(12) United States Patent
Brooks et al.

(10) Patent No.: US 7,192,982 B2
(45) Date of Patent: Mar. 20, 2007

(54) MODULATORS OF PEROXISOME PROLIFERATOR ACTIVATED RECEPTORS

(75) Inventors: Dawn Alisa Brooks, Indianapolis, IN (US); Alan M. Warshawsky, Carmel, IN (US); Chahrzad Montrose-Rafezadeh, Indianapolis, IN (US); Anne-Reifel Miller, Indianapolis, IN (US); Lourdes Prieto, Madrid (ES); Isabel Rojo, Madrid (ES); Jose Alfredo Martin, Madrid (ES); Maria Rosario Gonzales Garcia, Madrid (ES); Alicia Torrado, Madrid (ES); Rafael Ferritto Crespo, Madrid (ES); Carlos Lamas-Peteira, Madrid (ES); Robert J. Ardecky, Encinitas, CA (US); Maria Martin-Ortega Finger, Madrid (ES)

(73) Assignees: Ligand Pharmaceuticals, Inc., San Diego, CA (US); Eli Lilly and Company, Indianapolis, IN (US)

( * ) Notice: Subject to any disclaimer, the term of this patent is extended or adjusted under 35 U.S.C. 154(b) by 251 days.

(21) Appl. No.: 10/479,262

(22) PCT Filed: May 30, 2002

(86) PCT No.: PCT/US02/16950

§ 371 (c)(1), (2), (4) Date: Dec. 1, 2003

(87) PCT Pub. No.: WO02/100813

PCT Pub. Date: Dec. 19, 2002

(65) Prior Publication Data
US 2005/0020684 A1    Jan. 27, 2005

Related U.S. Application Data

(60) Provisional application No. 60/297,144, filed on Jun. 7, 2001.

(51) Int. Cl.
*A61K 37/00* (2006.01)
*C07C 59/00* (2006.01)

(52) U.S. Cl. .................. 514/557; 514/454; 514/456; 514/443; 514/451; 549/263; 549/273; 549/433; 549/434; 549/32; 549/31; 562/465; 562/463

(58) Field of Classification Search .......... 562/465, 562/463; 549/32, 31, 263, 273, 433, 434; 514/443, 451, 454, 456, 557
See application file for complete search history.

(56) References Cited

U.S. PATENT DOCUMENTS

| | | |
|---|---|---|
| 5,089,514 A | 2/1992 | Hulin |
| 5,232,945 A | 8/1993 | Hulin |
| 5,306,726 A | 4/1994 | Hulin |
| 5,387,672 A * | 2/1995 | Bucci et al. ............ 530/385 |
| 5,462,954 A * | 10/1995 | Baker et al. ............ 514/381 |
| 6,054,453 A | 4/2000 | Lohray et al. |
| 6,506,757 B1 | 1/2003 | Tajima et al. |

(Continued)

FOREIGN PATENT DOCUMENTS

CA    2 385 081    4/2001

(Continued)

OTHER PUBLICATIONS

Bucci et al., 1995, CAS : 122 :196942.*

(Continued)

*Primary Examiner*—Joseph K. McKane
*Assistant Examiner*—Robert Shiao
(74) *Attorney, Agent, or Firm*—Hamilton, Brook, Smith & Reynolds, P.C.

(57) ABSTRACT

Disclosed is a compound represented by Structural Formula (I): Ar is a substituted or unsubstituted aromatic group. Q is a covalent bond, —$CH_2$— or —$CH_2CH_2$—; W is a substituted or unsubstituted alkylene or a substituted or unsubstituted heteroalkylene linking group from two to ten atoms in length, preferably from two to seven atoms in length. Phenyl Ring A is optionally substituted with up to four substituents in addition to $R_1$ and W, $R_1$ is $(CH_2)_n$—CH($OR_2$)—$(CH_2)_m$$E_1$, —(CH)=C($OR_2$)—$(CH_2)_m$E, —$(CH_2)_n$—CH(Y)—$(CH_2)_m$E or (CH)=C(Y)—$(CH_2)_m$E; wherein E is $COOR_3$, $C_1$–$C_3$ alkylnitrile, carboxamide, sulfonamide, acylsulfonamide or tetrazole and wherein sulfonamide, acylsulfonamide and tetrazole are optionally substituted with one or more substituents independently selected from: $C_1$–$C_6$ alkyl, haloalkyl and aryl-$C_0$-4-alkyl; $R_2$ is H, an aliphatic group, a substituted aliphatic group, haloalkyl, an aromatic group, a substituted aromatic group, —$COR_4$, —$COOR_4$, —$CONR_5R_6$, —$C(S)R_4$, —$C(S)OR_4$ or $C(S)NR_5R_6$, $R_3$ is H, an aliphatic group, a substituted aliphatic group, an aromatic group or a substituted aromatic group. Y is O—, $CH_2$—, —$CH_2CH_2$— or CH=CH— and is bonded to a carbon atom in Phenyl Ring A that is ortho to $R_1$. $R_4$–$R_6$ are independently H, an aliphatic group, a substituted aliphatic group, an aromatic group or a substituted aromatic group. n and m are independently 0, 1 or 2

(I)

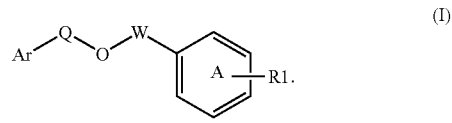

8 Claims, No Drawings

U.S. PATENT DOCUMENTS

| | | |
|---|---|---|
| 6,541,474 B2 | 4/2003 | Kikuchi et al. |
| 2002/0032202 A1 | 3/2002 | Kikuchi et al. |
| 2003/0153579 A1 | 8/2003 | Tajima et al. |

FOREIGN PATENT DOCUMENTS

| | | | |
|---|---|---|---|
| EP | 0 903 343 B1 | | 5/2003 |
| WO | WO 9636347 | * | 11/1996 |
| WO | WO99/62870 A1 | | 12/1999 |
| WO | WO99/62872 A1 | | 12/1999 |
| WO | WO/0220482 A1 | | 3/2002 |

OTHER PUBLICATIONS

Haigh, D., et al., "Non-thiazolidinedione Antihyperglycaemic Agents. Part 3: The Effects of Stereochemistry on the Potency of α-Methoxy-β-phenylpropanoic Acids," *Bioorganic & Medicinal Chemistry*, 7: 821-830 (1999).

Kersten, S., et al., "Roles of PPARs in Health and Disease," *Nature*, 405: 421-424 (2000).

* cited by examiner

MODULATORS OF PEROXISOME PROLIFERATOR ACTIVATED RECEPTORS

RELATED APPLICATIONS

This application claims the benefit of U.S. provisional application 60/297,144, filed 7 Jun. 2001, the entire teachings of which are incorporated herein by reference.

BACKGROUND OF THE INVENTION

The peroxisome proliferator activated receptors (PPARs) are members of the nuclear receptor gene family that are activated by fatty acids and fatty acid metabolites. The PPARs belong to the subset of nuclear receptors that function as heterodimers with the 9-cis retinoic acid receptor (RXR). Three subtypes, designated PPARα, PPARγ and PPARδ, are found in species ranging from *Xenopus* to humans.

PPARα is the main subtype in the liver and has facilitated analysis of the mechanism by which peroxisome proliferators exert their pleiopropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in low-density lipoprotein (LDL) cholesterol, and they are used particularly for the treatment of hypertriglyceridemia.

PPARγ is the main subtype in adipose tissue and involved in activating the program of adipocyte differentiation. PPARγ is not involved in stimulating peroxisome proliferation in the liver. There are two isomers of PPARγ: PPARγ1 and PPARγ2, which differ only in that PPARγ2 contains an additional 28 amino acids present at the amino terminus. The DNA sequences for the PPARγ receptors are described in Elbrecht, et al., BBRC 224; 431–437 (1996). Although peroxisome proliferators, including the fibrates and fatty acids, activate the transcriptional activity of PPAR's, only prostaglandin $J_2$ derivatives have been identified as natural ligands for PPARγ, which also binds the anti-diabetic agents thiazolidinediones with high affinity. The physiological functions of PPARα and PPARγ in lipid and carbohydrate metabolism were uncovered once it was recognized that they were the receptors for the fibrate and glitazone drugs, respectively.

PPARα and PPARγ receptors have been implicated in diabetes mellitus, cardiovascular disease, obesity, and gastrointestinal disease, such as inflammatory bowel disease and other inflammation related illnesses. Such inflammation related illnesses include, but are not limited to Alzheimer's disease, Crohn's disease, rheumatoid arthritis, psoriasis, and ischemia reprofusion injury. By contrast, PPARδ (also referred to as PPARβ and NUC1) is not reported to be receptor for any known class of drug molecules, and its role in mammalian physiology has remained undefined. The human nuclear receptor gene PPARδ (hPPARδ) has been cloned from a human osteosarcoma cell cDNA library and is fully described in A. Schmidt et al., *Molecular-Endocrinology*, 6:1634–1641 (1992).

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a propound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL (known as the "bad" cholesterol) which are risk factors in cardiovascular diseases. The constellation of symptoms which includes hyperinsulemia combined with hypertension, elevated body weight, elevated triglycerides and elevated LDL is known as Syndrome X.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. One form of hyperlipidemia is hypercholesterolemia, characterized by the existence of elevated LDL cholesterol levels. The initial treatment for hypercholesterolemia is often a diet low in fat and cholesterol coupled with appropriate physical exercise. Drug intervention is initiated if LDL-lowering goals are not met by diet and exercise alone. It is desirable to lower elevated levels of LDL cholesterol and increase levels of HDL cholesterol. Generally, it has been found that increased levels of HDL are associated with lower risk for coronary heart disease (CHD). See Gordon, et al., *Am. J. Med.*, 62, 707–714 (1977); Stampfer, et al., *N. England J. Med.*, 325, 373–381 (1991); and Kannel, et al., *Ann. Internal Med.*, 90, 85–91 (1979). An example of an HDL raising agent is nicotinic acid, but the quantities needed to achieve HDL elevation are associated with undesirable effects, such as flushing.

There are several treatments currently available for treating diabetes mellitus but these treatments still remain unsatisfactory and have limitations. While physical exercise and reduction in dietary intake of calories will improve the diabetic condition, compliance with this approach can be poor because of sedentary lifestyles and excess food consumption, in particular high fat-containing food. Therefore treatment with hypoglycemics, such as sulfonylureas (e.g., chlorpropamide, tolbutamide, tolazamide and acetohexamide) and biguanides (e.g. phenformin and metformin) are often necessary as the disease progresses. Sulfonylureas stimulate the β cells of the pancreas to secrete more insulin as the disease progresses. However, the response of the β cells eventually fails and treatment with insulin injections is necessary. In addition, both sulfonylurea treatment and insulin injection have the life threatening side effect of hypoglycemic coma, and thus patients using these treatments must carefully control dosage.

It has been well established that improved glycemic control in patients with diabetes (Type I and Type II) is accompanied by decreased microvasclular complications (DCCT and UKPDS). Due to difficulty in maintaining adequate glycemic control over time in patients with Type II diabetes, the use of insulin sensitizers in the therapy of Type II diabetes is growning. There is also a growing body of evidence that PPARγ agonist, insulin sensitizer, may have benefits in the treatment of Type II diabetes beyond their effects in improving glycemic control.

In the last decade a class of compounds known as thiazolidinediones (e.g. U.S. Pat. Nos. 5,089,514; 4,342,771; 4,367,234; 4,340,605; and 5,306,726) have emerged as effective anidiabetic agents that have been shown to increase the sensitivity of insulin sensitive tissues, such as skeletal muscle, liver and adipose, to insulin. Increasing insulin sensitivity rather than the amount of insulin in the blood reduces the likelihood of hypoglycemic coma. Although thiazolidinediones have been shown to increase insulin sensitivity by binding to PPARγ receptors, this treatment also produces unwanted side effects such as weight gain and, for troglitazone, liver toxicity.

In view of the above, there exists a need for new pharmaceutical agents which modulate these receptors to prevent, treat and/or alleviate these diseases or conditions while ameliorating side effects of current treatments.

SUMMARY OF THE INVENTION

Disclosed herein are novel α-methoxy cinnamates which are modulators of peroxisome proliferator activated receptors (PPAR). Many of these novel α-methoxy cinnamates have the advantage over previously known PPAR modulators in that they selectively bind at peroxisome proliferator activated receptor modulators. Based on this discovery, methods of modulating a peroxisome proliferator activated receptor in a subject in need of such modulation, methods of treating a subject for Type II diabetes, methods of treating a subject for cardiovascular disease, methods of treating a subject for Syndrome X and methods of treating a subject with other PPAR-mediated diseases and conditions are disclosed herein.

One embodiment of the present invention is a compound represented by Structural Formula (I):

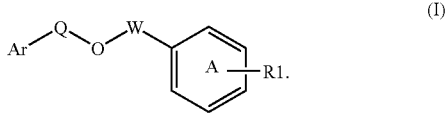

(I)

The variables in Structural Formula (I) are defined below.

Ar is a substituted or unsubstituted aromatic group. Preferably, Ar is an unsubstituted, monosubstituted or disubstituted aromatic group.

Q is a covalent bond, —CH$_2$—, —CH$_2$CH$_2$—, —CH$_2$CH$_2$CH$_2$— or —CH$_2$CH$_2$CH$_2$CH$_2$—. Preferably, Q is a covalent bond.

W is a substituted or unsubstituted alkylene group two to ten atoms in length or a substituted or unsubstituted heteroalkylene group, wherein the heteroalkylene group is an alkylene group from two to ten atoms in length in which one or more methylene groups have been replaced with a functional group selected from —CH=CH—, —C≡C—, —O—, —CO—, —NR$_7$—, —NR$_7$CO—, —C(=NOH)—, —S—, —S(O)—, —S(O)$_2$— or —CH(NR$_7$R$_8$)—.

Phenyl Ring A is optionally substituted with up to four substituents in addition to R$_1$ and W.

R$_1$ is —(CH$_2$)$_n$—CH(OR$_2$)—(CH$_2$)$_m$E, —(CH)=C(OR$_2$)—(CH$_2$)$_m$E, —(CH$_2$)$_n$—CH(Y)—(CH$_2$)$_m$E or —(CH)=C(Y)—(CH$_2$)$_m$E. E is COOR$_3$, C1–C3-alkylnitrile, carboxamide, sulfonamide, acylsulfonamide or tetrazole and wherein sulfonamide, acylsulfonamide and tetrazole are optionally substituted with one or more substituents independently selected from: C1–C6 alkyl, C1–C6 haloalkyl and aryl-C0–4-alkyl. Preferably R$_1$ is —(CH$_2$)$_n$—C(OR$_2$)—(CH$_2$)$_m$COOR$_3$, —(CH)=C(OR$_2$)—(CH$_2$)$_m$COOR$_3$, —(CH$_2$)$_n$—CH(Y)—(CH$_2$)$_m$COOR$_3$ or —(CH)=C(Y)—(CH$_2$)$_m$COOR$_3$. More preferably R$_1$ is meta or para to W and is represented by Structural Formula (II), even more preferably by Structural Formulas (III) or (IV) and even more preferably by Structural Formula (V):

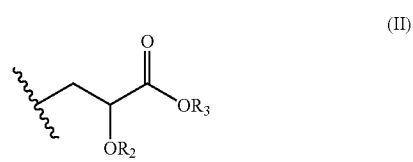

(II)

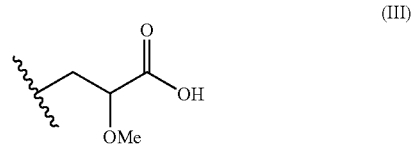

(III)

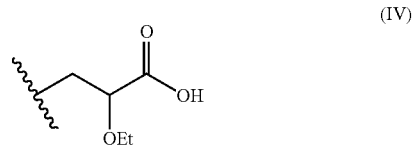

(IV)

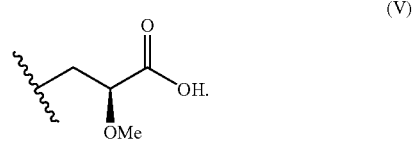

(V)

R$_2$ is —H, an aliphatic group, a substituted aliphatic group, haloalkyl, an aralkyl group, a substituted aralkyl group, an aromatic group, a substituted aromatic group, —COR$_4$, —COOR$_4$, —CONR$_5$R$_6$, —C(S)R$_4$, —C(S)OR$_4$ or —C(S)NR$_5$R$_6$.

Y is —O—, —CH$_2$—, —CH$_2$CH$_2$— or a —CH=CH— group that is bonded to a carbon atom in Phenyl Ring A that is ortho to R$_1$. Thus, Y, together with the two carbon atoms to which Y is bonded and the intervening carbon atoms, form a ring that is fused to Phenyl Ring A.

R$_3$–R$_8$ are independently —H, an aliphatic group, a substituted aliphatic group, an aromatic group or a substituted aromatic group.

n and m are independently 0, 1 or 2.

In Structural Formula (I), preferably, R$_2$ is a C1–C6 lower alkyl group, phenyl, benzyl or benzoyl; and R$_3$ is —H or a C1–C6 alkyl group (more preferably C$_1$–C$_3$ alkyl group).

In another embodiment, the compound of the present invention is represented by Structural Formula (VI):

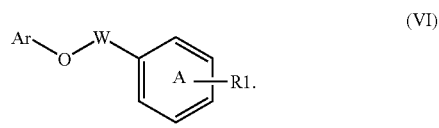

(VI)

The variables in Structural Formula (VI) are defined below.

Ar is a substituted or unsubstituted aromatic group. Preferably, Ar is an unsubstituted, monosubstituted or disubstituted aromatic group.

W is a substituted or unsubstituted alkylene linking group or a substituted or unsubstituted heteroalkylene linking group from two to ten atoms in length, preferably from two to seven atoms in length.

Phenyl Ring A is optionally substituted with up to four substituents in addition to $R_1$.

$R_1$ is —$(CH_2)_n$—$CH(OR_2)$—$(CH_2)_m COOR_3$, —$(CH)$=$C(OR_2)$—$(CH_2)_m COOR_3$, —$(CH_2)_n CH(Y)$—$(CH_2)_m COOR_3$ or —$(CH)$=$C(Y)$—$(CH_2)_m COOR_3$. Preferably $R_1$ is meta or para to W and is represented by Structural Formula (II), more preferably by Structural Formula (III) and even more preferably by Structural Formula (IV). Structural Formulas (II)–(V) are shown above.

$R_2$ is —H, an aliphatic group, a substituted aliphatic group, an aryl group, a substituted aryl group, —$COR_4$, —$COOR_4$, —$CONR_5 R_6$, —$C(S)R_4$, —$C(S)OR_4$ or —$C(S)NR_5 R_6$.

Y is —O—, —$CH_2$—, —$CH_2 CH_2$— or —CH=CH— and is bonded to a carbon atom in Phenyl Ring A that is ortho to $R_1$.

$R_3$–$R_6$ are independently —H, an aliphatic group, a substituted aliphatic group, an aryl group or a substituted aryl group.

n and m are independently 0, 1 or 2.

In Structural Formula (VI), preferably, $R_2$ is a C1–C6 lower alkyl group, phenyl, benzyl or benzoyl; and $R_3$ is —H or a $C_1$–$C_3$ lower alkyl group.

Another embodiment of the present invention is a method of modulating a peroxisome proliferator activated receptor (PPAR). The method comprises the step of contacting the receptor with at least one of the compounds of the present invention.

Another embodiment of the present invention is a method of modulating a peroxisome proliferator activated receptor gamma in a subject in need of modulation of the peroxisome proliferator activated receptor gamma, i.e., treating a PPAR-gamma mediated disease in a subject. The method comprises the step of administering to the subject an effective amount of a compound of the present invention.

Another embodiment of the present invention is a method for lowering blood-glucose in a subject in need of such treatment. The method comprises the step of administering to the subject an effective amount of a compound of the present invention.

Another embodiment of the present invention is a method of treating a subject for hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, polycystic ovarian syndrome, anorexia nervosa, cardiovascular disease or other diseases where insulin resistance is a component. The method comprises the step of administering to the subject an effective amount of a compound of the present invention.

Another embodiment of the present invention is a method of treating a subject with diabetes mellitus. The method comprises the step of administering to the subject an effective amount of a compound of the present invention Another embodiment of the present invention is a method of treating a subject for cardiovascular disease. The method comprises the step of administering to the subject an effective amount of a compound of the present invention.

Another embodiment of the present invention is a method of treating a subject for Syndrome X. The method comprises the step of administering to the subject an effective amount of a compound of the present invention.

Another embodiment of the present invention is a compound of the present invention for use in therapy. The therapy can be, for example, to treat Type II diabetes, cardiovascular disease, Syndrome X or a disorder modulated by a peroxisome proliferator activated receptor.

Another embodiment of the present invention is the use of a compound of the present invention for the manufacture of a medicament for the treatment of hyperglycemia, dyslipidemia, Type II diabetes, Type I diabetes, hypertriglyceridemia, syndrome X insulin resistance, heart failure, diabetic dyslipidemia, hyperlipidemia, hypercholesteremia, hypertension, obesity, anorexia bulimia, polycystic ovarian syndrome, anorexia nervosa, cardiovascular disease or other diseases where insulin resistance is a component or other disorders modulated by a peroxisome proliferator activated receptor.

Yet another embodiment of the present invention is a pharmaceutical composition which comprises a pharmaceutically acceptable carrier and at least one compound of the present invention.

Yet another embodiment of the present invention is a method of preparing a compound represented by Structural Formula (VII) from a starting compound represented by Structural Formula (VIII):

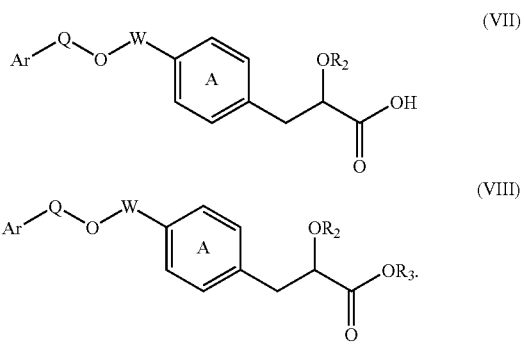

The method comprises the step of hydrolyzing the ester group in the starting compound. Phenyl Ring A, Ar, Q, W, $R_2$ and $R_3$ are as described for Structural Formulas (I) or (VI). Q in Structural Formulas (VII) and (VIII) is preferably a covalent bond.

Yet another embodiment of the present invention is one of the novel compounds described herein, wherein the compound is radioactively labeled, i.e., comprises a radioactive isotope (e.g., $^3H$ or $^{14}C$) at a specific site in the compound at level significantly greater than the natural abundance of the isotope. "Significantly greater than natural abundance" means that the amount of isotope greater than natural abundance can be assessed by suitable means (e.g., scintillation counting). Radiolabeled, preferably tritiated, (S)-3-{4-[3-(Biphenyl-4-yloxy)-propoxy]-phenyl}-2-methoxy-propionic acid is one example of a radiolabeled compound of the invention. Radiolabeled compounds, can be advantageously used to assess binding of test compound to PPARγ.

Yet another embodiment of the present invention is a method for determining whether a compound does or does not interact directly (e.g., binds) with PPARγ. The method comprises the step of specifically binding a radioactively labeled compound described herein to the ligand binding domain of a PPARγ receptor. The receptor is then combined with a test compound and the amount of specific binding of the radioactively labeled compound is assessed. Any decrease in the binding of the radiolabeled compound indicates that the test compound interacts directly with the peroxisome proliferator-activated receptor.

The compounds of the present invention and pharmaceutically acceptable salts, solvates and hydrates, stereoisomers thereof lower one or more of the following in mammals: glucose, insulin, triglycerides, fatty acids and/or cholesterol. They are therefore believed to be effective in treating hyperglycemia, dyslipidemia, Type II diabetes, Type I diabetes, hypertriglyceridemia, syndrome X insulin resistance, heart failure, diabetic dyslipidemia, hyperlipidemia, hypercholesteremia, hypertension, obesity, anorexia bulimia, polycystic ovarian syndrome, anorexia nervosa, cardiovascular disease or other diseases where insulin resistance is a component or other disorders modulated by a peroxisome proliferator activated receptor.

DETAILED DESCRIPTION OF THE INVENTION

In the Schemes, Preparations and Examples below, various reagent symbols and abbreviations have the following meanings:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DIAD | diisopropyl azodicarboxylate |
| DIPEA | diisopropylethylamine |
| DMAP | 4-dimethylamino pyridine |
| DMF | N,N-dimethylformamide |
| DMSO | dimethylsulfoxide |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| FMOC | 9-Flurorenylmethyl carbamate |
| HATU | O-(7-azabenzotriazol-1-yl)-N,N,N',N'-tetramethyluronium hexafluorophosphate |
| HOAT: | 1-hydroxy-7-azabenzotriazole |
| HOBT | 1-hydroxybenzotriazole hydrate |
| HPLC | high performance liquid chromatography |
| HRMS | high resolution mass |
| LRMS | low resolution mass |
| Me | methyl |
| Ms | methanesulfonyl |
| Pd$_2$(dba)$_3$ | tris(dibenzylideneacetone) dipalladium(0) |
| Ph | phenyl |
| Phe | phenylalanine |
| Pr | propyl |
| r.t. | room temperature |
| TBAF | tetrabutylammonium fluoride |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |

In one preferred embodiment, the compound of the present invention is represented by Structural Formula (IX):

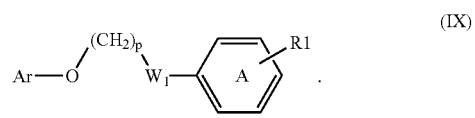

Ar, Phenyl Ring A and $R_1$ in Structural Formula (IX) are as defined in Structural Formulas (I) or (VI). $R_1$ is preferably para to $W_1$ and is represented by Structural Formula (II), more preferably Structural Formulas (III) or (IV) and even more preferably, Structural Formula (V).

p is an integer from one to nine, preferably one to four.

$W_1$ is —O—, —C(O), —OCH$_2$—, —CH$_2$—, —NR$_8$—, —NR$_8$CO—, —NR$_8$CH—, —C(═NOH)— or —CH(NR$_7$R$_8$)—.

$R_7$ and $R_8$ are independently —H, an aliphatic group, a substituted aliphatic group, an aromatic group or a substituted aromatic group.

In a more preferred embodiment, the compound of the present invention is represented by a structural formula selected from Structural Formulas (X)–(XVIII):

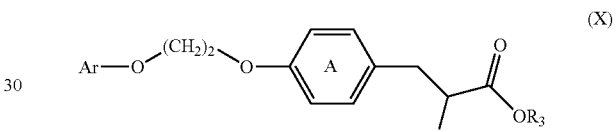

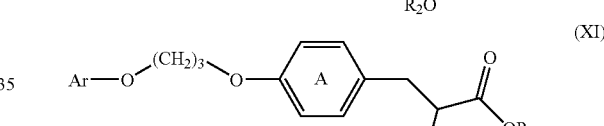

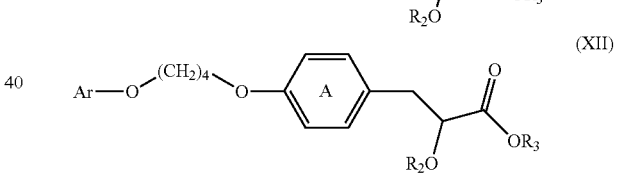

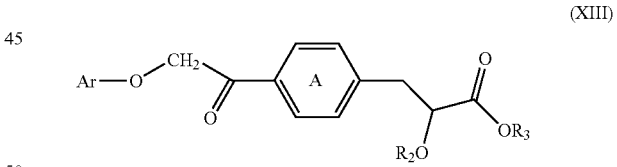

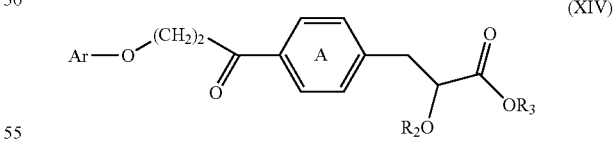

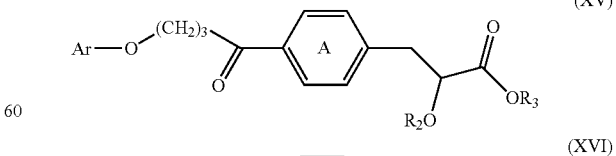

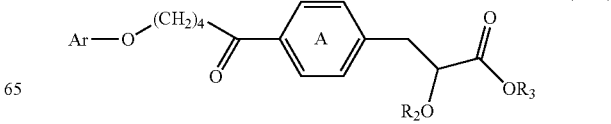

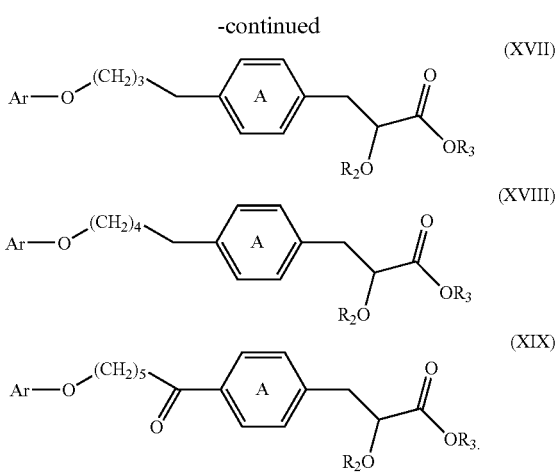

(XVII)

(XVIII)

(XIX)

Ar, Phenyl Ring A, $R_2$ and $R_3$ in Structural Formulas (X)–(XIX) are as described for Structural Formula (IX). Preferably, $R_2$ and $R_3$ are as described for Structural Formula (II). More preferably, —CH$_2$CH(OR$_2$)COOR$_3$ in Structural Formulas (X)–(XIX) is represented by Structural Formulas (III) or (IV) and even more preferably by Structural Formula (V).

In another preferred embodiment the compound of the present invention is represented by Structural Formula (XX):

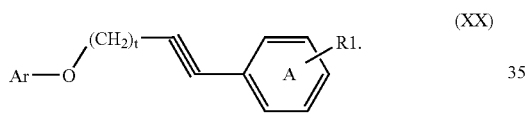

(XX)

Ar and Phenyl Ring A in Structural Formula (XX) are as described for Structural Formulas (I) or (VI) and t is an integer from 1 to about 5.

In a more preferred embodiment, $R_1$ in structural Formula (XX) is para to the carbon bonded to the alkyne group and is represented by Structural Formula (II), more preferably by Structural Formulas (III) or (IV) and even more preferably by Structural Formula (V). Preferably, t is 1, 2 or 3.

In another preferred embodiment, the compound of the present invention is represented by Structural Formula (XXI):

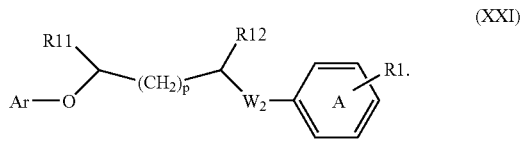

(XXI)

Ar and Phenyl Ring A in Structural Formula (XXI) are as described for Structural Formulas (I) or (VI).

p is zero, one or two.

$W_2$ is —O—, —C(O)—, —OCH$_2$—, —CH$_2$—, —NR$_8$—, —NR$_8$CO—, —NR$_8$CH—, —C(=NOH)— or —CH(NR$_7$R$_8$)—. $W_2$ is preferably —O—.

$R_7$ and $R_8$ are independently —H, an aliphatic group, a substituted aliphatic group, an aromatic group or a substituted aromatic group.

$R_{11}$ and $R_{12}$ are independently a C1–C6 alkyl group (preferably $C_1$–$C_3$ alkyl group), or, taken together are a substituted or unsubstituted ethylene, propylene or butylene group.

In a more preferred embodiment, the compound of the present invention is represented by a structural formula selected from Structural Formulas (XXII)–(XXVI):

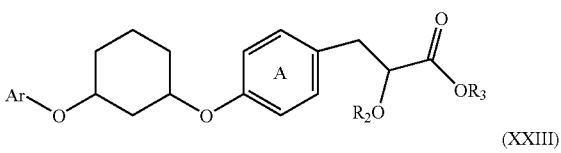

(XXII)

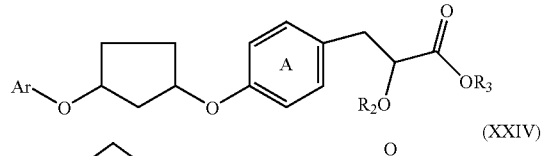

(XXIII)

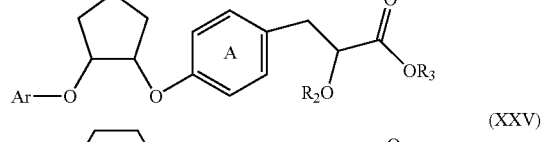

(XXIV)

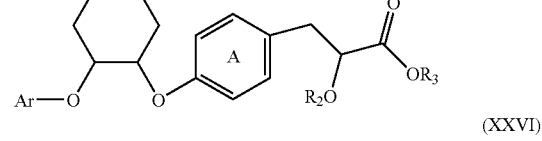

(XXV)

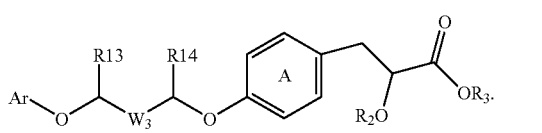

(XXVI)

Ar and Phenyl Ring A in Structural Formulas (XXII)–(XXVI) are as described for Structural Formula (XXI) and $R_2$ and $R_3$ in Structural Formulas (XXII)–(XXVI) are as described in Structural Formula (II). In Structural Formula (XXVI), $W_3$ is a covalent bond, methylene or ethylene and $R_{13}$ and $R_{14}$ are methyl, ethyl or propyl and are the same or different, preferably the same. Preferably, —CH$_2$CH(OR$_2$)COOR$_3$ in Structural Formulas (XXII)–(XXVI) is represented by Structural Formulas (III) or (IV), more preferably by Structural Formula (V).

In another preferred embodiment the compound of the present invention is represented by Structural Formula (XXVII):

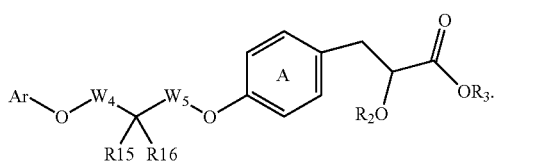

(XXVII)

Ar, Phenyl Ring A, $R_2$ and $R_3$ in Structural Formulas (XXVII) are as described for Structural Formulas (I) or (VI); $W_4$ and $W_5$ are independently methylene or ethylene; and $R_{15}$ is —H and $R_{16}$ is a C1–C6 alkyl group (preferably methyl ethyl or propyl), or $R_{15}$ and $R_{16}$, taken together, are =O or =$CH_2$. Preferably, —$CH_2CH(OR_2)COOR_3$ in Structural Formula (XXVII) is represented by Structural Formulas (III) or (IV), more preferably by Structural Formula (V).

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about 1 and about 10 carbon atoms, more typically between about 1 and about 6 carbon atoms. When cyclic, an aliphatic group typically contains between about 3 and about 10 carbon atoms, more typically between about 3 and about 7 carbon atoms. Aliphatic groups are preferably C1–C10 straight chained or branched alkyl groups (i.e., completely saturated aliphatic groups), more preferably C1–C6 straight chained or branched alkyl groups. Examples include methyl, ethyl, n-propyl, iso-propyl, n-butyl, sec-butyl and tert-butyl.

A "haloaliphatic group" is an aliphatic group, as defined above, substituted with one or more halogen atoms.

A "haloalkyl group" is an alkyl group (i.e., a saturated aliphatic group), as defined above, substituted with one or more halogen atoms. Examples included —$CF_3$, —$CHF_2$, —$CH_2F$, —$CF_2CF_3$ and the like.

An "aralkyl group" is an alkyl group substituted with an aromatic group, preferably a phenyl group. A preferred aralkyl group is a benzyl group. Suitable aromatic groups are described below and suitable alkyl groups are described above. Suitable substituents for an aralkyl group are described below.

An "aralkenyl group" is an alkenyl group substituted with an aromatic group. An "alkenyl group" is an aliphatic group with one or more carbon carbon double bonds. Suitable aromatic groups are described below. Suitable aliphatic groups are defined above. Suitable substituents for an aralkenyl group are described below.

An "allyl group" has the formula —$CH_2CH=CH_2$. Suitable substituents for an alkyl group are described below An "alkylene group" is a polymethylene group, i.e., —$(CH_2)_n$—, wherein n is a positive integer. Preferably, n is an integer from about 2 to about 10, more preferably from about 2 to about 7. A "substituted alkylene group" is an alkylene group in which one or more methylene hydrogen atoms are replaced with a substituent. Suitable substituents are described below.

An "arylene" is an aromatic group in which at least two carbon atoms are bonded to moieties other than hydrogen. Suitable arylene groups are those corresponding to the aromatic groups described herein.

A "sulfonamide group" is represented by —$S(O)_2NH_2$. A "substituted sulfonamide group" is represented by —$S(O)_2N(R)_2$, wherein each R is independently —H, C1–C6 alkyl, C1–C6 haloalkyl or aryl-C0–C4-alkyl and at least one R is not —H.

An "acylsulfonamide group" is represented by —$S(O)_2NH$—C(O)—R wherein R is —H or a C1–C6 alkyl group or a C1–C6 haloalkyl group. A "substituted acylsulfonamide group" is represented by —$S(O)_2NR'$—C(O)R, wherein R is —H or a C1–C6 alkyl group or C1–C6 haloalkyl group and R' is C1–C6 alkyl, C1–C6 haloalkyl or aryl-C0–C4-alkyl.

The term "heteroalkylene group" refers to an alkylene group in which one or more methylene groups have been replaced by a functional group, e.g., —$(CH_2)_p$-Z-$(CH_2)_q$— wherein p is a positive integer and q is zero or a positive integer such that p+q is less than 10 and Z is a functional group. Examples of suitable functional groups include —CH=CH—, —C≡C—, —O—, —CO—, —$NR_8$—, —$NR_8CO$—, —C(=NOH)—, —$S(O)_k$— and —CH($NR_7R_8$)— wherein each $R_7$ and each $R_8$ is independently —H, an aliphatic group, a substituted aliphatic group, an aromatic group or a substituted aromatic group; and k is 0, 1 or 2. Preferably, a heteroalkylene group is between about 2 and 10 atoms in length. For purposes of determining the length of a heteroalkylene group, in this application a functional group is considered to be one atom. Thus, for example, —$(CH_2)_3$—CO—NH$(CH_2)_2$— is six atoms in length (five methylene carbons and a functional group); and $CH_2)_3$—C(=NOH)—$(CH_2)_2$— is also six atoms in length (five methylene carbons and an oxime carbon). Examples of preferred heteroalkylene groups include —$(CH_2)_2$—O—, —$(CH_2)_3$—O—, —$(CH_2)_4$—O—, —$CH_2$—C≡CH—, —$(CH_2)_2$—C≡CH—, —$(CH_2)_3$—C≡CH—, —$(CH_2)_4$—C≡CH—, —$(CH_2)_5$—C≡CH—, —$(CH_2)CO$—, —$(CH_2)_2CO$—, —$(CH_2)_3CO$—, —$(CH_2)_4CO$—, —$(CH_2)_2$—C(=NOH)—, —$(CH_2)_3$—C(=NOH)—, —$(CH_2)_4$—(=NOH)—, —$(CH_2)_2$—$NR_8$—, —$(CH_2)_3$—$NR_8$—, —$(CH_2)_4$—$NR_8$—, —$(CH_2)_2$—$NR_8CO$—, —$(CH_2)_3$—$NR_8CO$—, —$(CH_2)_4$—$NR_8CO$—, —$(CH_2)_2$—$OCH_2$—, —$(CH_2)_3$—$OCH_2$—, —$(CH_2)_4$—$OCH_2$—, —$(CH_2)_2$—$NR_8CH_2$—, —$(CH_2)_3$—$NR_8CH_2$—, —$(CH_2)_4$—$NR_8CH_2$—, —$(CH_2)_2CH(NR_7R_8)$—, —$(CH_2)_3CH(NR_7R_8)$— and —$(CH_2)_4$—$CH(NR_7R_8)$—.

A "substituted heteroalkylene group" is a heteroalkylene group in which one or more methylene hydrogen atoms are replaced with a substituent. Preferred substituents include =O, =$CH_2$, C1–C6 alkyl and C2–C4 alkylene. When a heteroalkylene group is substituted with a C2–C4 alkylene group, the C2–C4 alkylene group together with the carbon atoms of the heteroalkylene group to which the two ends of the C2–C4 alkylene group are bonded and any intervening carbon atoms form a cycloalkyl ring. Structural Formula (XX) provides an example of a heteroalkylene group substituted with a C2–C4 alkylene group, which is represented by $R_{11}$ and $R_{12}$ taken together. Specifically, $R_{11}$ and $R_{12}$, taken together with —CH—$(CH_2)_p$CH— can form a cycloalkyl ring. Other examples of heteroalkylene groups substituted by an alkylene are shown in the following structural formulas:

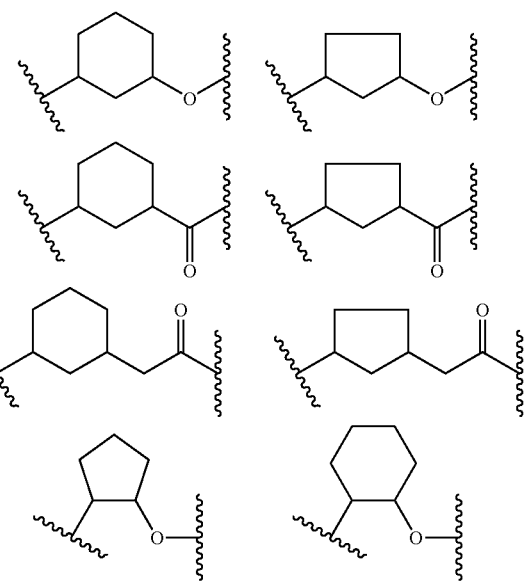

-continued

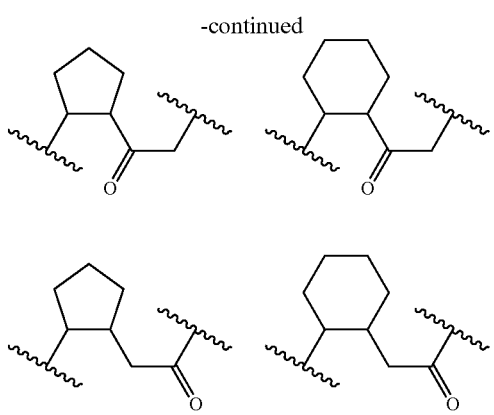

Other suitable substituents for a heteroalkylene group are described below.

A "nonaromatic heterocyclic ring" (or also referred to as a "heterocyclic ring") is a monocyclic, bicyclic, or tricyclic nonaromatic ring of 3 to 14 ring atoms which are saturated or partially saturated containing carbon and from one to four heteroatoms selected from N, O or S. The term "nonaromatic heterocyclic ring" includes nitrogen-containing heterocyclic rings, which contains from one to three nitrogen atoms and optionally further contains one other heteroatom selected from O or S. Examples include morpholinyl, thiomorphonlyl, pyrrolindinyl, pierazinyl, piperidinyl, azetidinyl, azacycloheptyl, or N-phenylpiperazinyl. The tern "non-aromatic heterocyclic ring" also includes non-aromatic heterocyclic rings fused to aromatic group, e.g., 1,3-benzodioxole, 4-chromanone, and phthalimide. A "non-aromatic heterocyclic ring" may be optionally substituted with a designated number of substituents, as described below.

An "aromatic group" (also referred to as an "aryl group") as used herein includes carbocyclic aromatic groups, heterocyclic aromatic groups (also referred to as "heteroaryl") and fused polycyclic aromatic ring system as defined herein.

A "carbocyclic aromatic group" is an aromatic ring of 5 to 14 carbons atoms, and includes a carbocyclic aromatic group fused with a 5-or 6-membered cycloalkyl group such as indan. Examples of carbocyclic aromatic groups include, but are not limited to, phenyl, 1-naphthyl, 2-naphyl, 1-anthracenyl 2-anthracenyl, phenanthrenyl, fluorene, 9-fluorenone, indan and the like. A carbocyclic aromatic group is optionally substituted with a designated number of substituents, described below for aromatic groups.

A "heterocyclic aromatic group" (or "heteroaryl") is a monocyclic, bicyclic or tricyclic aromatic ring of 5- to 14-ring atoms of carbon and from one to four heteroatoms selected from O, N, or S. Examples of heteroaryl include, but are not limited to N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl 2-pyranyl, 3-pyranyl, 4-pyrazolyl, 5-pyrazolyl, 2-thiazolyl, 4-thiazolyl, 5-thiazolyl, 2-oxazoyl, 4-oxazoyl, 5-oxazoyl, 2-imidazolyl, isoxazoyl, pyrrolyl, pyrazinyl, and purinyl and the like. Heterocyclic aromatic (or heteroaryl) as defined above may be optionally substituted with a designated number of substituents, as described below for aromatic groups.

A "fused polycyclic aromatic" ring system is a carbocyclic aromatic group or heteroaryl fused with one or more other heteroaryl or nonaromatic heterocyclic ring. Examples include 2,3-dihydrobenzofuran, dibenzothiophene, dibenzofuran, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzoimidazolyl, 2-qinolinyl, 3-quinolinyl, 1-isoqinolinyl, 3-quinolinyl, 1-isoinoldyl, 3-isoindolyl, benzotriazolyl and the like. Fused polycyclic aromatic ring systems may optionally be substituted with a designated number of substituents, as described below for aromatic groups.

"Halo" refers to fluoro, chloro, bromo and iodo.

Preferred examples of suitable values for Ar in Structural Formulas (I), and (VI)–(XXVII) are shown below:

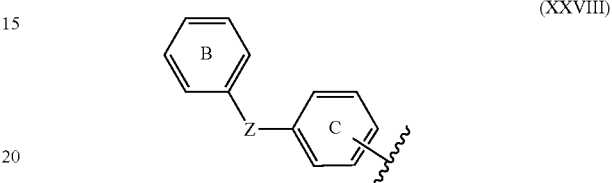

(XXVIII)

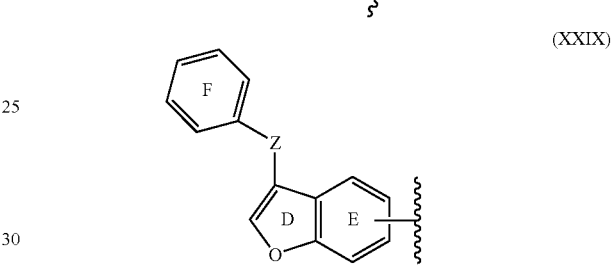

(XXIX)

(XXX)

(XXXI)


(XXXII)

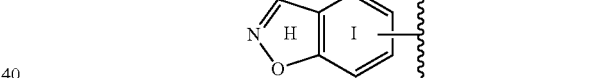

(XXXIII)

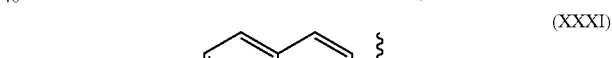

(XXXIV)

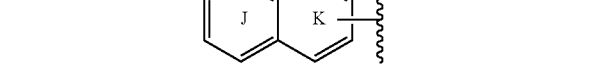


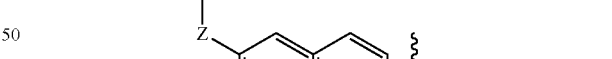

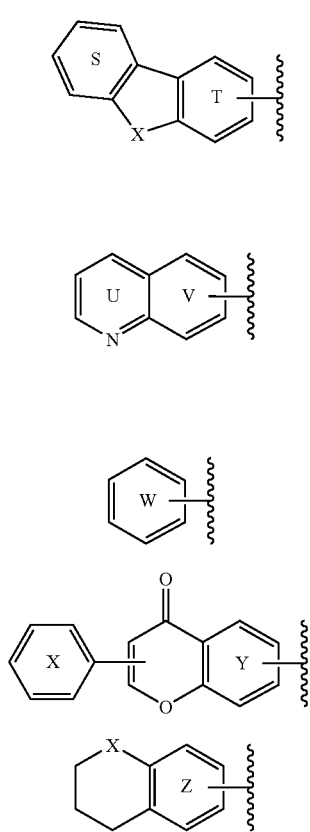

Rings B-Z are independently substituted or unsubstituted. Other examples of suitable groups for Ar include substituted or unsubstituted benzoylnaphthyl, thienylphenyl and naphthoylphenyl. Still other examples of suitable values for Ar are found in Examples 1–379. These aromatic groups, when used as values for Ar, can be substituted or unsubstituted, as shown in Examples 1–379, or, alternatively, can contain one or more other aromatic group substituents that are described herein.

X is —O—, —S—, —CH$_2$— or —C(O).

Z is a covalent bond, —O—, —(CH$_2$)$_q$—, —CH(CH$_3$)(CH$_2$)$_q$—, —C(CH$_3$)$_2$(CH$_2$)$_q$—, —(CH$_2$)$_q$CH(CH$_3$)—, —(CH$_2$)$_q$C(CH$_3$)$_2$—, —O(CH$_2$)$_q$—, —(CH$_2$)$_q$O—, —(CH$_2$)$_q$NH—, —(CH$_2$)$_q$NH—, —(CH$_2$)$_q$CHR$_{20}$—, —CHR$_{20}$(CH$_2$)$_q$—, —(CH$_2$)$_q$CR$_{20}$R$_{20}$—, —(CH$_2$)$_q$CR$_{20}$R$_{20}$—, —(CH$_2$)$_q$NR$_{20}$—, —NR$_{20}$(CH$_2$)$_q$—, —(CH$_2$)$_q$C(=NOH)—, —C(=NOH)(CH$_2$)$_q$—, —CH(OH)(CH$_2$)$_q$—, —(CH$_2$)$_q$—CH(OH)—, —CO—(CH$_2$q—, —(CH$_2$)$_q$—CO—, —COO—(CH$_2$)$_q$—, —OCO—(CH$_2$)$_q$—, —(CH$_2$)$_q$—OCO—, —(CH$_2$)$_q$COO—, —(CH$_2$)$_q$CO—NH—, —(CH$_2$)$_q$NH—CO—, —(CH$_2$)$_q$CONR$_{20}$—, —CONR$_{20}$(CH$_2$)$_q$—, —(CH$_2$)$_q$NR$_{20}$CO— or —NR$_{20}$CO(CH$_2$)$_q$—. Z is preferably a covalent bond, —C(=NOH), —O— or —C(O)— (more preferably —O— or —C(O)—); and q is 0, 1, 2 or 3, preferably 0 or 1.

Each R$_{20}$ is independently a C1–C5 alkyl group or halogenated C1–C5 alkyl group.

Especially preferred values groups for Ar in Structural Formulas (I) and (VI)–(XXVII) are shown below:

Phenyl Rings A' and A" are substituted or unsubstituted.

Suitable substituents for an aromatic group, including the aromatic group represented by Ar (e.g., Phenyl Rings A' and A" and Rings B-Z) and Phenyl Ring A, an aliphatic group, an alkyl group, an alkylene group, a heteroalkylene group, a non-aromatic heterocyclic group, an aralkyl group, an aralkenyl group and an alkyl group are those which do not significantly diminish the activity of the compound at the Peroxisome Proliferator Activated Receptors (PPARs), e.g., decrease the activity by more than a factor of five (preferably no more than a factor of two) compared with the corresponding compound without the substituent Examples of substituents include halogen (—Br, —Cl, —I and —F) —R, —OR, —CN, —NO$_2$, —N(R)$_2$, —COR, —COOR, —CON(R)$_2$, —SO$_k$R (k is 0, 1 or 2) and —NH—C(=NH)—NH$_2$. Other examples include sulfonamide, acylsulfonamide, —NR—CO—R, —OS(O)R, —OS(O)$_2$R, cycloalkyl groups, substituted or unsubstituted non-aromatic heterocyclic groups, —O(CH$_2$)$_r$COOH —O—O(CH$_2$)$_r$—N(R)$_2$, —O(CH$_2$)$_r$-(cycloalkyl), —O(CH$_2$)$_r$OH, —O(CH$_2$)$_r$—OSi(R)$_3$, and —(CH$_2$)$_a$CH(OR$_{30}$)(CH$_2$)$_b$COOR$_{31}$. Each R is independently —H, an aliphatic group, a substituted aliphatic group, a halogenated aliphatic group, a benzyl group, a substituted benzyl group, an aromatic group or a substituted aromatic group, and preferably —H, an alkyl group (e.g., a C1–C10 alkyl group), a halogenated alkyl group (e.g., a C1–C10 halogenated alkyl group), a phenyl group or a substituted phenyl group; R$_{30}$ is a C1–C6 alkyl group or C1–C6 halogenated alkyl group, R$_{31}$ is —H, a C1–C6 alkyl group or C1–C6 halogenated alkyl group; r is an integer from 1 to 6; a and b are independently 0, 1 or 2. An aromatic group, benzylic group, an aliphatic group, an alkyl group, an alkylene group, a heteroalkylene group, a non-aromatic heterocyclic group, aralkyl group and aralkenyl group can have more than one substituent. Other examples of suitable substituents for an aromatic group represented by Ar are those found at the corresponding position of the compounds descried in the Exemplification Section.

Preferred substituents for Rings B-Z include halogen, —R$_9$, —OR$_9$, —COR$_9$, —COOR$_9$, —CN, a non-aromatic heterocyclic group, an allylic group, —(CH$_2$)$_a$CH(OR$_{30}$)(CH$_2$)$_b$COOR$_{31}$ or —NR$_9$C(O)R$_9$. R$_9$ is —H, an alkyl group (e.g., a C1–C10 alkyl group), cycloalkyl, a halogenated alkyl group (e.g., a C1–C10 halogenated alkyl group) or an aromatic group. R$_{30}$, R$_{31}$, a and b are as described above; preferably R$_{30}$ is methyl or ethyl, R$_{31}$ is —H$_3$ and a and b are one.

More preferably, suitable substituents for Rings B-Z include one or more groups selected from halogen, C1–C8 straight chained or branched alkyl, C1–C8 straight chained or branched halogenated alkyl (e.g., —CF$_3$), C3–C8 cycloalkyl, C1–C8 straight chained or branched alkanoyl, C1–C8 straight chained or branched alkoxy (e.g., methoxy), —Br, —F, N-morpholino, —COOH, —OH, —CN, or C1–C8 straight chained or branched halogenated alkoxy (e.g., —OCF$_3$).

Suitable substituents for Phenyl Rings A' and A" are as described above for Rings B-Z.

Preferred substituents for Phenyl Ring A include halogen, —OR$_{10}$, —R$_{10}$, aromatic group, substituted aromatic group, aralkyl, substituted aralkyl, aralkenyl, substituted aralkenyl, allyl and substituted allyl and R$_{10}$ is —H, an alkyl group (e.g., a C1–C10 all group) or a halogenated alkyl group (e.g., a C1–C10 halogenated alkyl group). Specific examples of suitable substituents for Phenyl Ring A include —F, —Cl, —OCH$_3$, —OCF$_3$, —CH$_3$, ethyl, n-propyl, iso-propyl, alkyl, 2-phenylethenyl, 2-phenylethyl, phenyl, -o-biphenyl, -m-biphenyl, -p-biphenyl, -o-C$_6$H$_4$OCH$_3$, -m-C$_6$H$_4$OCH$_3$, -p-C$_6$H$_4$OCH$_3$, -o-C$_6$H$_4$F, -m-C$_6$H$_4$F and -p-C$_6$H$_4$F.

Another embodiment of the present invention is a compound represented by Structural Formula (XLII):

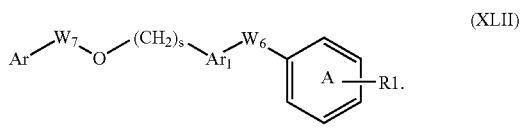

(XLII)

Ar and R$_1$ in Structural Formula (XLI) are as defined above in Structural Formulas (I) and (VI); s is 0, 1 or 2; Ar$_1$ is a substituted or unsubstituted arylene group; W$_6$ is a covalent bond, —W$_1$—, —CH$_2$W$_1$— or —W$_1$CH$_2$—; W$_7$ is a covalent bond or —CH$_2$— and W$_1$ is as defined above. Preferably R$_1$ is represented by Structural Formula (II), s is 0 or 1, Ar$_1$ is phenylene (ortho, meta or para substituted), W$_7$ is a covalent bond and W$_1$ is —O—. More preferably, Ar is represented by any one of Structural Formulas (XXVIII)–(XXXIX) and R$_1$ is represented by Structural Formulas (III) or (IV). Even more preferably, Ar is represented by Structural Formulas (XL) or (XLI) and R$_1$ is represented by Structural Formula (V).

Also included in the present invention are methods of treatment as described above, wherein the compound represented by Structural Formula (XLI) is administered as the therapeutic agent and the use of the compound for the manufacture of a medicament for the treatment of the PPAR mediated disorders described herein.

The following are specific examples of the compounds of the present invention:

(2S)-3-{4-[3-(Biphenyl-4-yloxy)-prop-1-ynyl]-phenyl}-2-methoxy-propionic acid (Compound 1);
(2S)-3-{4-[3-(4-Benzoyl-phenoxy)-prop-1-ynyl]-phenyl}-2-methoxy-propionic acid (Compound 2);
(2S)-2-Methoxy-3-{4-[3-phenoxy-phenoxy)-prop-1-ynyl]-phenyl}-propionic acid (Compound 3);
(2S)-3-{4-[3-(4-Fluoro-phenoxy)-prop-1-ynyl]-phenyl}-2-methoxy-propionic acid (Compound 4);
(2S)-2-Methoxy-3-{4-[3-(3-phenyl-benzofuran-6-yloxy)-prop-1-ynyl]-phenyl}-propionic acid (Compound 5);
(2S)-3-{4-[3-(4-Butyl-phenoxy)-prop-1-ynyl]-phenyl}-2-methoxy-propionic acid (Compound 6);
(2S)-2-Methoxy-3-(4-{3-[4-(4-trifluoromethyl-phenoxy)-phenoxy]-prop-1-ynyl}-phenyl)-propionic acid (Compound 7);
(2S)-2-Methoxy-3-{4-[3-(9-oxo-9H-fluoren-2-yloxy)-prop-1-ynyl]-phenyl}-propionic acid (Compound 8);
(2S)-2-Methoxy-3-{4-[3-(4-oxo-2-phenyl-4H-chromen-7-yloxy)-prop-1-ynyl]-phenyl}-propionic acid (Compound 9);
(2S)-3-(4-{3-[4-(2-Fluoro-benzoyl)-phenoxy]-prop-1-ynyl}-phenyl)-2-methoxy-propionic acid (Compound 10);
(2S)-2-Methoxy-3-{4-[3-(3-phenylamino-phenoxy)-prop-1-ynyl]-phenyl}-propionic acid (Compound 11);
(2S)-3-({3-[4-(4-Fluoro-benzoyl)-phenoxy]-prop-1-ynyl}-phenyl)-2-methoxy-propionic acid (Compound 12);
(2S)-2-Methoxy-3-{4-[3-(4-oxo-2-phenyl-4H-chromen-6-yloxy)-prop-1-ynyl]-phenyl}-propionic acid (Compound 13);
(2S)-3-(4-{3-[3-(4-Fluoro-phenyl)-benzofuran-6-yloxy]-prop-1-ynyl}-phenyl)-2-methoxy-propionic acid (Compound 14);
(2S)-2-Methoxy-3-(4-{3-[4-(1-methyl-1-phenyl-ethyl)-phenoxy]-prop-1-ynyl}-phenyl)-propionic acid (Compound 15);
(2S)-2-Methoxy-3-{4-[3-(4-phenylacetyl-phenoxy)-prop-1-ynyl]-phenyl}-propionic acid (Compound 16);
(2S)-3-{4-[3-(4-Benzyl-phenoxy)-prop-1-ynyl]-phenyl}-2-methoxy-propionic acid (Compound 17);
(2S)-3-[4-(3-{4-[(2-Fluoro-phenyl)-hydroxyimino-methyl]-phenoxy}-prop-1-ynyl)-phenyl]-2-methoxy-propionic acid (Compound 18);
(2S)-3-(4-{3-[4-(Hydroxyimino-phenyl-methyl)-phenoxy]-prop-1-ynyl}-phenyl)-2-methoxy-propionic acid (Compound 19);
(2S)-3-[4-(3-{4-[(4-Fluoro-phenyl)-hydroxyimino-methyl]-phenoxy}-prop-1-ynyl)-phenyl]-2-methoxy-propionic acid (Compound 20);
(2S)-3-{4-[5-(Biphenyl-4-yloxy)-pent-1-ynyl]-phenyl}-2-methoxy-propionic acid (Compound 21);
(2S)-2-Methoxy-3-{4-[5-(4-phenoxy-phenoxy)-pent-1-ynyl]-phenyl}-propionic acid (Compound 22),
(2S)-3-{4-[5-(4-Benzoyl-phenoxy)-pent-1-ynyl]-phenyl}-2-methoxy-propionic acid (Compound 23);
(2S)-3-{4-[5-(4-Benzyl-phenoxy)-pent-1-ynyl]-phenyl}-2-methoxy-propionic acid (Compound 24);
(2S)-3-(4-{5-[4-(4-Fluoro-benzoyl)-phenoxy]-pent-1-ynyl}-phenyl)-2-methoxy-propionic acid (Compound 25);
(2S)-2-Methoxy-3-(4-{5-[4-(4-trifluoromethyl-phenoxy)-phenoxy]-pent-1-ynyl}-phenyl)-propionic acid (Compound 26);
(2S)-2-Methoxy-3-{4-[5-(4-oxo-2-phenyl-4H-chromen-7-yloxy)-pent-1-ynyl]-phenyl}-propionic acid (Compound 27);
(2S)-2-Methoxy-3-{4-[5-(4-oxo-2-phenyl-4H-chromen-6-yloxy)-pent-1-ynyl]-phenyl}-propionic acid (Compound 28);
(2S)-2-Methoxy-3-(4-{5-[4-(1-methyl-1-phenyl-ethyl)-phenoxy]-pent-1-ynyl}-phenyl)-propionic acid (Compound 29);
(2S)-2-Methoxy-3-{4-[5-(9-oxo-9H-fluoren-2-yloxy)-pent-1-ynyl]-phenyl}-propionic acid (Compound 30);
(2S)-2-Methoxy-3-{4-[5-3-phenylamino-phenoxy)-pent-1-ynyl]-phenyl}-propionic acid (Compound 31);
(2S)-3-(4-{5-[4-(2-Fluoro-benzoyl)-phenoxy]-pent-1-ynyl}-phenyl)-2-methoxy-propionic acid (Compound 32);
(2S)-2-Methoxy-3-{4-[5-(3-phenyl-benzofuran-6-yloxy)-pent-1-ynyl]-phenyl}-propionic acid (Compound 33);

(2S)-3-(4-{5-[3-(4-Fluoro-phenyl)-benzofuran-6-yloxy]-pent-1-ynyl}-phenyl)-2-methoxy-propionic acid (Compound 34);

(2S)-2-Methoxy-3-{4-[5-(4-phenylacetyl-phenoxy)-pent-1-ynyl]-phenyl}-propionic acid (Compound 35);

(2S)-3-{4-[5-(4-Butyl-phenoxy)-pent-1-ynyl]-phenyl}-2-methoxy-propionic acid (Compound 36);

(2S)-3-[4-(5-{4-[(2-Fluoro-phenyl)-hydroxyimino-methyl]-phenoxy}-pent-1-ynyl)-phenyl]-2-methoxy-propionic (Compound 37);

(2S)-3-[4-(5-{4-[(4-Fluoro-Phenyl)-hydroxyimino-methyl]-phenoxy}-pent-1-ynyl)-phenyl]-2-methoxy-propionic acid (Compound 38);

(2S)-3-(4-{5-[4-(Hydroxyimino-phenyl-methyl)-phenoxy]-pent-1-ynyl}-phenyl)-2-methoxy-propionic acid (Compound 39);

(2S)-3-{4-[4-(Biphenyl-4-yloxy)-but-1-ynyl]-phenyl}-2-methoxy-propionic acid (Compound 40);

(2S)-2-Methoxy-3-{4-[4-(4-phenoxy-phenoxy)-but-1-ynyl]-phenyl}-propionic acid (Compound 41);

(2S)-3-{4-[4-(4-Benzoyl-phenoxy)-but-1-ynyl]-phenyl}-2-methoxy-propionic acid (Compound 42);

(2S)-3-(4-{4-[4-(Hydroxyimino-phenyl-methyl)-phenoxy]-but-1-ynyl}-phenyl)-2-methoxy-propionic acid (Compound 43);

(2S)-3-(4-{4-[4-Fluoro-benzoyl)-phenoxy]-but-1-ynyl}-phenyl)-2-methoxy-propionic acid (Compound 44);

(2S)-3-(4-{4-[3-(4-Fluoro-phenyl)-benzofuran-6-yloxy]-but-1-ynyl}-phenyl)-2-methoxy-propionic acid (Compound 45);

(2S)-2-Methoxy-3-(4-{4-[4-(4-trifluoromethyl-phenoxy)-phenoxy]-but-1-ynyl}-phenyl)-propionic acid (Compound 46);

(2S)-2-Methoxy-3-{4-[4-(4-oxo-2-phenyl-4H-chromen-7-yloxy)-but-1-ynyl]-phenyl}-propionic acid (Compound 47);

(2S)-2-Methoxy-3-{4-[4-(4-oxo-2-phenyl-4H-chromen-7-yloxy)-but-1-ynyl]-phenyl}-propionic acid (Compound 48);

(2S)-2-Methoxy-3-{4-[6-(4-phenoxy-phenoxy)-hex-1-ynyl]-phenyl}-propionic acid (Compound 49);

(2S)-3-{4-[6-(4-Benzoyl-phenoxy)-hex-1-ynyl]-phenyl}-2-methoxy-propionic acid (Compound 50);

(2S)-3-{4-[6-(Biphenyl-4-yloxy)-hex-1-ynyl]-phenyl}-2-methoxy-propionic acid (Compound 51);

(2S)-3-{4-[5-(Biphenyl-4-yloxy)-pentanoyl]-phenyl}-2-methoxy-propionic acid (Compound 52);

(2S)-3-{4-[5-(4-Benzoyl-phenoxy)-pentanoyl]-phenyl}-2-methoxy-propionic acid (Compound 53);

(2S)-2-Methoxy-3-{4-[5-(4-phenoxy-phenoxy)-pentanoyl]-phenyl}-propionic acid (Compound 54);

3-{4-[4-(4-Benzoyl-phenoxy)-butyryl]-phenyl}-2-methoxy-propionic acid (Compound 55);

(2S)-2-Methoxy-3-{4-[4-(4-phenoxy-phenoxy)-butyryl]-phenyl}-propionic acid (Compound 56);

(2S)-3-[4-(Biphenyl-4-yloxy)-butyryl-phenyl]-2-methoxy-propionic acid (Compound 57);

(2S)-3-{4-[6-(Biphenyl-4-yloxy)-hexanoyl]-phenyl}-2-methoxy-propionic acid (Compound 58);

(2S)-2-Methoxy-3-{4-[6-(4-phenoxy-phenoxy)-hexanoyl]-phenyl}-propionic acid (Compound 59);

(2S)-3-{4-[6-(4-Benzoyl-phenoxy)-hexanoyl]-phenyl}-2-methoxy-propionic acid (Compound 60);

(2S)-3-{4-[5-(Biphenyl-4-yloxy)-1-hydroxyimino-pentyl]-phenyl}-2-methoxy-propionic acid (Compound 61);

(2S,1'R*,2'S*)-3-(4-{2'-[4-(4-Fluoro-benzoyl)-phenoxy]-cyclopentyloxy}-phenyl)-2-methoxy-propionic acid (Compound 62);

(2S)-(1'R,3'R)-2-Methoxy-3-{4-[1',3'-dimethyl-3-(4-phenoxy-phenoxy)-propoxyl]-phenyl}-propionic acid (Compound 63);

(2S)-(1'R,3'R)-3-{4-[3-(4-Benzoylphenoxy)-1',3'-dimethyl-propoxyl]-phenyl}2-methoxy-propionic acid (Compound 64);

(2S)-(1'S,3'S)-2-Methoxy-3-{4-[1',3'-dimethyl-3-(4-phenoxy-phenoxy)-propoxyl]-phenyl}-propionic acid (Compound 65);

(2S)-(1'S,3'S)-3-{4-[3-(4-Benzoylphenoxy)-1',3'-dimethyl-propoxyl]-phenyl}2-methoxy-propionic acid (Compound 66);

(2S)-(1'R,2'R)-2-Methoxy-3-{4-[1',2'-dimethyl-(4-phenoxy-phenoxy)-ethoxyl]-phenyl}-propionic acid (Compound 67);

(2S)-(1'R,2'R)-3-{4-[1-(4-Benzoylphenoxy)-1',2'-dimethyl-ethoxyl]-phenyl}-2-methoxypropionic acid (Compound 68);

(2S)-(1'S,4'S)-2-Methoxy-3-{4-[1'-methyl-4'-(4-phenoxy-phenoxy)-pentyloxy]-phenyl}-propionic acid (Compound 69);

(2S)-(1'S,4'S)-3-{4-[4-(4-Benzoyl-phenoxy)-1-methyl-pentyloxy]-phenyl}-2-methoxy-propionic acid (Compound 70);

(2S)-(1'R,4'R)-2-Methoxy-3-{4-[1'-methyl-4'-(4-phenoxy-phenoxy)-pentyloxy]-phenyl}-propionic acid (Compound 71);

(2S)-(1'R,4'R)-3-{4-[4-(4-Benzoyl-phenoxy)-1-methyl-pentyloxy]-phenyl}-2-methoxy-propionic acid (Compound 72);

(2S)-(1'S,2'S)-2-Methoxy-3-{4-[1',2'-dimethyl-(4-phenoxy-phenoxy)-ethoxyl]-phenyl}-propionic acid (Compound 73);

(2S)-2-Methoxy-{4-[2-methylen-3-(4-phenoxy-phenoxy)-propoxyl]-phenyl}-propionic acid (Compound 74);

(2S)-2-Methoxy-{4-[2-oxo-3-(4-phenoxy-phenoxy)-propoxyl]-phenyl}-propionic acid (Compound 75);

(2S)-2-Methoxy-3-{4-[3-(4-phenoxy-phenoxymethyl)-benzyloxy]-phenyl}-propionic acid (Compound 76);

(2S)-2-Methoxy-3-{4-[2-(4-phenoxy-phenoxymethyl)-benzyloxy]-phenyl}-propionic acid (Compound 77);

(2S)-2-Methoxy-3-{4-[3-(4-phenoxy-phenoxy)-phenoxy]-phenyl}-propionic acid (Compound 78), (2S)3-[3'-(3-Benzoyl-phenoxymethyl)biphenyl-4-yl]-2-methoxy-propionic acid (Compound 79);

(2S)-3-[4'-(4-Benzoyl-phenoxymethyl)-biphenyl-4-yl-2-methoxy-propionic acid (Compound 80);

(2S)-(1'R*,3'R*)3-{4-[3'-(Biphenyl-4-yloxy)-1'-cyclopentyloxy]-phenyl}-2-methoxy-propionic acid (Compound 81);

(2S)-(1'R*,3'S*)3-{4-[3'-(Biphenyl-4-yloxy)-1'-cyclopentyloxy]-phenyl}-2-methoxy-propionic acid (Compound 82);

(2S)-(1'R*,3'R*)-2-Methoxy-3-{4-[3'-(4-phenoxy-phenoxy)-1'-cyclopentyloxy]-phenyl}-propionic acid (Compound 83);

(2S)-(1'R*,3'R*)-3-{4-[3-(4-Benzoyl-phenoxy)-cyclopentyloxy]-phenyl}-2-methoxy-propionic acid (Compound 84);

(2S)-(1'R*,3'R*)-2-Methoxy-3-{4-[3-(4-phenylacetyl-phenoxy)-cyclopentyloxy]-phenyl}-propionic acid (Compound 85);

(2S)-(1'R,3'S)3-{4-[3'-(Biphenyl-4-yloxy)-1'-cyclopentyloxy]-phenyl}-2-methoxy-propionic acid (Compound 86);
(2S)-(1'S,3'R)3-{4-[3'-(Biphenyl-4-yloxy)-1'-cyclopentyloxy]-phenyl}-2-methoxy-propionic acid (Compound 87);
(2S)-(1'S,3'S)3-{4-[3'-(Biphenyl-4-yloxy)-1'-cyclopentyloxy]-phenyl}-2-methoxy-propionic acid (Compound 88);
(2S)-(1'R,3'R)3-{4-[3'-(Biphenyl-4-yloxy)-1'-cyclopentyloxy]-phenyl}-2-methoxy-propionic acid (Compound 89);
(2S)-(1'R,3's)-3-{4-[3'-(Biphenyl-4-yloxy)-1'-cyclohexyloxy]-phenyl}-2-methoxy-propionic acid (Compound 90);
(2S)-(1'S,3'R)-3-{4-[3'-(Biphenyl-4-yloxy)-1'-cyclohexyloxy]-phenyl}-2-methoxy-propionic acid (Compound 91);
(2S)-(1'R,3'R)-3-{4-[3'-(Biphenyl-4-yloxy)-1'-cyclphenyloxy]-phenyl}-2-methoxy-propionic acid (Compound 92);
(2S)-(1'S,3'S)-3-{4-[3'-(Biphenyl-4-yloxy)-1'-cyclohexyloxy]-phenyl}-2-methoxy-propionic acid (Compound 93);
(2S)-3-{4-[3-(4-Benzoyl-phenoxy)-propoxy]-phenyl}-2-methoxy-propionic acid (Compound 94);
(2S)-3-(4-{3-[4-(4-Fluoro-benzoyl)-phenoxy]-propoxy}-phenyl)-2-methoxy-propionic acid (Compound 95);
(2S)-3-{4-[3-(4-Benzyl-phenoxy)-propoxy]-phenyl}-2-methoxy-propionic acid (Compound 96);
(2S)-2-Methoxy-3-{4-[3-(3-phenylamino-phenoxy)-propoxy]-phenyl}-propionic acid (Compound 97);
(2S)-3-{4-[3-Butyl-phenoxy)-propoxy]-phenyl}-2-methoxy-propionic acid (Compound 98);
(2S)-3-(4-{3-[4-(2-Fluoro-benzoyl)-phenoxy]-propoxy}-phenyl)-2-methoxy-propionic acid (Compound 99);
(2S)-2-Methoxy-3-{4-[3-(9-oxo-9H-fluoren-2-yloxy)-propoxy]-phenyl}-propionic acid (Compound 100);
(2S)-2-Methoxy-3-{4-[3-(2-methyl-benzothiazol-5-yloxy)-propoxy]-phenyl}-propionic acid (Compound 101);
(2S)-2-Methoxy-3-{4-[3-(3-morpholinyl-phenoxy)-propoxy]-phenyl}-propionic acid (Compound 102);
(2S)-3-{4-[3-(Biphenyl-2-yloxy)-propoxy]-phenyl}-2-methoxy-propionic acid (Compound 103);
(2S)-3-{4-[3-(4-Cylopentyl-phenoxy)-propoxy]-phenyl}-2-methoxy-propionic acid (Compound 104);
(2S)-3-{4-[3-(4-Cyano-3-fluoro-phenoxy)-propoxy]-phenyl}-2-methoxy-propionic acid (Compound 105);
(2S)-3-{4-[3-(2,4-Difluoro-phenoxy)-propoxy]-phenyl}-2-methoxy-propionic acid (Compound 106);
(2S)-2-Methoxy-3-{4-[3-(4-trifluoromethyl-phenoxy)-propoxy]-phenyl}-propionic acid (Compound 107);
(2S)-2-Methoxy-3-{4-[3-(3-trifluoromethyl-phenoxy)-propoxy]-phenyl}-propionic acid (Compound 108);
(2S)-2-Methoxy-3-{4-[3-(5-oxo-5,6,7,8-tetrahydro-naphthalen-2-yloxy)-propoxy]-phenyl}-propionic acid (Compound 109);
(2S)-3-{4-[3-(3,5-Difluoro-phenoxy)-propoxy]-phenyl}-2-methoxy-propionic acid (Compound 110);
(2S)-3-{4-[3-(Isoquinolin-5-yloxy)-propoxy]-phenyl}-2-methoxy-propionic acid (Compound 111);
(2S)-2-Methoxy-3-{4-[3-(4-trifluoromethoxy-phenoxy)-propoxy]-phenyl}-propionic acid (Compound 112);
(2S)-3-{4-[3-(4-Fluoro-phenoxy)-propoxy]-phenyl}-2-methoxy-propionic acid (Compound 113);
(2S)-2-Methoxy-3-{4-[3-(4-phenylacetyl-phenoxy)-propoxy]-phenyl}-propionic acid (Compound 114);

(2S)-2-Methoxy-3-(4-{3-[4-(1-methyl-1-phenyl-ethyl)-phenoxy]-propoxy}-phenyl)-propionic acid (Compound 115);
(2S)-2-Methoxy-3-{4-[3-(4-oxo-2-phenyl-4H-chromen-7-yloxy)-propoxy]-phenyl}-propionic acid (Compound 116);
4-{3-[4-(2-Carboxy-2-methoxy-ethyl)-phenoxy]-propoxy}-benzoic acid benzyl ester (Compound 117);
(2S)-2-Methoxy-3-{4-[3-(4-oxo-2-phenyl-chroman-6-yloxy)-propoxy]-phenyl}-propionic acid (Compound 118);
(2S)-2-Methoxy-3-{4-[3-(4-oxo-2-phenyl-chroman-6-yloxy)-propoxy]-phenyl}-propionic acid (Compound 119);
(2S)-2-Methoxy-3-{4-[3-(4-oxo-2-phenyl-chroman-7-yloxy)-propoxy]-phenyl}-propionic acid (Compound 120);
(2S)-2-Methoxy-3-(4-{3-[4-(4-trifluoromethyl-phenoxy)-phenoxy]-propoxy}-phenyl)-propionic acid (Compound 121);
(2S)-3-{4-[2-(4-benzoyl-phenoxy)-ethoxy]-phenyl}-2-methoxy-propionic acid (Compound 122);
(2S)-3-{4-[2-(Biphenyl-4-yloxy)-ethoxy]-phenyl}-2-methoxy-propionic acid (Compound 123);
(2S)-3-{4-[2-(Biphenyl-4-yloxy)-acetyl]-phenyl}-2-methoxy-propionic acid (Compound 124);
(2S)-2-Methoxy-3-{4-[2-(4-phenoxy-phenoxy)-acetyl]-phenyl}-propionic acid (Compound 125);
(2S)-3-{4-[2-(4-Benzoyl-phenoxy)-acetyl]-phenyl}-2-methoxy-propionic acid (Compound 126);
(2S)-3-{4-[3-(Biphenyl-4-yloxy)-propyl]-phenyl}-2-methoxy-propionic acid (Compound 127);
(2S)-3-{4-[4-(Biphenyl-4-yloxy)-butyl]-phenyl}-2-methoxy-propionic acid (Compound 128);
(2S)-3-{4-[5-(Biphenyl-4-yloxy)-pentyl]-phenyl}-2-methoxy-propionic acid (Compound 129);
3-{4-[3-(4-Benzoyl-phenoxy)-propoxy]-3-methoxy-propionic acid (Compound 130);
3-(4-{3-[4-(4-Fluoro-benzoyl)-phenoxy]-propoxy}-3-methoxy-phenyl)-2-methoxy-propionic acid (Compound 131);
3-{4-[3-(Biphenyl-4-yloxy)-propoxy]-3-methoxy-phenyl}-2-methoxy-propionic acid (Compound 132);
2-Methoxy-3-{3-methoxy-4-[3-(4-phenoxy-phenoxy)-propoxy]-phenyl}-propionic acid (Compound 133);
(2S)-3-(4-[3-phenyl-4-yloxy)-propoxy]-3-chloro-phenyl}-2-methoxy-propionic acid (Compound 134);
3-{3-Chloro-4-[3-(4-phenoxy-phenoxy)-propoxy]-phenyl}-2-methoxy-propionic acid (Compound 135);
'3-{4-[3-(4-Benzoyl-phenoxy)-propoxy]-3-chloro-phenyl}-2-methoxy-propionic acid (Compound 136);
3-{4-[3-(Biphenyl-4-yloxy)-propoxy]-3,5-dichloro-6-phenyl}-2-methoxy-propionic acid (Compound 137);
3-{4-[3-(Biphenyl-4-yloxy)-propoxy]-3-fluoro-phenyl}-2-methoxy-propionic acid (Compound 138);
3-{4-[3-(3-(Biphenyl-4-yloxy)-propoxy]-3-trifluoromethyl-phenyl}-2-methoxy-propionic acid (Compound 139);
(2S)-3-{6-[3-(Biphenyl-4-yloxy)-propoxy]-4'-methoxy-biphenyl-3-yl}-2-methoxy-propionic acid (Compound 140);
3-{6-[3-(Biphenyl-4-yloxy)-propoxy]-4'-fluoro-biphenyl-3-yl}-2-methoxy-propionic acid (Compound 141);
3-{6-[3-(Biphenyl-4-yloxy)-propoxy]-[1,1';4',1"]terphenyl-3-yl}-2-methoxy-propionic acid (Compound 142);
3-{6-[3-(Biphenyl-4-yloxy)-propoxy]-2'-methoxy-biphenyl-3-yl}-2-methoxy-propionic acid (Compound 143);
2-Methoxy-3-{6-[3-(4-phenoxy-phenoxy)-propoxy]-[1,1'; 4',1"]terphenyl-3-yl}-propionic acid (Compound 144);

3-{4-[3-(4-Benzoyl-phenoxy)-propoxy]-3-styryl-phenyl}-2-methoxy-propionic acid (Compound 145);

3-(4-{3-[4-(Hydroxy-phenyl-methyl)-phenoxy]-propoxy}-3-phenethyl-phenyl)-2-methoxy-propionic acid (Compound 146);

3-{4-[3-(4-Benzyl-phenoxy)-propoxy]-3-phenethyl-phenyl}-2-methoxy-propionic acid (Compound 147);

(2S)-3-{3-Allyl-4-[3-(4-phenoxy-phenoxy)-propoxy]-phenyl}-2-methoxy-propionic acid (Compound 148);

(2S)-2-Methoxy-3-{4-[3-(4-phenoxy-phenoxy)-propoxy]-3-propyl-phenyl}-propionic acid (Compound 149);

3-{4-[3-(Biphenyl-4-yloxy)-propoxy]-2-methyl-phenyl}-2-methoxy-acrylic acid (Compound 150);

3-{4-[3-(Biphenyl-4-yloxy)-propoxy]-2-methyl-phenyl}-2-methoxy-propionic acid (Compound 151), 3-{3-[3-(Biphenyl-4-yloxy)-propoxy]-phenyl}-2-methoxy-propionic acid (Compound 152);

'2-Methoxy-3-{3-[3-(4-phenoxy-phenoxy)-propoxy]-phenyl}-propionic acid (Compound 153);

3-{3-[3-(4-Benzoyl-phenoxy)-propoxy]-phenyl}-2-methoxy-propionic acid (Compound 154);

2-Methoxy-3-{3-[5-(4-phenoxy-phenoxy)-pent-1-ynyl]-phenyl}-propionic acid (Compound 155);

2-Methoxy-3-{3-[5-(4-phenoxy-phenoxy)-pentyl]-phenyl}-propionic acid (Compound 156);

2-Methoxy-3-{3-[5-(4-phenoxy-phenoxy)-pentanoyl]-phenyl}-propionic acid (Compound 157);

3-{4-[3-(3-Allyl-biphenyl-4-yloxy)-propoxy]-phenyl}-2-methoxy-propionic acid (Compound 158);

(2S)-2-Methoxy-3-{4-[3-(3-propyl-biphenyl-4-yloxy)-propoxy]-phenyl}-propionic acid (Compound 159);

(2S)-3-{4-[3-(2-Allyl-4-phenoxy-phenoxy)-propoxy]-phenyl}-2-methoxy-propionic acid (Compound 160);

(2S)-2-Methoxy-3-{4-[3-(4-phenoxy-2-propyl-phenoxy)-propoxy]-phenyl}-propionic acid (Compound 161);

3-{4-[3-(Biphenyl-4-yloxy)-propoxy]-3-methyl-phenyl}-2-methoxy-propionic acid (Compound 162);

2-Methoxy-3-{3-methyl-4-[3-(4-phenoxy-phenoxy)-propoxy]-phenyl}-propionic acid (Compound 163);

3-{4-[3-(4-Benzoyl-phenoxy)-propoxy]-3-methyl-phenyl}-2-methoxy-propionic acid (Compound 164);

(2S)-3-{4-[3-(Dibenzofuran-2-yloxy)-propoxy]-phenyl}-2-methoxy-propionic acid (Compound 165);

(2S)-3-[4-(3-{4-[(4-Fluoro-phenyl)-hydroxyimino-methyl]-phenoxy}-propoxy)-phenyl]-2-methoxy-propionic acid (Compound 166);

(2S)-3-[4-(3-{4-[(4-Fluoro-phenyl)-hydroxy-methyl]-phenoxy}-propoxy)-phenyl]-2-methoxy-propionic acid (Compound 167);

(2S)-2-Methoxy-3-(4-{3-[4-(4-piperidin-1-yl-benzoyl)-phenoxy]-propoxy}-phenyl)-propionic acid (Compound 168);

(2S)-2-Methoxy-3-(4-{3-[4-(4-morpholin-4-yl-benzoyl)-phenoxy]-propoxy}-phenyl)-propionic acid (Compound 169);

(2S)-3-(4-{3-[4-(4-Hydroxy-benzoyl)-phenoxy]-propoxy}-phenyl)-2-methoxy-propionic acid (Compound 170);

(2S)-2-methoxy-3-{4-[3-(4-phenoxy-phenoxy)-propoxy] phenyl}propanoic acid sodium salt (Compound 171);

(2S)-3-[4-(3-{4-[Hydroxyimino-(4-hydroxy-phenyl)-methyl]-phenoxy}-propoxy)-phenyl]-2-methoxy-propionic acid (Compound 172);

(2S)-3-{4-[3-(4-Benzoyl-3-hydroxy-phenoxy)-propoxy]-phenyl}-2-methoxy-propionic acid (Compound 173);

(2S)-3-(4-{3-[4-(2,4-Dimethoxy-benzoyl)-phenoxy]-propoxy}-phenyl)-2-methoxy-propionic acid (Compound 174);

3-{4-[3-(4-Benzyl-phenoxy)-propoxy]-3-methoxy-phenyl}-2-methoxy-propionic acid (Compound 175);

(S)-3-(4-benzyloxy-phenyl)-2-isopropoxy-propionic acid (Compound 176);

(2S)-2-isopropoxy-3-{4-[3-(4-phenoxy-phenoxy)-propoxy] phenyl}propanoic acid sodium salt (Compound 176A);

2-Methoxy-3-{3-methoxy-4-[3-(4-phenylacetyl-phenoxy)-propoxy]-phenyl}-propionic acid (Compound 177);

3-{4-[3-(4-Butoxy-phenoxy)-propoxy]-3-methoxy-phenyl}-2-methoxy-propionic acid (Compound 178);

2-Methoxy-3-{3-methoxy-4-[3-(4-oxo-2-phenyl-4H-chromen-6-yloxy)-propoxy]-phenyl}-propionic acid (Compound 179);

2-Methoxy-3-(3-methoxy-4-{3-[4-(4-trifluoromethyl-phenoxy)-phenoxy]-propoxy}-phenyl)-propionic acid (Compound 180);

3-{4-[3-(4-Benzyloxy-phenoxy)-propoxy]-3-methoxy-phenyl}-2-methoxy-propionic acid (Compound 181);

3-{4-[3-(4-Dibenzofuran-3-yl-phenoxy)-propoxy]-3-methoxy-phenyl}-2-methoxy-propionic acid (Compound 182);

(2S)-3-{4-[4-(Biphenyl-4-yloxy)-butoxy]-phenyl}-2-methoxy-propionic acid (Compound 183);

(2S)-3-{4-[4-(4-Benzoyl-phenoxy)-butoxy]-phenyl}-2-methoxy-propionic acid (Compound 184);

(2S)-2-Methoxy-3-{4-[4-(4-phenoxy-phenoxy)-butoxy]-phenyl}-propionic acid (Compound 185);

(2S)-2-Methoxy-3-{4-[2-(2,3,6-trifluoro-phenoxy)-ethoxy]-phenyl}-propionic acid (Compound 186);

(2S)-3-[4-(3-Benzyloxy-benzyloxy)-phenyl]-2-methoxy-propionic acid (Compound 187);

3-{4-[3-(Biphenyl-4-yloxy)-propoxy]-2-methoxy-phenyl}-2-methoxy-propionic acid (Compound 188);

3-{4-[3-(4-Benzoyl-phenoxy)-propoxy]-2-methoxy-phenyl}-2-methoxy-propionic acid (Compound 189);

2-Methoxy-3-{2-methoxy-4-[3-(4-phenoxy-phenoxy)-propoxy]-phenyl}-propionic acid (Compound 190);

3-{4-[3-(Biphenyl-4-yloxy)-propoxy]-2-chloro-phenyl}-2-methoxy-propionic acid (Compound 191);

3-{2-Chloro-4-[3-(4-phenoxy-phenoxy)-propoxy]-phenyl}-2-methoxy-propionic acid (Compound 192);

3-{4-[3-(4-Benzoyl-phenoxy)-propoxy]-2-chloro-phenyl}-2-methoxy-propionic acid (Compound 193);

(2S)-4-{3-[4-(2-Carboxy-2-methoxy-ethyl-phenoxy)-propoxy}-benzoic acid (Compound 194);

(2S)-3-{4-[3-(4-Dibenzothiophen-4-yl-phenoxy)-propoxy]-phenyl}-2-methoxy-propionic acid (Compound 195);

(2S)-3-{4-[3-(4'-Hydroxy-biphenyl-4-yloxy)-propoxy]-phenyl}-2-methoxy-propionic acid (Compound 196);

(2S)-4'-{3-[4-(2-Carboxy-2-methoxy-ethyl)-phenoxy]-propoxy}-biphenyl-4-carboxylic acid (Compound 197);

(2S)-3-{4-[2-(4-Benzoyl-phenoxy)-cyclohexyloxy]-phenyl}-2-methoxy-propionic acid (Compound 198);

(2S)-3-(4-{2-[4-(4-Fluoro-benzoyl)-phenoxy]-cyclohexyloxy}-phenyl)-2-methoxy-propionic acid (Compound 199);

(2S)-3-(4-{3-[3-(4-Fluoro-phenyl)-benzofuran-6-yloxy]-propoxy}-phenyl)-2-methoxy-propionic acid (Compound 200);

(2S)-2-Methoxy-3-{4-[3-(5,6,7,8-tetrahydro-naphthalen-2-yloxy)-propoxy]-phenyl}-propionic acid (Compound 201);

(2S)-3-{4-[3-(4-Benzyloxy-phenoxy)-propoxy]-phenyl}-2-methoxy-propionic acid (Compound 202);

(2S)-3-{4-[3-(4-Benzyloxy-phenoxy)-propoxy]-phenyl}-2-methoxy-propionic acid (Compound 203);

(2S)-3-{4-[3-(4-Heptyloxy-phenoxy)-propoxy]-phenyl}-2-methoxy-propionic acid (Compound 204);
(2S)-3-{4-[3-(6-Benzoyl-naphthalen-2 yloxy)-propoxy]-phenyl}-2-methoxy-propionic acid (Compound 205);
(2S)-3-{4-[3-(Benzo[1,3]dioxol-5-yloxy)-propoxy]-phenyl}-2-methoxy-propionic acid (Compound 206);
(2S)-3-{4-[3-(9H-Fluoren-2-yloxy)-propoxy]-phenyl}-2-methoxy-propionic acid (Compound 207);
(2S)-2-Methoxy-3-{4-[3-(4-octyl-phenoxy)-propoxy]-phenyl}-propionic acid (Compound 208);
(2S)-2-Methoxy-3-{4-[3-(naphthalen-1-yloxy)-propoxy]-phenyl}-propionic acid (Compound 209);
(2S)-3-{4-[3-(1H-Indol-7-yloxy)-propoxy]-phenyl}-2-methoxy-propionic acid (Compound 210);
(2S)-3-{4-[3-(4'-Fluoro-biphenyl-4-yloxy)-propoxy]-phenyl}-2-methoxy-propionic acid (Compound 211);
(2S)-3-{4-[3-(4'-Chloro-biphenyl-4-yloxy)-propoxy]-phenyl}-2-methoxy-propionic acid (Compound 212);
(2S)-3-{4-[3-(3',5'-Bis-trifluoromethyl-biphenyl-4-yloxy)-propoxy]-phenyl}-2-methoxy-propionic acid (Compound 213);
(2S)-3-{4-[3-(4-Dibenzofuran-4-yl-phenoxy)-propoxy]-phenyl}-2-methoxy-propionic acid (Compound 214);
(2S)-2-Methoxy-3-{4-[3-(4'-phenoxy-biphenyl-4-yloxy)-propoxy]-phenyl}-propionic acid (Compound 215);
(2S)-2-Methoxy-3-{4-[3-(4-thiophen-2-yl-phenoxy)-propoxy]-phenyl}-propionic acid (Compound 216);
(2S)-3-{4-[3-(3'-Chloro-biphenyl-4-yloxy)-propoxy]-phenyl}-2-methoxy-propionic acid (Compound 217);
(2S)-3-{4-[3-(2'-Chloro-biphenyl-4-yloxy)-propoxy]-phenyl}-2-methoxy-propionic acid (Compound 218);
(2S)-3-{4-[3-(2'-Fluoro-biphenyl-4-yloxy)-propoxy]-phenyl}-2-methoxy-propionic acid (Compound 219);
(2S)-3-{4-[3-(4-Benzo[1,3]dioxol-5-yl-phenoxy)-propoxy]-phenyl}-2-methoxy-propionic acid (Compound 220);
(2S)-3-{4-[3-(4'-tert-Butyl-biphenyl-4-yloxy)-propoxy]-phenyl}-2-methoxy-propionic acid (Compound 221);
(2S)-2-Methoxy-3-{4-[3-(3'-trifluoromethoxy-biphenyl-4-yloxy)-propoxy]-phenyl}-propionic acid (Compound 222);
(2S)-2-Methoxy-3-{4-[3-(4'-trifluoromethoxy-biphenyl-4-yloxy)-propoxy]-phenyl}-propionic acid (Compound 223);
(2S)-3-(4-{3-[4-(2-Chloro-benzoylamino)-phenoxy]-propoxy}-phenyl)-2-methoxy-propionic acid (Compound 224);
(2S)-2-Methoxy-3-(4-{3-[4-(2-methoxy-benzoylamino)-phenoxy]-propoxy}-phenyl)-propionic acid (Compound 225);
(2S)-3-(4-{3-[4-(2,2-Dimethyl-propionylamino)-phenoxy]-propoxy}-phenyl)-2-methoxy-propionic acid (Compound 226);
(2S)-3-(4-{3-[4-(3-Fluoro-benzoylamino)-phenoxy]-propoxy}-phenyl)-2-methoxy-propionic acid (Compound 227);
(2S)-2-Methoxy-3-(4-{3-[4-(3-methoxy-benzoylamino)-phenoxy]-propoxy}-phenyl)-propionic acid (Compound 228);
(2S)-2-Methoxy-3-(4-{3-[4-(3-methyl-benzoylamino)-phenoxy]-propoxy}-phenyl)-propionic acid (Compound 229);
(2S)-3-(4-{3-[4-(4-Fluoro-benzoylamino)-phenoxy]-propoxy}-phenyl)-2-methoxy-propionic acid (Compound 230);
(2)-3-(4-{3-[4-(4-Chloro-benzoylamino)-phenoxy]-propoxy}-phenyl)-2-methoxy-propionic acid (Compound 231);
(2S)-2-Methoxy-3-(4-{3-[4-(4-methoxy-benzoylamino)-phenoxy]-propoxy}-phenyl)-propionic acid (Compound 232);
(2S)-2-Methoxy-3-{4-[3-(4-phenylacetylamino-phenoxy)-propoxy]-phenyl}-propionic acid (Compound 233);
(2S)-3-(4-{3-[4-(2-Chloro-benzoyl)-phenoxy]-propoxy}-phenyl)-2-methoxy-propionic acid (Compound 234);
(2S)-2-Methoxy-3-(4-{3-[4-naphthalene-1-carbonyl)-phenoxy]-propoxy}-phenyl)-propionic acid (Compound 235);
(2S)-3-(4-{3-[4-(3-Fluoro-benzoyl)-phenoxy]-propoxy}-phenyl)-2-methoxy-propionic acid (Compound 236);
(2S)-2-Methoxy-3-(4-{3-[4-(3-methoxy-benzoyl)-phenoxy]-propoxy}-phenyl)-propionic acid (Compound 237);
(2S)-2-Methoxy-3-(4-{3-[4-(naphthalene-2-carbonyl)-phenoxy]-propoxy}-phenyl)-propionic acid (Compound 238);
(2S)-2-Methoxy-3-(4-{3-[4-(4-methyl-benzoyl)-phenoxy]-propoxy}-phenyl)-propionic acid (Compound 239);
(2S)-3-(4-{3-[4-(2,2-Dimethyl-propionyl)-phenoxy]-propoxy}-phenyl)-2-methoxy-propionic acid (Compound 240);
(2S)-3-{4-[3-(4-Isobutyryl-phenoxy)-propoxy]-phenyl}-2-methoxy-propionic acid (Compound 241);
(2S)-2-Methoxy-3-(4-{3-[4-(3-phenyl-propionyl)-phenoxy-]propoxy}-phenyl)-propionic acid (Compound 242);
3-{4-[3-(Biphenyl-4-yloxy)-propoxy]-2-fluoro-phenyl}-2-methoxy-propionic acid (Compound 243);
2-phenoxy-3-[4-(4-phenoxy-phenoxy)propoxyphenyl]propanoic acid (Compound 244);
(2S,2'S)-3-(4-{3-[4-(2'-Carboxy-2'-methoxy-ethyl)-phenoxy]-propoxy}-phenyl)-2-methoxy-propionic acid (Compound 245);
α-Methoxycinnamate Intermediate, ethyl (2S)-2-methoxy-3-(4-hydroxyphenyl) propanoate (Compound 246);
(2S)-2-methoxy-3-{4-[3-(4-phenoxy-phenoxy)-propoxy]phenyl}propanoic acid (Compound 247);
(2S)-(2'RS)-2-Methoxy-{4-[2'-methyl-3-(4-phenoxy-phenoxy)-propoxy]-phenyl}-propionic acid (Compound 248);
2(S)-3-[4-(3-Benzyloxy-propoxy)-phenyl]-2-methoxypropionic acid (Compound 249);
(2S)-3-[4-(5-Benzyloxy-pentyloxy)-phenyl]-2-methoxypropionic acid (Compound 250);
(2S)-2-ethoxy-{4-[3-(4-phenoxy-phenoxy)-propoxyl]-phenyl}-propionic acid (Compound 251);
(2S)-2-Benzyloxy-3-{4-[3-(4-phenoxy-phenoxy)-propoxy]-phenyl}-propionic acid (Compound 252);
(2S)-3-{4-[3-(4-{4-[2-(tert-Butyl dimethyl-silanyloxy)-ethoxy]-benzoyl}-phenoxy)-propoxy]-phenyl}-2-methoxy-propionic acid (Compound 253);
(2S)-3-[4-(3-{4-[4-(2-Hydroxy-ethoxy)-benzoyl]-phenoxy}-propoxy)-phenyl]-2-methoxy-propionic acid (Compound 254);
(2S)-3-{4-[3-(4-phenoxy-phenoxy)-propoxy]-phenyl}-2-propoxy-propionic acid (Compound 255);
(2S)-3-{4-[3-(4-Benzoyl-phenoxy)-propoxy]-phenyl}-2-ethoxy-propionic acid (Compound 256);
(2S)-3-{4-[3-(4-Benzyl-phenoxy)-propoxy]-phenyl}-2-ethoxy-propionic acid (Compound 257);
(2S)-3-{4-[3-(4-Benzoyl-phenoxy)-propoxy]-3-chloro-phenyl}-2-methoxy-propionic acid (Compound 258);
(2S)-4'-{3-[4-(2-Carboxy-2-methoxy-ethyl)-2-methoxy-phenoxy]-propoxy}-biphenyl-4-carboxylic acid (Compound 259);

(2S)-3-{4-[3-(4'-tert-Butyl-biphenyl-4-yloxy)-propoxy]-2-methoxy-propionic acid (Compound 260);

(2S)-3-(4-{3-[4-(4-Hydroxy-phenoxy)-phenoxy]-propoxy}-phenyl)-2-methoxy-propionic acid (Compound 261);

(2S)-2-Methoxy-3-(4-{3-[4-(2,2,3,3-tetrafluoro-propoxy)-phenoxy]-propoxy}-phenyl)-propionic acid (Compound 262);

(2S)-2-Methoxy-3-(4-{3-[4-(3-methyl-butoxy)-phenoxy]-propoxy}-phenyl)-propionic acid (Compound 263);

(2S)-3-3-{4-[3-(4-Isobutoxy-phenoxy)-propoxy]-phenyl}-2-methoxy-propionic acid (Compound 264);

(2S)-3-{4-[3-(4-Isopropoxy-phenoxy)-propoxy]-phenyl}-2-methoxy-propionic acid (Compound 265);

(2S)-3-{4-[3-(4-Cyclohexylmethoxy-phenoxy)-propoxy]-phenyl}-2-methoxy-propionic acid (Compound 266);

(2S)-2-Methoxy-3-{4-[3-(4-phenetyloxy-phenoxy)-propoxy]-phenyl}-propionic acid (Compound 267);

(2S)-3-(4-{3-[4-(3-Dimethylamino-propoxy)-phenoxy]-propoxy}-phenyl)-2-methoxy-propionic acid (Compound 268);

(2S)-3-{4-[3-(4-Carboxymethoxy-phenoxy)-propoxy]-phenyl}-2-methoxy-propionic acid (Compound 269);

(2S)-3-(4-{3-[4-(1H-Indol-5-yl)-phenoxy]-propoxy}-phenyl)-2-methoxy-propionic acid (Compound 270);

(2S)-Methoxy-3-{4-[3-(4-pyridin-3-yl-phenoxy)-propoxy]-phenyl}-propionic acid (Compound 271);

(2S)-2-Methoxy-3-{4-[3-(4-pyridin-4-yl-phenoxy)-propoxy]-phenyl}-propionic acid (Compound 272);

(2S)-2-Methoxy-3-{4-[3-(4-quinolin-8-yl-phenoxy)-propoxy]-phenyl}-propionic acid (Compound 273);

(2S)-3-{4-[3-(4'-Cyano-biphenyl-4-yloxy)-propoxy]-phenyl}-2-methoxy-propionic acid (Compound 274);

(2S)-2-Methoxy-3-(4-{3-[4)-(1H-tetrazol-5-yl)biphenyl-4-yloxy]-propoxy}-phenyl)-propionic acid (Compound 275);

(2)-3-{4-[3-(4-Imidazol-1-yl-phenoxy)-propoxy]-phenyl}-2-methoxy-propionic acid (Compound 276);

(2S)-3-(4-{3-[4-(1,3-Dioxo-1,3-dihydro-isoindol-2-yl)-phenoxy]-propoxy}-phenyl)-2-methoxy-propionic acid (Compound 277);

(2S)-3-(4-{3-[4-(4-Acetyl-piperazin-1-yl)-phenoxy]-propoxy}-phenyl)-2-methoxy-propionic acid (Compound 278);

(2S)-2-Methoxy-3-{4-[3-(4-piperazin-1-yl-phenoxy)-propoxy]-phenyl}-propionic acid (Compound 279);

(2S)-2-Methoxy-3-{4-[3-(4-morpholin-4-yl-phenoxy)-propoxy]-phenyl}-propionic acid (Compound 280);

(2S)-3-{4-[3-(Biphenyl-4-yloxy)-propoxy]-2-chloro-phenyl}-2-methoxy-propionic acid (Compound 281);

3-{4-[3-(4-Benzoyl-phenoxy)-propoxy]-2-chloro-phenyl}-2-methoxy-propionic acid (Compound 282);

(2S)-3-{4-[2-(biphenyl-4-yloxy)-ethoxy]-phenyl}-2-methoxy-propionic acid (Compound 283);

(2S)-2-methoxy-3-{4-[3-(3-trifluoromethyl-phenoxy)-propoxy]-phenyl}-propionic acid (Compound 284);

(2S)-2-methoxy-3-[4-(3-phenoxy-propoxy)-phenyl]-propionic acid (Compound 285);

(2S)-3-{4-[3-(biphenyl-3-yloxy)-propoxy]-phenyl}-2-methoxy-propionic acid (Compound 286);

(2S)-2-methoxy-3-{4-[3-(2-methyl-benzothiazol-5-yloxy)-propoxy]-phenyl}-propionic (Compound 287);

(2S)-2-methoxy-3-{4-[3-(3-morpholin-4-yl-phenoxy)-propoxy]-phenyl}-propionic acid (Compound 288);

(2S)-2-methoxy-3-{4-[3-(5,6,7,8-tetrahydro-naphthalen-2-yloxy)-propoxy]-phenyl}-propionic acid (Compound 289);

2-methoxy-3-{4-[2-(4-phenoxy-phenoxy)-ethoxy]-phenyl}-propionic acid (Compound 290);

3-{3-[3-(biphenyl-4-yloxy)-propoxy]-phenyl}-2-methoxy-propionic acid (isomer 1) (Compound 291);

3-{3-[3-(biphenyl-4-yloxy)-propoxy]-phenyl}-2-methoxy-propionic acid (Isomer 2) (Compound 292);

(2S)-3-{4-[3-(2-cyano-phenoxy)-propoxy]-phenyl}-2-methoxy-propionic acid (Compound 293);

(2S)-2-methoxy-3-{4-[3-(2-methoxy-phenoxy)-propoxy]-phenyl}-propionic acid (Compound 294);

(2S)-2-{3-[4-(2-carboxy-2-methoxy-ethyl)-phenoxy]-propoxy}-benzoic acid (Compound 295);

(2S)-3-{4-[3-(3-cyano-phenoxy)-propoxy]-phenyl}-2-methoxy-propionic acid (Compound 296);

(2S)-3-{4-[3-(3-dimethylamino-phenoxy)-propoxy]-phenyl}-2-methoxy-propionic acid (Compound 297);

(2S)-3-{3-[4-(2-carboxy-2-methoxy-ethyl)-phenoxy]-propoxy}-benzoic acid (Compound 298);

(2S)-3-{4-[3-(indan-5-yloxy)-propoxy]-phenyl}-2-methoxy-propionic acid (Compound 299);

(2S)-2-methoxy-3-{4-[3-(naphthalen-2-yloxy)-propoxy]-phenyl}-propionic acid (Compound 300);

(2S)-3-{4-[3-(1H-indol-5-yloxy)-propoxy]phenyl}-2-methoxy-propionic acid (Compound 301);

(2S)-2-methoxy-3-{4-[3-(quinolin-6-yloxy)-propoxy]-phenyl}-propionic acid (Compound 302);

(2S)-2-methoxy-3-{4-[3-(3-methoxy-phenoxy)-propoxy]-phenyl}-propionic acid (Compound 303);

(2S)-3-{4-[3-(3-fluoro-phenoxy)-propoxy]-phenyl}-2-methoxy-propionic acid (Compound 304);

(2S)-3-{4-[3-(2-isopropyl-phenoxy)-propoxy]-phenyl}-2-methoxy-propionic acid (Compound 305);

(2S)-2-methoxy-3-[4-(2-phenoxy-ethoxy)-phenyl]-propionic acid (Compound 306);

(2S)-3-{4-[2-(2-cyano-phenoxy)-ethoxy]-phenyl}-2-methoxy-propionic acid (Compound 307);

(2S)-2-methoxy-3-{4-[2-(2-methoxy-phenoxy)-ethoxy]-phenyl}-propionic acid (Compound 308);

(2S)-3-{4-[2-(biphenyl-2-yloxy)-ethoxy]-phenyl}-2-methoxy-propionic acid (Compound 309);

(2S)-2-{2-[4-(2-carboxy-2-methoxy-ethyl)-phenoxy]-ethoxy}-benzoic acid (Compound 310);

(2S)-3-{4-[2-(2-isopropyl-phenoxy)-ethoxy]-phenyl}-2-methoxy-propionic acid (Compound 311);

(2S)-3-{4-[2-(3-cyano-phenoxy)-ethoxy]-phenyl}-2-methoxy-propionic acid (Compound 312);

(2S)-3-{4-[2-(3-dimethylamino-phenoxy)-ethoxy]-phenyl}-2-methoxy-propionic (Compound 313);

(2S)-3-{4-[2-(biphenyl-3-yloxy)-ethoxy]-phenyl}-2-methoxy-propionic acid (Compound 314);

(2S)-3-{2-[4-(2-carboxy-2-methoxy-ethyl)-phenoxy]-ethoxy}-benzoic acid (Compound 315);

(2S)-3-{4-[2-(indan-5-yloxy)-ethoxy]-phenyl}-2-methoxy-propionic acid (Compound 316);

(2S)-2-methoxy-3-{4-[2-(naphthalen-2-yloxy)-ethoxy]-phenyl}-propionic acid (Compound 317);

(2S)-2-Methoxy-3-{4-[2-(quinolin-6-yloxy)-ethoxy]-phenyl}-propionic acid (Compound 318);

(2S)-2-Methoxy-3-{4-[2-(3-morpholin-4-yl-phenoxy)-ethoxy]-phenyl}-propionic acid (Compound 319);

(2S)-2-Methoxy-3-{4-[2-(2-methyl-benzothiazol-5-yloxy)-ethoxy]-phenyl}-propionic (Compound 320);

(2S)-2-methoxy-3-{4-[2-(3-methoxy-phenoxy)-ethoxy]-phenyl}-propionic acid (Compound 321);
(2S)-3-{4-[2-(3-fluoro-phenoxy)-ethoxy]-phenyl}-2-methoxy-propionic acid (Compound 322);
2-methoxy-3-[3-(3-phenoxy-propoxy)-phenyl]-propionic acid (isomer 1) (Compound 323);
3-{3-[3-(2-cyano-phenoxy)-propoxy]-phenyl}-2-methoxy-propionic acid (isomer 1) (Compound 324);
3-{3-[3-(3-cyano-phenoxy)-propoxy]-phenyl}-2-methoxy-propionic acid (isomer 1) (Compound 325);
2-methoxy-3-[3-(3-phenoxy-propoxy)-phenyl]-propionic acid (isomer 2) (Compound 326);
3-{3-[3-(2-cyano-phenoxy)-propoxy]-phenyl}-2-methoxy-propionic acid (isomer 2) (Compound 327);
3-{3-[3-(3-cyano-phenoxy)-propoxy]-phenyl}-2-methoxy-propionic acid (isomer 2) (Compound 328);
2-methoxy-3-{3-[3-(2-methoxy-phenoxy)-propoxy]-phenyl}-propionic acid (isomer 1) (Compound 329);
2-methoxy-3-{3-[3-(2-methoxy-phenoxy)-propoxy]-phenyl}-propionic acid (isomer 2) (Compound 330);
3-{3-[3-(2-isopropyl-phenoxy)-propoxy]-phenyl}-2-methoxypropionic acid (isomer 1) (Compound 331);
3-{3-[3-(2-isopropyl-phenoxy)-propoxy]-phenyl}-2-methoxy-propionic acid (isomer 2) (Compound 332);
3-{3-[3-(2-carboxy-2-methoxy-etyl)-phenoxy]-propoxy}-benzoic acid (isomer 1) (Compound 333);
3-{3-[3-(2-carboxy-2-methoxy-ethyl)-phenoxy]-propoxy}-benzoic acid (isomer 2) (Compound 334);
2-methoxy-3-{3-[3-(3-methoxy-phenoxy)-propoxy]-phenyl}-propionic acid (isomer 1) (Compound 335);
2-methoxy-3-{3-[3-(3-methoxy-phenoxy)-propoxy]-phenyl}-propionic acid (isomer 2) (Compound 336);
2-methoxy-3-{3-[3-(naphthalen-2-yloxy)-propoxy]-phenyl}-propionic acid (isomer 1) (Compound 337);
2-methoxy-3-{3-[3-(naphthalen-2-yloxy)-propoxy]-phenyl}-propionic acid (isomer 2) (Compound 338);
2-methoxy-3-{3-[3-(2-methyl-benzothiazol-5-yloxy)-propoxy]-phenyl}-propionic acid (isomer 1) (Compound 339);
2-methoxy-3-{3-[3-(2-methyl-benzothiazol-5-yloxy)-propoxy]-phenyl}-propionic acid (isomer 2) (Compound 340);
3-{3-]3-(2-chloro-phenoxy)-propoxy]-phenyl}-2-methoxy-propionic acid (isomer 1) (Compound 341);
3-{3-[3-(2-chloro-phenoxy)-propoxy]-phenyl}-2-methoxy-propionic acid (isomer 2) (Compound 342);
3-{3-[3-(3,4-dimethyl-phenoxy)-propoxy]-phenyl}-2-methoxy-propionic acid (isomer 1) (Compound 343);
3-{3-[3-(3,4-dimethyl-phenoxy)-propoxy]-phenyl}-2-methoxy-propionic acid (isomer 2) (Compound 344);
2-{3-[3-(2-carboxy-2-methoxy-ethyl)-phenoxy]-propoxy}-benzoic acid (isomer 1) (Compound 345);
3-{3-[3-(2-carboxy-2-methoxy-ethyl)-phenoxy]-propoxy}-benzoic acid (isomer 2) (Compound 346);
3-{3-[3-(biphenyl-3-yloxy)-propoxy]-phenyl}-2-methoxy-propionic acid isomer 1) (Compound 347);

3-{3-[3-(biphenyl-3-yloxy)-propoxy]-phenyl}-2-methoxy-propionic acid (isomer 2) (Compound 348);
2-methoxy-3-{3-[3-(quinolin-6-yloxy)-propoxy]-phenyl}-propionic acid (isomer 1) (Compound 349);
2-methoxy-3-{3-[3-(quinolin-6-yloxy)-propoxy]-phenyl}-propionic acid (isomer 2) (Compound 350);
3-{3-[2-(2-isopropyl-phenoxy)-ethoxy]-phenyl}-2-methoxy-propionic acid (isomer 2) (Compound 351);
2-methoxy-3-{3-[2-(3-methoxy-phenoxy)-ethoxy]-phenyl}-propionic acid (isomer 1) (Compound 352);
3-{3-[2-(3-fluoro-phenoxy)-ethoxy]-phenyl}-2-methoxy-propionic acid (isomer 1) (Compound 353);
2-methoxy-3-{3-[2-(5,6,7,8-tetrahydro-naphthalen-2-yloxy)-ethoxy]-phenyl}-propionic acid (isomer 1) (Compound 354);
2-methoxy-3-{3-[2-(3-methoxy-phenoxy)-ethoxy]-phenyl}-propionic acid (isomer 2) (Compound 355);
3-{3-[2-(3-fluoro-phenoxy)-ethoxy]-phenyl}-2-methoxy-propionic acid (isomer 2) (Compound 356);
2-methoxy-3-{3-[2-(5,6,7,8-tetrahydro-naphthalen-2-yloxy)-ethoxy]-phenyl}-propionic acid (isomer 2) (Compound 357);
(2S)-2-methoxy-3-{4-[2-(4-trifluoromethyl-phenoxy)-ethoxy]-phenyl}-propionic acid (Compound 358);
(2S)-2-methoxy-3-(4-{2-[4-(1-methyl-1-phenyl-ethyl)-phenoxy]-ethoxy}-phenyl)-propionic acid (Compound 359);
(2S)-3-{4-[2-(4-benzyl-phenoxy)-ethoxy]-phenyl}-2-methoxy-propionic acid (Compound 360);
(2S)-2-methoxy-3-{4-[2-(4-oxo-2-phenyl-4H-chromen-7-yloxy)-ethoxy]-phenyl}-propionic acid (Compound 361);
(2S)-3-{4-[2-(4-cyclopentyl-phenoxy)-ethoxy]-phenyl}-2-methoxy-propionic acid (Compound 362);
(2S)-3-{4-[2-(9H-fluoren-2-yloxy)-ethoxy]-phenyl}-2-methoxy-propionic acid (Compound 363);
(2S)-3-{4-[2-(4-butyl-phenoxy)-ethoxy]-phenyl}-2-methoxy-propionic acid (Compound 364);
(2S)-3-{4-[2-(2'-fluoro-biphenyl-4-yloxy)-ethoxy]-phenyl}-2-methoxy-propionic acid (Compound 365);
(2S)-3-(4-{2-[4-(2,2-dimethyl-propionyl)-phenoxy]-ethoxy}-phenyl)-2-methoxy-propionic acid (Compound 366);
3-(4-{2-[4-(2,2-dimethyl-propionylamino)-phenoxy]-ethoxy}-phenyl)-2-methoxy-propionic acid (Compound 367);
(2S)-3-(4-{2-[4-(cyclopentanecarbonyl-amino)-phenoxy]-ethoxy}-phenyl)-2-methoxy-propionic acid (Compound 368);
(2S)-3-[4-(2-{4-[(furan-2-carbonyl)-amino]-phenoxy}-ethoxy)-phenyl]-2-methoxy-propionic acid (Compound 369);
(2S)-2-methoxy-3-[4-(2-{4-[(pyridine-3-carbonyl)-amino]-phenoxy}-ethoxy)-phenyl]-propionic acid (Compound 370);
(2S)-2-methoxy-3-{4-[2-(2-pyrrolidin-1-yl-phenoxy)-ethoxy]-phenyl}-propionic acid (Compound 371);
(2S)-2-methoxy-3-{4-[2-(pyridin-2-yloxy)-ethoxy]-phenyl}-propionic acid (Compound 372);
(2S)-2-methoxy-3-{4-[2-(2-morpholin-4-yl-phenoxy)-ethoxy]-phenyl}-propionic acid (Compound 373);
(2S)-3-{4-[2-(4'-tert-butyl-biphenyl-4-yloxy)-ethoxy]-phenyl}-2-methoxy-propionic acid (Compound 374);
(2S)-2-ethoxy-3-{4-[2-(4-phenoxy-phenoxy)-ethoxy]-phenyl}-propionic acid (Compound 375);
(2R)-2-ethoxy-3-{4-[2-(4-phenoxy-phenoxy)-ethoxy]-phenyl}-propionic acid (Compound 376);
(2S)-3-{4-[2-(biphenyl-4-yloxy)-ethoxy]-phenyl}-2-propoxy-propionic acid (Compound 377);
3-{3-[3-(biphenyl-4-yloxy)-propoxy]-phenyl}-2-ethoxy-propionic acid (isomer 1) (Compound 378);
3-{3-[3-(biphenyl-4-yloxy)-propoxy]-phenyl}-2-ethoxy-propionic acid (isomer 2) (Compound 379).

The present invention also includes compounds represented by Structural Formula (I), wherein Ar is the corresponding aromatic group from any one of Compounds 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formulas (I) or (VI), wherein Phenyl Ring A is the corresponding phenyl or substituted phenyl group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_3$—O— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_4$—O— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_5$—O— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$CH_2$—C≡CH— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_2$—C≡CH— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_3$—C≡CH— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_4$—C≡CH— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_5$—C≡CH— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$CH_2CO$— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_2CO$— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is —$(CH_2)_3CO$— and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is represented by the following structural formula:

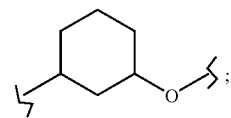

and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein W is represented by the following structural formula:

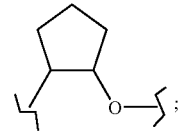

and Ar is the corresponding aromatic group from any one of Compounds 1–379 or from one of the compounds disclosed in Examples 1–379. Preferably, $R_1$ is para to the carbon atom bonded to W, $W_1$ or $W_2$ and is represented by Structural Formula (II), more preferably Structural Formula (III) or (IV) and even more preferably Structural Formula (V).

Also included are compounds represented by Structural Formula (I), wherein Ar—O—W— is the corresponding group from any one of Compounds 1–379 or from one of the compounds disclosed in Examples 1–379. Preferably, $R_1$ is para to the carbon atom bonded to W and is represented by Structural Formula (II), more preferably Structural Formula (III) or (IV) and even more preferably Structural Formula (V).

Also included are compounds represented by Structural Formula (I), wherein Ar is the corresponding aromatic group from any one of Compounds 1–379 or from one of the compounds disclosed in Examples 1–379, W is —CH(CH$_3$) W$_3$CH(CH$_3$)O— and W$_3$ is a covalent bond, methylene or ethylene. Preferably, $R_1$ is para to the carbon atom bonded to W and is represented by Structural Formula (II), more preferably Structural Formula (III) or (IV) and even more preferably Structural Formula (V).

Also included are compounds represented by Structural Formula (I), wherein Ar is the corresponding aromatic group from any one of Compounds 1–379 or from one of the compounds disclosed in Examples 1–379, W is —W$_4$C(=O)W$_5$O— or —W$_4$C(=CH$_2$)W$_5$O— and W$_4$ and W$_5$ are independently methylene or ethylene. Preferably, $R_1$ is para to the carbon atom bonded to W and is represented by Structural Formula (II), more preferably Structural Formula (III) or (IV) and even more preferably Structural Formula (V).

Prodrugs are compounds of the present invention, which have chemically or metabolically cleavable groups and become by solvolysis or under physiological conditions the compounds of the invention that are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy) alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of the present invention in a medium such as methanol with an acid or base esterification catalyst (e.g., NaOH, H$_2$SO$_4$). Ethyl ester prodrugs are prepared in similar fashion using ethanol in place of methanol.

Morpholinylethyl ester prodrugs may be prepared by reaction of the sodium salt of a compound of the present invention (in a medium such as dimethylformamide) with 4-(2-chloroethyl)morpholine hydrochloride (available from Aldrich Chemical Co., Milwaukee, Wis. USA, Item No. C4,220-3).

The term "pharmaceutically acceptable" means that the carrier, diluent, excipients and salt must be compatible with the other ingredients of the formulation, and not deleterious to the recipient thereof. Pharmaceutical formulations of the present invention are prepared by procedures known in the art using well-known and readily available ingredients.

Also included in the present invention are pharmaceutically acceptable salts, hydrates, stereoisomers and solvates of the compounds of the present invention and mixtures of such compounds, salts, hydrates, stereoisomers and/or solvates.

By virtue of its acidic moiety, certain compounds of the present invention form salts with pharmaceutically acceptable bases. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

Compounds of the present invention that are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures, succinates, benzoates and salts with amino acids such as glutamic acid.

Certain compounds of the present invention may contain one or more chiral centers, and exist in different optically active forms. When compounds of the present invention contain one chiral center, the compounds exist in two enantiomeric forms and the present invention includes both enatiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography, selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention has one or more chiral substituent it may exist in diastereoisomeric forms. The diastereoisomeric pairs may be separated by methods known to those skilled in the ark for example chromatography or crystallization and the individual enantiomers within each pair may be separated as described above. The present invention includes each diastereoisomer of such compounds and mixtures thereof.

Certain compounds of the present invention may exist in zwitterionic form and the present invention includes each zwitterionic form and mixtures thereof.

Certain compounds of the present invention and their salts may exist in more than one crystal form. Polymorphs of compounds of the present invention form part of this invention and may be prepared by crystallization of a given compound under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nmr spectroscopy, ir spectroscopy, differential scanning calorimetry, powder X-ray diffraction or such other techniques.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treatment" or "treating", as it is used herein, refers to both therapeutic treatment and prophylactic treatment. "Therapeutic treatment" refers to preventing the further progression or ameliorate the symptoms associated with a disease or condition. "Prophylactic treatment" refers to inhibiting, preventing or delaying the onset of the symptoms of a disease or condition in a subject who is at risk for the disease or condition. "Prophylactic treatment" also includes reducing the severity of the symptoms of a disease or condition by treating a subject at risk for developing the disease or condition before symptoms appear.

The language an "effective amount" or "pharmaceutically effective amount" is intended to include an amount that is sufficient to mediate a disease or condition and prevent its further progression or ameliorate the symptoms associated with the disease or condition. An "effective amount" or "pharmaceutically effective amount" can also include an amount sufficient to prevent or delay the onset of a disease or condition in a patient at risk for developing the disease or condition, i.e., prophylactic treatment. Such amount when administered prophylactically to a patient can also be effective to lessen the severity of the mediated condition. Such an amount is intended to include an amount that is sufficient to modulate a PPAR receptor, such as a PPARγ or PPARα receptor, which mediate a disease or condition. Conditions mediated by PPARα or PPARγ receptors include diabetes mellitus, cardiovascular disease, Syndrome X, obesity and gastrointestinal disease. Other such diseases are described below.

The compounds of the present invention and the pharmaceutically acceptable salts, solvates, stereoisomers and hydrates thereof have valuable pharmacological properties and can be used in pharmaceutical preparations containing the compound or pharmaceutically acceptable salts, esters or prodrugs thereof, in combination with a pharmaceutically acceptable carrier or diluent. They are useful as therapeutic substances in r treating (therapeutically or prophylactically) hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, polycystic ovarian syndrome, anorexia nervosa cardiovascular disease (especially atherosclerosis) or other diseases where insulin resistance is a component or other disorders mediated by a PPAR receptor. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein. Techniques for formulation and administration of the compounds of the instant invention can be found in Remington: the *Science and Practice of Pharmacy*, 19th edition, Mack Publishing Co., Easton, Pa. (1995).

For oral administration, the compound or salts thereof can be combined with a suitable solid or liquid carrier or diluent to form capsules, tablets, pills, powders, syrups, solutions, suspensions and the like.

The tablets, pins, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The active compounds can also be administered intranasally as, for example, liquid drops or spray. For oral or nasal inhalation, the compounds for use according to the present invention are conveniently delivered in the form of a dry powder inhaler; or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

For parental administration the compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally, subcutaneously, or intramuscularly, with intramuscular administration being preferred in humans.

The compounds may also be formulated in rectal compositions such as suppositories or retention enemas, e.g., containing conventional suppository bases such as cocoa butter or other glycerides.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The effective dosage of active ingredient employed may vary depending on the particular compound employed, the mode of administration, the condition being treated and the severity of the condition being treated.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the therapeutic treatment and/or prophylaxis of any one of or any combination of the following: hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, polycystic ovarian syndrome, anorexia nervosa, cardiovascular disease (especially atherosclerosis) or other diseases where insulin resistance is a component or other diosorders mediated by a PPAR receptor.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage formulation which contains a compound of the present invention and one or more additional active agents, as well as administration of a compound of the present invention and each active agent in its own separate pharmaceutical dosage formulation. For example, a compound of an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of the present invention and one or more additional active agents can be administered at essentially the same time, i.e., concurrently, or at separately staggered times, i.e., sequentially. Combination therapy is understood to include all these regimens.

An example of combination therapeutic or prophylactic treatment of atherosclerosis may be wherein a compound of the present invention or a salt thereof is administered in combination with one or more of the following active agents: antihyperlipidemic agents; plasma HDL-raising agents; antihypercholesterolemic agents, fibrates, vitamins, aspirin, and the like. As noted above, the compounds of the present invention can be administered in combination with more than one additional active agent.

Another example of combination therapy can be seen in treating (therapeutically or prophylactically) diabetes and related disorders wherein the compounds of the present invention and salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

Other examples of therapeutic agents which can be used in combination with the compounds of the present invention include insulin sensitizers, PPARγ agonists, glitazones, troglitizone, pioglitazone, englitazone, MCC-555, BRL 49653, biguanides, metformin, phenformin, insulin, insulin minetics, sulfonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrants, cholestyramine, colestipol, dialkylaminoalkyl derivatives of a cross-linked dextran, nicotinyl alcohol, nicotinic acid, a nicotinic acid salt, PPARα agonists, fenofibric acid derivatives, gemfibrozil, clofibrate, fenofibrate, benzafibrate, inhibitors of cholesterol absorption, beta-sitosterol, acyl CoA:cholesterol acyltransferase inhibitors, melinamide, probucol, PPARδ agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

An effective amount of a compound of the present invention can be used for the preparation of a medicament useful for treating (therapeutic and prophylactic) hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, polycystic ovarian syndrome, anorexia nervosa, cardiovascular disease (especially atherosclerosis), lowering tryglyceride levels, raising the plasma level of high density lipoprotein or other diseases where insulin resistance is a component or other disorders mediated by a PPAR receptor. Included is treating, preventing or reducing the risk of developing atherosclerosis, and for preventing or reducing the risk of having a first or subsequent atherosclerotic disease event in mammals, particularly in humans. In general an effective amount of a compound of the present invention (1) reduces serum glucose levels of a patient, or more specifically HbA1c, typically by about 0.7%; (2) reduces the serum triglyceride levels of a patient, typically by about 20%; and/or (3) increases the serum HDL levels in a patient, preferably about 30%.

Additionally, an effective amount of a compound of the present invention and an effective amount of one or more of the active agents listed above can be used together for the preparation of a medicament useful for the above-described treatments.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of the present invention or salts thereof) in a unit dose of composition is a therapeutically effective amount and may be varied according to the particular treatment involved. It may be appreciated that it may be necessary to make routine variations to the dosage depending on the age and condition of the patient. The dosage will also depend on the route of administration that may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) an effective amount of a compound of the invention together with a pharmaceutically acceptable carrier or diluent. The present pharmaceutical formulations are prepared by known procedures using well-known and readily available ingredients.

In making the compositions of the present invention, the active ingredient will usually be admixed with a carrier, or diluted by a carrier, or enclosed within a carrier that may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of about 0.05 to about 5.0 mg/ml in a 4% dextrose/0.5% Na citrate aqueous solution.

Solid form formulations include powders, tablets and capsules. A solid carrier can be one or more substance that may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or ac acia, and lubricating agents such as magnesium stearate, stearic acid, or talc.

In powders the carrier is a finely divided solid that is in admixture with the finely divided active ingredient. In tablets the active ingredient is mixed with a carrier having the necessary binding properties in suitable proportions and compacted in the shape and size desired.

Advantageously, compositions containing the compound of the present invention or the salts thereof may be provided in dosage unit form, preferably each dosage unit containing from about 1 to about 500 mg be administered although it will, of course, readily be understood that the amount of the compound or compounds of the present invention actually to be administered will be determined by a physician, in the light of all the relevant circumstances.

Powders and tablets preferably contain from about 1 to about 99 weight percent of the active ingredient that is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to the present invention or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| | |
|---|---|
| Active Ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| | |
|---|---|
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation maybe prepared as follows:

| | |
|---|---|
| Active Ingredient | 100 mg |
| Isotonic saline | 1,000 ml |

The solution of the above materials generally is administered intravenously to a subject at a rate of 1 ml per minute.

The compounds of the present invention, in general, may be prepared according to the Reaction Schemes described below. When describing various aspects of the present compounds, the terms "Tail", "Linker" and "Head" are used as their concept is illustrated below in General Reaction Scheme.

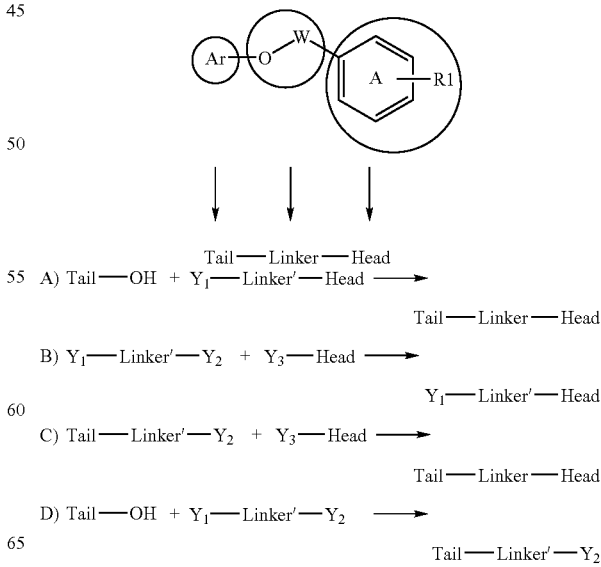

General Reaction Scheme

A) Tail—OH + $Y_1$—Linker'—Head ⟶ Tail—Linker—Head

B) $Y_1$—Linker'—$Y_2$ + $Y_3$—Head ⟶ Tail—Linker—Head

C) Tail—Linker'—$Y_2$ + $Y_3$—Head ⟶ $Y_1$—Linker'—Head

D) Tail—OH + $Y_1$—Linker'—$Y_2$ ⟶ Tail—Linker'—$Y_2$

-continued $Y_1$ = OH or LG (leaving grp)
$Y_2$ = $Y_1$ or H
$Y_3$ = OH, OTf, or I
Linker' = Linker modified to accomodate Y substitution As shown in General Reaction Scheme, the compounds of the present invention can be divided into three regions designated as Tail, Linker and Head. By a retrosynthetic analysis, key bond disconnections occur between each of these 3 regions. According to route A, a nucleophilic tailpiece is coupled to an electrophilic compound linker-headpiece, which in turn is derived by coupling the linker region with the headpiece by route B. Alternately according to route C, the headpiece can be coupled to the compound tailpiece-linker, derived by coupling the nucleophilic tailpiece with the electophilic linker by route D. The following reaction schemes illustrate more detailed synthetic routes to prepare the compounds of the present invention.

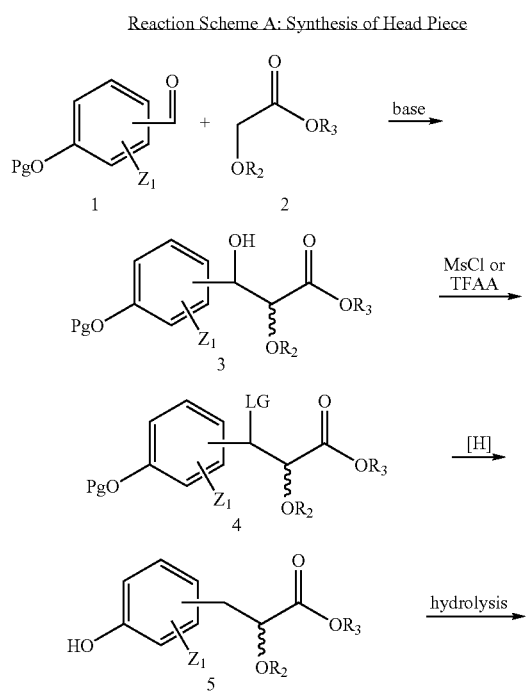

Reaction Scheme A: Synthesis of Head Piece

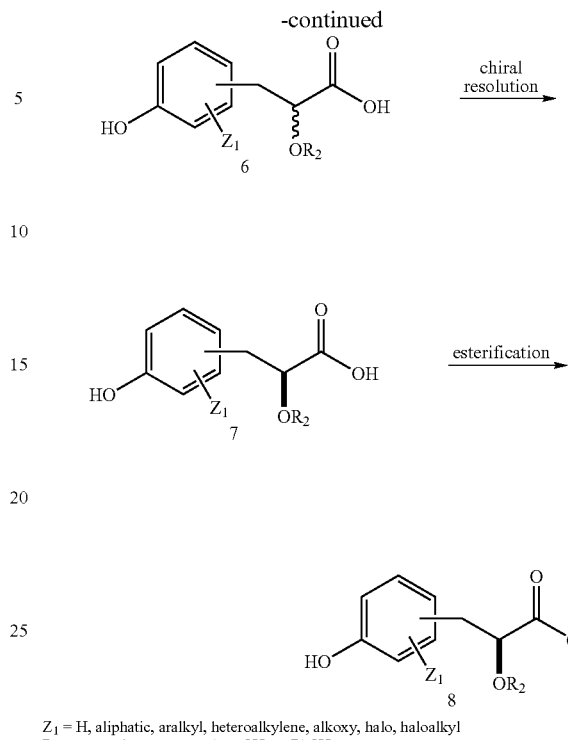

$Z_1$ = H, aliphatic, aralkyl, heteroalkylene, alkoxy, halo, haloalkyl
Pg = protecting group, such as $CH_3$ or $PhCH_2$ Reaction Scheme A shows the preparation of a general headpiece of the present compounds. Condensation of an aromatic aldehyde (1) with an alpha-alkoxyacetic acid ester (2) in the presence of a suitable base, such as lithium bis(trimethylsilyl)amide yields hydroxyester (3). The free hydroxyl group is converted into a leaving group by treatment with either methanesulfonyl chloride or trifluoroacetic anhydride. When the aromatic alcohol is protected as a benzyl ether (Pg is $PhCH_2$), exhaustive hydrogenolysis using hydrogen over Pd/C yields compound (5). Ester hydrolysis of (5) using aqueous hydroxide solution affords acid compound (6), which can be resolved into the corresponding enantiomers by using an appropriate chiral amine, such as (−)-cinchonidine. The acid (7) can be esterified using the appropriate alcohol under acidic conditions, such as ethanol and sulfuric acid, or an alkyl halide under basic conditions, such as cesium carbonate in DMF to give compound (8).

Reaction Scheme B: Synthesis of Head Piece

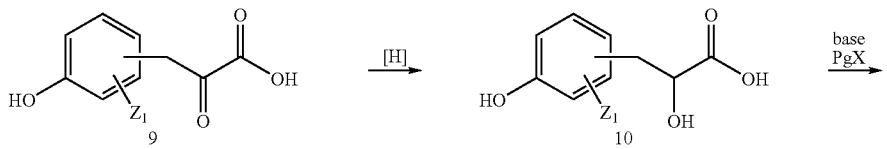

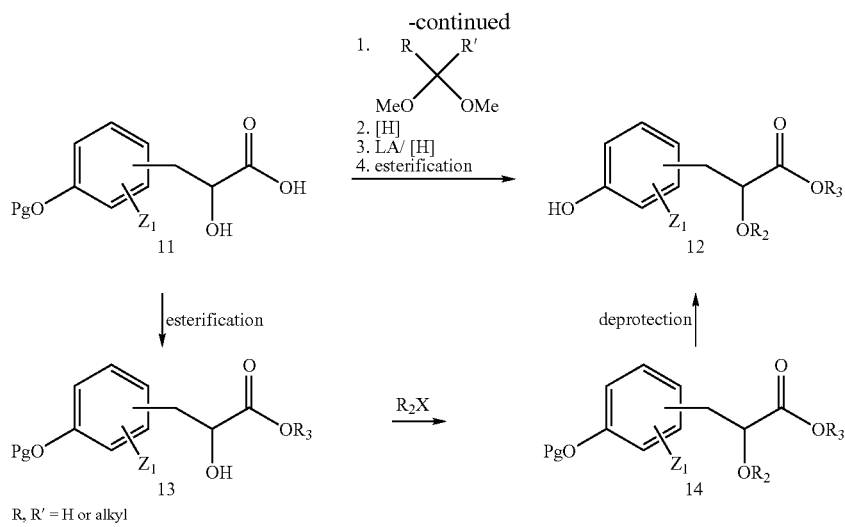

An alternate route to the headpiece is shown in Reaction Scheme B. The ketone function of ketoacid (9) is subjected to a reducing agent, such as B-chloro-diisopinocamphenylborane, to give hydroxyacid (10). The phenolic hydroxyl group is then protected with the protecting group to give compound (11). The compound (11) reacted with a dimethyl ketal followed by phenol ether cleavage gives an dioxolanone intermediate, which affords a 2-alkoxyacid upon treatment with a suitable Lewis acid, such as $TiCl_4$ and a reducing reagent, such as a trialkylsilane. Esterification yields 2-alkoxyester (12). Alternatively, acid (11) can be esterified to yield ester (13), which can be treated with an electrophile such as an alkyl halide, and an additive such as NaH or silver (I) oxide to afford ether compound (14).

As shown in Reaction Scheme C, a Claisen rearrangement can be used to alkylate the headpiece. Aryl alcohol (15) is treated with an alkyl bromide in the presence of a suitable base, such as NaH to give allyl ether (16). Heating the ether compound (16) in dimethylaniline affords the allylated headpiece compound (17).

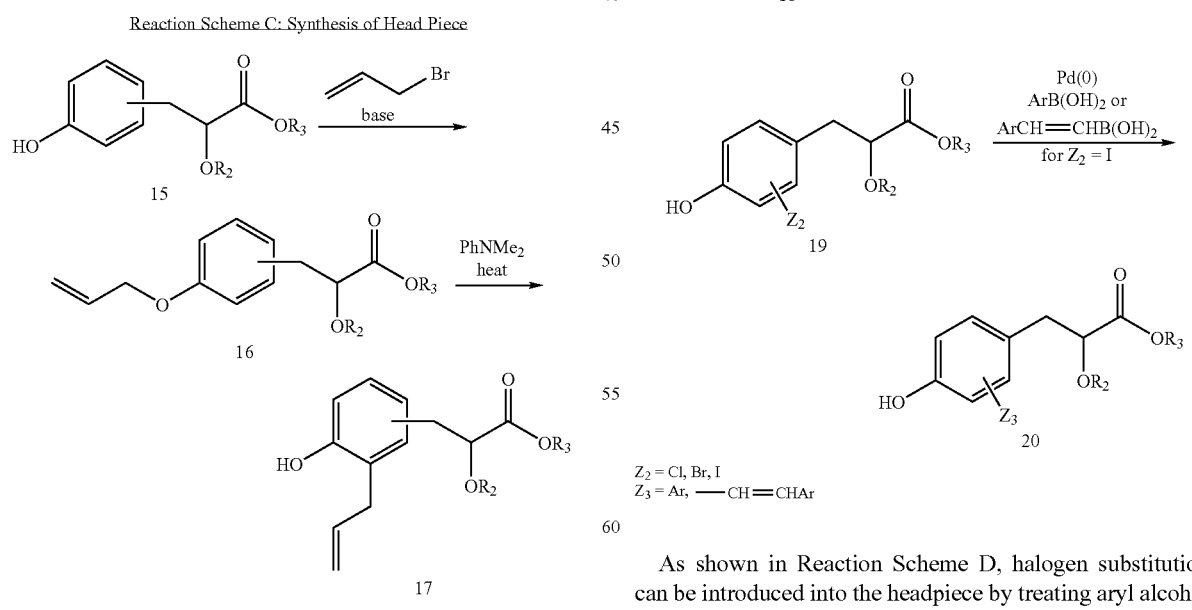

As shown in Reaction Scheme D, halogen substitution can be introduced into the headpiece by treating aryl alcohol (18) with an N-halosuccinimide in organic solvent to yield the compound (19). The compound (19) then undergoes a coupling reaction in the presence of palladium catalyst to yield the corresponding aryl and styrenyl compounds (20).

Reaction Scheme E: Synthesis of Head-Linker

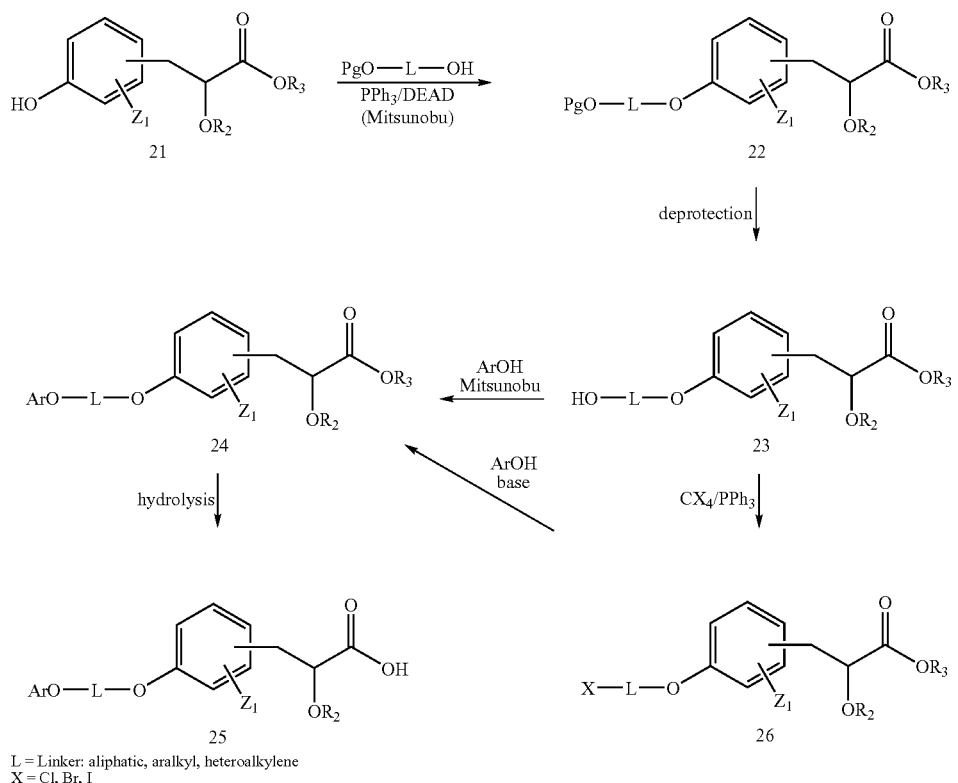

L = Linker: aliphatic, aralkyl, heteroalkylene
X = Cl, Br, I

Reaction Scheme E illustrates a synthesis of the present compounds by the general linker-headpiece route (General Scheme, routes A and B). The headpiece compoud (21) is coupled with a suitably monoprotected diol using a trialkylphosphine or triarylphosphine and an azodicarboxylate derivative (Mitsunobu conditions) to yield aryl ether (22). Deprotection of the alcohol function in the linker affords the compound (23), which then undergoes Mitsunobu coupling reaction with a tailpiece aryl alcohol (ArOH) to give compound (24). Further ester hydrolysis affords acid compound (25). Alternatively, the alcohol compound (23) can be converted to the corresponding halide (26) using a carbon tetrahalide and triphenylphosphine. Treatment of compound (26) with a tailpiece aryl alcohol (ArOH) in the presence of a suitable base, such as cesium carbonate affords compound (24), which then undergoes hydrolysis to give acid compound (25).

Reaction Scheme F: Synthesis of Head-Linker

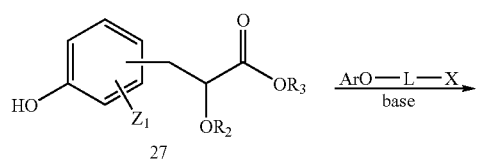

-continued

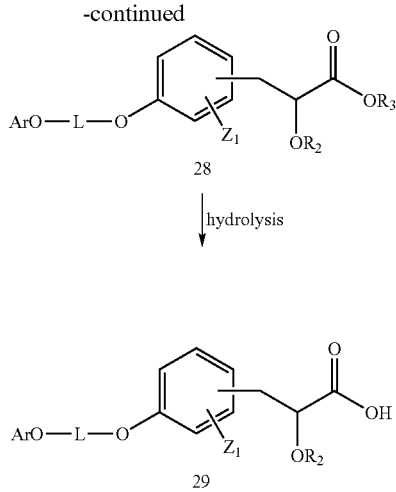

As shown in Reaction Scheme F, the compounds of the present invention can be prepared by the general tailpiece-linker to headpiece route (General Scheme, route C). The headpiece compound of alcohol (27) is treated with a tailpiece-inker halide (ArO-L-X) in the presence of a suitable base, such as potassium or cesium carbonate to afford the compound (28), which then undergoes ester hydrolysis to yield acid compound (29).

Reaction Scheme G: Solid Phase Synthesis

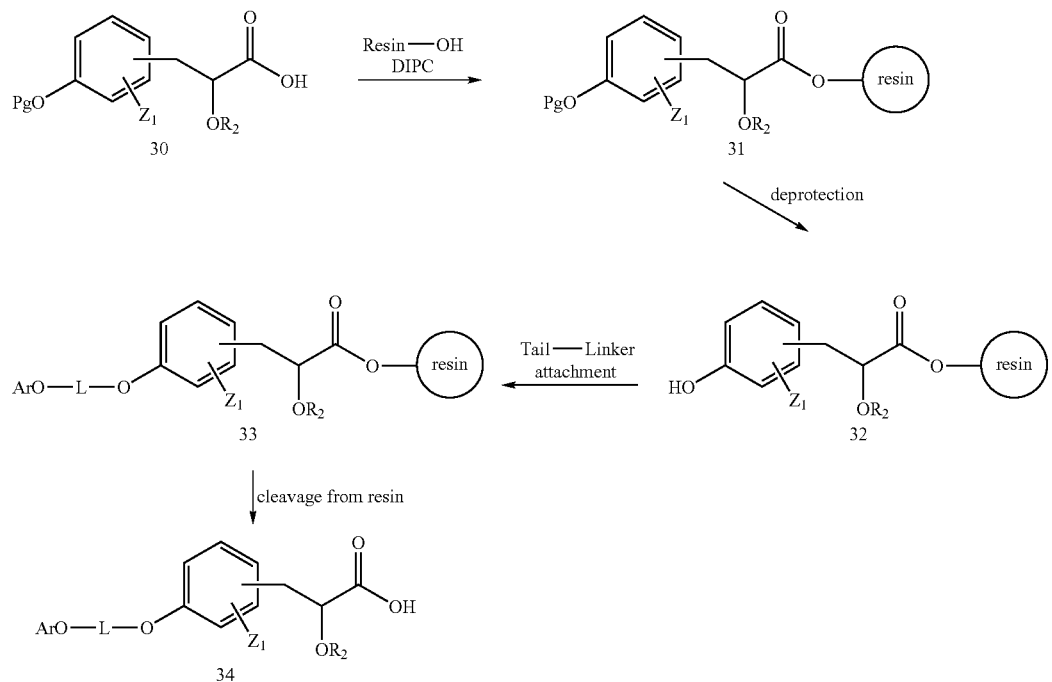

As shown in Reaction Scheme G, the headpiece can be attached to a resin allowing for a solid phase synthesis of the target compounds. Carboxylic acid (30) is attached to a suitable resin, such as the Wang resin, using an appropriate coupling reagent, such as diisopropyl carbodiimide (DIPC). Cleavage of the aryl alcohol protecting group, such as a tert-butyldimethylsilyl ether (t-BuMe$_2$Si) with the appropriate reagent, such as tetra-n-butylammonium fluoride gives aryl alcohol (32). The tail and linker regions are introduced as described in Reaction Schemes E and F to produce the compound (33). The carboxylic acid (34) can be released from the resin under suitable conditions, such as trifluoroacetic acid.

Reaction Scheme H: Synthesis of Head-Linker

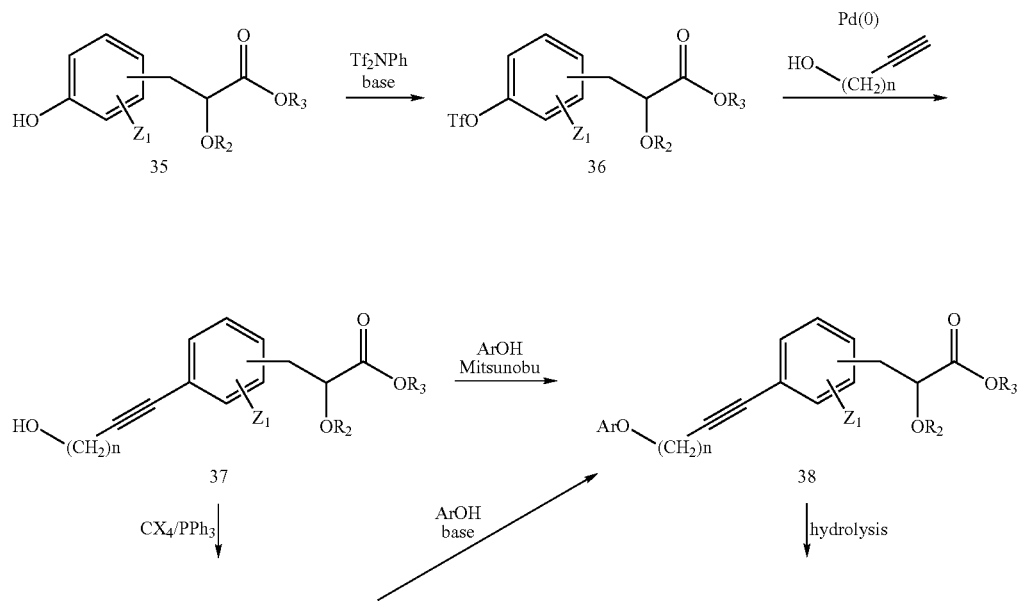

-continued

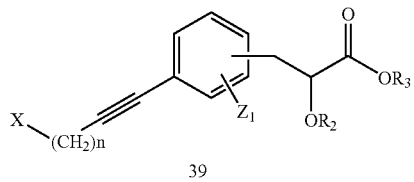
39

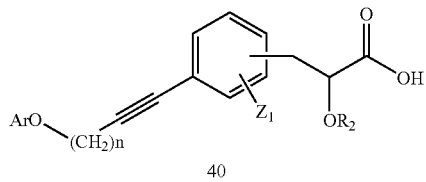
40

Reaction Scheme H illustrates a synthetic route to prepare the compounds of the present invention having alkynyl linkers. The headpiece compound (35) can be converted to the corresponding aryl triflate (36) (or aryl iodide) using phenyl triflamide and an appropriate base, such as NaH. The palladium catalyzed coupling reaction of compound (36) with an alkynyl alcohol gives the linker-headpiece intermediate (37). Coupling of compound (37) with various tailpiece alcohols can be achieved as described in Reaction Scheme E to afford the compound (38), which then undergoes a hydrolysis to yield the acid compound (40).

Reaction Scheme I: Synthesis of Head-Linker

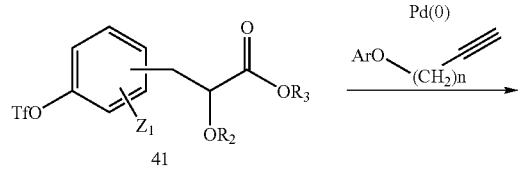

-continued

Alternative to Reaction Scheme H, the headpiece compound of triflate (41) can be combined with a tailpiece-linker to give the coupled compound (42) in one step as shown in Reaction Scheme I. The compound (42) then undergoes a hydrolysis to give the acid compound (43).

Reaction Scheme J: Synthesis of Head-Linker

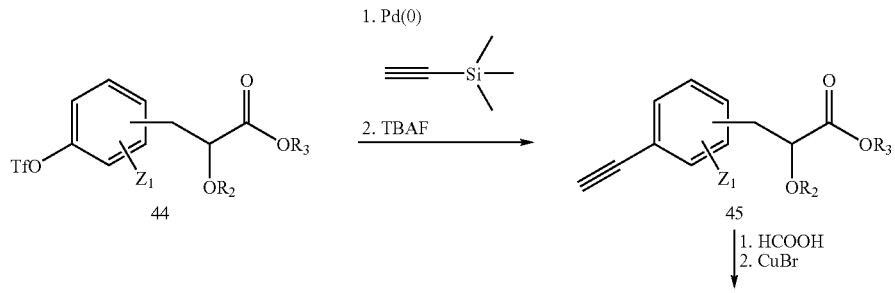

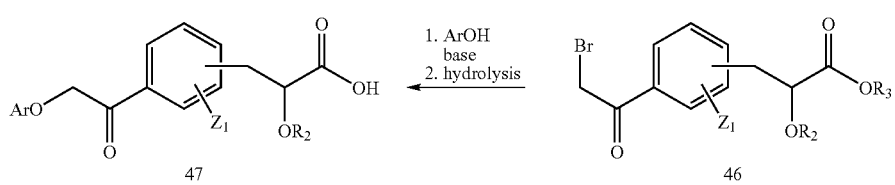

As shown in Reaction Scheme 3, the headpiece compound of triflate (44) can be coupled with trimethylsilylacetylene using palladium catalysis to give the acetylenic headpiece (45) after fluoride mediated cleavage of the silyl group. The alkyne (45) is hydrolyzed under aqueous acidic conditions to the methyl ketone, which is then brominated with a suitable agent, such as copper (I) bromide to give bromoketone (46). Treatment of the compound (46) with a tailpiece aryl alcohol in the presence of a suitable base, such as potassium carbonate and aqueous base hydrolysis affords the acid compound (47).

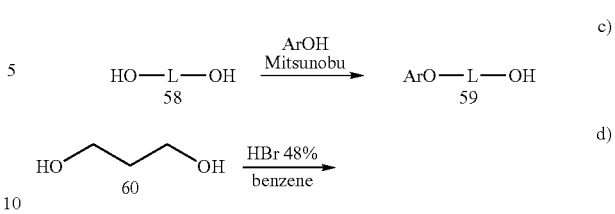

Reaction Scheme K: Alkyne-Linker Modification

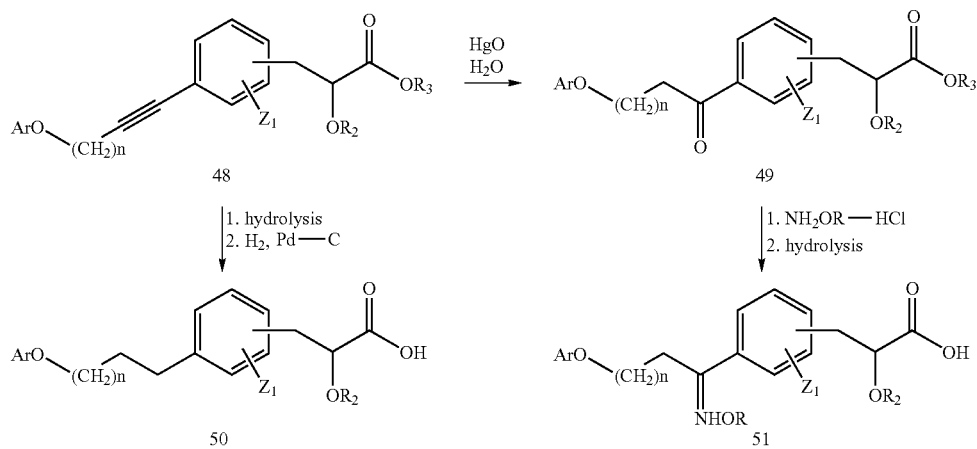

As shown in Reaction Scheme K, an alkyne function in the linker region of the present compounds can be modified. The alkyne can be oxidized to ketone to give compound (49) by using an appropriate oxidizing agent, such as mercuric oxide. The ketone can be further modified to the corresponding oximes (51) by treatment with an alkoxyamine followed by hydrolysis. Alternatively, the alkynyl function can be reduced to the alkylene as in compound (50) by using an appropriate reducing agent, such as hydrogen over palladium-on-carbon.

Reaction Scheme L: Synthesis of Linker

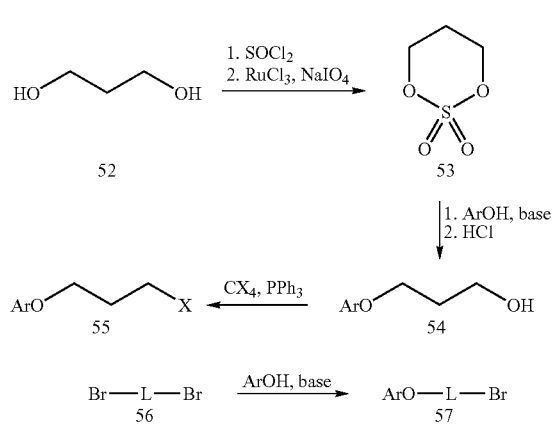

Reaction Scheme L illustrates various synthetic routes to the linker region. In route (a), 1,3-propane diol (52) is converted to the cyclic sulfonate ester (53) upon treatment with thionyl chloride followed by appropriate oxidation reagents, such as ruthenium trichloride and sodium periodate. Ring opening of the intermediate (53) is effected upon treatment with a tailpiece alcohol and a suitable base such as potassium tert-butoxide, followed by an acidic workup procedure to give the linker alcohol compound (54). The alcohol is then converted to the halide by using an appropriate reagent, such as a carbontetrahalide and a triarylphosphine to afford the compound (55). In route (b), the compound of dibromo-linker (56) is reacted with approximately one mole equivalent of the tailpiece aryl alcohol in the presence of a suitable base, such as potassium carbonate to give the bromo-ether compound (57).

In route (c), the compound of diol-linker (58) is coupled with approximately one mole equivalent of the tailpiece alcohol under Mitsunobu reaction conditions to give the hydroxy-ether compound (59).

In route (d), 1,3-propane diol (60) is converted to the halide (61), which is then reacted with the headpiece aryl alcohol under the Mitsunobu reaction condition to give the bromo-ether compound (62).

Reaction Scheme M: Synthesis of Modified Linker

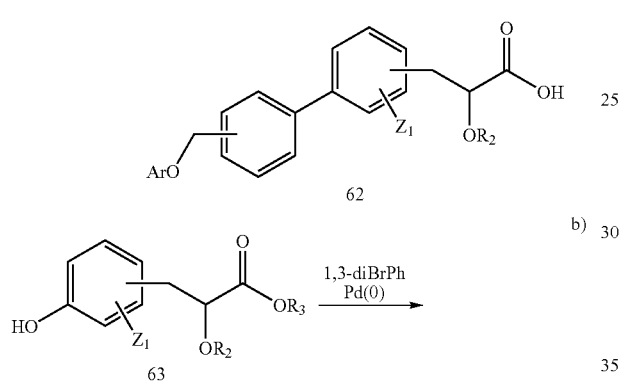

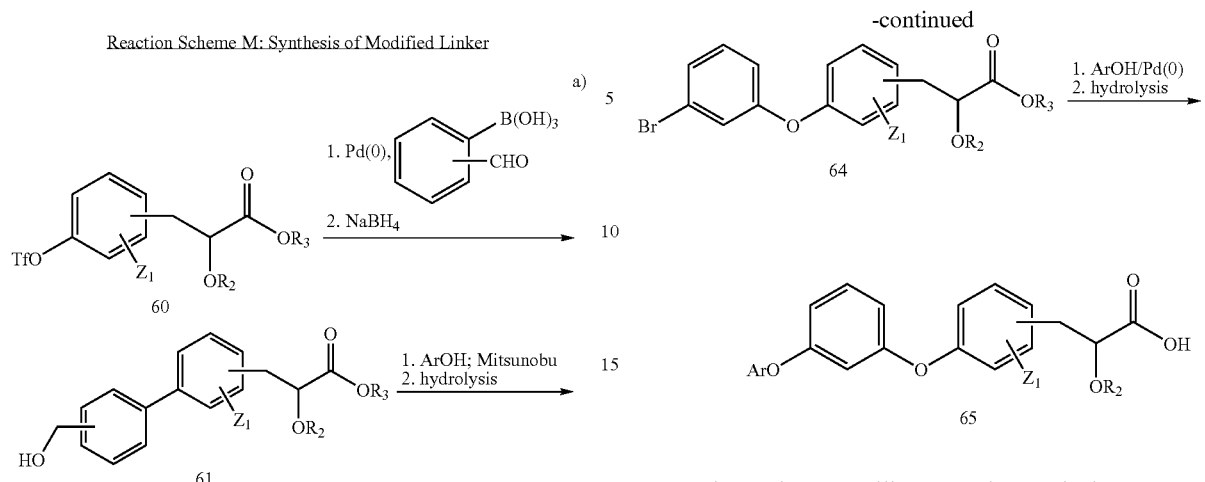

Reaction Scheme M illustrates the synthetic routes to compounds with aryl-containing linkers. In route (a), The compound of headpiece triflate (60) is coupled with an arylboronic acid in the presence of palladium catalyst. Reduction of the intermediate aldehyde using a suitable reagent such as sodium borohydride, affords the arylic alcohol compound (61). The compound (61) can be coupled with the tailpiece aryl alcohol (ArOH) under Mitsunobu conditions followed by ester hydrolysis to give the acid compound (62).

In route (b), the headpiece alcohol (63) is coupled with approximately one mole equivalent of aryl dibromide in the presence of palladium catalyst to give aryl bromide (64). The compound (64) is then coupled similarly to the tailpiece aryl alcohol (ArOH) followed by ester hydrolysis to afford the acid compound (65).

Reaction Scheme N: Tailpiece Modification

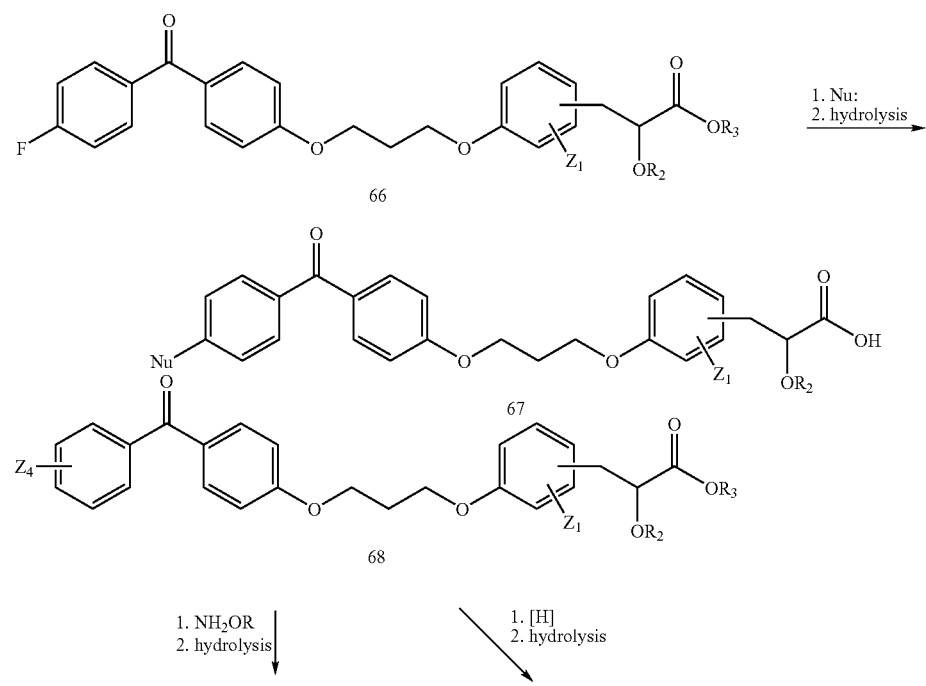

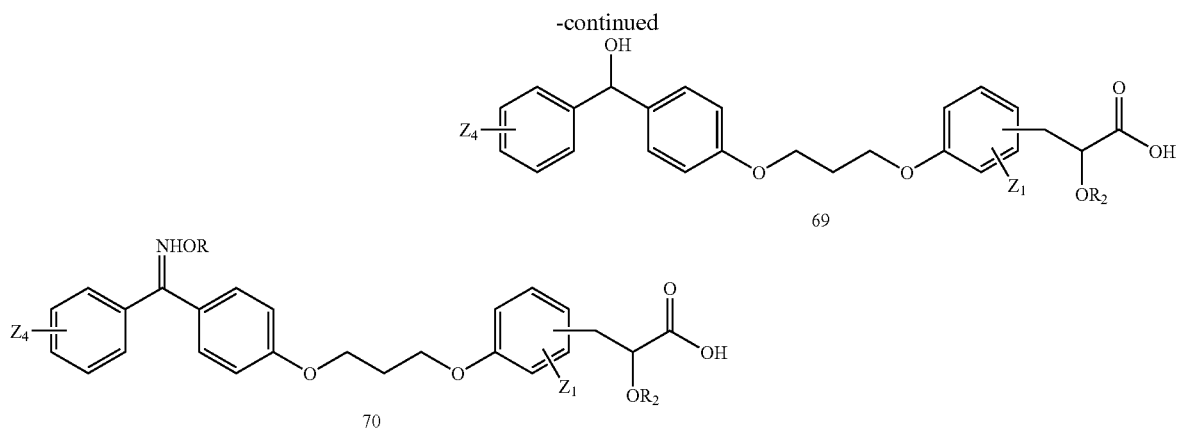

Nu: = nucleophile
Z₄ = suitable Ar substituent

Reaction Scheme N shows a synthetic route to modify the tailpiece region of the present compounds. The compound of para-fluorobenzophenone (66) is treated with a suitable nucleophile such as secondary amines and alkoxides, and then subjected to ester hydrolysis to give the acid compound (67).

The carbonyl function of benzophenone (68) can be reduced by using an appropriate reagent, such as hydrogen over palladium-on-carbon to yield the corresponding alcohol (69) after ester hydrolysis. The ketone moiety of compound (68) can be also modified to the corresponding oximes (70) by treatment with an alkoxyamine followed by hydrolysis.

Reaction Scheme O: Synthesis of Modified Tailpiece

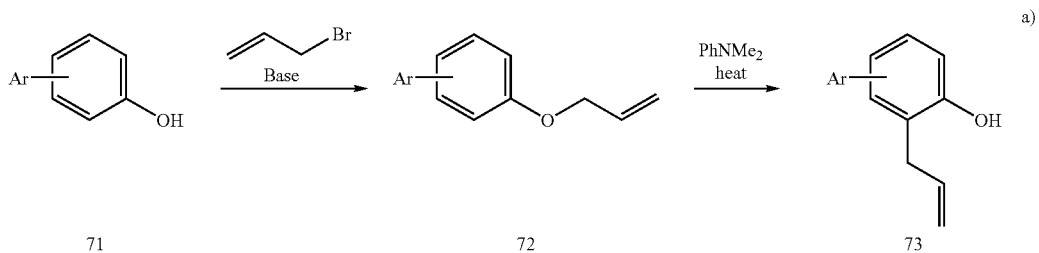

a)

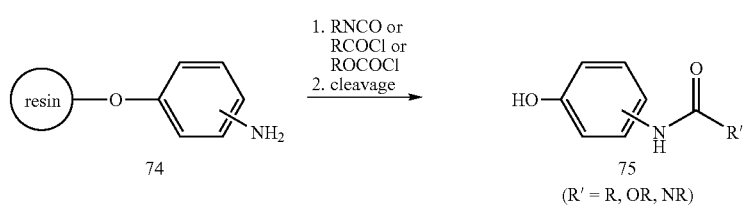

b)

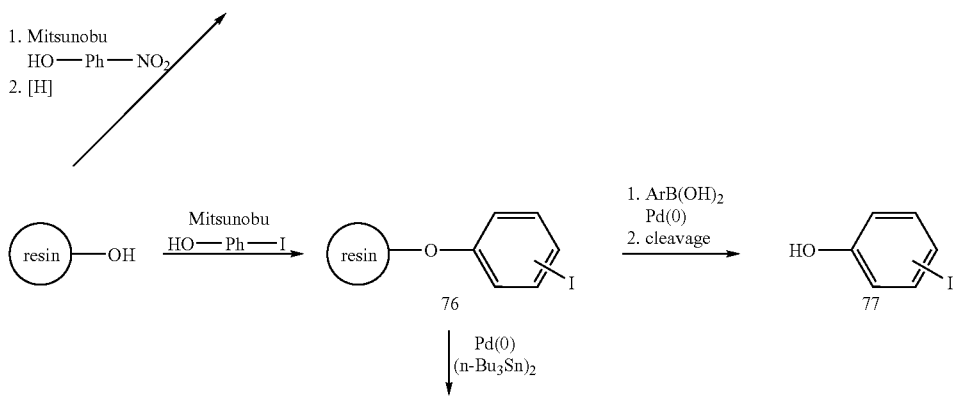

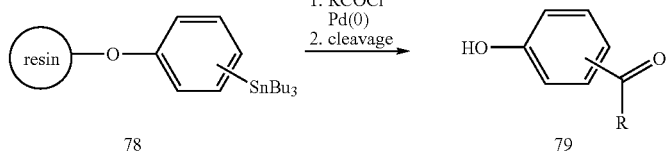

Reaction Scheme O shows the synthetic routes to prepare the tailpiece region of the compounds. A Claisen rearrangement is used to alkylate the tailpiece aryl ring as shown in route (a). Aryl alcohol (71) is treated with an alkyl bromide in the presence of a suitable base, such as NaH to give alkyl ether (72). Heating this ether in dimethylaniline gives the alkylated headpiece (73).

Solid phase methods to synthesize the tailpiece are described in route (b). Aryl alcohol is coupled to a suitable resin, such as the Wang resin under Mitsunobu conditions. Coupling the resin with a nitro aryl alcohol gives an intermediate that is reduced under-appropriate conditions, such as tin (II) chloride in DMF to give aniline (74). The nitrogen function is reacted further with suitable reagents, such as isocyanates, acid chlorides or chloroformates to give the corresponding ureas, carbamates and amides, respectively. Cleavage from the resin under acidic conditions, such as trifluoroacetic acid in dichloromethane affords the amino substituted tailpiece of aryl alcohol compound (75).

Alternatively, coupling the resin with an iodo aryl alcohol gives iodide intermediate (76). The aryl iodide (76) then can be coupled directly with aryl boronic acids under palladium catalysis to give biaryl tailpiece aryl alcohols (77) upon cleavage from the resin under acidic condition. Iodide intermediate (76) can also be converted to the trialkylstannane (78) in the presence of palladium catalyst. Subsequent palladium catalyzed coupling with suitable reagents, such as acid chloride and upon cleavage from the resin under acidic condition afford the carbonyl substituted tailpiece aryl alcohol compound (79).

EXEMPLIFICATION

Instrumental Analysis $^1$H NMR spectra were recorded on Varian 400 MHz, Bruker 200, 300 or 500 MHz spectromethers at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, and coupling constant (Hz). $^{13}$C NMR were recorded on a Bruker 200, 300 or 500 MHz spectromether at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light Standard Synthesis Procedures Certain standard synthesis procedures were used in preparing many of the exemplified compounds of the present invention. These Standard Procedures were:

Standard Procedure for Mitsounobu coupling hydrolysis procedure (A): A solution of triphenylphosphine (1.42 mmol) in 10 mL of dry THF was treated at 0° C. with diethylazodicarboxylate (1.42 mmol) and stirred for 20 min A solution of (2S)-3-[4-(3-Hydroxy-prop-1-ynyl)-phenyl]-2-methoxy-propionic acid ethyl ester (1.19 mmol) and 4-phenylphenol (1.42 mmol) in 5 mL of dry THF was added to the solution, and the mixture stirred at room temperature overnight. The mixture was concentrated to dryness under vacuum and purified by silica gel chromatography (silica gel, hexanes ethyl acetate 10:1 to 3:1). Fractions with Rfs 0.5 and 0.42 (hexanes/ethyl acetate 2:1) corresponding to the couple compound and starting phenol, respectively, were combined and concentrated to dryness. The mixture was dissolved in 4 mL of 1N NaOH and 12 mL of methanol and stirred at room temperature until TLC indicated the disappearance of starting material. The methanol was removed under vacuum, and the aqueous solution was diluted with 20 mL of brine and washed with diethyl ether (3×15 mL). The aqueous phase was acidified with 1N HCl (pH 1-2) and extracted with ethyl acetate (3×15 mL). The organic layer dried (MgSO$_4$) and concentrated under vacuum.

Standard Procedure for the Mitsounobu coupling procedure (B): A solution of triphenylphosphine (1.42 mmol) in 10 mL toluene or THF was treated at 0° C. with DEAD or DIAD (1.42 mmol) and stirred for 20 min. A solution of (2S)-3-(4-Hydroxy-phenyl)-2-methoxy-propionic acid ethyl ester (1.19 mmol) and the corresponding alcohol (1.42 mmol) in 5 mL of toluene or THF was added to the solution, and the mixture stirred at room temperature overnight. The mixture was concentrated to dryness under-vacuum and purified by silica gel chromatography Standard hydrolysis Procedure (C): (2S)-3-{4-[4-(Biphenyl-4-yloxy)-but-1-ynyl]-phenyl}-2-methoxy-propionic acid ethyl ester (0.5 g, 1.17 mmol) was dissolved in 20 mL of 1N NaOH (or LiOH) and 60 mL of methanol and was stirred at room temperature until TLC indicated the disappearance of starting material (ca. 3 h). The methanol was removed under vacuum, and the aqueous solution diluted with 20 mL of brine and washed with diethyl ether (3×60 mL). The aqueous phase was acidified with 1N HCl (until pH 1-2) and extracted with ethyl acetate (3×60 mL). The organic layer dried (MgSO$_4$) and concentrated under vacuum.

Standard Procedure for Monoprotection of diols (D): A solution of the corresponding diol (1 eq) in dry THF was cooled to 0° C. Sodium hydride (1 eq) was added, and the mixture reaction was stirred 30 min at that temperature. Tert-butyldimethylsilyl chloride (0.95 eq) was added, and the mixture was stirred at room temperature overnight. Then a 10% Na$_2$CO$_3$ solution was added and the mixture was extracted with ethyl acetate. The combined organic layers were washed with brine; dried (MgSO$_4$) and concentrated in vacuo. The residue was purified by silica gel chromatography.

Standard Procedure for the cleveage of the protected alcohols (E): A mixture solution of the corresponding protected alcohol in THF was treated with tetrabutylamonium fluoride (1M in THF) (2 eq). The solution was stirred at room temperature until reaction is completed by TLC, then quenched with water and extracted with Ethyl Acetate to give a crude product which was purified by silica gel chromatography.

Standard Procedure (F): The reaction was carried out in a polypropylene syringe equipped with a polypropylene frit. A suspension of the resin-linked phenol (1 eq) was suspended in THF (0.02 M). A solution of 1,3-propanediol (5 eq) in THF was added followed by a mixture of triphenylphosphine (5 eq) and diisopropylazo-dicarboxylate (5 eq) in THF. The mixture was shaken at room temperature overnight. The reaction solvent was removed, and the resin was washed sequentially with THF (2×), $CH_2Cl_2$ (2×), DMF (2×), $CH_2Cl_2$ (2×), methanol and $CH_2Cl_2$ (3×). The resultant polymer was dried under vacuum overnight to produce the targeted immobilized alcohol.

Standard Procedure (G): The reaction was carried out in a polypropylene syringe equipped with a polypropylene frit. A suspension of the resin-linked alcohol (1 eq) was suspended in a mixture 1:1 THF/$CH_2Cl_2$ (0.015 M. A solution of phenol (10 eq) dissolved in a mixture of 1:1 THF/$CH_2Cl_2$ was added followed by a mixture of triphenylphosphine (5 eq) and diisopropylazo-dicarboxylate (5 eq) in THF/$CH_2Cl_2$ 1:1. The mixture was shaken at room temperature overnight, and the reaction solvent was removed. The resin was washed sequentially with 1:1 THF/$CH_2Cl_2$ (2×), THF (2×), $CH_2Cl_2$ (2×), DMF (2×), $CH_2Cl_2$ (2×), methanol, and $CH_2Cl_2$ (2×). The resin was dried under vacuum for 5 h and treated with 50% TFA in $CH_2Cl_2$. The solution was filtered and concentrated, and the residue was purified by HPLC-MS chromatography to produce the desired product.

Standard Procedure (H): Lithium hydroxide 1N solution in water (0.245 mL) was added to a solution of the ester (0.073 mmol) in tetrahydrofuran (1 mL) at room temperature. The reaction mixture was stirred at room temperature for 1.5 hours, diluted with water (10 mL) and extracted with diethyl ether (3×10 mL). The aqueous layer was acidified with 1N HCl to pH 1 and extracted with Diethyl ether (5×15 mL). The combined organic layers were dried ($MgSO_4$), filtered and concentrated under vacuum to produce the corresponding acid.

Standard Procedure (I): A mixture of the corresponding phenol (1 eq) and the bromoalkyl derivative (1 eq) with $K_2CO_3$ (3 eq) were refluxed in acetonitrile overnight. Cooled the mixture reaction and concentrated to dryness to give a crude which was purified by chromatography in silica gel to give the product.

Standard Procedure (J). A mixture of the corresponding phenol (1.5 eq), and the bromoalkyl derivative (1 eq) in DMF were treated with $Cs_2CO_3$ (3 eq). The mixture reaction was stirred at room temperature overnight and then filtered. Removed the DMF under vacuo and added methanol to the residue treating the mixture with NaOH 1M (10 eq) and stirred for 3 h. The solvent was evaporated and the salts were dissolved in water. The aqueous phase was acidified to pH 2 and extracted with dichloromethane, filtered through a hydrophobic syringe and the organic layer purified by HPLC-MS.

Example 1

(2S)-3-{4-[3-(Biphenyl-4-yloxy)-prop-1-ynyl]-phenyl}-2-methoxy-propionic acid

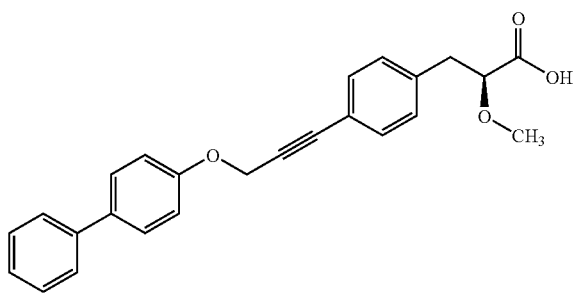

Step A (2S)-2-Methoxy-3-(4-trifluoromethanesulfoxy-phenyl)-propionic acid ethyl ester

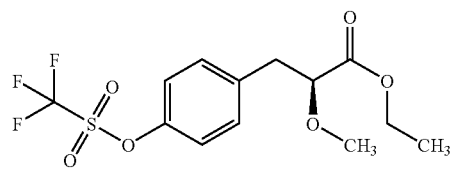

To a solution of (S)-2-methoxy-3-hydroxyphenyl-propionic acid ethyl ester (0.388 g, 1.73 mmol) in 40 mL of dry THF cooled to −20° C. was added sodium hydride (0.073 g, 1.82 mmol, 60% oil dispersion). The mixture was stirred at −20° C. for 30 min. Phenyl triflimide (0.68 g, 1.90 mmol) was added in one portion, and the solution was stirred at room temperature overnight and concentrated to dryness under vacuum. The residue was partitioned between water (20 mL) and diethyl ether (20 mL). The layers were separated, and the aqueous solution was extracted with diethyl ether (2×20 ml). The combined organic layers were washed with 10% $Na_2CO_3$ (6×20 mL) and brine (20 mL), dried ($MgSO_4$), and concentrated to a yellow oil (574 mg, 97%).
$^1$H-NMR (200.15 MHz, $CDCl_3$): δ 7.34–7.16 (m, 4H), 4.18 (q, 2H, J=7.0), 3.93 (dd, 1H, J=7.3, 5.6), 3.36 (s, 3H), 3.05 (s, 1H), 3.02 (d, 1H, J=2.4 Hz), 1.22 (t, 3H, J=7.25).

Step B (2S)-3-[4-(3-Hydroxy-prop-1-ynyl)-phenyl]-2-methoxy-propionic acid ethyl ester

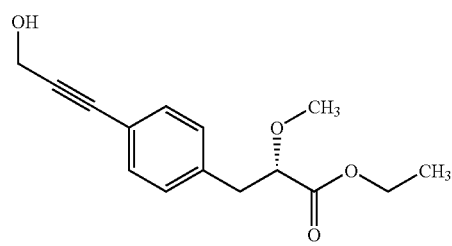

A solution of (2S)-2-methoxy-3-(4-trifluoromethane-sulfonyloxy-phenyl)-propionic acid ethyl ester (0.861 g, 2.53 mmol), propargyl alcohol (0.88 mL, 15.18 mmol), triethylamine (1.41 mL, 10.12 mmol) and dichlorobis(triphenylphosphine)palladium (II) in 10 mL of dry DMF was heated to 90° C. for 2 hours. The reaction mixture was cooled to room temperature, diluted with 50 mL of water, and extracted with diethyl ether (3×30 mL). The combined organic layers were washed with 0.5 N HCl (2×20 mL) and brine (20 mL), dried (MgSO$_4$), and concentrated. The residue purified by column chromatography (silica gel, hexanes/ethyl acetate 2:1, R$_f$0.17) to give a yellow-brown oil (0.211 g, 32%). $^1$H-NMR (200.15 MHz, CDCl$_3$): δ 7.35 (d, 2H, J=8.1), 7.18 (d, 2H, J=8.1), 4.48 (s, 2H), 4.17 (q, 2H, J=7.3), 3.93 (dd, 1H, J=7.3, 5.7), 3.34 (s, 3H), 3.02 (s, 1H), 2.99 (d, 1H, J=2.2), 1.8 (s, 1H), 1.22 (t, 3H, J=7.3).

Step C (2S)-3-{4-[3-(Biphenyl-4-yloxy)-prop-1-ynyl]-phenyl}-2-methoxy-propionic acid The title compound was prepared from (2S)-3-[4-(3-hydroxy-prop-1-ynyl)-phenyl]-2-methoxy-propionic acid ethyl ester using the standard Mitsunobu coupling-hydrolysis procedure (Standard Procedure A) to produce a white solid. Mp 111–112° C. $^1$H-NMR (200.15 MHz, CDCl$_3$): δ 7.58–7.52 (m, 4H), 7.45–7.30 (m, 5H), 7.19 (d, 1H, J=8.3), 7.10 (dd, 3H, J=6.7, 1.9), 4.94 (s, 2H), 3.98 (dd, 1H, J=7.5, 4.3); 3.37 (s, 3H), 3.13 (dd, 1H, J=14.5, 4.6), 2.99 (dd, 1H, J=14.2, 7.8). MS (ES) for C$_{25}$H$_{22}$O$_4$ [M+NH$_4$]$^+$: 404, [M+Na]$^+$:409.

Example 2

(2S)-3-{4-[3-(4-Benzoyl-phenoxy)-prop-1-ynyl]-phenyl}-2-methoxy-propionic acid:

The title compound was prepared from (2S)-3-[4-(3-hydroxy-prop-1-ynyl)-phenyl]-2-methoxy-propionic acid ethyl ester (from Example 1, Step B) via the standard Mitsunobu coupling-hydrolysis procedure (Standard Procedure A) to produce a white oily solid. $^1$H-NMR (200.15 MHz, CDCl$_3$): δ 7.84–7.71 (m, 4H), 7.55–7.33 (m, 5H), 7.17 (d, 2H, J=8.0), 7.07 (d, 2H, J=8.8), 4.96 (s, 2H), 3.96 (dd, 1H, J=7.7, 4.4), 3.35 (s, 3H), 3.11 (dd, 1H, J=14.3, 4.4), 2.97 (dd, 1H, J=14.3, 7.3).

Example 3

(2S)-2-Methoxy-3-{4-[3-(4-phenoxy-phenoxy)-prop-1-ynyl]-phenyl}-propionic acid:

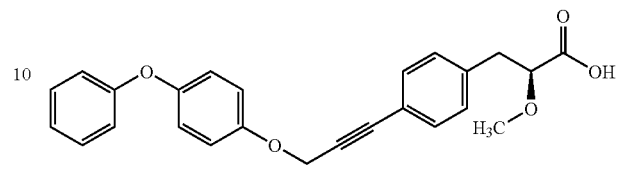

The title compound was prepared from (2S)-3-[4-(3-Hydroxy-prop-1-ynyl)-phenyl]-2-methoxy-propionic acid ethyl ester via (from Example 1, Step B) the standard Mitsunobu coupling-hydrolysis procedure (Standard Procedure A) to produce a white oily solid (41%). $^1$H-NMR (200.15 MHz, CDCl$_3$): δ 7.38–7.15 (m, 5H), 7.02–6.76 (m, 8H); 4.86 (s, 2H), 3.98 (dd, 1H, J=7.3, 4.4), 3.36 (s, 3H), 3.12 (dd, 1H, J=14.3, 4.4), 2.98 (dd, 1H, J=14.3, 7.3). MS (ES) for C$_{25}$H$_{22}$O$_5$ [M+NH$_4$]$^+$: 420.2, [M+Na]$^+$:425.2.

Example 4

(2S)-3-{4-[3-(4-Fluoro-phenoxy)-prop-1-ynyl]-phenyl}-2-methoxy-propionic acid

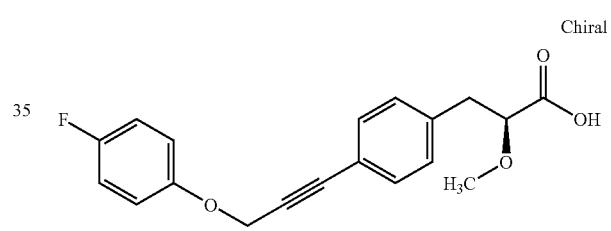

The title compound was prepared from (2S)-3-[4-(3-Hydroxy-prop-1-ynyl)-phenyl]-2-methoxy-propionic acid ethyl ester (from Example 1, Step B) via the standard Mitsunobu coupling-hydrolysis procedure (Standard Procedure A) to produce a white solid of the title compound. $^1$H-NMR (CDCl$_3$, 200.15 MHz): δ 7.34 (d, J=8.1 Hz, 2 H); 7.16 (d, J=8.0 Hz, 2 H); 6.98–6.86 (m, 4 H); 4.84 (s, 2 H); 3.97 (dd, J=7.7, 4.4 Hz, 1 H); 3.36 (s, 3 H); 3.12 (dd, J=14.3, 4.4 Hz, 1 H); 2.98 (dd, J=14.3, 7.3 Hz, 1 H). MS (ES) for C$_{19}$H$_{17}$FO$_4$ [M+NH$_4$]$^+$: 346, [M+Na]$^+$: 351.

Example 5

(2S)-2-Methoxy-3-{4-[3-(3-phenyl-benzofuran-6-yloxy)-prop-1-ynyl]-phenyl}-propionic acid

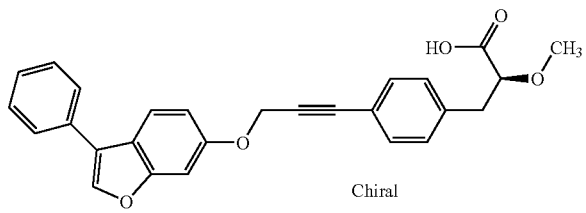

Step A (2S)-3-[4-(3-Chloro-prop-1-ynyl)-phenyl]-2-methoxy-propionic acid ethyl ester

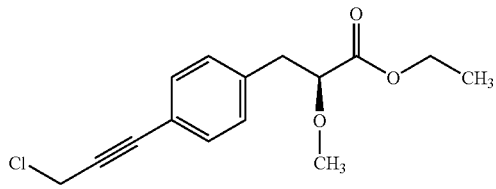

The title compound was prepared from (2S)-3-[4-(3-hydroxy-prop-1-ynyl)-phenyl]-2-methoxy-propionic acid ethyl ester (0.060 g, 0.23 mmol) (from Example 1, Step B) in dry DMF (5 ml) and treated with triethyl amine (0.69 mmol) and mesylchloride (0.46 mmol). The mixture reaction was stirred overnight and the crude product was extracted with $H_2O$/Ether. The organic layer was dried and concentrated to give a product that was purified in silica using Hexane/Ethyl Acetate (5/1) to give the title compound as an oil (0.020 g, 30% yield). MS (ES) for $C_{15}H_{17}ClO_3$ [M+H]$^+$: 281.2

Step B (2S)-2-Methoxy-3-{4-[3-(3-phenyl-benzofuran-6-yloxy)-prop-1-ynyl]-phenyl}-propionic acid A solution of (2S)-3-[4-(3-Chloro-prop-1-ynyl)-phenyl]-2-methoxy-propionic acid ethyl ester from Step A (0.071 mmol, 1 eq) in 0.7 ml of DMF in a 16×100 mm tube treated with 3-phenyl-6-hydroxybenzofurane (0.078 mmol, 1.1 eq) Cesium Carbonate (0.213 mmol 3 eq) and NaI (0.071 mmol, 1 eq) and stirred at room temperature overnight. The reactants were filtered and washed with DMF several times. The solvent was evaporated under vacuo and the residue reconstituted in a mixture of Ethanol (2 ml) and NaOH (1M) (1 ml) and stirred at room temperature until reaction is completed by HPLC-MS. Then HCl (1M) was added (until pH=3) and the solvent were eliminated under vacuo. The residue was reconstituted in $CH_2Cl_2/H_2O$ and filtered through a hidrofobic syringer. The organic layer was separated, concentrated and purified by HPLC-MS to get the title compound. MS(ES) for $C_{27}H_{22}O_5$ [M+H]$^+$: 427.2.

Example 6

(2S)-3-{4-[3-(4-Butyl-phenoxy)-prop-1-ynyl]-phenyl}-2-methoxy-propionic acid

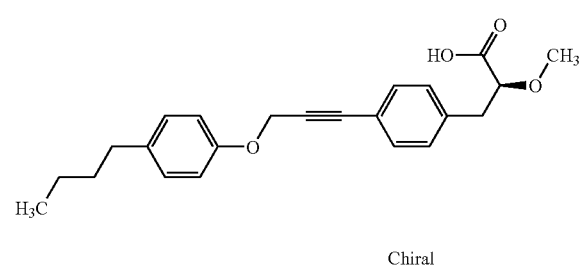

The title compound was prepared from (2S)-3-[4-(3-Chloro-prop-1-ynyl)-phenyl]-2-methoxy-propionic acid ethyl ester from Example 5, Step A and 4-n-butylphenol in a manner analogous to that described for Example 5, Step B. MS(ES) for $C_{23}H_{26}O_4$ [M–H]$^-$: 365.2

Example 7

(2S)-2-Methoxy-3-(4-{3-[4-(4-trifluoromethyl-phenoxy)-phenoxy]-prop-1-ynyl}-phenyl)-propionic acid

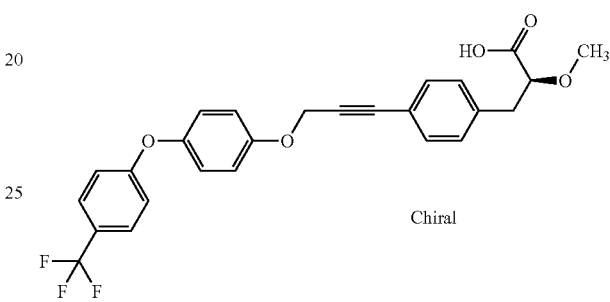

The title compound was prepared from (2S)-3-[4-(3-Chloro-prop-1-ynyl)-phenyl]-2-methoxy-propionic acid ethyl ester from Example 5 Step A and 4-(4-trifluoromethylPhenoxy)-phenol in a manner analogous to that described for Example 5, Step B. MS(ES) for $C_{26}H_{21}F_3O_5$ [M–H]$^-$: 469.2

Example 8

(2S)-2-Methoxy-3-{4-[3-(9-oxo-9H-fluoren-2-yloxy)-prop-1-ynyl]-phenyl}-propionic acid

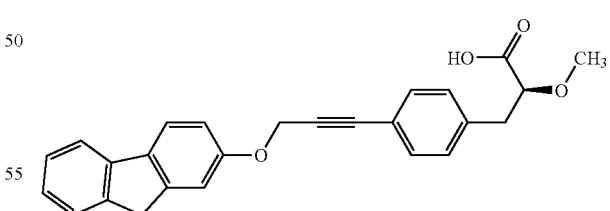

The title compound was prepared from (2S)-3-[4-(3-Chloro-prop-1-ynyl)-phenyl]-2-methoxy-propionic acid ethyl ester from Example 5 Step A and 2-hydroxy-9-fluorenone in a manner analogous to that described for Example 5, Step B. MS(ES) for $C_{26}H_{20}O_5$ [M–H]$^-$: 411.2

Example 9

(2S)-2-Methoxy-3-{4-[3-(4-oxo-2-phenyl-4H-chromen-7-yloxy)-prop-1-ynyl]-phenyl}-propionic acid

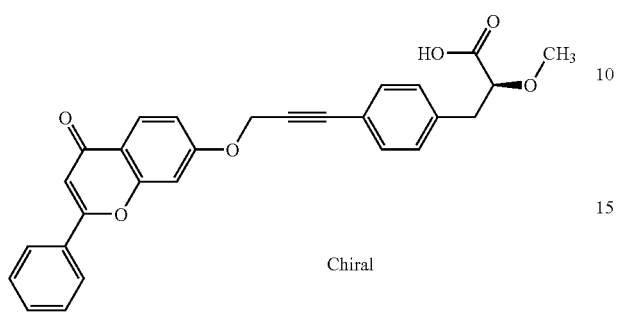

Chiral

The title compound was prepared from (2S)-3-[4-(3-Chloro-prop-1-ynyl)-phenyl]-2-methoxy-propionic acid ethyl ester from Example 5, Step A and 7-hydroxyflavone in a manner analogous to that described for Example 5, Step B. MS(ES) for $C_{28}H_{22}O_6$[M+H]$^+$: 455.2.

Example 10

(2S)-3-(4-{3-[4-(2-Fluoro-benzoyl)-phenoxy]-prop-1-ynyl}-phenyl)-2-methoxy-propionic acid

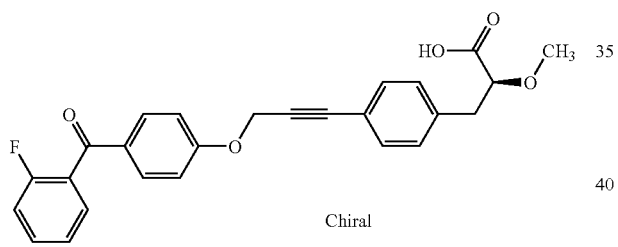

Chiral

The title compound was prepared from (2S)-3-[4-(3-Chloro-prop-1-ynyl)-phenyl]-2-methoxy-propionic acid ethyl ester from Example 5, Step A and 2-fluoro-4-hydroxybenzophenone in a manner analogous to that described for Example 5, Step B. MS(ES) for $C_{26}H_{21}FO$[M+H]$^+$: 433.2.

Example 11

(2S)-2-Methoxy-3-{4-[3-(3-phenylamino-phenoxy)-prop-1-ynyl]-phenyl}-propionic acid

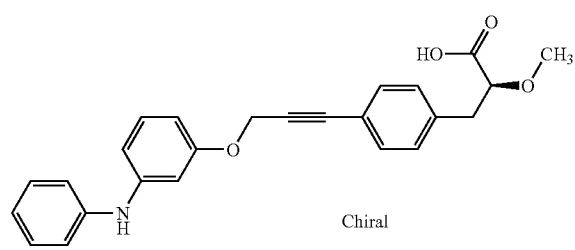

Chiral

The title compound was prepare from (2S)-3-[4-(3-Chloro-prop-1-ynyl)-phenyl]-2-methoxy-propionic acid ethyl ester from Example 5, Step A and 3-hydroxydiphenylamine in a manner analogous to that described for Example 5, Step B. MS(ES) for $CH_{23}H_{23}NO$ [M+H]$^+$: 402.2.

Example 12

(2S)-3-(4-{3-[4-(4-Fluoro-benzoyl)-phenoxy]-prop-1-ynyl}-phenyl)-2-methoxy-propionic acid

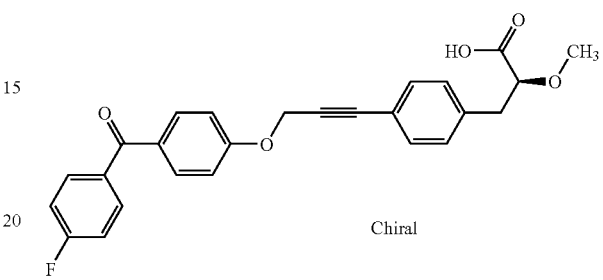

Chiral

The title compound was prepared from (2S)-3-[4-(3-Chloro-prop-1-ynyl)-phenyl]-2-methoxy-propionic acid ethyl ester from Example 5, Step A and 4-fluoro-4'-hydroxybenzophenone in a manner analogous to that described for Example 5, Step B. MS(ES) for $C_{26}H_{21}FO$[M+H]$^+$: 433.2.

Example 13

(2S)-2-Methoxy-3-{4-[3-(4-oxo-2-phenyl-4H-chromen-6-yloxy)-prop-1-ynyl]-phenyl}-propionic acid

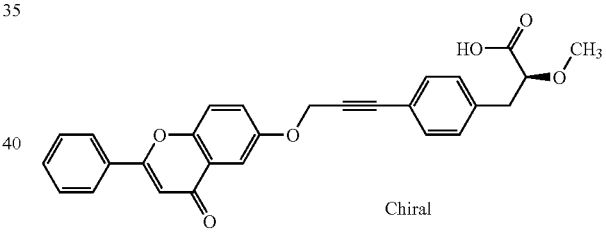

Chiral

The title compound was prepared from (2S)-3-[4-(3-Chloro-prop-1-ynyl)-phenyl]-2-methoxy-propionic acid ethyl ester from Example 5, Step A and 6-hydroxyflavone in a manner analogous to that described for Example 5, Step B. MS(ES) for $C_{28}H_{22}O_6$[M+H]$^+$: 455.2.

Example 14

(2S)-3-(4-{3-[3-(4-Fluor-phenyl)-benzofuran-6-yloxy]-prop-1-ynyl}-phenyl)-2-methoxy-propionic acid

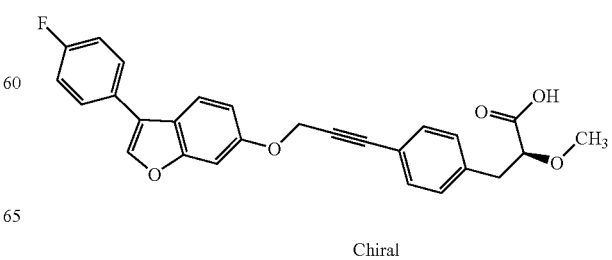

Chiral

The title compound was prepared from (2S)-3-[4-(3-Chloro-prop-1-ynyl)-phenyl]-2-methoxy-propionic acid ethyl ester from Example 5, Step A and 6-hydroxy-3-(4-fluorophenyl)benzofurane in a manner analogous to that described for Example 5, Step B. MS(ES) for $C_{27}H_{21}FO_5$ [M−H]⁻: 443.2.

Example 15

(2S)-2-Methoxy-3-(4-{3-[4-(1-methyl-1-phenyl-ethyl)-phenoxy]-prop-1-ynyl}-phenyl)-propionic acid

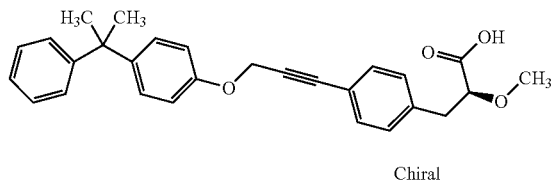

Chiral

The title compound was prepared from (2S)-3-[4-(3-Chloro-prop-1-ynyl)-phenyl]-2-methoxy-propionic acid ethyl ester from Example 5, Step A and 4-cumylphenol in a manner analogous to that described for Example 5, Step B. MS(ES) for $C_{28}H_{28}O_4[M+NH_4]^+$: 446.2.

Example 16

(2S)-2-Methoxy-3-{4-[3-(4-phenylacetyl-phenoxy)-prop-1-ynyl]-phenyl}-propionic acid

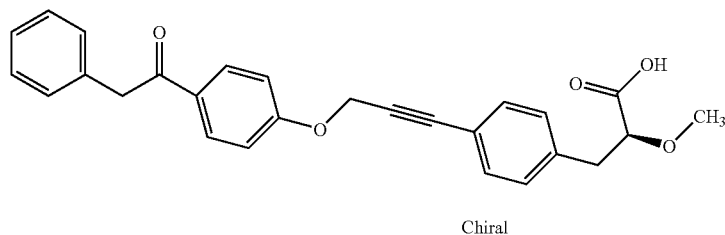

Chiral

The title compound was prepared from (2S)-3-[4-(3-Chloro-prop-1-ynyl)-phenyl]-2-methoxy-propionic acid ethyl ester from Example 5, Step A and benzyl-4-hydroxyphenylketone in a manner analogous to that described for Example 5, Step B. MS(ES) for $C_{27}H_{24}O_5$ [M−H]⁻: 427.2.

Example 17

(2S)-3-{4-[3-(4-Benzyl-phenoxy)-prop-1-ynyl]-phenyl}-2-methoxy-propionic acid

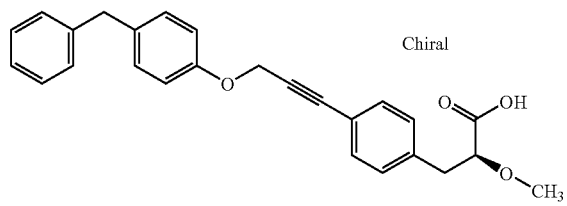

Chiral

The title compound was prepared from (2S)-3-[4-(3-Chloro-prop-1-ynyl)-phenyl]-2-methoxy-propionic acid ethyl ester from Example 5, Step A and 4-hydroxydiphenylmethane in a manner analogous to that described for Example 5, Step B. MS(ES) for $C_{26}H_{24}O_4[M−H]^-$: 399.

Example 18

(2S)-3-[4-(3-{4-[(2-Fluoro-phenyl)-hydroxyimino-methyl]-phenoxy}-prop-1-ynyl)-phenyl]-2-methoxy-propionic acid

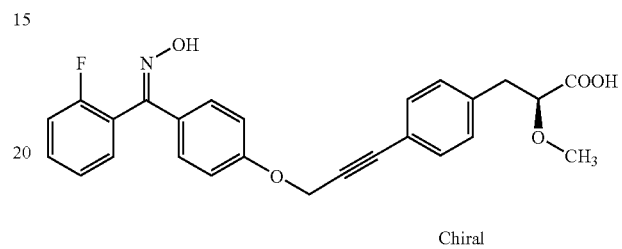

Chiral (2S)-3-(4-{3-[4-(2-Fluoro-benzoyl)-phenoxy]-prop-1-ynyl}-phenyl)-2-methoxy-propionic acid from Example 10, (0.01 mmol, 1 eq) was mixed with Hydroxylamine chlorydrate (4 eq), pyrydine (10 eq) and Ethanol (2 ml) and the mixture reaction was stirred overnight. The ethanol was evaporated under vacuo and HCl 0.5% was added to the residue to pH=3. Extracted with ethyl acetate and concentrated to give the title product as a mixture of two oximes. MS(ES) for $C_{26}H_{22}FNO_5$ [M+H]⁺: 448.2, [M−H]⁻: 446.2.

Example 19

(2S)-3-(4-{3-[4-(Hydroxyimino-phenyl-methyl)-phenoxy]-prop-1-ynyl}-phenyl)-2-methoxy-propionic acid

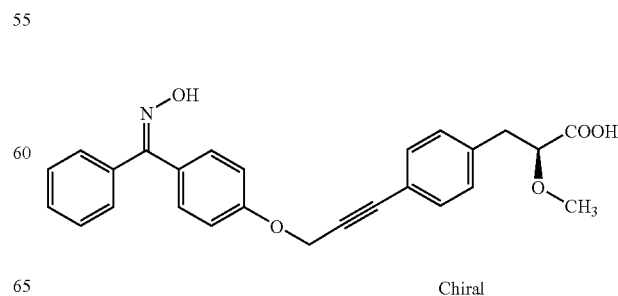

Chiral (2S)-3-{4-[3-(4-Benzoyl-phenoxy)-prop-1-ynyl]-phenyl}-2-methoxy-propionic acid (0.01 mmol, 1 eq) (Example 2) was mixed with Hydroxylamine chlorydrate (4 eq), pyrydine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes. MS(ES) for $C_{26}H_{23}NO_5$ [M+H]$^+$: 430.2, [M−H]$^−$: 428.2.

Example 20

(2S)-3-[4-(3-{4-[(4-Fluoro-phenyl)-hydroxyimino-methyl]-phenoxy}-prop-1-ynyl)-phenyl]-2-methoxy-propionic acid

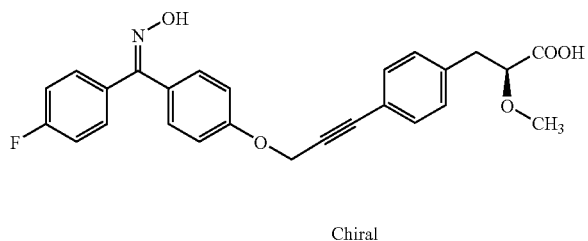

Chiral (2S)-3-(4-{3-[4-(4-Fluoro-benzoyl)-phenoxy]-prop-1-ynyl}-phenyl)-2-methoxy-propionic acid from Example 12 (0.01 mmol, 1 eq) was mixed with Hydroxylamine chlorydrate (4 eq), pyridine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes. MS(ES) for $C_{26}H_{22}FNO_5$ [M+H]$^+$: 448.2, [M−H]$^−$: 446.2.

Example 21

(2S)-3-{4-[5-(Biphenyl-4-yloxy)-pent-1-ynyl]-phenyl}-2-methoxy-propionic acid

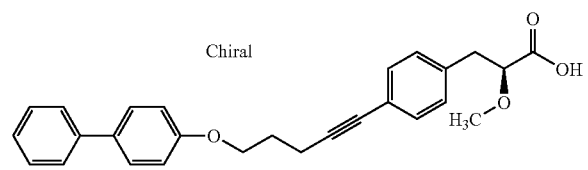

Chiral

Step A (2S)-3-[4-(5-Hydroxy-pent-1-ynyl)-phenyl]-2-methoxy-propionic acid ethyl ester

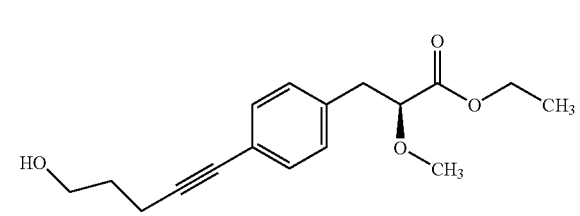

This compound was prepared form 4-pentyn-1-ol following the procedure described in Example 1, Step B. Yellow-brown oil. $^1$H-NMR (200.15 MHz, CDCl$_3$): δ 7.33 (d, 2H, J=8.1), 7.16 (d, 2H, J=8.1), 4.17 (q, 2H, J=7.3), 3.92 (dd, 1H, J=7.3, 5.7), 3.80 (t, 2H, J=6.5), 3.34 (s, 3H), 3.01 (s, 1H), 2.98 (d, 1H, J=2.4), 2.68 (t, 2H, J=6.2), 1.86 (br, 1H), 1.23 (t, 3H, J=7.3).

Step B (2S)-3-{4-[5-(Biphenyl-4-yloxy)-pent-1-ynyl]-phenyl}-2-methoxy-propionic acid The title compound was prepared from (2S)-3-[4-(5-hydroxy-pent-1-ynyl)-phenyl]-2-methoxy-propionic acid ethyl ester and 4-phenylphenol via the standard Mitsunobu coupling-hydrolysis procedure (Standard Procedure A) to produce a white oily solid. $^1$H-NMR (200.15 MHz, CDCl$_3$): δ 7.56–7.28 (m, 9H), 7.15 (d, 2H, J=8.4), 6.98 (d, 2H, J=8.8), 4.15 (t, 2H, J=6.2), 3.97 (dd, 1H, J=7.7, 4.4), 3.36 (s, 3H), 3.11 (dd, 1H, J=14.3, 4.4), 2.97 (dd, 1H, J=14.3, 7.7), 2.62 (t, 2H, J=7.0), 2.08 (qn, 2H, J=6.6).

Example 22

(2S)-2-Methoxy-3-{4-[5-(4-phenoxy-phenoxy)-pent-1-ynyl]-phenyl}-propionic acid

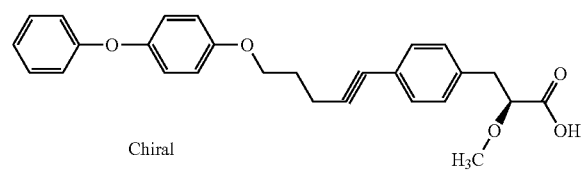

Chiral

The title compound was prepared from (2S)-3-[4-(5-hydroxy-pent-1-ynyl)-phenyl]-2-methoxy-propionic acid (Example 21, Step A) and 4-phenoxyphenol via the standard Mitsunobu coupling-hydrolysis procedure (Standard Procedure A) to produce a white oily solid. $^1$H-NMR (200.15 MHz, CDCl$_3$): δ 7.26–7.19 (m, 4H), 7.07 (d, 2H, J=8.3), 6.98–6.78 (m, 7H), 4.01 (t, 2H, J=5.9), 3.91 (dd, 1H, J=7.3, 4.3), 3.30 (s, 3H), 3.05 (dd, 1H, J=14.2, 4.3), 2.90 (dd, 1H, J=14.2, 7.5), 2.54 (t, 2H, J=6.7), 1.98 (qn, 2H, J=6.4). MS (ES) for $C_{27}H_{26}O_5$[M+NH$_4$]$^+$: 448, [M+Na]$^+$: 453.

Example 23

(2S)-3-{4-[5-(4-Benzoyl-phenoxy)-pent-1-ynyl]-phenyl}-2-methoxy-propionic acid

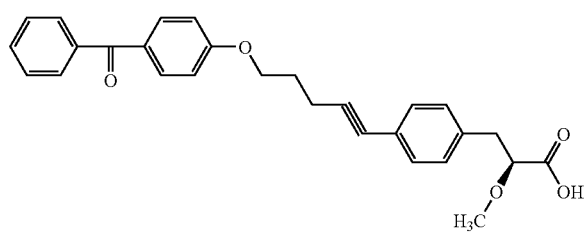

The title compound was prepared from (2S)-3-[4-(5-hydroxy-pent-1-ynyl)-phenyl]-2-methoxy-propionic acid (Example 21, Step A) and 4-hydroxybenzophenone via the standard Mitsunobu coupling-hydrolysis procedure (Standard Procedure A) to produce a white oily solid. $^1$H-NMR (200.15 MHz, CDCl$_3$): δ 7.82–7.70 (m, 3H), 7.54–7.43 (m, 4H), 7.31–7.23 (m, 2H), 7.14 (d, 2H, J=8.1), 6.95 (d, 2H, J=8.8), 4.19 (d, 2H, J=5.9), 3.96 (dd, 1H, J=7.7, 4.4), 3.34 (s, 3H), 3.09 (dd, 1H, J=14.3, 4.4), 2.95 (dd, 1H, J=14.3, 7.7), 2.61 (t, 2H, J=7.0), 2.08 (qn, 2H, J=0.6).

Example 24

(2S)-3-{4-[5-(4-Benzyl-phenoxy)-pent-1-ynyl]-phenyl}-2-methoxy-propionic acid

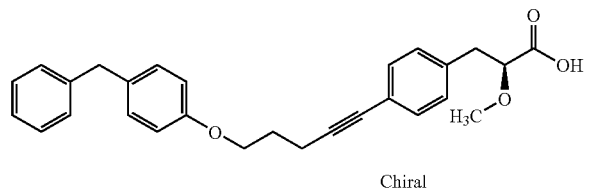

Chiral

Step A

3-[4-(5-Bromo-pent-1-ynyl)-phenyl]-2-methoxy-propionic acid ethyl ester

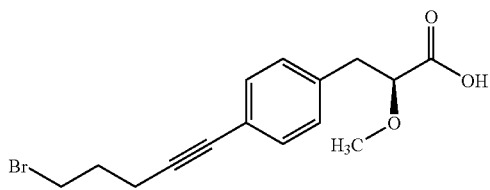

Chiral

To a solution of (2S)-3-[4-(5-Hydroxy-pent-1-ynyl)-phenyl]-2-methoxy-propionic acid ethyl ester from Example 21, Step A (0.17 mmol, 1 eq) in dichloromethane (5 ml) and CBr$_4$ (0.34 mmol, 2 eq) at 0° C., Ph$_3$P was added (0.34 mmol, 2 eq) partionwise and the mixture reaction was stirred 1 hour the solvent was removed under vacuo and the residue purified by flash chromatography using Hexane/Ethyl acetate as eluent (6:1) to give the title product in 85% yield.

Step B (2S)-3-{4-[5-(4-Benzyl-phenoxy)-pent-1-ynyl]-phenyl}-2-methoxy-propionic acid A solution of 3-[4-(5-Bromo-pent-1-ynyl)-phenyl]-2-methoxy-propionic acid ethyl ester from Step A (0.1 mmol, 1 eq) in 0.7 ml of DMF in a 16×100 mm tube treated with 4-hydroxydiphenylmethane (0.11 mmol, 1.1 eq) and Cesium Carbonate (0.3 mmol, 3 eq) and stirred at room temperature overnight. The reactants were filtered and washed with DMF several times. The solvent was evaporated under vacuo and the residue reconstituted in a mixture of Ethanol (2 ml) and NaOH (1M) (1 ml) and stirred at room temperature until reaction is completed by HPLC-MS. Then HCl (1M) was added (until pH=3) and the solvent were eliminated under vacuo. The residue was reconstituted in CH$_2$Cl$_2$/H$_2$O and filtered through a hidrofobic syringer. The organic layer was separated, concentrated and purified by HPLC-MS to get the title compound. MS(ES) for C$_{28}$H$_{28}$O$_4$[M+NH$_4$]$^+$: 446.2.

Example 25

(2S)-3-(4-{5-[4-(4-Fluoro-benzoyl)-phenoxy]-pent-1-ynyl}-phenyl)-2-methoxy-propionic acid

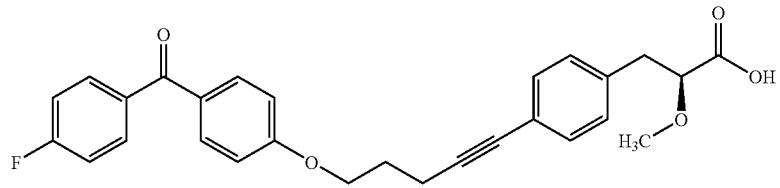

Chiral

The title compound was prepared from 3-[4-(5-Bromo-pent-1-ynyl)-phenyl]-2-methoxy-propionic acid ethyl ester from Example 24, Step A and 4-fluoro-4-hydroxybenzophenone in a manner analogous to that described for Example 24, Step B. MS(ES) for $C_{28}H_{25}F_3O_5[M+H]^+$: 461.2.

Example 26

(2S)-2-Methoxy-3-(4-{5-[4-(4-trifluoromethyl-phenoxy)-phenoxy]-pent-1-ynyl}-phenyl)-propionic acid

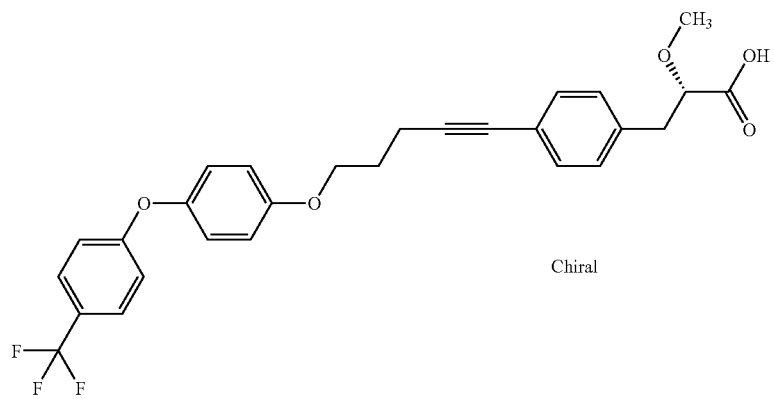

The title compound was prepared from 3-[4-(5-Bromo-pent-1-ynyl)-phenyl]-2-methoxy-propionic acid ethyl ester
From Example 24, Step A and 4-(4-trifluoromethylphenoxy)phenol in a manner analogous to that described for Example 24, Step B. MS(ES) for $C_{28}H_{25}F_3O_5[M+NH_4]^+$: 516.2.

Example 27

(2S)-2-Methoxy-3-{4-[5-(4-oxo-2-phenyl-4H-chromen-7-yloxy)-pent-1-ynyl]-phenyl}-propionic acid

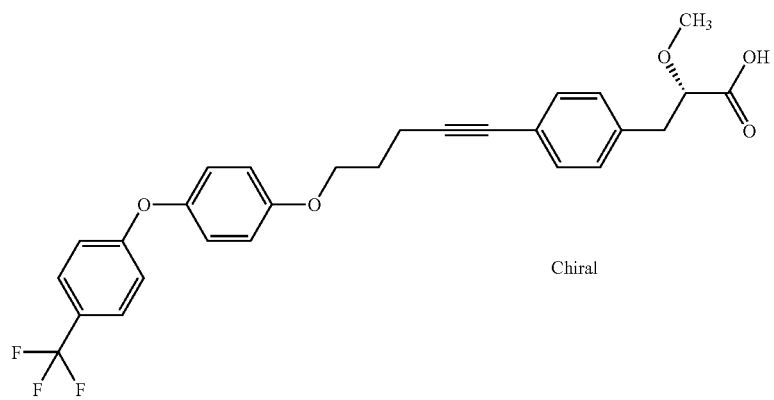

The title compound was prepared from 3-[4-(5-Bromo-pent-1-ynyl)-phenyl]-2-methoxy-propionic acid ethyl ester from Example 24, Step A and 7-hydroxyflavone in a manner analogous to that described for Example 24, Step B. MS(ES) for $C_{30}H_{26}O_6[M+H]^+$:483.2.

Example 28

(2S)-2-Methoxy-3-{4-[5-(4-oxo-2-phenyl-4H-chromen-6-yloxy)-pent-1-ynyl]-phenyl}-propionic acid

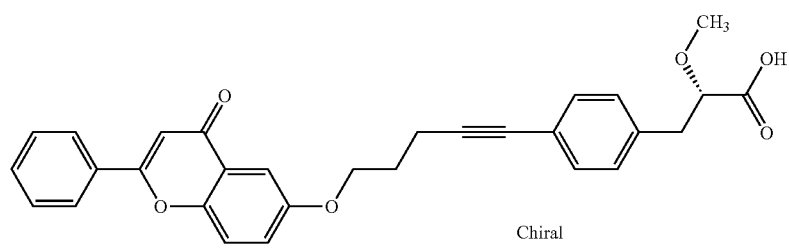

The title compound was prepared from 3-[4-(5-Bromo-pent-1-ynyl)-phenyl]-2-methoxy-propionic acid ethyl ester from Example 24, Step A and 6-hydroxyflavone in a manner analogous to that described for Example 24, Step B. MS(ES) for $C_{30}H_{26}O_6[M+H]^+$:483.2

Example 29

(2S)-2-Methoxy-3-(4-{5-[4-(1-methyl-1-phenyl-ethyl)-phenoxy]-pent-1-ynyl}-phenyl)-propionic acid

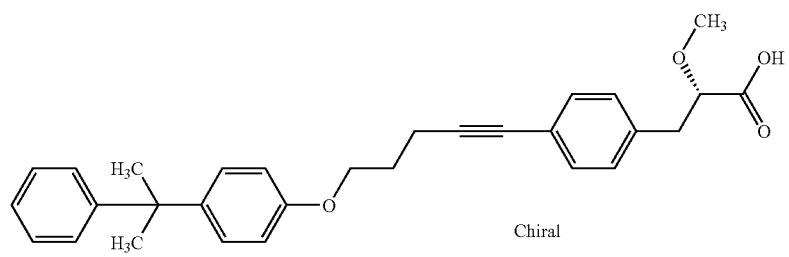

The title compound was prepared from 3-[4-(5-Bromo-pent-1-ynyl)-phenyl]-2-methoxy-propionic acid ethyl ester from Example 24, Step A and 4-cumylphenol in a manner analogous to that described for Example 24, Step B. MS(ES) for $C_{30}H_{32}O_4$ [M+NH$_4$]$^+$: 474.3

Example 30

(2S)-2-Methoxy-3-{4-[5-(9-oxo-9H-fluoren-2-yloxy-pent-1-ynyl]-phenyl}-propionic acid

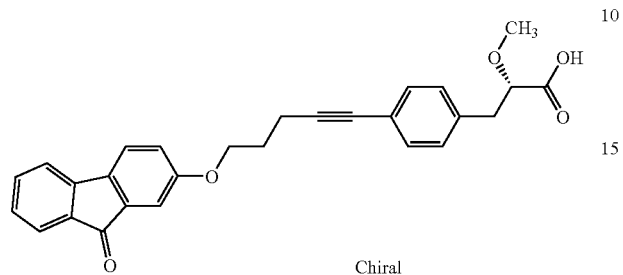

Chiral

The title compound was prepared from 3-[4-(5-Bromo-pent-1-ynyl)-phenyl]-2-methoxy-propionic acid ethyl ester from Example 24, Step A and 2-hydroxy-9-fluorenone in a manner analogous to that described for Example 24, Step B. MS(ES) for $C_8H_{24}O_5$[M+H]$^+$:441.2.

Example 31

(2S)-2-Methoxy-3-{4-[5-(3-phenylamino-phenoxy)-pent-1-ynyl]-phenyl}-propionic acid

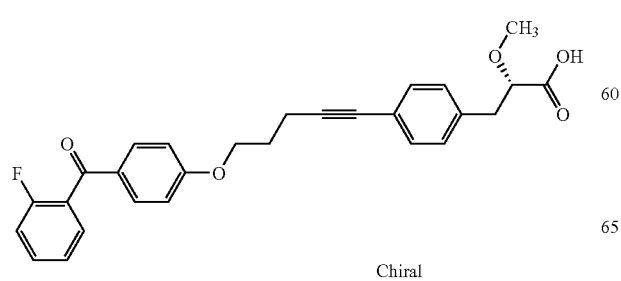

Chiral

The title compound was prepared from 3-[4-(5-Bromo-pent-1-ynyl)-phenyl]-2-methoxy-propionic acid ethyl ester from Example 24 Step A and 3-hydroxydiphenylamine in a manner analogous to that described for Example 24, Step B. MS(ES) for $C_{27}H_{27}NO_4$[M+H]$^+$:430.2.

Example 32

(2S)-3-(4-{5-[4-(2-Fluoro-benzoyl)-phenoxy]-pent-1-ynyl}-phenyl)-2-methoxy-propionic acid

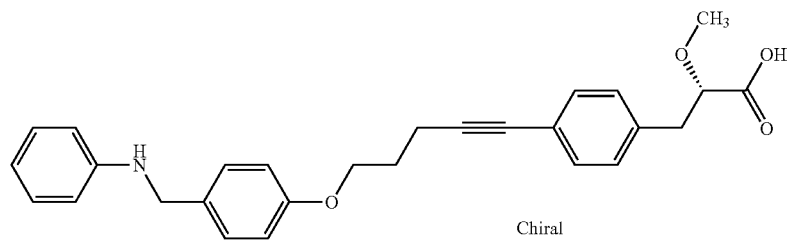

Chiral

The title compound was prepared from 3-[4-(5-Bromo-pent-1-ynyl)-phenyl]-2-methoxy-propionic acid ethyl ester from Example 24, Step A and 2-fluoro-4'-hydroxybenzophenone in a manner analogous to that described for Example 24, Step B. MS(ES) for $C_{28}H_{25}FO_5$[M+H]$^+$:461.2.

Example 33

(2S)-2-Methoxy-3-{4-[5-(3-phenyl-benzofuran-6-yloxy)-pent-1-ynyl]-phenyl}-propionic acid

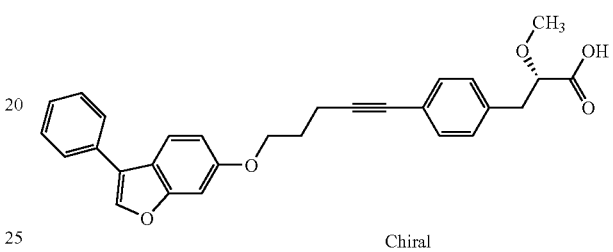

Chiral

The title compound was prepared from 3-[4-(5-Bromo-pent-1-ynyl)-phenyl]-2-methoxy-propionic acid ethyl ester from Example 24, Step A and 6-hydroxy-4-phenylbenzophenone in a manner analogous to that described for Example 24, Step B. MS(ES) for $C_{29}H_{26}O_5$[M+H]$^+$:455.2.

Example 34

(2S)-3-(4-{5-[3-(4-Fluoro-phenyl)-benzofuran-6-yloxy]-pent-1-ynyl}-phenyl)-2-methoxy-propionic acid

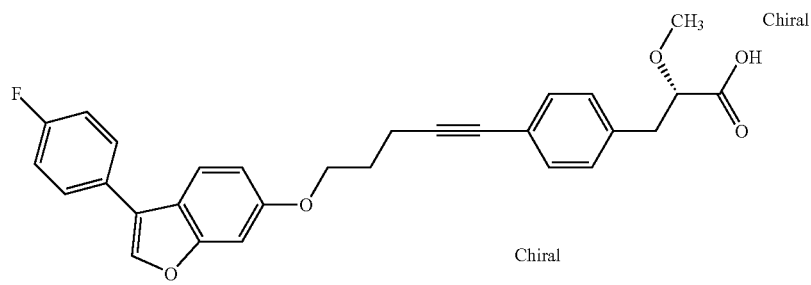

The title compound was prepared from 3-[4-(5-Bromo-pent-1-ynyl)-phenyl]-2-methoxy-propionic acid ethyl ester from Example 24, Step A and 3-(4'-fluorophenyl)-6-hydroxybenzophenone in a manner analogous to that described for Example 24, Step B. MS(ES) for $C_{29}H_{25}PO_5[M+H]^+$: 473.2.

Example 35

(2S)-2-Methoxy-3-{4-[5-(4-phenylacetyl-phenoxy)-pent-1-ynyl]-phenyl}-propionic acid

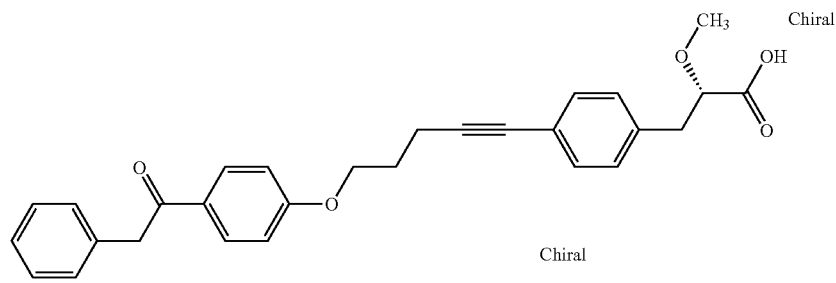

The title compound was prepared from 3-[4-(5-Bromo-pent-1-ynyl)-phenyl]-2-methoxy-propionic acid ethyl ester from Example 24, Step A and benzyl-4-hydroxyphenylketone in a manner analogous to that described for Example 24, Step B. MS(ES) for $C_{29}H_{25}O_5[M-H]^-$:455.2.

Example 36

(2S)-3-{4-[5-Butyl-phenoxy)-pent-1-ynyl]-phenyl}-2-methoxy-propionic acid

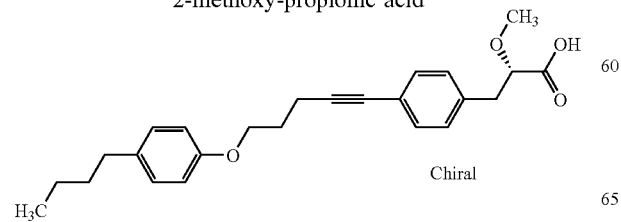

The title compound was prepared from 3-[4-(5-Bromo-pent-1-ynyl)-phenyl]-2-methoxy-propionic acid ethyl ester from Example 24, Step A and 4-N-butylphenol in a manner analogous to that described for Example 24, Step B. MS(ES) for $C_{25}H_{30}O_4$[M−H]⁻:393.2.

Example 37

(2S)-3-[4-(5-{4-[(2-Fluoro-phenyl)-hydroxyimino-methyl]-phenoxy}-pent-1-ynyl)-phenyl]-2-methoxy-propionic

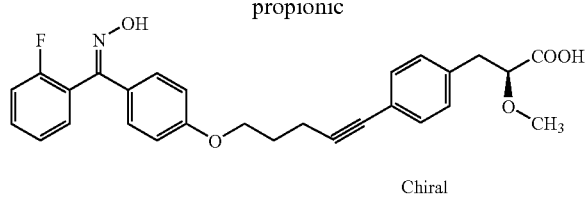

Chiral (2S)-3-(4-{5-[4-(2-Fluoro-benzoyl)-phenoxy]-pent-1-ynyl}-phenyl)-2-methoxy-propionic acid from Example 32, (1 eq) was mixed with Hydroxylamine chlorydrate (4 eq), pyridine (10 eq) and Ethanol (2 ml) and the mixture reaction was stirred overnight. The ethanol was evaporated under vacuo and HCl 6.5% was added to the residue to pH=3. Extracted with Ethyl Acetate and concentrated to give the title product as a mixture of two oximes. MS(ES) for $C_{28}H_{26}FNO_5$ [M+H]⁺: 476.2, [M−H]⁻: 474.2.

Example 38

(2S)-3-[4-(5-{4-[(4-Fluoro-phenyl)-hydroxyimino-methyl]-phenoxy}-pent-1-ynyl)-phenyl]-2-methoxy-propionic acid

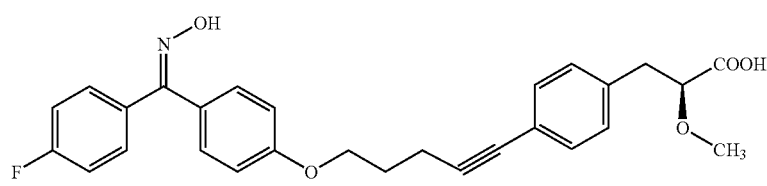

Chiral (2S)-3-(4-{5-[4-(4-Fluoro-benzoyl)-phenoxy]-pent-1-ynyl}-phenyl)-2-methoxy-propionic acid from Example 25 (1 eq) was mixed with Hydroxylamine chlorydrate (4 eq), pyridine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes. MS(ES) for $C_{28}H_{26}FNO_5$ [M+H]⁺: 476.2, [M−H]⁻: 474.2.

Example 39

(2S)-3-(4-{5-[4-Hydroxyimino-phenyl-methyl)-phenoxy]-pent-1-ynyl}-phenyl)-2-methoxy-propionic acid

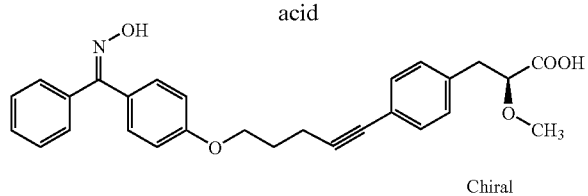

Chiral (2S)-3-{4-[5-(4-Benzoyl-phenoxy)-pent-1-ynyl]-phenyl}-2-methoxy-propionic acid from Example 23, (1 eq) was mixed with Hydroxylamine chlorydrate (4 eq), pyridine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes: MS(ES) for $C_{28}H_{27}NO_5$ [M+H]⁺: 458.2.

Example 40

(2S)-3-{4-[4-(Biphenyl-4-yloxy)-but-1-ynyl]-phenyl}-2-methoxy-propionic acid

Step A

Toluene-4-sulfonic acid but-3-ynyl ester

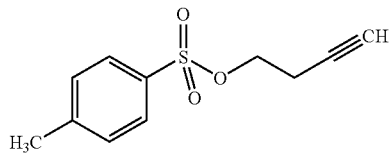

A solution of 3-butyn-1-ol (1 mL, 13.31 mmol), p-toluenesulphenyl chloride (2.519 g, 13.21 mmol), triethylamine (2.03 mL, 14.53 mmol) and 4-dimethylaminopyridine (0.081 g, 0.66 mmol) in 20 mL of dichloromethane were stirred at room temperature overnight. The solution was diluted with dichloromethane (20 mL), washed with 0.5N-HCl (40 mL) and brine (40 mL), dried (MgSO₄), and concentrated to produce an oil (2.82 g, 95%). ¹H-NMR (200.15 MHz, CDCl₃): δ 7.80 (d, 2H, J=8.3), 7.35 (d, 2H, J=8.1), 4.10 (t, 2H, J=7.0), 2.55 (dt, 2H, J=2.7, 7.0), 2.45 (s, 3H), 1.97 (t, 1H, J=2.7).

Step B

4-But-3-ynyloxy-biphenyl

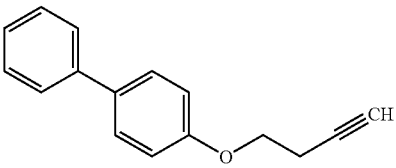

A solution of 4-phenylphenol (0.774 g, 4.55 mmol) and potassium tert-butoxide (0.51 g, 4.55 mmol) in toluene (20 mL) was stirred for 1 h at room temperature. Sodium iodide (0.068 g, 0.45 mmol) and toluene-4-sulfonic acid but-3-ynyl ester (1.02 g, 4.55 mmol) were added, and the mixture heated to reflux for 24 hours. The mixture was cooled to room temperature, diluted with diethyl ether (20 mL), washed with water (2×20 mL). The organic layer was dried (MgSO$_4$) and concentrated under vacuum. The residue was purified by silica gel chromatography (silica gel, hexanes/ethyl acetate 3:1, R$_f$0.57) to give an oil (140 mg, 14%). $^1$H-NMR (200.15 MHz, CDCl$_3$): δ 7.57–7.50 (m, 4H), 7.46–7.38 (m, 2H), 7.32 (d, 1H, J=7.3), 7.02–6.95 (m, 2H), 4.15 (t, 2H, J=7.0), 2.71 (dt, 2H, J=2.7, 7.3), 2.06 (t, 1H, J=2.7).

Step C (2S)-3-{4-[4-(Biphenyl-4-yloxy)-but-1-ynyl]-phenyl}-2-methoxy-propionic acid ethyl ester

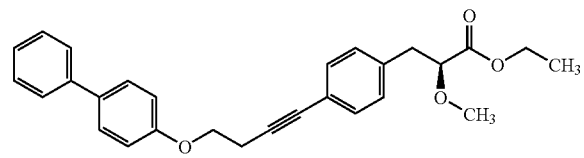

To a solution of (2S)-2-methoxy-3-(4-trifluoro-methanesulfonyloxy-phenyl)-propionic acid ethyl ester (1.157 g, 3.4 mmol) (Example 1, Step A) in 30 mL of degassed piperidine was added 4-but-3-ynyloxy-biphenyl (0.9 g, 4.85 mmol), tetrakis(triphenylphosphine)palladium (0) (0.196 g, 0.17 mmol), triphenylphosphine (0.09 g, 0.34 mmol), and cooper (I) iodide (0.065 g, 0.34 mmol). The solution was stirred for 3 h at 80° C. and cooled to room temperature. The solvent was evaporated under vacuum, and the residue was purified by column chromatography (silica gel, hexanes/diethyl ether 9:1, R$_f$0.27) to a brown oil (0.7 g, 48%). $^1$H-NMR (200.15 MHz, CDCl$_3$): δ 7.58–7.30 (m, 9H), 7.17 (d, 2H, J=8.0), 7.02 (d, 2H, J=8.9), 4.22 (t, 2H, J=7.3), 4.18 (q, 2H, J=7.0), 3.93 (dd, 1H, J=7.3, 5.6), 3.35 (s, 3H), 3.02 (s, 1H), 2.99 (d, 1H, J=2.4), 2.92 (t, 2H, J=7.3), 1.24 (t, 3H, J=7.3).

Step D (2S)-3-{4-[4-(Biphenyl-4-yloxy)-but-1-ynyl]-phenyl}-2-methoxy-propionic acid The title compound was prepared from (2S)-3-{4-[4-(biphenyl-4-yloxy)-but-1-ynyl]-phenyl}-2-methoxy-propionic acid ethyl ester via the standard hydrolysis procedure C. The residue was purified by chromatography (silica gel hexanes/ethyl acetate/acetic acid 50:50:1, R$_f$0.25) to produce a white solid (86%). $^1$H-NMR (200.15 MHz, CDCl$_3$): δ 7.57–7.51 (m, 4H), 7.45–7.30 (m, 5H), 7.19 (d, 2H, J=8.0), 7.01 (d, 2H, J=8.8), 4.20 (t, 2H, J=6.9), 3.98 (dd, 1H, J=7.7, 4.4), 3.37 (s, 3H), 3.11 (dd, 1H, J=14.3, 4.4), 3.00 (dd, 1H, J=14.3, 7.7), 2.91 (t, 2H, J=7.0).

Example 41

(2S)-2-Methoxy-3-{4-[4-(4-phenoxy-phenoxy)-but-1-ynyl]-phenyl}-propionic acid

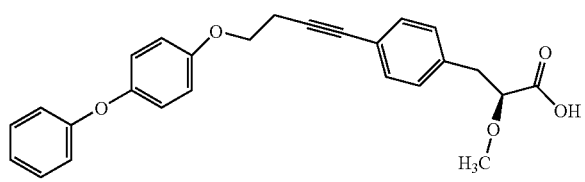

Step A

1-But-3-ynyloxy-4-phenyloxybenzene

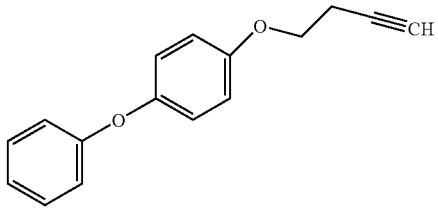

This compound was prepared from 4-phenoxyphenol and toluene-4-sulfonic acid but-3-ynyl ester (Example 40, Step A) following the procedure described in Example 40, Step B. $^1$H-NMR (200.15 MHz, CDCl$_3$): δ 77.35–7.26 (m, 2H), 7.05–6.87 (m, 5H), 4.09 (t, 2H, J=7.0), 2.69 (dt, 2H, J=2.4, 7.0), 2.05 (t, 1H, J=2.1).

Step B (2S)-2-Methoxy-3-{4-[4-(4-phenoxy-phenoxy)-but-4-ynyl]-phenyl}-propionic acid The title compound was prepared from 1-but-3-ynyloxy-4-phenyloxybenzene and (2S)-2-methoxy-3-(4-trifluoromethanesulfonyloxy-phenyl)-propionic acid ethyl ester (Example 1, Step A) following the procedure described in Example 40, Step C. The ethyl ester derivative was contaminated with starting triflate. The mixture was hydrolyzed using the Standard Procedure C. The residue was purified by chromatography (silica gel, hexanes/ethyl acetate-Acetic acid 50:50:1, R$_f$0.25) to produce a white solid (7%): $^1$H-NMR (200.15 MHz, CDCl$_3$): δ 7.35–7.28 (m, 4H), 7.16 (d, 2H, J=8.0), 7.02–6.87 (1H, 7H), 4.13 (t, 2H, J=7.0), 3.97 (dd, 1H, J=7.7, 4.4), 3.36 (s, 3H), 3.11 (dd, 1H, J=14.3, 4.4), 2.97 (dd, 1H, J=14.3, 7.7), 2.87 (t, 2H, J=7.0). MS (ES) fro C$_{26}$H$_{24}$O$_5$ [M+NH$_4$]$^+$: 434.2, [M+Na]$^+$: 439.2.

Example 42

(2S)-3-{4-[4-(4-Benzoyl-phenoxy)-but-1-ynyl]-phenyl}-2-methoxy-propionic acid

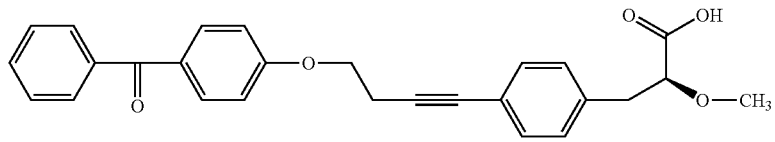

Step A (4-But-3-ynyloxy-phenyl)-phenyl-methanone

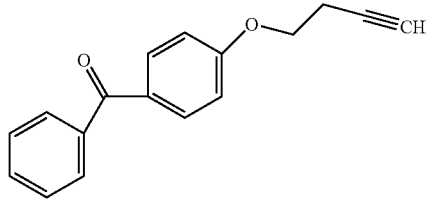

This compound was prepared from 4-hydroxybenzophenone and toluene-4-sulfonic acid but-3-ynyl ester (Example 40, Step A) following the procedure described in Example 40, Step B (8%). $^1$H-NMR (200.15 MHz, CDCl$_3$): δ 7.84–7.73 (m, 4 H), 7.57–7.43 (m, 3H), 6.97 (d, 2H, J=8.6), 4.18 (t, 2H, J=7.0), 2.73 (dt, 2H, J=2.7, 7.0), 2.06 (t, 1H, J=2.7).

Step B (2S)-3-{4-[4-(4-Benzoyl-phenoxy)-but-1-ynyl]-phenyl}-2-methoxy-propionic acid ethyl ester

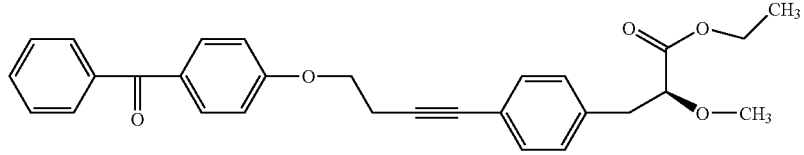

This compound was prepared from (4-but-3-ynyloxy-phenyl)-phenylmethanone and (2S)-2-Methoxy-3-(4-trifluoromethane-sulfonyloxy-phenyl)-propionic acid ethyl ester (Example 1, Step A) following the procedure described in Example 38, Step C (66%). $^1$H-NMR (200.15 MHz, CDCl$_3$): δ 37.85–7.73 (m, 4H), 7.57–7.43 (m; 3H), 7.34 (d, 2H, J=8.1), 7.16 (d, 2H, J=8.3), 7.00 (d, 2H, J=8.6), 4.25 (t, 2H, J=7.0), 4.18 (q, 2H, J=7.0), 3.92 (dd, 1H, J=7.3, 5.6), 3.34 (s, 3H), 3.01 (s, 1H), 2.98 (d, 1H, J=3.5), 2.93 (t, 2H, J=7.0), 1.23 (t, 3H, J=7.3).

Step C (2S)-3-{4-[4-(4-Benzoyl-phenoxy)-but-1-ynyl]-phenyl}-2-methoxy-propionic acid The title compound was prepared from (2S)-3-{4-[4-(4-benzoyl-phenoxy)-but-1-ynyl]-phenyl}-2-methoxy-propionic acid ethyl ester via the standard hydrolysis procedure C to produce a white solid. $^1$H-NMR (200.15 MHz, CDCl$_3$): δ 7.83–7.71 (m, 4H), 7.55–7.44 (m, 3H), 7.32 (d, 2H, J=8.0), 7.16 (d, 2H, J=8.4), 6.97 (d, 2H, J=9.1), 4.22 (t, 2H, J=7.0), 3.96 (dd, 1H, J=7.7, 4.4), 3.35 (s, 3H), 3.10 (dd, 1H, J=13.9, 4.4), 2.98 (dd, 1H, J=13.9, 7.7), 2.91 (t, 2H, J=7.0).

Example 43

(2S)-3-(4-{4-[4-(Hydroxyimino-phenyl-methyl)-phenoxy]-but-1-ynyl}-phenyl)-2-methoxy-propionic acid

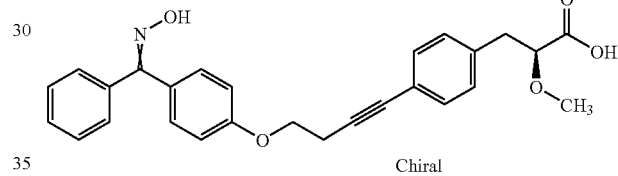

(2S)-3-{4-[4-(4-Benzoyl-phenoxy)-but-1-ynyl]-phenyl}-2-methoxy-propionic acid from Example 42, (1 eq) was mixed with Hydroxylamine chlorydrate (4 eq), pyridine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes. MS (ES) for C$_{27}$H$_{25}$NO$_5$ [M+H]$^+$: 444.2.

Example 44

(2S)-3-(4-{4-[4-(4-Fluoro-benzoyl)-phenoxy]-but-1-ynyl}-phenyl)-2-methoxy-propionic acid

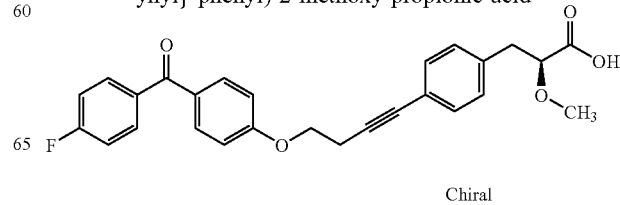

Step A (4-But-3-ynyloxy-phenyl)-(4-fluoro-phenyl)-methanone

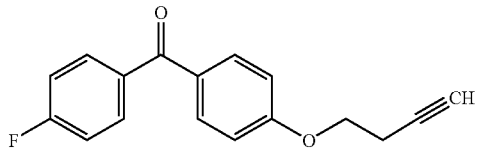

This compound was prepared from 4-fluoro-hydroxybenzophenone and toluene-4-sulfonic acid but-3-ynyl ester (Example 40, Step A) following the procedure described in Example 40, Step B.

Step B (2S)-3-(4-{4-[4-(4-Fluoro-benzyl)-phenoxy]-but-1-phenyl)-2-methoxy-propionic acid The title compound was prepared from (4-But-3-ynyloxy-phenyl)-(4-fluoro-phenyl)-methanone and (2S)-2-methoxy 3-(4-trifluoromethanesulfonyloxy-phenyl)-propionic acid ethyl ester (Example 1, Step A) following the procedure described in Example 40, Step C. The ethyl ester derivative was contaminated with starting triflate. The mixture was hydrolyzed using the standard hydrolysis procedure C. The residue was purified by chromatography. MS(ES) for $C_{27}H_{23}FO$ $[M+H]^+$: 447.2.

Example 45

(2S)-3-(4-{4-[3-(4-Fluoro-phenyl)-benzofuran-6-yloxy]-but-1-ynyl}-phenyl)-2-methoxy-propionic acid

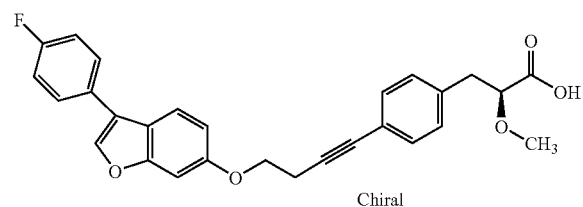

Step A

6-But-3-ylnyloxy-3-(4-fluoro-phenyl)-benzofuran

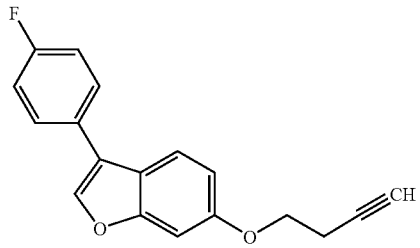

This compound was prepared from 6-hydroxy-3-(4-fluorophenyl)benzofurane and toluene-4-sulfonic acid but-3-ynyl ester (Example 40, Step A) following the procedure described in Example 40, Step B.

Step B (2S)-3-(4-{4-[3-(4-Fluoro-phenyl)-benzofuran-6-yloxy]-but-1-ynyl}-phenyl)-2-methoxy-propionic acid The title compound was prepared from 6-But-3-ynyloxy-3-(4-fluoro-phenyl)-benzofuran and (2S)-2-methoxy-3-(4-trifluoromethanesulfonyloxy-phenyl)-propionic acid ethyl ester Example 1, Step A) following the procedure described in Example 40, Step C. The ethyl ester derivative was contaminated with starting triflate. The mixture was hydrolyzed using the Standard Procedure C. The residue was purified by chromatography. MS(ES) for $C_{28}H_{23}FO_5$ $[M-H]^-$: 457.2.

Example 46

(2S)-2-Methoxy-3-(4-{4-[4-(4-trifluoromethyl-phenoxy)-phenoxy]-but-1-ynyl}-phenyl)-propionic acid

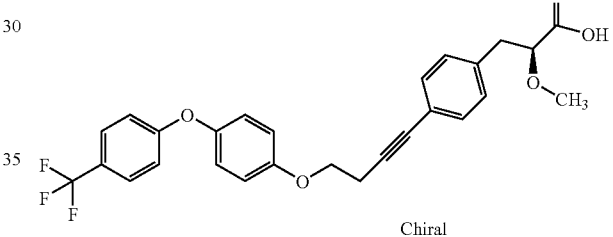

Step A 4-(3-butynyloxy)-4'-trifluoromethylphenyloxy phenyl

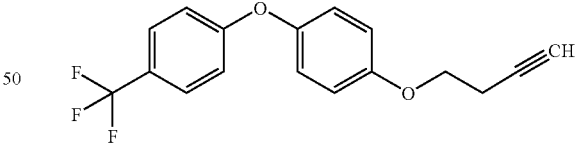

This compound was prepared from trifluoromethylphenoxyphenol and toluene-4-sulfonic acid but-3-ynyl ester Example 40, Step A) following the procedure described in Example 40, Step B.

Step B (2S)-2-Methoxy-3-(4-{4-[4-(4-trifluoromethyl-phenoxy)-phenoxy]-but-1-ynyl}-phenyl)-propionic acid The title compound was prepared from 4-(3-butynyloxy)-4'-trifluoromethylphenyloxy phenyl and (2S)-2-methoxy-3-

(4-trifluoromethanesulfonyloxy-phenyl)-propionic acid ethyl ester (Example 1, Step A) following the procedure described in Example 40, Step C. The ethyl ester derivative was contaminated with starting triflate. The mixture was hydrolyzed using the Standard Procedure C. The residue was purified by chromatography. MS(ES) for $C_{27}H_{23}F_3O_5$ [M−H]⁻: 483.2.

Example 47

(2S)-2-Methoxy-3-{4-[4-(4-oxo-2-phenyl-4H-chromen-7-yloxy-but-1-ynyl]-phenyl}-propionic acid

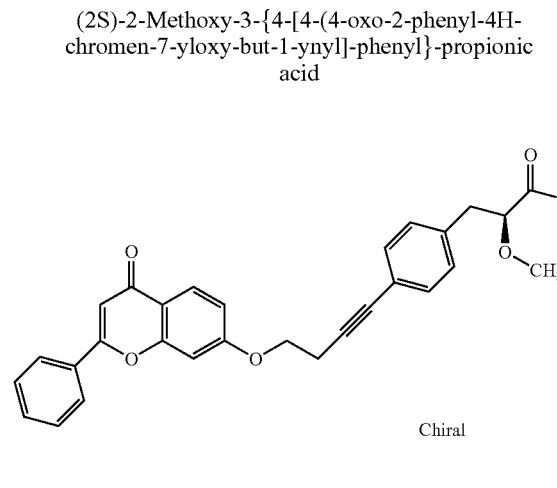

Chiral

Step A

3-[4-(4-Hydroxy-but-1-ynyl)-phenyl]-2-methoxy-propionic acid ethyl ester

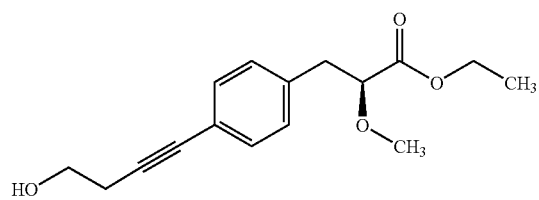

This compound was prepared form 4-butyn-1-ol following the procedure described in Example 1, Step B.

Step B (2S)-2-Methoxy-3-{4-[4-(4-oxo-2-phenyl-4H-chromen-7-yloxy)-but-1-ynyl]-phenyl}-propionic acid The title compound was prepared from 7-hydroxyflavone by the Standard coupling-hydrolisis Procedure A but using for the Mitsounobu reaction toluene as solvent and DIAD instead DEAD. MS(ES) for $C_{29}H_{24}O_6$ [M+H]⁺: 429.2.

Example 48

(2S)-2-Methoxy-3-{4-[4-(4-oxo-2-phenyl-4H-chromen-6-yloxy)-but-1-ynyl]-phenyl}-propionic acid

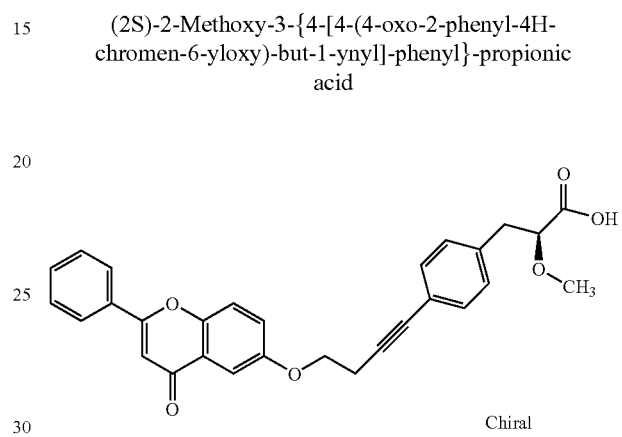

Chiral

The title compound was prepared from 3-[4-(4-Hydroxy-but-1-ynyl)-phenyl]-2-methoxy-propionic acid ethyl ester from Example 47, Step A and 6-hydroxyflavone following the standard coupling-hydrolysis procedure A using toluene as solvent and DIAD instead DEAD. MS(ES) for $C_{29}H_{24}O_6$ [M+H]⁺: 469.2.

Example 49

(2S)-2-Methoxy-3-{4-[6-(4-phenoxy-phenoxy)-hex-1-ynyl]-phenyl}-propionic acid

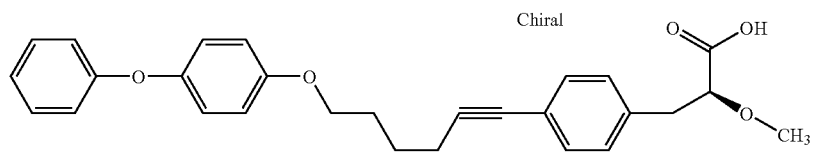

Step A (2S)-3-[4-(6-Hydroxy-hex-1-ynyl)-phenyl]-2-methoxy-propionic acid ethyl ester

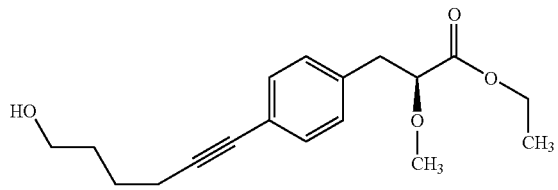

To a solution of (2S)-(3-(4-iodophenyl)-2-methoxy-propionic acid ethyl ester (1.6 g, 4.81 mmol) in 100 mL of degassed piperidine was added 5-hexin-1-ol (0.709 g, 724 mmol), tetrakis(triphenylphosphine)palladium (0) (0.278 g, 0.24 mmol), triphenylphosphine (0.125 g, 0.48 mmol), and cooper (I) iodide (0.091 g, 0.48 mmol). The solution was stirred for 3 hours at 80° C. and cooled to room temperature. The solvent was evaporated under vacuum, and the residue was purified by column chromatography (silica gel, hexanes/ethyl acetate 3:1 to give title compound as a yellow oil (1.18 g, 74% yield). MS(ES) for $C_{18}H_{24}O_4[M+NH_4]^+$: 322.2.

Step B (2S)-2-Methoxy-3-{4-[6-(4-phenoxy-phenoxy)-hex-1-ynyl]-phenyl}-propionic acid The title compound was prepared from 3-[4-(6-Hydroxy-hex-1-ynyl)-phenyl]-2-methoxy-propionic acid ethyl ester and 4-phenoxyphenol via the standard Mitsunobu coupling-hydrolysis procedure (Standard Procedure A) to produce the title compound. MS(ES) for $C_{28}H_{28}O_5[M+H]^+$: 445.2

Example 50

(2S)-3-{4-[6-(4-Benzoyl-phenoxy)-hex-1-ynyl]-phenyl}-2-methoxy-propionic acid

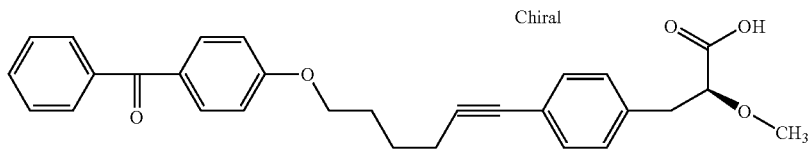

The title compound was prepared from 3-[4-(6-Hydroxy-hex-1-ynyl)-phenyl]-2-methoxy-propionic acid ethyl ester (Example 49, Step A) and 4-hydroxybenzophenone via the standard Mitsunobu coupling-hydrolysis procedure (Standard Procedure A) to produce the title compound. MS(ES) for $C_{29}H_{28}O_5 [M+H]^+$: 457.2.

Example 51

(2S)-3-{4-[6-(Biphenyl-4-yloxy)-hex-1-ynyl]-phenyl}-2-methoxy-propionic acid

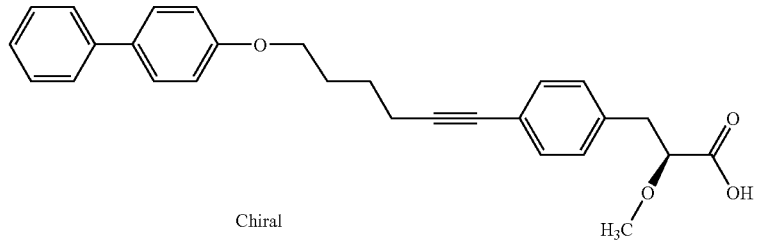

The title compound was prepared from 3-[4-(6-Hydroxy-hex-1-ynyl)-phenyl]-2-methoxy-propionic acid ethyl ester (Example 49, Step A) and 4-phenylphenol via the standard Mitsunobu coupling-hydrolysis procedure (Standard Procedure A) to produce the title compound. MS(ES) for $C_{28}H_{28}O_4[M+NH_4]^+$: 446.2.

Example 52

(2S)-3-{4-[5-(Biphenyl-4-yloxy)-pentanoyl]-phenyl}-2-methoxy-propionic acid

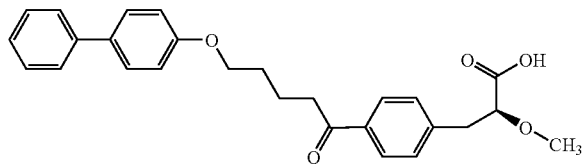

A solution of triphenylphosphine (0.24 g, 0.915 mmol) in 5 mL of dry THF was treated at 0° C. with diethylazodicarboxylate (0.159 g, 0.915 mmol) and stirred for 20 min. A solution of (2S)-3-[4-(5-hydroxy-pent-1-ynyl)-phenyl]-2-methoxy-propionic acid ethyl ester (Example 21, Step A) (0.18 g, 0.61 mmol) and 4-phenylphenol (0.156 g, 0.915 mmol) in 2 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mixture of 75 mg of mercury (II) oxide and 4% sulfuric acid in water. The solution was stirred at 55° C. for 3 h, cooled to room temperature, diluted with saturated aqueous $NaHCO_3$ (20 mL), and extracted with dichloromethane (4×20 mL). The combined organic layers were washed with brine (20 mL), dried ($MgSO_4$), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL). The combined extracts were dried ($MgSO_4$) and concentrated to a white solid (19%). $^1$H-NMR (200.15 MHz, $CDCl_3$): δ 7.89 (d, 2H, J=8.4), 7.55–7.23 (m, 9H), 6.93 (d, 2H, J=8.8), 4.06–3.99 (m, 3H), 3.38 (s, 3H), 3.18 (dd, 1H, J=4.3, 4.4), 3.03 (t+m, 3 H, J=6.9), 1.96–1.86 (m, 4H).

Example 53

(2S)-3-{4-[5-(4-Benzoyl-phenoxy)-pentanoyl]-phenyl}-2-methoxy-propionic acid

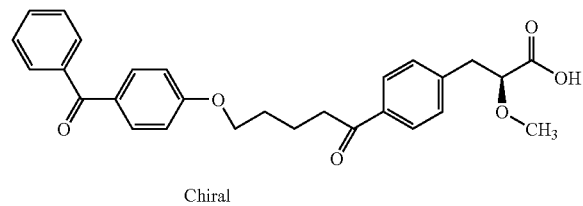

Chiral

A solution of triphenylphosphine (0.915 mmol) in 5 mL of dry THF was treated at 0° C. with diethylazodicarboxylate (0.915 mmol) and stirred for 20 min. A solution of (2S)-3-[4-(5-hydroxy-pent-1-ynyl)-phenyl]-2-methoxy-propionic acid ethyl ester (Example 21, Step A) (0.61 mmol) and 4-benzoylphenol (0.915 mmol) in 2 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mixture of 75 mg of mercury (II) oxide and 4% sulfuric acid in water. The solution was stirred at 55° C. for 3 hours, cooled to room temperature, diluted with saturated aqueous $NaHCO_3$ (20 mL), and extracted with dichloromethane (4×20 mL). The combined organic layers were washed with brine (20 mL), dried ($MgSO_4$), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL) then concentrated to give the title compound. $^1$H-NMR ($CDCl_3$, 200.15 MHz): 7.91–7.72 (m, 5H), 7.56–7.32 (m, 6H), 6.92 (d, 2H, J=8.9), 4.12–4.03 (m, 3H), 3.42 (s, 3H), 3.19–3.05 (m, 4H), 1.95–1.92 (m, 4H).

Example 54

(2S)-2-Methoxy-3-{4-[5-(4-phenoxy-phenoxy)-pentanoyl]-phenyl}-propionic acid

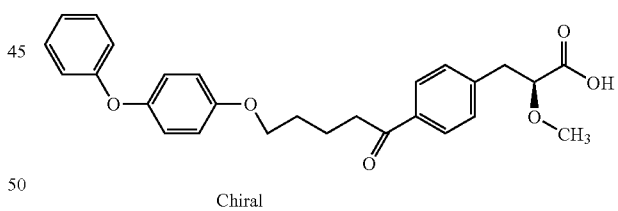

Chiral

A solution of triphenylphosphine (0.915 mmol) in 5 mL of dry THF was treated at 0° C. with diethylazodicarboxylate (0.915 mmol) and stirred for 20 min. A solution of (2S)-3-[4-(5-hydroxy-pent-1-ynyl)-phenyl]-2-methoxy-propionic acid ethyl ester (Example 21, Step A) (0.61 mmol) and 4-phenoxyphenol (0.915 mmol) in 2 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mire of 75 mg of mercury (II) oxide and 4% sulfuric acid in water. The solution was stirred at 55° C. for 3 hours, cooled to room temperature, diluted with saturated aqueous NaHCO₃ (20 mL), and extracted with dichloromethane (4×20 mL). The combined organic layers were washed with brine (20 mL), dried (MgSO₄), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL) then concentrated to give the title compound. ¹H-NMR (CDCl3, 200.15 MHz): 7.91 (d, 2H, J=8.3), 7.36–7.27 (m, 4H), 7.07–6.83 (m, 7H), 4.08–3.96 (m, 3H), 3.41 (s, 3H), 3.22 (dd, 1H, J=14.0, 4.3), 3.14–3.01 (m, 4H), 1.26 (s, 1H).

3.19 (t, 2H, J=7.0), 3.08 (d, 1H, J=5.1), 3.07 (d, 1H, J=7.5), 2.27 (qn, 2H, J=6.2), 1.24 (t, 3H, J=7.3).

Step B

3-{4-[4-(4-Benzoyl-phenoxy)-butyryl]-phenyl}-2-methoxy-propionic acid

The title compound was prepared from (2S)-3-{4-[4-(4-benzoyl-phenoxy)-butyryl]-phenyl}-2-methoxy-propionic acid ethyl ester via the standard hydrolysis procedure C. White solid (71%). ¹H-NMR (200.15 MHz, CDCl₃): δ 7.90 (d, 2H, J=8.0), 7.80–7.70 (m, 4H), 7.58–7.39 (m, 3H), 7.32 (d, 2H, J=8.4), 6.92 (d, 3H, J=9.1), 4.13 (t, 2H, J=6.2), 4.02 (dd, 1H, J=7.3, 4.4), 3.38 (s, 3H), 3.20–3.00 (m, 4H), 2.25 (qn, 2H, J=6.2).

Example 55

3-{4-[4-(4-Benzoyl-phenoxy)-butyryl]-phenyl}-2-methoxy-propionic acid

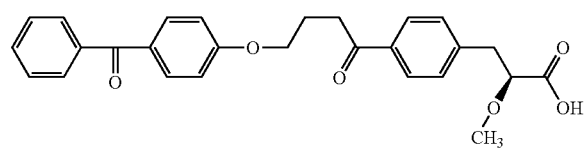

Step A (2S)-3-{4-[4-(4-Benzoyl-phenoxy)-butyryl]-phenyl}-2-methoxy-propionic acid ethyl ester

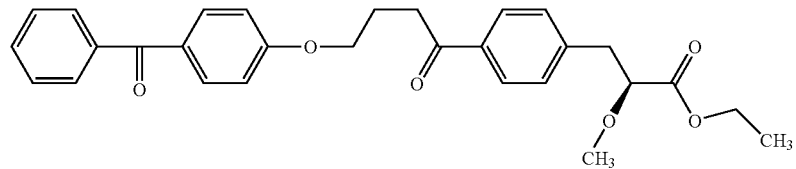

(2S)-3-{4-[4-(4-Benzoyl-phenoxy)-but-1-ynyl]-phenyl}-2-methoxy-propionic acid ethyl ester (Example 42, Step B) (0.08 g, 0.17 mmol) was dissolved in 4 mL of methanol. To this solution was added 3 mL of a solution of 0.075 g, of mercury (II) oxide in 12 mL of 4% sulfuric acid. The mixture was stirred at 55° C. for 3 hours, cooled to room temperature, and diluted with 20 mL saturated NaHCO₃ solution.

The mixture was extracted with of dichloromethane (4×20 mL), and the combined organic layers were dried (MgSO₄), and concentrated. The residue was purified by silica gel chromatography (silica gel, hexanes/ethyl acetate 3:1) to give a yellow oil (72%). ¹H-NMR (200.15 MHz, CDCl₃): δ 7.92 (d, 2H, J=8.6), 7.83–7.72 (m, 4H), 7.60–7.42 (m, 3H), 7.34 (d, 2H, J=8.6), 6.95 (d, 2H, J=8.9), 4.19 (q, 2H, J=7.3), 4.15 (t, 2H, J=6.2), 3.97 (dd, 1H, J=7.3, 5.4), 3.35 (s, 3H),

Example 56

(2S)-2-Methoxy-3-{4-[4-(4-phenoxy-phenoxy)-butyryl]-phenyl}-propionic acid

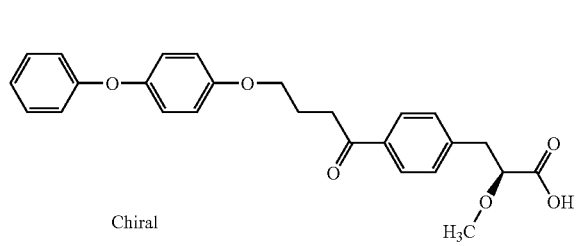

Step A

2S)-3-{4-[4-(4-phenoxy-phenoxy)-butyryl]-phenyl}-2-methoxy-propionic acid ethyl ester

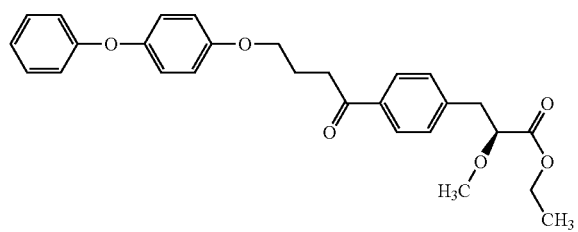

(2S)-2-Methoxy-3-{4-[4-(4-phenoxy-phenoxy)-but-1-ynyl]-phenyl}-propionic acid ethyl ester (0.17 mmol) from Example 41, was dissolved in 4 ml of methanol. To this solution was added 3 ml of a solution of 0.075 g, of mercury (II) oxide in 12 mL of 4% sulfuric acid. The mixture was stirred at 55° C. for 3 hour, cooled to room temperature, and diluted with 20 mL saturated NaHCO₃ solution. The mixture was extracted with of dichloromethane (4×20 mL), and the combined organic layers were dried (MgSO₄), and concentrated. The residue was purified by silica gel chromatography (silica gel, hexanes/ethyl acetate 3:1) to give a yellow oil.

Step B (2S)-2-Methoxy-3-{4-[4-(4-phenoxy-phenoxy)-butyryl]-phenyl}-propionic acid The title compound was prepared from (2S)-3-{4-[4-(4-phenoxy-phenoxy)-butyryl]phenyl}-2-methoxy-propionic acid ethyl ester via the standard hydrolysis procedure C. MS (ES) for $C_{26}H_{26}O_6$ [M+H]⁺: 435.2.

Example 40, Step C, was dissolved in 4 ml of methanol. To this solution was added 3 ml of a solution of 0.075 g, of mercury (II) oxide in 12 mL of 4% sulfuric acid. The mixture was stirred at 55° C. for 3 hours, cooled to room temperature, and diluted with 20 mL saturated NaHCO₃ solution. The mixture was extracted with of dichloromethane (4×20 mL), and the combined organic layers were dried (MgSO₄), and concentrated. The residue was purified by silica gel chromatography (silica gel, hexanes/ethyl acetate 3:1) to give a yellow oil.

Step B (2S)-3-[4-(Biphenyl-4-yloxy)-butyryl-phenyl]-2-methoxy-propionic acid

The title compound was prepared from (2S)-3-{4-[4-(4-phenylphenoxy)-butyryl]-phenyl}-2-methoxy-propionic acid ethyl ester via the standard hydrolysis procedure C. MS (ES) for $C_{26}H_{26}O_5$ [M+H]⁺: 419.2.

Example 58

(2S)-3-{4-[6-(Biphenyl-4-yloxy)-hexanoyl]-phenyl}-2-methoxy-propionic acid

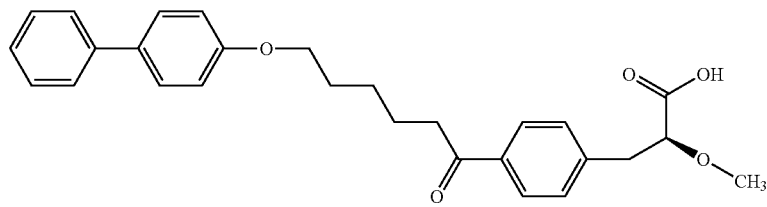

Chiral

Example 57

(2S)-3-[4-(Biphenyl-4-yloxy)-butyryl-phenyl]-2-methoxy-propionic acid

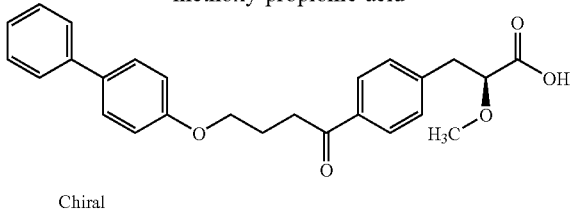

Chiral

Step A (2S)-3-{4-[4-(4-phenylphenoxy)-butyryl]-phenyl}-2-methoxy-propionic acid ethyl ester

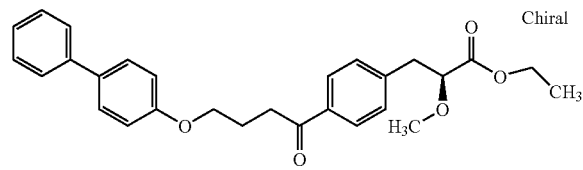

(2S)-3-{4-[4-(Biphenyl-4-yloxy)-but-1-ynyl]-phenyl}-2-methoxy-propionic acid ethyl ester (0.17 mmol) from A solution of triphenylphosphine (0.474 g, 1.8 mmol) in 50 mL of dry THF was treated at 0° C. with diethylazodicarboxylate (1.8 mmol) and stirred for 20 min. A solution of 3-[4-(6-Hydroxy-hex-1-ynyl)-phenyl]-2-methoxy-propionic acid ethyl ester (Example 49, Step A) (0.365 g, 1.2 mmol) and 4-phenylphenol (0.307 g, 1.8 mmol) in 10 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mixture of 0–712 mg of mercury (II) oxide and 12 ml of 4% sulfuric acid in water. The solution was stirred at 55° C. for 3 hours, cooled to room temperature, diluted with saturated aqueous NaHCO₃ (20 mL), and extracted with dichloromethane (4×20 mL). The combined organic layers were washed with brine (20 mL), dried (MgSO₄), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL). The combined extracts were dried (MgSO₄) and concentrated to give the title compound. MS(ES) for $C_{28}H_{30}O_5$[M+H]⁺: 447.2.

Example 59

(2S)-2-Methoxy-3-{4-[6-(4-phenoxy-phenoxy)-hexanoyl]-phenyl}-propionic acid

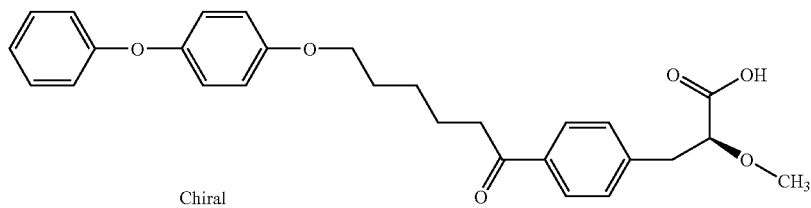
Chiral

A solution of triphenylphosphine (1.8 mmol) in 50 mL of dry THF was treated at 0° C. with diethylazodicarboxylate (1.8 mmol) and stirred for 20 min. A solution of 3-[4-(6-Hydroxy-hex-1-ynyl)-phenyl]-2-methoxy-propionic acid ethyl ester (Example 49, Step A) (1.2 mmol) and 4-phenoxyphenol (1.8 mmol) in 10 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mixture of 0.712 mg of mercury (II) oxide and 12 ml of 4% sulfuric acid in water. The solution was stirred at 55° C. for 3 hours, cooled to room temperature, diluted with saturated aqueous $NaHCO_3$ (20 mL), and extracted with dichloromethane (4×20 mL). The combined organic layers were washed with brine (20 mL), dried ($MgSO_4$), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL). The combined extracts were dried ($MgSO_4$) and concentrated to give the title compound. MS(ES) for $C_{28}H_{30}O_6[M+H]^+$: 463.2.

Example 60

(2S)-3-{4-[6-(4-Benzoyl-phenoxy)-hexanoyl]-phenyl}-2-methoxy-propionic acid

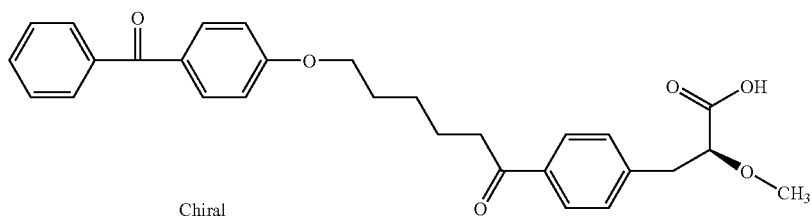
Chiral

A solution of triphenylphosphine (1.8 mmol) in 50 mL of dry THF was treated at 0° C. with diethylazodicarboxylate (1.8 mmol) and stirred for 20 min. A solution of 3-[4-(6-Hydroxy-hex-1-ynyl)-phenyl]-2-methoxy-propionic acid ethyl ester (Example 49, Step A) (1.2 mmol) and 4-phydroxybenzophenone (1.8 mmol) in 10 mL of dry THF was added, and the mixture was stirred at room temperature overnight. The mixture was concentrated under vacuum and purified by silica gel chromatography (silica gel, hexanes/ethyl acetate 10:1 to 3:1). Fractions with $R_f$s 0.48 and 0.45 (hexanes/ethyl acetate 2:1) corresponding to the coupled compound and starting phenol, respectively, were combined and concentrated. The mixture was dissolved in 5 mL of methanol and was treated with a mixture of 0.712 mg of mercury (II) oxide and 12 ml of 4% sulfuric acid in water. The solution was stirred at 55° C. for 3 hours, cooled to room temperature, diluted with saturated aqueous $NaHCO_3$ (20 mL), and extracted with dichloromethane (4×20 mL). The combined organic layers were washed with brine (20 mL), dried ($MgSO_4$), and concentrated. The residue was dissolved in 6 mL of methanol and 2 mL of 1N NaOH and stirred for 2 hours. The methanol was evaporated under vacuum, and the aqueous solution was diluted with brine (6 mL) and washed with diethyl ether (3×15 mL). The aqueous layer was acidified with 1N HCl (pH 1–2) and extracted with ethyl acetate (3×15 mL). The combined extracts were dried ($MgSO_4$) and concentrated to give the title compound. MS(ES) for $C_{29}H_{30}O_6$[M+H]$^+$: 475.2.

Example 61

(2S)-3-{4-[5-(Biphenyl-4-yloxy)-1-hydroxyimino-pentyl]-phenyl}-2-methoxy-propionic acid

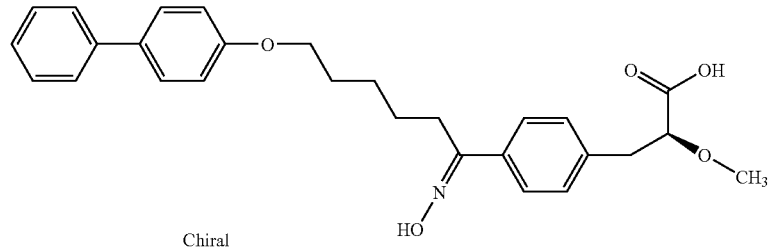

Chiral (2S)-3-{4-[5-(Biphenyl-4-yloxy)-pentanoyl]-phenyl}-2-methoxy-propionic acid from Example 52, (1 eq) was mixed with Hydroxylamine chlorydrate (4 eq), pyrydine (10 eq) and Ethanol (2 ml) and the mixture reaction was stirred overnight. The ethanol was evaporated under vacuo and HCl 0.5% was added to the residue to pH=3. Extracted with Ethyl Acetate and concentrated to give the title product as a mixture of two oximes. MS(ES) for $C_{27}H_{29}NO_5$ [M+H]$^+$: 448.2.2, [M–H]$^-$: 446.2.

Example 62

(2S,1'R*,2'S*)-3-(4-{2'-[4-(4-(Fluoro-benzoyl)-phenoxy]-cyclopentyloxy}-phenyl)-2-methoxy-propionic acid

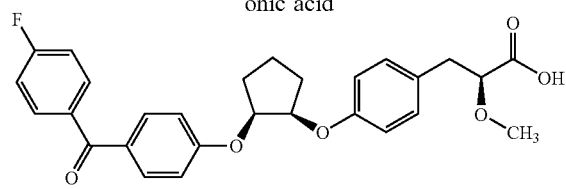

Step A cis-2-(tert-Butyl-dimethyl-silanyloxy)-cyclopentanol

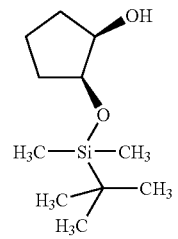

The title compound was prepared from meso-1,2-cyclopentanediol via the Standard Procedure D for the monoprotection of diols. The residue was purified by silica gel chromatography (hexanes/ethyl 3:1, $R_f$0.55) (50%). $^1$H-NMR (200.15 MHz, CDCl$_3$): δ 4.04 (dt, 1H, J=4.6, 6.2), 3.95–3.89 (m, 1H), 2.59 (d, 1H, J=3.8), 1.88–1.49 (m, 6H), 0.91 (s, 9H), 0.09 (s, 6H).

Step B (2S,1'R,2'R) 3-[4-(2'-Hydroxy-cyclopentyloxy)-phenyl]-2-methoxy-propionic acid ethyl ester

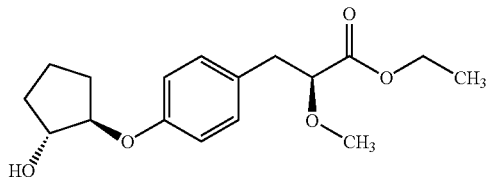

A solution of triphenylphosphine (0.634 g, 2.23 mmol) in 15 mL of dry THF was treated, at 0° C. with diethylazodicarboxylate (0.368 mL, 0.2.45 mmol) and stirred for 20 min. A solution of (2S)-2-methoxy-3-hydroxyphenylpropionic acid ethyl (0.5 g, 2.23 mmol) and cis-2-(tert-butyl-dimethylsilanyloxy)cyclopentanol (0.531 g, 0.245 mmol) min 5 mL of dry THF was added to the solution, and the mixture was stirred at room temperature overnight. The mixture was concentrated under vacuum and the residue was purified by silica gel chromatography (silica gel, hexanes/ethyl acetate 6:1). Fraction with $R_f$s 0.55 (hexanes/ethyl acetate 3:1) corresponding to the coupled compound and starting phenol, respectively, were collected and concentrated. The residue was dissolved in 4 mL of THF, and tetrabutylammonium fluoride (2.23 mL, 1 M in THF) was added. The solution was stirred for 2 hours at room temperature, diluted with 30 mL of diethyl ether, and washed with 1N HCl (2×20 mL). The organic solution was dried (MgSO$_4$) and concentrated. The residue was purified by silica gel chromatography (silica gel, hexanes/ethyl acetate 3:1, $R_f$ 0.9) to the product (60%). $^1$H-NMR (200.15 MHz, CDCl$_3$): δ 7.11 (d, 2H, J=8.6), 6.80 (d, 2H, J=8.9), 4.43–4.40 (m, 1H), 4.23–4.12 (m, 4H); 3.90 (dd, 1H, J=7.0, 5.9); 3.35 (s, 3H); 2.95 (d, 2H, J=6.7), 2.16–1.60 (m, 6H), 1.22 (t, 3H, J=7.0), 0.88 (s, 9H), 0.05 (d, 3H, J=2.2).

Step C (2S,1'R*,2'S*) 3-(4-{2'-[4-(4-Fluoro-benzoyl)-phenoxy]-cyclopentyloxy}-phenyl)-2-methoxy-propionic acid The title compound was prepared from (2S,1'R,2'R)-3-[4-(2'-hydroxy-cyclopentyloxy)-phenyl]-2-methoxy-propionic acid ethyl ester and 4-fluoro-4-hydroxybenzophenone via the Standard Procedure A. $^1$H-NMR (200.15 MHz, CDCl$_3$): δ 7.82–7.67 (m, 4H), 7.18–7.06 (m, 4H), 6.93 (d, 2H, J=8.9), 6.76 (d, 2H, J=8.6), 4.88–4.74 (m, 2H), 3.97–3.94 (m, 1H), 3.39 (s, 3H); 3.09–2.89 (m, 2H); 2.23–1.98 (m, 6H). MS (ES) for $C_{28}H_{27}FO_6$ [M+H]$^+$: 479.2, [M+Na]$^+$: 501.2.

Example 63

(2S)-(1'R,3'R)-2-Methoxy-3-{4-[1',3'-dimethyl-3-(4-phenoxy-phenoxy)-propoxy]-phenyl}-propionic acid Chiral

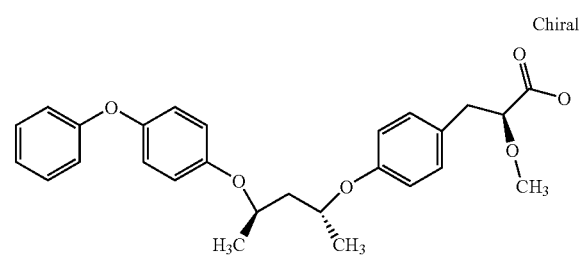

Step A (2S,4S)-4-(tert-Butyl-dimethyl-silanyloxy)-pentan-2-ol

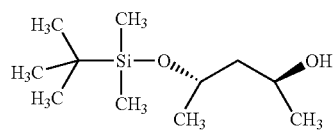

The title compound was prepared starting from (2S,4S) pentanediol using the Standard Procedure D. MS (ES) for $C_{11}H_{26}O_2Si$ [M+H]$_+$: 219.2.

Step B (2S)-(1'R,3'S)-3-{4-[3'-(tert-Butyl-dimethyl-silanloxy)-1'-methyl-butoxy]-phenyl}-2-methoxy-propionic acid ethyl ester

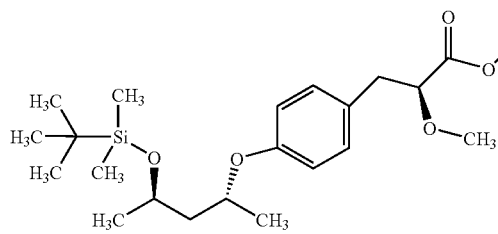

The title compound was prepared using the Standard Procedure for the Mitsounobu coupling B to give the product.

Step C (2S)-(1'R,3'S)-3-[4-(3'-Hydroxy-1'-methyl-butoxy)-phenyl]-2-methoxy-propionic acid methyl ester

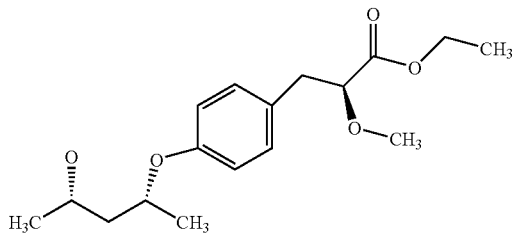

The title compound was prepared folowing the Standard Procedure E to give the product. MS (ES) for $C_{17}H_{26}O_5$ [M+H]$^+$: 328.2.

Step D (2S)-(1'R,2'R)-2-Methoxy-3-{4-[1'-methyl-3'-(4-phenoxy-phenoxy)-butoxy]-phenyl}-propionic acid ethyl ester

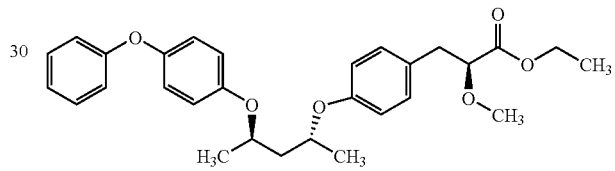

The title compound was prepared following the Standard Mitsounobu coupling procedure B to give the corresponding product. MS (ES) for $C_{29}H_{34}O_6$ [M+NH$_4$]$^+$: 496.2.

Step E (2S)-(1'R,3'R)-2-Methoxy-3-{4-[1',3'-dimethyl-3-(4-phenoxy-phenoxy)-propoxyl]-phenyl}-propionic acid The title compound was prepared by the Standard hydrolysis procedure C of the compound from Step D to give the final compound as a gummy solid. $^1$H-NMR (CDCl$_3$, 200.15 MHz): 7.32–7.24 (m, 2H), 7.10–6.75 (m, 11H), 4.70–4.50 (m, 2H), 3.95 (dd, 1H, J=7.3, 4.3), 3.36 (s, 3H), 3.06 (dd, 1H, J=14.5, 4.6), 2.92 (dd, 1H, J=14.2, 7.5),1.96 (dd, 2H, J=6.7, 5.4), 1.31 (d, 6H, J=6.2).ppm. MS(ES) for $C_{27}H_{30}O_6$ [M+NH$_4$]$^+$: 468.2, [M–H]$^-$: 449.2.

Example 64

(2S)-(1'R,3'R)-3-{4-[3-(4-Benzoylphenoxy)-1',3'-dimethylpropoxyl]-phenyl}2-methoxy-propionic acid

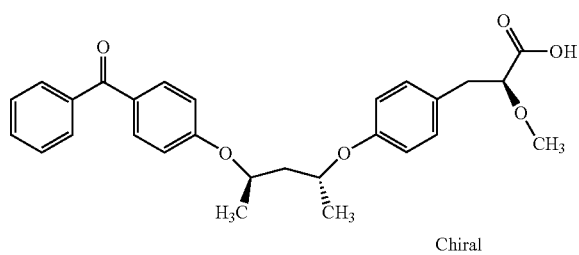

Chiral

The title compound was prepared in a manner analogous that Example 63, starting from the (2S,4S)-pentanediol to give the final compound. ¹H-NMR (CDCl₃, 200.15 MHz): 9.24 (s, 1H), 7.75 (t, 1H, J=1.6), 7.70 (t, 1H, J=1.9), 7.69 (dd, 2H, J=12.6, 2.2), 7.59–7.40 (m, 3H), 7.04 (d, 2H, J=8.6), 6.85 (d, 2H, J=9.1), 6.69 (d, 2H, J=8.9), 4.87–4.72 (m, 1H), 4.62–4.47 (m, 1H), 3.94 (dd, 1H, J=7.0, 5.6), 3.37 (s, 3H), 3.05–2.86 (m, 2H), 1.99 (dd, 2H, J=6.7, 5.4), 1.36 (d, 3H, J=6.2), 1.30 (d, 3H, J=6.2).

Example 65

(2S)-(1'S,3'S)-2-Methoxy-3-{4-[1',3'-dimethyl-3-(4-phenoxy-phenoxy)-propoxyl]-phenyl}-propionic acid

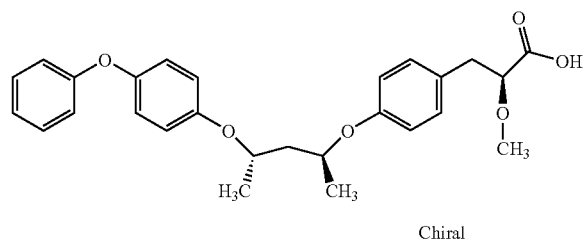

Chiral

The title compound was prepared in a manner analogous that Example 63, starting from the (2R,4R)-pentanediol to give the final compound. ¹H-NMR (CDCl₃, 200.15 MHz): 7.33–7.25 (m, 2H), 7.12–6.76 (m, 11H), 4.71–4.49 (m, 2H), 3.95 (dd, 1H, J=7.5, 4.6), 3.36 (s, 3H), 3.05 (dd, 1H, J=14.5, 4.6), 2.93 (dd, 1H, J=14.2, 7.5), 1.96 (dd, 2H, J=7.0, 5.7), 1.31 (d, 6H, J=6.2). MS(ES) for C₂₇H₃₀O₆ [M+NH₄]⁺: 468.2, [M–H]⁻: 449.2.

Example 66

(2S)-(1'S,3'S)-3-{4-[3-(4-Benzoylphenoxy-1',3'-dimethylpropoxyl]-phenyl}2-methoxy-propionic acid

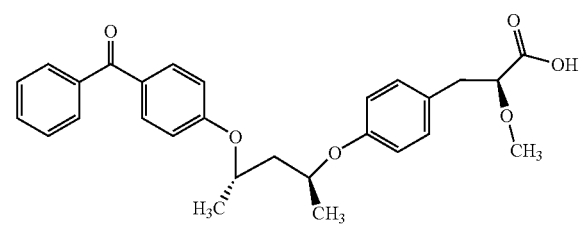

The title compound was prepared in a manner analogous that Example 63, starting from the (2R,4R)-pentanediol to give the final compound ¹H-NMR (CDCl₃, 200.15 MHz): 7.76–7.41 (m, 7H), 7.02 (d, 2H, J=8.6), 6.83 (d, 2H, J=8.9), 6.67 (d, 2H, J=8.9), 4.78 (dd, 1H, J=12.1, 6.2), 4.63–4.47 (m, 1H), 3.99 (dd, 1H, J=6.2, 4.8), 3.41 (s, 3H), 3.08–2.87 (m, 2H), 2.00 (dd, 2H, J=5.6, 12.4), 1.33 (dd, 6H, J=11.6, 6.2). MS(ES) for C₂₈H₃₀O₆ [M+H]⁺: 463.2, [M–H]⁻: 461.3.

Example 67

(2S)-(1'R,2'R)-2-Methoxy-3-{4-[1',2'-dimethyl-(4-phenoxy-phenoxy)-ethoxyl]-phenyl}-propionic acid

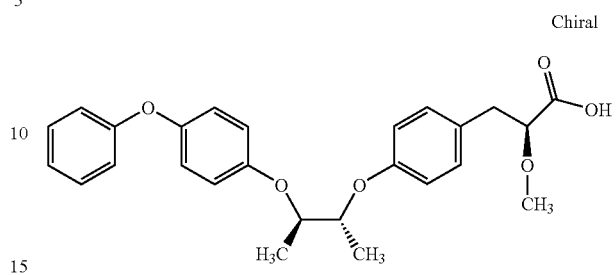

Chiral

The title compound was prepared in a manner analogous that 63, starting from the (2S,3S)-butane-2,3-diol to give the final compound. ¹H-NMR (CDCl₃, 200.15 MHz): 7.94 (m, 1H), 7.34–7.26 (m, 3H), 7.17–6.83 (m, 10H), 4.59–4.38 (m, 2H), 3.98 (dd, 1H, J=7.5, 4.6), 3.39 (s, 3H), 3.08 (dd, 1H, J=14.2, 4.3), 2.95 (dd, 1H, J=14.2, 7.5), 1.36 (d, 6H, J=6.2). MS(ES) for C₂₆H₂₈O₆ [M+NH₄]⁺: 454.2, [M–H]⁻: 435.2.

Example 68

(2S)-(1'R,2'R)-3-{4-[1-(4-Benzoylphenoxy)-1',2'-dimethyl-ethoxyl]-phenyl}-2-methoxypropionic acid

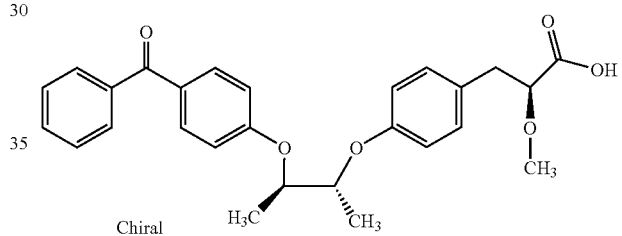

Chiral

The title compound was prepared in a manner analogous that Example 63, starting from the (2S,3S)butane-2,3-diol to give the final compound. ¹H-NMR (CDCl₃, 200.15 MHz): 7.77 (t, 3H, J=8.9), 7.74 (s, 1H), 7.60–7.42 (m, 3H), 7.14 (d, 2H, J=8.6), 6.96 (d, 2H, J=8.9), 6.84 (d, 2H, J=8.9), 4.72–4.60 (m, 1H), 4.59–4.47 (m, 1H), 3.98 (dd, 1H, J=7.5, 4.6), 3.39 (s, 3H), 3.08 (dd, 1H, J=14.5, 4.6), 2.95 (dd, 1H, J=14.2, 7.3), 1.42 (d, 3H, J=6.2), 1.37 (d, 3H, J=6.2). MS(ES) for C₂₇H₂₈O₆ [M+H]⁺: 449.2, [M–H]⁻: 447.2.

Example 69

(2S)-(1'S,4'S)-2-Methoxy-3-{4-[1'-methyl-4'-(4-phenoxy-phenoxy)-pentyloxy]-phenyl}-propionic acid

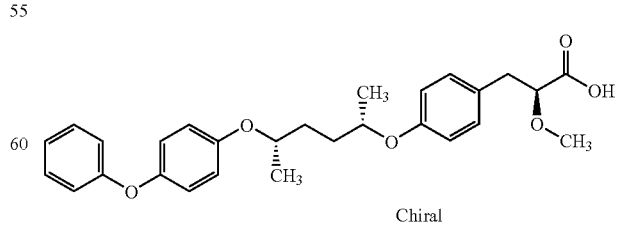

Chiral

The title compound was prepared in a manner analogous that Example 63, starting from the (2R,5R)-hexane-2,5-diol to give the final compound. ¹H-NMR (200.15 MHz, CDCl₃): 7.3–7.2 (m, 2H), 7.14 (d, 2H, J=8.6), 7.1–6.8 (m, 9H), 4.4–4.3 (m, 2H), 3.97 (dd, 1H, J=7.6, 4.4), 3.39 (s, 3H), 3.08 (dd, 1H, J=14.2, 4.4), 2.95 (dd, 1H, J=14.4, 7.6), 2.0–1.7 (m, 4H), 1.31 (d, 6H, J=6.2) ppm.

Example 70

(2S)-(1'S,4'S)-3-{4-[4-(4-Benzoyl-phenoxy)-1-methyl-pentyloxy]-phenyl}-2-methoxy-propionic acid

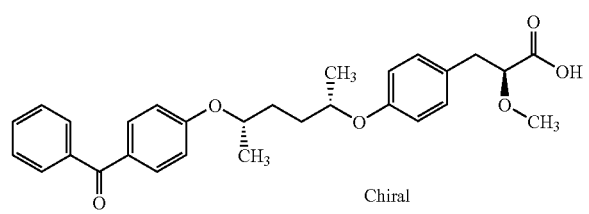

Chiral

The title compound was prepared in a manner analogous that Example 63, starting from the (2R,5R)-hexane-2,5-diol to give the final compound. ¹H-NMR (200.15 MHz, CDCl₃): 7.8–7.7 (m, 4H), 7.6–7.5 (m, 3H), 7.13 (d, 2H, J=8.6), 6.90 (dd, 2H, J=7.0, 2.0), 6.79 (d, 2H, J=8.6), 4.51 (c, 1H, J=6.0), 4.35 (c, 1H, J=6.0), 3.98 (dd, 1H, J=7.2, 4.8), 3.39 (s, 3H), 3.08 (dd, 1H, J=14.4, 4.8), 2.95 (dd, 1H, J=14.4, 7.2), 2.0–1.7 (m, 4H), 1.35 (d, 3H, J=6.0), 1.30 (d, 3H, J=6.0) ppm.

Example 71

(2S)-(1'R,4'R)-2-Methoxy-3-{4-[1'-methyl-4'-(4-phenoxy-phenoxy)-pentyloxy]-phenyl}-propionic acid

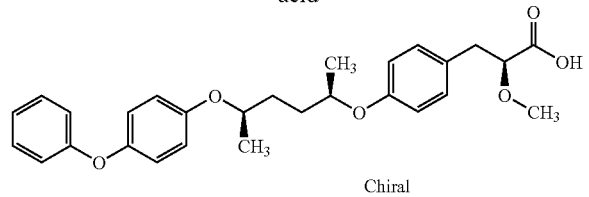

Chiral

The title compound was prepared in a manner analogous that Example 63, starting from the (2S,5S)-hexane-2,5-diol to give the final compound. ¹H-NMR (200.15 MHz, CDCl₃). 7.3–7.2 (m, 2H), 7.14 (d, 2H, J=8.4), 7.1–6.7 (m, 9H), 4.4–4.2 (m, 2H), 3.96 (dd, 1H, J=7.4, 4.4), 3.37 (s, 3H), 3.07 (dd, 1H, J=14.4, 4.4), 2.93 (dd, 1H, J=14.4, 7.4), 2.0–1.6 (m, 4H), 1.30 (d, 6H, J=6.0) ppm.

Example 72

(2S)-(1'R,4'R)-3-{4-[4-(4-Benzoyl-phenoxy)-1-methyl-pentyloxy]-phenyl}-2-methoxy-propionic acid

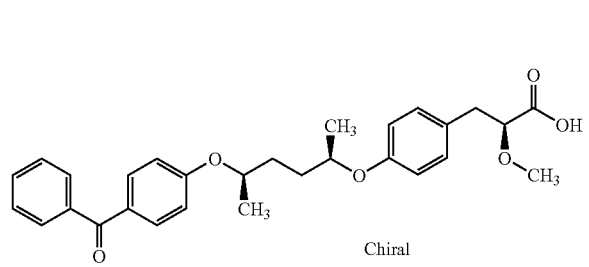

Chiral

The title compound was prepared in a manner analogous that Example 63, starting from the (2S,5S)-hexane-2,5-diol to give the final compound. ¹H-NMR (200.15 MHz, CDCl₃): 7.8–7.5 (m, 3H), 7.5–7.4 (m, 3H), 7.06 (d, 2H, J=5.6), 6.82 (d, 2H, J=6.0), 6.71 (d, 2H, J=5.8), 4.44 (c, 1H, J=3.6), 4.28 (c, 1H, J=3.6), 3.88 (dd, 1H, J=9.6, 2.8), 3.29 (s, 3H), 2.98 (dd, 1H, J=9.6, 2.8), 2.86 (dd, 1H, J=9.6, 5.0), 1.9–1.6 (m, 4H), 1.27 (d, 3H, J=4.0), 1.21 (d, 3H, J=4.0) ppm.

Example 73

(2S)-(1'S,2'S)-2-Methoxy-3-{4-[1',2'-dimethyl-(4-phenoxy-phenoxy)-ethoxy]-phenyl}-propionic acid

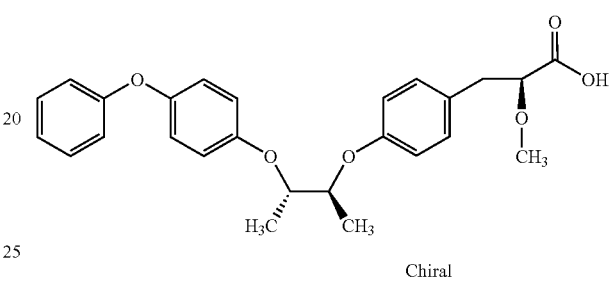

Chiral

Step A (2R,3S)-3-(4-phenoxy-phenoxy)-butan-2-ol

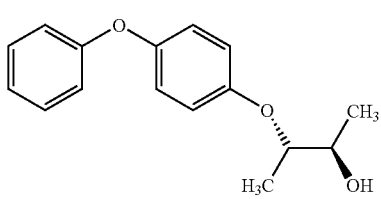

A solution of (2R,3R)-butane-2,3-diol was monoprotected with tert-butyldimethylsilyl chloride using the Standard Procedure D, after purification by chromatography, the compound was coupling with 4-phenoxyphenol using Standard Procedure B (in THF) and deprotected with tetrabutylamonium fluoride as Standard Procedure E to give the title compound as an oil. MS (ES) for C₁₆H₁₈O₃ [M+NH₄]⁺: 276.2.

Step B (1R,2S)-Toluene-4-sulfonic acid 1-methyl-2-(4-phenoxy-phenoxy)-propyl ester

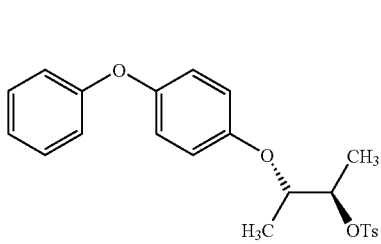

To a solution of compound from Step A (1 eq) in neat pyridine, p-Toluenesulfonic chloride (1.5 eq) was added and the mixture reaction was stirred at room temperature over two days. The reaction was quenched with HCl 1N and extracted with ethyl acetate and washing the organic layers with brine (3 times). The organic layers were dry and concentrated in vacuo to give a residue which was purified by silica gel chromatography to give the title product. MS (ES) for $C_{23}H_{24}O_5S$ [M+NH$_4$]$^+$: 430.1.

Step C (2S)-(1'S,2'S)-2-Methoxy-3-{4-[1',2'-dimethyl-(4-phenoxy-phenoxy)-ethoxyl]-phenyl}-propionic acid ethyl ester

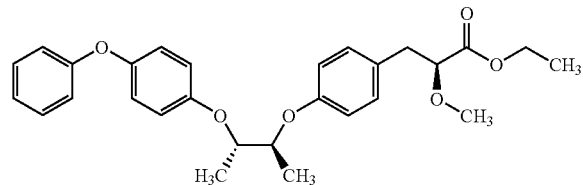

A solution of (1R,2S)-Toluene-4-sulfonic acid 1-methyl-2-(4-phenoxy-phenoxy)-propyl ester from above Step (1 eq), potassium carbonate (3 eq) and 2S)-3-(4-Hydroxyphenyl)-2-methoxy-propionic acid ethyl ester (1 eq) in acetonitrile was refluxed overnight. The solution was evaporated to dryness and chromatographied to get the title compound. MS (ES) for $C_{27}H_{30}O_7$ [M+NH$_4$]$^+$: 482.4.

Step D (2S)-(1'S,2'S)-2-Methoxy-3-{4-[1',2'-dimethyl-(4-phenoxy-phenoxy)-ethoxyl]-phenyl}-propionic acid The title compound was prepared using the Standard hydrolysis Procedure C to give the final product as an oil. $^1$H-NMR (CDCl$_3$, 200.15 MHz): 7.34–7.26 (m, 3H), 7.16–6.83 (m, 10H), 4.58–4.41 (m, 2H), 3.98 (dd, 1H, J=7.3, 4.3), 3.39 (s, 3H), 3.14–2.89 (m, 2H), 1.35 (d, 6H, J=6.2). MS(ES) for $C_{26}H_{28}O_6$ [M+NH$_4$]$_+$: 454.3, [M–H]$_-$: 435.1.

Example 74

(2S)-2-Methoxy-{4-[2-methylen-3-(4-phenoxy-phenoxy)-propoxyl]-phenyl}-propionic acid

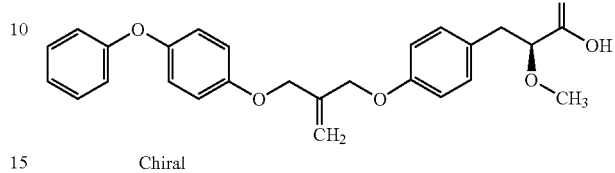

Chiral

Step A 2-(4-phenoxy-phenoxymethyl)-prop-2-en-1-ol

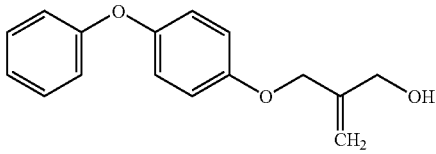

A solution of triphenylphosphine (1 eq) in toluene at 0° C. was treated with diethylazodicarboxylate (1 eq) and stirred for 20 min. Then a solution of 4-pehoxyphenol and 2-Methylene-propane-1,3-diol in toluene was added to the solution and the mixture reaction was stirred overnight. Concentrated to dryness and chromatographied to give the title compound.

Step B (2S)-2-Methoxy-{4-[2-methylen-3-(4-phenoxy-phenoxy)-propoxyl]-phenyl}-propionic acid ethyl ester

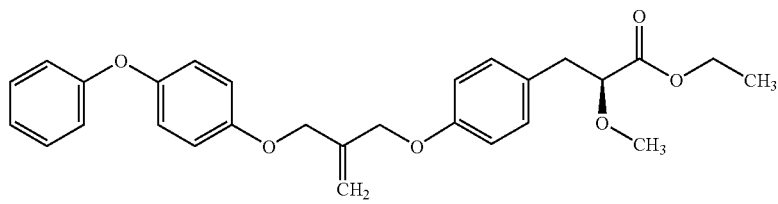

The title compound was prepared using Standard Mitsounobu coupling conditions B.

Step C (2S)-2-Methoxy-{4-[2-methylen-3-(4-phenoxy-phenoxy)-propoxy]-phenyl}-propionic acid The title compound was prepared by using the Standard Procedure for hydrolysis C to give the final product as an oil. ¹H-NMR (CDCl₃, 200.15 MHz): 8.09 (s, 1H), 7.34–6.86 (m, 13H), 5.41 (s, 2H), 4.62 (s, 4H), 3.98 (dd, 1H, J=7.5, 4.6), 3.40 (s, 3H), 3.09 (dd, 1H, J=14.5, 4.6), 2.97 (dd, 1H, J=14.5, 7.5).

Example 75

(2S)-2-Methoxy-{4-[2-oxo-3-(4-phenoxy-phenoxy)-propoxy]-phenyl}-propionic acid

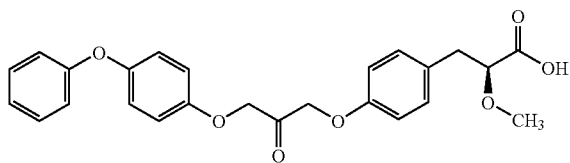

Chiral

A solution of (2S)-2-Methoxy-{4-[2-methylen-3-(4-phenoxy-phenoxy)-propoxyl]-phenyl}-propionic acid from Example 74, in dichloromethane at −78° C. was treated with ozone until the solution turned blue. Washed with brine, dry and concentrated to dryness to give the title compound. ¹H-NMR (CDCl₃, 200.15 MHz): 7.35–6.83 (m, 13H), 4.86 (d, 4H, J=3.0), 3.98 (dd, 1H, J=7.3, 4.3), 3.40 (s, 3H), 3.10 (dd, 1H, J=14.2, 4.0), 2.97 (dd, 1H, J=14.5, 7.3). MS(ES) for C₂₅H₂₄O₇ [M+NH₄]⁺: 454.2, [M−H]⁻: 435.2.

Example 76

(2S)-2-Methoxy-3-{4-[3-(4-phenoxy-phenoxymethyl)-benzyloxy]-phenyl}-propionic acid

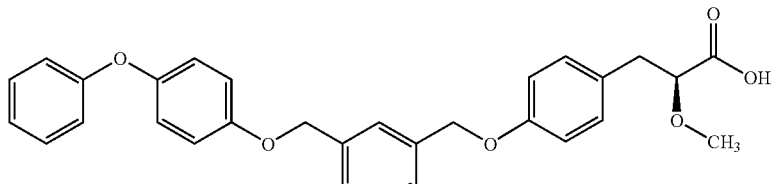

Chiral

The title compound was prepared in a manner analogous that Example 74, starting from (3-Hydroxymethyl-phenyl)-ethanol to give the final compound. ¹H-NMR (200.15 MHz, CDCl₃): 7.50 (s, 1H), 7.40 (s, 2H), 7.28 (d, 2H, J=8.6), 7.17 (d, 2H, J=8.6), 7.1–6.9 (m, 10H), 5.06 (s, 4H), 3.99 (dd, 1H, J=7.2, 4.4), 3.40 (s, 3H), 3.10 (dd, 1H, J=14.4, 4.6), 2.97 (dd, 1H, J=14.2, 7.4) ppm.

Example 77

(2S)-2-Methoxy-3-{4-[2-(4-phenoxy-phenoxymethyl)-benzyloxy]-phenyl}-propionic acid

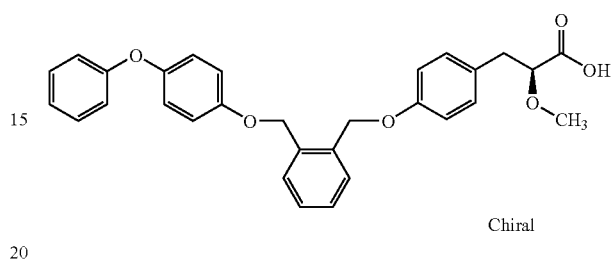

Chiral

The title compound was prepared in a manner analogous that Example 63, starting from (2-Hydroxymethyl-phenyl)-methanol to give the final compound. ¹H-NMR (200.15 MHz, CDCl₃): 7.5–7.4 (m, 2H), 7.4–7.3 (m, 2H), 7.28 (d, 2H, J=8.0), 7.16 (d, 2H, J=8.6), 7.1–6.9 (m, 9H), 5.14 (s, 4H), 3.95 (dd, 1H, J=7.4, 4.6), 3.37 (s, 3H), 3.07 (dd, 1H, J=14.2, 4.4), 2.94 (dd, 1H, J=14.2, 7.6) ppm.

Example 78

(2S)-2-Methoxy-3-{4-[3-(4-phenoxy-phenoxy-phenoxy]-phenyl}-propionic acid

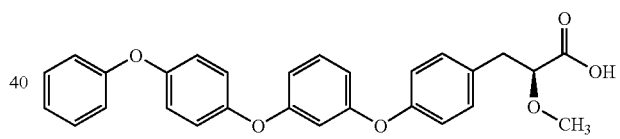

Chiral

Step A (2S)-3-[4-(3-Bromo-phenoxy)-phenyl]-2-methoxy-propionic acid ethyl ester

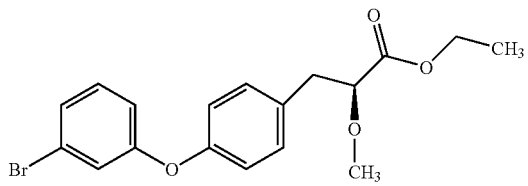

An ovendried resealable Schlenk tube was fitted with a rubber septum and was cooled to room temperature under $N_2$ purge. The tube was charge with $Pd(OAc)_2$ (2.0 mol %), 2-(ditert-butylphosphino)biphenyl (0.03 eq), potassium phosphate (2 eq), 1,3-dibromobenzene (1 eq) and (2S)-3-(4-Hydroxy-phenyl)-2-methoxy-propionic acid ethyl ester (1,2 eq). The tube was capped with the septum and purged with N2, and then toluene was added through the septum. The tube was sealed with a teflon screwcap, and the reaction mixture was stirred at 100° C. for 16 hours. The solvent was removed and the residue was purified by chromatography to afford the title compound.

Step B (2S)-2-Methoxy-3-{4-[3-(phenoxy-phenoxy)-phenoxy]-phenyl}-propionic acid ethyl ester

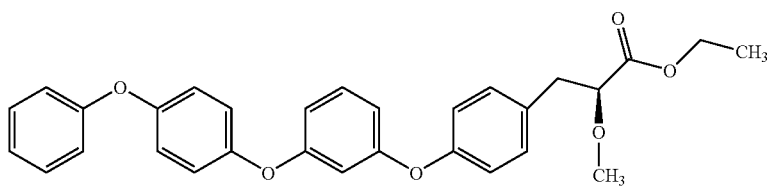

The title compound was porcepared using the same coupling procedure described above for Step A with 4-phenoxyphenol and (2S)-3-[4-(3-Bromo-phenoxy)-phenyl]-2-methoxy-propionic acid ethyl ester.

Step C (2S)-2-Methoxy-3-{4-[3-(4-phenoxy-phenoxy)-phenoxy]-phenyl}-propionic acid The title compound was prepared from Step B by using Standar Procedure for the hydrolysis C. MS (ES) for $C_{28}H_{24}O_6$ [M+Na]$^+$: 479.

Example 79

(2S)-3-[3'-(3-Benzoyl-phenoxymethyl)-biphenyl-4-yl]-2-methoxy-propionic acid

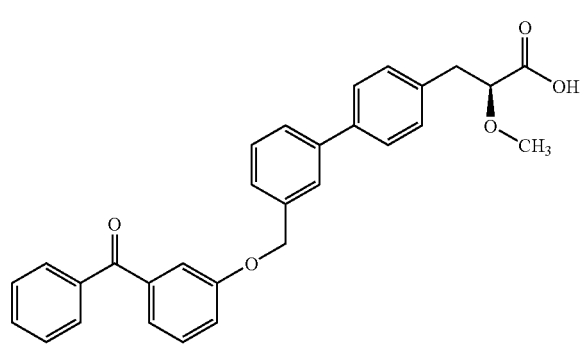

Step A (2S)-3-(3'-Hydroxymethyl-biphenyl-4-yl)-2-methoxy-propionic acid ethyl ester

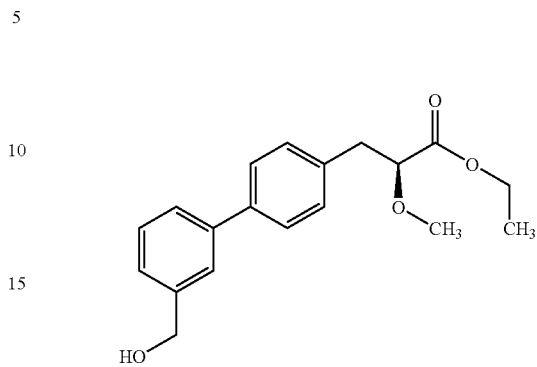

A solution of (2S) 2-Methoxy-3-(4-trifluoromethanesulfonyloxy-phenyl)-propionic acid ethyl ester (Example 1, Step A) (150 mg, 0.42 mmol), 3-formylphenyl boronic acid (126 mg, 0.842 mmol) and tetrakis(triphenylphosphine)-palladium (0) (15 mg, 0.013 mmol) in 11 ml of a mixture 20:1 toluene/ethanol together with 2 ml of a 2N $Na_2CO_3$ was heated to 120° C. for 6 hours under nitrogen atmosphere.

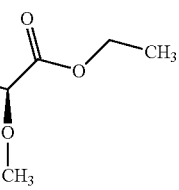

The reaction mixture was cooled to room temperature and dilute with EtOAc (20 ml). It was washed with $H_2O$ (3×5 ml) and sodium tartrate (3×5 ml). The combined organic layers were dried (MgSO$_4$), filtered and concentrated in vacuum. The resultant crude was purified by column chromatography (silica gel, hexanes/ethyl acetate 3:1). Fractions corresponding to the desired compound (R$_f$: 0.27) were collected and concentrate to dryness. The product was dissolved in MeOH cooled at 0° C., and sodium borohydride (3 eq) was added. The solution was stirred for 1 h. and then diluted with Ethyl-acetate (20 ml). It was washed with $H_2O$ (3×5 ml) and NaHCO$_3$ (3×5 ml). The combined organic layers were dried (MgSO$_4$), filtered and concentrated in vacuum. The resultant crude was purified by column (silica gel, hexanes/ethyl acetate 2:1). Obtained a colorless oil (60 mg, 45%). $^1$H-NMR (200.15 MHz, CDCl$_3$): δ 7.55–7.23 (m, 8H), 4.71 (s, 2H), 4.18 (q, 2H, J=7.0), 3.93 (dd, 1H, J=7.3, 5.6), 3.35 (s, 3H), 3.05 (s, 1H), 3.02 (s, 1H), 1.25 (t, 3H, J=7.25)

Step B (2S)-3-[3'-(3-Benzoyl-phenoxymethyl)-biphenyl-4-yl]-2-methoxy-propionic acid The title compound was prepared from (2S) 3-(3'-Hydroxymethyl-biphenyl-4-yl)-2-methoxy-propionic acid ethyl ester (Step A) and 4-Hydroxybenzophenone via the standard Mitsunobu coupling-hydrolisis procedure (Standard Procedure A) to produce a white oily solid. $^1$H-NMR (200.15 MHz, CDCl$_3$): δ 7.83–7.33 (m, 15H), 7.03 (d, 2H, J=8.1), 5.17 (s, 2H), 4.07 (dd, 1H, J=6.9, 3.7), 3.40 (s, 3H), 3.16 (dd, 1H, J=14.1, 3.6), 3.06 (dd, 1H, J=14.1, 7.0).

Example 80

(2S)-3-[4'-(4-Benzoyl-phenoxymethyl)-biphenyl-4-yl]-2-methoxy-propionic acid

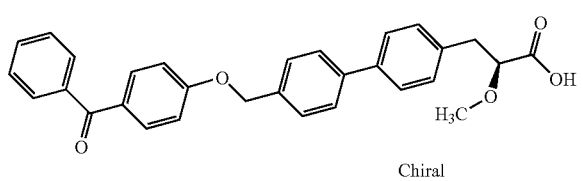

Chiral

Step A (2S)-3-(4'-Hydroxymethyl-biphenyl-4-yl)-2-methoxy-propionic acid ethyl ester

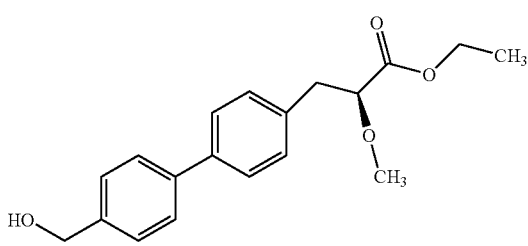

A mixture of (2S)-2-Methoxy-3-(4-trifluoromethanesulfonyloxy-phenyl)-propionic acid ethyl ester from Example 1, Step A (1 eq), tetrakis(triphenylphosphine) palladium(0) (0.03 eq), sodium carbonate (1.5 eq) and 4-hydroxymethylphenylboronic acid (2 eq) in Toluene/Ethanol (20:1) was refluxed till the reaction is completed by TLC. The mixture was diluted with ethyl acetate, extracted and washed with water, NaHCO$_3$, sodium tartrate and brine. The organic layer was concentrated to dryness and chromatographied to afford the title compound.

Step B (2S)-3-[4'-(4-Benzoyl-phenoxymethyl)-biphenyl-4-yl]-2-methoxy-propionic acid (2S)-3-(4'-Hydroxymethyl-biphenyl-4-yl)-2-methoxypropionic acid ethyl ester from Step A, was treated with 4-hydroxybenzophenone under the standard Mitsunobu coupling procedure B (THF). The product obtained after chromatography was hydrolyzed using the Standard Procedure C to get the title compound. $^1$H-NMR (CDCl$_3$, 200.15 MHz): 7.86–7.73 (m, 4H), 7.63–7.43 (m, 9H), 7.34–7.29 (m, 2H), 7.05 (d, 2H, J=9.1), 5.18 (s, 2H), 4.06 (dd, 1H, J=7.3, 4.0), 3.42 (s, 3H), 3.20 (dd, 1H, J=14.5, 4.0), 3.06 (dd, 1H, J=14.5, 7.3). MS (ES) for C$_{30}$H$_{26}$O$_5$ [M+H]$^+$: 467.2, [M+Na]$^+$: 489.2.

Example 81

(2S)-(1'R*,3'R*)3-{4-[3'-(Biphenyl-4-yloxy)-1'-cyclopentyloxy]-phenyl}-2-methoxy-propionic acid

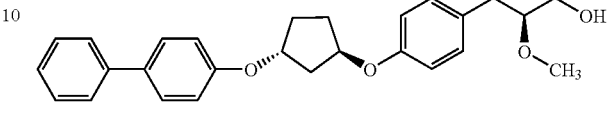

Step A (1RS,3RS)-3-(tert-Butyl-dimethyl-silanyloxy)-cyclopentanol

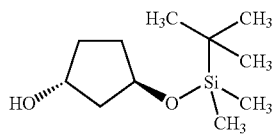

To a solution of rac-1,3-pentanediol (0.46 g, 4.5 mmol) in 23 mL of THF at 0° C. was added sodium hydride (0.18 g, 4.5 mmol, 60% oil dispersion). The mixture was stirred at 0° C. for 1 h. Tert-butyldimethylsilyl chloride (0.678 g, 4.5 mmol) was added, and the mixture was stirred overnight at room temperature. The mixture compounds were concentrated and purified by silica gel chromatography (silica gel, hexanes/ethyl acetate 3:1) to give 0.682 g, of the title compound trans and 0.157 g (6%) of the other cis isomer (1R*,3S*)-3-(tert-Butyl-dimethyl-silanyloxy)-cyclopentanol. $^1$H-NMR (200.15 MHz, CDCl$_3$): δ 4.48–4.36 (m, 2H), 2.19–1.89 (m, 2H), 1.85–1.79 (m, 2H), 1.58–1.46 (m, 2H), 0.89 (s, 9H), 0.04 (s, 6H).

Step B (1R*,3S*)-[3-(Biphenyl-4-yloxy)-cyclopentyloxy]-tert-butyl-dimethyl-silane

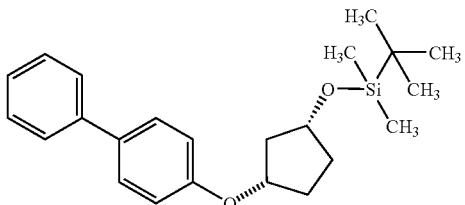

A solution of triphenylphosphine (0.195 g, 0.742 mmol) in 5 mL of dry THF was treated at 0° C. with diethylazodicarboxylate (0.117 mL, 0.742 mmol) and stirred for 20 min. A solution of (1R*,3R*)-3-(tert-butyldimethylsilanyloxy) cyclopentanol (0.146 g, 0.675 mmol) and 4-phenyl phenol (0.126 g, 0.0.724 mmol) in 5 mL of dry THF was added to the solution, and the mixture was stirred at room temperature overnight. The solution was concentrated under vacuum and purified by silica gel chromatography (silica gel, hexanes/ ethyl acetate 6:1, R$_f$0.66). $^1$H-NMR (200.15 MHz, CDCl$_3$): δ 7.58–7.29 (m, 7H); 6.93 (d, 2H, J=8.92), 4.76–4.65 (m, 1H), 4.32–4.21 (m, 1H), 2.38 (qn, 1H, J=7.0), 2.04–1.94 (m, 2H), 1.87–1.78 (m, 3H), 0.90 (s, 9H), 0.07 (s, 3H), 0.06 (s, 3H).

Step C (1R*,3S*)-3-(Biphenyl-4-yloxy)-cyclopentanol

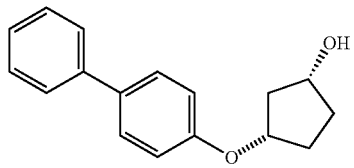

(1R*,3S*)-[3-(Biphenyl-4-yloxy)-cyclopentyloxy]-tert-butyldimethylsilane (0.25 g, 0.67 mmol) was dissolved in 2 mL of THF and tetrabutylammonium fluoride (0.67 mL, 1M in THF) and stirred at room temperature for 2 hours. The solution was diluted with 15 mL of diethyl ether and washed with 1N HCl (2×15 mL). The organic layer was dried (MgSO$_4$) and concentrated. The residue was purified by silica gel chromatography (silica gel, hexanes/ethyl acetate 3:1, R$_f$0.09) to give the product (100%). $^1$H-NMR (200.15 MHz, CDCl$_3$): δ 7.58–7.26 (m, 7H), 6.95 (d, 2H, J=8.9), 4.92–4.84 (m, 1H), 4.40–4.38 (m, 1H), 2.18–1.92 (m, 7H).

Step D (2S)-(1'R*,2'R*)3-{4-[3-(Biphenyl-4-yloxy)-cyclopentyloxy]-phenyl}-2-methoxy-propionic acid The title compound was prepared from (1R*,3S*) 3-(Biphenyl-4-yloxy)-cyclopentanol and (2S)-2-methoxy-3-hydroxyphenylpropionic acid ethyl ester via the Standard Procedure A. Oily solid. $^1$H-NMR (CDCl$_3$, 200.15 MHz): δ 7.57–7.29 (m, 7H), 7.15 (d, 2H, J=8.6), 6.94 (d, 2H, J=8.9), 6.81 (d, 2H, J=8.6), 4.99–4.91 (m, 2H), 3.99 (dd, 1H, J=7.3, 4.6), 3.41 (s, 3H), 3.10 (dd, 1H, J=14.2, 4.6), 2.96 (dd, 1H, J=14.5, 7.3), 2.31 (t, 2H, J=4.8), 2.26–1.97 (m, 4H).

Example 82

(2S)-(1'R*,3'S*)3-{4-[3'-(Biphenyl-4-yloxy)-1'-cyclopentyloxy]-phenyl}-2-methoxy-propionic acid

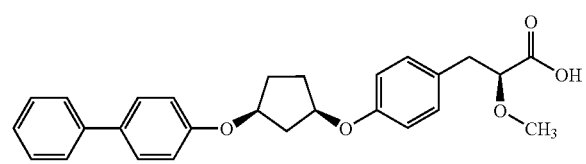

Step A (1R*,3S*)-3-(tert-Butyl-dimethyl-silanyloxy)-cyclopentanol

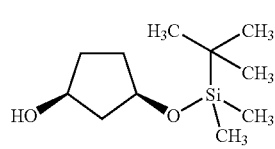

The title compound was isolated from Example 81, Step A in a 6% yield.

Step B (2S)-(1'R*,3'S*)3-{4-[3'-(Biphenyl-4-yloxy)-1'-cyclopentyloxy]-phenyl}-2-methoxy-propionic acid The title compound was prepared starting from compound from Step A and following the same procedure as in Example 81, to give the final product. MS (ES) for C$_{27}$H$_{28}$O$_5$ [M+NH$_4$]$^+$: 450.2, [M+Na]$^+$: 455.23.

Example 83

(2S)-(1'R*,3'R*)-2-Methoxy-3-{4-[3'-(4-phenoxy-phenoxy)-1'-cyclopentyloxy]-phenyl}-propionic acid

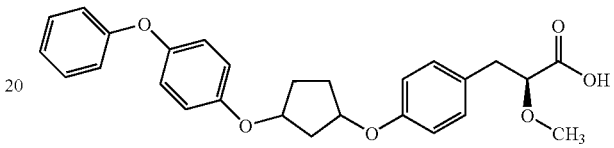

Chiral

Step A (2S)-(1R*,3S*)-3-{4-[3'-(tert-Butyl-dimethyl-silanyloxy)-1'-cyclopentyloxy]-phenyl}-2-methoxy-propionic acid ethyl ester

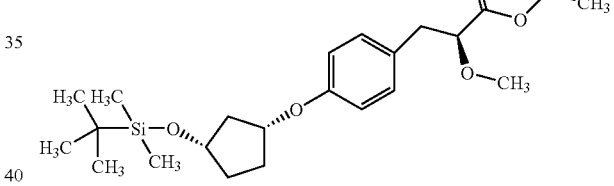

A solution of triphenylphosphine (0.634 g, 2.23 mmol) in 15 mL of dry THF was treated at 0° C. with diethylazodicarboxylate (0.2.45 mmol) and stirred for 20 min. A solution of (2S)-2-methoxy-3-hydroxyphenylpropionic acid ethyl (2.23 mmol) and 1R*,3R*-tert-butyldimethylsylyloxy-cyclopentanol (0.245 mmol) in 5 mL of dry THF was added to the solution, and the mixture was stirred at room temperature overnight. The mixture was concentrated under vacuum and the residue was purified by silica gel chromatography.

Step B (2S)-(1R*,3S*)-3-[4-(3'-Hydroxy-1'-cyclopentyloxy)-phenyl]-2-methoxy-propionic acid ethyl ester

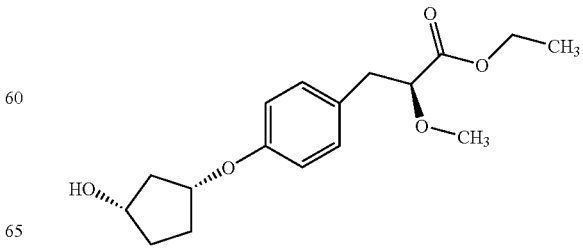

The title compound was prepared folowing the Standard Procedure E to give the product.

Step C (2S)-(1'R*,3'R*)-2-Methoxy-3-{4-[3'-(4-phenoxy-phenoxy)-1'-cyclopentyloxy]-phenyl}-propionic acid (2S)-(1R*,3S*)-3-[4-(3'-Hydroxy-1'-cyclopentyloxy)-phenyl]-2-methoxy-propionic acid ethyl ester from Step A, was treated with 4-phenoxyphenol under the standard Mitsounobu coupling procedure B (THF). The product obtained after chromatography was hydrolyzed using the standard hydrolysis procedure C to get the title compound. $^1$H-NMR (CDCl$_3$, 200.15 MHz): 7.34–7.26 (m, 2H), 7.17–7.04 (m, 3H), 7.00–6.92 (m, 4H), 6.88–6.78 (m, 4H), 4.94–4.89 (m, 2H), 3.99 (dd, 1H, J=7.3, 4.3), 3.41 (s, 3H), 3.10 (dd, 1H, J=14.2, 4.6), 2.96 (dd, 1H, J=14.2, 7.3), 2.28 (t, 2H, J=4.8), 2.21–1.89 (m, 4H). MS (ES) for C$_{27}$H$_{26}$O$_6$ [M+NH$_4$]$^+$: 466.2, [M+Na]$^+$: 471.2.

Example 84

(2S)-(1'R*,3'R*)-3-{4-[3-(4-Benzoyl-phenoxy)-cyclopentyloxy]-phenyl}-2-methoxy-propionic acid

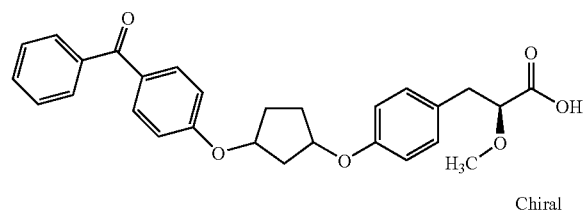

Chiral

The title compound was prepared as manner analogous in Example 83, starting from (1R*,3R*)-3-(tert-Butyl-dimethyl-silanyloxy)-cyclopentanol and 4-hydroxy nezophenone. $^1$H-NMR (CDCl$_3$, 200.15 MHz): 7.83–7.73 (m, 4H), 7.56–7.42 (m, 3H), 7.15 (d, 2H, J=8.3), 6.92 (dd, 2H, J=7.0, 1.9), 6.80 (d, 2H, J=8.6), 5.03–5.01 (m, 1H), 4.96–4.92 (m, 1H), 3.98 (dd, 1H, J=7.3, 4.6), 3.39 (s, 3H), 3.09 (dd, 1H, J=14.5, 4.6), 2.95 (dd, 1H, J=14.2, 7.3), 2.40–1.91 (m, 6H). MS (ES) for C$_{28}$H$_{28}$O$_6$ [M+H]$^+$: 461.2, [M+Na]$^+$: 483.2.

Example 85

(2S)-(1'R*,3'R*)-2-Methoxy-3-{4-[3-(4-phenylacetyl-phenoxy)-cyclopentyloxy]-phenyl}-propionic acid Chiral

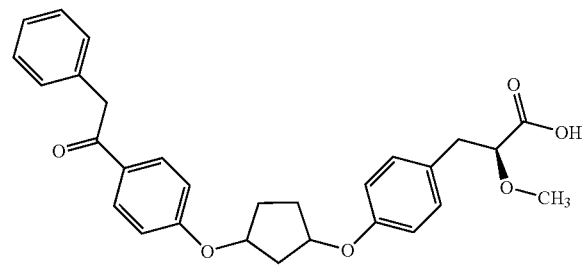

The title compound was prepared as manner analogous in Example 83, starting from (1R*,3R*)-3-(tert-Butyl-dimethyl-silanyloxy)-cyclopentanol and 1-(4-Hydroxy-phenyl)-2-phenyl-ethanone. MS (ES) for C$_{29}$H$_{30}$O$_6$ [M+H]$^+$: 475.2, [+Na]$^+$: 497.2. $^1$H-NMR (CDCl$_3$, 200.15 MHz): 7.97 (d, 2H, J=8.9), 7.32–7.23 (m, 5H); 7.15 (d, 2H, J=8.6), 6.91–6.77 (m, 4H), 5.01–4.91 (m, 2H), 4.22 (s, 2H), 3.98 (dd, 1H, J=7.3, 4.6), 3.40 (s, 3H), 3.09 (dd, 1H, J=14.2, 4.6), 2.96 (dd, 1H, J=14.5, 7.3), 2.33–1.92 (m, 6H).

Example 86

(2S)-(1'R,3'S)3-{4-[3'-(Biphenyl-4-yloxy)-1'-cyclopentyloxy]-phenyl}-2-methoxy-propionic acid

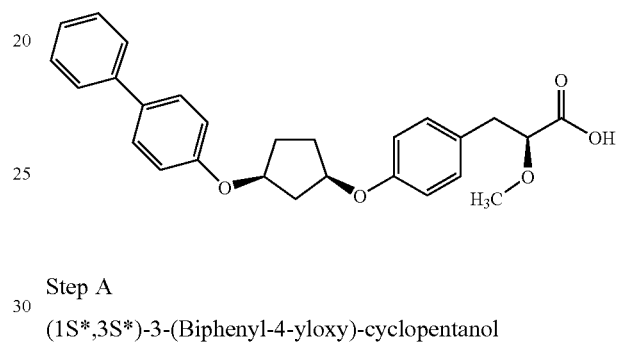

Step A (1S*,3S*)-3-(Biphenyl-4-yloxy)-cyclopentanol

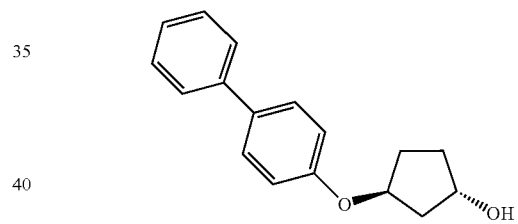

The title compound was prepared starting from (1R*,3S*)-3-(tert-Butyl-dimethyl-silanyloxy)-cyclopentanol of Example 82, Step A, and running a Standard Mitsounobu coupling reaction B (toluene) with 4-phenylphenol. The product then was deprotected by Standard Procedure E to give the compound after purification by chromatography.

Step B (1'S,2S,3'S)-3,3,3-Trifluoro-2-methoxy-2-phenyl-propionic acid 3'-(biphenyl-4-yloxy)-1'-cyclopentyl ester

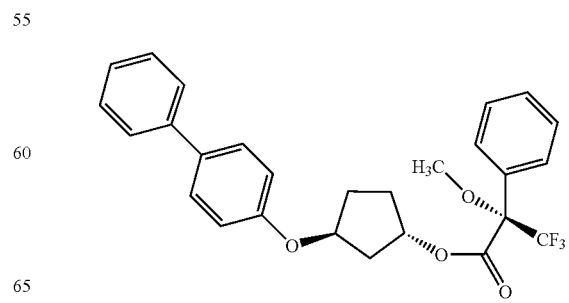

A mixture of (1S*,3S*)-3-(Biphenyl-4-yloxy)-cyclopentanol From Step A (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. overnight. The reaction mixture was cooled and concentrated to dryness. Reconstituted in ether and washed with HCl 1N, and NaHCO₃. Dry over MsSO4 and concentrated in vacuo to give a crude that was purify by silica gel chromatography to give a diastereomeric mixture which was separated using chiral HPLC.

Step C (1S,3S)-3-(Biphenyl-4-yloxy)-cyclopentanol

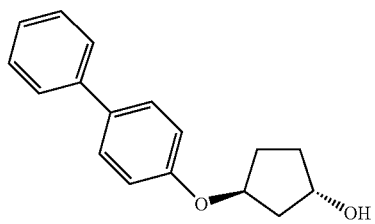

To a solution of compound from Step C in ethanol an excess of NaOH 1N was added and the mixture reaction was stirred at room temperature. The solution was concentrated in vacuo and diluted with brine. Extracted with ether and concentrated to yield the title compound.

Step D (2S)-(1'R,3*S)-3-{4-[3'-(Biphenyl-4-yloxy)-1'-cyclopentyloxy]-phenyl}-2-methoxy-propionic acid The title compound was prepared using the Standard Procedure for Mitsounobu coupling-hydrolysis A in Toluene to give the final compound. MS (ES) for C₂₇H₂₈O₅ [M+NH₄]⁺: 450.2, [M+Na]⁺: 455.2. ¹H-NMR (CDCl₃, 200.15 MHz): 7.56–7.28 (m, 6H), 7.15–7.08 (m, 3H), 6.95 (d, 2H, J=8.9), 6.84–6.73 (m, 2H), 4.81–4.79 (m, 2H), 3.98 (dd, 1H, J=7.0, 4.3), 3.40 (s, 3H), 3.10 (dd, 1H, J=14.2, 4.0), 2.95 (dd, 1H, J=14.2, 7.3), 2.58–2.44 (m, 1H), 2.19–2.02 (m, 5H).

Example 87

(2S)-(1'S,3'R)3-{4-[3'-(Biphenyl-4-yloxy)-1'-cyclopentyloxy]-phenyl}-2-methoxy-propionic acid

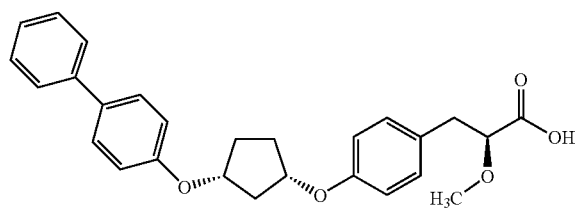

Step A (1'R,2S,3'R)-3,3,3-Trifluoro-2-methoxy-2-phenyl-propionic acid 3'-(biphenyl-4-yloxy)-1'-cyclopentyl ester

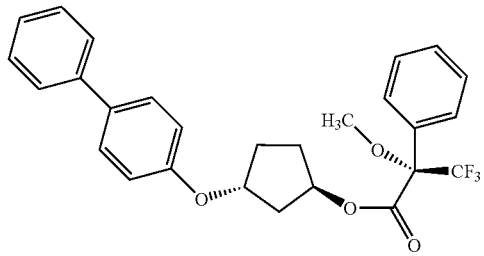

A mixture of (1S*,3S*)-3-(Biphenyl-4-yloxy)-cyclopentanol from Step A (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. overnight. The reaction mixture was cooled and concentrated to dryness. Reconstituted in ether and washed with HCl 1N, and NaHCO₃. Dry over MsSO4 and concentrated in vacuo to give a crude that was purify by silica gel chromatography to give a diastereomeric mixture which was separated using chiral HPLC.

Step B (2S)-(1'S,3'R)3-{4-[3'-(Biphenyl-4-yloxy)-1'-cyclopentyloxy]-phenyl}-2-methoxy-propionic acid The title compound was prepared using the same procedures as in Example 86, Steps C and D, to give the final compound. MS (ES) for C₂₇H₂₈O₅ [M+NH₄]⁺: 450.2, [M+Na]⁺: 455.2. ¹H-NMR (CDCl₃, 200.15 MHz): 7.56–7.28 (m, 6H), 7.15–7.08 (m, 3H), 6.95 (d, 2H, J=8.9), 6.84–6.73 (m, 2H), 4.81–4.79 (m, 2H), 3.98 (dd, 1H, J=7.0, 4.3), 3.40 (s, 3H), 3.10 (dd, 1H, J=14.2, 4.0), 2.95 (dd, 1H, J=14.2, 7.3), 2.58–2.44 (m, 1H), 2.19–2.02 (m, 5H).

Example 88

(2S)-(1'S,3'S)3-{4-[3'-(Biphenyl-4-yloxy)-1'-cyclopentyloxy]-phenyl}-2-methoxy-propionic acid

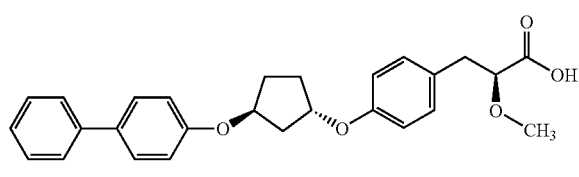

Chiral

The title compound was prepared from (2S)-(1'R*,2'R*)-3-{4-[3-(Biphenyl-4-yloxy)-cyclopentyloxy]-phenyl}-2-methoxy-propionic acid from 0, Step D, which was purified by chiral-HPLC to give the corresponding enantiomer. MS (ES) for C₂₇H₂₈O₅ [M+NH₄]⁺: 450.2, [M+Na]⁺: 455.2. ¹H-NMR (CDCl₃, 200.15 MHz): δ 7.57–7.29 (m, 7H), 7.15 (d, 2H, J=8.6), 6.94 (d, 2H, J=8.9), 6.81 (d, 2H, J=8.6), 4.99–4.91 (m, 2H), 3.99 (dd, 1H, J=7.3, 4.6), 3.41 (s, 3H), 3.10 (dd, 1H, J=14.2, 4.6), 2.96 (dd, 1H, J=14.5, 7.3), 2.31 (t, 2H, J=4.8), 2.26–1.97 (m, 4H).

Example 89

(2S)-(1'R,3'R)-3-{4-[3'-(Biphenyl-4-yloxy)-1'-cyclopentyloxy]-phenyl}-2-methoxy-propionic acid

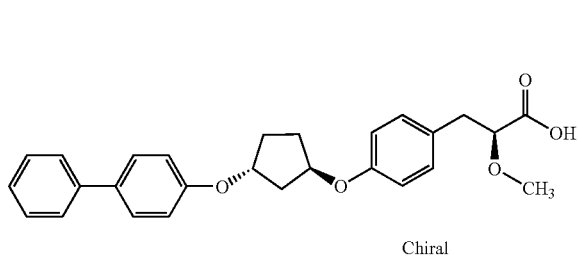

Chiral

The title compound was prepared from (2S)-(1'R*,2'R*) 3-{4-[3-(Biphenyl-4-yloxy)cyclopentyloxy]-phenyl}-2-methoxy-propionic acid from Example 81, Step D, which was purified by chiral-HPLC to give the corresponding enantiomer. $^1$H-NMR (CDCl$_3$, 200.15 MHz): d 7.57–7.29 (m, 7H), 7.15 (d, 2H, J=8.6), 6.94 (d, 2H, J=8.9), 6.81 (d, 2H, J=8.6), 4.99–4.91 (m, 2H), 3.99 (dd, 1H, J=7.3, 4.6), 3.41 (s, 3H), 3.10 (dd, 1H, J=14.2, 4.6), 2.96 (dd, 1H, J=14.5, 7.3), 2.31 (t, 2H, J=4.8), 2.26–1.97 (m, 4H). MS (ES) for C$_{27}$H$_{28}$O$_5$ [M+Na]$^+$: 455.

Example 90

(2S)-(1'R,3'S)-3-{4-[3'-(Biphenyl-4-yloxy)-1'-cyclohexyloxy]-phenyl}-2-methoxy-propionic acid

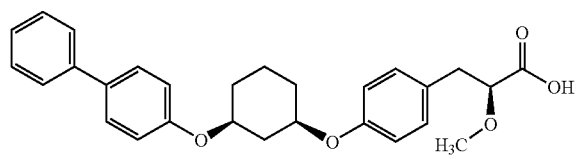

Step A 3-(tert-Butyl-dimethyl-silanyloxy)-cyclohexanol

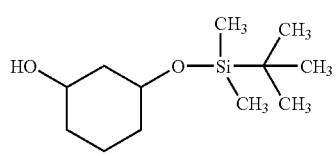

The title compound was prepared following the Standar Procedure D for the monoprotection of diols, to give the product as a colorless oil.

Step B

[3-(Biphenyl-4-yloxy)-cyclohexyloxy]-tert-butyl-dimethyl-silane

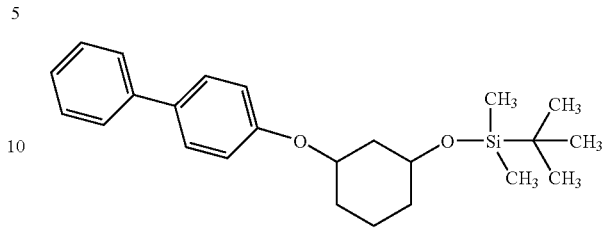

The title compound was prepared using the Standard Procedure for Mitsounobu coupling B (Toluene) to give the product as a colorless oil. MS (ES) for C$_{24}$H$_{34}$O$_2$Si: [M+H]$^+$: 383.3.

Step C 3-(Biphenyl-4-yloxy)-cyclohexanol

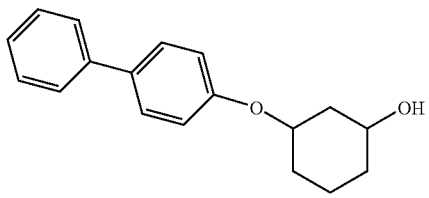

The title compound was prepared by the Standard Procedure E for cleveage the protected alcohols to give a mixture of the four isomers of the compounds. The mixture was purified by silicagel chromatography to give the corresponding two isomers (trans). (1S*,3S*)-3-(Biphenyl-4-yloxy)-cyclohexanol $^1$H-NMR (CDCl3, 500.00 MHz): 7.55 (d, J=7.3 Hz, 2H), 7.51 (d, J=8.5 Hz, 2H); 7.41 (t, J=7.9 Hz, 2H); 7.30 (t, J=7.3 Hz, 1H); 6.97 (d, J=8.5 Hz, 2H); 4.74–4.72 (m, 1H); 4.20–4.15 (m, 1H); 2.09–2.04 (m, 1H); 1.86–1.70 (m, 6H); 1.53–1.27 (m, 3H)ppm and (cis)(1R*, 3S)-3-(Biphenyl-4-yloxy)-cyclohexanol $^1$H-NMR (CDCl$_3$, 500.00 MHz): 7.54 (d, J=7.6 Hz, 2H); 7.51 (d, J=8.5 Hz, 2H); 7.41 (t, J=7.6 Hz, 2H); 7.30 (t, J=7.3 Hz, 1H); 6.97 (d, J=8.5 Hz, 2H); 4.39–4.36 (m, 1H); 3.83–3.80 (m, 1H); 2.31 (d, J=12.3 Hz, 1H); 2.04–1.85 (m, 4H); 1.72–1.34 (m, 10H)ppm.

Step D (1R,3S)-(2S)-3,3,3-Trifluoro-2-methoxy-2-phenyl-propionic acid 3-(biphenyl-4-yloxy)-1-cyclohexyl ester

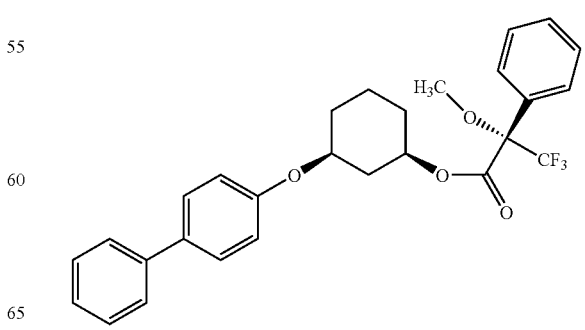

A mixture of (1R*,3S*)-3-(Biphenyl-4-yloxy)-cyclohexanol from Step C (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. over night. The reaction mixture was cooled and concentrated to dryness. Reconstituted in: ether and washed with HCl 1N, and NaHCO₃. Dry over MsSO₄ and concentrated in vacuo to give a crude that was purified by silica gel chromatography to give a diastereomeric mixture which was separated using chiral HPLC Step E
(1R,3S)-3-(Biphenyl-4-yloxy)-cyclohexanol

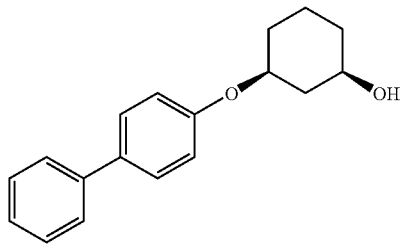

To a solution of compound from Step D in ethanol an excess of NaOH 1N was added and the mixture reaction was stirred at room temperature. The solution was concentrated in vacuo and diluted with brine. Extracted with ether and concentrated to yield the title compound.

Step F (2S)-(1'S,3'R)-3-{4-[3'-(Biphenyl-4-yloxy)-1'-cyclohexyloxy]-phenyl}-2-methoxy-propionic acid The title compound was prepared using the Standard Procedure for Mitsounobu coupling-hydrolysis A in Toluene to give the final compound. ¹H-NMR (CDCl₃, 200.15 MHz): 7.73–7.28 (m, 7H), 7.12 (dd, 2H, J=10.2, 8.6), 7.00–6.93 (m, 1H), 6.86–6.73 (m, 2H), 4.34–4.19 (m, 2H), 3.98 (dd, 1H, J=7.3, 4.3), 3.39 (s, 3H), 3.09 (dd, 1H, J=14.2, 4.0), 2.94 (dd, 1H, J=14.5, 7.3), 2.67–2.61 (m, 1H), 2.27–2.18 (m, 1H), 1.96–1.93 (m, 1H), 1.71–1.54 (m, 1H), 1.46–1.37 (m, 3H).

Example 91

(2S)-(1'S,3'R)-3-{4-[3'-(Biphenyl-4-yloxy)-1'-cyclohexyloxy]-phenyl}-2-methoxy-propionic acid

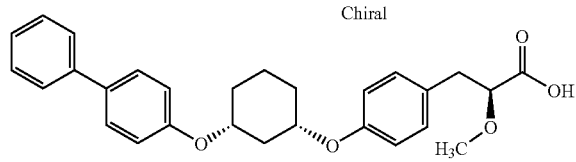

Step A (1S,3R)-(2S)-3,3,3-Trifluoro-2-methoxy-2-phenyl-propionic acid 3-(biphenyl-4-yloxy)-1-cyclohexyl ester

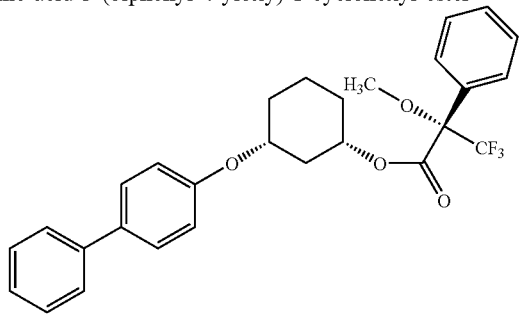

A mixture of (1R*,3S*)-3-(Biphenyl-4-yloxy)-cyclohexanol from Example 90, Step C (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. over night. The reaction mixture was cooled and concentrated to dryness. Reconstituted in ether and washed with HCl 1N, and NaHCO₃. Dry over MsSO₄ and concentrated in vacuo to give a crude that was purified by silica gel chromatography to give a diastereomeric mixture which was separated using chiral HPLC.

Step B (1S,3R)-3-(Biphenyl-4-yloxy)-cyclohexanol

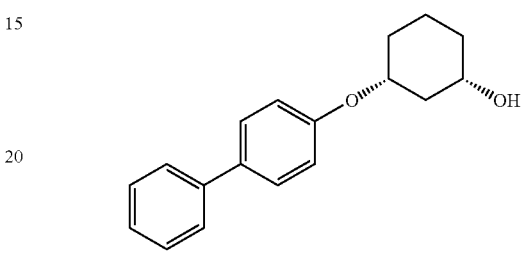

The compound was prepared using the same procedure as in Example 90, Step E.

Step C (2S)-(1'S,3'R)-3-{4-[3'-(Biphenyl-4-yloxy)-1'-cyclohexyloxy]-phenyl}-2-methoxy-propionic acid The title compound was prepared using the Standard Procedure for Mitsounobu coupling-hydrolysis A in toluene to give the final compound. ¹H-NMR (CDCl₃, 200.15 MHz): 7.73–7.28 (m, 7H), 7.12 (dd, 2H, J=10.2, 8.6), 7.00–6.93 (m, 1H), 6.86–6.73 (m, 2H), 4.34–4.19 (m, 2H), 3.98 (dd, 1H, J=7.3, 4.3), 3.39 (s, 3H), 3.09 (dd, 1H, J=14.2, 4.0), 2.94 (dd, 1H, J=14.5, 7.3), 2.67–2.61 (m, 1H), 2.27–2.18 (m, 1H), 1.96–1.93 (m, 1H), 1.71–1.54 (m, 1H), 1.46–1.37 (m, 3H).

Example 92

(2S)-(1'R,3'R)-3-{4-[3'-(Biphenyl-4-yloxy)-1'-cyclohexyloxy]-phenyl}-2-methoxy-propionic acid

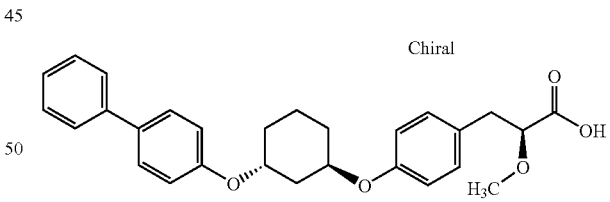

Step A (1R,3S)-(2S)-3,3,3-Trifluoro-2-methoxy-2-phenyl-propionic acid 3-(biphenyl-4-yloxy)-1-cyclohexyl ester

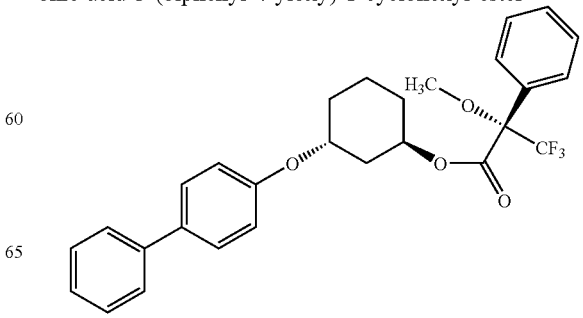

A mixture of (1R*,3R*)-3-(Biphenyl-4-yloxy)-cyclohexanol (trans), from Example 90, Step C (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. over night. The reaction mixture was cooled and concentrated to dryness. Reconstituted in ether and washed with HCl 1N, and NaHCO₃. Dry over MsSO4 and concentrated in vacuo to give a crude that was purify by silcagel chromatography to give a diastereomeric mixture which was separated using chiral HPLC.

Step B (1R,3R)-3-(Biphenyl-4-yloxy)-cyclohexanol

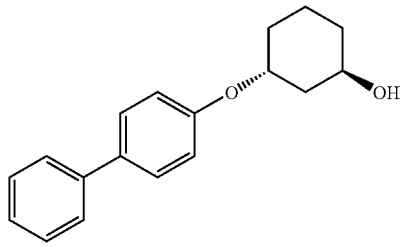

The compound was prepared using the same procedure as in Example 90, Step E.

Step C (2S)-(1'R,3'R)-3-{4-[3'-(Biphenyl-4-yloxy)-1'-cyclohexyloxy]-phenyl}-2-methoxy-propionic acid The title compound was prepared using the Standard Procedure for Mitsounobu coupling-hydrolysis A in toluene to give the final compound. ¹H-NMR (CDCl₃, 200.15 MHz): 7.57–7.27 (m, 7H), 7.13 (d, 2H, J=8.6), 6.96 (dd, 2H, J=6.7, 2.1), 6.83 (d, 2H, J=8.9), 4.75–4.72 (m, 2H), 4.00–3.95 (m, 1H), 3.38 (s, 3H), 3.09 (dd, 1H, J=14.8, 4.3), 2.94 (dd, 1H, J=14.5, 7.5), 2.12–2.05 (m, 3H), 1.80–1.78 (m, 5H).

Example 93

(2S)-(1'S,3'S)-3-{4-[3'-(Biphenyl-4-yloxy)-1'-cyclohexyloxy]-phenyl}-2-methoxy-propionic acid

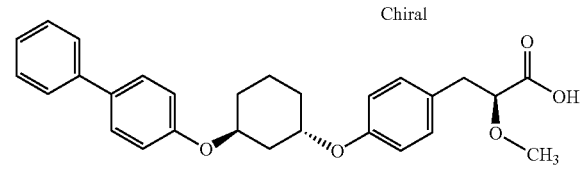
Chiral

Step A (1S,3S)-(2S)-3,3,3-Trifluoro-2-methoxy-2-phenyl-propionic acid 3-(biphenyl-4-yloxy)-1-cyclohexyl ester

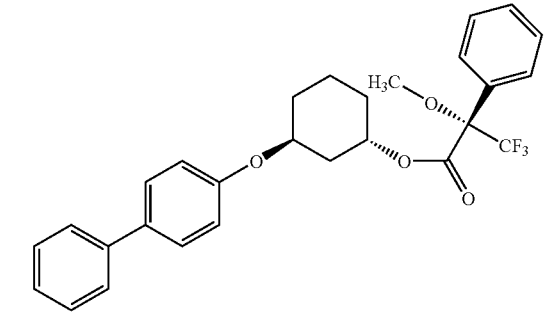

A mixture of (1R*,3R*)-3-(Biphenyl-4-yloxy)-cyclohexanol (trans), from Example 90, Step C (1 eq) with (S)-(−)-α-methoxy-α-(trifluoromethyl)-phenylacetic acid (1 eq), DMAP (0.1 eq) and EDCI (1.2 eq) in dichloromethane was stirred at 36° C. over night. The reaction mixture was cooled and concentrated to dryness. Reconstituted in ether and washed with HCl 1N, and NaHCO₃. Dry over NaSO4 and concentrated in vacuo to give a crude that was purify by silica gel chromatography to give a diastereomeric mixture which was separated using chiral HPLC.

Step B (1S,3S)-3-(Biphenyl-4-yloxy)-cyclohexanol

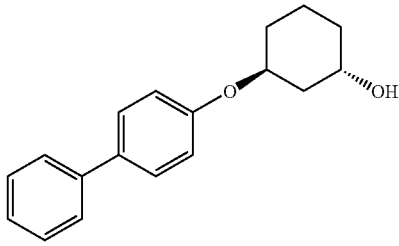

The compound was prepared using the same procedure as in Example 90, Step E.

Step C (2S)-(1'S,3'S)-3-{4-[3'-(Biphenyl-4-yloxy)-1'-cyclohexyloxy]-phenyl}-2-methoxy-propionic acid The title compound was prepared using the Standard Procedure for Mitsounobu coupling-hydrolysis A in toluene to give the final compound. ¹H-NMR (CDCl₃, 200.15 MHz): 7.57–7.27 (m, 7H), 7.13 (d, 2H, J=8.6), 6.96 (dd, 2H, J=6.7, 2.1), 6.83 (d, 2H, J=8.9), 4.75–4.72 (m, 2H), 4.00–3.95 (m, 1H), 3.38 (s, 3H), 3.09 (dd, 1H, J=14.8, 4.3), 2.94 (dd, 1H, J=14.5, 7.5), 2.12–2.05 (m, 3H), 1.80–1.78 (m, 5H).

Example 94

(2S)-3-{1-[3-(4-Benzoyl-phenoxy)-propoxy]-phenyl}-2-methoxy-propionic acid

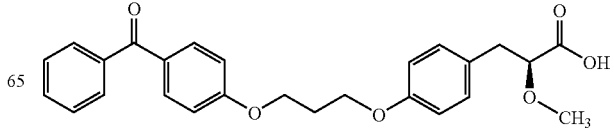

Step A (2S)-3-[4-(tert-Butyl-dimethyl-silanyloxy)-phenyl]-2-methoxy-propionic acid

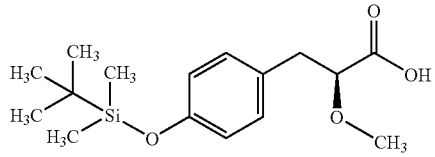

To a solution of (2S)-3-hydroxyphenyl-2-methoxy-propionic acid (7.30 g, 37.2 mmol) in 40 mL of dry DMF was added tert-butyldimethylsilyl chloride (11.80 g, 78.2 mmol) and imidazole (5.32 g, 78.2 mmol). The solution was stirred at room temperature overnight. Water (40 mL) was added, and the aqueous phase was extracted with hexanes (40 mL). The organic layer was washed with water (50 mL), dried ($MgSO_4$), and concentrated. The crude material was dissolved in THF (20 mL), and saturated $NaHCO_3$ solution (20 mL) was added. The resulting mixture was stirred for 2 hours at room temperature. The aqueous layer was extracted with ethyl acetate (40 mL), acidified to pH 3, and extracted again with ethyl acetate (3×40 mL). The combined organic layers were washed with brine (60 mL) and dried (MgSO4), and concentrated to a yellow oil (11.5 g, 99%). $^1$H-NMR (200.15 MHz, $CDCl_3$): δ 7.09 (d, 2H, J=8.3), 6.76 (d, 2H, J=8.6), 3.97 (dd, 1H, J=7.5, 4.3), 3.38 (s, 3H), 3.09 (dd, 1H, J=14.5, 4.3), 2.93 (dd, 1H, J=14.2, 7.3), 0.97 (s, 9H), 0.18 (6H, s).

Step B

Preparation of (2S)-3-[4-(tert-Butyl-dimethyl-silanyloxy)-phenyl]-2-methoxy-propionic acid linked to Wang's Resin

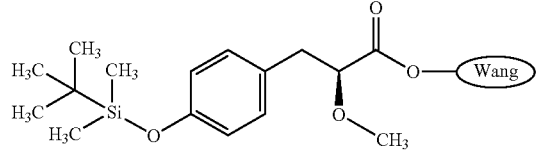

The reaction was carried out in a polypropylene syringe equipped with a polypropylene frit. Wang's resin (1 eq, ca. 1.2 mmol/g resin) was suspended in dichloromethane (0.05 M) and (2S)-3-[4-(tert-butyldimethylsilanyloxy)phenyl]-2-methoxypropionic acid (1.5 eq), disopropylcarbodiimide (2.0 eq), and a catalytic amount of dimethylaminopyridine were added. The mixture was shaken at room temperature overnight. The reaction solvent was removed, and the resin was washed sequentially with $CH_2Cl_2$ (2×), DMF (2×), $CH_2Cl_2$ (2×), methanol, and $CH_2Cl_2$ (2×). The resin was dried under vacuum for 5 hours. The resin was suspended in $CH_2Cl_2$ (0.05 M) and treated with acetic anhydride (5 eq) and a catalytic amount of dimethyaminopyridine for 2 hours. The solvent was removed and the resin washed sequentially with a mixture of 1:1 acetic acid/$CH_2Cl_2$ (3×), $CH_2Cl_2$ (2×), methanol, $CH_2Cl_2$ (2×) and dried under vacuum overnight to give (2S)-3-[4-(tert-butyldimethylsilanyloxy)-phenyl]-2-methoxy-propionic acid linked to Wang's Resin.

Step C

Preparation of (2S)-3-(4-Hydroxy-phenyl)-2-methoxy-propionic acid linked to Wang's Resin

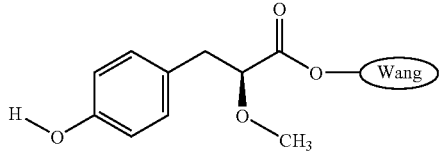

The reaction was carried out in a polypropylene syringe equipped with a polypropylene frit. To a suspension of (2S)-3-[4-(tert-butyldimethylsilanyloxy)-phenyl]-2-methoxy-propionic acid linked to Wang's Resin (1 eq) in dichloromethane (0.05 M) was added tetrabutylammonium fluoride (ca 5 eq). The mixture was shaken at room temperature for 3 hours. The solvent was removed, and the resin was washed sequentially with $CH_2C_2$ (2×), DMF (2×), $CH_2Cl_2$ (2×), is methanol, and $CH_2Cl_2$ (2×). The resin was dried under vacuum overnight to produce (2S) 3-(4-hydroxy-phenyl)-2-methoxy-propionic acid linked to Wang's Resin. Cleavage of 20 mg of the resin in TFA/$CH_2Cl_2$ 1:1 followed by evaporation of the solvent produced (S)-3-(4-hydroxy-phenyl)-2-methoxy-propionic acid as an oil. $^1$H-NMR (200.15 MHz, $CDCl_3$): δ 7.10 (d, 2H, J=8.6), 6.76 (d, 2H, J=8.6), 3.99 (dd, 1H, J=7.0, 4.6), 3.41 (s, 3H), 3.10 (dd, 1H, J=14.5, 4.6), 2.95 (dd, 1H, J=14.5, 7.5).

Step D

Preparation of (2S)-3-[4-(3-Hydroxy-propoxy phenyl]-2-methoxy-propionic acid linked to Wang's Resin

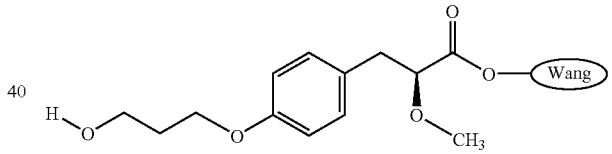

The title compound was prepared from (2S)-3-(4-hydroxy-phenyl)-2-methoxy-propionic acid linked to Wang's Resin via Mitsunobu coupling (Standard Procedure F) to produce (2S)-3-[4-(3-hydroxy-propoxy)-phenyl]-2-methoxy-propionic acid linked to Wang's Resin. Cleavage of 20 mg of the resin in TFA/$CH_2Cl_2$ 1:1 followed by evaporation of the solvent produced (2S)-3-[4-(3-hydroxy-propoxy)-phenyl]-2-methoxy-propionic acid as an oil. $^1$H-NMR (200.15 MHz, $CDCl_3$): δ 7.16 (d, 2H, J=8.6), 6.82 (d, 2H, J=8.6), 4.56 (t, 1H, J=6.2), 4.09 (2H, dd, J=13.2, 5.9), 3.99 (dd, 1H, J=6.7, 4.0), 3.90 (1H, t, J=5.9), 3.40 (s, 3H), 3.10 (dd, 1H, J=14.2, 4.0), 2.96 (dd, 1H, J=14.2, 7.3), 2.22 (qn, 1H, J=5.9), 2.05 (qn, 1H, J=5.9).

Step E (2S)-3-{4-[3-(4-Benzoyl-phenoxy)-propoxy]-phenyl}-2-methoxy-propionic acid The title compound was prepared from (2S)-3-[4-(3-hydroxy-propoxy)-phenyl]-2-methoxy-propionic acid linked to Wang's Resin via the Mitsunobu coupling-cleavage from the resin procedure (Standard Procedure G) to give 1.6 mg of a white solid (6%). $^1$H-NMR (200.15 MHz, $CDCl_3$): δ 7.82–7.72 (m, 4H), 7.57–7.43 (m, 3H), 7.14 (d, 2H, J=8.8), 6.96 (d, 2H, J=8.8), 6.84 (d, 2H, J=8.8), 4.25 (t, 2H, J=6.0), 4.14 (t, 2H, J=6.0), 4.00 (dd, 1H, J=6.8, 4.6 Hz), 3.41 (s, 3H), 3.10 (dd, 1H, J=14.1, 4.6), 2.97 (dd, 1H, J=14.1, 6.8), 2.28 (qn, 2H, J=6.0).

Example 95

(2S)-3-(4-{3-[4-(4-Fluoro-benzoyl)-phenoxy]-propoxy}-phenyl)-2-methoxy-propionic acid

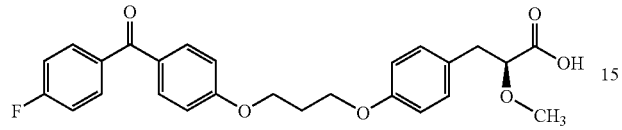

The title compound was prepared from (2S)-3-[4-(3-hydroxy-propoxy)-phenyl]-2-methoxy-propionic acid linked to Wang's Resin (Example 94, Step D) via Mitsunobu coupling with 4-hydroxybenzophenone and cleavage from the resin (Standard Procedure G) gave an oil (7%). $^1$H-NMR (200.15 MHz, CDCl$_3$): δ 7.82–7.73 (m, 4H), 7.19–7.10 (m, 4H), 6:96 (d, 2H, J=8.9), 6.84 (d, 2H, J=8.9), 4.25 (t, 2H, J=6.0), 4.15 (t, 2H, J=6.0), 4.00 (dd, 1H, J=6.7, 4.6), 3.41 (s, 3H), 3.10 (dd, 1H, J=14.1, 4.6), 2.97 (dd, dd, J=14.1, 6.8), 2.28 (qn, 2H, J=6.0). MS (ES) for C$_{26}$H$_{25}$FO$_6$ [M+H]$^+$: 453.2, [M+Na]$^+$: 475.2.

Example 96

(2S)-3-{4-[3-(4-Benzoyl-phenoxy)-propoxy]-phenyl}-2-methoxy-propionic acid

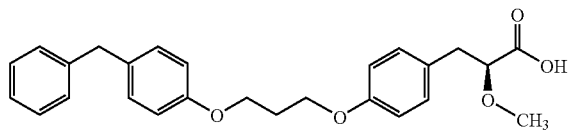

The title compound was prepared from (2S)-3-[4-(3-hydroxy-propoxy)-phenyl]-2-methoxy-propionic acid linked to Wang's Resin (Example 94, Step D) via Mitsunobu coupling with 4-hydroxydiphenylmethane and cleavage from the resin (Standard Procedure G) produced a white solid (5%). $^1$H-NMR (200.15 MHz, CDCl$_3$): δ 7.29–7.13 (m, 6H), 7.08 (d, 2H, J=8.9), 6.82 (d, 2H, J=8.6), 4.12 (t, 4H, J=6.2), 3.97 (dd, 1H, J=6.6, 4.0), 3.39 (s, 3H), 3.10 (dd, 1H, J=14.2, 4.0), 2.95 (dd, 1H, J=14.2, 6.6), 2.22 (qn, 2H, J=6.2).

Example 97

(2S)-2-Methoxy-3-{4-[3-(3-phenylamino-phenoxy)-propoxy]-phenyl}-propionic acid

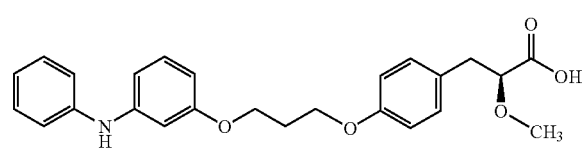

The title compound was prepared from (2S)-3-[4-(3-hydroxy-propoxy)-phenyl]-2-methoxy-propionic acid linked to Wang's Resin (Example 94, Step D) via Mitsunobu coupling with 3-hydroxydiphenylamine and cleavage from the resin (Standard Procedure G) gave an oily solid (4%). $^1$H-NMR (200.15 MHz, CDCl$_3$): δ 7.31–6.81 (m, 8H), 6.83 (d, 2H, J=8.6), 6.65–6.62 (m, 2H), 6.48 (dd, 1H, J=8.2, 2.1), 4.12 (t, 4H, J=6.2), 3.99 (dd, 1H, J=7.0, 4.4), 3.40 (s, 3H), 3.10 (dd, 1H, J=14.2, 4.4), 2.95 (dd, 1H, J=14.2, 7.0), 2.22 (qn, 2H, J=6.2).

Example 98

(2S)-3-{4-[3-(4-Butyl-phenoxy)-propoxy]-phenyl}-2-methoxy-propionic acid

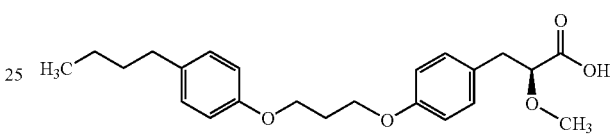

The title compound was prepared from (2S)-3-[4-(3-hydroxy-propoxy)-phenyl]-2-methoxy-propionic acid linked to Wang's Resin (Example 94, Step D) via Mitsunobu coupling with 4-n-butylphenol and cleavage from the resin (Standard Procedure G) gave an oily solid (7%). $^1$H-NMR (200.15 MHz, CDCl$_3$): δ 7.11 (dd, 4H, J=12.7, 8.6), 6.82 (dd, 4H, J=8.6, 3.2), 4.12 (t, 4H, J=6.2), 3.97 (dd, 1H, J=7.7, 4.4), 3.38 (s, 3H), 3.30 (dd, 1H, J=14.5, 4.4), 2.94 (dd, 1H, J=14.5, 7.7), 2.54 (t, 2H, J=7.7), 2.23 (qn, 2H, J=6.2), 1.63–1.48 (m, 2H), 1.42–1.24 (m, 2H), 0.91 (t, 3H, J=7.2).

Example 99

(2S)-3-(4-{3-[4-(2-Fluoro-benzoyl)-phenoxy]-propoxy}-phenyl)-2-methoxy-propionic acid

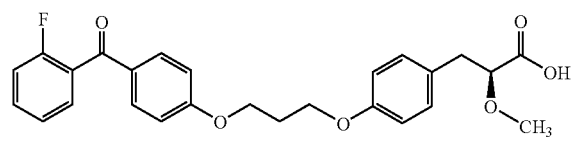

The title compound was prepared from (2S)-3-[4-(3-Hydroxy-propoxy)-phenyl]-2-methoxy-propionic acid linked to Wang's Resin (Example 94, Step D) via Mitsunobu coupling with 2-fluoro-4'-hydroxybenzophenone and cleavage from the resin (Standard Procedure G) gave an oily solid (7%). $^1$H-NMR (200.15 MHz, CDCl$_3$): δ 7.81 (dd, 2H, J=8.8, 1.3), 7.54–7.45 (m, 2H), 7.28–7.09 (m, 4H), 6.94 (d, 2H, J=8.6), 6.83 (d, 2H, J=8.6), 4.24 (t, 2H, J=6.2), 4.14 (t, 2H, J=6.2), 3.98 (dd, 1H, J=7.0, 4.6), 3.40 (s, 3H), 3.09 (dd, 1H, J=14.2, 4.6), 2.96 (dd, 1H, J=14.2, 7.0), 2.28 (q, 2H, J=6.2).

Example 100

(2S)-2-Methoxy-3-{4-[3-(9-oxo-9H-fluoren-2-yloxy)-propoxy]-phenyl}-propionic acid

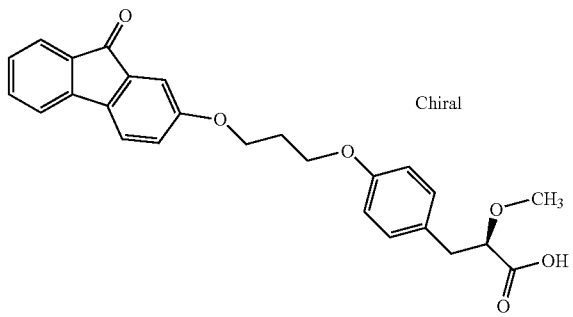

The title compound was prepared from (2S)-3-[4-(3-Hydroxy-propoxy)-phenyl]-2-methoxy-propionic acid linked to Wang's Resin (Example 94, Step D) via Mitsunobu coupling with 2-hydroxy-9-fluorenone and cleavage from the resin (Standard Procedure G) gave an oily solid. $^1$H-NMR (200.15 MHz, CDCl$_3$): 7.59 (d, 1H, J=7.0); 7.43–7.37 (m, 3H); 7.26–7.13 (m, 4H); 6.98 (dd, 1H, J=8.1, 2.4); 6.85 (d, 2H, J=8.6); 4.17 (qui, 4H, J=5.6); 3.99 (dd, 1H, J=7.0, 4.6); 3.40 (s, 3H); 3.10 (dd, 1H, J=14.2, 4.6); 2.96 (dd, 1H, J=14.2, 7.0); 2.32–2.23 (m, 4H) ppm.

Example 101

(2S)-2-Methoxy-3-{4-[3-(2-methyl-benzothiazol-5-yloxy)-propoxy]-phenyl}-propionic acid

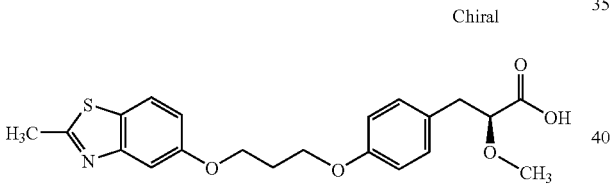

The title compound was prepared from (2S)-3-[4-(3-Hydroxy-propoxy)-phenyl]-2-methoxy-propionic acid linked to Wang's Resin (Example 94, Step D) via Mitsunobu coupling with 2-methyl-5-benzothiazolol and cleavage from the resin (Standard Procedure G) to give an oily solid. $^1$H-NMR (200.15 MHz, CDCl$_3$): 7.65 (d, 1 H, J=8.9), 7.36–7.35 (m, 1 H), 7.16 (d, 2 H, J=8.9), 7.03 (dd, 1 H, J=8.9, 2.4), 6.86 (dd, 2 H, J=6.5, 1.9), 4.22 (t, 2 H, J=35.9), 4.18 (t, 2 H, J=6.2), 4.01 (dd, 2 H, J=6.4, 5.4), 3.43 (s, 3 H), 3.14–2.94 (m, 2 H), 2.87 (s, 3 H), 2.27 (qn, 2 H, J=6.2) ppm.

Example 102

(2S)-2-Methoxy-3-{4-[3-(3-morpholin-4-yl-phenoxy)-propoxy]-phenyl}-propionic acid

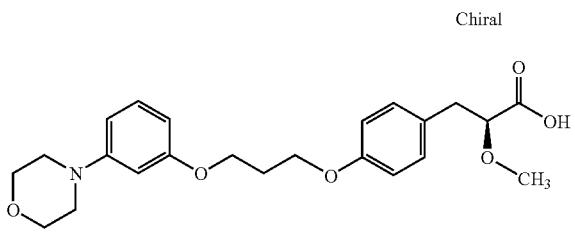

The title compound was prepared from (2S)-3-[4-(3-Hydroxy-propoxy)-phenyl]-2-methoxy-propionic acid linked to Wang's Resin (Example 94, Step D) via Mitsunobu coupling with 3-(4-morpholino)phenol and cleavage from the resin (Standard Procedure G) gave an oily solid. $^1$H-NMR (200.15 MHz, CDCl$_3$): 7.32–7.23 (m, 1 H), 7.14–7.10 (m, 2 H), 6.84–6.69 (m, 5 H), 4.14 (q, 4 H, J=5.6), 4.02–3.94 (m, 5 H), 3.40 (s, 3 H), 3.33–3.28 (m, 4 H), 3.13–2.91 (m, 2 H), 2.23 (qn, 2 H, J=5.9) ppm.

Example 103

(2S)-3-{4-[3-(Biphenyl-2-yloxy)-propoxy]-phenoxy}-2-methoxy-propionic acid

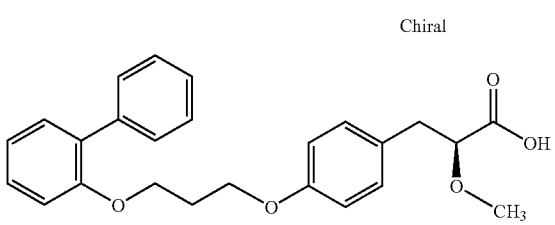

The title compound was prepared from (2S)-3-[4-(3-Hydroxy-propoxy)-phenyl]-2-methoxy-propionic acid linked to Wang's Resin (Example 94, Step D) via Mitsunobu coupling with 2-phenylphenol and cleavage from the resin (Stand Procedure G) to give the title compound. $^1$H-NMR (200.15 MHz, CDCl$_3$): 7.51–7.43 (m, 2 H), 7.38–7.29 (m, 5 H), 7.15–6.98 (m, 4 H), 6.79–6.72 (m, 2 H), 4.15 (t, 2 H, J=5.9 Hz), 4.04–3.96 (m, 3 H), 3.39 (s, 3 H), 3.15–2.90 (m; 2 H), 2.15 (qn, 2 H, J=5.9 Hz) ppm.

Example 104

(2S)-3-{4-[3-(4-Cyclopentyl-phenoxy)-propoxy]-phenyl}-2-methoxy-propionic acid

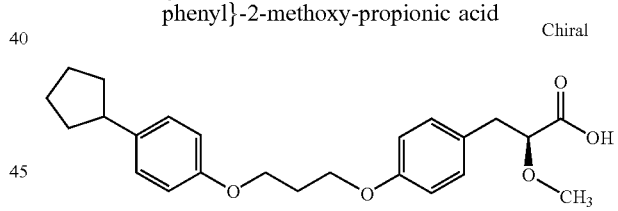

The title compound was prepared from (2S)-3-[4-(3-Hydroxy-propoxy)-phenyl]-2-methoxy-propionic acid linked to Wang's Resin (Example 94, Step D) via Mitsunobu coupling with 4-cyclopentylphenol and cleavage from the resin (Standard Procedure G) gave an oily solid.

Example 105

(2S)-3-{4-[3-(4-Cyano-3-fluoro-phenoxy)-phenyl]}-2-methoxy-propionic acid

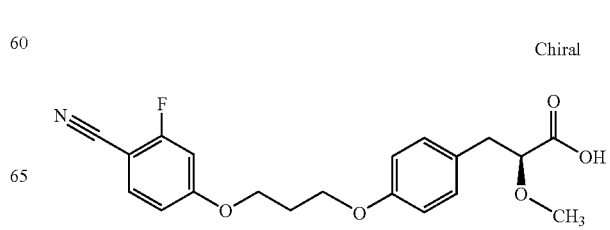

The title compound was prepared from (2S)-3-[4-(3-Hydroxy-propoxy)-phenyl]-2-methoxy-propionic acid linked to Wang's Resin (Example 94, Step D) via Mitsunobu coupling with 2-fluoro-4-hydroxybenzonitrile and cleavage from the resin (Standard Procedure G) gave an oily solid.

Example 106

(2S)-3-{4-[3-(2,4-Difluoro-phenoxy)-propoxy]-phenyl}-2-methoxy-propionic acid

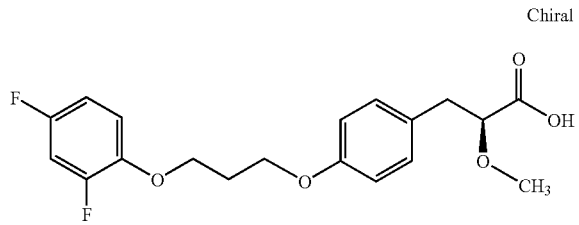

The title compound was prepared from (2S)-3-[4-(3-Hydroxy-propoxy)-phenyl]-2-methoxy-propionic acid linked to Wang's Resin (Example 94, Step D) via Mitsunobu coupling with 2,4-difluorophenol and cleavage from the resin (Standard Procedure G) gave an oily solid.

Example 107

(2S)-2-Methoxy-3-{4-[3-(4-trifluoromethyl-phenoxy)-propoxy]-phenyl}-propionic acid

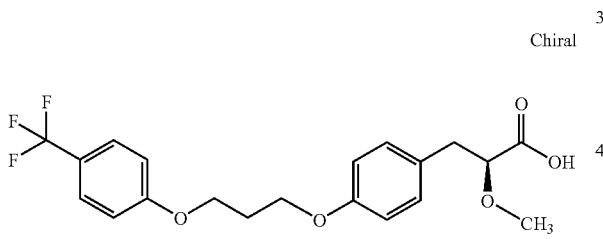

The title compound was prepared from (2S)-3-[4-(3-Hydroxy-propoxy)-phenyl]-2-methoxy-propionic acid linked to Wang's Resin (Example 94, Step D) via Mitsunobu coupling with 4-trifluoromethylphenol and cleavage from the resin (Standard Procedure G) gave an oily solid.

Example 108

(2S)-2-Methoxy-3-{4-[3-(3-trifluoromethyl-phenoxy)-propoxy]-phenyl}-propionic acid

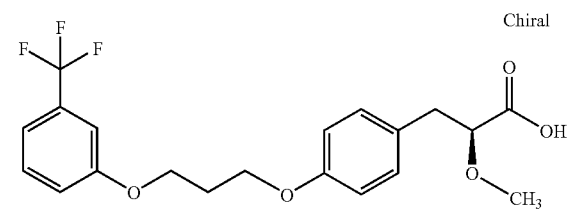

The title compound was prepared from (2S)-3-[4-(3-Hydroxy-propoxy)-phenyl]-2-methoxy-propionic acid linked to Wang's Resin Example 94, Step D) via Mitsunobu coupling with 3-trifluoromethylphenol and cleavage from the resin (Standard Procedure CG) gave an oily solid.

Example 109

(2S)-2-Methoxy-3-{4-[3-(5-oxo-5,6,7,8-tetrahydro-naphthalen-2-yloxy)-propoxy]-phenyl}-propionic acid

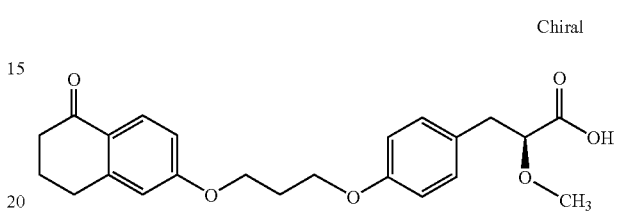

The title compound was prepared from (2S)-3-[4-(3-Hydroxy-propoxy)-phenyl]-2-methoxy-propionic acid linked to Wang's Resin (Example 94, Step D) via Mitsunobu coupling with 6-hydroxy-1,2,3,4-tetrahydronaphtalenone and cleavage from the resin (Standard Procedure G) gave an oily solid.

Example 110

(2S)-3-{4-[3-(3,5-Difluoro-phenoxy)-propoxy]-phenyl}-2-methoxy-propionic acid

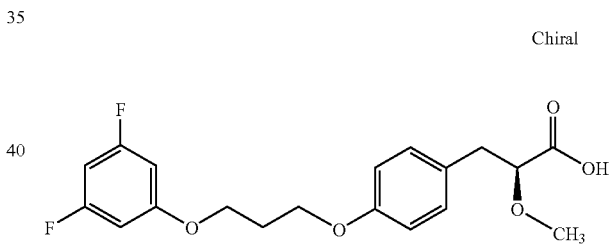

The title compound was prepared from (2S)-3-[4-(3-Hydroxy-propoxy)-phenyl]-2-methoxy-propionic acid linked to Wang's Resin (Example 94, Step D) via Mitsunobu coupling with 3,5-difluorophenol and cleavage from the resin (Standard Procedure G) gave an oily solid.

Example 111

(2S)-3-{4-[3-(Isoquinolin-5-yloxy)-propoxy]-phenyl}-2-methoxy-propionic acid

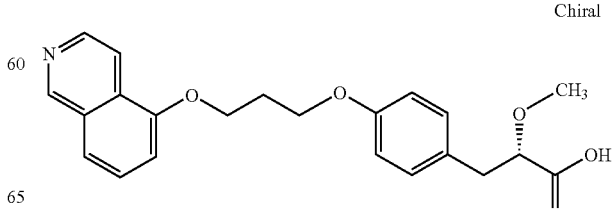

The title compound was prepared from (2S)-3-[4-(3-Hydroxy-propoxy)-phenyl]-2-methoxy-propionic acid linked to Wang's Resin (Example 94, Step D) via Mitsunobu coupling with 5-hydroxyisoquinolyne and cleavage from the resin (Standard Procedure G) gave an oily solid.

Example 112

(2S)-2-Methoxy-3-{4-[3-(4-trifluoromethoxy-phenoxy)-propoxy]-phenyl}-propionic acid

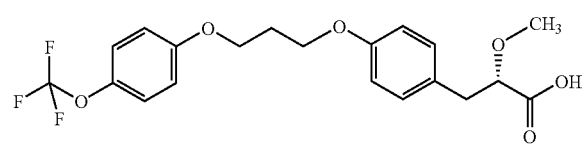

The title compound was prepared from (2S)-3-[4-(3-Hydroxy-propoxy)-phenyl]-2-methoxy-propionic acid linked to Wang's Resin (Example 94, Step D) via Mitsunobu coupling with 4-trifluoromethoxyphenol and cleavage from the resin (Standard Procedure G) gave an oily solid.

Example 113

(2S)-3-{4-[3-(4-Fluoro-phenoxy)-propoxy]-phenyl}-2-methoxy-propionic acid

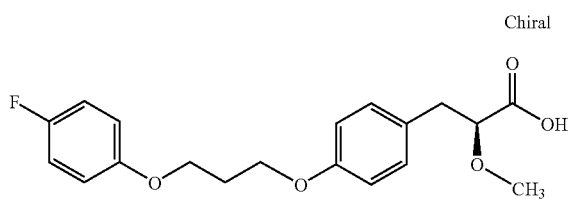

The title compound was prepared from (2S)-3-[4-(3-Hydroxy-propoxy)-phenyl]-2-methoxy-propionic acid linked to Wang's Resin (Example 94, Step D) via Mitsunobu coupling with 4-fluorophenol and cleavage from the resin (Standard Procedure G) gave an oily solid.

Example 114

(2S)-2-Methoxy-3-{4-[3-(4-phenylacetyl-phenoxy)-propoxy]-phenyl}-propionic acid

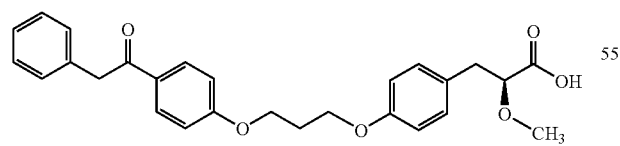

The title compound was prepared from (2S)-3-[4-(3-Hydroxy-propoxy)-phenyl]-2-methoxy-propionic acid linked to Wang's Resin (Example 94, Step D) via Mitsunobu coupling with benzyl-4-hydroxyphenylketone and cleavage from the resin (Standard Procedure G) gave an oily solid.

Example 115

(2S)-2-Methoxy-3-(4-{3-[4-(1-methyl-1-phenyl-ethyl)-phenoxy]-propoxy}-phenyl)-propionic acid

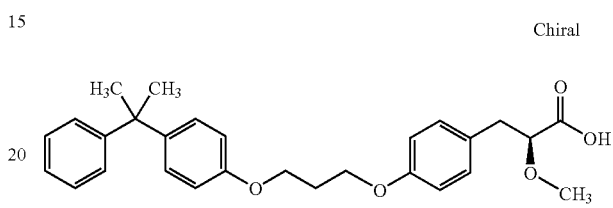

The title compound was prepared from (2S)-3-[4-(3-Hydroxy-propoxy)-phenyl]-2-methoxy-propionic acid linked to Wang's Resin (Example 94, Step D) via Mitsunobu coupling with 4-cumylphenol and cleavage from the resin (Standard Procedure G) gave an oily solid.

Example 116

(2S)-2-Methoxy-3-{4-[3-(4-oxo-2-phenyl-4H-chromen-7-yloxy)-propoxy]-phenyl}-propionic acid

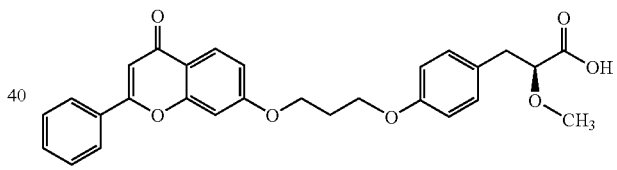

The title compound was prepared from (2S)-3-[4-(3-Hydroxy-propoxy)-phenyl]-2-methoxy-propionic acid linked to Wang's Resin (Example 94, Step D) via Mitsunobu coupling with 7-hydroxyflavone and cleavage from the resin (Standard Procedure G) gave an oily solid.

Example 117

4-{3-[4-(2-Carboxy-2-methoxy-ethyl)-phenoxy]-propoxy}-benzoic acid benzyl ester

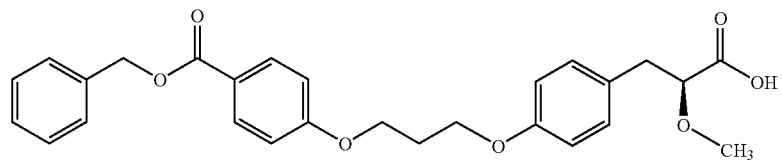

The title compound was prepared from (2S)-3-[4-(3-Hydroxy-propoxy)-phenyl]-2-methoxy-propionic acid linked to Wang's Resin (Example 94, Step D) via Mitsunobu coupling with benzyl 4-hydroxybenzoate and cleavage from the resin (Standard Procedure G) gave an oily solid.

Example 118

(2S)-2-Methoxy-3-{4-[3-(4-oxo-2-phenyl-chroman-6-yloxy)-propoxy]-phenyl}-propionic acid

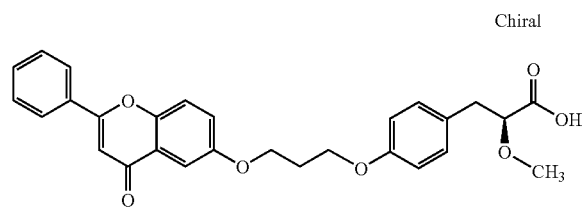

The title compound was prepared from (2S)-3-[4-(3-Hydroxy-propoxy)-phenyl]-2-methoxy-propionic acid linked to Wang's Resin (Example 94, Step D) via Mitsunobu coupling with 6-hydroxyflavone and cleavage from the resin (Standard Procedure G) gave an oily solid.

Example 119

(2S)-2-Methoxy-3-{4-[3-(4-oxo-2-phenyl-chroman-6-yloxy)-propoxy]-phenyl}-propionic acid

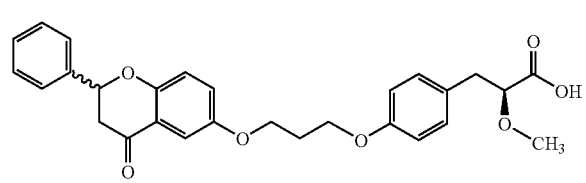

The title compound was prepared from (2S)-3-[4-(3-Hydroxy-propoxy)-phenyl]-2-methoxy-propionic acid linked to Wang's Resin (Example 94, Step D) via Mitsunobu coupling with 6-hydroxyflavanone and cleavage from the resin (Standard Procedure G) gave an oily solid.

Example 120

(2S)-2-Methoxy-3-{4-[3-(4-oxo-2-phenyl-chroman-7-yloxy)-propoxy]-phenyl}-propionic acid

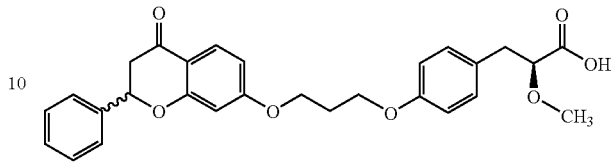

The title compound was prepared from (2S)-3-[4-(3-Hydroxy-propoxy)-phenyl]-2-methoxy-propionic acid linked to Wang's Resin Example 94, Step D) via Mitsunobu coupling with 7-hydroxyflavanone and cleavage from the resin (Standard Procedure G) gave an oily solid.

Example 121

(2S)-2-Methoxy-3-(4-{3-[4-(4-trifluoromethyl-phenoxy)-phenoxy]-propoxy}-phenyl)-propionic acid

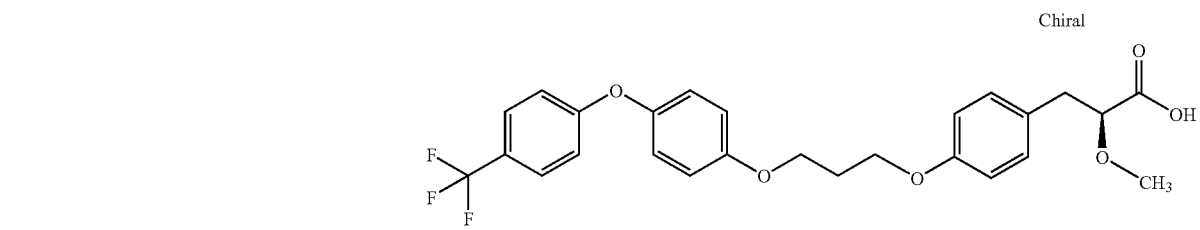

The title compound was prepared from (2S)-3-[4-(3-Hydroxy-propoxy)-phenyl]-2-methoxy-propionic acid linked to Wang's Resin (Example 94, Step D) via Mitsunobu coupling with 4-(4-trifluoromethyl)phenoxyphenol and cleavage from the resin (Standard Procedure G) gave an oily solid.

Example 122

(2S)-3-{4-[2-(4-benzoyl-phenoxy)-ethoxy]-phenyl}-2-methoxy-propionic acid

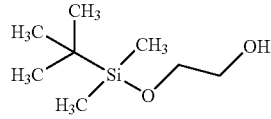

Step A 2-(tert-Butyl-dimethyl-silanyloxy)-ethanol

To a solution of ethylene glycol (1.00 g, 16.1 mmol) in THF (80 mL) was added NaH (0.65 mg, 16.1 mmol, 60% oil dispersion) at 0° C. The reaction was stirred 1 hour, tert-butyldimethylsilyl chloride (2.35 g, 16.1 mmol) was added, and the reaction mixture was allowed to warm to room temperature. After 3 hours at room temperature, $Na_2CO_3$ saturated solution (80 mL) was added, and the aqueous layer was extracted with ethyl acetate (3×50 mL). The combined organic layers were washed with water (80 mL) and brine (80 mL), dried over ($MgSO_4$), and concentrated under vacuum. The reaction crude was purified by silica gel column chromatography (silica gel, hexanes/ethyl acetate, 2:3) to produce 1.93 g, (85%) of a yellow oil. $^1$H-NMR (200.15 MHz, $CDCl_3$): δ 3.74–3.59 (m, 4H), 0.91 (s, 9H), 0.08 (s, 6H).

Step B

Preparation of (2S)-3-{4-[2-(tert-Butyl-dimethyl-silanyloxy)-ethoxy]-phenyl}-2-methoxy-propanoic acid linked to Wang's Resin

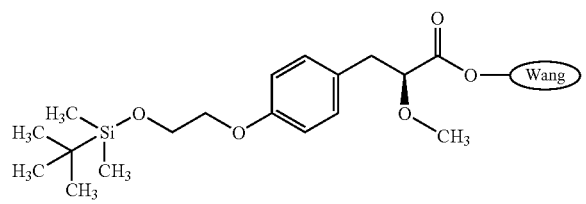

The title compound was prepared from (2S)-3-(4-hydroxy-phenyl)-2-methoxy-propionic acid linked to Wang's Resin (Example 94, Step D) via the Mitsunobu coupling procedure with 2-(tert-butyldimethylsilanyloxy)ethanol (Standard Procedure B).

Step C

Preparation of (2S)-3-[4-[2-Hydroxyethoxy]-phenyl}-2-methoxy-propanoic acid linked to Wang's Resin

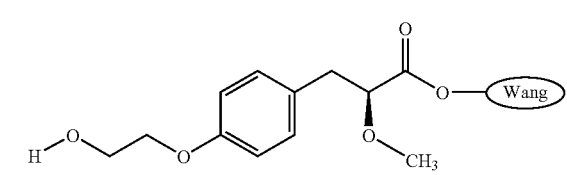

The title compound was prepared from 3-{4-[2-tert-butydimethylsilanyloxy)ethoxy]-phenyl}-2-methoxy-propanoic acid linked to Wang's Resin when treated with tetrabutylammonium fluoride in THF as described in Standard Procedure E. Cleavage of 20 mg of the resin in $TFA/CH_2Cl_2$ (1:1) followed by evaporation of the solvent produced (2S)-3-[4-[2-hydroxy-ethoxy]-phenyl}-2-methoxy-propanoic acid as an oil. $^1$H-NMR (200.15 MHz, $CDCl_3$): δ 7.16 (d, 2H, J=8.6), 6.85 (d, 2H, J=8.9), 4.09–3.93 (m, 5H), 3.41 (s, 3H), 3.11 (dd, 1H, J=14.5, 4.0), 2.97 (dd, 1H, J=14.5, 7.2).

Step D (2S)-3-{4-[2-(4-Benzoyl-phenoxy)-ethoxy]-phenyl}-2-methoxy-propionic acid

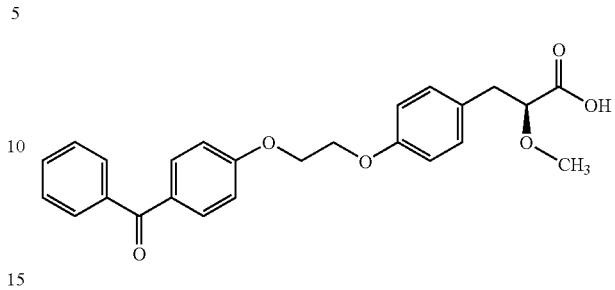

The title compound was prepared from (2S)-3-(4-hydroxy-phenyl)-2-methoxy-propionic acid linked to Wang's Resin via Mitsunobu coupling Standard Procedure G. Cleavage from the resin gave an oily solid. $^1$H-NMR (200.15 MHz, $CDCl_3$): δ 7.84–7.72 (m, 4H), 7.60–7.41 (m, 3H), 7.18 (d, 2H, J=8.6), 6.99 (d, 2H, J=8.9), 6.87 (d, 2H, J=8.7), 4.43–4.32 (m, 4H), 3.96 (dd, 1H, J=7.5, 4.6), 3.65 (s, 3H), 3.09 (dd, 1H, J=14.2, 4.2), 2.95 (dd, 1H, J=14.2, 7.8)ppm.

Example 123

(2S)-3-{4-[2-(Biphenyl-4-yloxy)-ethoxy]-phenyl}-2-methoxy-propionic acid

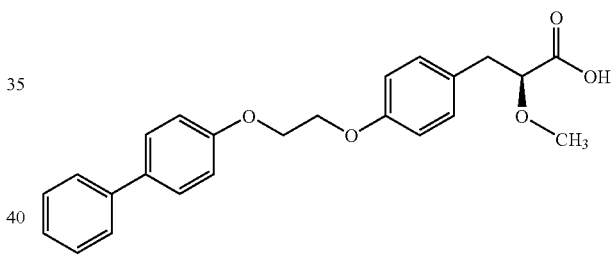

Step A (Biphenyl-4-yloxy)-acetic acid ethyl ester

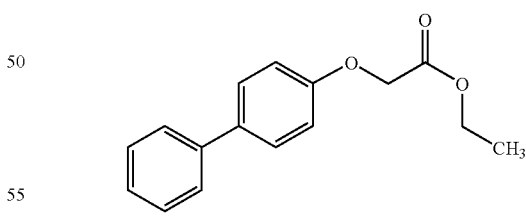

To a solution of 4-phenylphenol (1.02 g, 5.99 mmol) in 10 mL of DMF at −20° C. was added sodium hydride (0.24 g, 5.99 mmol, 60% oil dispersion) and the mixture stirred at 0° C. for 30 min. 2-bromoethyl acetate (0.66 mL, 5.99 mmol) was added and the mixture stirred at room temperature overnight. The solution was diluted with water (50 mL) and extracted with diethyl ether (3×20 mL). The combined extracts were washed with water (4×20 mL), dried ($MgSO_4$) and concentrated under vacuum. 0.63 g (41%). $^1$H-NMR ($CDCl_3$, 200.15 MHz): 7.57–7.56 (m, 4H), 7.45–7.26 (m, 3H), 6.98 (dd, 2H, J=6.4, 2.1), 4.66 (s, 2H), 4.29 (q, 2H, J=7.3), 1.31 (t, 5H, J=7.3) ppm.

Step B 2-(Biphenyl-4-yloxy)-ethanol

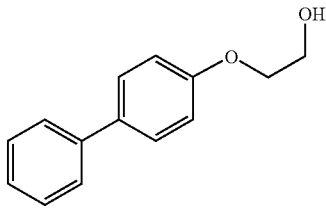

To a solution of (Biphenyl-4-yloxy)-acetic acid ethyl ester (0.63 g, 2.46 mmol) in dry toluene (15 mL) at −78° C. was added DIBAL-H 1M in toluene (4.92 mL, 4.92 mmol). The solution was stirred at −78° C. for 1 hour, warmed to room temperature and quenched with mixture of a solution of sodium tartrate in water and ethyl acetate for 1 hour. The layers were separated and the aqueous phase further extracted with ethyl acetate. The combined organic layers were dried (MgSO$_4$), concentrated under vacuum and the residue purified bu column chromatography (silica gel, hexanes/Ethyl acetate 4:1, R$_f$0.1), 48%. $^1$H-NMR (CDCl$_3$, 200.15 MHz): 7.58–7.26 (m, 8H); 7.00 (d, 2H, J=8.6), 4.14 (t, 2H, J=4.6), 4.02–3.98 (m, 2H); 2.04 (t, 1H, J=5.4).

Step C (2S)-3-{4-[2-(Biphenyl-4-yloxy)-ethoxy]-phenyl}-2-methoxy-propionic acid

The title compound was prepared from 2-(Biphenyl-4-yloxy)-ethanol and (2S)-2-Methoxy-3-hydroxyphenyl propionic acid ethyl ester using the general procedure A (34%). $^1$H-NMR (CDCl$_3$, 200.15 MHz): δ 7.55–7.49 (m, 4H); 7.43–7.35 (m, 2H); 7.29 (d, 1H, J=7.3); 7.15 (d, 2H, J=8.8); 7.00 (d, 2H, J=8.8); 6.88 (d, 2H, J=8.8); 4.36–4.29 (m, 4H); 3.98 (dd, 1H, J=7.0, 4.4); 3.39 (s, 3H); 3.10 (dd, 1H, J=14.3, 4.4); 2.95 (dd, 1H, J=14.3, 7.3)ppm. MS (ES) for C$_{24}$H$_{24}$O$_5$ [M+NH$_4$]$^+$: 410.

Example 124

(2S)-3-{4-[2-(Biphenyl-4-yloxy)-acetyl]-phenyl}-2-methoxy-propionic acid

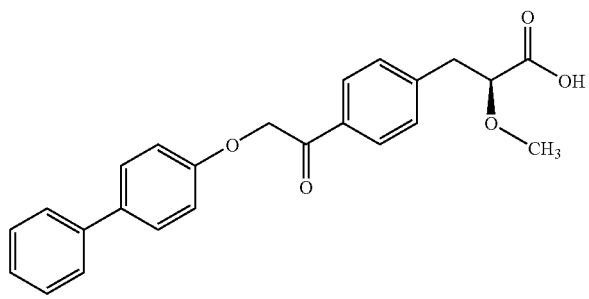

Step A (2S)-3-(4-Ethynyl-phenyl)-2-methoxy-propionic acid ethyl ester

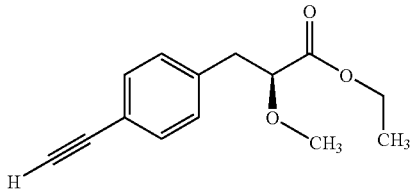

To a solution of (2S)-2-Methoxy-3-(4-trifluoromethanesulfonyloxy-phenyl)-propionic acid ethyl ester (0.100 g, 0.29 mmol) (Example 1, Step A) in 10 mL of degassed piperidine, was added (trimethylsilyl)acetylene (99,6 mg, 1.015 mmol), tetrakis(triphenylphosphine) Palladium (0) (0.017 g, 0.015 mmol), triphenylphosphine (7.7 mg, 0.029 mmol) and cooper (I) Iodide (5.5 mg, 0.029 mmol). The solution was stirred for 2 hours at 120° C. and then cooled to room temperature. The solvent was evaporated under vacuum. The residue was dissolved in dry THF and 0.4 mL of a solution of tetrabutylamonium fluoride (1.0 M in THF) and 0.02 mL of water were added. The mixture was stirred at room temperature for 5 min. The solvent was evaporated under vacuum and the residue partitioned between water (20 ml) and diethyl ether (20 mL). The layers were separated and the aqueous solution extracted twice with 20 ml of diethylether. The combined organic layers were washed with 10% Na$_2$CO$_3$ (6×20 ml) and brine (20 ml) and dried (MgSO$_4$). Concentration produced a yellow oil (38 mg, 56%) $^1$H-NMR (200.15 MHz, CDCl$_3$): δ 7.95 (d, 1H, J=7.3), 7.25 (d, 1H, J=7.3), 4.18 (q, 2H, J=7.0), 3.97 (dd, 1H, J=7.3, 5.6), 3.36 (s, 3H), 3.05 (d, 1H, J=5.3), 3.02 (d, 1H, J=2.4 Hz), 1.22 (t, 3H, J=7.25).

Step B (2S) 3-(4-Acetyl-phenyl)-2-methoxy-propionic acid ethyl ester

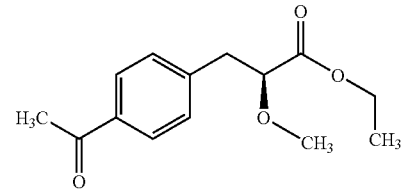

To (2S)-3-(4-Ethynyl-phenyl)-2-methoxy-propionic acid ethyl ester (36 Mg, 0.15 mmol) (Example 29, Step A) were added 4 ml of formic acid. The solution was stirred for 1 hour at 100° C. and then cooled to room temperature. The mixture was taken up with methylene chloride and the solution was washed with water, sodium carbonate, and water, dried (MgSO$_4$) and the solvent was evaporated under vacuum. Obtained a brown liquid (0.035 g, 95%). $^1$H-NMR (200.15 MHz, CDCl$_3$): δ 7.43 (d, 1H, J=73), 7.12 (d, 1H, J=7.3), 4.18 (q, 2H, J=7.0), 3.97 (dd, 1H, J=7.3, 5.6), 3.32 (s, 3H), 3.06 (s, 1H), 3.03 (d, 1H, J=2.4 Hz), 2.56 (s, 2H), 1.22 (t, 3H, J=7.25).

Step C (2S) 3-[4-(2-Bromo-acetyl)-phenyl]-2-methoxy-propionic acid ethyl ester

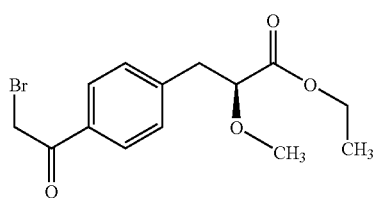

Powdered cupric bromide (62 mg, 0.28 mmol) was added portionwise to a solution of (2S)-3-(4-Acetyl-phenyl)-2-methoxy-propionic acid ethyl ester (35 mg, 0.14 mmol) in $CHCl_3$ (5 ml) and ethyl acetate (5 mL). The solution was stirred for 1 hour at 65° C. and then cooled to room temperature. The mixture was filtered and the solvent evaporated under vacuum. The residue was purified by chromatography (silica gel, hexanes/Ethyl Ether 8:2, $R_f$ 0.20) to produce a colorless oil (25 mg, 54%). $^1$H-NMR (200.15 MHz, $CDCl_3$): δ 7.935 (d, 1H, J=7.3), 7.38 (d, 1H, J=7.3), 4.50 (s, 2H), 4.12 (q, 2H, J=7.0), 3.97 (dd, 1H, J=7.3, 5.6), 3.38 (s, 3H), 3.10 (s, 1H), 3.06 (d, 1H, J=2.4 Hz), 1.22 (t, 3H, J=7.25).

Step D (2S)-3-{4-[2-(Biphenyl-4-yloxy)-acetyl]-phenyl}-2-methoxy-propionic acid

The title compound was prepared from a solution of (2S)-3-[4-(2-Bromo-acetyl)-phenyl]-2-methoxy-propionic acid ethyl ester (25 mg, 0.076 mmol) in acetonitrile (5 ml). 4-phenylphenol (29 mg, 0.152 mmol) and $K_2CO_3$ (31,5 mg, 0.23 mmol) were added. The solution was stirred for 30 min at 80° C. and then cooled to room temperature. The mixture was concentrated to dryness under vacuum and chromatographed in silica gel (hexanes/Ethyl ether 8:2 to 7:3). Fractions corresponding to the coupled compound were collected ($R_f$ 0.27) and concentrated to dryness. The mixture thus obtained was dissolved in 4 mL of NaOH 1N and 12 mL of Methanol and stirred at room temperature until TLC indicates the disappearance of starting material. The methanol was eliminated under vacuum and the aqueous solution diluted with 20 mL of brine and washed with diethyl ether (3×15 mL). The aqueous phase was acidulated with HCl 1N (until pH 3); extracted with ethyl acetate (3×15 mL) and the organic layer dried ($MgSO_4$) and concentrated under vacuum. Obtained a colorless oil (9.6 mg, 32%). $^1$H-NMR (200.15 MHz; $CDCl_3$): δ 7.96 (d, 2H, J=8.4), 7.55–7.23 (m, 9H), 6.99 (d, 2H, J=8.8), 5.26 (s, 2H), 4.03 (dd, 1H, J=7.3, 5.6), 3.39 (s, 3H), 3.22 (dd, 1H, J=14.3, 5.5), 3.03 (dd, 1H, J=14.3, 7.2).

Example 125

(2S)-2-Methoxy-3-{4-[2-(4-phenoxy-phenoxy)-acetyl]-phenyl}-propionic acid

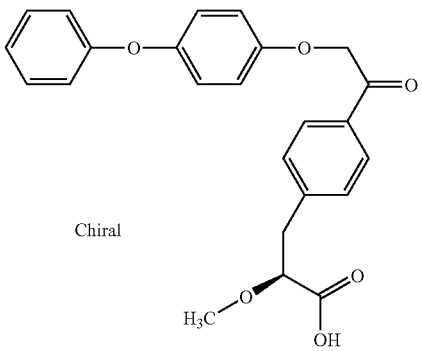

Chiral

The title compound was prepared from a solution of (2S)-3-[4-(2-Bromo-acetyl)-phenyl]-2-methoxy-propionic acid ethyl ester (0.076 mmol) from Example 124, Step C in acetonitrile (5 ml). 4-phenoxyphenol (0.152 mmol) and $K_2CO_3$ (0.23 mmol) were added. The solution was stirred for 30 min at 80° C. and then cooled to room temperature. The mixture was concentrated to dryness under vacuum and chromatographed in silica gel (hexanes/Ethyl ether 8:2 to 7:3). Fractions corresponding to the coupled compound were collected ($R_f$: 0.27) and concentrated to dryness. The mixture thus obtained was dissolved in 4 mL of NaOH 1N and 12 mL of Methanol and stirred at room temperature until TLC indicates the disappearance of starting material. The methanol was eliminated under vacuum and the aqueous solution diluted with 20 mL of brine and washed with diethyl ether (3×15 mL). The aqueous phase was acidulated with HCl 1N (until pH 3); extracted with ethyl acetate (3×15 mL) and the organic layer dried ($MgSO_4$) and concentrated under vacuum. Obtained a colourless oil. $^1$H-NMR (200.15 MHz, $CDCl_3$): 7.96 (d, 2H, J=8.4), 7.55–7.33 (m, 5H), 7.04–6.83 (m, 6H), 5.24 (s, 2H), 4.08 (dd, 1H, J=7.4, 4.4), 3.40 (s, 3H), 3.22 (dd, 1H, J=14.3, 4.4), 3.15 (dd, 1H, J=14.3, 7.2).

Example 126

(2S)-3-{4-[2-(4-Benzoyl-phenoxy)-acetyl]-phenyl}-2-methoxy-propionic acid

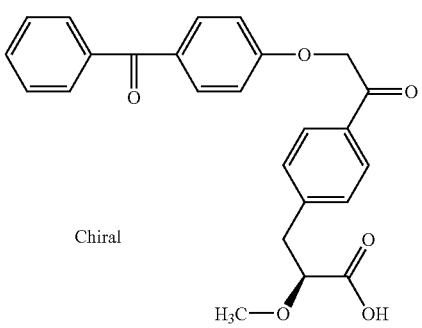

Chiral

The title compound was prepared from a solution of (2S) 3-[4-(2-Bromo-acetyl)-phenyl]-2-methoxy-propionic acid ethyl ester (0.076 mmol) from Example 124, Step C in acetonitrile (5 ml). 4-hydroxybenzophenone (0.152 mmol) and $K_2CO_3$ (0.23 mmol) were added. The solution was stirred for 30 min at 80° C. and then cooled to room temperature. The mixture was concentrated to dryness under vacuum and chromatographed in silica gel (hexanes/Ethyl ether 8:2 to 7:3). Fractions corresponding to the coupled compound were collected ($R_f$ 0.27) and concentrated to dryness. The mixture thus obtained was dissolved in 4 mL of NaOH 1N and 12 mL of Methanol and stirred at room temperature until TLC indicates the disappearance of starting material. The methanol was eliminated under vacuum and the aqueous solution diluted with 20 mL of brine and washed with diethyl ether (3×15 mL). The aqueous phase was acidulated with HCl 1N (until pH 3); extracted with ethyl acetate (3×15 ml) and the organic layer dried ($MgSO_4$) and concentrated under vacuum. Obtained a colorless oil. $^1$H-NMR (200.15 MHz, $CDCl_3$): 7.96–7.71 (m, 6H), 7.57–7.46 (m, 5H), 6.97 (d, 2H, J=8.1), 5.35 (s, 2H), 4.08 (dd, 1H, J=7.4, 4.2), 3.26 (s, 3H), 3.20 (dd, 1H, J=14.1, 4.1), 3.09 (dd, 1H, J=14.1, 7.2).

Example 127

(2S)-3-{4-[3-(Biphenyl-4-yloxy)-propyl]-phenyl}-2-methoxy-propionic acid

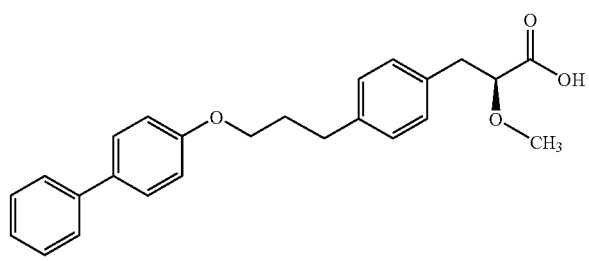

The title compound was prepared as follows: (2S) 3-{4-[3-(Biphenyl-4-yloxy)-prop-1-ynyl]-phenyl}-2-methoxy-propionic acid (0, Step C) (0.0325 g, 0.08 mmol) was dissolved in methanol (10 mL). Palladium 10% an activated carbon (0.004 g, 0.004 mmol) was added and the solution saturated with hydrogen (1 Atm) and stirred for 5 hours. The mixture was filtered through a pad of celite and concentrated under vacuum. The residue was purified by column chromatography (silica gel, hexanes/Ethyl acetate-Acetic acid 50:50:1, $R_f$ 0.23) (85%). $^1$H-NMR ($CDCl_3$, 200.15 MHz): δ 7.56–7.24 (m, 11H), 6.94 (d, 2H, J=8.8), 4.02–3.95 (m, 3H), 3.38 (s, 3H), 3.11 (dd, 1H, J=14.3, 4.4), 2.98 (dd, 1H, J=14.3, 7.3), 2.79 (t, 2H, J=8.1), 2.16–2.03 (m, 3H). MS (ES) for $C_{25}H_{26}O_4$ [M+$NH_4$]$^+$: 408.2, [M+Na]$^+$: 413.2.

Example 128

(2S)-3-{4-[4-(Biphenyl-4-yloxy)-butyl]-phenyl}-2-methoxy-propionic acid

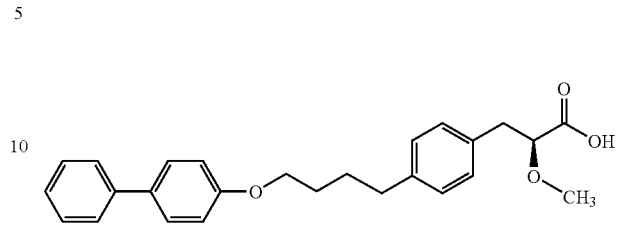

Step A (2S)-3-[4-(4-Hydroxy-butyl)-phenyl]-2-methoxy-propionic acid ethyl ester

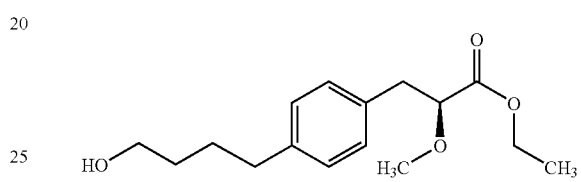

(2S)-3-[4-(3-Hydroxy-prop-1-ynyl)-phenyl]-2-methoxy-propionic acid ethyl ester (0.294 g, 1.06 mmol) was dissolved in ethyl acetate (50 mL). Palladium 10% on activated carbon (0.057 g, 0.05 mmol) was added and the solution saturated with hydrogen (1 Atm) and stirred for 2 hours. The mixture was filtered through a pad of celite and concentrated under vacuum. (100%). $^1$H-NMR ($CDCl_3$, 200.15 MHz): δ 7.12 (dd, 4H, J=11.3, 8.6), 4.17 (q, 2H, J=7.0), 3.94 (dd, 1H, J=7.0, 6.2), 3.65 (t, 2H, J=5.9); 3.35 (s, 3H), 3.00 (s, 1H), 2.97 (s, 1H), 2.61 (t, 2H, J=7.3), 1.73–1.60 (m, 4H), 1.22 (t, 3H, J=7.0).

Step B (2S)-3-{4-[4-(Biphenyl-4-yloxy)-butyl]-phenyl}-2-methoxy-propionic acid

The title compound was prepared from (2S)-3-[4-(4-Hydroxy-butyl)-phenyl]-2-methoxy-propionic acid ethyl ester and 4-phenylphenol following the Standard Procedure of coupling-hydrolysis A. $^1$H-NMR ($CDCl_3$, 200.15 MHz): δ 7.55–7.23 (m, 7H); 7.14 (d, 4H, J=1.1); 6.93 (d, 2H, J=8.4); 4.02–3.96 (m, 3H); 3.37 (s, 3H); 3.11 (dd, 1H, J=14.3, 4.4); 2.97 (dd, 1H, J=14.3, 7.3); 2.66 (t, 2H, J=7.0); 1.83–1.80 (m, 4H). MS (ES) for $C_{26}H_{28}O_4$ [M+$NH_4$]$^+$: 422.2, [M+Na]$^+$: 427.2.

Example 129

(2S)-3-{4-[5-(Biphenyl-4-yloxy)-pentyl]-phenyl}-2-methoxy-propionic acid

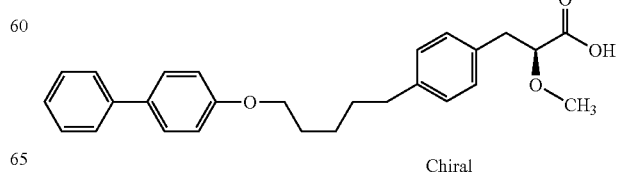

Chiral

The title compound was prepared as follows: (2S)-3-{4-[5-(Biphenyl-4-yloxy)-pent-1-ynyl]-phenyl}-2-methoxy-propionic acid from Example 21 (0.08 mmol) was dissolved in methanol (10 mL). Palladium 10% on activated carbon (0.004 g, 0.004 mmol) was added and the solution saturated with hydrogen (1 Atm) and stirred for 5 hours. The mixture was filtered through a pad of celite and concentrated under vacuum. The residue was purified by column chromatography. MS (ES) for $C_{27}H_{30}O_4$ [M−H]⁻: 417.3.

Example 130

3-{4-[3-(4-Benzoyl-phenoxy-propoxy]-3-methoxy-propionic acid

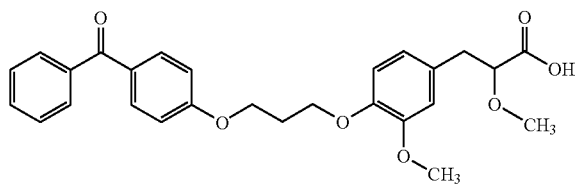

Step A 3-(4-Benzyloxy-3-methoxy-phenyl)-3-hydroxy-2-methoxy-propionic acid methyl ester

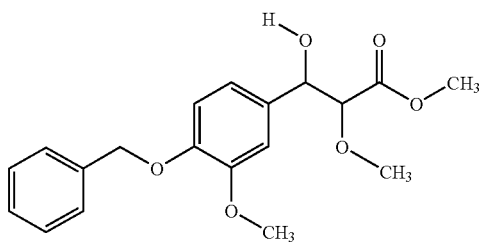

A solution of 4-benzyloxy-3-methoxy-benzaldehyde (0.44 g, 1.92 mmol) and methyl methoxyacetate (0.19 mL, 1.92 mmol) in THF (10 mL) at −78° C. was added dropwise to sodium bis(trimethylsilyl)amide (20 mL, 2.11 mmol, 1N in THF) at −78° C. The reaction mixture was stirred for 3 h and quenched with 1N HCl (5 mL). The mixture was allowed to warm to room temperature, diluted with water (15 mL), and extracted with ethyl acetate (3×15 mL). The combined organic layers were dried (MgSO₄) and concentrated. The residue was purified by silica gel column chromatography (silica gel, hexanes/ethyl acetate, 1:1) to produce 3-(4-benzyloxy-3-methoxy-phenyl)-3-hydroxy-2-methoxy-propionic acid methyl ester as an oil (350 mg, 52%); ¹H-NMR (200.15 MHz, CDCl₃): δ 7.45–7.20 (m, 5H), 6.9 (s, 1H), 6.8 (b, 2H), 5.1 (s, 2H), 4.90–4.80 (m, 1H), 4.10 (m, 1H), 3.90 (s, 3H), 3.65 (s, 3H), 3.31 (s, 3H), 3.10–2.96 (m, 1H).

Step B 3-(4-Hydroxy-3-methoxy-phenyl-2-methoxy-propionic acid methyl ester

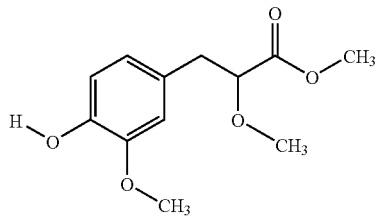

Trifluoroacetic anhydride (0.62 mL, 4.36 mmol) and triethylamine (0.62 mL, 4.36 mmol) were added to a solution of 3-(4-benzyloxy-3-methoxy-phenyl)-3-hydroxy-2-methoxy-propionic acid methyl ester (1.01 g, 2.91 mmol) in methylene chloride (30 mL) at 0° C. The resulting mixture was stirred for 4 hours at room temperature and was concentrated under vacuum. The residue was dissolved in ethyl acetate (30 mL), and 10% palladium on carbon (0.3 g) was added to the solution. The mixture was stirred under hydrogen pressure (4 atm) for 16 hours. The mixture was filtered through Celite and concentrated under vacuum. The residue was purified by silica gel column chromatography (silica gel, hexanes/ethyl acetate 7:3) to produce 3-(4-hydroxy-3-methoxy-phenyl)-2-methoxy-propionic acid methyl ester as an oil (598 mg, 86%). ¹H-NMR (200.15 MHz, CDCl₃): δ 6.80 (d, 1H, J=7.8), 6.7 (s, 1H), 6.62 (d, 1H, J=7.8), 3.96 (dd, 1H, J=7.8, 4.0), 3.80 (s, 3H), 3.68 (s, 3H), 3.30 (s, 3H), 3.09 (dd, 1H, J=14.2, 4.0), 2.91 (dd, 1H, J=14.2, 7.8).

Step C 3-(4-Hydroxy-3-methoxy-phenyl)-2-methoxy-propionic acid

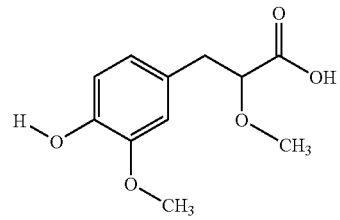

A 1N aqueous lithium hydroxide solution was added to a solution of 3-(4-hydroxy-3-methoxy-phenyl)-2-methoxy-propionic acid methyl ester (280 mg, 1.17 mmol) in THF at room temperature, and the reaction mixture stirred overnight. The aqueous phase was extracted with ethyl acetate (20 mL), acidified to pH 2, and extracted with ethyl acetate (3×15 mL). The later organic layers were combined and washed with water (15 mL) and brine (10 mL), dried (MgSO4), filtered, and concentrated under vacuum to produce 3-(4-hydroxy-3-methoxy-phenyl)-2-methoxy-propionic acid as an oil (183 mg, 74%). ¹H-NMR (250.13 MHz, CDCl₃): δ 6.83 (1H, d, J=7.8), 6.74 (1H, s), 6.72 (1H, d, J=7.8), 3.99 (1H dd, J=7.8, 4.0), 3.85 (s, 3H), 3.40 (s, 3H), 3.09 (1H, dd, J=14.2, 4.0), 2.91 (1H dd, J=14.2, 7.8).

Step D

3-[4-(tert-Butyl-dimethyl-silanyloxy)-3-methoxy-phenyl]-2-methoxy-propionic acid

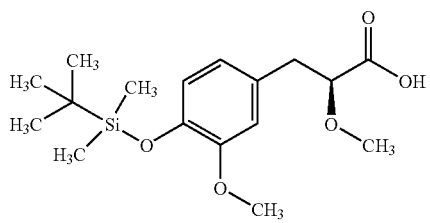

To a solution of 3-(4-hydroxy-3-methoxy-phenyl)-2-methoxy-propionic acid (1.02 g, 4.87 mmol) in CH$_2$Cl$_2$-DMF (20 mL=10:1) was added tert-butyl-dimethylsilyl chloride (1.75 g, 11.68 mmol) and imidazole (0.70 g, 10.24 mmol). The resulting solution was stirred at room temperature overnight. Water (15 mL) was added, and the aqueous phase was extracted with hexanes (30 mL). The hexanes layer was washed with water (10 mL), dried (MgSO$_4$), filtered, and concentrated. The crude product was dissolved in ethyl acetate (10 mL), and a saturated solution of K$_2$CO$_3$ (5 mL) was added. The resulting mixture was stirred for 2 hours at room temperature. The aqueous layer was extracted with ethyl acetate (10 mL), acidified to pH 3, and extracted again with ethyl acetate (3×10 mL). The later organic layers were combined and washed with brine (20 mL), dried (MgSO4), and concentrated to a yellow oil (1.2 g, 77%). $^1$H-NMR (200.15 MHz, CDCl$_3$): δ 6.78–6.67 (m, 3H), 3.96 (dd, 1H, J=7.8, 4.0), 3.78 (s, 3H), 3.35 (s, 3H), 3.09 (dd, 1H, J=14.2, 4.0), 2.91 (dd, 1H, J=14.2, 7.8), 0.98 (s, 9H), 0.13 (6H, s).

Step E

Preparation of 3-[4-(tert-Butyl-dimethyl-silanyloxy)-3-methoxy-phenyl]-2-methoxy-propionic acid linked to Wang's Resin

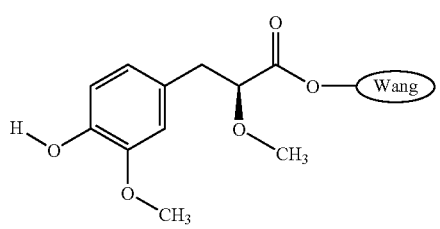

The title compound was prepared following the procedure as in Example 95, Step B.

Step F

Preparation of 3-(4-hydroxy-3-methoxy-phenyl)-2-methoxy-propionic acid linked to Wang's Resin

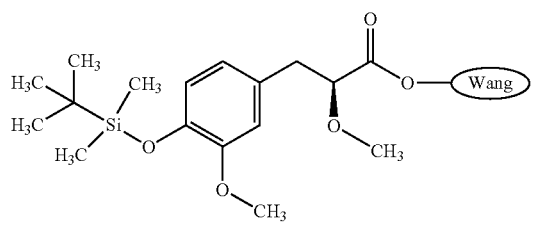

The title compound was prepared following the procedure as in Example 95, Step C.

Step G

Preparation of 3-[4-(3-hydroxy-propoxy)-3-methoxy-phenyl]-2-methoxy-propionic acid linked to Wang's Resin.

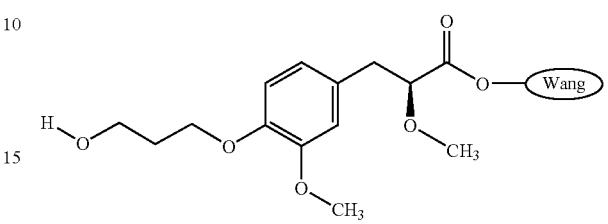

The title compound was prepared from 3-(4-hydroxy-3-methoxy-phenyl)-2-methoxy-propionic acid linked to Wang's Resin via Mitsunobu coupling (Standard Procedure F) to produce 3-[4-(3-hydroxy-propoxy)-3-methoxy-phenyl]-2-methoxy-propionic acid linked to Wang's Resin.

Step H

3-{4-[3-(4-Benzoyl-phenoxy)-propoxy]-3-methoxy-phenyl}-2-methoxy-propionic acid

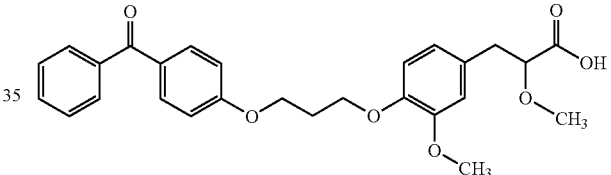

The title compound was prepared from 3-(4-(3-hydroxy-propoxy)-3-methoxy-phenyl)-2-methoxy-propionic acid linked to Wang's Resin via the Mitsunobu coupling-cleavage from the resin procedure (Standard Procedure G) to produce an oily solid (4%). $^1$H-NMR (200.15 MHz, CDCl$_3$): δ 7.81–7.72 (m, 4H), 7.57–7.43 (m, 3H), 6.96 (d, 2H, J=8.9), 6.81–6.73 (m, 3H), 4.28 (t, 2H, J=6.2), 4.20 (t, 2H, J=6.2), 4.01 (dd, 1H, J=7.0, 4.6), 3.83 (s, 3H), 3.42 (s, 3H), 3.09 (dd, 1H, J=14.5, 4.0), 2.97 (dd, 1H, J=14.5, 7.0), 2.33 (qn, 2H, J=6.2).

Example 131

3-(4-{3-[4-(4-Fluoro-benzoyl)-phenoxy]-propoxy}-3-methoxy-phenyl-2-methoxy-propionic acid

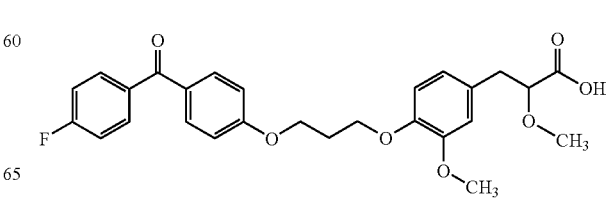

The title compound was prepared from 3-(4-(3-hydroxy-propoxy)-3-methoxy-phenyl)-2-methoxy-propionic acid linked to Wang's Resin via the Mitsunobu coupling-cleavage from the resin procedure (Standard Procedure G) to produce an oily solid (4%). $^1$H-NMR (200.15 MHz, CDCl$_3$): δ 7.83–7.74 (m, 4H), 7.15 (t, 2H, J=8.6 Hz), 6.96 (d, 2H, J=8.6), 6.85–6.74 (m, 3H), 4.28 (t, 2H, J=6.2), 4.20 (t, 2H, J=6.2), 4.01 (dd, 1H, J=7.0, 4.6), 3.84 (s, 3H), 3.42 (s, 3H), 3.10 (dd, 1H, J=14.2, 4.6), 2.97 (dd, 1H, J=14.2, 7.0), 2.33 (qn, 2H, J=6.2).

Example 132

3-{4-[3-(Biphenyl-4-yloxy)-propoxy]-3-methoxy-phenyl}-2-methoxy-propionic acid

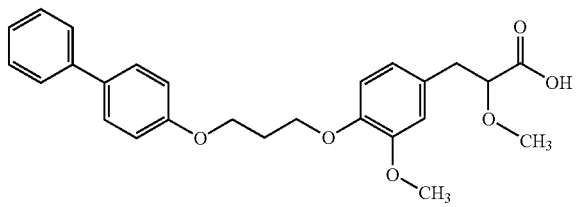

Step A 3-(4-Hydroxy-3-methoxy-phenyl)-2-methoxy-propionic acid ethyl ester

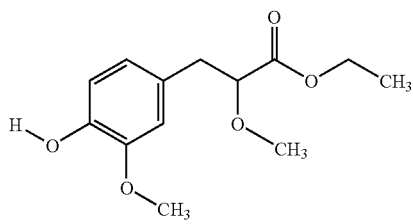

To a solution of 3-[4-(tert-butyl-dimethyl-silanyloxy)-3-methoxy-phenyl]-2-methoxy-propionic acid (356 mg, 1.05 mmol) in absolute ethanol (8 mL) was added concentrated sulfuric acid (0.033 mL, 0.63 mmol). The reaction mixture was allowed to stir at room temperature for 17 hours. The solution was concentrated under vacuum, and water (10 mL) and solid NaHCO$_3$ were added to neutralize the residue. The aqueous phase was extracted with ethyl acetate (2×10 mL). The combined organic layers were washed with water (20 mL) and brine (20 mL), dried (MgSO4), filtered, and concentrated to produce 3-(4-hydroxy-3-methoxy-phenyl)-2-methoxy-propionic acid ethyl ester (260 mg, 98%). $^1$H-NMR (200.15 MHz, CDCl$_3$): δ 6.83 (d, 1H, J=8.1 Hz), 6.76–6.69 (m, 2H), 4.19 (q, 2H, J=7.3 Hz), 3.97–3.90 (m, 1H), 3.87 (s, 3H), 3.36 (s, 3H), 2.96–2.92 (m, 2H), 1.25 (t, 3H, J=7.3 Hz).

Step B

[1,3,2]Dioxathiane 2,2-dioxide

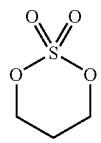

To a solution of 1,3-propanodiol (30 g, 394 mmol) in CCl$_4$ (278 mL) was added thionyl chloride (36 mL, 491 mmol) via syringe. The resulting mixture was heated at reflux for 1.5 h and was cooled to 0° C. to evaporate the solvent under vacuum. The residue was dissolved in a mixture of CCl$_4$/CH$_3$CN/H$_2$O (2:2:3=500 mL) and cooled to 0° C. Ruthenium trichloride trihydrate (0.556 g, 2.68 mmol) was added, followed by addition of solid NaIO$_4$ (14.35 g, 197 mmol). The mixture was stirred at room temperature for 1 h, H$_2$O (1 L) was added, and the aqueous phase was extracted with diethyl ether (4×300 mL). The combined organic layers were washed with brine (2×100 mL), dried (MgSO4), and filtered through a pad of silica gel to remove the ruthenium salts. The solvent was evaporated and hexanes (200 mL) was added to the resulting oil. After cooling, a gray solid precipitated. The solid was filtered and washed with hexanes. Recrystallization from hexanes/ether yielded a white, crystalline solid (18.15 g, 33%). $^1$H-NMR (200.15 MHz, CDCl$_3$): δ 4.73 (t, 4H, J=5.6), 2.13 (qn, 2H, J=5.6).

Step C 3-(Biphenyl-4-yloxy)-propan-1-ol

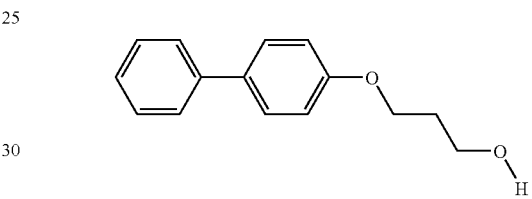

A solution of 4-phenylphenol (4.9 g, 29.0 mmol) and potassium tert-butoxide (3.64 g, 30.3 mmol) in THF (100 mL) was stirred at room temperature for 30 min. The solution was cooled at 0° C. and [1,3,2]dioxathiane 2,2-dioxide (3.6 g, 26.34 mmol) in THF (25 mL) was added. The resulting mixture was stirred at room temperature for 5 hours, and the solvent was removed under vacuum. The residue was dissolved in 6N HCl (15 mL) and heated at 100° C. for 16 hours. The mixture was cooled to room temperature, and the aqueous phase was extracted with ethyl acetate (3×30 mL). The combined organic layers were washed with H$_2$O (3×25 mL) and brine (25 mL), dried (MgSO4), filtered, and concentrated to produce 3-(biphenyl-4-yloxy)-propan-1-ol as a white solid (4.16 g, 63%). $^1$H-NMR (200.15 MHz, CDCl$_3$): δ 7.57–7.49 (m, 4H), 7.45–7.37 (m, 3H), 6.98 (dd, 2H, J=6.72, 2.14), 4.17 (t, 2H, J=5.9), 3.88 (q, 2H, J=5.9), 2.07 (qn, 2H, J=5.9).

Step D 4-(3-Bromo-propoxy)-biphenyl

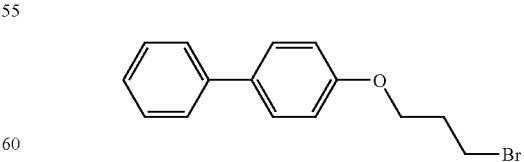

To a solution of 3-(biphenyl-4-yloxy)-propan-1-ol (1.00 g, 4.38 mmol) in CH$_2$Cl$_2$ (20 mL) at 0° C. was added triphenylphosphine (1.61 g, 6.14 mmol) and carbon tetrabromide (1.81 g, 5.47 mmol). The reaction mixture was allowed to warm to room temperature, stirred for 1 hour, and extracted with ethyl acetate (50 mL). The organic layer was washed with H₂O (3×50 mL) and bine (3×25 mL), dried (MgSO4), filtered and concentrated. The crude product was purified by silica gel column chromatography (silica gel, hexanes/ethyl acetate, 9:1) to produce 4-(3-bromo-propoxy)-biphenyl (1.22 g, 95%). ¹H-NMR (200.15 MHz, CDCl₃): δ 7.57–7.29 (m, 7H), 6.98 (dd, 2H, J=6.72, 1.88), 4.15 (t, 2H, J=5.92), 3.62 (t, 2H, J=6.44), 2.34 (qn, 2H, J=5.92).

Step E

3-{4-[3-(Biphenyl-4-yloxy)-propoxy]-3-methoxy-phenyl}-2-methoxy-propionic acid ethyl ester

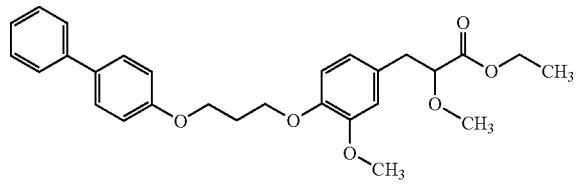

To a solution of 3-(4-hydroxy-3-methoxy-phenyl)-2-methoxy-propionic acid ethyl ester (Example 132, Step A) (0.080 g, 0.31 mmol) in acetonitrile (10 mL) was added 4-(3-bromo-propoxy)biphenyl (Example 132, Step D) (0.101 g, 0.35 mmol) and potassium carbonate (0.115 g, 0.945 mmol). The resulting suspension was stirred at 85° C. overnight. After cooling, the reaction mixture was diluted with ethyl acetate (10 mL), and water (10 mL) was added. The organic layer was washed with water (10 mL) and brine (10 mL), dried (MgSO4), and concentrated. The crude product was purified by silica gel column chromatography (silica gel, hexanes/ethyl acetate, 7:3) to produce 3-{4-[3-(biphenyl-4-yloxy)-propoxy]-3-methoxy-phenyl}-2-methoxy-propionic acid ethyl ester (0.086 g, 59%). ¹H-NMR (200.15 MHz, CDCl₃): δ 7.57–7.26 (m, 7H), 6.98 (d, 2H, J=8.6), 6.87–6.73 (m, 3H), 4.25–4.17 (m, 6H), 3.91 (dd, 1H, J=7.0, 5.6), 3.83 (s, 3H), 3.35 (s, 3H), 2.97–2.93 (m, 2H), 2.31 (qn, 2H, J=5.9), 1.24 (t, 3H, J=7.3).

Step F

3-{4-[3-(Biphenyl-4-yloxy)-propoxy]-3-methoxy-phenyl}-2-methoxy-propionic acid

The title compound was prepared from 3-{4-[3 (biphenyl-4-yloxy)-propoxy]-3-methoxy-phenyl}-2-methoxy-propionic acid ethyl ester following the hydrolysis procedure described in Example 130, Step C. ¹H-NMR (200.15 MHz, CDCl₃): δ 7.56–7.25 (m, 7H), 6.97 (d, 2H, J=8.9), 6.89–6.79 (m, 3H), 5.07 (b, 1H), 4.17 (q, 4H, J=5.6), 3.95 (dd, 1H, J=7.5, 3.5), 3.82 (s, 3H), 3.32 (s, 3H), 3.11–2.86 (m, 2H), 2.28 (qn, 2H, J=6.2).

Example 133

2-Methoxy-3-{3-methoxy-{3-(4-phenoxy-phenoxy)-propoxy]-phenyl}-propionic acid

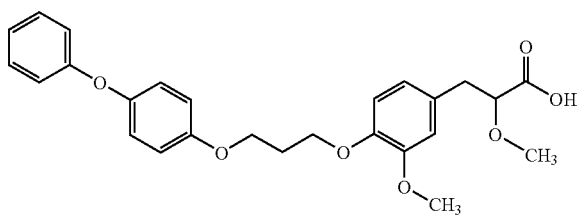

The title compound was prepared following the procedure described for Example 132 (Steps A–E). ¹H-NMR (200.15 MHz, CDCl₃): δ 7.32–7.24 (m, 2H), 7.06–6.75 (m, 10H), 4.16 (q, 4H, J=6.2), 3.97 (dd, 1H, J=7.8, 4.3), 3.82 (s, 3H), 3.37 (s, 3H), 3.08 (dd, 1H, J=14.2, 4.0), 2.94 (dd, 1H, J=14.5, 7.8); 2.27 (qn, 2H, J=6.2).

Example 134

(2S)-3-(4-[3-(Biphenyl-4-yloxy)-propoxy]-3-chloro-phenyl}-2-methoxy-propionic acid

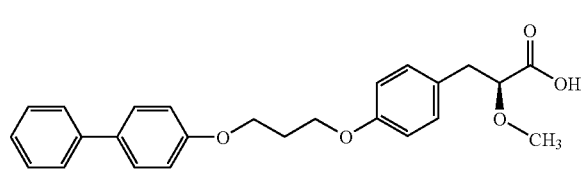

Step A (2S)-3-(3-Chloro-4-hydroxy-phenyl)-2-methoxy-propionic acid ethyl ester

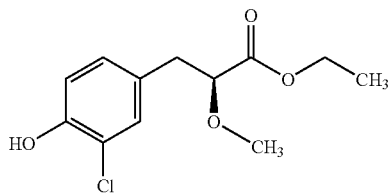

To a solution of 3-(4-hydroxy-phenyl)-2-methoxy-propionic acid ethyl ester (0.113 g, 0.5 mmol) in CH₃CN (3 mL) cooled to 0° C., N-chlorosuccinimide (0.067 g, 0.5 mmol,) was added in various portions. The mixture was allowed to warm to room temperature and was stirred for 8 hours. The mixture-was concentrated under vacuum, and the resulting oil was washed with CCl₄ (4 mL). The precipitate which formed was filtered, and the filtrate was concentrated to give a mixture of 3-(3-chloro-4-hydroxy-phenyl)-2-methoxy-propionic acid ethyl ester and 3-(3,5-Dichloro-4-hydroxy-phenyl)-2-methoxy-propionic acid ethyl ester as a brown oil which was purified by ultraviolet-directed HPLC. A colorless oil was obtained (0.020 g, 14%). ¹H-NMR (200.15 MHz, CDCl₃): δ 7.18 (d, 1H, J=2.15), 7.02 (dd, 1H, J=8.32, 2.15), 6.91 (d, 1H, J=8.32), 4.18 (q, 2H, J=7.25), 3.88 (dd, 1H, J=7.24, 5.62), 3.35 (s, 3H), 2.92 (dd, 2H, J=6.31, 2.42), 1.24 (t, 3H, J=7.2).

Step B (2S)-3-{4-[3-(Biphenyl-4-yloxy)-propoxy]-3-chloro-phenyl}-2-methoxy-propionic acid ethyl ester

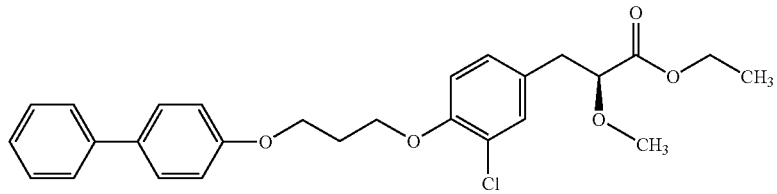

3-(3 Chloro-4-hydroxy-phenyl)-2-methoxy-propionic acid ethyl ester (0.020 g, 0.077 mmol) was dissolved in CH₃CN (3 mL) and 4-(3-bromo-propoxy)-biphenyl (Example 132, Step D), (0.025 g 0.085 mmol) and K₂CO₃ (0.032 g, 0.23 mmol) were added. The mixture was heated to 85° C. and stirred for 5 hours. After cooling, water (2 mL) was added. The mixture was extracted in EtOAc (3×10 mL), washed with H₂O (2×5 mL) and brine (2×5 mL). The organic layer was dried (MgSO₄), filtered, and concentrated in vacuo. The crude product was purified by silica gel column chromatography (silica gel, hexanes/ethyl acetate 9:1) to produce 3-{4-[3-(Biphenyl-4-yloxy)-propoxy]-3-chloro-phenyl}-2-methoxy-propionic acid ethyl ester (0.017 mg, 48%). ¹H-NMR (200.15 MHz, CDCl₃): δ 7.57–7.24 (m, 9H), 7.02–6.89 (m, 3H), 4.28–4.12 (m, 5H), 3.89 (dd, 1H, J=7.24, 5.62), 3.62 (t, 1H, J=6.44), 3.36 (s, 3H), 2.93 (dd, 2H, J=6.31, 2.42), 2.32 (qn, 2H, J=5.10), 1.25 (t, 3H, J=7.2).

Step C (2S)3-{4-[3-(Biphenyl-4-yloxy)-propoxy]-3-chloro-phenyl}-2-methoxy-propionic acid The title compound was prepared as follows: 3-{4-[3-(Biphenyl-4-yloxy)-propoxy]-3-chloro-phenyl}-2-methoxy-propionic acid ethyl ester (0.017 g, 0.037 mmol) was dissolved in 0.25 M ethanolic NaOH solution (0.3 mL, 0.075 mmol). The mixture was stirred 16 hours at room temperature and water was added. The aqueous layer was extracted with Et₂O (3×5 mL). The aqueous layer was acidified to pH=1 with 1 N HCl and extracted with Et₂O (5×10 mL). The organic layer was dried (MgSO₄) and concentrated under vacuum to give the title compound as a yellow oil (0.006 mg, 38%). ¹H-NMR (200.15 MHz, CDCl₃): δ 7.57–7.25 (m, 9H), 7.0–6.86 (m, 3H), 4.23 (q, 4H, J=6.18), 3.96 (dd, 1H, J=7.24, 4.28), 3.40 (s, 3H), 3.06 (dd, 1H, J=14.5, 4.28), 2.92 (dd, 1H, J=14.5, 7.24), 2.32 (qn, 2H, J=5.92).

Example 135

3-{3-Chloro-4-[3-(4-phenoxy-phenoxy)-propoxy]-phenyl}-2-methoxy-propionic acid

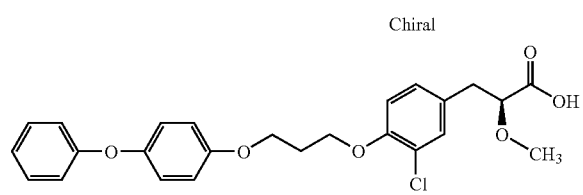

The title compound was prepared as a same manner in Example 134, but using 4-(3-bromopropoxy)-1-phenoxy-benzene as material for the coupling reaction Example 136

'3-{4-[3-(4-Benzoyl-phenoxy)-propoxy]-3-chloro-phenyl}-2-methoxy-propionic acid

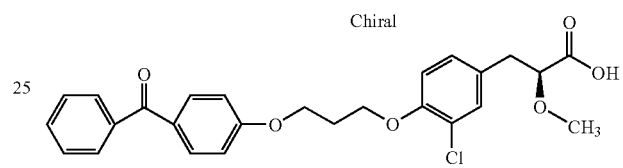

The title compound was prepared as a same manner in Example 134, but using [4-(3-Bromo-propoxy)-phenyl]-phenyl-methanoneas material for the coupling reaction Example 137

3-{4-[3-(Biphenyl-4-yloxy)-propoxy]-3,5-dichloro-phenyl}-2-methoxy-propionic acid

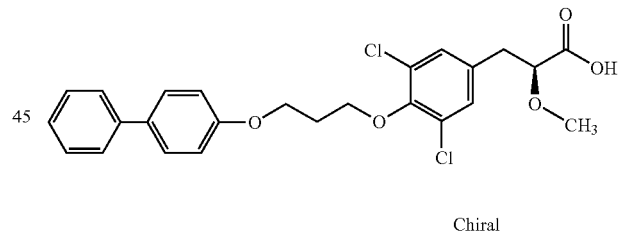

Step A 3-(3,5-Dichloro-4-hydroxy-phenyl)-2-methoxy-propionic acid ethyl ester

To a solution of 3-(4-hydroxy-phenyl)-2-methoxy-propionic acid ethyl ester (0.113 g, 0.5 mmol) in CH₃CN (3 mL) cooled to 0° C., N-chlorosuccinimide (0.067 g, 0.5 mmol,) was added in various portions. The mixture was allowed to warm to room temperature and was stirred for 8 hours. The mixture was concentrated under vacuum, and the resulting oil was washed with CCl₄ (4 mL). The precipitate which formed was filtered and the filtrate was concentrated to give a mixture of 3-(3-chloro-4-hydroxy-phenyl)-2-methoxy-propionic acid ethyl ester and 3-(3,5-Dichloro-4-hydroxy-phenyl)-2-methoxy-propionic acid ethyl ester as a brown oil which was purified by ultraviolet-directed HPLC.

Step B

3-{4-[3-(Biphenyl-4-yloxy)-propoxy]-3,5-dichloro-phenyl}-2-methoxy-propionic acid The title compound was prepared staring from compound from Step A and using the same procedure as in 0.

Example 138

3-{4-[3-(Biphenyl-4-yloxy)-propoxy]-3-fluoro-phenyl}-2-methoxy-propionic acid

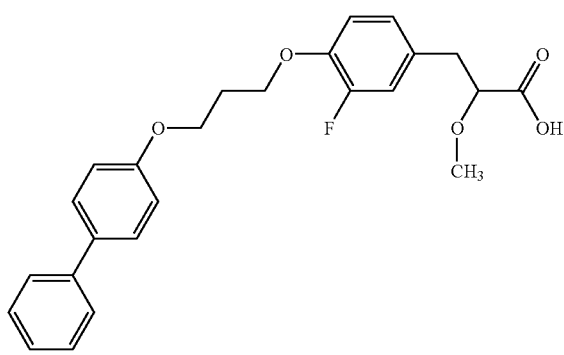

Step A 2-(3-Fluoro-4-methoxy-phenyl)-[1,3]-dioxolane

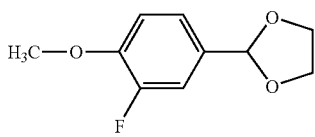

A solution of 3-fluoro-4-methoxy-benzaldehyde (463 mg, 3 mmol), ethylene glycol (0.86 mL, 15 mmol) and PPTs (75 mg, 0.3 mmol) in toluene (15 mL) was heated at reflux with aceotropic removal of water for 6 hours. The solvent was evaporated and the residue was diluted with methylene chloride (20 mL), washed with water (2×10 mL) and dried (MgSO$_4$). Concentration produced 2-(3-Fluoro-4-methoxy-phenyl)-[1,3]-dioxolane as a colorless oil (550 mg, 92%). $^1$H-NMR (CDCl3, 200.15 MHz): δ 7.24–7.15 (m, 2H), 6.92 (t, 1H, J=8.5), 5.71 (s, 1H), 4.10–3.98 (m, 4H), 3.86 (s, 3H).

Step B

4-[1,3]Dioxolan-2-yl-2-fluorophenol

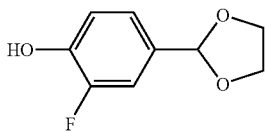

A solution of 2-(3-Fluoro-4-methoxy-phenyl)-[1,3]-dioxolane (250 mg, 1.26 mmol) and Sodium thiomethoxide (106 mg, 1.51 mmol) in dry N,N-dimethylformamide (3.5 mL) was heated at 100° C. under nitrogen for 4 hours. Then a saturated solution of ammonium chloride (15 mL) was added and the aqueous layer extracted with methylene chloride (4×10 mL). The combined organic layers were dried (Na$_2$SO$_4$), filtered and concentrated under vacuum. The residue was chromatographed (silica gel, hexanes/ethyl acetate 7:3) to produce 4-[1,3]dioxolan-2-yl-2-fluoro-phenol as a pale brown oil (120 mg, 52%). $^1$H-NMR (CDCl3, 200.15 MHz): δ 7.24–7.01 (m, 2H), 6.88 (t, 1H, J=8.4), 6.07 (s$_a$, 1H), 5.71 (s, 1H), 4.13–3.95 (m, 4H).

Step C

3-Fluoro-4-hydroxy-benzaldehyde

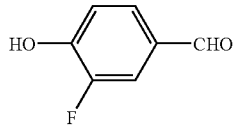

A solution of 1N HCl (1 mL) and 4-[1,3]dioxolan-2-yl-2-fluoro-phenol (250 mg, 1.35 mmol) in THF (2 mL) was stirred, at room temperature for 1 hour. The mixture was diluted with water and extracted with methylene chloride (4×10 mL). The combined organic layers were dried (Na$_2$SO$_4$), filtered and concentrated under vacuum. The residue was chromatographed (silica gel, hexanes/ethyl acetate 1:1) to produce 3-Fluoro-4-hydroxy-benzaldehyde as a white solid (180 mg, 95%). $^1$H-NMR (CDCl3, 200.15 MHz): 9.84 (d, 1H, J=2.4), 7.68–7.59 (m, 2H), 7.15 (t, 1H, J=8.5), 6.5 (s$_a$, 1H).

Step D

4-[3-(Biphenyl-4-yloxy)-propoxy]-3-fluoro-benzaldehyde

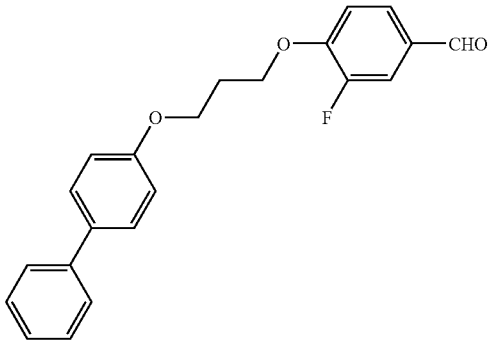

Potassium tert-butoxide (198 mg, 1.76 mmol) was added, at 0° C., to a solution of 3-Fluoro-4-hydroxy-benzaldehyde (235 mg, 1.68 mmol) in dry N,N-dimethylformamide (2 mL). The mixture was stirred for 10 minutes. 4-(3-Bromo-propoxy)-biphenyl (example 23, Step D) (539 mg, 1.84 mmol) was added and the reaction was stirred for 24 hours at room temperature. The mixture was diluted with water (15 mL) and extracted with ethyl acetate (4×15 mL). The combined organic layers were dried (Na$_2$SO$_4$), filtered, and concentrated under vacuum to produce a solid which was washed with hexanes to produce 4-[3-(Biphenyl-4-yloxy)-propoxy]-3-fluoro-benzaldehyde as a pale brown solid (490 mg, 83%). $^1$H-NMR (CDCl3, 200.15 MHz): δ 9.83 (d, 1H, J=2.2), 7.64–7.23 (m, 9H), 7.09 (t, 1H, J=8.2), 6.96 (d, 2H, J=8.8), 4.32 (t, 2H, J=5.9), 4.21 (t, 2H, J=5.9), 2.35 (qn, 2H, J=5.9).

Step E

3-{4-[3-(Biphenyl-4-yloxy)-propoxy]-3-fluoro-phenyl}-3-hidroxy-2-methoxy-propionic acid methyl ester

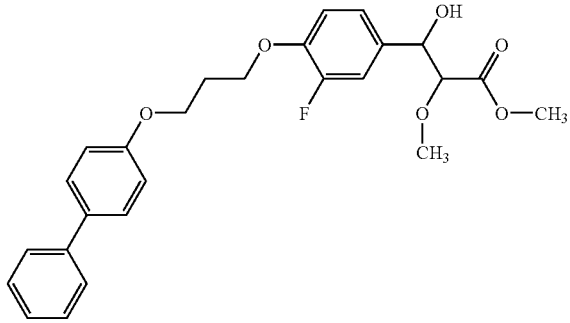

To a solution of sodium bis(trimethylsilyl)amide 1N (0.71 mL, 0.71 mmol) in dry THF (5 mL), was added dropwise methyl methoxyacetate (57 µL, 0.57 mmol) at −78° C. The solution was stirred for 1 hour. 4-[3-(Biphenyl-4-yloxy)-propoxy]-3-fluoro-benzaldehyde (220 mg, 0.626 mmol) was added and the mixture warmed to 0° C. and stirred for 3 additional hours. The mixture was quenched with 1N HCl (2 mL), diluted with water (20 mL) and extracted with dichloromethane (4×15 mL). The combined organic layers were dried (Na$_2$SO$_4$), filtered and concentrated under vacuum. The residue was chromatographed (silica gel, hexanes/ethyl acetate 7:3) to produce 3-{4-[3-(Biphenyl-4-yloxy)-propoxy]-3-fluoro-phenyl}-3-hidroxy-2-methoxy-propionic acid methyl ester as a colourless oil (62 mg, 24%). $^1$H-NMR (CDCl3, 200.15 MHz): δ 7.55–7.25 (m, 8H), 7.15–6.89 (m, 5H), 4.91–4.79 (m, 1H), 4.24–4.18 (m, 4H), 3.92 and 3.81 (2d, 1H, J=5.86 and 5.48), 3.67 and 3.64 (2s, 3H), 3.40 and 3.36 (2s, 3H), 3.01 and 2.94 (2d, 1H, 5.12 and 5.12), 2.29 (qn, 2H, J=5.9).

Step F

3-{4-[3-(Biphenyl-4-yloxy)-propoxy]-3-fluoro-phenyl}-2-methoxy-propionic acid methyl ester

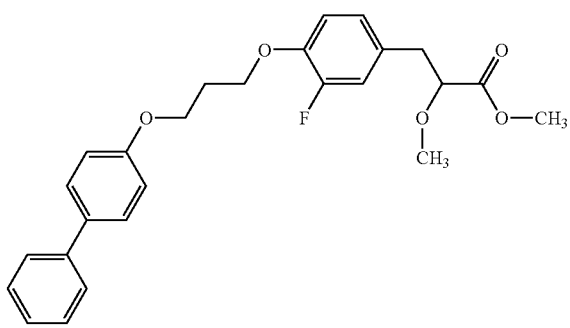

Trifluoroacetic anhydride (0.056 mL, 0.395 mmol) and pyridine (0.048 mL, 18.9 mmol) were added to a solution of 3-{4-[3-(Biphenyl-4-yloxy)-propoxy]-3-fluoro-phenyl}-3-hidroxy-2-methoxy-propionic acid methyl ester (90 mg, 0.197 mmol) in methylene chloride (2; mL) at 0° C. The mix was stirred for 4 hours at room temperature and quenched with 1N HCl (10 mL). The layers were separated and the aqueous extracted with methylene chloride (3×20 mL). The combined organic layers were evaporated and the residue dissolved in ethyl acetate (50 mL). 10% palladium on carbon (90 mg) was added to the solution and mixture was stirred under hydrogen pressure (5 atm) for 16 hours, filtered through a pad of celite and concentrated under vacuum. The residue was chromatographed (silica gel, hexanes/ethyl acetate 4:1) to produce 3-{4-[3-(Biphenyl-4-yloxy)-propoxy]-3-fluoro-phenyl}-2-methoxy-propionic acid methyl ester as a colorless oil (40 mg, 46%). $^1$H-NMR (CDCl3, 200.15 MHz): δ 7.58–7.49 (m, 4H), 7.46–7.37 (m, 2H), 7.34–7.24 (m, 1H), 7.01–6.90 (m, 5H), 4.22 (t, 4H, J=5.9), 3.93 (dd, 1H, J=7.3, 5.3), 3.73 (s, 3H), 3.37 (s, 3H), 2.97–2.92 (m, 2H), 2.31 (qn, 2H, J=5.9).

Step G

3-{4-[3-(Biphenyl-4-yloxy)-propoxy]-3-fluoro-phenyl}-2-methoxy-propionic acid

The title compound was prepared from 3-{4-[3-(Biphenyl-4-yloxy)-propoxy]-3-fluoro-phenyl}-2-methoxy-propionic acid methyl ester following the Standard Procedure E: white solid (38 mg, 98%). $^1$H-NMR (CDCl3, 200.15 MHz): δ 7.58–7.49 (m, 4H), 7.46–7.37 (m, 2H), 7.34–7.24 (m,1H), 7.01–6.90 (m, 5H), 4.23 (t, 2H, J=5.9), 4.22 (t, 2H, J=5.9), 3.97 (dd, 1H, J=7.4, 4.4), 3.4 (s, 3H), 3.12–2.89 (m, 2H), 2.31 (qn, 2H, J=5.9).

Example 139

3-{4-[3-(Biphenyl-4-yloxy)-propoxy]-3-trifluoromethyl-phenyl}-2-methoxy-propionic acid

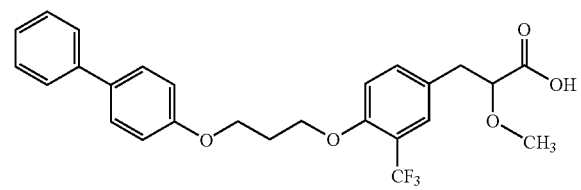

Step A

3-Bromo-4-hydroxy-benzaldehyde

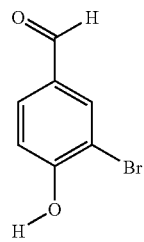

A solution of bromine (0.88 mL, 17.18 mmol) in chloroform (20 mL) was added dropwise at room temperature to a solution of 4-hydroxybenzaldehyde (2 g, 16.36 mmol) in chloroform (40 mL) and the mixture was stirred for 0.5 hour at room temperature and 1 more hour at 40° C. A saturated solution of NaHCO$_3$ (30 mL) was added and the organic layer separated. The aqueous layer was extracted with methylene chloride (3×20 mL). Thee combined organic layers were dried (Na$_2$SO$_4$), filtered and concentrated under vacuum. The residue was chromatographed (silica gel, methylene chloride-methanol 98:2) to afford 3-Bromo-4- hydroxy-benzaldehyde as a white solid (1.1 g, 34%).
¹H-NMR (CDCl₃, 200.15 MHz): 9.80 (s, 1H), 8.02 (d, 1H, J=1.8), 7.75 (dd, 1H, J=8.4, 1.8), 7.12 (d, 1H, J=8.4), 6.19 (s, 1H).

Step B

4-Benzyloxy-3-bromo-benzaldehyde

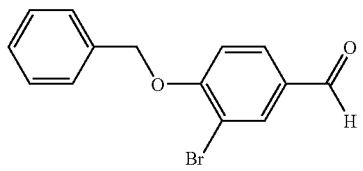

3-Bromo-4-hydroxy-benzaldehyde (1.9 g, 9.45 mmol) was added slowly, at 0° C., to a suspension of NaH 95% (290 mg, 11.34 nol) in dry N,N-dimethylformamide (45 mL). The mixture was stirred for 0.5 hours. Benzyl chloride (1.3 mL, 11.34 mmol) was added and the reaction stirred at room temperature overnight. 1N HCl (40 mL) was added and the layers separated. The aqueous layer was extracted with diethyl ether (5×50 mL) and the combined organic layers were dried (Na₂SO₄), filtered, and concentrated under vacuum. The residue was chromatographed (silica gel, hexanes/ethyl acetate 9:1) to produce 4-Benzyloxy-3-bromo-benzaldehyde as a white solid (2.47 g, 90%). ¹H-NMR (CDCl3, 200.15 MHz): δ 9.82 (s, 1H), 8.09 (d, 1H, J=1.8), 7.76 (dd, 1H, J=8.4, 1.8), 7.47–7.32 (m, 5H), 7.02 (d, 1H, J=8.4), 5.24 (s, 2H.

Step C

4-Benzyloxy-3-trifluoromethyl-benzaldehyde

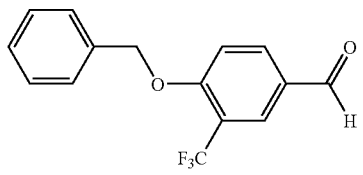

Methyl 2,2-difluoro-2-(fluorosulfonyl)-acetate (1.25 mL, 9.78 mmol) was added to a suspension of dry CuI (745 mg, 3.91 mmol) and 4-Benzyloxy-3-bromo-benzaldehyde (570 mg, 1.96 mmol) in dry N,N-dimethylformamide (10 mL). The mixture was stirred under nitrogen at 120° C. for 6 hours in a sealed tube. The reaction mixture was cooled to room temperature and diluted with water (20 mL). The aqueous layer was extracted with diethyl ether (4×20 mL) and the combined organic layers were dried (Na₂SO₄), filtered and concentrated under vacuum. The residue was chromatographed (silica gel, hexanes/ethyl acetate 9:1) to produce 4-Benzyloxy-3-trifluoromethyl-benzaldehyde as a white solid (120 mg, 22%). ¹H-NMR (CDCl3, 200.15 MHz): δ 9.88 (s, 1H), 8.11 (d, 1H, J=1.8), 7.98 (dd, 1H, J=8.6, 1.8), 7.44–7.31 (m, 5H), 7.14 (d, 1H, J=8.6), 5.27 (s, 2H).

Step D 3-(4-hydroxy-3-trifluoromethyl-phenyl)-2-methoxy-acrylic acid methyl ester

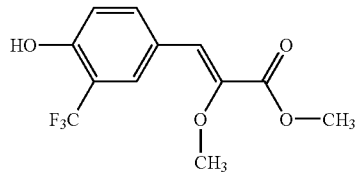

To a solution of sodium bis(trimethylsilyl)amide 1N (0.8 mL, 0.8 mmol) in THF (4 mL), was added dropwise methyl methoxyacetate (0.066 mL, 0.66 mmol) at −78° C. After allowing the mixture to stir for 1 hour, 4-Benzyloxy-3-trifluoromethyl-benzaldehyde (185 mL, 0.66 mmol) was added dropwise. When the addition was finished the mixture was warmed to room temperature and stirred for 3 additional hours. Trifluoroacetic anhydride (0.28 mL, 1.98 mmol) was added and the mixture was stirred at room temperature for 4 hours. The solvent was evaporated and the residue dissolved in ethyl acetate (50 mL). 10% palladium on carbon (200 mg) was added to the solution and the mixture stirred under hydrogen pressure (5 atm) for 16 hours, filtered through a pad of celite and concentrated under vacuum. The residue was chromatographed (silica gel, hexanes/ethyl acetate 4:1) to produce 3-(4 hydroxy-3-trifluoromethyl-phenyl)-2-methoxy-acrylic acid methyl ester as a white solid (72 mg, 40%). ¹H-NMR ((CD₃)₂CO, 200.15 MHz): δ 9.65 (b, 1H), 8.02 (d, 1H, J=1.8), 7.87 (dd, 1H, J=8.4, 1.8), 7.08 (d, 1H, J=8.4), 6.90 (s, 1H), 3.77 (s, 3H), 3.75 (s, 3H).

Step E

3-{4-[3-(biphenyl-4-yloxy)-propoxy]-3-trifluoromethyl-phenyl}-2-methoxy-acrylic acid methyl ester

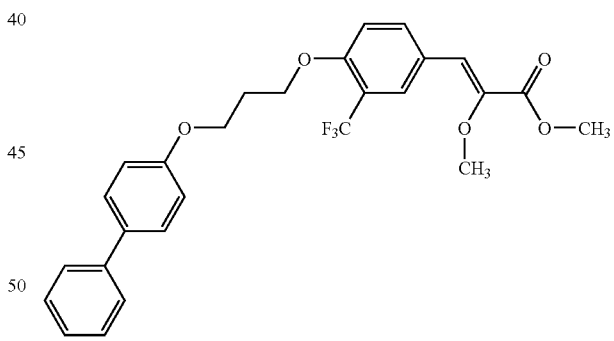

Potassium tert-butoxide (15 mg, 0.13 mmol) was added at 0° C. to a solution of 3-(4-hydroxy-3-trifluoromethyl-phenyl)-2-methoxy-acrylic acid methyl ester (35 mg, 0.126 mmol) in dry N,N-dimethylformamide (0.6 mL). The mixture was stirred for 0.5 hours and 4-(3-Bromo-propoxy)-biphenyl (example 23, Step D) (45 mg, 0.15 mmol) was added. The reaction was stirred for 6 hours at room temperature and quenched with a saturated solution of ammonium chloride (10 mL). The aqueous layer was separated and extracted with methylene chloride (5×10 mL). The combined organic layers were dried (Na₂SO₄), filtered and concentrated under vacuum. The residue was chromatographed (silica gel, hexanes/ethyl acetate 8:2) to produce 3-{4-[3-(biphenyl-4-yloxy)-propoxy]-3-fluoromethyl-phenyl}-2-methoxy-acrylic acid methyl ester as a colorless oil (35 mg, 57%). ¹H-NMR (CDCl3, 200.15 MHz): δ 8.00 (d, 1H, J=1.6), 7.89 (dd, 1H, J=8.6, 1.6), 7.46–7.26 (m, 7H), 7.05–6.93 (m, 4H), 4.33–4.20 (m, 4H), 3.86 (s, 3H), 3.79 (s, 3H), 2.33 (qn, 2H, J=5.9).

Step F

3-{4-[3-(biphenyl-4-yloxy)-propoxy]-3-trifluoromethyl-phenyl}-2-methoxy-acrylic acid

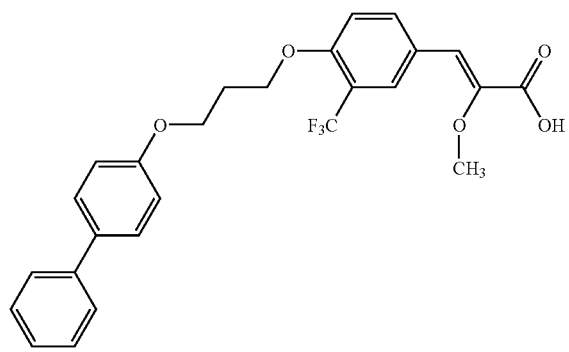

The title compound was prepared 3-{4-[3-(biphenyl-4-yloxy)-propoxy]-3-trifluoromethyl-phenyl}-2-methoxy-acrylic acid methyl ester (35 mg, 0.072 mmol) following the Standard Procedure E: white solid (31 mg, 92%). ¹H-NMR (CDCl3, 200.15 MHz): δ 8.02 (d, 1H, J=1.8), 7.88 (dd, 1H, J=8.6, 1.8), 7.57–7.28 (m, 7H), 7.08–6.96 (m, 4H), 4.35–4.21 (m, 4H), 3.81 (s, 3H), 2.34 (qn, 2H, J=5.8).

Step G

3-{4-[3-(biphenyl-4-yloxy)-propoxy]-3-trifluoromethoxy-phenyl}-2-methoxy-propionic acid The title compound was prepared as follows: A mixture of 3-{4-[3-(biphenyl-4-yloxy)-propoxy]-3-trifluoromethyl-phenyl}-2-methoxy-acrylic (20 mg, 0.041 mmol) and magnesium (20 mg, 0.82 mmol) in methanol (1 mL) was stirred at room temperature for 80 hours. The reaction mixture was quenched with 1N HCl (10 mL). The aqueous layer was extracted with methylene chloride (5×10 mL). The combined organic layers were dried (MgSO4), filtered and concentrated under vacuum to give 3-{4-[3-(biphenyl-4-yloxy)-propoxy]-3-trifluoromethoxy-phenyl}-2-methoxy-propionic acid as a white solid (7 mg, 35%). ¹H-NMR (CDCl3, 200.15 MHz): δ 7.57–7.32 (m, 9H), 7.00–6.95 (m, 3H), 4.27–4.19 (m, 4H), 3.97 (dd, 1H, J=7.3, 4.3), 3.41 (s, 3H), 3.16–2.93 (m, 2H), 2.31 (qn, 2H, J=5.8).

Example 140

(2S)-3-{6-[3-(Biphenyl-4-yloxy)-propoxy]-4'-methoxy-biphenyl-3-yl}-2-methoxy-propionic acid

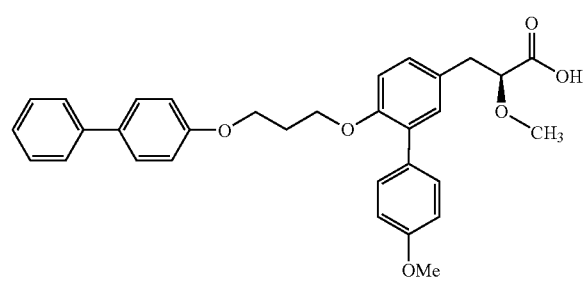

Step A (4-Hydroxy-3-iodide)-2-methoxy dihidroinnamic acid

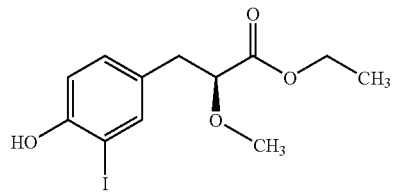

(4-Hydroxy)-2-methoxy dihydrocinnamic acid (1 g, 4.4 mmol) was dissolved in 30 mL of CH3CN and cooled to −20° C. NIS was added (0.99 g, 4.43 mmol) and the mixture was stirred for 8 hours. The solvent was evaporated under vacuum and the crude oil was washed with CCl4 with formation of a white solid. The solid was removed by filtration, and the filtrate was concentrated and purified by column chromatography (silica gel, dichloromethane/MeOH 0.5%) Yellow oil (924 mg, 60%). ¹H-NMR (200.15 MHz, CDCl3): δ 7.49 (d, 1H, J=2), 7.04 (dd, 1H, J=2, 8.2), 6.80 (d, 1H, J=8.2), 6.03 (bs, 1H), 4.17 (q, 2H, J=7.2), 3.88 (dd, 1H, J=5.6, 7), 3.33 (s, 3H), 2.88 (dd, 2H, J=2.4, 5.0), 1.21 (t, 3H, J=7.2)

Step B (2S)-3-(6-Hydroxy-4'-methoxy-biphenyl-3-yl)-2-methoxy-propionic acid

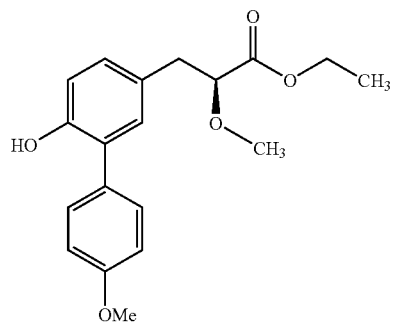

A solution of (2S)(4-Hydroxy-3-iodide-)-2-methoxy dihydrocinnamic acid (197 mg, 0.56 mmol), 4-methoxyphenyl boronic acid (170.7 mg, 1.12 mmol) and tetrakis(triphenylphosphine)-palladium (0) (8.7 mg, 0.5 mmol) in 11 mL of a mixture 20:1 toluene/ethanol together with 2 mL of a 2N Na2CO3 was heated to 120° for 16 hours under nitrogen atmosphere. The reaction mixture was cooled to room temperature and dilute with ethyl acetate (20 mL). It was washed with H2O (3×5 mL) and brine (3×5 mL). The combined organic layers were dried (MgSO4), filtered and concentrated under vacuum. The resultant crude was purified by column chromatography (silica gel, hexanes/ethyl acetate 8:2). Colorless oil (123 mg, 67%). ¹H-NMR (200.15 MHz, CDCl3): δ 7.39 (dd, 2H, J=2.1, 6.4), 7.08–7.03 (m, 2H), 6.97 (dd, 2H, J=2.1, 6.7), 6.85 (dd, 1H, J=1.3, 7.5), 5.60 (s, 1H), 4.17 (q, 2H, J=7.0), 3.95 (dd, 1H, J=5.9, 6.4), 3.82 (s, 3H), 3.35 (s, 3H), 2.97 (d, 2H, J=6.4), 1.22 (t, 3H, J=7.2)

Step C (2S)-3-{6-[3-(Biphenyl-4-yloxy)-propoxy]-4'-methoxy-biphenyl-3-yl}-2-methoxy-propionic acid ethyl ester

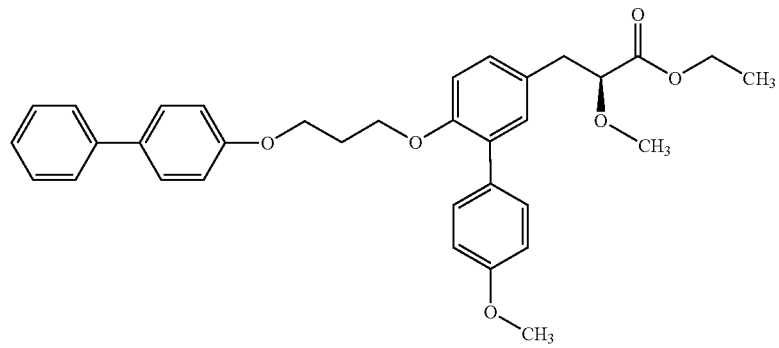

3-{6-[3-(Biphenyl-4-yloxy)-propoxy]4'-methoxy-biphenyl-3-yl}-2-methoxy-propionic acid ethyl ester was prepared following the Standard Procedure B (THF). The residue was purified by chromatography (silica gel, hexanes/ethyl acetate 8:2). White solid (13 mg, 17%). $^1$H-NMR (200.15 MHz, CDCl$_3$): δ 7.57 (m, 10H), 7.14 (dd, 2H, J=2.1, 7.8), 6.94–6.87 (m, 4H), 4.24–4.04 (m, 6H), 3.94 (dd,1H, J=5.9, 6.9), 3.81 (s, 3H), 3.36 (s, 3H), 2.99 (d, 2H, J=6.9), 2.18 (qn, 2H, J=5.9), 1.22 (t, 3H, J=7.2).

Step D (2S)-3-{6-[3-(Biphenyl-4-yloxy)-propoxy]-4'-methoxy-biphenyl-3-yl}-2-methoxy-propionic acid The title compound was prepared following the procedure described in example 25 (Step C). $^1$H-NMR (200.15 MHz, CDCl$_3$): δ 7.57–6.87 (m, 16 H), 4.15 (t, 2H, J=6.1), 4.07 (t, 2H, J=6.1), 4.01 (dd, 1H, J=7.2, 4.5), 3.80 (s, 3H), 3.41 (s, 3H), 3.13 (dd, 1H, J=4.5, 14.4), 2.99 (dd, 1H, J=7.1, 14.4), 2.21 (qn, 2H, J=5.9).

Example 141

3-{6-[3-{-(Biphenyl-4-yloxy)-propoxy]-4'-fluoro-biphenyl-3-yl}-2-methoxy-propionic acid

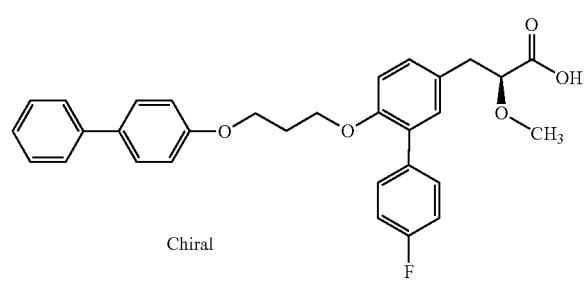

The title compound was prepared as in Example 140, with 4-fluorophenyl boronic acid. $^1$H-NMR (200.15 MHz, CDCl$_3$): δ 7.57–6.87 (m, 16 H), 4.15 (t, 2H, J=5.9), 4.04 (t, 2H, J=5.9), 4.02 (dd, 1H, J=7.2, 4.5), 3.41 (s, 3H), 3.13 (dd, 1H, J=4.5, 14.2), 3.00 (dd, 1H, J=7.5, 14.2), 2.17 (qn, 2H, J=5.9).

Example 142

3-{6-[3-(Biphenyl-4-yloxy)-propoxy]-[1,1';4',1"]terphenyl-3-yl}-2-methoxy-propionic acid

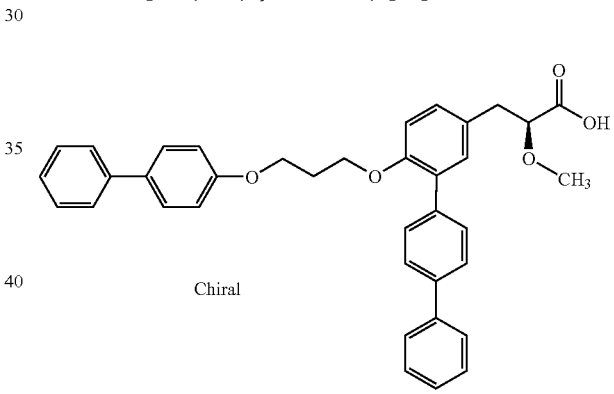

The title compound was prepared as in Example 140, with 4-phenylphenyl boronic acid Example 143

3-{6-[3-(Biphenyl-4-yloxy)-propoxy]-2'-methoxy-biphenyl-3-yl}-2-methoxy-propionic acid

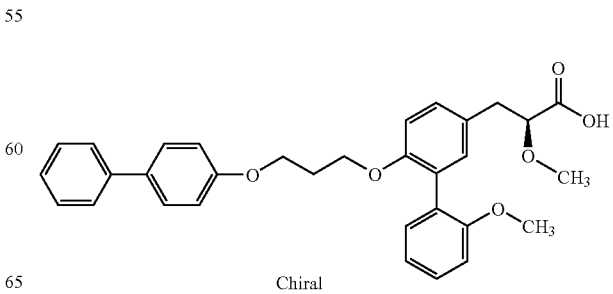

The title compound was prepared as in Example 140, with 2-methoxyphenyl boronic acid.

Example 144

2-Methoxy-3-{6-[3-(4-phenoxy-phenoxy)-propoxy]-[1,1':4',1"]terphenyl-3-yl}-propionic acid

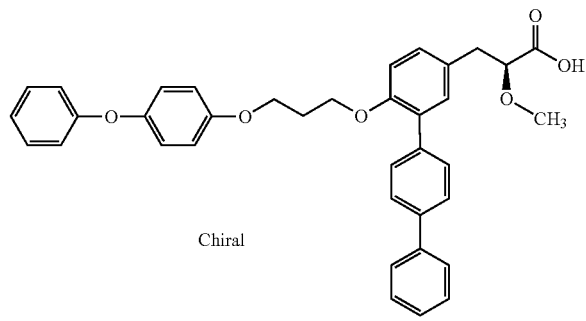

The title compound was prepared as in Example 140, with 4-diphenyl boronic acid.

Example 145

3-{4-[3-(4-Benzoyl-phenoxy)-propoxy]-3-styryl-phenyl}-2-methoxy-propionic acid

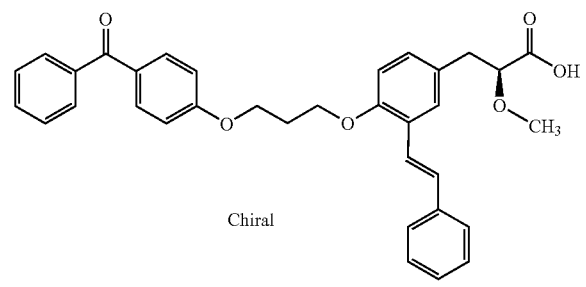

The title compound was prepared as in Example 140, with trans-2-phenylvinyl boronic acid

Example 146

3-(4-{3-[4-(Hydroxy-phenyl-methyl)-phenoxy]-propoxy}-3-phenethyl-phenyl)-2-methoxy-propionic acid

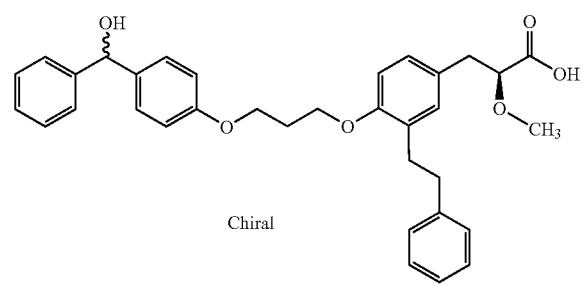

A solution of 3-{4-[3-(4-Benzoyl-phenoxy)-propoxy]-3-styryl-phenyl}-2-methoxy-propionic acid ethyl ester from Example 145, was dissolved in ethanol and treated with $H_2$ under balloon pressure. Filtered through a pad of celite and concentrated to dryness. The compound thus obtained was treated under standard hydrolysis procedure C to give the title compound.

Example 147

3-{4-[3-(4-Benzyl-phenoxy)-propoxy]-3-phenethyl-phenyl}-2-methoxy-propionic acid

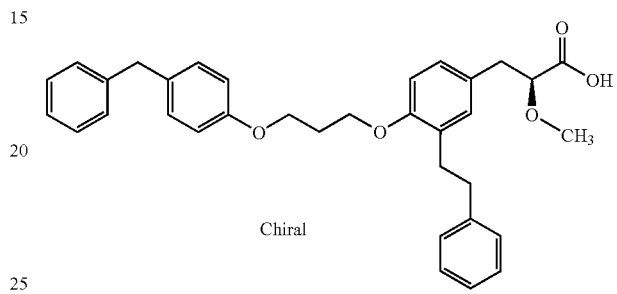

The title compound was obtained as a secondary product of the reduction of 3-{4-[3-(4-Benzoyl-phenoxy)-propoxy]-3-styryl-phenyl}-2-methoxy-propionic acid ethyl ester (from Example 145) as in Example 146, and was hydrolyzed under the standard hydrolysis procedure C to afford the product.

Example 148

(2S)-3-{3-Allyl-4-[3-(4-phenoxy-phenoxy)-propoxy]-phenyl}-2-methoxy-propionic acid

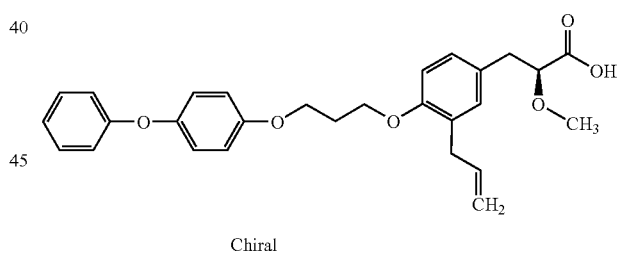

Step A (2S)-3-(3-Allyl-4-hydroxy-phenyl)-2-methoxy-propionic acid ethyl ester

To a solution of 3-(4-hydroxy-phenyl)-2-methoxy-propionic acid ethyl ester (1 eq) in acetone, K₂CO₃ (2 eq) and alkyl bromide (1.2 eq) were added and the mixture reaction was stirred at 55° C. over night. Quenched with water and extracted with ethyl acetate. The organic layer was dried (MgSO₄) and concentrated to give 3-(4-alkyloxy-phenyl)-2-methoxy-propionic acid ethyl ester. This crude product was dissolved in Me₂NPh and heated to reflux for 6 hours and then stirred at room temperature over 3 days. Refluxed again for 8 hours and then poured into and ice-cold HCl 1M solution, extracted with ethyl acetate and washed with water. Dried and concentrated to give a crude product which was purified by chromatography to give the title product.

Step B (2S)-3-{3-Allyl-4-[3-(4-phenoxy-phenoxy)-propoxy]-phenyl}-2-methoxy-propionic acid ethyl ester

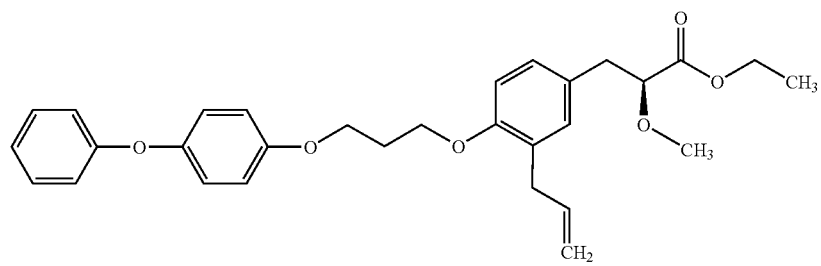

(2S)-3-(3-Allyl-4-hydroxy-phenyl)-2-methoxy-propionic acid ethyl ester from Step A was allowed to react with 4-(3-bromopropoxy)-1-phenoxybenzene under the Standard Procedure I to give the title compound.

Step C (2S)-3-{3-Allyl-4-[3-(4-phenoxy-phenoxy)-propoxy]-phenyl}-2-methoxy-propionic acid (2S)-3-{3-Allyl-4-[3-(4-phenoxy-phenoxy)-propoxy]-phenyl}-2-methoxy-propionic acid ethyl ester from Step B was hydrolyzed under the standard hydrolysis procedure C to afford the product.

Example 149

(2S)-2-Methoxy-3-{4-[3-(4-phenoxy-phenoxy)-propoxy]-3-propyl-phenyl}-propionic acid

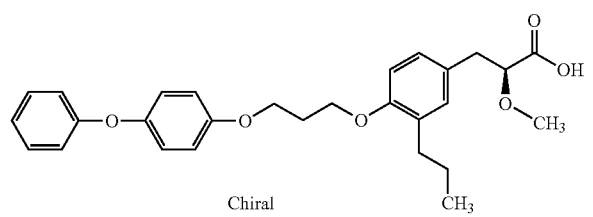

A solution of (2S)-3-{3-Allyl-4-[3-(4-phenoxy-phenoxy)-propoxy]-phenyl}-2-methoxy-propionic acid ethyl ester, from Example 148, Step B, was dissolved in ethanol and treated with H₂ under balloon pressure. Filtered through a pad of celite and concentrated to dryness. The compound thus obtained was treated under, standard hydrolysis procedure C to give the title compound.

Example 150

3-{4-[3-(Biphenyl-4-yloxy)-propoxy]-2-methyl-phenyl}-2-methoxy-acrylic acid

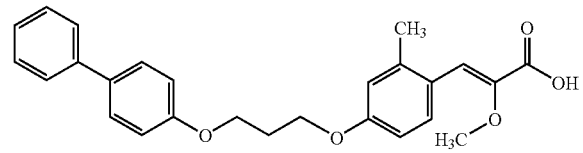

Step A

4-Triisopropylsilanloxy-benzaldehyde

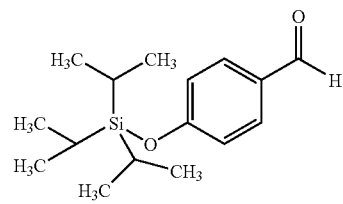

4-hydroxybenzaldehyde (3 g, 24.57 mmol), triisopropylsilyl chloride (5.52 mL, 25.79 mmol) and imidazol (2 g, 29.48 mmol) were dissolved in 60 mL of DMF and the solution stirred at room temperature overnight. Water (120 mL) was added to the solution and the mixture extracted with diethyl ether (3×50 mL). The combined extracts were washed with water (5×30 mL), saturated ammonium chloride (2×30 mL) and brine (20 mL) and dried (MgSO₄). Concentration produced an oil that was purified by chromatography (silica gel, hexanes/Ethyl acetate 20:1, $R_f$ 0.4) (75%).

¹H-NMR (CDCl₃, 200.15 MHz): 9.85 (s, 1H), 7.75 (d, 2H, J=8.9), 6.95 (d, 2H, J=8.4), 1.31–1.20 (m, 3H), 1.10 (s, 18H).

Step B

2-Methyl-4-triisopropylsilanyloxy-benzaldehyde

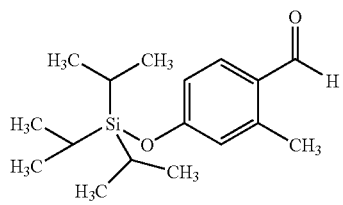

To a solution of trimethylethylenediamine (0.45 mL, 3.48 mmol) in THF (9 mL) at −20° C. was added Butyllithium 1.6M in hexanes (2.11 mL, 3.8 mmol). The solution was stirred at −20° C. for 15 min. A solution of 4-Triisopropylsilanyloxy-benzaldehyde (0.922 g, 3.31 mmol) was added dropwise and the solution stirred for 15 min at −20° C. Bu 16M in hexanes (6.21 ml, 9.93 mmol) was added dropwise and the solution kept in the freezer at −20° C. for 26 hours. The solution was cooled to 40° C. and methyl iodide (3.71 mL, 59.60 mmol) was added. The solution was allowed to reach room temperature and further stirred 30 ml. The reaction was quenched with saturated ammonium chloride (20 mL) and extracted with ethyl acetate (3×30 mL). The combined extracts were dried (MgSO$_4$), concentrated under vacuum and purified by column chromatography (silica gel, hexanes/Ethyl acetate 20:1, R$_f$0.085) (49%). $^1$H-NMR (CDCl$_3$, 200.15 MHz): δ 10.1 (s, 1H), 7.69 (d, 1H, J=8.3), 6.80 (dd, 1H, J=8.6, 2.4), 6.72 (s, 1H), 0.61 (s, 3H), 1.33–1.19 (m, 3H), 1.12 (s,18H).

Step C

3-{4-[3-(Biphenyl-4-yloxy)-propoxy]-2-methyl-phenyl}-2-methoxy-acrylic acid methyl ester

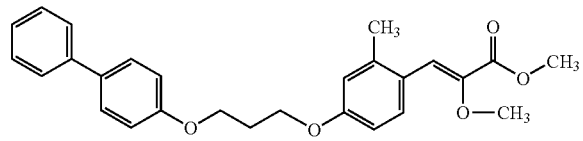

Methyl 2-methoxyacetate (0.450 mL, 4.53 mmol) was added to a solution of NaHDMS (4.74 mmol) in 40 mL of THF cooled to −78° C. The mixture was stirred at −78° C. for 30 min and then a solution of 2-Methyl-4-trisopropylsilanyloxy-benzaldehyde (1.26 g, 4.3 mmol) in 20 mL of THF was added dropwise. The solution was allowed to warm to 0° C. and stirred for 2.5 hours. The mixture was quenched with HCl 1N (50 mL) at 0° C., extracted with dichloromethane (3×40 mL), dried (MgSO$_4$) and concentrated under vacuum. The residue was dissolved in dichloromethane (50 mL) and cooled to 0° C. To the solution was added trifluoroacetic anhidride (0.82 mL, 5.84 mmol), N,N-dimethylaminopyridine (0.025 g, 0.21 mmol), and pyridine (0.379 mL, 4.59 mmol). And stirred at room temperature for 4 hours. The volatiles were eliminated under vacuum and the residue dissolved in 100 mL of ethyl acetate. Palladium 10% on activated carbon (0.9 g) was added and the mixture hydrogenated at room temperature (5 Atm H$_2$) for 14 hours. The solution was filtered through a pad of celite and concentrated under vacuum. The residue was purified by column chromatography (silica gel, hexanes/Ethyl acetate 3:1) the fractions with R$_f$0.08 were collected and concentrated under vacuum (0.249 g containing 3-(4-Hydroxy-2-methyl-phenyl)-2-methoxy-acrylic acid c.a. 85% pure by NMR). The residue was added to a solution of 4-(3-Bromo-propoxy)-biphenyl (example 23, Step D) (0.359 g, 1.23 mmol), sodium iodide (0.05 g) and potassium tert-butoxide (126 mg, 1.12 mmol) in 5 mL of dimethylformamide. The solution was stirred at room temperature 24 hours, diluted with water and extracted with diethylether (3×30 mL). The combined organic layers were washed with water (5×30 ml), dried (MgSO$_4$) and concentrated under vacuum. The residue was purified by column chromatography (silica gel, hexane:ethyl acetate 6:1, R$_f$0.22). (0.18 mg, 10%). $^1$H-NMR (CDCl$_3$, 200.15 MHz): δ 7.98 (d, 1H, J=8.6), 7.57–7.25 (m, 7H), 7.16 (s, 1H); 6.98 (dd, J=6.7, 2.1), 6.80–6.76 (m, 2H), 4.20 (t, 4H, J=5.9), 3.85 (s, 3H), 3.69 (s, 3H), 2.36 (s, 3H), 2.29 (t, 2H, J=6.2).

Step D

3-{4-[3-(Biphenyl-4-yloxy)-propoxy]-2-methyl-phenyl}-2-methoxy-acrylic acid

The title compound was prepared from 3-{4-[3-(Biphenyl-4-yloxy)-propoxy]-2-methyl-phenyl}-2-methoxy-acrylic acid methyl ester following the general procedure B. $^1$H-NMR (CDCl$_3$, 200.15 MHz): 7.97 (d, 1H, J=8.4), 7.55–7.47 (m, 4H), 7.43–7.27 (m, 4H), 6.96 (dd, 2H, J=6.6, 2.2), 6.79–6.75 (m, 2H), 4.19 (t, 4H, J=6.2), 3.69 (s, 3H), 2.35 (s, 3H), 2.27 (t, 2H, J=6.2).

Example 151

3-{4-[3-(Biphenyl-4-yloxy)-propoxy]-2-methyl-phenyl}-2-methoxy-propionic acid

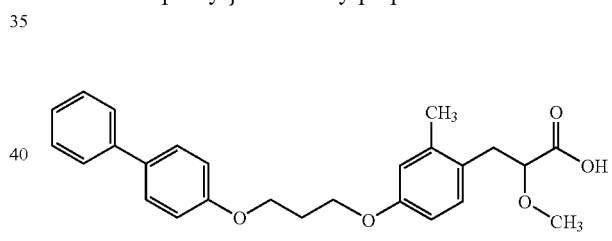

Step A

3-{4-[3-(Biphenyl-4-yloxy)-propoxy]-2-methyl-phenyl}-2-methoxy-propionic acid methyl ester

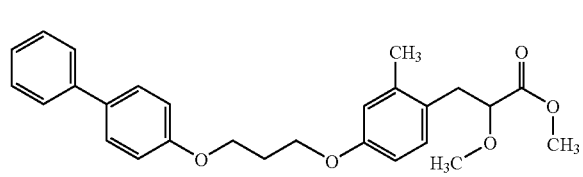

Magnesium turnings (0.101 g, 4.17 mmol) was added to a solution of 3-{4-[3-(Biphenyl-4-yloxy)-propoxy]-2-methyl-phenyl}-2-methoxy-acrylic acid methyl ester (Example 37, Step C) (0.09 g, 0.21 mmol) in methanol (2 mL) and diethyl ether (2 mL). The mixture was stirred at room temperature overnight and then quenched with HCl 3N until pH 7. A saturated solution of ammonium chloride (10 mL) was added and the mixture extracted with ethyl ether (3×10 mL). The combined extracts were dried (MgSO$_4$) and con centrated under vacuum. The residue was purified by column chromatography. (Silica Gel, hexanes/Ethyl acetate 4.5:1, R$_f$ 0.31) (48%). $^1$H-NMR (CDCl$_3$, 200.15 MHz): 7.57–7.29 (m, 7H), 7.07 (d, 1H, J=8.1); 6.98 (dd, 2H, J=6.7, 2.1), 6.73 (s, 1H); 6.71 (d, 1H, J=11.8); 4.18 (dt, 4H, J=9.7, 6.2), 3.91 (dd, 1H, J=7.3, 6.2), 3.72 (s, 3H), 3.32 (s, 3H), 2.97 (d, 2H, J=6.4), 2.31 (s, 3H); 2.27 (t, 2H, J=6.2).

Step B

3-{4-[3-(Biphenyl-4-yloxy)-propoxy]-2-methyl-phenyl}-2-methoxy-propionic acid

The title compound was prepared from 3-{4-[3-(Biphenyl-4-yloxy)-propoxy]-2-methyl-phenyl}-2-methoxy-propionic acid methyl ester following the general procedure B. (71%). $^1$H-NMR (CDCl$_3$, 200.15 MHz): δ 7.55–7.27 (m, 7H); 7.09 (d, 1H, J=8.1); 6.96 (d, 2H, J=9.2); 6.71–6.67 (m, 2H); 4.15 (dt, 4H, J=9.1, 6.2); 3.92 (dd, 1H, J=8.4, 4.4); 3.31 (s, 3H); 3.08 (dd, 1H, J=14.6, 4.4); 2.93 (dd, 1H, J=14.3, 8.4); 2.30 (s, 3H); 2.25 (qn, 2H, J=6.2).

Example 152

3-{3-[3-(Biphenyl-4-yloxy)-propoxy]-phenyl}-2-methoxy-propionic acid

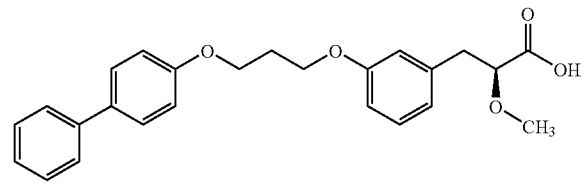

Step A 3-(3-Benzyloxy-phenyl)-3-hydroxy-2-methoxy-propionic acid methyl ester

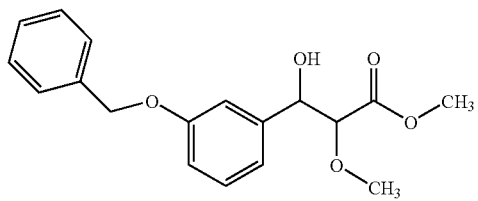

To a solution of NaHMDS (1.1 eq) in dry THF at −78° C. a mixture of 3-benzyloxy-benzaldehyde (1 eq) and methoxy-acetic acid methyl ester (1.25 eq) in THF were added dropwise and the mixture reaction at this temperature over 1.5 hours. Then the reaction was quenched with HCl 3N and allowed to rise room temperature. Washed with brine and extracted with ether. The organic layer was dried and concentrated to dryness to, give after chromatography in silica gel the title product.

Step B 3-(3-Benzyloxy-phenyl)-2-methoxy-acrylic acid methyl ester

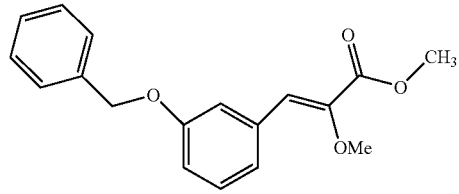

A mixture of 3-(3-Benzyloxy-phenyl)-3-hydroxy-2-methoxy-propionic acid methyl ester (1 eq), mesylchloride (1 eq) triethylamine (4 eq) and a catalytic amount of DMAP (0.1 eq) in dichloromethane was stirred at room temperature overnight. The Reaction mixture was diluted with ether and washed with HCl 1N. Dried and concentrated in vacuo to give a residue which was chromatographed in silica gel to yield the title compound.

Step C 3-(3-Benzyloxy-phenyl)-2-methoxy-propionic acid methyl ester

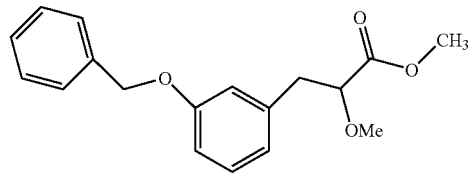

Compound from Step B was dissolved in methanol and treated with magnesium. The flask was placed in an ice bath for 5 min and then the reaction mixture was stirred at room temperature for 4 hours. Washed with HCl 3N and extracted with ether. Dry and concentrated to dryness to get the title compound.

Step D 3-(3-Hydroxy-phenyl)-2-methoxy-propionic acid methyl ester

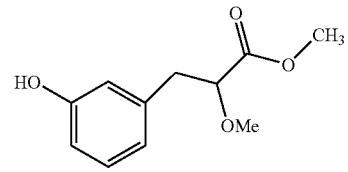

A solution of 3-(3-Benzyloxy-phenyl)-2-methoxy-propionic acid methyl ester in methanol was treated with a catalytic amount of C—Pd (0.1 eq) and then H$_2$ was bubbled through the mixture and stirred overnight. The mixture reaction was concentrated and reconstituted in ethyl acetate, filtered through a pad of celite and concentrated in vacuo to give the title compound.

Step E

3-{3-[3-(Biphenyl-4-yloxy)-propoxy]-phenyl}-2-methoxy-propionic acid

A mixture of 3-(3-Hydroxyphenyl)-2-methoxy-propionic acid methyl ester (1 eq) from Step D, Cesium Carbonate (3 eq) and 4-(3-bromopropoxy)biphenyl (1 eq) in DMF and in a 10 mL tube was shaked in an orbital agitator over a weekend. The mixture was filtered through a hydrofobic syringer and evaporated in a speed-vac apparatus. Then diluted with NaOH 1N-Ethanol and stirred overnight. Then HCl 3N was added and the reaction mixture was concentrated to remove the ethanol in vacuo, reconstituted in dichloromethane and filtered through a hydrofobic syringe. The organic layer was evaporated to give the title compound. MS (ES) for $C_{25}H_{26}O_5$ [M+NH$^4$]$^+$: 424.2, [M+Na]$^+$: 429.2. $^1$H-NMR (CDCl$_3$, 200.15 MHz): 7.57–7.17 (m, 9H), 6.98 (dd, 2H, J=6.7, 1.9), 6.84–6.81 (m, 3H), 4.19 (dd, 4H, J=14.0, 6.4), 4.03 (dd, 1H, J=7.3, 4.3), 3.40 (s, 3H), 3.13 (dd, 1H, J=14.2, 4.6), 2.98 (dd, 1H, J=14.0, 7.5), 2.28 (qui, 2H, J=5.9)ppm.

Example 153

'2-Methoxy-3-{3-[3-(4-phenoxy-phenoxy)-propoxy]-phenyl}-propionic acid

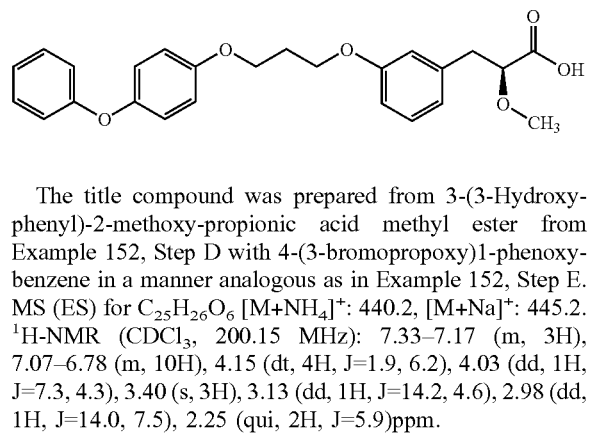

The title compound was prepared from 3-(3-Hydroxy-phenyl)-2-methoxy-propionic acid methyl ester from Example 152, Step D with 4-(3-bromopropoxy)1-phenoxy-benzene in a manner analogous as in Example 152, Step E. MS (ES) for $C_{25}H_{26}O_6$ [M+NH$_4$]$^+$: 440.2, [M+Na]$^+$: 445.2. $^1$H-NMR (CDCl$_3$, 200.15 MHz): 7.33–7.17 (m, 3H), 7.07–6.78 (m, 10H), 4.15 (dt, 4H, J=1.9, 6.2), 4.03 (dd, 1H, J=7.3, 4.3), 3.40 (s, 3H), 3.13 (dd, 1H, J=14.2, 4.6), 2.98 (dd, 1H, J=14.0, 7.5), 2.25 (qui, 2H, J=5.9)ppm.

Example 154

3-{3-[3-Benzoyl-phenoxy)-propoxy]-phenyl}-2-methoxy-propionic acid

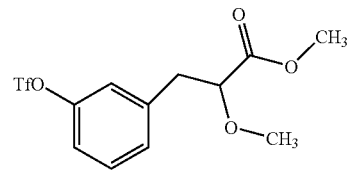

The title compound was prepared from 3-(3-Hydroxy-phenyl)-2-methoxy-propionic acid methyl ester from Example 152, Step D with [4-(3-Bromo-propoxy)-phenyl]-phenyl-methanone in a manner analogous as in Example 152, Step E. MS (ES) for $C_{26}H_{26}O_6$ M+H]$^+$: 435.2, [M+Na]$^+$: 457.2. 1H-NMR (CDCl3, 200.15 MHz): 7.83–7.72 (m, 4H), 7.56–7.42 (m, 3H), 7.21 (dd, 2H, J=9.1, 7.0), 6.97 (d, 2H, J=8.9), 6.82 (d, 1H, J=14.2), 6.82 (s, 2H), 4.25 (t, 2H, J=6.2), 4.16 (t, 2H, J=5.9), 4.02 (dd, 1H, J=7.5, 4.3), 3.40 (s, 3H), 3.12 (dd, 1H, J=14.0, 4.3), 2.98 (dd, 1H, J=14.2, 7.5), 2.29 (qui, 2H, J=5.9).

Example 155

2-Methoxy-3-{3-[5-(4-phenoxy-phenoxy)-pent-1-ynyl]-phenyl}-propionic acid

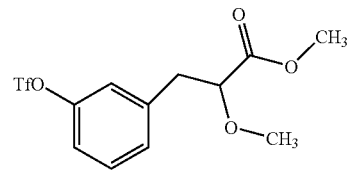

Step A

2-Methoxy-3-(3-trifluoromethanesulfonyloxy-phenyl)-propionic acid methyl ester

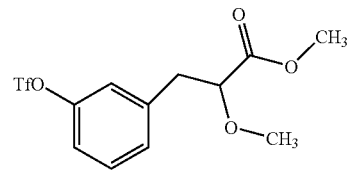

The title compound was prepared using the same procedure as in Example 1, Step A starting from 3-(3-Hydroxy-phenyl)-2-methoxy-propionic acid methyl ester.

Step B

3-[3-(5-Hydroxy-pent-1-ynyl)-phenyl]-2-methoxy-propionic acid methyl ester

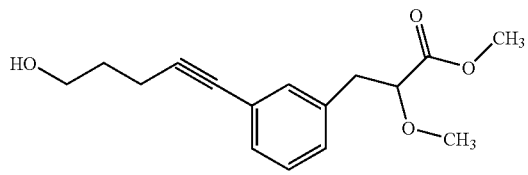

The title compound was prepared from 4-butyn-1-ol following the procedure described, in Example 1, Step B.

Step C

3-[3-(5-Bromo-pent-1-ynyl)-phenyl]-2-methoxy-propionic acid methyl ester

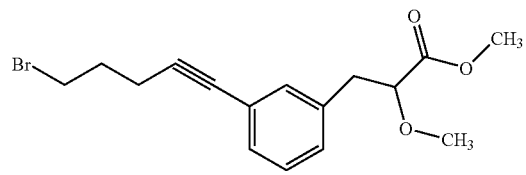

To a solution of 3-[3-(5-Hydroxy-pent-1-ynyl)-phenyl]-2-methoxy-propionic acid methyl ester, and CBr$_4$ dissolved in dichloromethane at 0° C., triphenylphosphine was added and the mixture reaction was stirred at room temperature over 5 hours.

The reaction then was diluted with water and extracted with ether.

Chromatographied to give the title compound.

Step D

2-Methoxy-3-{3-[5-(4-phenoxy-phenoxy)-pent-1-ynyl-3-phenyl]-propionic acid methyl ester

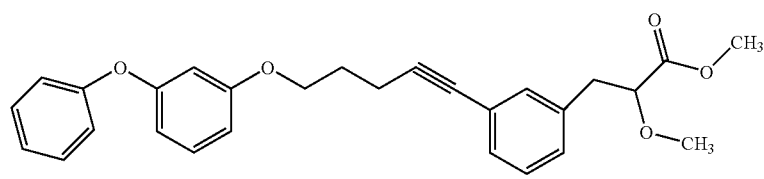

A mixture of 3-[3-(5-Bromo-pent-1-ynyl)-phenyl]-2-methoxy-propionic acid methyl ester (1 eq), 4-phenoxyphenol (1 eq) and Cesium carbonate (3 eq), in DMF was stirred overnight. Then diluted in water and extracted with ether to give after dry in vacuo the title compound.

Step E

2-Methoxy-3-{3-[5-(4-phenoxy-phenoxy)-pent-1-ynyl]-phenyl}-propionic acid

The title compound was prepared following the Standard Hydrolysis Procedure C and starting from 2-Methoxy-3-{3-[5-(4-phenoxy-phenoxy)-pent-1-ynyl]-phenyl}-propionic acid methyl ester from Step D. MS (ES) for C$_{27}$H$_{26}$O$_5$ [M+NH$^4$]$^+$: 448.2, [M+Na]$^+$: 453.2. $^1$H-NMR (CDCl$_3$, 200.15 MHz): 7.33–7.17 (m, 7H), 7.07–6.88 (m, 7H), 4.11 (t, 2H, J=0.2), 4.00 (dd, 1H, J=7.5, 4.0), 3.39 (s, 3H), 3.11 (dd, 1H, J=14.0, 4.3), 2.96 (dd, 1H, J=14.5, 7.8), 2.63 (t, 2H, J=7.0), 2.08 (qui, 2H, J=6.7).

Example 156

2-Methoxy-3-{3-[5-(4-phenoxy-phenoxy)-pentyl]-phenyl}-propionic acid

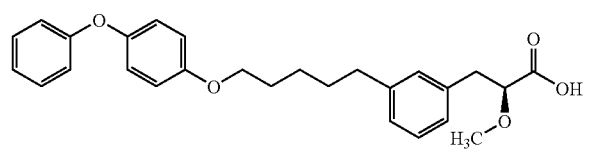

The title compound was prepared from 2-Methoxy-3-{3-[5-(4-phenoxy-phenoxy)-pent-1-ynyl]-phenyl}-propionic acid of Example 155, Step E, and treated with Pd—C (0.1 eq) in ethyl acetate and H$_2$. Filtered through celite and concentrated to give the compound. MS (ES) for C$_{27}$H$_{30}$O$_5$ [M+H]$^+$: 435.2, [M+NH$_4$]$^+$: 452.2. $^1$H-NMR (CDCl$_3$, 200.15 MHz): 7.34–7.19 (m, 3H), 7.09–6.84 (m, 10H), 4.02 (dd, 1H, J=7.5, 4.6), 3.94 (t, 2H, J=6.5), 3.39 (s, 3H), 3.13 (dd, 1H, J=14.0, 4.3), 3.00 (dd, 1H, J=14.0, 7.5), 2.63 (t, 2H, J=7.8), 1.88–1.45 (m, 6H)ppm.

Example 157

2-Methoxy-3-{3-[5-(4-phenoxy-phenoxy)-pentanoyl]-phenyl}-propionic acid

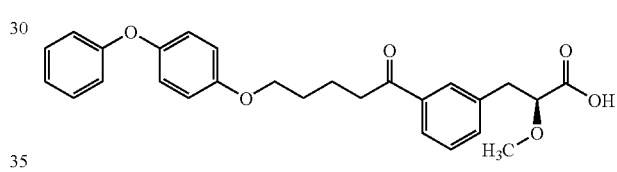

The title compound was prepared from 2-Methoxy-3-{3-[5-(4-phenoxy-phenoxy)-pent-1-ynyl]-phenyl}-propionic acid methyl ester (Example 155, Step D) and following the same procedure as in Example 57, and a standard hydrolysis procedure C to get the compound.

Example 158

3-{4-[3-(3-Allyl-biphenyl-4-yloxy)-propoxy]-phenyl}-2-methoxy-propionic acid

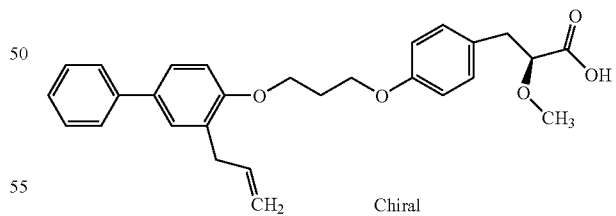

Step A

2-Allyl-4-phenoxy-phenol

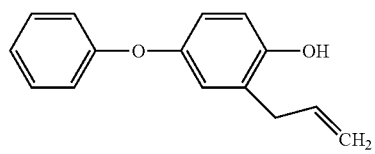

To a solution of 4-phenylphenol (1 eq) in acetone, K₂CO₃ (2 eq) and alkyl bromide (1.2 eq) were added and the mixture reaction was stirred at 55° C. overnight. Quenched with water and extracted with ethyl acetate. The organic layer was dried (MgSO₄) and concentrated to give 4-allyloxybiphenyl. This crude product was dissolved in Me₂NPh and heated to reflux for 6 hours and then stirred at room temperature over 3 days. Refluxed again for 8 hours and then poured into and ice-cold HCl 1M solution, extracted with ethyl acetate and washed with water. Dried and concentrated to give a crude product which was purified by chromatography to give the title product.

Step B 3-(3-Allyl-biphenyl-4-yloxy)-propan-1-ol

The product obtained in Step A (1.1 eq) was dissolved in THF and treated with t-BuOK (1.15 eq) and allowed to react for 2 hours. Then a solution of [1,3,2]Dioxathiolane 2,2-dioxide (1.0 eq) was added and the mixture reaction was stirred overnight quenched with HCl 6N and refluxed the reaction overnight. Extracted with ethyl acetate, washed with brine and concentrated to give the title compound.

Step C

3-{4-[3-(3-Allyl-biphenyl-4-yloxy)-propoxy]-phenyl}-2-methoxy-propionic acid ethyl ester

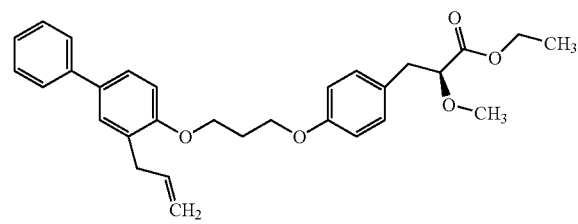

A solution of compound from Step B in dichloromethane was treated with CBr₄ (1.12 eq) and PPh₃ (1.4 eq) and allow to react for 1.5 hours. The product isolated after chromatography of this reaction was treated under Standard Procedure I with (2S)-3-(4-hydroxy-phenyl)-2-methoxy-propionic acid ethyl ester to give the title compound.

Step D

3-{4-[3-(3-Allyl-biphenyl-4-yloxy)-propoxy]-phenyl}-2-methoxy-propionic acid

The title compound was prepared by using the standard Hydrolysis Procedure (NaOH) C.

Example 159

(2S)-2-Methoxy-3-{4-[3-(3-propyl-biphenyl-4-yloxy)-propoxy]-phenyl}-propionic acid

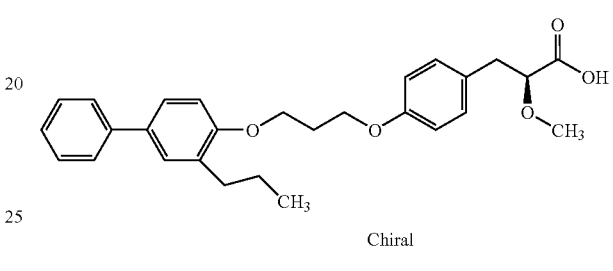

3-{4-[3-(3-Allyl-biphenyl-4-yloxy)-propoxy]-phenyl}-2-methoxy-propionic acid from Example 158, Step D dissolved in ethyl acetate was treated with Pd(C) 10% under balloon pressure for 6 hours. Filtered through celite and concentrated to dryness to give the title compound.

Example 160

(2S)-3-{4-[3-(2-Allyl-4-phenoxy-phenoxy)-propoxy]-phenyl}-2-methoxy-propionic acid Step A 2-Allyl-4-phenoxyphenol

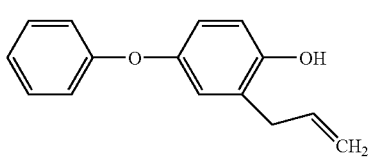

The title compound was prepared in a same manner as in Example 158, Step A, starting from 4-phenoxyphenol.

Step B

2-{4-[3-(2-Allyl-4-phenoxy-phenoxy)-propoxy]-phenyl}-3-methoxy-propionic acid ethyl ester

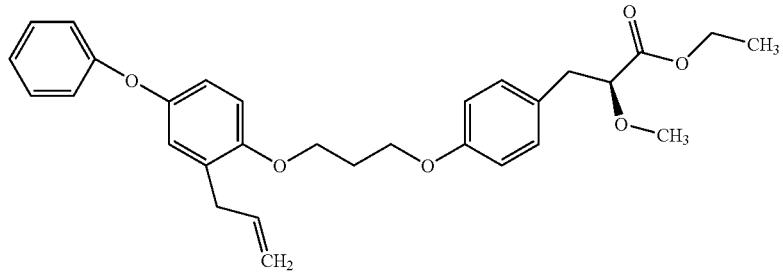

3-[4-(3-Bromo-propoxy)-phenyl]-2-methoxy-propionic acid ethyl ester and 2-Allyl-4-phenoxy-phenol from Step A were allowed to react under Standard Procedure I to give the title compound.

Step C (2S)-3-{4-[3-(2-Allyl-4-phenoxy-phenoxy)-propoxy]-phenyl}-2-methoxy-propionic acid The title compound was prepared by using the standard Hydrolysis Procedure C (NaOH) to yield the compound.

Example 161

(2S)-2-Methoxy-3-{4-[3-(4-phenoxy-2-propyl-phenoxy)-propoxy]-phenyl}-propionic acid

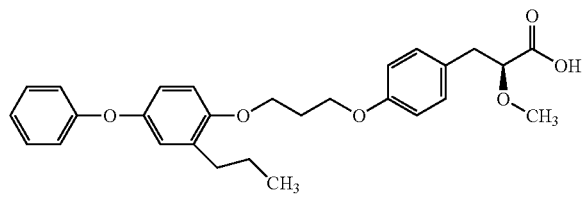

The title compound was prepared from 2-{4-[3-(2-Allyl-4-phenoxy-phenoxy)-propoxy]-phenyl}-3-methoxy-propionic acid ethyl ester from Example 160, Step B which was treated in ethyl acetate with Pd(C) and $H_2$ in balloon presure to give after filtration the corresponding reduced product which was hydrolyzed under Standard Procedure C to give the title compound.

Example 162

3-{4-[3-Biphenyl-4-yloxy)-propoxy]-3-methyl-phenyl}-2-methoxy-propionic acid

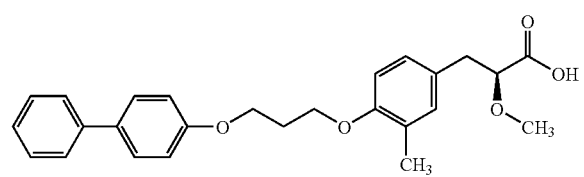

Step A

4-Benzyloxy-3-methyl-benzaldehyde

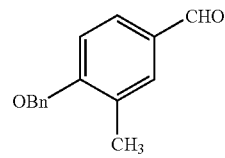

A mixture of benzyl bromide and 4-hydroxy-3-methyl-benzaldehyde were treated under Standard Procedure I to give the title product.

Step B 3-(4-Benzyloxy-3-methyl-phenyl)-3-hydroxy-2-methoxy-propionic acid ethyl ester

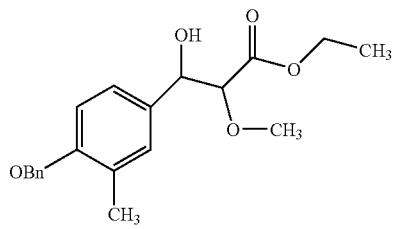

To a solution of NaHMDS (1.1 eq) in dry THF at −78° C. a mixture of 4-Benzyloxy-3-methyl-benzaldehyde (1 eq) and Methoxy-acetic acid methyl ester (1.25 eq) in THF were added dropwise and the mixture reaction at this temperature over 1.5 hours. Then the reaction was quenched with HCl 3N and allowed to rise room temperature. Washed with brine and extracted with ether. The organic layer was dried and concentrated to dryness to give after chromatography in silica gel the title product.

Step C 3-(4-Benzyloxy-3-methyl-phenyl-2-methoxy-acrylic acid ethyl ester

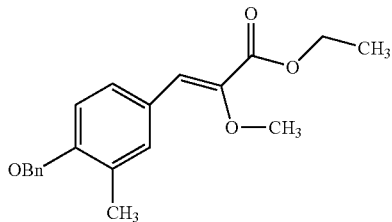

A mixture of 3-(4-Benzyloxy-3-methyl-phenyl)-3-hydroxy-2-methoxy-propionic acid ethyl ester (1 eq), Mesylchloride (1 eq) triethylamine (4 eq) and a catalytic amount of DMAP (0.1 eq) in dichloromethane was stirred at room temperature over night. The reaction mixture was diluted with ether and washed with HCl 1N. Dried and concentrated in vacuo to give a residue which was chromatographed in silica gel to yield the title compound.

Step D 3-(4-Benzyloxy-3-methyl-phenol)-2-methoxy-propionic acid ethyl ester

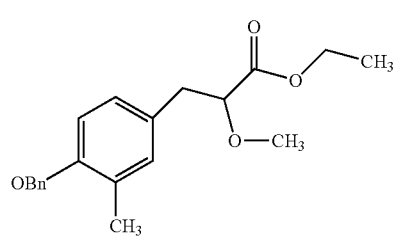

Compound from Step C was dissolved in methanol and treated with magnesium.

The flask was placed in an ice bath for 5 min and then the reaction mixture was stirred at room temperature for 4 hours. Washed with HCl 3N and extracted with ether. Dry and concentrated to dryness to get the title compound.

Step E 3-(4-Hydroxy-3-methyl-phenyl)-2-methoxy-propionic acid ethyl ester

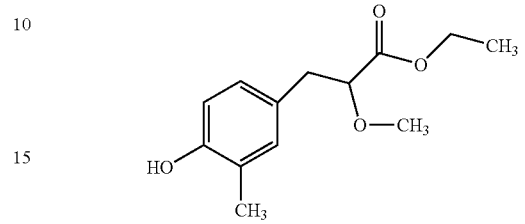

A solution of 3-(4-Benzyloxy-3-methyl-phenyl)-2-methoxy-propionic acid ethyl ester in ethyl acetate was treated with a catalytic amount of C—Pd (0.1 eq) and then H$_2$ was bubbled through the mixture and stirred 2 hours. The mixture reaction was filtered through a pad of celite and concentrated in vacuo to give the title compound.

Step F (2S)-3-{4-[3-(Biphenyl-4-yloxy)-propoxy]-3-methyl-phenyl}-2-methoxy-propionic acid ethyl ester

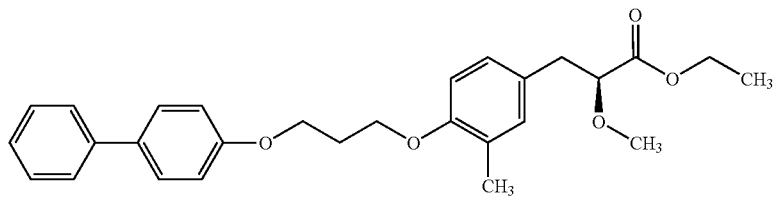

A mixture of 3-(4-Hydroxy-3-methyl-phenyl)-2-methoxy-propionic acid ethyl ester and from Step E and 4-(3-bromopropoxy)biphenyl were treated under standard condition I to give the title product.

Step G

3-{4-[3-(Biphenyl-4-yloxy)-propoxy]-3-methyl-phenyl}-2-methoxy-propionic acid

The title compound was prepared from compound from Step F under Standard hydrolysis procedure C using NaOH.

Example 163

2-Methoxy-3-{3-methyl-4-[3-(4-phenoxy-phenoxy)-propoxy]-phenyl}-propionic acid

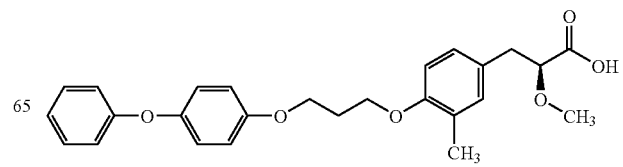

Step A

2-Methoxy-3-{3-methyl-4-[3-(4-phenoxy-phenoxy)-propoxy]-phenyl}-propionic acid ethyl ester

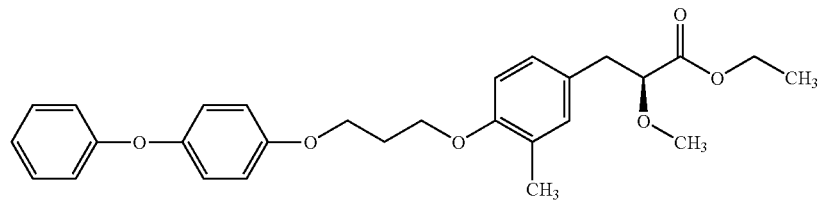

A mixture of 3-(Hydroxy-3-methyl-phenyl)-2-methoxy-propionic acid ethyl ester and from Example 162, Step E and 4-(3-bromopropoxy)-phenoxyphenyl were treated under standard condition I to give the title product.

Step B

The title compound was prepared from compound from Step A under Standard hydrolysis procedure C using NaOH.

Example 164

3-{4-[3-(4-Benzoyl-phenoxy)-propoxy]-3-methyl-phenyl}-2-methoxy-propionic acid

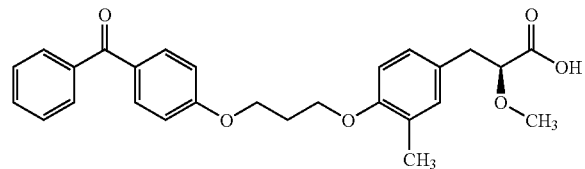

Step A

3-[4-(3-Benzoyl-phenoxy)-propoxy]-3-methyl-phenyl}-2-methoxy-propionic acid ethyl ester

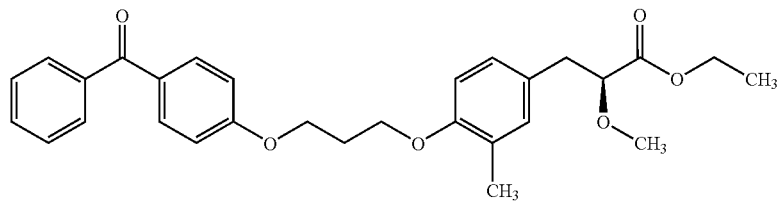

A mixture of 3-(4-Hydroxy-3-methyl-phenyl)-2-methoxy-propionic acid ethyl ester and from Example 162, Step E and [4-(3-Bromo-propoxy)-phenyl]-phenyl-methanone were treated under standard condition I to give the title product.

Step B

3-{4-[3-(4-Benzoyl-phenoxy)-propoxy]-3-methyl-phenyl}-2-methoxy-propionic acid

The title compound was prepared from compound from Step A under Standard hydrolysis procedure C using NaOH.

Example 165

(2S)-3-{4-[3-(Dibenzofuran-2-yloxy)-propoxy]-phenyl}-2-methoxy-propionic acid

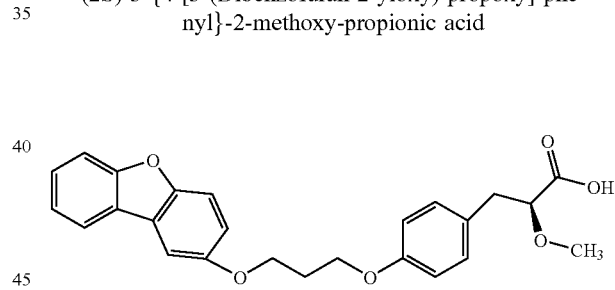

Step A

3-(Dibenzofuran-2-yloxy-propan-1-ol

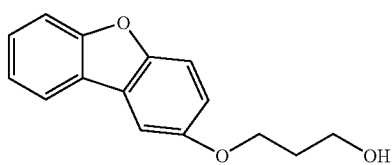

A solution of 2-hydroxydibenzofurane, potassium tert-butoxide and [1,2,3]dioxathiane-2,2-dioxide were treated as the same manner as in Example 132, Step C, to give the title product.

Step B

2-(3-Bromo-propoxy)-dibenzofuran

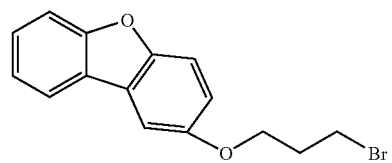

Starting from compound of Step A and following the procedure described in Example 132, Step D we obtained the title compound.

Step C

3-{4-[3-(Dibenzofuran-2-yloxy)-propoxy]-phenyl}-2-methoxy-propionic acid ethyl ester

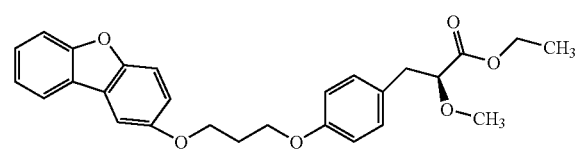

A mixture of 2-(3-Bromo-propoxy)-dibenzofuran and (2S)-3-(4-hydroxy-phenyl)-2-methoxy propionic acid ethyl ester were allowed to react under the Standard Procedure I to give the title compound.

Step D

(2S)-3-{4-[3-(Dibenzofuran-2-yloxy)-propoxy]-phenyl}-2-methoxy-propionic acid The title compound was prepared from Step C using the standard hydrolysis procedure C (NaOH).

Example 166

(2S)-3-[4-(3-{4-[(4-Fluoro-phenyl)-hydroxyimino-methyl]-phenoxy}-propoxy)-phenyl]-2-methoxy-propionic acid

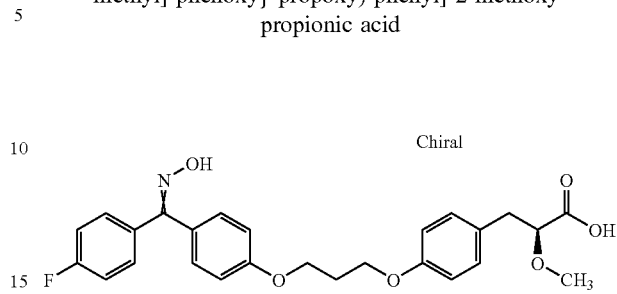

The title compound was prepared from (2S)-3-(4-{3-[4-(4-Fluoro-benzoyl)-phenoxy]-propoxy}-phenyl)-2-methoxy-propionic acid (Example 95), and was treated under the same conditions as in Example 61, to give the title compound.

Example 167

(2S)-3-[4-(3-{4-[(4-Fluoro-phenyl)-hydroxy-methyl]-phenoxy}-propoxy)-phenyl]-2-methoxy-propionic acid

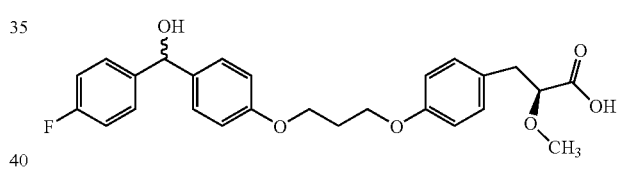

Step A (2S)-3-[4-(3-{4-[(4-Fluoro-phenyl)-hydroxy-methyl]-phenoxy}-propoxy)-phenyl]-2-methoxy-propionic acid ethyl ester

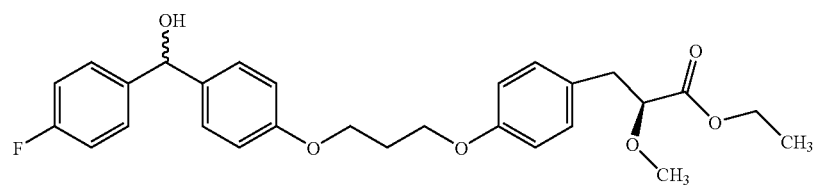

The title compound was prepared from (2S)-3-(4-{3-[4-(4-Fluoro-benzoyl)-phenoxy]-propoxy}-phenyl)-2-methoxy-propionic acid ethyl ester (Example 95) which was dissolved in methanol and treated at 0° C. with NaBH$_4$ (2 eq) for 6 hours. Washed with water and extracted with dichloromethane to give after purification by chromatography the title compound.

Step B

2S)-3-[4-(3-{4-[(4-Fluoro-phenyl)-hydroxy-methyl]-phenoxy}-propoxy)-phenyl]-2-methoxy-propionic acid The title compound was prepared from Step A by standard hydrolysis procedure C (NaOH).

Example 168

(2S)-2-Methoxy-3-(4-{3-[4-(4-piperidin-1-benzoyl]-propoxy}-phenyl)-propionic acid

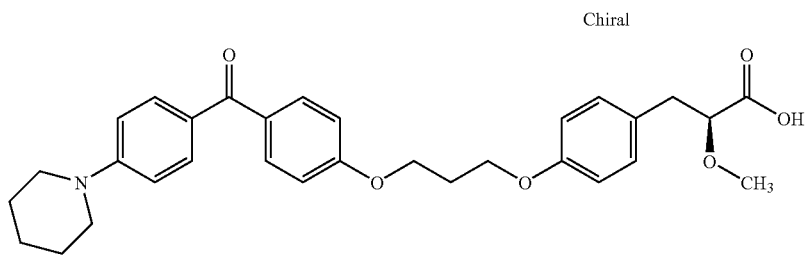

Step A (2S)-2-Methoxy-3-(4-{3-[4-(4-piperidin-1-yl-benzoyl)-phenoxy]-propoxy}-phenyl)-propionic acid ethyl ester

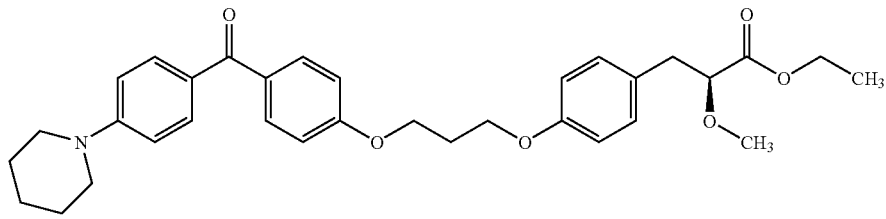

To a solution of (2S)-3-(4-{3-[4-(4-Fluoro-benzoyl)-phenoxy]-propoxy}-phenyl)-2-methoxy-propionic acid ethyl ester (Example 95) in DMSO, piperydine (3 eq) was added and the mixture reaction was heated to 140° C. for 2 days. The reaction was extracted with ethyl acetate and washed (several times) with water. Concentrated to dryness and chromatographied to give the title compound.

Step B (2S)-2-Methoxy-3-(4-{3-[4-(4-piperidin-1-yl-benzoyl)-phenoxy]-propoxy}-phenyl)-propionic acid The title compound was prepared from Step A by standard hydrolysis procedure C (LiOH). MS (ES) for $C_{31}H_{35}NO_6$ [M+H]$^+$: 518.

Example 169

(2S)-2-Methoxy-3-(4-{3-[4-(4-morpholin-4-yl-benzoyl)-phenoxy]-propoxy}-phenyl)-propionic acid

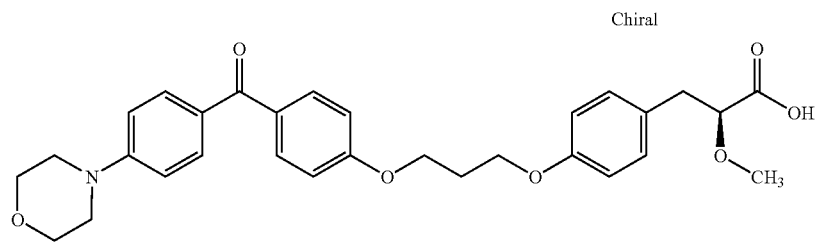

Step A (2S)-2-Methoxy-3-(4-{3-[4-(4-morpholin-4-yl-benzoyl)-phenoxy-propoxy}-phenyl)-propionic acid ethyl ester

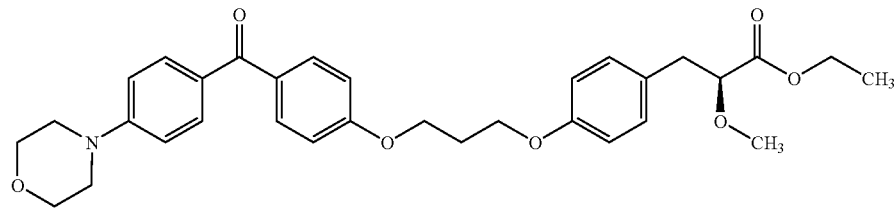

To a solution of (2S)-3-(4-{3-[4-(4-Fluoro-benzoyl)-phenoxy]-propoxy}-phenyl)-2-methoxy-propionic acid ethyl ester (Example 95) in DMSO, morpholyne (3 eq) was added and the mixture reaction was heated to 140° C. for 2 days. The reaction was extracted with ethyl acetate and washed (several times) with water. Concentrated to dryness and chromatographed to give the title compound.

Step B (2S)-2-Methoxy-3-(4-{3-[4-(4-morpholin-4-benzoyl)-phenoxy]-propoxy}-phenyl)-propionic acid The title compound was prepared from Step A by standard hydrolysis procedure C (LiOH). MS (ES) for $C_{30}H_{33}NO_7$ [M+H]$^+$: 520.

Example 170

(2S)-3-(4-{3-[4-(4-Hydroxy-benzoyl)-phenoxy]-propoxy}-phenyl)-2-methoxy-propionic acid

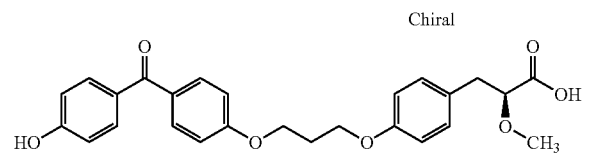

A solution of (2S)-3-(4-{3-[4-(4-Fluoro-benzoyl)-phenoxy]-propoxy}-phenyl)-2-methoxy-propionic acid (85 mg) (Example 95) and KOH (100 mg) in chlorobenzene (0.3 ml) with water (1 ml) were heated in sealed tube at 200° C. for 3 days. Extracted with ethyl acetate, dried and concentrated to dryness to give a crude product which was purified by chromatography to give the title compound. MS (ES) for $C_{26}H_{26}O_7$ [M+H]$^+$: 451.

Example 171

2S-2-methoxy-3-{4-[3-(4-phenoxy-phenoxy)-propoxy]phenyl}propanoic acid sodium salt

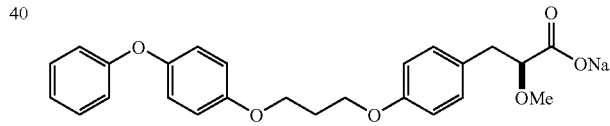

Step 1: 1-chloro-3-(4-phenoxyphenyl propane (a)

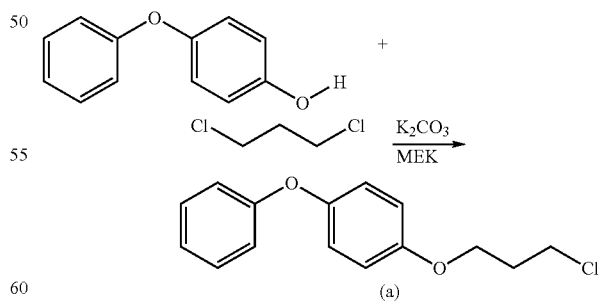

The compound of 4-phenoxyphenol (81.03 g, 435.5 mmol) was dissolved in 810 ml MEK at ambient temperature under Nitrogen. Powdered potassium carbonate (577.16 g, 4,176.27 mmol) was added followed by 1,3-dichloropropane (300.00 g, 2,655.1 mmol), and the resulting solution was heated to reflux for 15.5 hours. The solution was cooled to room temperature, filtered and washed with 750 ml MEK. The filtrate was concentrated under vacuum to give a crude orange liquid. The crude liquid was dissolved in 260 ml absolute MeOH at ambient temperature and stirred 5 minutes, which was then cooled in an ice/acetone/water bath for 1.5 hours. White precipitate was filtered off and washed with 480 ml cold absolute MeOH. The white solid was collected and dried under vacuum at 30° C. for 16 hours to afford about 81.87 g of compound (a).

Step 2: 2S-2-methoxy-3-{4-[3-(4-phenoxy-phenoxy)-propoxy]-phenyl}-propanoic acid sodium salt

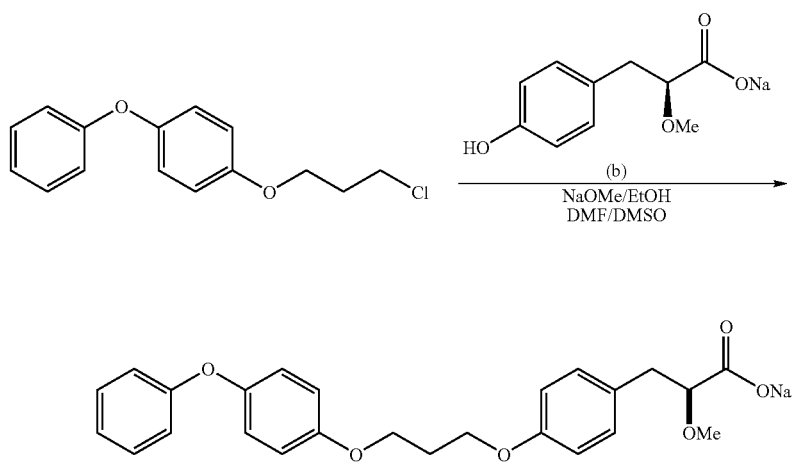

The compound (b) (10.9 g, 50 mmol) was dissolved in 50 ml absolute ethanol at ambient temperature. Sodium methoxide (4.05 g, 75 mmol) was added all at once, and the resulting solution was heated to reflux for 30 minutes. The solution was cooled to 40° C. and the compound (a) (15.72 g, 75 mmol) was added all at once followed by 50 ml DMF and 50 ml DMSO. The clear red solution was heated to reflux for 30 minutes, and cooled to ambient temperature. The ethanol was removed under vacuum at 60° C., and a mixture 100 ml of water and 100 ml MTBE was added. The top organic layer was separated and discarded Fresh MTBE (100 ml) was added and crystallization occurred. The biphasic slurry was stirred at ambient temperature for 30 minutes, filtered and washed with 250 ml MTBE. The white solid was dried under vacuum at 60° C. for 16 hours to afford about 15.34 g of the title compound.

Example 172

(2S)-3-[4-(3-{4-[Hydroxyamino-(4-hydroxy-phenyl)-methyl]-phenoxy}-propoxy)-phenyl]-2-methoxy-propionic acid

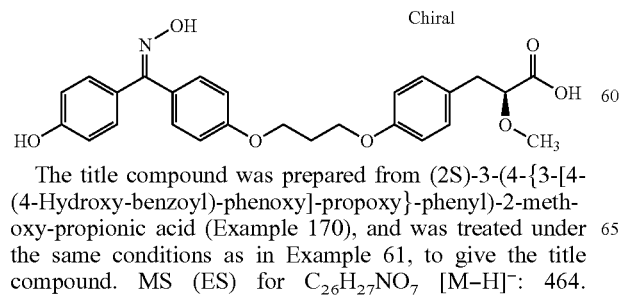

The title compound was prepared from (2S)-3-(4-{3-[4-(4-Hydroxy-benzoyl)-phenoxy]-propoxy}-phenyl)-2-methoxy-propionic acid (Example 170), and was treated under the same conditions as in Example 61, to give the title compound. MS (ES) for $C_{26}H_{27}NO_7$ [M–H]$^-$: 464.

Example 173

(2S)-3-{4-[3-(4-Benzoyl-3-hydroxy-phenoxy)-propoxy]-phenyl}-2-methoxy-propionic acid

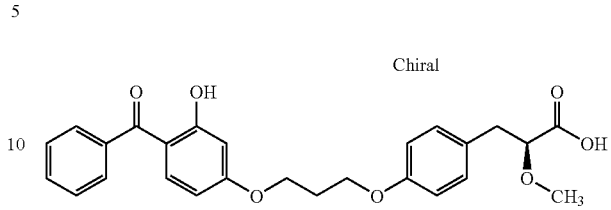

Step A (2S)-3-[4-(3-Bromo-propoxy)-phenyl]-2-methoxy-propionic acid ethyl ester

The title compound was prepared from (2S)-3-[4-(3-Hydroxy-propoxy)-phenyl]-2-methoxy-propionic acid ethyl ester from Example 171, Step B, and following the procedure described in Example 132, Step D we obtained the title compound.

Step B

3-{4-[3-(4-Benzoyl-3-hydroxy-phenoxy)-propoxy]-phenyl}-2-methoxy-propionic acid ethyl ester

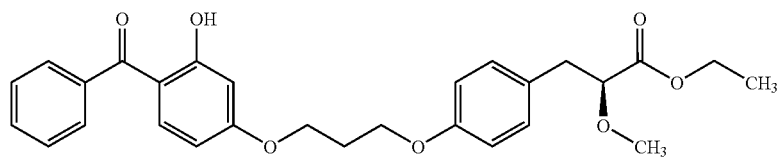

A mixture of (2S)-3-[4-(3-Bromo-propoxy)-phenyl]-2-methoxy-propionic acid ethyl ester from Step A and 2,4-dihydroxybenzophenone were allowed to react under the Standard Procedure I to get to title compound.

Step C (2S)-3-{4-[3-(4-Benzoyl-3-hydroxy-phenoxy)-propoxy]-phenyl}-2-methoxy-propionic acid The title compound was prepared from Step B by standard hydrolysis procedure C (LiOH). MS (ES) for $C_{26}H_{26}O_7$ [M–H]$^-$: 449.

Example 174

(2S)-3-(4-{3-[4-(2,4-Dimethoxy-benzoyl)-phenoxy]-propoxy}-phenyl)-2-methoxy-propionic acid

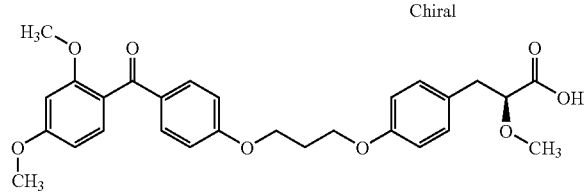

Step A 3-(4-{3-[4-(2,4-Dimethoxy-benzoyl)-phenoxy]-propoxy}-phenyl)-2-methoxy-propionic acid ethyl ester

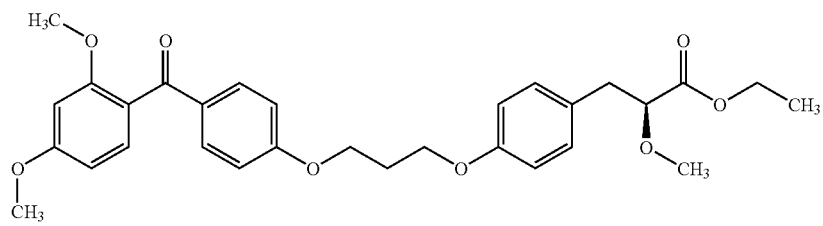

A mixture of (2S)-3-[4-(3-Bromo-propoxy)-phenyl]-2-methoxy-propionic acid ethyl ester from 0, Step A and 2,4-dimethoxy-4'hydroxybenzophenone were allowed to react under the Standard Procedure I to get to title compound.

Step B (2S)-3-(4-{3-[4-(2,4-Dimethoxy-benzoyl)-phenoxy]-propoxy}-phenyl)-2-methoxy-propionic acid The title compound was prepared from Step A by standard hydrolysis procedure C (LiOH). MS (ES) for $C_{28}H_{30}O_8$ [M–H]$^-$: 493.

Example 175

3-{4-[3-(4-Benzyl-phenoxy-propoxy]-3-methoxy-phenyl}-2-methoxy-propionic acid

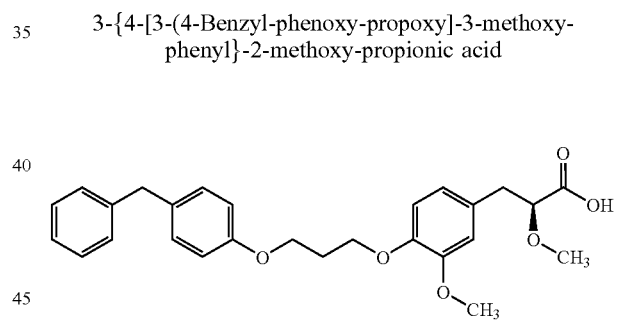

Step A

3-[4-(3-Hydroxy-propoxy)-3-methoxy-phenyl]-2-methoxy-propionic acid

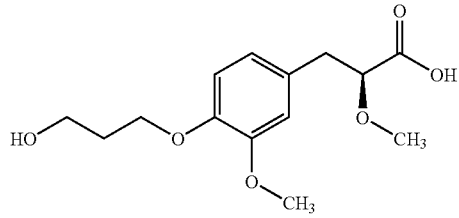

A mixture of 3-(4-Hydroxy-3-methoxy-phenyl)-2-methoxy-propionic acid ethyl ester (Example 130, Step A) and 3-(tert-Butyl-dimethyl-silanyloxy)-propan-1-ol were treated under Mitsounobu coupling standard conditions B using DIAD and toluene. The product thus obtained was treated under Standard Procedure E for cleaveage protected alcohols to give the title product.

Step B

3-[4-(3-Bromo-propoxy)-3-methoxy-phenyl]-2-methoxy-propionic acid

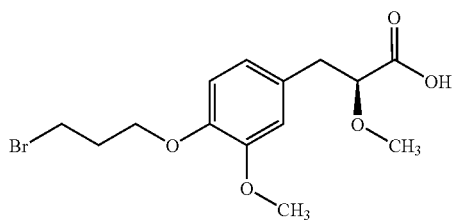

The title compound was prepared from 3-[4-(3-Hydroxy-propoxy)-3-methoxy-phenyl]-2-methoxy-propionic acid and following the procedure described in Example 132, Step D we obtained the title compound.

Step C

3-{4-[3-(4-Benzyl-phenoxy)-propoxy]-3-methoxy-phenyl}-2-methoxy-propionic acid

The title compound was prepared from 3-[4-(3-Bromo-propoxy)-3-methoxy-phenyl]-2-methoxy-propionic acid and 4-benzylphenol following the Standard Procedure J. MS (ES) for $C_{27}H_{30}O_6$ [M+NH$_4$]$^+$: 468, [M+Na]$^+$: 473.

Example 176

(S)-3-(4-benzyloxy-phenyl)-2-isopropoxy-propionic acid

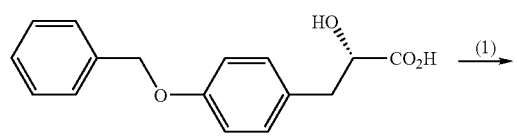

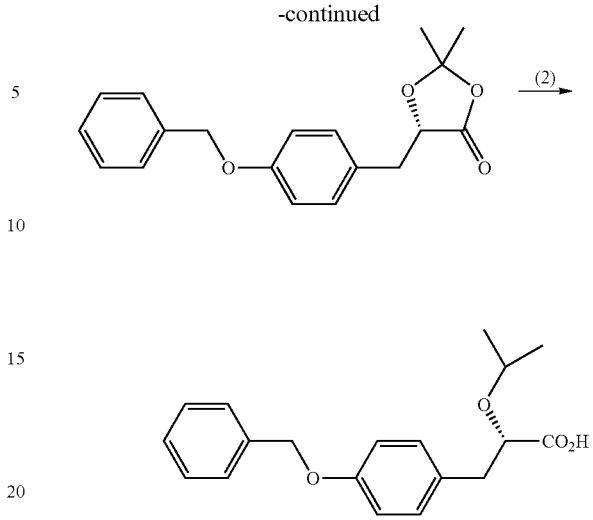

Step 1: A solution containing (S)-5-(4-benzyloxy-benzyl)-2,2-dimethyl-[1,3]dioxolan-4-one (S)-3-(4-benzyloxy-phenyl)-2-hydroxy-propionic acid (2.0 g, 7.34 mmol), 2,2-dimethoxypropane (18.63 g, 0.179 mol) and pyrididium p-toluene sulfonate (0.92 g, 3.66 mmol) in chloroform (80 mL) was heated to reflux for 40 minutes under $N_2$. The reaction was cooled, diluted with water and extracted with $CH_2Cl_2$. The organic layer was dried ($Na_2SO_4$) and the solvent was removed in vacuo to give crude product which was purified by a flash chromatography using 10:1 hexanes: acetone to afford about 2.01 g (88%) of (S)-5-(4-benzyloxy-benzyl)-2,2-dimethyl-[1,3]dioxolan-4-one. $^1$H NMR (400 MHz, CDCl$_3$) δ 7.43–7.29 (m, 5H), 7.17 (d, 2H, J=8.80 Hz), 6.91 (d, 2H, J=8.80 Hz), 5.04 (s, 2H), 4.61 (dd, 1H, J=6.36 Hz, J=4.40 Hz), 3.12 (dd, 1H, J=14.67 Hz, J=4.40 Hz), 2.99 (dd, 1H, J=14.67 Hz, J=6.36 Hz), 1.49 (s, 3H), 1.36 (s, 3H). MS (ES$^+$) m/z exact mass calculated for $C_{19}H_{20}O_4$ (M+NH$_4$) 330. Found m/z 330.

Step 2: (S)-3-(4-benzyloxy-phenyl)-2-isopropoxy-propionic acid A −78° C. solution of (S)-5-(4-benzyloxy-benzyl)-2,2-dimethyl-[1,3]dioxolan-4-one (0.20 g, 0.64 mmol) and triethylsilane (0.223 g, 1.92 mmol) in $CH_2Cl_2$ (8 mL) was treated dropwise with a 1 molar solution of $TiCl_4$ in $CH_2Cl_2$ (0.64 mL, 0.64 mmol) under $N_2$. The solution was stirred at −78° C. for 15 minutes and then quenched with water. The mixture was extracted with EtOAc, and the organic layer was dried ($Na_2SO_2$). The organic layer was filtered, and the solvent was removed in vacuo to give crude product which was purified by a flash chromatography using 5:1 hexanes: acetone to afford 0.171 g (85%) (S)-3-(4-benzyloxy-phenyl)-2-isopropoxy-propionic acid. $^1$H NMR (400 MHz, DMSO-d$_6$) δ 12.50 (bs, 1H), 7.42–7.27 (m, 5H), 7.12 (d, 2H, J=8.80 Hz), 6.88 (d, 2H, J=8.80 Hz), 5.02 (s, 2H), 3.96 (dd, 1H, J=7.83 Hz, J=4.89 Hz), 3.47 (hp, 1H, J=5.87 Hz), 2.83 (dd, 1H, J=13.69 Hz, J=4.89 Hz), 2.71 (dd, 1H, J=13.69 Hz, J=8.31 Hz), 1.02 (d, 2H, J=5.87 Hz), 0.86 (d, 2H, J=5.87 Hz). IR (KBr) 3012, 2977, 2931, 1767, 1722, 1610, 1511, 1380, 1240, 1116, 1020. HRMS (TOF ES$^-$) m/z exact mass calculated for $C_{19}H_{21}O_4$ (M−1) 13.1440. Found m/z 313.1434.

Example 176A (2S)-2-isopropoxy-3-{4-[3-(4-phenoxy)-phenoxy)-propoxy]phenyl}propanoic acid sodium salt

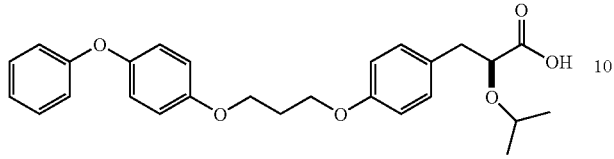

Scheme

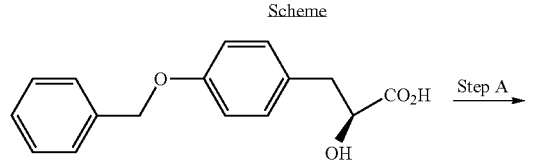

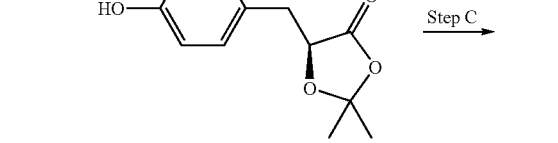

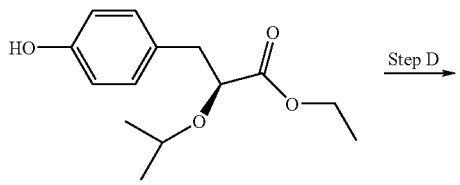

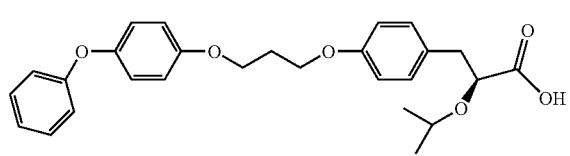

(S)-3-(4-hydroxy-phenyl)-2-methoxy-propionic-acid ethyl ester

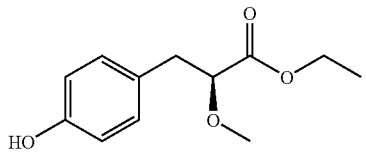

A solution of (S)-3-(4-hydroxy-phenyl)-2-methoxy-propionic acid (20 g, 100 mmol) in 3 A ethanol (140 mL) was treated dropwise with concentrated sulfuric acid (5.7 mL)) and stirred at room temperature overnight. The solution was concentrated and is water (110 mL) was added. Sodium bicarbonate was added to bring the pH to 7–8. The mixture was extracted with ethyl acetate (3×50 mL). The combined organic layers were washed with 20% NaCl solution (50 ml), dried (MgSO$_4$), filtered, and concentrated to a golden oil (18 g, 80%). $^1$H-NMR (CDCl$_3$): 7.1(d, 2H); 6.7(d, 2H); 4.2(m, 2H); 3.9(m, 1H); 3.6(s, 3H); 2.95(m, 2H); 125(t, 3H). MS (ES): 223.2 (M−1).

(S)-3-(4-benzyloxy-phenyl)-2-hydroxy-propionic acid

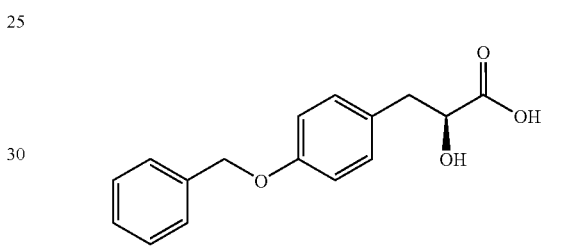

(S)-2-Hydroxy-3-(4-hydroxy-phenyl)-propionic acid (121 g, 0.664 mol) (Wang et al. *Tetrahedron Lett.* 1998, 39, 5501) in absolute EtOH (2 L) was treated with potassium carbonate (184 g, 1.33 mol) and benzyl chloride 169 g, 1.34 mol). The mixture was heated at reflux overnight and concentrated to about half the volume under vacuum. Aqueous 5N NaOH (100 mL) was added, and the mixture was stirred at ambient temperature overnight and then concentrated. The residue was acidified with concentrated HCl. The yellow sold was collected by filtration and dried overnight under vacuum at 50° C. The crude product in isopropanol (1.8 L) was heated at reflux for about 30 minutes, cooled to ambient temperature, and stirred for about 16 hours. The slurry was filtered and dried under vacuum at 70° C. overnight to give the title compound as a white solid (137 g, 76%).

Step A: (S)-5-(4-benzyloxy-benzyl)-2,2-dimethyl-[1,3]dioxolan-4-one (S)-3-(4-Benzyloxy-phenyl)-2-hydroxy-propionic acid (2.0 g, 7.34 mmol), 2,2-dimethoxypropane (18.63 g, 0.179 mol) and pyridinium p-toluene sulfonate (0.92 g, 3.66 mmol) in chloroform (80 mL) was heated to reflux for 40 minutes under N$_2$. The mixture was cooled, diluted with water, and extracted with CH$_2$Cl$_2$. The organic layer was dried (Na$_2$SO$_4$) and concentrated in vacuo to give crude product that was purified by flash chromatography using 10:1 hexanes:acetone to afford the title compound (2.01 g, 88%). $^1$H-NMR (400 MHz, CDCl$_3$) δ 7.43–7.29 (m, 5H), 7.17 (d, 2H, J=8.80 Hz), 6.91 (d, 2H, J=8.80 Hz), 5.04 (s, 2H), 4.61 (dd, 1H, J=6.36 Hz, J=4.40 Hz), 3.12 (dd, 1H, J=14.617 Hz, J=4.40 Hz), 2.99 (dd, 1H, J=14.67 Hz, J=6.36 Hz), 1.49 (s, 3H), 1.36 (s, 3H). MS (ES$^+$) m/z calc'd for C$_{19}$H$_{20}$O$_4$ (M+NH$_4$) 330. Found m/z 330.

Step B: (S)-5-(4-hydroxy-benzyl)-2,2-dimethyl-[1,3]dioxolane-4-one (S)-5-(4-benzyloxy-benzyl)-2,2-dimethyl-[1,3]dioxolan-4-one (1.0 g, 3.2 mmol) was combined with 10% Pd/C (0.75 g) in EtOAc (40 mL) and purged with $N_2$ then $H_2$ and then stirred under a hydrogen balloon for 3 hours. Sodium sulfate was added, and the mixture was filtered through Celite. The solvent was removed in vacuo to afford the title compound (0.747 g, 100%). $^1$H NMR (400 MHz, CDCl$_3$) δ 7.11 (d, 2H, J=8.31 Hz), 6.76 (d, 2H, J=8.31 Hz), 4.93 (bs, 1H), 4.61 (dd, 1H, J=6.36 Hz, J=4.40 Hz), 3.11 (dd, 1H, J=14.67 Hz, J=4.40 Hz), 2.98 (dd, 1H, J=14.67 Hz, J=5.86 Hz), 1.49 (s, 3H), 1.36 (s, 3H). MS (ES$^-$) m/z mass calc'd for $C_{12}H_{14}O_4$ (M−1) 221. Found m/z 221.

Step C: (S)-3-(4-hydroxy-phenyl)-2-isopropoxy-propionic acid ethyl ester

A 0° C. solution of (S)-5-(4-hydroxy-benzyl)-2,2-methyl-[1,3]dioxolan-4-one (0.20 g, 0.90 mmol) and triethylsilane (1.05 g, 9.02 mmol) in CH$_2$Cl$_2$ (10 mL) was treated dropwise with TiCl$_4$ (0.90 mL, 0.90 mmol, 1M CH$_2$Cl$_2$) under $N_2$. The solution was stirred at 0° C. for about 15 min and warmed to room temperature. After about 45 minutes, the mixture was quenched with water and extracted with EtOAc. The organic layer was dried (Na$_2$SO$_2$), filtered, and concentrated in vacuo to give of crude product (0.32 g). This material was combined with ethanol (25 mL) and conc. H$_2$SO$_2$ (1 mL) and stirred for 17 hours at room temperature under $N_2$. The mixture was concentrated and partitioned between EtOAc and water. The organic layer was dried (Na$_2$SO$_2$), filtered, and concentrated in vacuo. The crude product was purified by flash chromatography using 5:1 hexanes:acetone to afford the title compound (0.158 g, 70%). $^1$H NMR (400 MHz, CDCl$_3$) δ 7.11 (d, 2H, J=8.31 Hz), 6.76 (d, 2H, J=8.31 Hz), 4.79 (bs, 1H), 4.20–4.12 (m, 2H), 3.99 (dd, 1H, J=8.56 Hz, J=4.89 Hz), 3.49 (hp, 1H, J=6.36 Hz), 2.94–2.83 (m, 2H), 1.23 (t, 3H, J=6.85 Hz), 1.14 (d, 3H, J=6.36 Hz), 0.96 (d, 3H, J=6.36 Hz). MS (ES$^-$) m/z calc'd for $C_{14}H_{20}O_4$ (M−1) 251. Found m/z 251.

Step D: (S)-2-isopropoxy-3-{4-[3-(4-phenoxy-phenoxy)-propoxy]-phenyl}-propionic acid The synthesis of 2S-2-isopropoxy-3-{4-o3-(4-phenoxy-phenoxy)-propoxy]phenyl}propanoic acid sodium salt was completed according to procedures described in Example 171. $^1$H NMR (400 MHz, CDCl$_3$): δ 0.96 (d, 3 H, J=5.9 Hz), 1.09 (d, 3 H, J=6.3 Hz), 2.22 (quartet, 2H, J=5.9 Hz), 2.82 (dd, 1 H, J=9.3 Hz, 13.7 Hz), 3.01 (dd, 1 H, J=2.5 Hz, 13.7 Hz), 3.43 (q, 1 H, J=5.9 Hz), 4.01 (dd, 1 H, J=3.4, 8.8 Hz), 4.11 (q, 4 H, J=6.4 Hz), 6.80 (d, 2 H, J=8.3 Hz), 6.88 (d, 2 H, J=8.8 Hz), 6.90–7.00 (m, 4 H), 7.01–7.05 (m, 1 H), 7.17 (d, 2 H, J=8.3 Hz), 7.28 (d, 2 H, J=8.8 Hz). MS: 451.2 (MH$^+$).

Example 177

2-Methoxy-3-{3-methoxy-4-[3-(4-phenylacetyl-phenoxy)-propoxy]-phenyl}-propionic acid

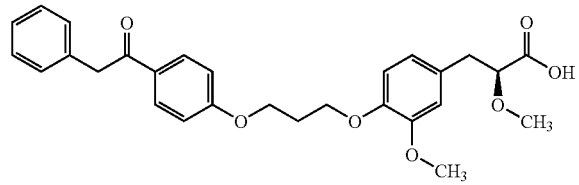

The title compound was prepared from 3-[4-(3-Bromo-propoxy)-3-methoxy-phenyl]-2-methoxy-propionic acid (Example 175, Step B) and 1-(4-Hydroxy-phenyl)-2-phenyl-ethanone following the Standard Procedure J. MS (ES) for $C_{28}H_{30}O_7$ [M+H]$^+$: 479.

Example 178

3-{4-[3-(4-Butoxy-phenoxy)-propoxy]-3-methoxy-phenyl}-2-methoxy-propionic acid

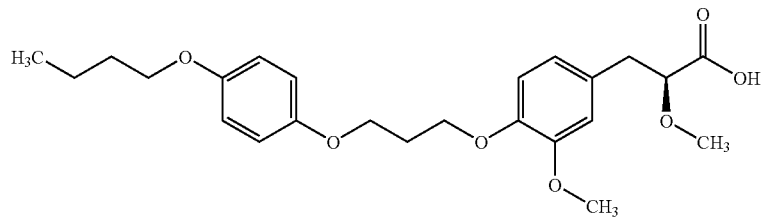

The title compound was prepared from 3-[4-(3-Bromo-propoxy)-3-methoxy-phenyl]-2-methoxy-propionic acid (Example 175, Step B) and 4-Butoxy-phenol following the Standard Procedure J. MS (ES) for $C_{24}H_{32}O_7$ [M+Na]$^+$: 455.

Example 179

2-Methoxy-3-{3-methoxy-4-[3-(4-oxo-2-phenyl-4H-chromen-6-yloxy)-propoxy]-phenyl}-propionic acid

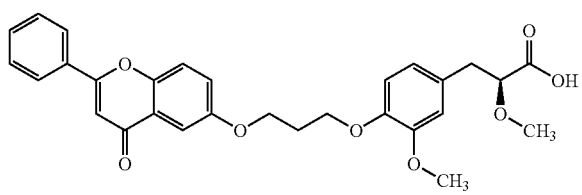

The title compound was prepared from 3-[4-(3-Bromopropoxy)-3-methoxy-phenyl]-2-methoxy-propionic acid (Example 175, Step B) and 6-Hydroxy-2-phenyl-chromen-4-one following the Standard Procedure J. $^1$H-NMR (200.15 MHz, CDCl$_3$): 8.0–7.9 (m, 2H), 7.6–7.5 (m, 5H), 7.30 (dd, 1H, J=9.0, 3.0), 6.9–6.8 (m, 4H), 4.3–4.2 (m, 4H), 4.00 (dd, 1H, J=7.2, 4.6), 3.83 (s, 3H), 3.41 (s, 3H), 3.09 (dd, 1H, J=14.2, 4.6), 2.96 (dd, 1H, J=14.2, 7.2), 2.33 (qn, 2H, J=6.2) ppm.

Example 180

2-Methoxy-3-(3-methoxy-4-{3-[4-(4-trifluoromethyl-phenoxy)-phenoxy]-propoxy}-phenyl)-propionic acid

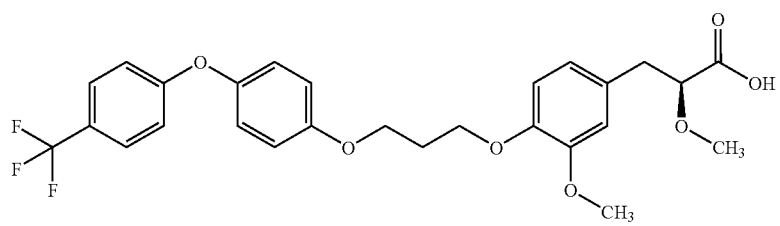

The title compound was prepared from 3-[4-(3-Bromopropoxy)-3-methoxy-phenyl]-2-methoxy-propionic acid (Example 175, Step B) and 4-(4-Trifluoromethyl-phenoxy)-phenol following the Standard Procedure J. MS (ES) for C$_{27}$H$_{27}$F$_3$O$_7$ [M+Na]$^+$: 543.

Example 181

3-{4-[3-(4-Benzyloxy-phenoxy)-propoxy]-3-methoxy-phenyl}-2-methoxy-propionic acid

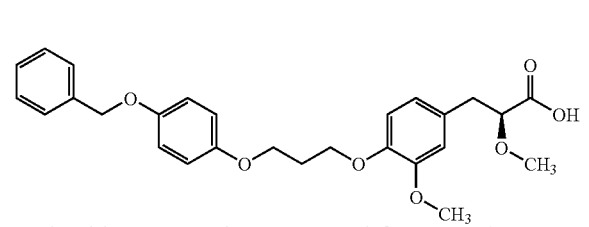

The title compound was prepared from 3-[4-(3-Bromopropoxy)-3-methoxy-phenyl]-2-methoxy-propionic acid (Example 175, Step B) and 4-Benzyloxy-phenol following the Standard Procedure J. MS (ES) for C$_{27}$H$_{30}$O$_7$ [M+Na]$^+$: 489.

Example 182

3-{4-[3-(4-Dibenzofuran-3-yl-phenoxy)-propoxy]-3-methoxy-phenyl}-2-methoxy-propionic acid

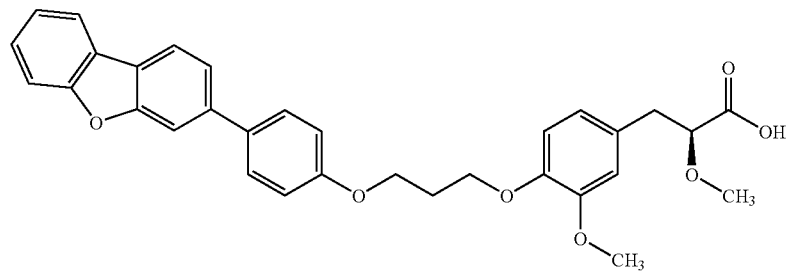

The title compound was prepared from 3-[4-(3-Bromopropoxy)-3-methoxy-phenyl]-2-methoxy-propionic acid (Example 175, Step B) and 4-Dibenzofuran-3-yl-phenol following the Standard Procedure J. MS (ES) for C$_{32}$H$_{30}$O$_7$ [M+NH$_4$]$^+$:544, [M+Na]$^+$: 549.

Example 183

(2S)-3-{4-[4-(Biphenyl-4-yloxy)-butoxy]-phenyl}-2-methoxy-propionic acid

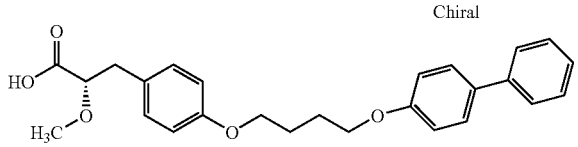

Step A (2S)-3-[4-(4-Hydroxy-butoxy-phenyl]-2-methoxy-propionic acid ethyl ester

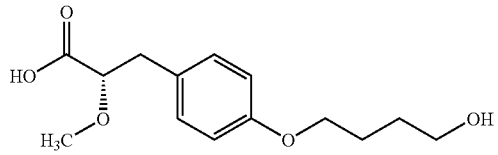

A mixture of 3-(4-Hydroxy-phenyl)-2-methoxy-propionic acid ethyl ester and 3-(tert-Butyl-dimethyl-silanyloxy)-butan-1-ol were treated under Mitsounobu coupling Standard conditions B using DIAD and THF. The product thus obtained was treated under Standard Procedure E for cleaveage protected alcohols to give the title product.

Step B (2S)-3-[4-(4-Bromo-butoxy-phenyl]-2-methoxy-propionic acid ethyl ester

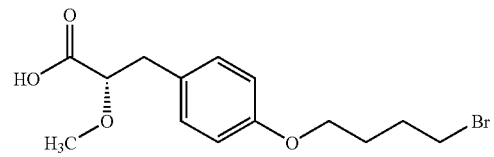

The title compound was prepared from (2S)-3-[4-(4-Hydroxy-butoxy)-phenyl]-2-methoxy-propionic acid ethyl ester and following the procedure described in Example 132, Step D we obtained the title compound.

Step C (2S)-3-{4-[4-(Biphenyl-4yloxy-butoxy]-phenyl}-2-methoxy-propionic acid ethyl ester

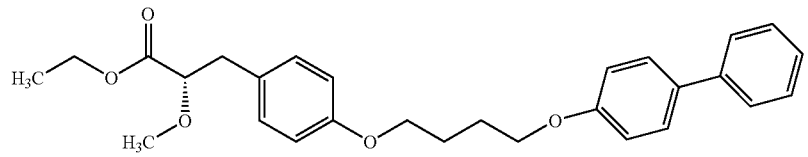

The title compound was prepared from (2S)-3-[4-(4-Bromo-butoxy)-phenyl]-2-methoxy-propionic acid ethyl ester (Step B) and 4-phenylphenol under the Standard Procedure I to give the product.

Step D

2S)-3-{4-[4-(Biphenyl-4-yloxy)-butoxy]-phenyl}-2-methoxy-propionic acid

The title compound was prepared from (2S)-3-{4-[4-(Biphenyl-4-yloxy)-butoxy]-phenyl}-2-methoxy-propionic acid ethyl ester from Step C under the standard Hydrolysis procedure C. (LiOH). $^1$H-NMR (200.15 MHz, CDCl$_3$): 7.57–7.49 (m, 4H); 7.45–7.37 (m, 2H); 7.32–7.11 (m, 3H); 6.97 (d, 2H, J=8.9); 6.84 (d, 2H, J=8.9); 4.11–3.93 (m, 5H); 3.40 (s, 3H); 3.10 (dd, 1H, J=14.0, 4.3); 2.96 (dd, 1H, J=14.5, 7.0); 1.99–1.97 (m, 4H) ppm.

Example 184

(2S)-3-{4-[4-(4-Benzoyl-phenoxy)-butoxy]-phenyl}-2-methoxy-propionic acid

Chiral

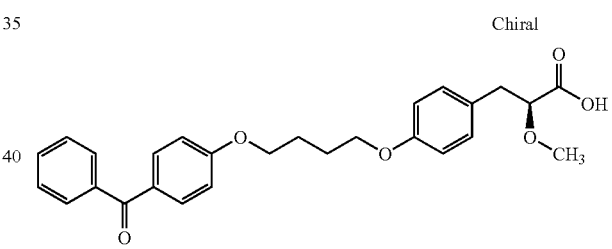

Step A (2S)-3-{4-[4-(4-Benzoyl-phenoxy)-butoxy]-phenyl}-2-methoxy-propionic acid ethyl ester

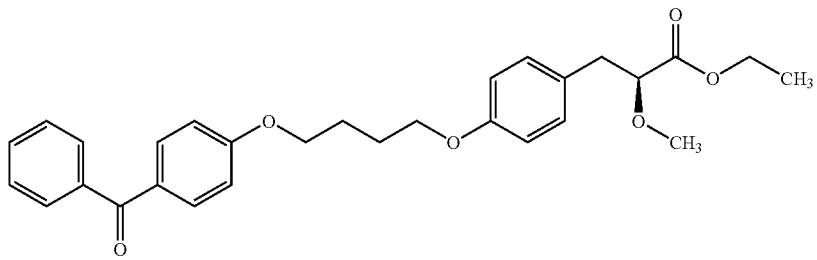

The title compound was prepared from (2S)-3-[4-(4-Bromo-butoxy)-phenyl]-2-methoxy-propionic acid ethyl ester (Example 183, Step B) and 4-hydroxybenzophenone under the Standard Procedure I to give the product.

Step B (2S)-3-{4-[4-(4-Benzoyl-phenoxy)-butoxy]-phenyl}-2-methoxy-propionic acid The title compound was prepared from (2S)-3-{4-[4-(4-Benzoyl-phenoxy)-butoxy]-phenyl}-2-methoxy-propionic acid ethyl ester from Step A under the Standard hydrolysis procedure C. (LiOH). $^1$H-NMR (200.15 MHz; CDCl$_3$): 7.81 (d, 2H, J=8.9), 7.75 (dd, 2H, J=8.3, 1.4), 7.6–7.4 (m, 3H), 7.15 (d, 2H, J=8.6), 6.81 (d, 2H, J=8.3), 4.2–3.9 (m, 5H), 3.37 (s, 3H), 3:08 (dd, 1H, J=14.2, 4.3), 2.94 (dd, 1H, J=14.2, 7.5), 2.1–1.9 (m, 4H) ppm.

Example 185

(2S)-2-Methoxy-3-{4-[4-(4-phenoxy-phenoxy)-butoxy]-phenyl}-propionic acid

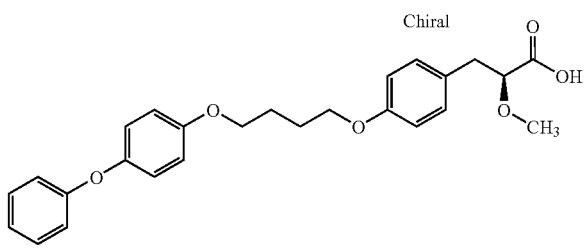

Step A (2S)-2-Methoxy-3-{4-[4-(4-phenoxy-phenoxy)-butoxy]-phenyl}-propionic acid ethyl ester The title compound was prepared from (2S)-3-[4-(4-Bromo-butoxy)-phenyl]-2-methoxy-propionic acid ethyl ester (Example 183, Step B) and 4-phenoxyphenol under the Standard Procedure I to give the product.

Step B (2S)-2-Methoxy-3-{4-[4-(4-phenoxy-phenoxy)-butoxy]-phenyl}-propionic acid The title compound was prepared from (2S)-2-Methoxy-3-{4-[4-(4-phenoxy-phenoxy)-butoxy]-phenyl}-propionic acid ethyl ester, from Step A under the Standard hydrolysis procedure C. (LiOH). $^1$H-NMR (200.15 MHz, CDCl$_3$): 7.4–7.2 (m, 2H), 7.15 (d, 2H, J=8.6), 7.1–6.7 (m, 9H), 4.0–3.9 (m, 5H), 3.34 (s, 3H), 3.08 (dd, 1H, J=14.0, 4.0), 2.93 (dd, 1H, J=14.0, 7.8), 2.1–1.9 (m, 4H) ppm.

Example 186

(2S)-2-Methoxy-3-{4-[2-(2,3,6-trifluoro-phenoxy)-ethoxy]-phenyl}-propionic acid

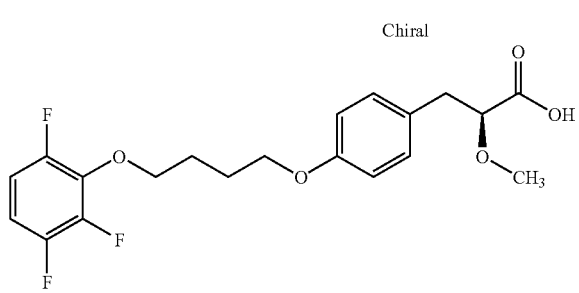

The title compound was prepared from (2S)-3-[4-(3-hydroxy-phenyl]-2-methoxypropionic acid linked to Wang's Resin (Example 94, Step C) via the Mitsounobu coupling-cleveage (Standard Procedure G) with 2-(2,3,6-Trifluoro-phenoxy)-ethanol to give the desire product. $^1$H-NMR (200.15 MHz, CDCl$_3$): 7.15 (d, 2H, J=8.6), 6.9–6.8 (m, 4H), 4.51 (t, 2H, J=4.0), 4.27 (t, 2H, J=4.8), 3.97 (dd, 1H, J=7.2, 4.3), 3.39 (s, 3H), 3.09 (dd, 1H, J=14.5, 4.5), 2.95 (dd, 1H, J=14.5, 7.5) ppm.

Example 187

(2S)-3-[4-(3-Benzyloxy-benzyloxy)-phenyl]-2-methoxy-propionic acid

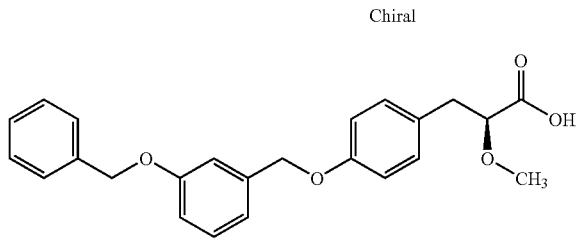

The title compound was prepared from (2S)-3-[4-(3-hydroxy-phenyl]-2-methoxypropionic acid linked to Wang's Resin (Example 94, Step C) via the Mitsounobu coupling-cleveage (Standard Procedure G) with (3-Benzyloxy-phenyl)-methanol to give the desire product. $^1$H-NMR (200.15 MHz, CDCl$_3$): 7.5–7.2 (m, 5H), 7.2–6.8 (m, 8H), 5.07 (s, 2H), 5.01 (s, 2H), 3.99 (dd, 1H, J=7.0, 4.6), 3.40 (s, 3H), 3.10 (dd, 1H, J=14.2, 4.3), 2.96 (ad, 1H, J=14.5, 7.2) ppm.

Example 188

3-{4-[3-(Biphenyl-4-yloxy)-propoxy]-2-methoxy-phenyl}-2-methoxy-propionic acid

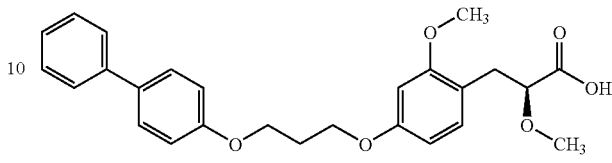

Step A

3-[4-(tert-Butyl-dimethyl-silanyloxy)-2-methoxy-phenyl]-3-hydroxy-2-methoxy-propionic acid methyl ester

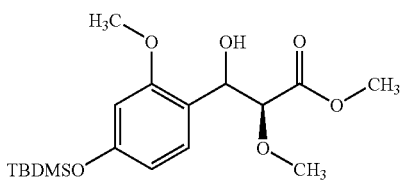

A solution of 4-tert-butyldimethylsilanyloxy-2-methoxy benzaldehyde (1 eq) and methyl methoxyacetate (1.25 eq) in THF (10 mL) at −78° C. was added dropwise to sodium bis(trimethylsilyl)amide (1.25 eq, 1N in THF) at −78° C. The reaction mixture was stirred for 3 h and quenched with 1N HCl (5 mL). The mixture was allowed to warm to room temperature, diluted with water (15 mL), and extracted with ethyl acetate (3×15 mL). The combined organic layers were dried (MgSO$_4$) and concentrated. The residue was purified by silica gel column to obtain the title compound.

Step B

3-[4-(tert-Butyl-dimethyl-silanyloxy)-2-methoxy-phenyl]-2-methoxy-propionic acid methyl ester

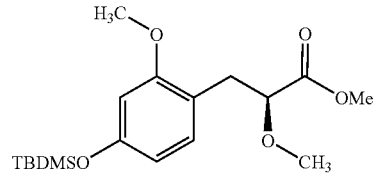

A mixture of 3-[4-(tert-Butyl-dimethyl-silanyloxy)-2-methoxy-phenyl]-3-hydroxy-2-methoxy-propionic acid methyl ester (1 eq), Mesylchloride (1 eq) triethylamine (4 eq) and a catalytic amount of DMAP (0.1 eq) in dichloromethane was stirred at room temperature over night. The reaction mixture was diluted with ether and washed with HCl 1N. Dried and concentrated in vacuo to give a residue which was chromatographed in silica gel to yield a compound which was dissolved in methanol was treated with Mg (20 eq) and stirred until gas evolution was observed. Cooled to 0° C. and stirred for 4 hours. The solvent was removed and the residue reconstituted in ether washed with HCl 1N and brine and concentrated to give the title product.

Step C 2-(4-Hydroxy-2-methoxy-benzyl)-butyric acid methyl ester

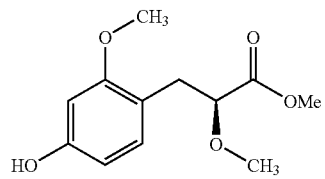

3-[4-(tert-Butyl-dimethyl-silanyloxy)-2-methoxy-phenyl]-2-methoxy-propionic acid methyl ester from Step B was treated under the Standard Procedure E to cleveage the protected silyl group and obtained the product.

Step D

3-{4-[3-(Biphenyl-4-yloxy)-propoxy]-2-methoxy-phenyl}-2-methoxy-propionic acid

A mixture solution of 2-(4-hydroxy-2-methoxy-benzyl)-butyric acid methyl ester from Step C and 3-(biphenyl-4-yloxy)-propan-1-ol was reacted under the Standard Mitsounobu coupling conditions B (DIAD/toluene) to give the corresponding coupled product, which afforded the title compound via the Standard hydrolysis procedure C (NaOH). MS(ES) for $C_{26}H_{28}O_6$ $[M+NH_4]^+$: 454.

Example 189

3-{4-[3-(4-Benzoyl-phenoxy)-propoxy]-2-methoxy-phenyl}-2-methoxy-propionic acid

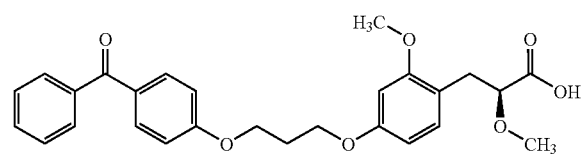

A mixture solution of 2-(4-Hydroxy-2-methoxy-benzyl)-butyric acid ethyl ester from Example 188, Step C and [4-(3-Hydroxy-propoxy)-phenyl]-phenyl-methanone were allowed to react under the Standard Mitsounobu coupling conditions B (DIAD/toluene) to give the corresponding coupled product which by the Standard hydrolysis procedure C (NaOH) yield the title compound. MS (ES) for $C_{27}H_{28}O_7$ $[M+H]^+$: 465.

Example 190

2-Methoxy-3-{2-methoxy-4-[3-(4-phenoxy-phenoxy)-propoxy]-phenyl}-propionic acid

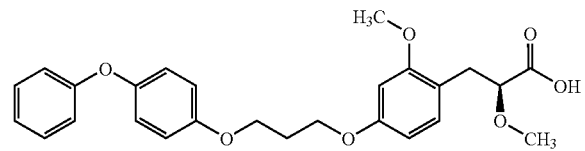

A mixture solution of 2-(4-Hydroxy-2-methoxy-benzyl)-butyric acid ethyl ester from Example 188, Step C and 3-(4-phenoxy-phenoxy)-propan-1-ol were allowed to react under the Standard Mitsounobu coupling conditions B (DIAD/toluene) to give the corresponding coupled product which by the Standard hydrolysis procedure C (NaOH) yielded the title compound. MS (ES) for $C_{26}H_{28}O_7$ $[M+Na]^+$: 475.

Example 191

3-{4-[3-(Biphenyl-4-yloxy)-propoxy]-2-chloro-phenyl}-2-methoxy-propionic acid

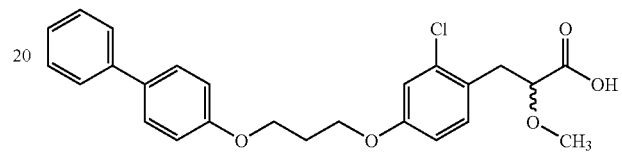

Step A

4-Benzyloxy-2-chloro-benzoic acid benzyl ester

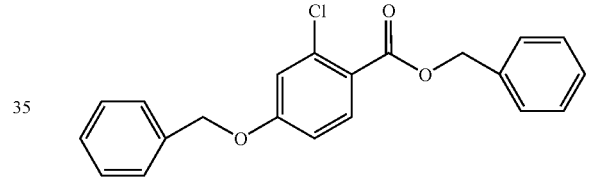

A mixture solution of 2-chloro-4-hydroxybenzoic (1 eq) acid with benzyl bromide (2 eq) and $K_2CO_3$ (3 eq) in acetonitrile were heated at 85° C. Then filtered and concentrated to dryness to give after chromatography in silica gel the title compound.

Step B (4-Benzyloxy-2-chloro-phenyl)-methanol

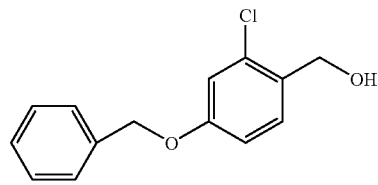

A mixture of 4-Benzyloxy-2 chloro-benzoic acid benzyl ester from Step A with DIBAL-H 1M in toluene (2.2 eq) in THF were stirred at room temperature for 3 hours. The quenched with tartrate saturated solution and extracted with ethyl acetate. Concentrated to dryness and purified by chromatography to afford the title compound.

Step C

4-Benzyloxy-2-chloro-benzaldehyde

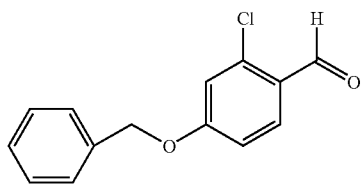

To a solution of (4-Benzyloxy-2-chloro-phenyl)-methanol in dichloromethane, $MnO_2$ (10 eq) were added and the mixture reaction stirred overnight. Filtered through a pad of celite and purified by chromatography in silica gel to give the title product.

Step D 3-(4-Benzyloxy-2-chloro-phenyl)-3-hydroxy-2-methoxy-propionic acid ethyl ester

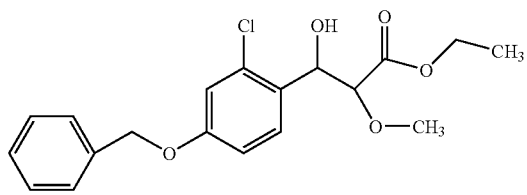

A solution of 4'-Benzyloxy-2-chloro-benzaldehyde (1 eq) and methyl methoxyacetate (1.25 eq) in THF (10 mL) at −78° C. was added dropwise to sodium bis(trimethylsilyl) amide (1.25 eq, 1N in THF) at −78° C. The reaction mixture was stirred for 3 h and quenched with 1N HCl (5 mL). The mixture was allowed to warm to room temperature, diluted with water (15 mL), and extracted with ethyl acetate (3×15 mL). The combined organic layers were dried ($MgSO_4$) and concentrated. The residue was purified by silica gel column to obtained the title compound.

Step E 3-(4-Benzyloxy-2-chloro-phenyl)-2-methoxy-propionic acid ethyl ester

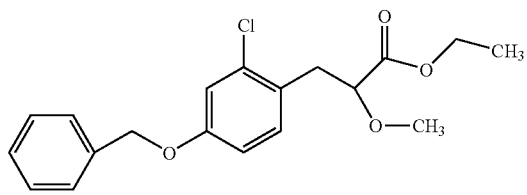

A mixture of 3-(4-Benzyloxy-2-chloro-phenyl)-3-hydroxy-2-methoxy-propionic acid ethyl ester (1 eq), Mesyl-chloride (1 eq) triethylamine (4 eq) and a catalytic amount of DMAP (0.1 eq) in dichloromethane was stirred at room temperature over night. The reaction mixture was diluted with ether and washed with HCl 1N. Dried and concentrated in vacuo to give a residue which was chromatographed in silica gel to yield a compound which was dissolved in methanol was treated with Mg (20 eq) and stirred until gas evolution was observed. Cooled to 0° C. and stirred for 4 hours. The solvent was removed and the residue reconstituted in ether washed with HCl 1N and brine and concentrated to give the title product.

Step F 3-(2-Chloro-4-hydroxy-phenyl)-2-methoxy-propionic acid ethyl ester

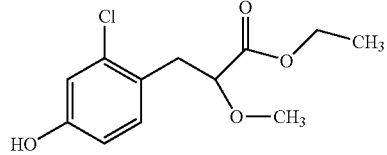

3-(4-Benzyloxy-2-chloro-phenyl)-2-methoxy-propionic acid ethyl ester in ethyl acetate was treated with Pd(C) and $H_2$ under balloon pressure. Then filtered through celite and concentrated to give the title compound.

Step G

3-{4-[3-(Biphenyl-4-yloxy)-propoxy]-2-chloro-phenyl}-2-methoxy-propionic acid

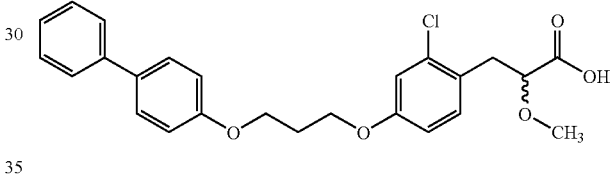

A mixture solution of 3-(2-Chloro-4-hydroxy-phenyl)-2-methoxy-propionic acid ethyl ester from Step F and 3-(Biphenyl-4-yloxy)-propan-1-ol were allowed to react under the Standard Mitsounobu coupling conditions B (DIAD/toluene) to give the corresponding coupled product which by the Standard hydrolysis procedure C (NaOH) yield the title compound. MS (ES) for $C_{25}H_{25}ClO_5$ $[M+NH_4]^+$: 458.

Example 192

3-{2-Chloro-4-[3-(4-phenoxy-phenoxy)-propoxy]-phenyl}-2-methoxy-propionic acid

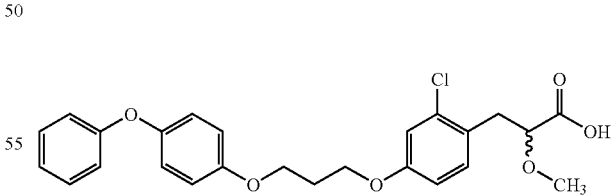

A mixture solution of 3-(2-Chloro-4-hydroxy-phenyl)-2-methoxy-propionic acid ethyl ester from Example 191, Step F and 3-(4-phenoxy-phenoxy)-propan-1-ol were allowed to react under the Standard Mitsounobu coupling conditions B (DIAD/toluene) to give the corresponding coupled product which by the Standard hydrolysis procedure C (NaOH) yield the title compound. MS (ES) for $C_{25}H_{25}ClO_6$ $[M+NH_4]^+$: 474.

Example 193

3-{4-[3-(4-Benzoyl-phenoxy)-propoxy]-2-chloro-phenyl}-2-methoxy-propionic acid

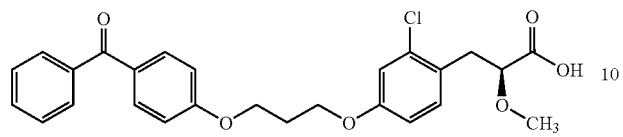

A mixture solution of 3-(2-Chloro-4-hydroxy-phenyl)-2-methoxy-propionic acid ethyl ester from Example 132, Step F and [4-(3-Hydroxy-propoxy)-phenyl]-phenyl-methanone were allowed to react under the Standard Mitsounobu coupling conditions B (DIAD/toluene) to give the corresponding coupled product which by the Standard hydrolysis procedure C (NaOH) yield the title compound. MS (ES) for $C_{26}H_{25}ClO_6$ [M+H]$^+$: 469.

Example 194

(2S)-4-{3-[4-(2-Carboxy-2-methoxy-ethyl)-phenoxy]-propoxy}-benzoic acid

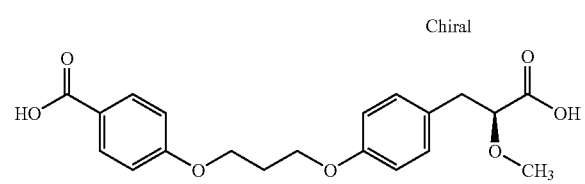

Step A (2S)-4-{3-[4-(2-Ethoxycarbonyl-2-methoxy-ethyl)-phenoxy]-propoxy}-benzoic acid benzyl ester

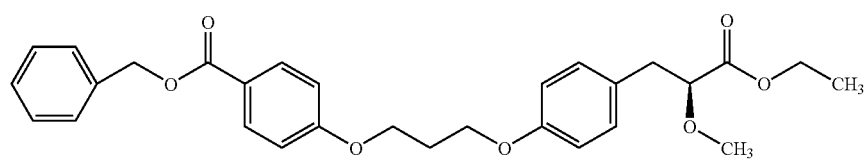

(2S)-3-[4-(3-Hydroxy-propoxy)-phenyl]-2-methoxy-propionic acid ethyl ester from 0, Step B and 4-Hydroxy-benzoic acid benzyl ester were treated under Mitsounobu Standard coupling conditions B to give the title compound.

Step B (2S)-4-{3-[4-(2-Carboxy-2-methoxy-ethyl)-phenoxy]-propoxy}-benzoic acid The title compound was prepared from (2S)-4-{3-[4-(2-Ethoxycarbonyl-2-methoxy-ethyl)-phenoxy]-propoxy}-benzoic acid benzyl ester (Step A) by Standard Hydrolysis procedure C (NaOH). MS (ES) for $C_{20}H_{22}O_7$ [M+Na]$^+$: 397.

Example 195

(2S)-3-{4-[3-(4-Dibenzothiophen-4-yl-phenoxy)-propoxy]-phenyl}-2-methoxy-propionic acid

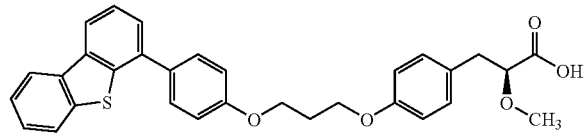

Step A (2S)-3-{4-[3-(4-Dibenzothiophen-4-yl-phenoxy)-propoxy]-phenyl}-2-methoxy-propionic acid ethyl ester

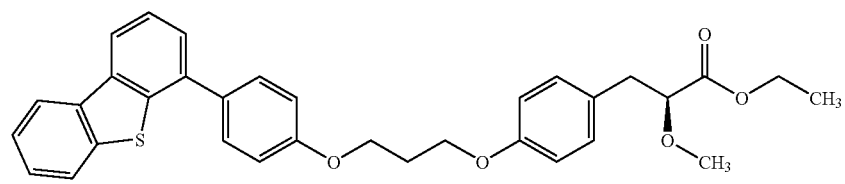

(2S)-3-[4-(3-Hydroxy-propoxy)-phenyl]-2-methoxy-propionic acid ethyl ester from Example 171, Step B and 4-Dibenzothiophen-4-yl-phenol were treated under Mitsounobu Standard coupling conditions B to give the title compound.

Step B (2S)-3-{4-[3-(4-Dibenzothiophen-4-yl-phenoxy)-propoxy]-phenyl}-2-methoxy-propionic acid The title compound was prepared from (2S)-3-{4-[3-(4-Dibenzothiophen-4-yl-phenoxy)-propoxy]-phenyl}-2-methoxy-propionic acid ethyl ester (Step A) by Standard Hydrolysis procedure C (NaOH). MS (ES) for $C_{31}H_{28}O_5S$ [M+NH$_4$]$^+$: 530.

Filtered and concentrated in vacuo to give the title compound.

Step B (2S)-3-{4-[3-(4'-Hydroxy-biphenyl-4-yloxy)-propoxy]-phenyl}-2-methoxy-propionic acid The title compound was prepared from (2S)-3-(4-{3-[4'-(tert-Butyl-dimethyl-silanyloxy)-biphenyl-4-yloxy]-propoxy}-phenyl)-2-methoxy-propionic acid ethyl ester (Step A) by Standard Hydrolysis procedure C (NaOH). MS (ES) for $C_{25}H_{26}O_6$ [M+Na]$^+$: 445.

Example 197

(2S)-4'-{3-[4-(2-Carboxy-2-methoxy-ethyl)-phenoxy]-propoxy}-biphenyl-4-carboxylic acid

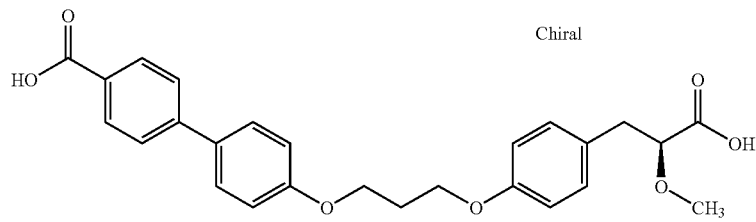

Example 196

(2S)-3-{4-[3-(4'-Hydroxy-biphenyl-4-yloxy)-propoxy]-phenyl}-2-methoxy-propionic acid

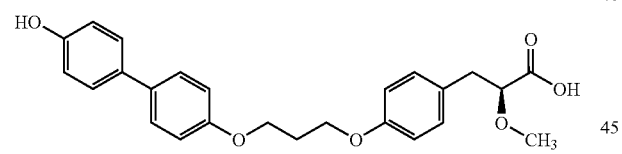

Step A (2S)-3-(4-{3-[4'-(tert-Butyl-dimethyl-silanyloxy)-biphenyl-4-yloxy]-propoxy}-phenyl)-2-methoxy-propionic acid ethyl ester

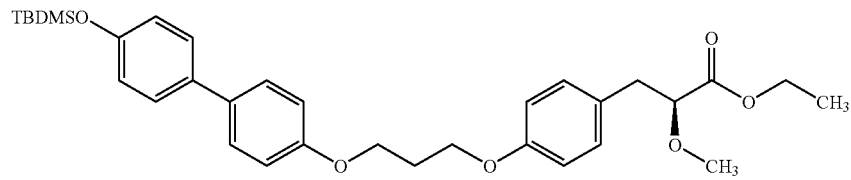

(2S)-3-[4-(3-Bromo-propoxy)-phenyl]-2-methoxy-propionic acid ethyl ester from Example 173, Step A, and 4-(tert-Butyl-dimethyl-silanyloxy)-biphenyl-4-ol were treated with CsCO$_3$ (3 eq) in DMF and stirred at room temperature over night.-

Step A (2S)-4'-{3-[4-(2-Ethoxycarbonyl-2-methoxy-ethyl)-phenoxy]-propoxy}-biphenyl-4-carboxylic acid methyl ester

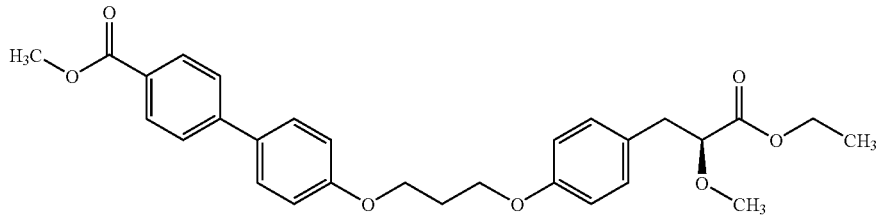

(2S)-3-[4-(3-Hydroxy-propoxy)-phenyl]-2-methoxy-propionic acid ethyl ester from Example 171, Step B and 4'-Hydroxy-biphenyl-4-carboxylic acid methyl ester were treated under Mitsounobu Standard coupling conditions B to give the title compound.

Step B (2S)-4'-{3-[4-(2-Carboxy-2-methoxy-ethyl)-phenoxy]-propoxy}-biphenyl-4-carboxylic acid The title compound was prepared from (2S)-4'-{3-[4-(2-Ethoxycarbonyl-2-methoxy-ethyl)-phenoxy]-propoxy}-biphenyl-4-carboxylic acid methyl ester (Step A) by Standard Hydrolysis procedure C (NaOH). MS (ES) for $C_{26}H_{26}O_7$ $[M+NH_4]^+$: 468, $[M+Na]^+$: 473.

Example 198

(2S)-3-{4-[2-(4-Benzoyl-phenoxy)-cyclohexyloxy]-phenyl}-2-methoxy-propionic acid

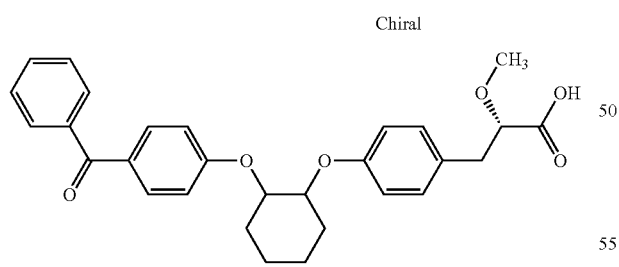

The title compound was prepared from (2S)-3-(4-hydroxyphenyl)-2-methoxy-propionic acid linked to Wang's resin Example 94, Step C) via Mitsounobu coupling (Standard Procedure F) to give 3-[4-(2-Hydroxy-cyclohexyloxy)-phenyl]-2-methoxy-propionic acid linked to the resin. A second Mitsounobu coupling reaction with 4-hydroxybenzophenone via Standard Procedure G allow us to get the title compound. $^1$H-NMR (CDCl$_3$, 200 MHz): 7.75 (d, 4H, J=8.6); 7.57–7.43 (m, 3H); 7.13 (d, 2H, J=8.9); 6.89 (d, 2H, J=9.1); 6.79 (d, 2H, J=8.6); 4.53–4.36 (m, 2H); 4.04–3.99 (m, 1H); 3.43 (s, 3H); 3.08–2.94 (m, 2H); 1.38–1.29 (m, 8H) ppm.

Example 199

(2S)-3-(4-{2-[4-(4-Fluoro-benzoyl)-phenoxy]-cyclohexyloxy}-phenyl)-2-methoxy-propionic acid

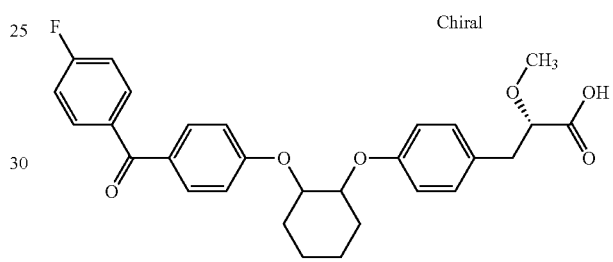

The title compound was prepared from (2S)-3-(4-hydroxyphenyl)-2-methoxy-propionic acid linked to Wang's resin (Example 94, Step C) via Mitsounobu coupling (Standard Procedure F) to give 3-[4-(2-Hydroxy-cyclohexyloxy)-phenyl]-2-methoxy-propionic acid linked to the resin. A second Mitsounobu coupling reaction with 4-fluoro-4'-hydroxybenzophenone via Standard Procedure G allows us to get the title compound. $^1$H-NMR (CDCl$_3$, 200 MHz): 7.83–7.69 (m, 4H); 7.19–7.11 (m, 4H); 6.89 (d, 2H, J=8.9); 6.79 (d, 2H, J=8.6); 4.53–4.33 (m, 2H); 4.02 (dd, 1H, J=6.5, 4.8); 3.43 (s, 3H); 3.10 (dd, 1H, J=14.4, 4.8); 2.98 (dd, 1H, J=14.4, 6.5); 1.38–1.29 (m, 8H) ppm.

Example 200

(2S)-3-(4-{3-[3-(4-Fluoro-phenyl)-benzofuran-6-yloxy]-propoxy}-phenyl)-2-methoxy-propionic acid

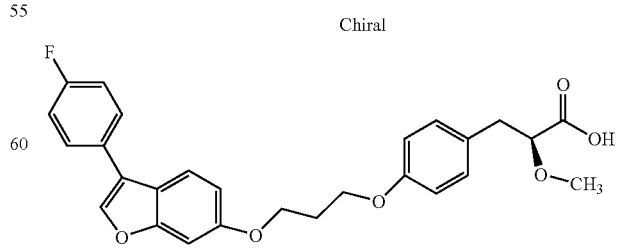

(2S)-3-[4-(3-Bromo-propoxy)-phenyl]-2-methoxy-propionic acid ethyl ester from Example 173, Step A was treated with 3-(4-Fluoro-phenyl)-benzofuran-6-ol under the Standard Procedure J. The compound thus obtained was allowed to react under Standard hydrolysis procedure C (NaOH) to give the title compound. MS(ES) for $C_{27}H_{25}FO_6$ $[M+NH_4]^+$: 482, $[M+Na]^+$: 487, $[M+H]^+$: 464.

Example 201

(2S)-2-Methoxy-3-{4-[3-(5,6,7,8-tetrahydro-naphthalen-2-yloxy)-propoxy]-phenyl}-propionic acid

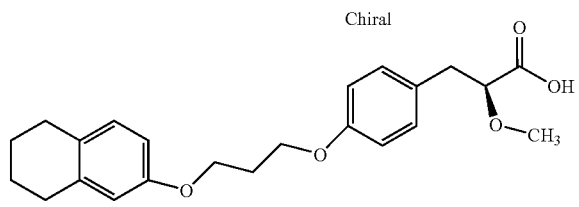

(2S)-3-[4-(3-Bromo-propoxy)-phenyl]-2-methoxy-propionic acid ethyl ester from Example 173, Step A was treated with 5,6,7,8-Tetrahydro-naphthalen-2-ol under the Standard Procedure J. The compound thus obtained was allowed to react under Standard Hydrolysis Procedure C (NaOH) to give the title compound. MS(ES) for $C_{23}H_{28}NO_5$ $[M+Na]^+$: 407, $[M+H]^+$: 385.

Example 202

(2S)-3-{4-[3-(4-Benzyloxy-phenoxy)-propoxy]-phenyl}-2-methoxy-propionic acid

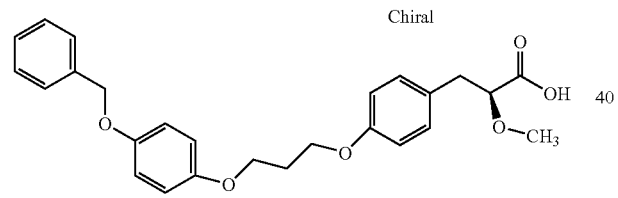

(2S)-3-[4-(3-Bromo-propoxy)-phenyl]-2-methoxy-propionic acid ethyl ester from Example 173, Step A was treated with 4-Benzyloxy-phenol under the Standard Procedure J. The compound thus obtained was allowed to react under Standard hydrolysis procedure C (NaOH) to give the title compound. MS(ES) for $C_{26}H_{28}O_6$ $[M-H]^-$: 435.

Example 203

(2S)-3-{4-[3-(4-Butoxy-phenoxy)-propoxy]-phenyl}-2-methoxy-propionic acid

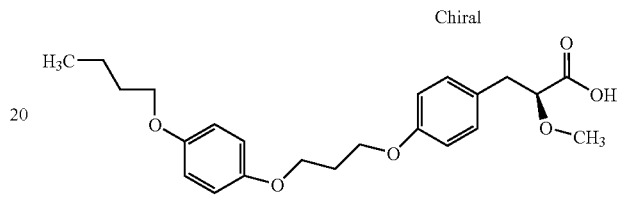

(2S)-3-[4-(3-Bromo-propoxy)-phenyl]-2-methoxy-propionic acid ethyl ester from Example 173, Step A was treated with 4-Butoxy-phenol under the Standard Procedure J. The compound thus obtained was allowed to react under Standard hydrolysis procedure C (NaOH) to give the title compound. MS(ES) for $C_{23}H_{30}O_6$ $[M+NH_4]^+$: 420, $[M+Na]^+$: 425, $[M+H]^+$: 403.

Example 204

(2S)-3-{4-[3-(4-Heptyloxy-phenoxy)-propoxy]-phenyl}-2-methoxy-propionic acid

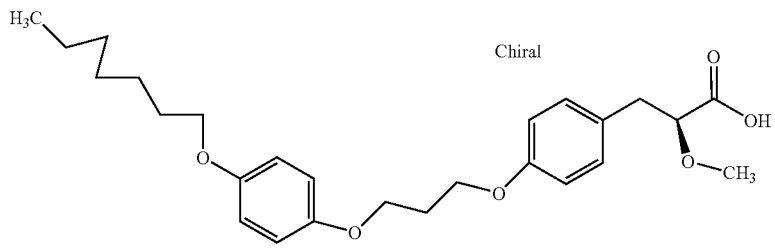

(2S)-3-[4-(3-Bromo-propoxy)-phenyl]-2-methoxy-propionic acid ethyl ester from Example 173, Step A was treated with 4-Heptyloxy-phenol under the Standard Procedure J. The compound thus obtained was allowed to react under Standard hydrolysis procedure C (NaOH) to give the title compound. MS(ES) for $C_{36}H_{36}O_6$ [M+Na]$^+$: 467, [M+H]$^+$: 445.

Example 205
(2S)-3-{4-[3-(6-Benzoyl-naphthalen-2-yloxy)-propoxy]-phenyl}-2-methoxy-propionic acid

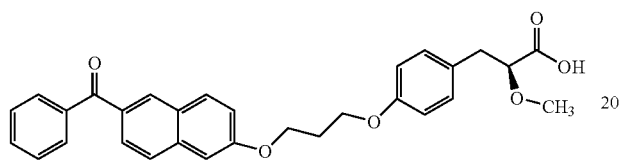

(2S)-3-[4-(3-Bromo-propoxy)-phenyl]-2-methoxy-propionic acid ethyl ester from Example 173, Step A was treated with (6-Hydroxy-naphthalen-2-yl)-phenyl-methanone under the Standard Procedure J. The compound thus obtained was allowed to react under Standard hydrolysis procedure C(NaOH) to give the title compound. MS(ES) for $C_{30}H_{28}O_6$ [M+Na]$^+$: 507, [M+H]$^+$: 485.

Example 206
(2S)-3-{4-[3-(Benzo[1,3]dioxol-5-yloxy)-propoxy]-phenyl}-2-methoxy-propionic acid

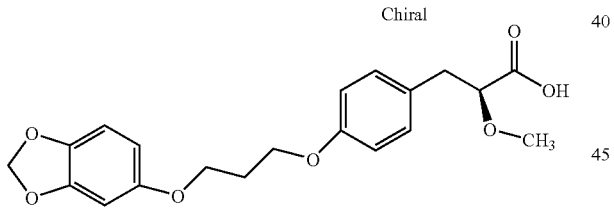

(2S)-3-[4-(3-Bromo-propoxy)-phenyl]-2-methoxy-propionic acid ethyl ester from Example 173, Step A was treated with Benzo[1,3]dioxol-5-ol under the Standard Procedure J. The compound thus obtained was allowed to react under Standard hydrolysis procedure C (NaOH) to give the title compound. MS(ES) for $C_{20}H_{22}O_7$ [M+Na]$^+$: 397, [M+H]$^+$: 375.

Example 207
(2S)-3-{4-[3-(9H-Fluoren-2-yloxy)-propoxy]-phenyl}-2-methoxy-propionic acid

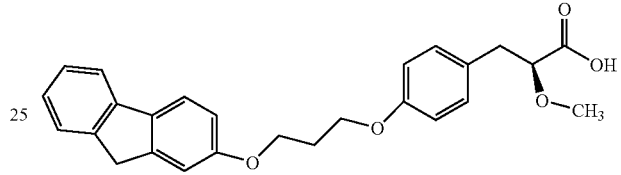

(2S)-3-[4-(3-Bromo-propoxy)-phenyl]-2-methoxy-propionic acid ethyl ester from Example 173, Step A was treated with 9H-Fluoren-2-ol under the Standard Procedure J. The compound thus obtained was allowed to react under Standard hydrolysis procedure C (NaOH) to give the title compound. MS(ES) for $C_{26}H_{26}O_5$ [M+Na]$^+$: 441.

Example 208
(2S)-2-Methoxy-3-{4-[3-(4-octyl-phenoxy)-propoxy]-phenyl}-propionic acid

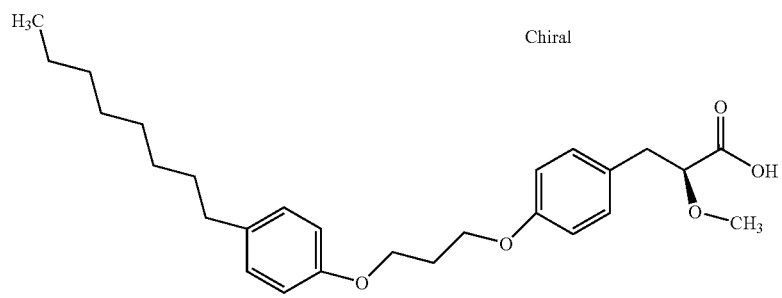

(2S)-3-[4-(3-Bromo-propoxy)-phenyl]-2-methoxy-propionic acid ethyl ester from Example 173, Step A was treated with 4-Octyl-phenol under the Standard Procedure J. The compound thus obtained was allowed to react under Standard hydrolysis procedure C (NaOH) to give the title compound. MS(ES) for $C_{27}H_{38}O_5$ [M+Na]$^+$: 466.

Example 209

(2S)-2-Methoxy-3-{4-[3-(naphthalen-1-yloxy)-propoxy]-phenyl}-propionic acid

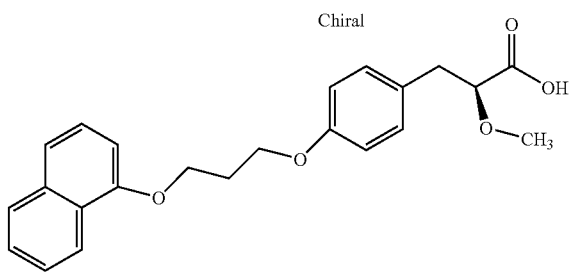

(2S)-3-[4-(3-Bromo-propoxy)-phenyl]-2-methoxy-propionic acid ethyl ester from Example 173, Step A was treated with Naphthalen-1-ol under the Standard Procedure J. The compound thus obtained was allowed to react under Standard hydrolysis procedure C (NaOH) to give the title compound. MS(ES) for $C_{23}H_{24}O_5$ [M+Na]$^+$: 403, [M+H]$^+$: 381.

Example 210

(2S)-3-{4-[3-(1H-Indol-7-yloxy)-propoxy]-phenyl}-2-methoxy-propionic acid

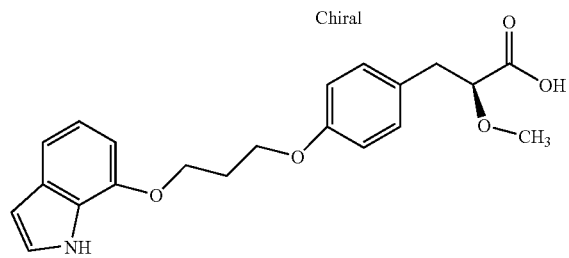

(2S)-3-[4-(3-Bromo-propoxy)-phenyl]-2-methoxy-propionic acid ethyl ester from Example 173, Step A was treated with 1H-Indol-7-ol under the Standard Procedure J. The compound thus obtained was allowed to react under Standard hydrolysis procedure C (NaOH) to give the title compound. MS(ES) for $C_{21}H_{23}NO_5$ [M+Na]$^+$: 392; [M+H]$^+$: 370.

Example 211

(2S)-3-{4-[3-(4'-Fluoro-biphenyl-4-yloxy)-propoxy]-phenyl}-2-methoxy-propionic acid

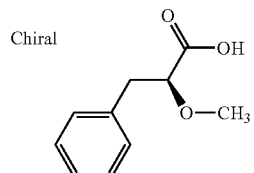

Step A

Preparation of p-Iodophenol Linked to the Wang's Resin

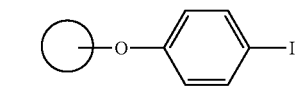

Wang' resin, (1 eq), p-iodophenol (4.5 eq) and PPh$_3$ (5–8 eq) were suspended in a vial and cooled to 0° C. then DIAD was added (5 eq). The mixture reaction was allowed to get room temperature and stirred overnight. Filtered of and washed with MeOH—CH$_2$Cl$_2$-THF—HClaq and CH$_2$Cl$_2$ to give the product.

Step B

4'-Fluoro-biphenyl-4-ol

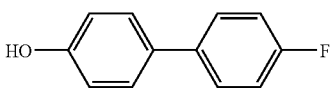

A mixture of p-Iodophenol linked to the Wang's resin from Step A (1 eq), 4-fluorobenzene boronic acid (6 eq), K$_2$CO$_3$ (12 eq) and Pd(OAc)$_2$ (0.5 eq) were suspended in a mixture of dioxane/water (6/1) and the mixture was heated at 100° C. and stirring for 36 hours. The resin was washed with DMF/H$_2$O and MeOH/THF/HCl diluted and MeOH/CH$_2$Cl$_2$. After it was dried, was suspended in dichloromethane, and TFA 95% was added. The mixture was stirred at room temperature for 30 min then filtered and washed with MeOH and dichloromethane. The solvents were concentrated to dryness to give the title product.

Step C (2S)-3-{4-[3-(4'-Fluoro-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 4'-Fluoro-biphenyl-4-ol from Step B under the Standard Procedure J. The compound thus obtained was allowed to react under Standard hydrolysis procedure C (NaOH) to give the title compound. MS(ES) for $C_{25}H_{25}FO_5$ [M+NH$_4$]$^+$: 442, [M+Na]$^+$: 447.

Example 212

(2S)-3-{4-[3-(4'-Chloro-biphenyl-4-yloxy)-propoxy]-phenyl}-2-methoxy-propionic acid

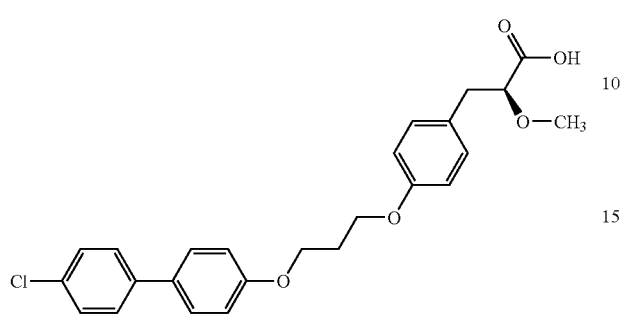

Step A 4-chlorobiphenyl-4-ol

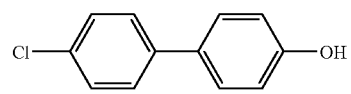

The title compound was prepared following the procedure described in Example 211, Step B with 4-chlorophenyl boronic acid.

Step B (2S)-3-{4-[3-(4'-Chloro-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with chloro-biphenyl-4-ol from Step A under the Standard Procedure J. The compound thus obtained was allowed to react under Standard hydrolysis procedure C (NaOH) to give the title compound. MS(ES) for $C_{25}H_{25}ClO_5$ [M+Na]$^+$: 463, [M+H]$^+$: 441.

Example 213

(2S)-3-{4-[3-(3',5'-Bis-trifluoromethyl-biphenyl-4-yloxy)-propoxy]-phenyl}-2-methoxy-propionic acid

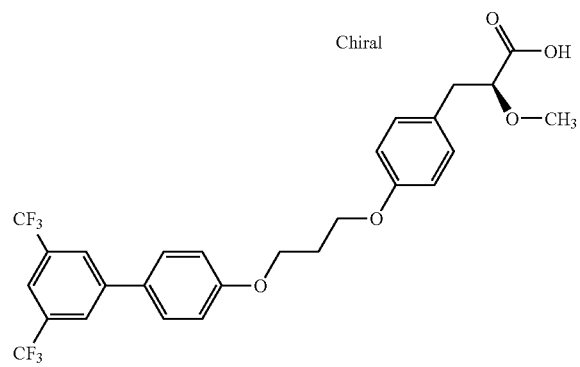

Step A

3',5'-Bis-trifluoromethyl-biphenyl-4-ol

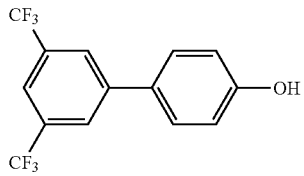

The title compound was prepared following the procedure described in Example 211, Step B with 3,5-bis(trifluoromethyl)-phenyl boronic acid.

Step B (2S)-3-{4-[3-(3',5'-Bis-trifluoromethyl-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 3',5'-Bis-trifluoromethyl-biphenyl-4-ol from Step A under the Standard Procedure J. The compound thus obtained was allowed to react under Standard hydrolysis procedure C (NaOH) to give the title compound. MS(ES) for $C_{27}H_{24}F_6O_5$ [M+Na]$^+$: 565, [M+H]$^+$: 543.

Example 214

(2S)-3-{4-[3-(4-Dibenzofuran-4-yl-phenoxy)-propoxy]-phenyl}-2-methoxy-propionic acid

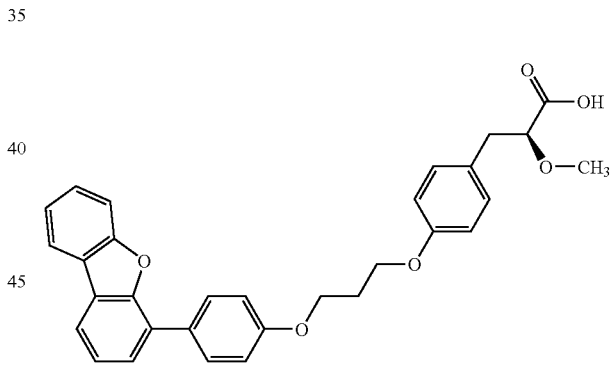

Step A

4-Dibenzofuran-4-yl-phenol

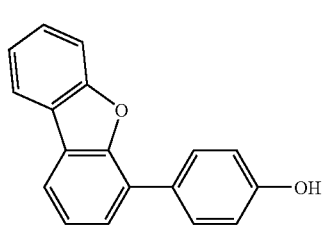

The title compound was prepared following the procedure described in Example 211, Step B with 4-benzofurane boronic acid.

Step B (2S)-3-{4-[3-(4-Dibenzofuran-4-yl-phenoxy)-propoxy]-phenyl}-2-methoxy-propionic acid (2S)-3-[4-(3-Bromo-propoxy)-phenyl]-2-methoxy-propionic acid ethyl ester from 0, Step A was treated with 4-Dibenzofuran-4-yl-phenol from Step A under the Standard Procedure J. The compound thus obtained was allowed to react under Standard hydrolysis procedure C (NaOH) to give the title compound. MS(ES) for $C_{31}H_{30}O_6$ [M+Na]$^+$: 519.

Example 215

(2S)-2-Methoxy-3-{4-[3-(4'-phenoxy-biphenyl-4-yloxy)-propoxy]-phenyl}-propionic acid

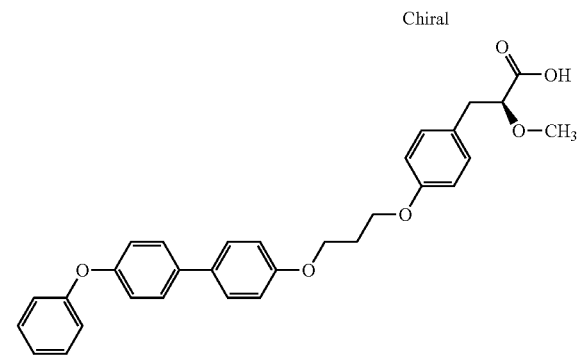

Step A

4'-phenoxy-biphenyl-4-ol

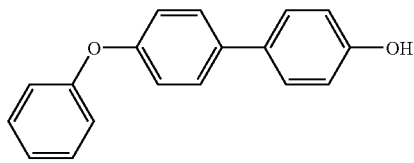

The title compound was prepared following the procedure described in Example 211, Step B with 4-phenoxyphenyl boronic acid.

Step B (2S)-2-Methoxy-3-{4-[3-(4'-phenoxy-biphenyl-4-yloxy)-propoxy]-phenyl}-propionic acid (2S)-3-[4-(3-Bromo-propoxy)-phenyl]-2-methoxy-propionic acid ethyl ester from Example 173, Step A was treated with 4'-phenoxy-biphenyl-4-ol from Step A under the Standard Procedure J. The compound thus obtained was allowed to react under Standard hydrolysis procedure C (NaOH) to give the title compound. MS(ES) for $C_{31}H_{30}O_6$ [M+NH$_4$]$^+$: 516, [M+Na]$^+$: 521.

Example 216

(2S)-2-Methoxy-3-{4-[3-(4-thiophen-2-yl-phenoxy)-propoxy]-phenyl}-propionic acid

Step A

4-Thiophen-2-yl-phenol

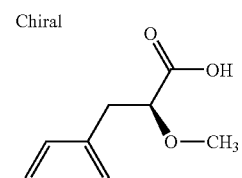

The title compound was prepared following the procedure described in Example 211, Step B with tiophene-2-boronic acid.

Step B (2S)-2-Methoxy-3-{4-[3-(4-thiophen-2-yl-phenoxy)-propoxy]-phenyl}-propionic acid 2S)-3-[4-(3-Bromo-propoxy)-phenyl]-2-methoxy-propionic acid ethyl ester from Example 173, Step A was treated with 4-Thiophen-2-yl-phenol from Step A under the Standard Procedure J. The compound thus obtained was allowed to react under Standard hydrolysis procedure C (NaOH) to give the title compound. MS(ES) for $C_{23}H_{24}O_5S$ [M+NH$_4$]$^+$: 430, [M+Na]$^+$: 435.

Example 217

(2S)-3-{4-[3-(3'-Chloro-biphenyl-4-yloxy)-propoxy]-phenyl}-2-methoxy-propionic acid Step A 3'-Chloro-biphenyl-4-ol

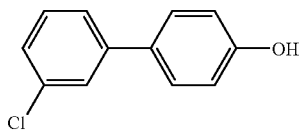

The title compound was prepared following the procedure described in Example 211, Step B with 3-chlorophenyl boronic acid.

Step B (2S)-3-{4-[3-(3-Chloro-biphenyl-4-yloxy)-propoxy]-phenyl}-2-methoxy-propionic acid (2S)-3-[4-(3-Bromo-propoxy)-phenyl]-2-methoxy-propionic acid ethyl ester from 0, Step A was treated with 3'-Chloro-biphenyl-4-ol from Step A under the Standard Procedure J. The compound thus obtained was allowed to react under Standard hydrolysis procedure C (NaOH) to give the title compound. MS(ES) for $C_{25}H_{25}ClO_5$ [M+NH_4]^+: 458, [M+Na]^+: 463.

Example 218

(2S)-3-{4-[3-(2'-Chloro-biphenyl-4-yloxy)-propoxy]-phenyl}-2-methoxy-propionic acid

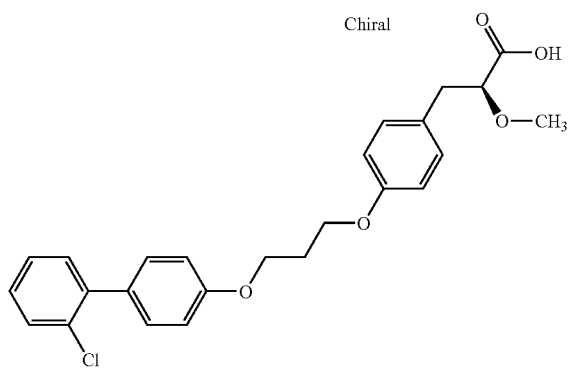

Step A

2'-Chloro-biphenyl-4-ol

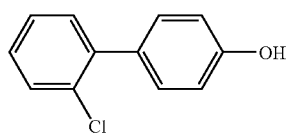

The title compound was prepared following the procedure described in Example 211, Step B with 2-chlorophenyl boronic acid Step B (2S)-3-{4-[3-(2'-Chloro-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 2-Chloro-biphenyl-4-ol from Step A under the Standard Procedure J. The compound thus obtained was allowed to react under Standard hydrolysis procedure C (NaOH) to give the title compound. MS(ES) for $C_{25}H_{25}ClO_5$ [M+NH_4]^+: 458, [M+Na]^+: 463.

Example 219

(2S)-3-{4-[3-(2'-Fluoro-biphenyl-4-yloxy)-propoxy]-phenyl}-2-methoxy-propionic acid

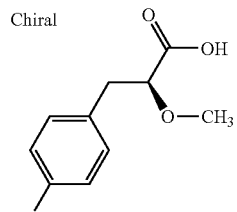

Step A

2'-Fluoro-biphenyl-4-ol

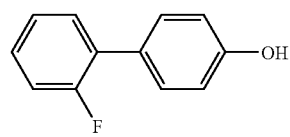

The title compound was prepared following the procedure described in Example 211, Step B with 2-fluorophenyl boronic acid Step B (2S)-3-{4-[3-(2'-Fluoro-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 2-fluoro-biphenyl 4 from Step A under the Standard Procedure J. The compound thus obtained was allowed to react under Standard hydrolysis procedure C (NaOH) to give the title compound. MS(ES) for $C_{25}H_{25}FO_5$ [M+NH_4]^+: 442, [M+Na]^+: 447.

Example 220

(2S)-3-{4-[3-(4-Benzo[1,3]dioxol-5-yl-phenoxy)-propoxy]-phenyl}-2-methoxy-propionic acid

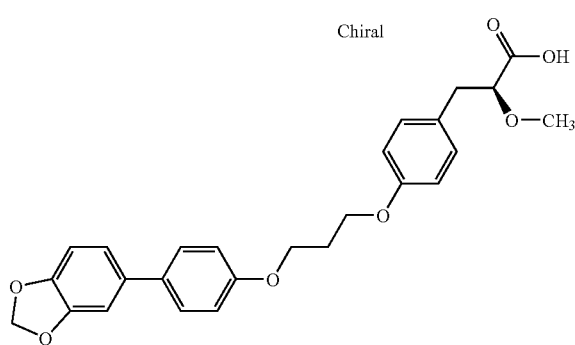

Step A

4-Benzo[1,3]dioxol-5-yl-phenol

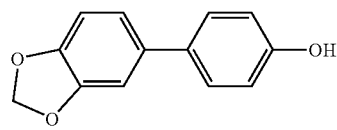

The title compound was prepared following the procedure described in Example 211, Step B with 3,4-methylenedioxophenyl boronic acid

Step B (2S)-3-{4-[3-(4-Benzo[1,3]dioxol-5-yl-phenoxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 4-Benzo[1,3]dioxol-5-yl-phenol from Step A under the Standard Procedure J. The compound thus obtained was allowed to react under Standard hydrolysis procedure C (NaOH) to give the title compound. MS(ES) for $C_{26}H_{26}O_7$ $[M+NH_4]^+$: 468, $[M+Na]^+$: 473.

Example 221

(2S)-3-{4-[3-(4'-tert-Butyl-biphenyl-4-yloxy)-propoxy]-phenyl}-2-methoxy-propionic acid

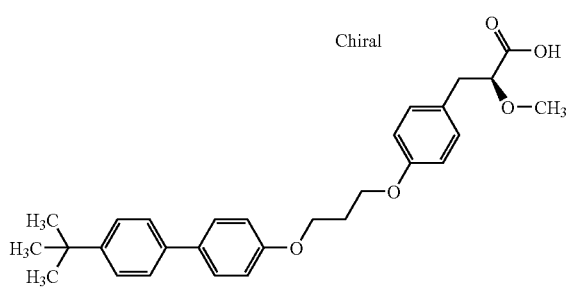

Step A

4'-tert-Butyl-biphenyl-4-ol

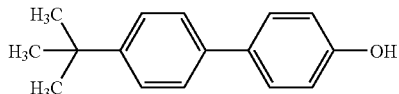

The title compound was prepared following the procedure described in Example 211, Step B with 4-tert-butylphenyl boronic acid

Step B (2S)-3-{4-[3-(4'-tert-Butyl-biphenyl-4-yloxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 4'-tert-Butyl-biphenyl-4-ol from Step A under the Standard Procedure J. The compound thus obtained was allowed to react under Standard hydrolysis procedure C (NaOH) to give the title compound. MS(ES) for $C_{29}H_{34}O_5$ $[M+NH_4]^+$: 480, $[M+Na]^+$: 485.

Example 222

(2S)-2-Methoxy-3-{4-[3-(3'-trifluoromethoxy-biphenyl-4-yloxy)-propoxy]-phenyl}-propionic acid

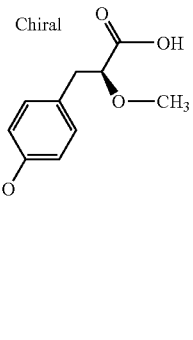

Step A

3'-Trifluoromethoxy-biphenyl-4-ol

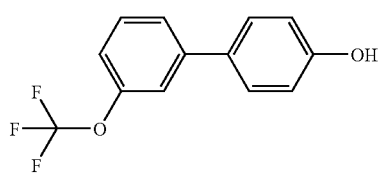

The title compound was prepared following the procedure described in Example 211, Step B with 3-trifluoromethoxy-benzebe boronic acid Step B (2S)-2-Methoxy-3-{4-[3-(3'-trifluoromethoxy-biphenyl-4-yloxy)-propoxy]-phenyl}-propionic acid (2S)-3-[4-(3-Bromo-propoxy)-phenyl]-2-methoxy-propionic acid ethyl ester from Example 173, Step A was treated with 3'-Trifluoromethoxy-biphenyl-4-ol from Step A under the Standard Procedure J. The compound thus obtained was allowed to react under Standard hydrolysis procedure C (NaOH) to give the title compound. MS(ES) for $C_{26}H_{25}F_3O_6$ [M+Na]$^+$: 513, [M+H]$^+$: 491.

Example 223

(2S)-2-Methoxy-3-{4-[3-(4'-trifluoromethoxy-biphenyl-4-yloxy)-propoxy]-phenyl}-propionic acid

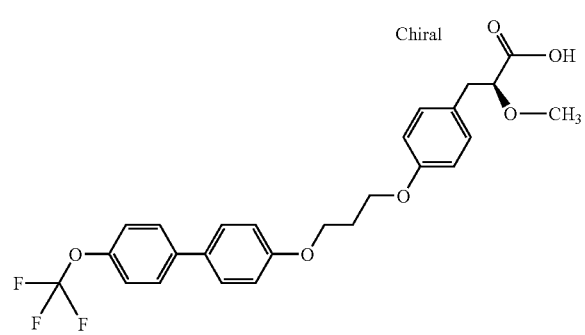

Step A

4'-Trifluoromethoxy-biphenyl-4-ol

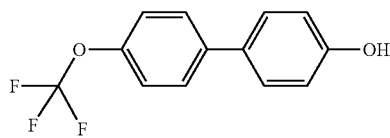

The title compound was prepared following the procedure described in Example 211, Step B with 4-trifluoromethoxy-benzebe boronic acid Step B (2S)-2-Methoxy-3-{4-[3-(4'-trifluoromethoxy-biphenyl-4-yloxy)-propoxy]-phenyl}-propionic acid (2S)-3-[4-(3-Bromo-propoxy)-phenyl]-2-methoxy-propionic acid ethyl ester from Example 173, Step A was treated with 4'-Trifluoromethoxy-biphenyl-4-ol from Step A under the Standard Procedure J. The compound thus obtained was allowed to react under Standard hydrolysis procedure C (NaOH) to give the title compound. MS(ES) for $C_{26}H_{25}F_3O_6$ [M+NH$_4$]$^+$: 508, [M+Na]$^+$: 513.

Example 224

(2S)-3-(4-{3-[4-(2-Chloro-benzoylamino)-phenoxy]-propoxy}-phenyl)-2-methoxy-propionic acid

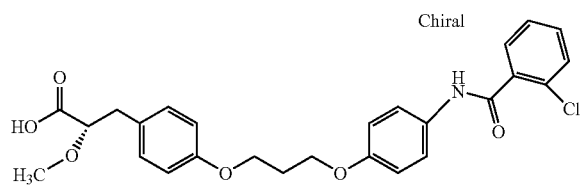

Step A p-Aminophenol Linked to Wang's Resin

A suspension of Wang's resin in THF/CH$_2$Cl$_2$ was treated with DIAD (5 eq), Ph3P (5 eq) and p-nitrophenol (5 eq). The mixture was stirred overnight and then the resin was filtered through and washed with MeOH/CH$_2$Cl$_2$ several times. After dried the resin was suspended in DAD and treated with SnCl2 (10 eq) and stirred again overnight. Filtered and washed with MeOH/CH$_2$Cl$_2$ several times and dried to give th product.

Step B

2-Chloro-N-(4-hydroxy-phenyl)-benzamide

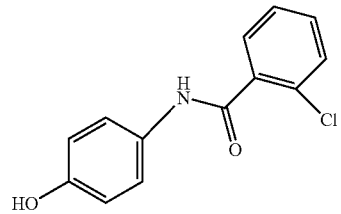

A suspension of p-aminophenol linked to the Wang's resin from Step A (1 eq) in dichloromethane was treated with triethylamine (2 ml/mmol) and 2-chloro-benzoyl chloride (10 eq). The mixture reaction was stirred for 1 hour and then the resin was filtered, washed with MeOH/CH$_2$Cl$_2$ several times and dried. The resin was then treated with TEA 95% H$_2$O 5% and stirred at room temperature for 30 minutes. Filtered and washed with dichloromethane/methanol and concentrated to dryness to afford the title compound.

Step C (2)-3-{3-[4-(2-Chloro-benzoylamino)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with 2-Chloro-N-(4-hydroxy-phenyl)-benzamide from Step B under the Standard Procedure J. The compound thus obtained was allowed to react under Standard hydrolysis procedure C (NaOH) to give the title compound. MS(ES) for $C_{26}H_{26}ClNO_6$ [M+H]$^+$: 484.

Example 225

(2S)-2-Methoxy-3-(4-{3-[4-(2-methoxy-benzoy-lamino)-phenoxy]-propoxy}-phenyl)-propionic acid

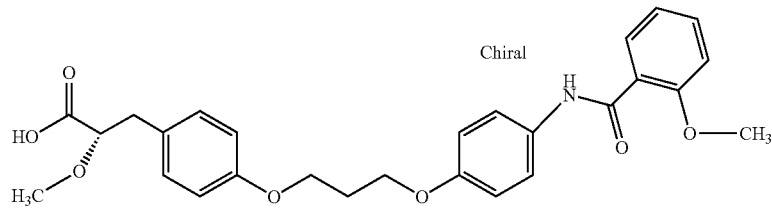

Step A
N-(4-Hydroxy-phenyl)-2-methoxy-benzamide

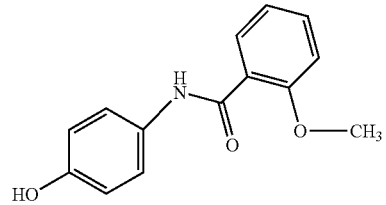

The title compound was prepared following the procedure described in 0, Step B with 2-methoxy-benzoyl chloride.

Step B
(2S)-2-Methoxy-3-(4-{3-[4-(2-methoxy-benzoylamino)-phenoxy]-propoxy}-phenyl)-propionic acid (2S)-3-[4-(3-Bromo-propoxy)-phenyl]-2-methoxy-propionic acid ethyl ester, from Example 173, Step A was treated with N-(4-Hydroxy-phenyl)-2-methoxy-benzamide from Step A under the Standard Procedure J. The compound thus obtained was allowed to react under Standard hydrolysis procedure C (NaOH) to give the title compound. MS(ES) for $C_{27}H_{29}NO_7$ [+H]$^+$: 480.

Example 226

(2S)-3-(4-{3-[4-(2,2-Dimethyl-propionylamino)-phenoxy]-propoxy}-phenyl)-2-methoxy-propionic acid

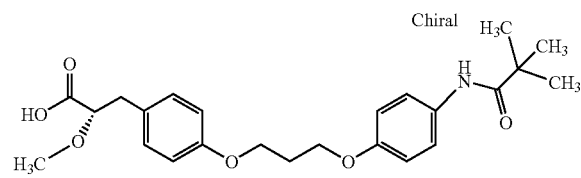

Step A
N-(4-Hydroxy-phenyl)-2,2-dimethyl-propionamide

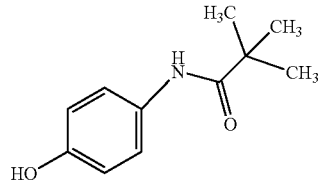

The title compound was prepared following the procedure described in Example 224, Step B with 2,2-Dimethyl-propionyl chloride.

Step B
(2S)-3-(4-{3-[4-(2,2-Dimethyl-propionylamino)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with N-(4-Hydroxy-phenyl)-2,2-dimethyl-propionamide from Step A under the Standard Procedure J. The compound thus obtained was allowed to react under Standard hydrolysis procedure C (NaOH) to give the title compound. MS(ES) for $C_{24}H_{31}NO_6$ [M+H]$^+$: 430.

Example 227

(2S)-3-(4-{3-[4-(3-Fluoro-benzoylamino)-phenoxy]-propoxy}-phenyl)-2-methoxy-propionic acid

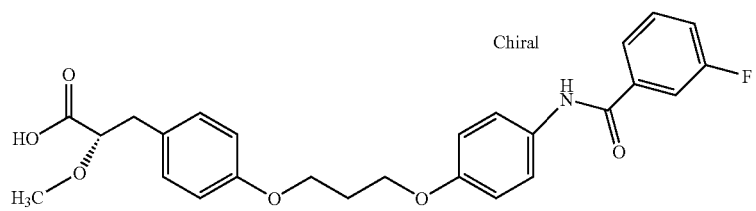

Step A

3-Fluoro-N-(4-hydroxy-phenyl)benzamide

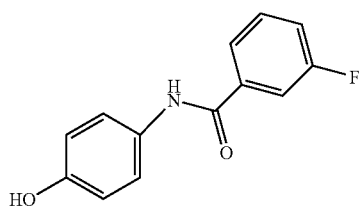

The title compound was prepared following the procedure described in Example 224, Step B with 3-Fluoro-benzoyl chloride.

Step B (2S)-3-(4-{3-[4-(3-Fluoro-benzoylamino)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with 3-Fluoro-N-(4-hydroxy-phenyl)-benzamide from Step A under the Standard Procedure J. The compound thus obtained was allowed to react under Standard hydrolysis procedure C (NaOH) to give the title compound. MS(ES) for $C_{26}H_{26}FNO_6$ [M+H]$^+$: 468.

Example 228

(2S)-2-Methoxy-3-(4-{3-[4-(4-(3-methoxy-benzoylamino)-phenoxy]-propoxy}-phenyl)-propionic acid Step A N-(4-Hydroxy-phenyl)-3-methoxy-benzamide

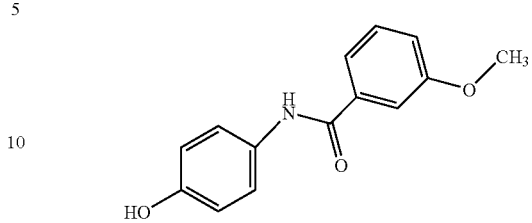

The title compound was prepared following the procedure described in Example 224, Step B with 3-methoxy-benzoyl chloride.

Step B (2S)-2-Methoxy-3-(4-{3-[4-(3-methoxy-benzoylamino)-phenoxy]-propoxy}-phenyl)-propionic acid (2S)-3-[4-(3-Bromo-propoxy)-phenyl]-2-methoxy-propionic acid ethyl ester from Example 173, Step A was treated with N-(4-Hydroxy-phenyl-3-methoxy-benzamide from Step A under the Standard Procedure J. The compound thus obtained was allowed to react under Standard hydrolysis procedure C NaOH) to give the title compound. MS(ES) for $C_{27}H_{29}NO_7$ [M+H]$^+$: 480.

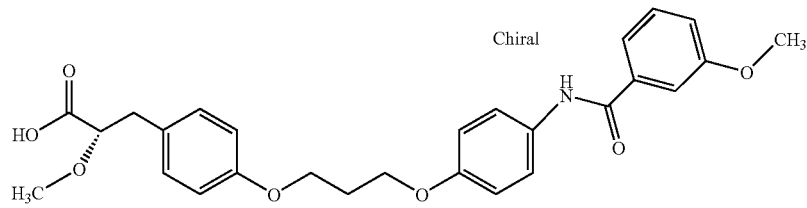

Example 229

(2S)-2-Methoxy-3-(4-{3-[4-(3-methyl-benzoylamino)-phenoxy]-propoxy}-phenyl)-propionic acid

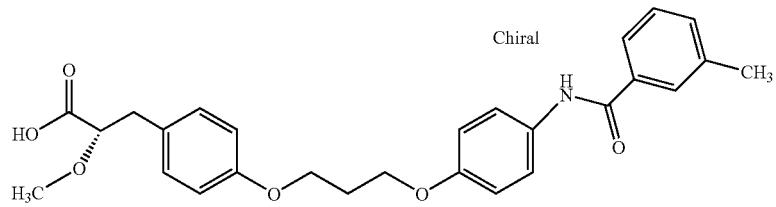

Step A
N-(4-Hydroxy-phenyl)-3-methyl-benzamide

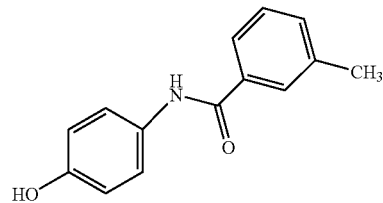

The title compound was prepared following the procedure described in Example 224, Step B with 3-methyl-benzoyl chloride.

Step B
(2S)-2-Methoxy-3-(4-{3-[4-(3-methyl-benzoylamino-phenoxy]-propoxy}-phenyl)-propionic acid (2S)-3-[4-(3-Bromo-propoxy)-phenyl]-2-methoxy-propionic acid ethyl ester from Example 173, Step A was treated with N-(4-Hydroxy-phenyl)-3-methyl-benzamide from Step A under the Standard Procedure J. The compound thus obtained was allowed to react under Standard hydrolysis procedure C (NaOH) to give the title compound. MS(ES) for $C_{27}H_{29}NO_6$ [M+H]$^+$: 464.

Example 230

(2S)-3-(4-{3-[4-(4-Fluoro-benzoylamino)-phenoxy]-propoxy}-phenyl)-2-methoxy-propionic acid

Step A
4-Fluoro-N-(4-hydroxy-phenyl)-benzamide

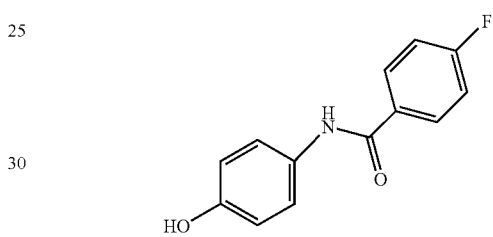

The title compound was prepared following the procedure described in Example 224, Step B with 4-Fluoro benzoyl chloride.

Step B (2S)-3-(4-{3-[4-(4-Fluoro-benzoylamino)-phenoxy]-propoxy}-phenyl)-2-methoxy-propionic acid (2S)-3-[4-(3-Bromopropoxy)-phenyl]-2-methoxy-propionic acid ethyl ester from Example 173, Step A was treated with 4-Fluoro-N-(4-hydroxy-phenyl)-benzamide from Step A under the Standard Procedure J. The compound thus obtained was allowed to react under Standard hydrolysis procedure C (NaOH) to give the title compound. MS(ES) for $C_{26}H_{26}FNO_6$ [M+H]$^+$: 468.

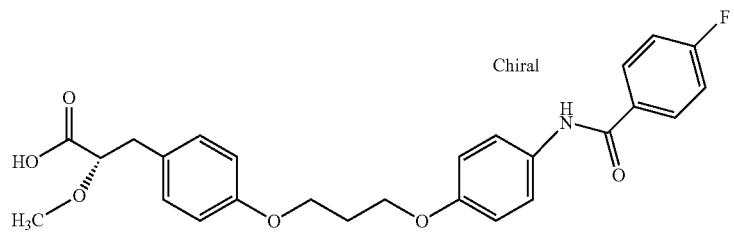

Example 231

(2S)-3-(4-{3-[4-(4-Chloro-benzoylamino)-phenoxy]-propoxy}-phenyl)-2-methoxy-propionic acid

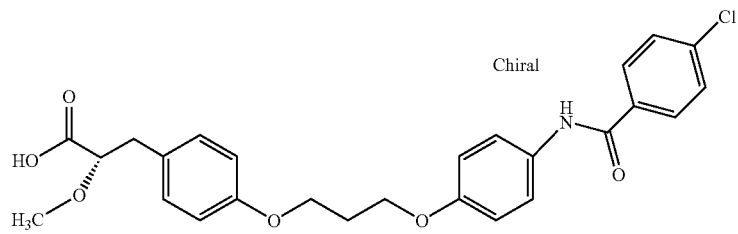

Step A
4-Chloro-N-(4-hydroxy-phenyl)-benzamide

The title compound was prepared following the procedure described in Example 224, Step B with 4-chloro-benzoyl chloride.

Step B
(2S)-3-(4-{3-[4-(4-Chloro-benzylamino)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with 4-chloro-N-(4-hydroxyphenyl)benzamide from Step A under the Standard Procedure J. The compound thus obtained was allowed to react under Standard hydrolysis procedure C (NaOH) to give the title compound. MS(ES) for $C_{26}H_{26}ClNO_6$ [M+H]$^+$: 484.

Example 232

(2S)-2-Methoxy-3-(4-{3-[4-(4-methoxy-benzoylamino)-phenoxy]-propoxy}-phenyl)-propionic acid

Step A
N-(4-Hydroxy-phenyl)-4-methoxy-benzamide

The title compound was prepared following the procedure described in Example 224, Step B with 4-methoxy-benzoyl chloride.

Step B
(2S)-2-Methoxy-3-(4-{3-[4-(4-methoxy-benzoylamino)-phenoxy]-propoxy}-phenyl)-propionic acid (2S)-3-[4-(3-Bromo-propoxy)-phenyl]-2-methoxy-propionic acid ethyl ester from Example 173, Step A was treated with 4-methoxy-N-4-hydroxy-phenyl)benzamide from Step A under the Standard Procedure J. The compound thus obtained was allowed to react under Standard hydrolysis procedure C (NaOH) to give the title compound. MS(ES) for $C_{27}H_{29}NO_7$ [M+H]$^+$: 480.

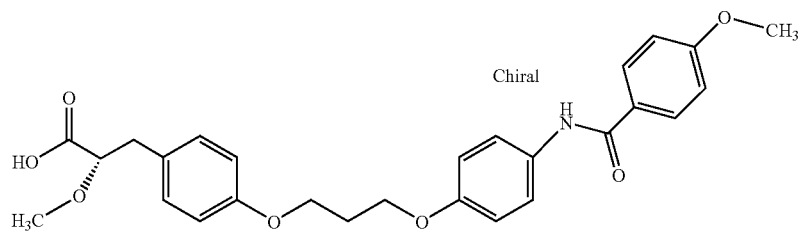

Example 233

(2S)-2-Methoxy-3-{4-[3-(4-phenylacetylamino-phenoxy)-propoxy]-phenyl}-propionic acid

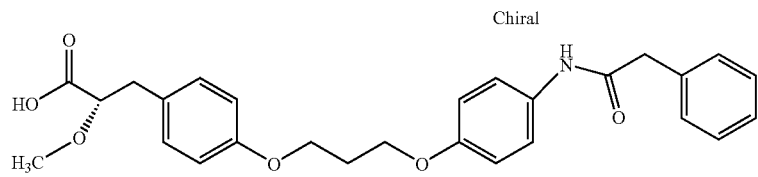

Step A
N-(4-Hydroxy-phenyl)-2-phenyl-acetamide

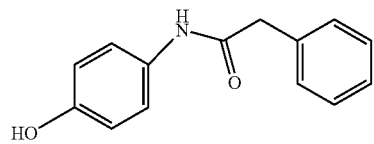

The title compound was prepared following the procedure described in Example 224, Step B with Phenyl-acetyl chloride.

Step B
(2S)-2-Methoxy-3-{4-[3-(4-phenylacetylamino-phenoxy)-propoxy]-phenyl}-propionic acid (2S)-3-[4-(3-Bromo-propoxy)-phenyl]-2-methoxy-propionic acid ethyl ester from Example 173, Step A was treated with N-(4-Hydroxy-phenyl)-2-phenyl-acetamide from Step A under the Standard Procedure J. The compound thus obtained was allowed to react under Standard hydrolysis procedure C (NaOH) to give the title compound. MS(ES) for $C_{27}H_{29}NO_6$ [M+H]$^+$: 484.

Example 234

(2S)-3-(4-{3-[4-(2-Chloro-benzoyl)-phenoxy]-propoxy}-phenyl)-2-methoxy-propionic acid

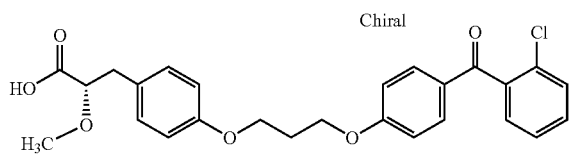

Step A
4-Tributylstannanyl-Phenol Linked to Wang's Resin

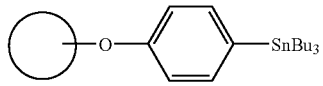

p-Iodophenol linked to Wang's resin from Example 211, Step A, was suspended in toluene and bis-tributyltin was added (5 eq). The mixture reaction was stirred at 100° C. overnight. Then filtered through and the resin was washed with $CH_2Cl_2$/MeOH/Hexane/MeOH/$CH_2Cl_2$ to give the compound.

Step B
(2-Chloro-phenyl)-(4-hydroxy-phenyl)-methanone

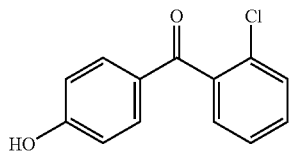

4-Tributylstannanyl-phenol linked to Wang's resin from Step A (1 eq), $Pd_2(dba)_3$ (0.3 eq) and $K_2CO_3$ (70 mg) were suspended in THF/Diisopropilmethylamine. To this mixture 2-chloro-benzoyl chloride was added and stirred for 2 hours. The suspension was filtered and the resin washed with MeOH/$CH_2Cl_2$/DMF, then HCl diluted/dioxane and $Na_2CO_3$ 5%(dioxane) and DMF/MeOH/$CH_2Cl_2$. Once the resin was dried TFA 95% and $CH_2Cl_2$ were added and the mixture stirred at room temperature for 30 min. The resin was filtered and washed with MeOH/$CH_2Cl_2$. The solvents were collected and concentrated to dryness to give the title product.

Step C
(2S)-3-(4-{3-[4-(2-Chloro-benzoyl)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with (2-Chloro-phenyl)-(4-hydroxy-phenyl)-methanone from Step B under the Standard Procedure J. The compound thus obtained was allowed to react under Standard hydrolysis procedure C (NaOH) to give the title compound. MS(ES) for $C_{26}H_{25}ClO_6$ [M+NH$_4$]$^+$: 491, [M+H]$^+$: 469.

Example 235

(2S)-2-Methoxy-3-(4-{3-[4-(naphthalene-1-carbonyl)-phenoxy]-propoxy}-phenyl)-propionic acid

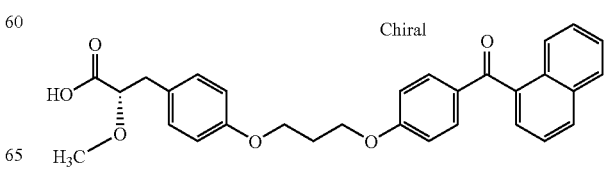

Step A (4-Hydroxy-phenyl)-naphthalen-1-yl-methanone

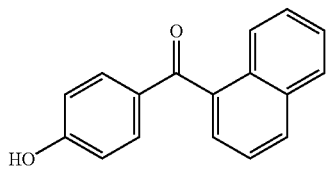

The title compound was prepared following the procedure described in Example 234, Step B with naphthalene-1-carbonyl chloride.

Step B (2S)-2-Methoxy-3-(4-{3-[4-(naphthalene-1-carbonyl)-phenoxy]-propoxy}-phenyl)-propionic acid (2S)-3-[4-(3-Bromo-propoxy)-phenyl]-2-methoxy-propionic acid ethyl ester from Example 173, Step A wag treated with (4-Hydroxy-phenyl)-naphthalen-1-yl-methanone from Step A under the Standard Procedure J. The compound thus obtained was allowed to react under Standard hydrolysis procedure C (NaOH) to give the title compound. MS(ES) for $C_{30}H_{28}O_6$ [M+NH$_4$]$^+$: 507, [M+H]+485.

The title compound was prepared following the procedure described in Example 234, Step B with 3-Fluoro-benzoyl chloride.

Step B (2S)-3-(4-{3-[4-(3-Fluoro-benzoyl)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with (3-Fluoro-phenyl)-(4-hydroxy-phenyl)-methanone from Step A under the Standard Procedure J. The compound thus obtained was allowed to react under Standard hydrolysis procedure C (NaOH) to give the title compound. MS(ES) for $C_{26}H_{25}FO_6$ [M+H]$^+$: 453.5.

Example 237

(2S)-2-Methoxy-3-(4-{3-[4-(3-methoxy-benzoyl)-phenoxy]-propoxy}-phenyl)-propionic acid

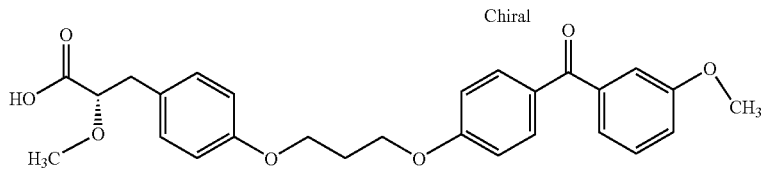

Example 236

(2S)-3-(4-{3-[4-(3-Fluoro-benzoyl)-phenoxy]-propoxy}-phenyl-2-methoxy-propionic acid

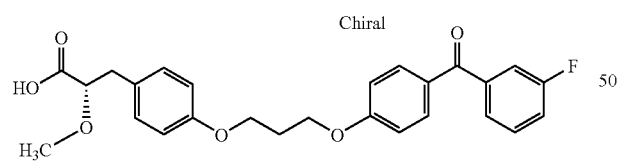

Step A (3-Fluoro-phenyl)-(4-hydroxy-phenyl)-methanone

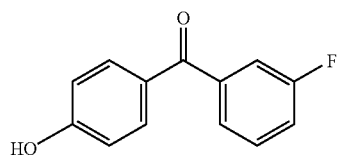

Step A (4-Hydroxy-phenyl)-(3-methoxy-phenyl)-methanone

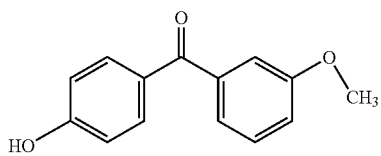

The title compound was prepared following the procedure described in Example 234, Step B with 3-methoxy-benzoyl chloride.

Step B (2S)-2-Methoxy-3-(4-{3-[4-(3-methoxy-benzoyl)-phenoxy]-propoxy}-phenyl)-propionic acid (2S)-3-[4-(3-Bromo-propoxy)-phenyl]-2-methoxy-propionic acid ethyl ester from Example 173, Step A was treated with (4-Hydroxy-phenyl)-(3-methoxy-phenyl)-methanone from Step A under the Standard Procedure J. The compound thus obtained was allowed to react under Standard hydrolysis procedure C (NaOH) to give the title compound. MS(ES) for $C_{27}H_{28}O_7$ [M+H]$^+$: 465.

Example 238

(2S)-2-Methoxy-3-(4-{3-[4-(naphthalen-2-carbonyl)-phenoxy]-propoxy}-phenyl)-propionic acid

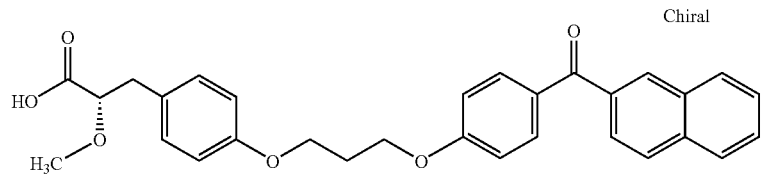

Step A (4-Hydroxy-phenyl)-naphthalen-2-yl-methanone

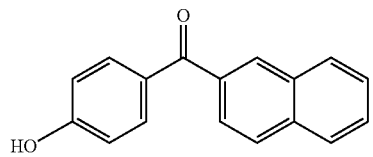

The title compound was prepared following the procedure described in Example 234, Step B with naphtalene-2-carbonyl chloride.

Step B (2S)-2-Methoxy-3-(4-{3-[4-(naphthalene-2-carbonyl)-phenoxy]-propoxy}-phenyl)-propionic acid (2S)-3-[4-(3-Bromo-propoxy)-phenyl]-2-methoxy-propionic acid ethyl ester from Example 173, Step A was treated with (4-Hydroxy-phenyl)-naphthalen-2-yl-methanone from Step A under the Standard Procedure J. The compound thus obtained was allowed to react under Standard hydrolysis procedure C (NaOH) to give the title compound. MS(ES) for $C_{30}H_{28}O_6$ [M+H]$^+$: 485.

Example 239

(2)-2-Methoxy-3-(4-{3-[4-(4-methyl-benzoyl)-phenoxy]-propoxy}-phenyl)-propionic acid

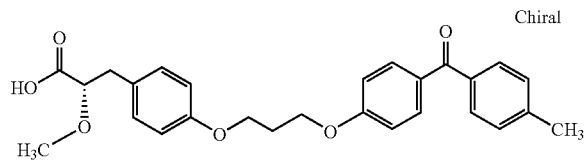

Step A (4-Hydroxy-phenyl)-p-tolyl-methanone

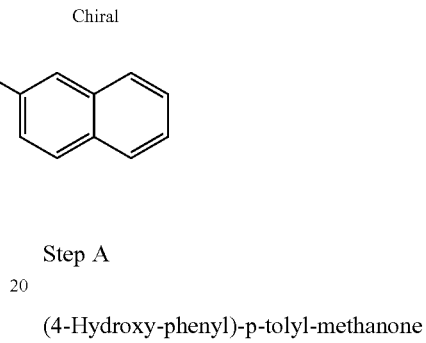

The title compound was prepared folowing the procedure described in Example 234, Step B with 4-mehyl-benzoyl chloride.

Step B (2S)-2-Methoxy-3-(4-{3-[4-(4-methyl-benzoyl)-phenoxy]-propoxy}-phenyl)-propionic acid (2S)-3-[4-(3-Bromo-propoxy)-phenyl]-2-methoxy-propionic acid ethyl ester from Example 173, Step A was treated with (4Hydroxy-phenyl)-p-tolyl-methanone from Srep A under the Standar Procedure J. The compound thus obtained was allowed to react under Standar hydrolysis procedure C (NaOH) to give the title compound. Ms(ES) for $C_{27}H_{28}O_6$ [M+NH$_4$]$^+$: 471 [M+H]$^+$: 449.

Example 240

(2S)-3-(4-{3-[4-(2,2-Dimethyl-propionyl)-phenoxy]-propoxy}-phenyl)-2-methoxy-propionic acid

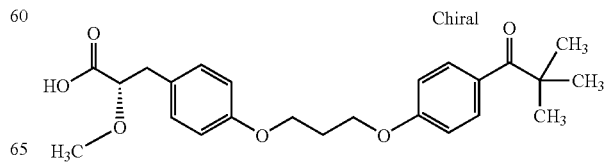

Step A 1-(4-Hydroxy-phenyl)-2,2-dimethyl-propan-1-one

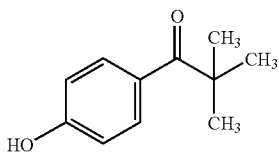

The title compound was prepared following the procedure described in Example 234, Step B with 2,2-Dimethyl-propionyl chloride.

Step B (2S)-3-(4-{3-[4-(2,2-Dimethyl-propionyl)-phenoxy]-propoxy}-phenyl)-2-methoxy-propionic acid (2S)-3-[4-(3-Bromo-propoxy)-phenyl]-2-methoxy-propionic acid ethyl ester from Example 173, Step A was treated with 1-(4-Hydroxyphenyl)-2,2-dimethyl-propan-1-one from Step A under the Standard Procedure J. The compound thus obtained was allowed to react under Standard hydrolysis procedure C (NaOH) to give the title compound. MS(ES) for $C_{24}H_{30}O_6$ $[M+NH_4]^+$: 437 $[M+H]^+$: 415.

The title compound was prepared following the procedure described in Example 234, Step B with Isobutyryl chloride.

Step B (2S)-3-{4-[3-(4-Isobutyryl-phenoxy)-propoxy]-phenyl}-2-methoxy-propionic acid (2S)-3-[4-(3-Bromo-propoxy)-phenyl]-2-methoxy-propionic acid ethyl ester from Example 173, Step A was treated with 1-(4-Hydroxy-phenyl)-2-methyl-propan-1-one from Step A under the Standard Procedure J. The compound thus obtained was allowed to react under Standard hydrolysis procedure C (NaOH) to give the title compound. MS(ES) for $C_{23}H_{28}O_6$ $[M+NH_4]^+$: 423 $[M+H]^+$: 401.

Example 242

(2S)-2-Methoxy-3-(4-{3-[4-(3-phenyl-propionyl)-phenoxy]-propoxy}-phenyl)-propionic acid

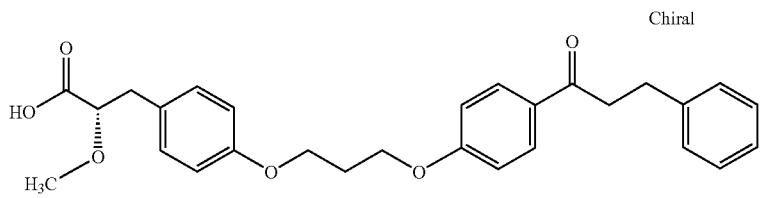

Example 241

(2S)-3-{4-[3-(4-Isobutyryl-phenoxy)-propoxy]-phenyl}-2-methoxy-propionic acid

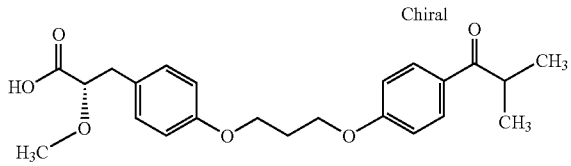

Step A 1-(4-Hydroxy-phenyl)-2-methyl-propan-1-one

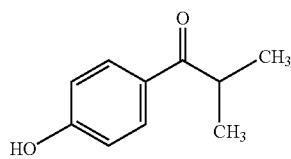

Step A 1-(4-Hydroxy-phenyl)-3-phenyl-propan-1-one

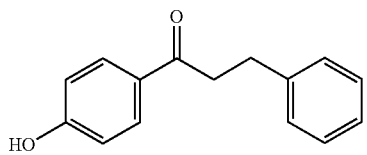

The title compound was prepared following the procedure described in Example 234, Step B with 3-Phenyl-propionyl chloride.

Step B (2S)-2-Methoxy-3-(4-{3-[4-(3-phenyl-propionyl)-phenoxy]-propoxy}-phenyl)-propionic acid (2S)-3-[4-(3-Bromo-propoxy)-phenyl]-2-methoxy-propionic acid ethyl ester from Example 173, Step A was treated with 1-(4-Hydroxy-phenyl)-3-phenyl-propan-1-one from Step A under the Standard Procedure J. The compound thus obtained was allowed to react under Standard hydrolysis procedure C (NaOH) to give the title compound. MS(ES) for $C_{28}H_{30}O_6$ $[M+NH_4]^+$: 485 $[M+H]^+$: 463.

Example 243

3-{4-[3-(Biphenyl-4-yloxy)-propoxy]-2-fluoro-phenyl}-2-methoxy-propionic acid

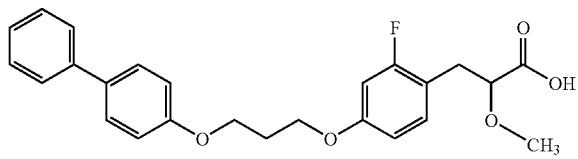

Step A

2-Fluoro-4-hydroxy-benzaldehyde

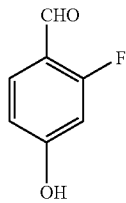

2-Fluoro-4-methoxy-benzaldehyde (1 g, 6.49 mmol) was added to a suspension of anhydrous potassium iodide (2.15 g, 13 mmol) and aluminum trichloride (1.04 g, 7.8 mmol) in anhydrous toluene (10 mL), and the mixture was stirred at 40° C. for 3 hours. Aluminum trichloride (2.15 g, 13 mmol) and anhydrous potassium iodide (0.86 g, 6.49 mmol) were added, and the mixture was stirred for 3 hours. The mixture was diluted with water (10 mL) and extracted with ethyl acetate (5×20 mL). The combined organic layers were dried ($MgSO_4$), filtered, and concentrated under vacuum. The residue was purified by silica gel chromatography (silica gel, hexanes/ethyl acetate 4:1) to give 2-fluoro-4-hydroxy-benzaldehyde as a white solid (260 mg, 29%). $^1$H NMR (200 MHz, Acetone-$d_6$): δ 10.08 (s, 1H), 9.77 (b, 1H), 7.69 (t, 1H, J=8.4), 6.78 (dd, 1H, J=8.8, 2.6), 6.65 (dd, 1H, J=12.5, 2.2)ppm.

Step B

4-[3-(Biphenyl-4-yloxy)-propoxy]-2-fluoro-benzaldehyde

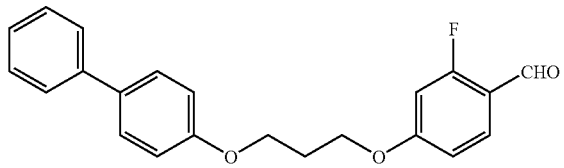

Potassium tert-butoxide (0.217 g, 1.93 mmol) was added to a solution of 2-fluoro-4-hydroxy-benzaldehyde (0.246 g, 1.76 mmol) in anhydrous DMF (5 mL) at 0° C., and the mixture was stirred for 30 min. 4-(3-Bromo-propoxy)-biphenyl (0.564 g, 1.93 mmol, Example 132, Step D) was added, and the mixture stirred at room temperature for 24 hours. The reaction mixture was diluted with water and extracted with EtOAc (5×15 mL). The combined organic layers were dried ($MgSO_4$), filtered, and concentrated under vacuum. The residue was purified by silica gel chromatography (silica gel, hexanes/ethyl acetate 4:1) to give 4-[3-(biphenyl-4-yloxy)-propoxy]-2-fluoro-benzaldehyde as a white solid (540 mg, 88%). $^1$H NMR (200 MHz, $CDCl_3$): δ 10.19 (s, 1H), 7.80 (t, 1H, J=8.4); 7.55–7.48 (m, 4H); 7.42–7.27 (m, 3H); 6.99–6.93 (m, 2H); 6.78 (dd, 1H, J=8.8, 2.6); 6.64 (dd, 1H, J=12.4, 2.2); 4.27–4.15 (m, 4H); 2.30 (qn, 2H, J=5.9)ppm.

Step C

3-{4-[3-(Biphenyl-4-yloxy)-propoxy]-2-fluoro-phenyl}-3-hydroxy-2-methoxy-propionic acid methyl ester

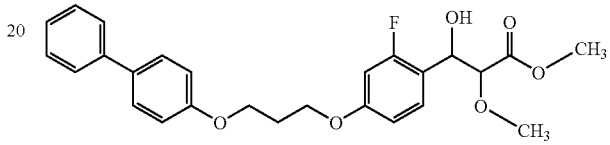

A solution of 4-[3-(biphenyl-4-yloxy)-propoxy]-2-fluoro-benzaldehyde (0.320 g, 0.91 mmol) and methyl methoxyacetate (0.099 mL, 1 mmol) in THF (10 mL) at −78° C. was added dropwise to sodium bis(trimethylsilyl)amide (1 mL, 1 mmol, 1N in THF) at −78° C. The reaction mixture was stirred for 3 hours, quenched with 1N HCl (1 mL), and allowed to warm to room temperature. The mixture was diluted with water (10 mL) and extracted with ethyl acetate (3×30 mL). The combined organic layers were dried ($MgSO_4$), filtered, and concentrated under vacuum. The residue was purified by silica gel chromatography (silica gel, hexanes/ethyl acetate 2:1) to give a 1:1 diastereomeric mixture of 3-{4-[3-(biphenyl-4-yloxy)-propoxy]-2-fluoro-phenyl}-3-hydroxy-2-methoxy-propionic acid methyl ester as a white solid (250 mg, 60%). $^1$H NMR (200 MHz, $CDCl_3$): 7.55–7.47 (m, 4H), 7.42–7.23 (m, 4H), 6.95 (d, 2H, J=8.4), 6.73–6.66 (m, 1H), 6.59 (dd, 1H, J=12.4, 2.6), 5.19 (dd, 1H, J=15.4, 4.8), 4.18–4.04 (m, 4H), 3.93 (d, 1H, J=5.1), 3.68 and 3.63 (2 s, 3H), 3.39 and 3.37 (2 s, 3H), 3.12 (b, 1H), 2.24 (qn, 2H, J=6.2)ppm.

Step D

3-{4-[3-(Biphenyl-4-yloxy)-propoxy]-2-fluoro-phenyl}-2-methoxy-propionic acid methyl ester

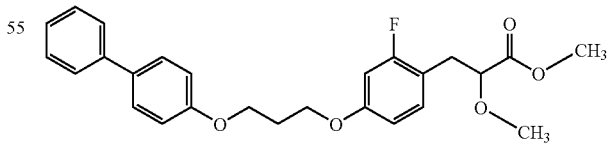

Trifluoroacetic anhydride (0.043 mL, 0.37 mmol) and pyridine (0.074 mL, 0.93 mmol) were added to a solution of 3-{4-[3-(biphenyl-4-yloxy)-propoxy]-2-fluoro-phenyl}-3-hydroxy-2-methoxy-propionic acid methyl ester (0.142 g, 0.31 mmol) in methylene chloride (1 mL) at 0° C. The resulting mixture was stirred for 4 hours at room tempera ture and was concentrated under vacuum. The residue was dissolved in ethyl acetate (50 mL) and 10% palladium on carbon (0.064 g) was added to the solution. The mixture was stirred under hydrogen pressure (5 atm) for 16 hours. The mixture was filtered through celite and concentrated under vacuum. The residue was purified by silica gel chromatography (silica gel, hexanes/ethyl acetate 4:1) to give 3-{4-[3-(biphenyl-4-yloxy)-propoxy]-2-fluoro-phenyl}-2-methoxy-propionic acid methyl ester as a white solid (30 mg, 22%). $^1$H NMR (200 MHz, CDCl$_3$): 7.60–7.50 (m, 4H); 7.46–7.27 (m, 3H); 7.18–7.09 (m, 1H); 7.03–6.96 (m, 2H); 6.70–6.61 (m, 2H); 4.17 (dt, 4H, J=9.1, 6.2); 4.00 (dd, 1H, J=7.3, 5.9); 3.74 (s, 3H); 3.37 (s, 3H); 3.13–2.93 (m, 2H); 2.28 (qn, 2H, J=6.2).

Step E

3-{4-[3-(Biphenyl-4-yloxy)-propoxy]-2-fluoro-phenyl}-2-methoxy-propionic acid 1N aqueous lithium hydroxide solution (1.37 mL) was added to a solution of 3-{4-[3-(biphenyl-4-yloxy)-propoxy]-2-fluoro-phenyl}-2-methoxy-propionic acid methyl ester (0.075 g, 0.17 mmol) in THF (2 mL) at room temperature. The reaction mixture was stirred overnight, diluted with water (10 mL), and extracted with diethyl ether (3×20 mL). The aqueous layer was acidified with 1N HCl to pH 1 and extracted with ethyl acetate (3×25 mL). The combined organic layers were dried (MgSO$_4$), filtered, and concentrated to give 3-{4-[3-(biphenyl-4-yloxy)-propoxy]-2-fluoro-phenyl}-2-methoxy-propionic acid as a white solid (60 mg, 83%). $^1$H-NMR (200 MHz, CDCl$_3$): 7.56–7.29 (m, 7H), 7.18–7.09 (m, 1H), 6.98 (d, 2H, J=8.6), 6.66–6.60 (m, 2H), 4.17 (dt, 4H, J=8.9, 5.9), 4.03 (dd, 1H, J=6.7, 4.8), 3.40 (s, 3H), 3.23–3.14 (m, 1H), 2.97 (dd, 1H, J=14.0, 6.7), 2.26 (q, 2H, J=5.9)ppm.

Example 244

2-phenoxy-3-[4-(4-phenoxy-phenoxy)-propoxyphenyl]propanoic acid

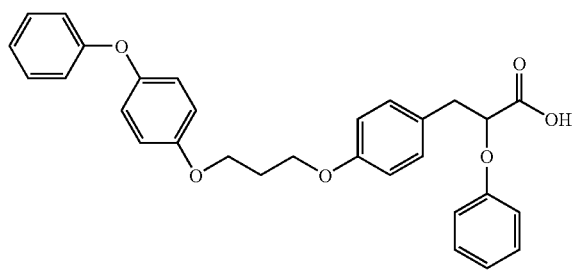

Step A 1-(3-bromopropoxy)-4-phenoxybenzene

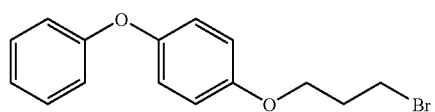

The title compound was prepared from 4-phenoxyphenol following the same procedure as in Example 132, Step D. $^1$H-NMR (200.15 MHz, CDCl$_3$): δ 7.35–7.25 (m, 2H), 7.09–6.87 (m, 7H), 4.10 (t, 2H, J=5.9), 3.62 (t, 2H, J=6.1), 2.55–2.21 (m, 2H)ppm.

Step B

4-Benzyloxyphenyl-2-hydroxypropanoic acid methyl ester

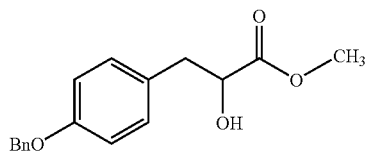

A solution of DL-4-hydroxyphenyllactic acid (0.5 g, 2.74 mmol) was stirred over night in MeOH/HCl saturated solution. The reaction was concentrated to dryness and the crude product (0.545 g, 2.7 mmol) was treated with K$_2$CO$_3$ (3 eq.) and benzyl bromide (0.507 g, 2.97 mmol) in acetonitrile (20 ml) and refluxed overnight. The crude reaction was filtered off and concentrated to produce a crude product. The residue was purified by chromatography (silca-gel, hexanes/Ethyl acetate (3:1) to give a white oil (97%). $^1$H-NMR (200.15 MHz, CDCl$_3$): δ 7.43–7.35 (m, 5H), 7.14 (d, 2H, J=8.59), 6.92 (d, 2H, J=8.59), 5.04 (s, 2H), 4.42 (dd, 1H, J=10.7, 6.1), 2.97 (ddd, 2H, J=4.5, 13.9, 31.1), 2.73 (d, 1H, J=6.1).

Step C

4-Benzyloxyphenyl-2-(4-chlorophenoxy)propanoic acid methyl ester

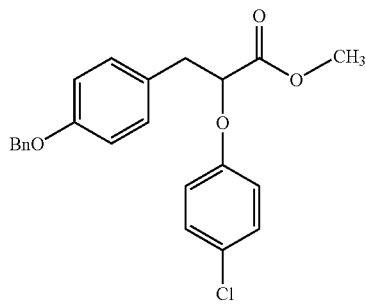

A solution of triphenylphosphin(0.1 g, 0.38 mmol) in 5 ml of dry THF was treated at 0° C. with DEAD (0.066 g, 0.38 mmol) and stirred over 30 min. Then a solution of 4-Benzyloxyphenyl-2-hydroxypropanoic acid methyl ester (0.1 g, 0.35 mmol) and p-chlorophenol (0.048 g, 0.38 mmol) in 2 ml of THF was added to the solution and the mixture reaction was stirred at room temperature overnight. The mixture was concentrated to dryness and chromatographed in silicagel (hexanes/Ethyl acetate 3:1) to give 0.082 g of product (60%). $^1$H-NMR (200.15 MHz, CDCl$_3$): δ 7.46–7.31 (m, 5H), 7.28–7.13 (m, 4H), 6.93 (d, 2H, J=8.8), 6.75 (d, 2H, J=8.8), 5.04 (s, 2H), 4.73(t, 1H, J=6.1), 3.71 s (s, 3H), 3.18 (d, 2H, J=6.4).

Step D

4-Hydroxyphenyl-2-phenoxypropanoic acid methyl ester

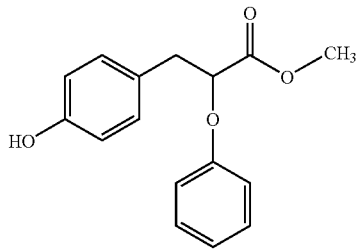

A solution of 4-Benzyloxyphenyl-2-(4-chlorophenoxy) propanoic acid methyl ester in ethanol with 10% Pd/C (5 wt %) was stirred under hydrogen atmosphere (1 tm) over 2 hours. The catalyst was removed via filtration through a pad of celite and the filtrated concentrated in vacuo to produce the title compound (90%). $^1$H-NMR (200.15 MHz, CDCl$_3$): δ 7.25–7.14 (m, 4H), 7.94–7.73 (m, 4H), 4.81–4.69 (m, 1H), 3.70 (s, 3H), 3.16 (d, 2H, J=4.1).

Step E 2-phenoxy-3-[4-(4-phenoxy phenoxy)propoxyphenyl]propanoic acid methyl ester

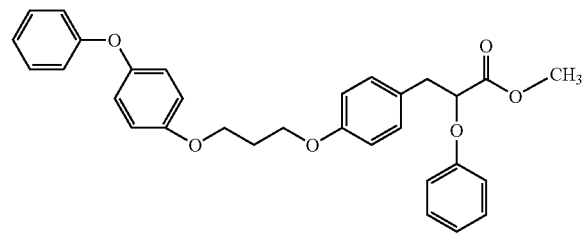

A mixture of 3-(4-hydroxyphenyl)-2-phenoxypropanoic acid methyl ester (0.055 g, 0.18 mmol) with 1-(3-bromopropoxy)-4-phenoxybenzene (Step A) (0.055 g, 0.18 mmol) and potassium tert-butoxide (0.020 g, 0.18 mmol) were stirred in DMF (5 mL) overnight. The mixture reaction concentrated in vacuo with toluene (2 times), reconstituted in Ethyl acetate and washed with water (3 times) and brine, dryed (Na$_2$SO$_4$) and concentrated to afford a crude product that was purified by chromatographied in silicagel (hexanes/ Ethyl acetate, 3:1) to give 0.022 g of the title compound (23%). $^1$H-NMR (200.15 MHz, CDCl$_3$): δ 7.34–7.15 (m, 6H), 7.07–6.71 (m, 12H), 4.80–4.68 (m, 1H), 4.13 (t, 4H, J=15.1), 3.71 (s, 3H), 3.20–3.15 (m, 2H), 2.30–2.18 (q, 2H).

Step F 2-phenoxy-3-[4-(4-phenoxy phenoxy)propoxphenyl]propanoic acid

The title compound was prepared from 2-phenoxy-3-[4-(4-phenoxy phenoxy)propoxyphenyl]propanoic acid methyl ester (0.022 g, 0.04 mmol). That was stirred with an excess of LiOH 3N (5 eq.) in THF (3 ml) overnight. The solution was acidulate with HCl 1N (to pH 1–2) and extracted with ethyl acetate. The organic layer was dried (Na$_2$SO$_4$) and concentrated under vacuum to produce an oily solid (80%). $^1$H-NMR (200.15 MHz, CDCl$_3$): δ 7.33–7.16 (m, 6H), 7.03–6.70 (m, 12H), 4.84–4.71 (m, 1H), 4.13 (t, 4H, J=6.1), 3.24–3.19 (m, 2H)ppm.

Example 245

(2S,2'S)-3-(4-{3-[4-(2'-Carboxy-2'-methoxy-ethyl)-phenoxy]-propoxy}-phenyl)-2-methoxy-propionic acid

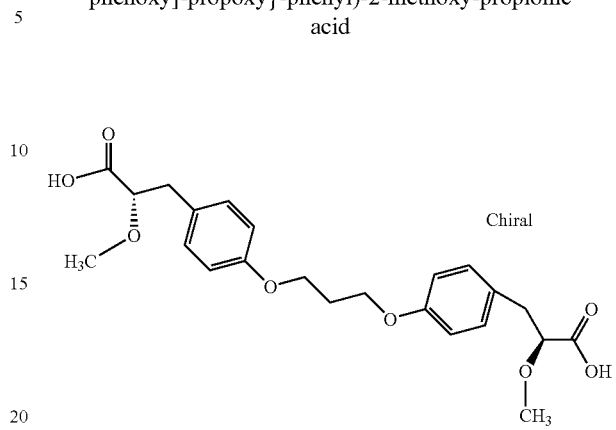

A mixture of (2S)-3-[4-(3-hydroxy-phenyl]-2-methoxypropionic acid ethyl ester (2 eq), and propylene glycol (1.3 eq) were allowed to react under the Standard Mitsounobu coupling conditions B (DIAD/Toluene), and the resulting product of this reaction was treated following the Standard hydrolysis conditions C to give the title compound. MS(ES) for C$_{23}$H$_{28}$O$_8$ [M+NH$_4$]$^+$: 450, [M+H]$^+$: 433.

Example 246

Synthesis of α-Methoxycinnamate Intermediate, ethyl (2S)-2-methoxy-3-(4-hydorxphenyl)propanoate (e)

Scheme

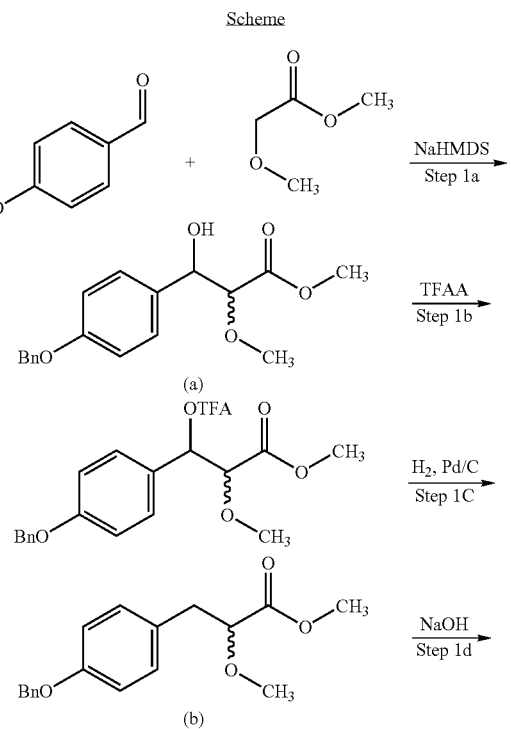

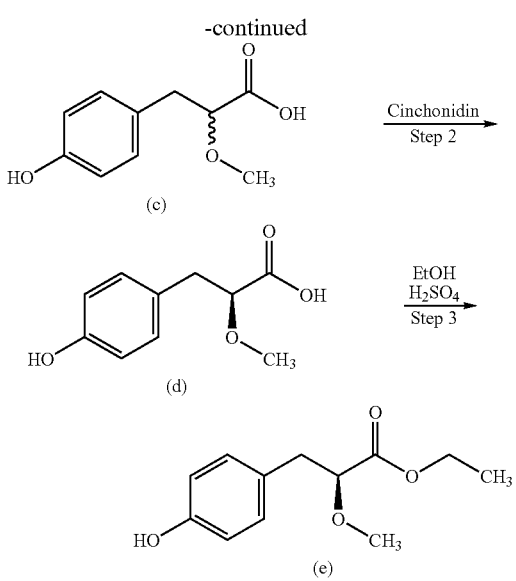

Step 1a: methyl 3-hydroxy-2-methoxy-3-[4(phenylmethoxy)phenyl]propanoate (a)

Sodium bis-(trimethylsilyl)amide (440 mL 0.44 mol 1.0 M in THF) was cooled to −70° C. under a nitrogen atmosphere. A solution of 4-benzyloxybenzaldehyde (85 g, 0.4 mol) and methyl methoxyacetate (52 g, 0.5 mol) in THF (0.5 L) was added dropwise at −70° C. over 2 hours, and the mixture was stirred for an hour. A solution of concentrated HCl (85 mL) and water (85 mL) was added at −70° C. The resulting solution was allowed to warm to ambient temperature and was extracted with MTBE (2×0.5 L). The combined extracts were washed with brine (0.5 L), dried (MgSO$_4$), filtered, and concentrated under to give 133 g of a red oil.

Step 1b and Step 1c: methyl 3-(4-hydroxyphenyl)-2-methoxypropanoate (b)

Methyl 3-hydroxy-2-methoxy-3-[4-(phenylmethoxy)phenyl]propanoate (133 g, crude from above) was dissolved in CH$_2$Cl$_2$ (700 mL), and pyridine (129 mL, 1.6 mol) was added. The resulting solution was cooled in a water bath and trifluoroacetic anhydride (85 mL, 0.6 mol) was added dropwise under nitrogen. The bath was removed, and the mixture was stirred at ambient temperature for 16 hours. The solution was cooled to 0° C. and concentrated HCl (150 mL) in water (1 L) was added dropwise. The organic layer was separated and concentrated, and ethyl acetate (0.5 L) was added. The resulting solution was treated with hydrogen gas under 50 psi in the presence of 5% Pd—C (80 g, 50% water wet) at ambient temperature for 16 hours. The catalyst was filtered, and the filtrate was concentrated under vacuum to give 122 g oil. $^1$H-NMR (CDCl$_3$): 7.1 (2H, d); 6.7 (d, 2H); 5.4 (s, 1H); 4.0 (m, 1H); 3.7 (s, 3H); 3.4 (s, 3H); 3.0 (m, 1H). MS (ES)=209.2 (M−1).

Step 1d: 3-(4-hydroxphenyl)-2-methoxypropanoic acid (c)

Methyl 3-(4-hydroxyphenyl)-2-methoxypropanoate (132 g, 0.631 mol) was dissolved in methanol (700 mL) and 5N sodium hydroxide (631 mL, 3.16 mol) was added dropwise at ambient temperature. The solution was stirred for 16 hours at ambient temperature. The methanol was removed under vacuum, and water (500 mL) was added. The mixture was extracted with MTBE (2×500 mL). The aqueous solution was brought to pH=1 with concentrated HCl and then extracted with MTBE (2×500 mL). The organic extracts were dried (MgSO$_4$), filtered, and concentrated under vacuum to give the racemic acid as an oil (110 g) which was crystallized upon standing. $^1$H-NMR (DMSO): 7.0 (d, 2H); 6.6 (d, 2H); 4.0 (m, 1H); 2.8 (m, 2H). MS (ES)=195.1 (M−1).

Step 2: (2S)-3-(4-hydroxyphenyl)-2-methoxypropanoic acid (d)

Cinchonidine salt of (2S)-3-(4-hydroxyphenyl)-2-methoxypropanoic acid.

A slurry consisting of 3-(4-hydroxyphenyl)-2-methoxypropanoic acid (21.21 g, 0.1081 mol), (−)-cinchonidine (31.83 g, 0.1081 mol), and THF (424 mL) was heated briefly at reflux to give a red-brown solution. The mixture was cooled to ambient temperature and stirred for 3 days. The resulting-slurry was cooled to 0° C. for 4 hours and filtered to give about 17.06 g of the cinchonidine salt (71.2% ee by chiral HPLC). The cinchonidine salt was slurried in THF, heated to reflux for 1 hour, and cooled to ambient temperature overnight. The mixture was cooled to 0° C. for 2 hours and filtered to give about 14.87 g of the cinchonidine salt (83.0% ee by chiral HPLC). The cinchonidine salt was slurried again in THF, and heated to reflux for 1 hour, and cooled to ambient temperature. The mixture was cooled to 0° C. for 2 hours and filtered to give about 12.87 g (24%) of the cinchonidine salt of (2S)-3-(4-hydroxyphenyl)-2-methoxypropanoic acid (91.4% ee by chiral HPLC).

(2S)-3-(4-hydroxyphenyl)-2-methoxypropanoic acid

The cinchonidine salt of (2S)-3-(4-hydroxyphenyl)-2-methoxypropanoic acid (73.59 g, 0.15 mol) (98.1% ee by chiral HPLC) was suspended in 1N HCl solution (750 mL) and extracted with methyl tert butyl ether (3×200 mL). The combined extracts were dried (Na$_2$SO$_4$) and concentrated to give about 24.12 g (82%) of (2S)-3-(4-hydroxyphenyl)-2-methoxypropanoic acid (96.7% ee by chiral HPLC). $^1$H NMR (DMSO-d$_6$): δ 2.72–2.89 (m, 2H), 3.21 (s, 3H), 3.8–3.87 (m, 1H), 6.64–6.67 (d, 2H), 6.97–7.02 (d, 2H), 9.15 (s, broad, 1H), 12.62 (s, broad, 1H). MS (ES$^+$): m/z 219.0 ([M+Na]$^+$). MS (ES$^-$) m/z 195.1 ([M−H]$^-$). [α]$_D$=−2.2° (c=1, MeOH).

Step 3: ethyl (2S)-2-methoxy-3-(4-hydroxyphenyl)propanoate (e)

A solution of (2S)-3-(4-hydroxyphenyl)-2-methoxypropanoic acid (35 g) in 140 ml of ethanol was mixed with 5.66 ml of concentrated sulfuric acid and stirred at room temperature until complete as indicated by HPLC. The ethanol was removed via vacuum distillation (55° C./28"Hg) and 110 ml of water was added. The pH was adjusted to about 7 to 8 with sodium bicarbonate, and the mixture was extracted with add 50 ml ethyl acetate (3×50 ml). The organic layers were combined, washed with 50 ml 20% NaCl solution, dried with 15 g of magnesium sulfate, and concentrate product to afford ethyl (2S)-2-methoxy-3-(4-hydorxyphenyl)propanoate as an oil. $^1$H-NMR (CDCl$_3$): 7.1 (d, 2H); 6.7(d, 2H); 4.2(m, 2H); 3.9(m, 1H); 3.6(s, 3H); 2.95(m, 2H); 1.25(t, 3H). MS (ES): 223.2 (M−1).

Example 247

Synthesis of (2S)-2-methoxy-3-{4-[3-(4-phenoxy-phenoxy)-propoxy]phenyl}propanoic acid

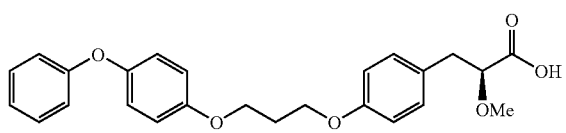

Scheme

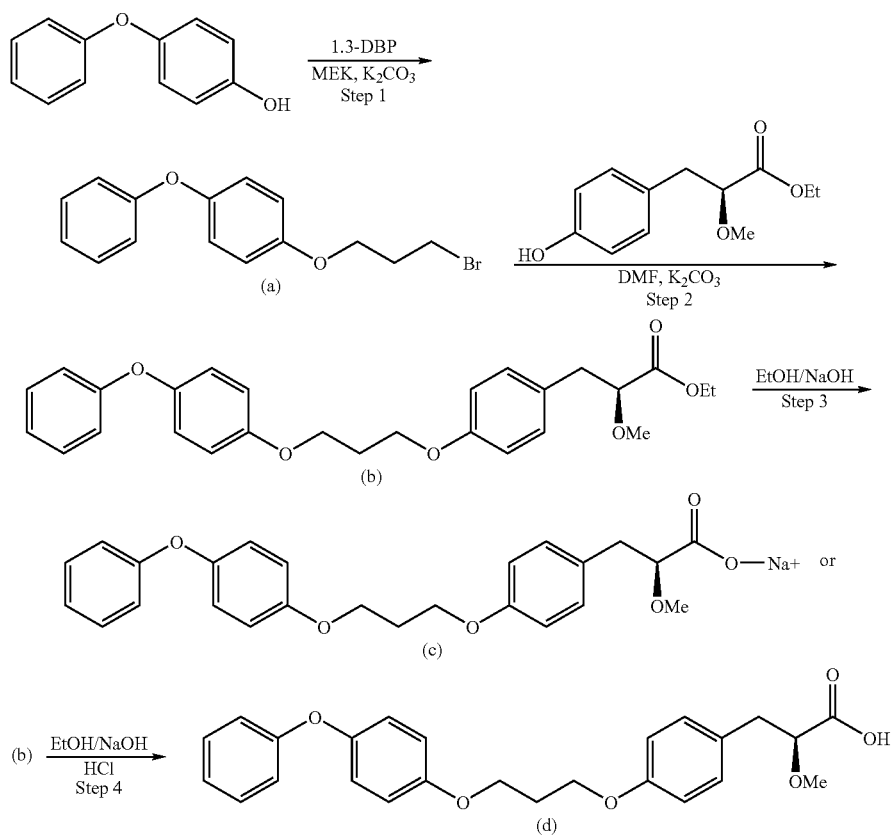

Step 1: 1-bromo-3-(4-phenoxyphenyl)propane (a)

To a 22 L flask was added 4-phenoxyphenol (900 g), 1,3-dibrompropane (5858 g), powered potassium carbonate (1335 g), and methyl ethyl ketone (9 L). The mixture was stirred for 30 minutes at 22° C. The off-white slurry was heated to a gentle reflux (~83° C.) and held at that temperature for 16 hours. The off white slurry was cooled to 25° C. and vacuum filtered, washing the cake of inorganic salts with methyl ethyl ketone (4 L). The filtrate was concentrated on a rotary evaporator while increasing the temperature to 90° C. under house vacuum. After the condensation had stopped, the oil was held at 90° C. under vacuum for an additional two hours to ensure the remaining 1,3-dibrompropane below 8% by GC analysis. The residue was dissolved in 3 L of methyl alcohol, and the white slurry was cooled slowly to about 0–5° C. and held at that temperature overnight. The product was filtered, washed with cold methyl alcohol (6 L), and dried at 30° C. for about 20 hours to afford about 1234 g of compound (a) in 84% yield (99.4% pure by GC). $^1$H-NMR (CDCl$_3$): 7.3(2H, m), 7.1(2H, m), 7.0(2H, m), 6.9(2H, m), 4.1(2H, m); 3.6(2H, m); 2.3(2H, m).

Step 2: ethyl (2S)-2-methoxy-3-{4-[3-(4-phenoxy-phenoxy)-propoxy]phenyl}propanoate (b)

1-Bromo-3-(4-phenoxyphenyl)propane (1337 g), ethyl (2S)-2-methoxy-3-(4-hydorxyphenyl)propanoate (957 g) and dimethylformamide (5 L) were charged to a 22 L flask. After a solution was obtained, powered-potassium carbonate (1770 g) was added. The mixture was stirred for 16 hours at ambient temperature and then quenched by adding water (6.5 L) while maintaining temperature at 20 to 30° C. The aqueous layer was extracted three times with ethyl acetate (5 L each). The combined organic layers were washed with water (3×4 L) and brine (4 L). The organic layer was then dried with sodium sulfate (1000 g), filtered, and washed with ethyl acetate. The filtrate was concentrated to afford about 1974 g of crude (b). $^1$H-NMR (CDCl$_3$): 7.3(m, 2H); 7.2(d, 2H); 7.0(m, 1H); 6.95(m,4H); 6.9(d, 2H); 6.85(d, 2H); 4.2(m, 2H); 4.15(m, 4H); 3.9(t, 1H); 3.39(s, 3H); 2.99(m, 2H); 2.25(m, 2H); 1.25(m, 3H). MS (ES)=468.2 (M+NH$_4$).

Step 3: 2S-2-methoxy-3-{4-[3-(4-phenoxy-phenoxy)-propoxy]phenyl}propanoic acid, sodium salt (c)

To a 22 L flask, a solution of compound (b) (987 g) in ethanol (10 L) was added and stirred, followed by adding 5 N NaOH (4.4 L) for over 60 minutes at a temperature at 20 to 30° C. The slurry was stirred for about an hour at ambient temperature and then cooled to 10–15° C. where the mixture was held at that temperature for 1 hour and filtered. The solid was washed with alcohol (8 L) and MTBE (50 L) to afford the compound (c), which can be further purified by recrystallizing from ethyl acetate: $^1$H-NMR (DMSO): 7.35(m, 2H); 7.1(m, 3H); 7.0(m, 4H), 6.9(d, 2H); 6.8(d, 2H); 4.1(m, 4H); 3.4(t, 1H); 3.1(s, 3H); 2.8(dd, 1H); 2.6(m, 1H); 2.15(m, 2H). MS (ES): 421.2 (M−1).

Step 4: 2S-2-methoxy-3-{4-[3-(4-phenoxy-phenoxy)-propoxy]-phenyl}propanoic acid (d)

2-Methoxy-3-{4-[3-(4-phenoxy-phenoxy)-propoxy]-phenyl}-propionic acid ethyl ester (b) (12.15 g, 27 mmol) was dissolved in ethanol (250 ml) at ambient temperature, and 5N NaOH (54 ml, 270 mmol) was added dropwise. The slurry was stirred at ambient temperature for 2 hours. The mixture was diluted with water (250 ml), and conc. HCl (33 ml) was added dropwise. The resulting slurry was stirred at ambient temperature for about 2 hours. The white solid was filtered and dried under vacuum at 70° C. for 16 hours to afford about 10.5 g of the compound (d). $^1$H-NMR (CDCl$_3$): 7.3 (m, 2H), 7.18 (d, 2H), 7.07 (t, 1H), 6.9 (m, 8H), 4.19 (m, 4H), 4.0 (m, 1H), 3.4 (s, 3H), 3.0 (m, 2H), 2.25 (m, 2H). MS (ES): 421.2 (M−1).

Example 248

(2S)-(2'RS)-2-Methoxy-{4-[2'-methyl-3-(4-phenoxy-phenoxy)-propoxy]-phenyl}-propionic acid

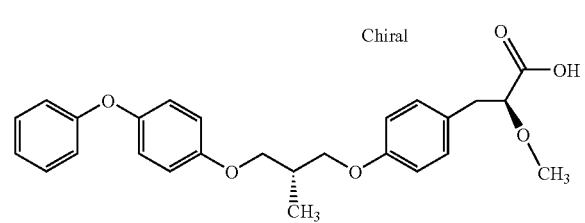

A solution of (2S)-2-Methoxy-3-{4-[2-(4-phenoxy-phenoxy)-propoxy]-phenyl}-propionic acid {4-[2-methylen-3-(4-phenoxy-phenoxy)-propoxy]-phenyl}-propionic acid from Example 74, in ethanol was treated with Pd/C and H$_2$ for over 2 hours at 1 atm. The mixture was filtered through celite and concentrated to dryness to afford the title compound as a mixture of isomers. MS (ES) for C$_{26}$H$_{28}$O$_6$ [M+NH$_4$]$^+$: 454.2, [M−H]$^−$: 435.2.

Example 249

2(S)-3-[4-(3-Benzyloxy-propoxy)-phenyl]-2-methoxypropionic acid

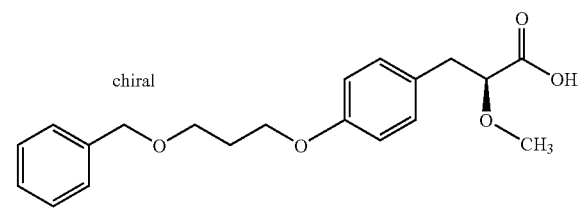

The title compound was prepared from (2S)-3-[4-(3-hydroxy-phenyl]-2-methoxypropionic acid linked to Wang's Resin (Example 94, Step C) via the Mitsunobu reaction-cleavage (Standard Procedure G). $^1$H-NMR (200.15 MHz, CDCl$_3$): 7.4–7.2 (m, 5H), 7.14 (d, 2H, J=8.6), 6.82 (d, 2H, J=8.6), 4.52 (s, 2H), 4.06 (t, 2H, J=6.2), 3.97 (dd, 1H, J=7.2, 4.6), 3.65 (t, 2H, J=6.2), 3.39 (s, 3H), 3.09 (dd, 1H, J=14.4, 4.4), 2.95 (dd, 1H, J=14.4, 7.2), 2.07 (qn, 2H, J=6.2).

Example 250

(2S)-3-[4-(5-Benzyloxy-pentyloxy)-phenyl]-2-methoxypropionic acid

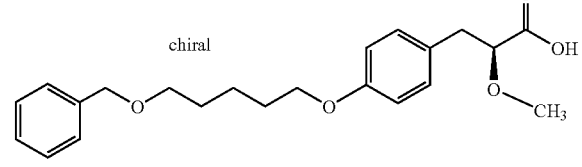

The title compound was prepared from (2S)-3-[4-(3-hydroxy-phenyl]-2-methoxy-propionic acid linked to Wang's Resin (Example 94, Step C) via the Mitsunobu reaction-cleavage (Standard Procedure G) with 5-benzyloxy-pentan-1-ol. $^1$H-NMR (200.15 MHz, CDCl$_3$): 7.4–7.3 (m, 5H), 7.14 (d, 2H, J=8.6), 6.81 (d, 2H, J=8.6), 4.51 (s, 2H), 4.0–3.9 (m, 3H), 3.50 (t, 2H, J=6.2), 3.39 (s, 3H), 3.08 (dd, 1H, J=14.2, 4.3), 2.95 (dd, 1H, J=14.2, 7.5), 1.9–1.5 (m, 6H).

Example 251

(2S)-2-ethoxy-{4-[3-(4-phenoxy-phenoxy)-propoxy]-phenyl}-propionic acid

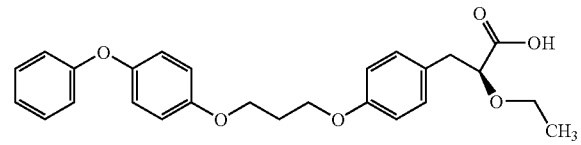

Step A (2S)-2-Hydroxy-3-(4-hydroxy-phenyl)-propionic acid ethyl ester

A solution of (2S)-2-hydroxy-3-(4-hydroxy-phenyl)-propionic acid in ethanol and H$_2$SO$_4$ (catalytic) was stirred overnight. The mixture was concentrated to dryness and reconstituted in ethyl acetate. The organic layer was washed with NaHCO$_3$, dried over MgSO$_4$ and concentrated to dryness to give the title product. $^1$H-NMR (CDCl$_3$, 200.15 MHz): δ 7.03 (d, 2H, J=8.6), 7.00 (d, 2H, J=8.7), 6.72–6.77 (m, 1H), 4.44–4.30 (m, 1H), 4.22 (q, 2H, J=7.9), 3.13–2–77 (m, 2H), 1.24 (t, 3H, J=7.9).

Step B (2S)-2-Hydroxy-3-{4-[3-(4-phenoxy-phenoxy)-propoxy]-phenyl}-propionic acid ethyl ester To a solution of compound (Step A) in DMF, CsCO₃ (1.0 eq) and 4-(3-bromopropoxy)-1-phenoxybenzene (1.1 eq) (Example 244, Step A) were added. The mixture was stirred at room temperature overnight. The solvent was concentrated in vacuum and ethyl acetate was added. The organic layer was washed with water and concentrated to affrod, after chromatography on silica gel, the title compound.
$^1$H-NMR (CDCl₃, 200.15 MHz): δ 7.28 (dd, 2H, J=8.3, 0.8), 7.17–6.84 (m, 11H), 4.44–4.36 (m, 1H), 4.28–4.12 (m, 6H), 3.13–2.87 (m, 2H), 2.79–2.76 (m, 1H), 2.32–2.19 (m, 2H), 1.29 (t, 3H, J=7.9).

Step C

2-Ethoxy-3-{4-[3-(4-phenoxy-phenoxy)-propoxy]-phenyl}-propionic acid ethyl ester A solution of (2S)-2-hydroxy-3-{4-[3-(4-phenoxy-phenoxy)-propoxy]-phenyl}-propionic acid ethyl ester, AgO₂ (1.5 eq) and ethyl iodide (excess) in dichloromethane was stirred over 10 days. The crude mixture was filtered through celite and concentrated to dryness. The compound was purified by chromatography to give the title product.
$^1$H-NMR (CDCl₃, 200.15 MHz): δ 7.34–7.26 (m, 2H), 7.18–6.82 (m, 11H), 4.18–4.17 (m, 6H), 4.01–3.94 (m, 1H), 3.68–3.53 (m, 1H), 3.43–3.28 (m, 1H), 2.96 (d, 2H, J=6.5), 2.25 (qn, 2H, J=6.2), 1.20 (dt, 6H, J=12.6, 7.3).

Step D (2S)-2-ethoxy-{4-[3-(4-phenoxy-phenoxy)-propoxy]-phenyl}-propionic acid The title compound was prepared from 2-ethoxy-3-{4-[3-(4-phenoxy-phenoxy)-propoxy]-phenyl}-propionic acid ethyl ester (Step C) by standard hydrolysis procedure C (LiOH). MS (ES) for C₂₆H₂₈O₆ [M+NH₄]⁺: 454.2, [M–H]⁻: 435.2.

Example 252

(2S)-2-Benzyloxy-3-{4-[3-phenoxy-phenoxy)-propoxy]-phenyl}-propionic acid

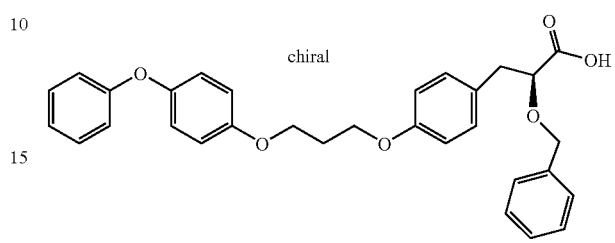

The title compound was prepared as in Example 251 using benzyl bromide as alkylating agent. Hydrolysis under the Standard Procedure C of the corresponding ethyl ester derivative gave us the title compound. MS(ES) for C₃₁H₃₀O₆ [M+NH₄]⁺: 516.2, [M–H]⁻: 497.2.

Example 253

(2S)-3-{4-[3-(4-{4-[2-(tert-Butyl-dimethyl-silanyloxy)-ethoxy]-benzoyl}-phenoxy)-propoxy]-phenyl}-2-methoxy-propionic acid

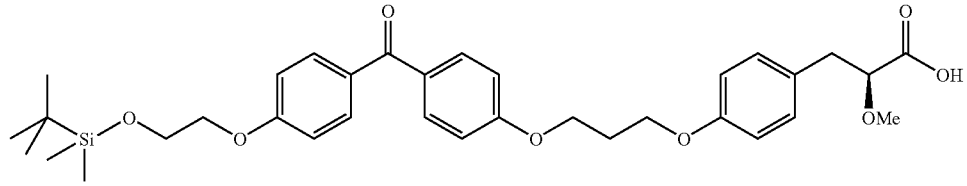

Step A (2S)-3-(4-{3-[4-(4-hydroxy-benzoyl)-phenoxy]-propoxy}-phenyl)-2-methoxy-propionic acid ethyl ester

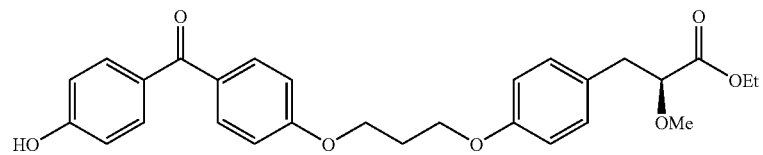

Concentrated sulfuric acid (0.05 mL) was added to a solution of (2S)-3-(4-{3-[4-(4-hydroxy-benzoyl)-phenoxy]- propoxy}-phenyl)-2-methoxy-propionic acid (0.18 mmol, 80 mg) (example 170) in ethanol (20 mL) at room temperature. The mixture was stirred at room temperature for three days, and the solvent was concentrated under vacuum. After addition of water, the mixture was neutralized with solid NaHCO$_3$ and extracted with ethyl acetate (3×15 mL). The combined organic layers were dried over MgSO$_4$, filtered and concentrated under vacuum to afford the title compound. $^1$H-NMR (200.15 MHz, CDCl$_3$): δ 7.76 (d, 2H, J=8.6), 7.71 (d, 2H, J=8.8), 7.13 (d, 2H, J=8.6), 6.91–6.80 (m, 6H), 6.37 (br s, 1H), 4.25–4.10 (m, 6H), 3.93 (dd, 1H, J=7.0, 5.6), 3.35 (s, 3H), 2.95 (m, 2H), 2.27 (qn, 2H, J=5.9), 1.23 (t, 3H, J=7.1).

Step B (2S)-3-{4-[3-(4-{4-[2-(tert-Butyl-dimethyl-silanyloxy)-ethoxy]-benzoyl}-phenoxy)-propoxy]-phenyl}-2-methoxy-propionic acid ethyl ester Step C (2S)-3-{4-[3-(4-{4-[2-(tert-Butyl dimethyl-silanyloxy)-ethoxy]-benzoyl}-phenoxy)-propoxy]-phenyl}-2-methoxy-propionic acid The title compound was prepared from (2S)-3-{4-[3-(4-{4-[2-tert-Butyl-dimethyl-silanyloxy)-ethoxy]-benzoyl}-phenoxy)-propoxy]-phenyl}-2-methoxy-propionic acid ethyl ester by the standard hydrolysis procedure C (LiOH). $^1$H-NMR (200.15 MHz, CDCl$_3$): δ 7.76 (dd, 4H, J=8.6, 1.6), 7.15 (d, 2H, J=8.6), 6.95 (dd, 4H, J=8.8, 1.6), 6.83 (d, 2H, 8–0.6), 4.24 (t, 2H, J=6.0), 4.17–4.09 (m, 5H), 4.02–3.94

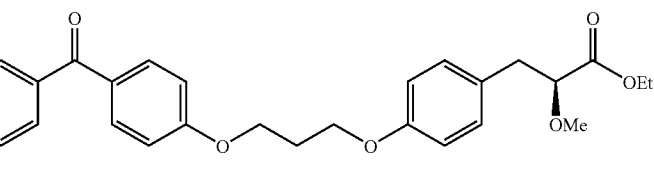

Diisopropyl azodicarboxilate (0.2 mmol, 0.04 mL) was added dropwise to a solution of 2-(tert-butyl-dimethyl-silanyloxy)-ethanol (0.26 mmol, 46 mg) (Example 122, Step A), (2S)-3-(4-{3-[4-(4-hydroxy-benzoyl)-phenoxy]-propoxy}-phenyl)-2-methoxy-propionic acid ethyl ester (0.13 mmol, 65 mg) and triphenylphosphine (0.2 mmol, 38 mg) in anhydrous toluene (2 mL) at 0° C. under nitrogen. The mixture was stirred overnight at room temperature, quenched with water and extracted with ethyl acetate (3×15 mL). The combined organic layers were dried over MgSO$_4$, filtered and concentrated under vacuum. The crude mixture was chromatographed on silica gel using a 4/1 hexane/EtOAc mixture as eluent to afford the title product $^1$H-NMR (200.15 MHz, CDCl$_3$): δ 7.76 (d, 4H, J=8.9), 7.13 (d, 2H, J=8.6), 6.96 (d, 4H, J=8.6), 6.83 (d, 2H, J=8.6), 4.26–4.09 (m, 8H), 4.02–3.87 (m, 3H), 3.35 (s, 3H), 2.97 (m, 2H), 2.28 (qn, 2H, J=5.9), 1.23 (t, 3H, J=7.1), 0.91 (s, 9H), 0.11 (s, 6H).

(m, 3H), 3.39 (s, 3H), 3.12–2.90 (m, 2H), 2.27 (qn, 2H, J=6.0), 0.91 (s, 9H), 0.11 (s, 6H).

Example 254
(2S)-3-[4-(3-{4-[4-(2-Hydroxy-ethoxy)-benzoyl]-phenoxy}-propoxy)-phenyl]-2-methoxy-propionic acid

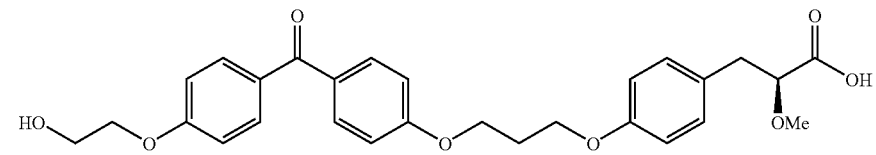

The compound of (2S)-3-{4-[3-(4-{4-[2-(tert-butyl-dimethyl-silanyloxy)-ethoxy]-benzoyl}-phenoxy)-propoxy]-phenyl}-2-methoxy-propionic acid (Example 253, Step C) (0.05 mmol, 30 mg) was dissolved in 5 mL of a mixture of acetic acid, THF and H$_2$O (3:1:1) and stirred at room temperature for 2 hours. The mixture was diluted with H$_2$O and extracted with ethyl acetate (4×20 mL). The combined organic layers were dried over MgSO$_4$, filtered and concentrated under vacuum to afford the title compound. MS(ES) for C$_{28}$H$_{30}$O$_8$ [M+H]$^+$: 495.1

Example 255

(2S)-3-{4-[3-(4-phenoxy-phenoxy)-propoxy]-phenyl}-2-propoxy-propionic acid

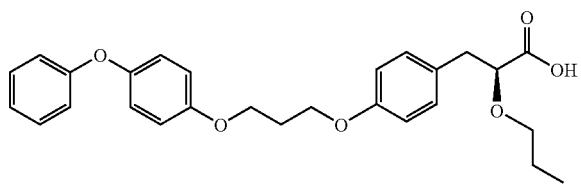

Step A 3-(4-Benzyloxy-phenyl-2-hydroxy-propionic acid ethyl ester

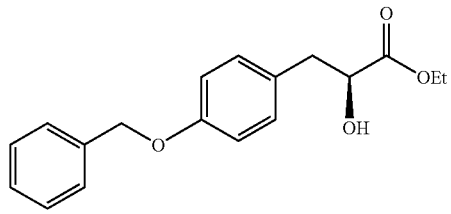

A mixture of 2-hydroxy-3-(4-hydroxy-phenyl)-propionic acid ethyl ester (Example 251, Step A) (5.2 mmol, 1.1 g), benzyl bromide (5.2 mmol, 0.62 mL) and potassium carbonate (15.7 mmol, 2.2 g) in acetonitrile (20 mL) was refluxed overnight. The mixture was cooled down to room temperature and concentrated to dryness to give a crude, which was purified by column chromatography on, silica gel to afford the title product.

MS (ES) for $C_{18}H_{20}O_4$ [M+NH$_4$]$^+$: 318.3

Step B (2S)-2-Allyloxy-3-(4-benzyloxy-phenyl)-propionic acid ethyl ester

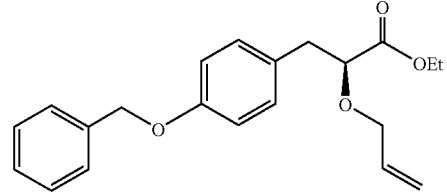

Silver (I) oxide (5.7 mmol, 1.3 g) was added to a mixture of (S)-3-(4-benzyloxy-phenyl)-2-hydroxy-propionic acid ethyl ester (3.8 mmol, 1.2 g) and alkyl bromide (19 mmol, 1.6 mL) in DMF (10 mL) at room temperature, and the reaction mixture was heated at 50° C. for 20 hours. After cooling to room temperature, the mixture was diluted with H$_2$O and extracted with ethyl acetate (5×25 mL). The combined organic layers were washed with water (4×20 mL) and brine; dried over MgSO$_4$, filtered and concentrated under vacuum. The crude mixture was chromatographed on silica gel using a 4/1 hexane/ethyl acetate mixture as eluent to afford the title product. $^1$H-NMR (200.15 MHz, CDCl$_3$): δ 7.46–7.32 (m, 5H), 7.18 (d, 2H, J=8.9), 6.91 (d, 2H, J=8.9), 5.91–5.72 (m, 1H), 5.25–5.12 (m, 2H), 5.05 (s, 2H), 4.11–4.03 (4H, m), 3.94–3.84 (m, 1H), 2.99 (d, 2H, J=7.0), 1.23 (t, 3H, J=7.0).

Step C (2S)-3-(4-Hydroxy-phenyl)-2-propoxy-propionic acid ethyl ester

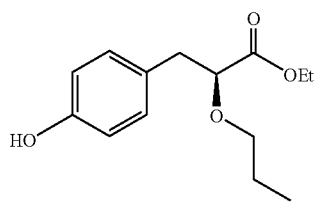

A mixture of (S)-2-allyloxy-3-(4-benzyloxy-phenyl)-propionic acid ethyl ester (1.33 mmol, 450 mg) and 10% Pd/C (45 mg) in EtOH (15 mL) were stirred under hydrogen atmosphere (1 atm) for 18 hours. The mixture was filtered through celite and concentrated under vacuum to afford the title product. $^1$H-NMR (200.15 MHz, CDCl$_3$): δ 7.10 (d, 4H, J=8.6), 6.73 (d, 2H, J=8.4), 5.90 (brs, 1H), 4.16 (q, 2H, J=7.3), 3.94 (t, 1H, J=6.7), 3.53–3.45 (m, 1H), 3.27–3.16 (m, 1H), 2.93 (d, 2H, J=6.5), 1.54 (m, 2H), 1.22 (t, 3H, J=7.3), 0.84 (t, 3H, J=7.5).

Step D (2S)-3-{4-[3-(4-Phenoxy-phenoxy)-propoxy]-phenyl}-2-propoxy-propionic acid ethyl ester

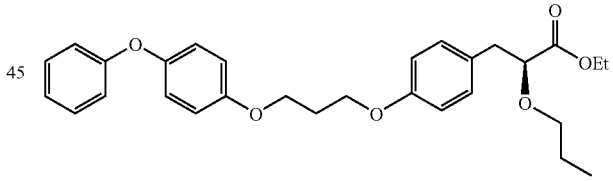

The title compound was prepared from (S)-3-(4-hydroxy-phenyl)-2-propoxy-propionic acid ethyl ester and 3-(4-phenoxy-phenoxy)-propyl bromide (Example 244) using the Standard Procedure L. The product was purified by column chromatography on silica gel using 9/1 Hexan/Ethyl acetate mixture as eluent to afford the title product. MS(ES) for $C_{29}H_{34}O_6$ [M+NH$_4$]$^+$: 496.3

Step E (2S)-3-{4-[3-(4-Phenoxy-phenoxy)-propoxy]-phenyl}-2-propoxy-propionic acid The title compound was prepared from (S)-3-{4-[3-(4-Phenoxy-phenoxy)-propoxy]-phenyl}-2-propoxy-propionic acid ethyl ester by the standard hydrolysis procedure C (LiOH). MS(ES) for $C_{27}H_{30}O_6$ [M−H]$^-$: 449.2

Example 256

(2S)-3-{4-[3-(4-Benzoyl phenoxy)-propoxy]-phenyl}-2-ethoxy-propionic acid

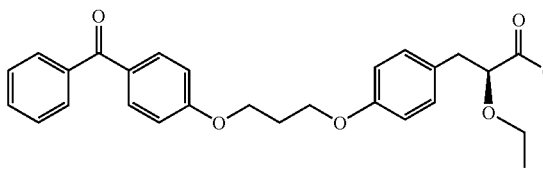

Step A (2S)-3-{4-[3-(4-Benzoyl-phenoxy)-propoxy]-phenyl}-2-ethoxy-propionic acid methyl ester

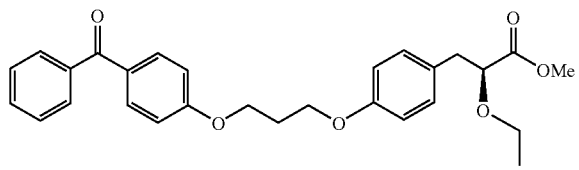

The title compound was prepared from 2-ethoxy-3-(4-hydroxy-phenyl)-propionic acid methyl ester and [4-(3-bromo-propoxy)-phenyl]-phenyl-methanone (prepared from 4-hydroxybenzophenone following the same procedure as in (Example 132, Steps B to D) using the Standard Procedure I. The product was purified by column chromatography on silica gel using a hexane/ethyl acetate mixture (4/1) as eluent to give the racemic product. This racemic mixture was subjected to chiral HPLC separation to give the pure enantiomer. $^1$H-NMR (200.15 MHz, CDCl$_3$): δ 7.83–7.72 (m, 4H), 7.57–7.42 (m, 3H), 7.14 (d, 2H, J=8.8), 6.96 (d, 2H, J=8.8), 6.83 (d, 2H, J=8.6), 4.25 (t, 2H, J=6.1), 4.15 (t, 2H, J=6.2), 3.98 (dd, 1H, J=7.1, 6.0), 3.70 (s, 3H), 3.58 (dd, 1H, J=9.1, 7.0), 3.33 (dd, 1H, J=9.1, 7.0), 2.94 (m, 2H), 2.28 (qn, 2H, J=6.2), 1.25 (t, 3H, J=7.3).

Step B (2S)-3-{4-[3-(4-Benzoyl-phenoxy)-propoxy]-phenyl}-2-ethoxy-propionic acid The title compound was prepared from (S)-3-{4-[3-(4-Benzoyl-phenoxy)-propoxy]-phenyl}-2-ethoxy-propionic acid methyl ester by the standard hydrolysis procedure C (LiOH). MS(ES) for C$_{27}$H$_{28}$O$_6$ [M–H]$^-$: 447.1

Example 257

(2S)-3-{4-[3-(4-Benzyl-phenoxy)-propoxy]-phenyl}-2-ethoxy-propionic acid

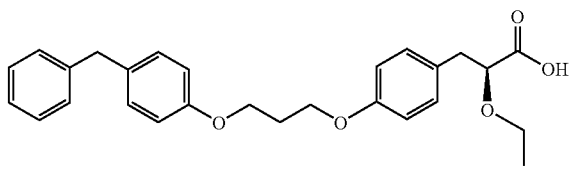

Step A (2S)-3-{4-[3-(4-Benzyl-phenoxy)-propoxy]-phenyl}-2-ethoxy-propionic acid ethyl ester

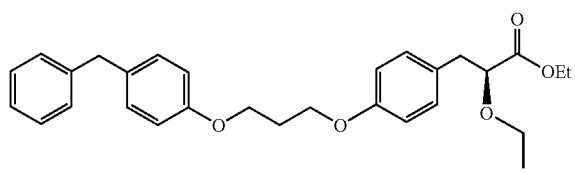

The title compound was prepared from (S)-2-ethoxy-3-(4-hydroxy-phenyl)-propionic acid ethyl ester and 3-(4-benzyl-phenoxy)-propyl bromide (prepared from 4-benzylphenol following the same procedure as in (Example 132, Steps B to D) using the Standard Procedure I. The product was purified by column chromatography on silica gel using a hexae/ethyl acetate mixture (4/1) as eluent to give the title product. MS(ES) for C$_{29}$H$_{34}$O$_5$ [M+NH$_4$]$^+$: 480.2.

Step B (2S)-3-{4-[3-(4-Benzyl-phenoxy)-propoxy]-phenyl}-2-ethoxy-propionic acid The title compound was prepared from (S)-3-{4-[3-(4-Benzyl-phenoxy)-propoxy]-phenyl}-2-ethoxy-propionic acid ethyl ester by the standard hydrolysis procedure C (LiOH). MS(ES) for C$_{27}$H$_{30}$O$_5$ [M–H]$^-$: 433.1

Example 258

(2S)-3-{4-[3-(4-Benzoyl-phenoxy)-propoxy]-3-chloro-phenyl}-2-ethoxy-propionic acid

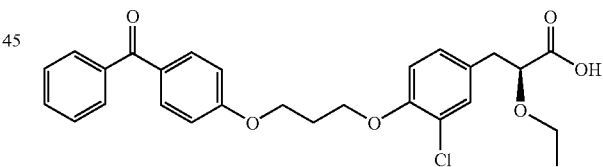

Step A (2S)-3-(3-Chloro-4-hydroxy-phenyl)-2-ethoxy-propionic acid ethyl ester

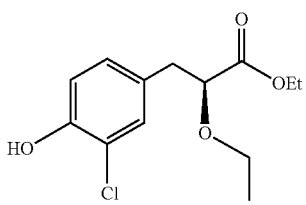

N-Chlorosuccinimide (2.1 mmol) was added to a solution of (S)-2-ethoxy-3-(4-hydroxy-phenyl)-propionic acid ethyl ester (2.1 mmol) in acetonitrile (12 mL) at room temperature, and the mixture was stirred at the same temperature for 5 days. Solvent was evaporated under vacuum, and the residue was washed with CCl$_4$. The resulting suspension was filtered, and the filtrate was concentrated under vacuum and chromatographed on silica gel using a 9/1 hexane/EtOAc mixture as eluent to afford title product. MS(ES) for C$_{13}$H$_{17}$ClO$_4$ [M−H]$^-$: 271.0

Step B (2S)-3-{4-[3-(4-benzoyl-phenoxy)-propoxy]-3-chloro-phenyl}-2-ethoxy-propionic acid ethyl ester

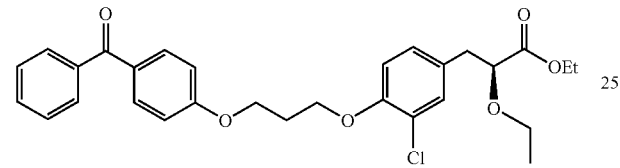

The title compound was prepared from (S)-2-ethoxy-3-(3-chloro-4-hydroxy-phenyl)-propionic acid ethyl ester and [4-(3-bromo-propoxy)-phenyl]-phenyl-methanone (Example 256) using the Standard Procedure I. The product was purified by column chromatography on silica gel using a 4/1 Hexane/Ethyl acetate mixture as eluent to give the title product. MS(ES) for C$_{29}$H$_{31}$ClO$_6$ [M+H]$^+$: 511.1

Step C (2S)-3-{4-[3-(4-benzoyl-phenoxy)-propoxy]-3-chloro-phenyl}-2-ethoxy-propionic acid The title compound was prepared from (S)-3-{4-[3-(4-benzoyl-phenoxy)-propoxy]-3-chloro-phenyl}-2-ethoxy-propionic acid methyl ester by the standard hydrolysis procedure C (LiOH). $^1$H-NMR (200.15 MHz, CDCl$_3$): δ 7.82–7.72 (m, 4H), 7.56–7.43 (m, 3H), 7.07 (dd, 1H, J=8.8, 2.0), 6.97 (d, 2H, J=8.9), 6.86 (d, 2H, J=8.3), 4.31 (t, 2H, J=6.0), 4.21 (t, 2H, J=6.0), 4.10–4.02 (m, 1H), 3.66–3.44 (m, 2H), 3.10–2.87 (m, 2H), 2.33 (qn, 2H, J=6.2), 1.20 (t, 3H, J=7.0).

Example 259

(2S)-4'-{3-[4-(2-Carboxy-2-methoxy-ethyl)-2-methoxy-phenoxy]-propoxy}-biphenyl-4-carboxylic acid

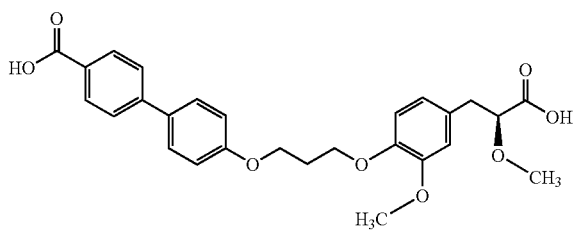

Step A

3-[4-(3-Hydroxy-propoxy)-3-methoxy-phenyl]-2-methoxypropionic acid methyl ester

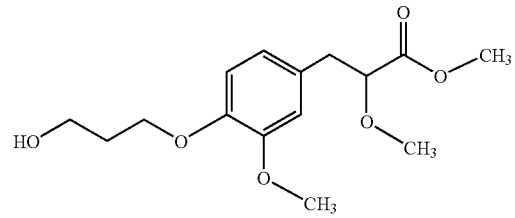

A mixture of 3-(4-Hydroxy-3-methoxy-phenyl)-2-methoxypropionic acid methyl ester (Example 130, Step B) and 3-(tert-butyl-dimethyl-silanyloxy)-propan-1-ol were treated under Mitsunobu standard conditions B using DIAD and toluene. The product obtained was treated under Standard Procedure E for cleavage protected alcohols to give the title product. The 2S isomer was separated from the 2R isomer by chiral. $^1$H-NMR (CDCl$_3$, 200.15 MHz): δ 6.84–6.72 (m, 3H), 4.17 (t, 2H, J=5.9), 3.94 (dd, 2H, J=7.0, 5.4), 3.87 (t, 2H, J=5.4), 3.84 (s, 3H), 3.73 (s, 3H), 3.35 (s, 3H), 2.97–2.93 (m, 2H), 2.11–2.00 (m, 2H).

Step B (2S)-4'-{3-[2-Methoxy-4-(2-methoxy-2-methoxycarbonyl-ethyl)-phenoxy]-propoxy}-biphenyl-4-carboxylic acid methyl ester

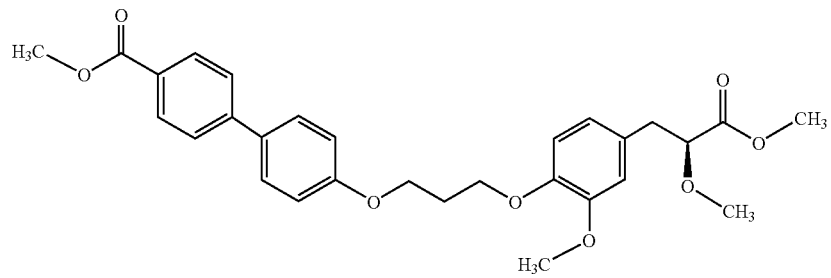

3-[4-(3-Bromo-propoxy)-3-methoxy-phenyl]-2-methoxypropionic acid methyl ester (Step A) and 4'-hydroxy-biphenyl-4-carboxylic acid methyl ester (Example 197, Step A) were treated under Mitsunobu standard condition B. The crude was purified by chromatography on silica gel (hexanes/ethyl acetate 7:3) to afford the title compound.

¹H-NMR (CDCl₃, 200.15 MHz): δ 8.07 (d, 2H, J=8.6), 7.58 (dd, 4H, J=10.8, 8.9), 7.14 (d, 2H, J=8.9), 6.99 (d, 2H, J=8.9), 6.84 (d, 2H, J=8.6), 4.24–4.12 (m, 6H), 3.94–3.90 (m, 4H), 3.35 (s, 3H), 2.97–2.94 (m, 2H), 2.27 (qn, 2H, J=5.9), 1.23 (t, 3H, J=7.0).

Step C (2S)-4'-{3-[4-(2-Carboxy-2-methoxy-ethyl)-2-methoxy-phenoxy]-propoxy}-biphenyl-4-carboxylic acid The title compound was prepared from 4'-{3-[2-methoxy-4-(2-methoxy-2-methoxycarbonyl-ethyl)-phenoxy]-propoxy}-biphenyl-4-carboxylic acid methyl ester (Step B) by standard hydrolysis procedure C (NaOH). ¹H-NMR (MeOD, 300.15 MHz):

δ 8.07 (d, 2H, J=8.5), 7.69 (d, 2H, J=8.5), 7.63 (d, 2H, J=8.7), 7.06 (d, 2H, J=8.7), 6.91–6.88 (m, 2H), 6.78 (dd, 1H, J=8.1, 1.6), 4.25 (t, 2H, J=6.3), 4.18 (t, 2H, J=6.0), 3.94 (dd, 1H, J=7.9, 4.4), 3.82 (s, 3H), 3.33 (s, 3H), 3.01 (dd, 1H, J=14.1, 4.4), 2.88 (dd, 1H, J=13.9, 7.7), 2.26 (qn, 2H, J=6.0).

Example 260

(2S)-3-{4-[3-(4'-tert-Butyl-biphenyl-4-yloxy)-propoxy]-2-methoxy-propionic acid

Step B

3-[4-(3-Bromo-propoxy)-2-methoxy-phenyl]-2-methoxy-propionic acid methyl ester

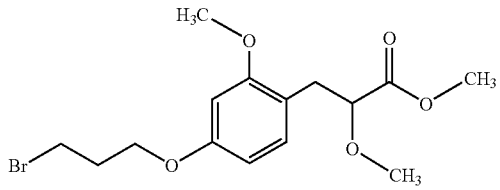

3-(4-Hydroxy-2-methoxy-phenyl)-2-methoxy-propionic acid methyl ester (Example 188, Step C) and 3-bromo-propan-1-ol (Step A) were treated in the standard Mitsunobu conditions B (DIAD/toluene) to afford the title compound. ¹H-NMR (CDCl₃, 200.15 MHz): δ 7.01 (d, 1H, J=8.3), 6.39 (m, 2H), 4.06 (t, 2H, J=5.9), 4.00–3.96 (m, 1H), 3.78 (s, 3H), 3.67 (s, 3H), 3.57 (t, 2H, J=6.4), 3.31 (s, 3H), 2.99 (dd, 1H, J=13.7, 6.2), 2.91 (dd, 1H, J=13.7, 7.5), 2.34–2.22 (m, 2H).

Step C (2S)-3-{4-[3-(4'-tert-Butyl-biphenyl-4-yloxy)-propoxy-2-methoxy-phenyl]-2-methoxy-propionic acid methyl ester

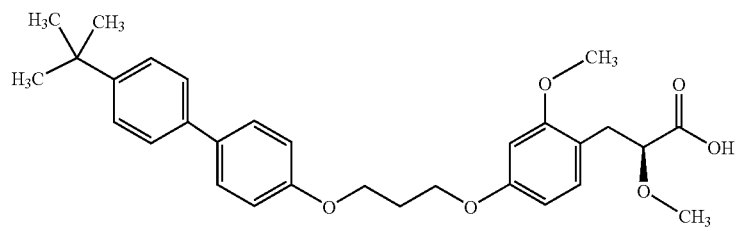

Step A

3-Bromopropan-1-ol

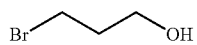

To a solution of 1,3-propanediol (5 g, 66 mmol) and benzene (132 mL) was added hydrobromic acid 48% (8 mL). The resulting mixture was heated at reflux for 20 hours while trapping the water formed using a Dean-Stark water separator. The mixture was washed with 2N NaOH solution, 5% HCl, water and brine. The organic layer was dried (Na₂SO₄) and evaporated under reduced pressure. ¹H-NMR (CDCl₃, 300.15 MHz): δ 3.78 (2H, t, J=6.0), 3.52 (2H, t, J=6.0), 2.07 (2H, m).

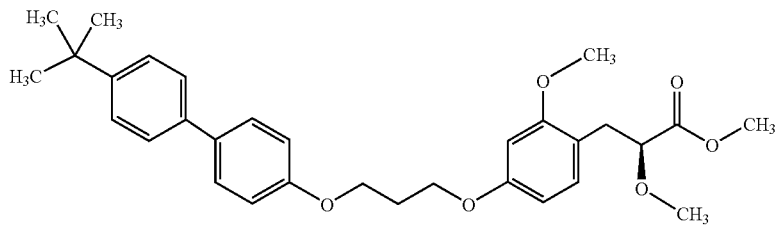

3-[4-(3-Bromo-propoxy)-2-methoxy-phenyl]-2-methoxy-propionic acid methyl ester (Step B) and 4'-tert-butyl-biphenyl-4-ol (Example 221, Step A) were treated under Standard Procedure K. The enantiomers were separated by chiral HPLC. The (2S) isomer was separated from the 2R isomer by chiral HPLC (Chiralpack AD, Hexane 0.05% TFA/IPA, 75/25, isocratic mode, 1 mL/min; RT=7.70 min). $^1$H-NMR (CDCl$_3$, 200.15 MHz): δ 7.53–7.41 (m, 6H), 7.05–6.95 (m, 3H), 6.45–6.40 (m, 2H), 4.21 (d, 2H, J=6.2), 4.14 (d, 2H, J=6.2), 4.05–3.98 (m, 1H), 3.80 (s, 3H), 3.69 (s, 3H), 3.33 (s, 3H), 3.01 (dd, 1H, J=13.4, 6.2), 2.92 (dd, 1H, J=13.4, 7.5), 2.27 (qn, 2H, J=6.2).

Step D (2S)-3-{4-[3-(4'-tert-Butyl-biphenyl-4-yloxy)-propoxy]-2-methoxy-phenyl}-2-methoxy-propionic acid The title compound was prepared from (2S)-3-{4-[3-(4'-tert-butyl-biphenyl-4-yloxy)-propoxy]2-methoxy-phenyl}-2-2-methoxy-propionic acid methyl ester (Step C) by standard hydrolysis procedure C (NaOH). $^1$H-NMR (Acetone-d$_6$, 300.15 MHz): δ 7.57 (d, 2H, J=8.7), 7.53 (d, 2H, J=8.7), 7.45 (d, 2H, J=8.5), 7.06–7.02 (m, 3H), 6.55 (d, 1H, J=2.0), 6.46 (dd, 1H, J=8.3, 2.2), 4.26–4.17 (m, 4H), 3.96 (dd, 1H, J=7.9, 5.7), 3.81 (s, 3H), 3.26 (s, 3H), 2.25 (qn, 2H, J=6.3), 1.33 (s, 9H).

Example 261

(2S)-3-(4-{3-[4-(4-Hydroxy-phenoxy)-phenoxy]-propoxy}-phenyl)-2-methoxy-propionic acid Step A (2S)-3-{4-[3-(tert-Butyl-dimethyl-silanyloxy)-propoxy]-phenyl}-2-methoxy-propionic acid ethyl ester

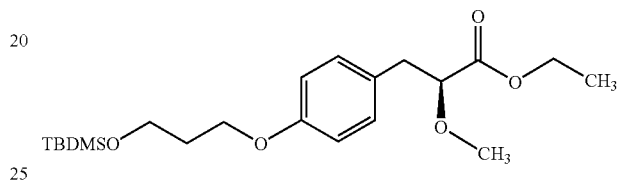

A mixture of (2S)-3-(4-hydroxy-phenyl)-2-methoxy propionic acid ethyl ester and 3-(tert-Butyl-dimethyl-silanyloxy)-propan-1-ol were treated under Mitsounobu coupling standard conditions B using DIAD and toluene.

Step B (2S)-3-[4-(3-Hydroxy-propoxy)-phenyl]-2-methoxy-propionic acid ethyl ester

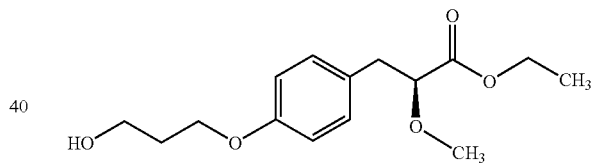

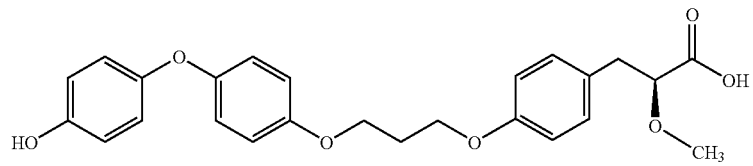

A solution of (2S)-3-{4-[3-(tert-Butyl-dimethyl-silany-loxy)-propoxy]-phenyl}-2-methoxy-propionic acid ethyl ester was treated under Standard Procedure E for cleaveage protected alcohols to give the title product.

Step C 3-(4-{3-[4'-(tert-Butyl-dimethyl-silanyloxy)-biphenyl-4-yloxy]-propoxy}-phenyl)-2-methoxy-propionic acid ethyl ester

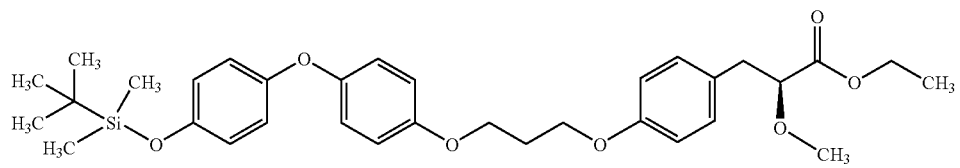

(2S)-3-[4-(3-Hydroxy-propoxy)-phenyl]-2-methoxy-propionic acid ethyl ester and 4'-(tert-butyl-dimethyl-silanyloxy)-biphenyl-4-ol (Example 196, Step A) were treated under Mitsunobu procedure B (DIAD, toluene), to afford the title compound.

Step D (2S)-3-(4-{3-[4-(4-Hydroxy-propoxy)-phenoxy]-propoxy}-phenyl)-2-methoxy-propionic acid The title compound was prepared from 3-(4-{3-[4'-(tert-butyl-dimethyl-silanyloxy)-biphenyl-4-yloxy]-propoxy}-phenyl)-2-methoxy-propionic acid ethyl ester (Step A) by standard hydrolysis procedure C (NaOH). $^1$H-NMR (CDCl$_3$, 200.15 MHz): δ 7.15 (d, 2H, J=8.6), 6.92–6.74 (m, 10H), 4.15–4.09 (m, 4H), 3.98 (dd, 1H, J=7.3, 4.6), 3.39 (s, 3H), 3.09 (dd, 1H, J=14.2, 4.6), 2.95 (dd, 1H, J=14.2, 7.3), 2.23 (qn, 2H, J=5.9).

Example 262

(2S)-2-Methoxy-3-(4-{3-[4-(2,2,3,3-tetrafluoro-propoxy)-phenoxy]-propoxy}-phenyl)-propionic acid Step A 4-(2,2,3,3-tetrafluoro-propoxy)-1-benzyloxy-phenol

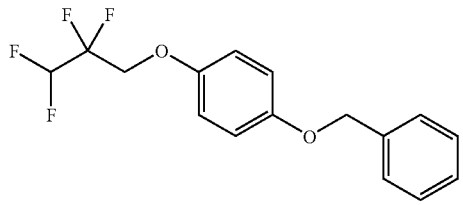

To a solution of methanesulfonic acid 2,2,3,3-tetrafluoropropyl ester (obtained from 2,2,3,3-tetrafluoropropanol and methanesulfonyl chloride as described in (Example 268, Step A) (0.35 mmol, 74 mg) and 4-benzyloxy-phenol (0.175 mmol, 35 mg) in DMF (1 mL) was added K$_2$CO$_3$, and the was stirred at 100° C. for 20 hours. Waiter: was added and the aqueous layer was extracted twice with hexane and once with ethyl acetate. The combined organic layers were dried (Na$_2$SO$_4$), filtered and evaporated. The crude was purified by chromatography on silica gel (hexane/ethyl acetate 4:1) to afford the title compound. $^1$H-NMR (CDCl$_3$, 200.15

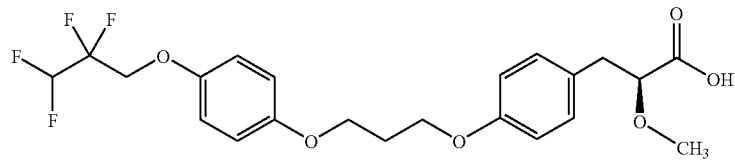

MHz): δ 7.42–7.32 (m, 5H, 6.96–6.84 (m, 4H), 6.06 (tt, 1H, J=53.0, 5.1), 5.03 (s, 2H), 4.29 (dt, J=12.0, 1.6).

Step B 4-(2,2,3,3-Tetrafluoro-propoxy)-phenol

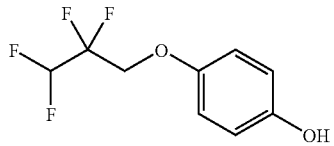

4-(2,2,3,3-tetrafluoro-propoxy)-benzyloxy-phenol (0.09 mmol, 28 mg) (Step A) was dissolved in MeOH (2 mL) and Pd(C) (40% weight, 10 mg) was added. The mixture was stirred for 90 minutes under $H_2$ atmosphere (1 atm), and filtered through a celite pad (EtOH). The filtrate was concentrated to give the title compound. $^1$H-NMR (CDCl$_3$, 200.15 MHz): δ 6.85–6.75 (m, 4H), 6.05 (dt, J=53.2, 4.8), 4.28 (dt, 2H, J=12.1, 1.6).

Step C (2S)-2-Methoxy-3-(4-{3-[4-(2,2,3,3-tetrafluoro-propoxy)-phenoxy]-propoxy}-phenyl)-propionic acid ethyl ester 3-[4-(3-Bromo-propoxy)-phenyl]-2-methoxy-propionic acid ethyl ester (Example 173, Step A) and 4-(2,2,3,3-tetrafluoro-propoxy)-phenol (Step B) were treated under ester K to afford the title compound $^1$H-NMR (CDCl$_3$, 200.15 MHz): δ 7.13 (d, 2H, J=8.6), 6.85–6.80 (m, 6H), 6.05 (dt, 1H, J=53.2, 5.1), 4.22–4.08 (m, 8H), 3.90 (dd, 1H, J=7.0, 5.6), 3.35 (s, 3H), 3.04–2.86 (m, 2H), 2.22 (qn, 2H, J=6.2).

Step D (2S)-2-Methoxy-3-(4-{3-[4-(2,2,3,3-tetrafluoro-propoxy)-phenoxy]-propoxy}-phenyl)-propionic acid The title compound was prepared from (2S)-2-methoxy-3-(4-{3-[4-(2,2,3,3-tetrafluoro-propoxy)-phenoxy]-propoxy}-phenyl)-propionic acid ethyl ester (Step C) by standard hydrolysis procedure C (NaOH). $^1$H-NMR (CDCl$_3$,

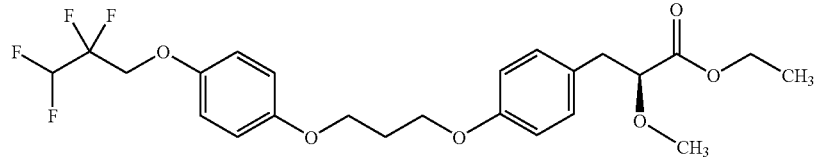

200.15 MHz): δ 7.14 (d, 2H, J=8.6), 6.84–6.79 (m, 6H), 6.04 (tt, 1H, J=53.0, 4.8), 4.27 (t, 2H, J=12.0), 4.09 (t, 4H, J=5.9), 3.97–3.91 (m, 1H), 3.34 (s, 3H), 3.11–2.87 (m, 2H), 2.20 (qn, 2H, J=5.9).

Example 263

(2S)-2-Methoxy-3-(4-{3-[4-(3-methyl-butoxy)-phenoxy]-propoxy}-phenyl)-propionic acid

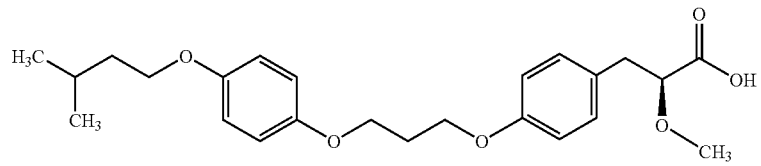

Step A

2S)-3-{4-[3-(4-benzyloxy-phenoxy]-phenoxy}-phenyl)-2-methoxy propionic acid ethyl ester

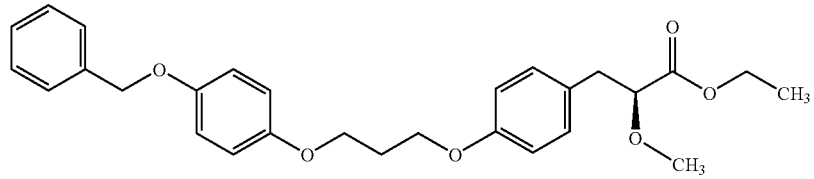

3-[4-(3-Bromo-propoxy)-3-methoxy-phenyl]-2-methoxy-propionic acid methyl ester (Example 175, Step B) and 4-benzyloxy-phenol were treated under Mitsunobu standard conditions B to afford the title compound. ¹H-NMR (CDCl₃, 200.15 MHz): δ 7.44–7.30 (m, 5H), 7.13 (d, 2H, J=8.6), 6.93–6.73 (m, 6H), 5.01 (s, 2H), 4.20–4.06 (m, 6H), 3.90 (dd, 1H, J=7.0, 5.6), 3.35 (s, 3H), 3.00–2.93 (m, 2H), 2.22 (qn, 2H, J=6.2), 1.23 (t, 3H, J=7.2).

Step B (2S)-3-{4-[3-(4-Hydroxy-phenoxy)-propoxy]-phenyl}-2-methoxy-propionic acid ethyl ester

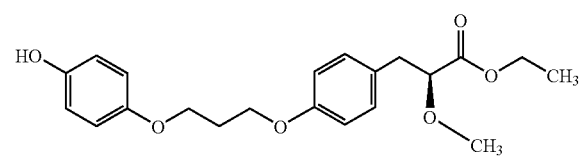

The title compound was obtained following the hydrogenation procedure (Example 261, Step B), starting from (2S)-3-{4-[3-(4-benzyloxy-phenoxy]-propoxy}-phenyl)-2-methoxy propionic acid ethyl ester. ¹H-NMR (CDCl₃, 200.15 MHz): δ 7.13 (d, 2H, J=8.9), 6.84–6.71 (m, 6H), 4.23–4.06 (m, 6H), 3.91 (dd, 1H, J=7.3, 5.9), 3.35 (s, 3H), 2.97–2.93 (m, 2H), 2.21 (qn, 2H, J=6.2), 1.23 (t, 3H, J=7.3).

Step C (2S)-2-Methoxy-3-(4-{3-[3-methyl-butoxy)-phenoxy]-propoxy}-phenyl)-propionic acid ethyl ester (2S)-3-{4-[3-(4-Hydroxy-phenoxy)-propoxy]-phenyl}-2-methoxy-propionic acid ethyl ester (Step A) was reacted under Mitsunobu procedure B (DIAD, toluene) with 3-methyl-butanol to afford the title compound. ¹H-NMR (CDCl₃, 200.15 MHz): δ 7.13 (d, 2H, J=8.6), 6.85–6.81 (m, 6H), 4.18 (q, 4H, J=7.0), 4.08 (d, 2H, J=5.9), 3.96–3.87 (m, 3H), 3.35 (s, 3H), 2.97–2.93 (m, 2H), 2.22 (qn, 2H, J=6.2), 1.86–1.60 (m, 3H), 1.23 (t, 5H, J=7.0), 0.95 (d, 6H, J=6.4).

Step D (2S)-2-Methoxy-3-(4-{3-[3-methyl-butoxy)-phenoxy]-propoxy}-phenyl)-propionic acid The title compound was prepared from (2S)-2-methoxy-3-(4-{3-[4-(3-methyl-butoxy)-phenoxy]-propoxy}-phenyl)-propionic acid ethyl ester (Step B) by standard hydrolysis procedure C (NaOH). ¹H-NMR (CDCl₃, 200.15 MHz): δ 7.12 (d, 2H, J=8.4), 6.84–6.80 (m, 6H), 4.09 (q, 4H, J=6.2), 3.99–3.88 (m, 3H), 3.37 (s, 3H), 3.07 (dd, 1H, J=14.3, 4.4), 2.93 (dd, 1H, J=14.3, 7.0), 2.19 (qn, 2H, J=6.2), 1.90–1.71 (m, 1H), 1.62 (q, 2H, J=6.9), 0.93 (d, 6H, J=6.6).

Example 264

(2S)-3-{4-[3-(4-Isobutoxy-phenoxy)-propoxy]-phenyl}-2-methoxy-propionic acid

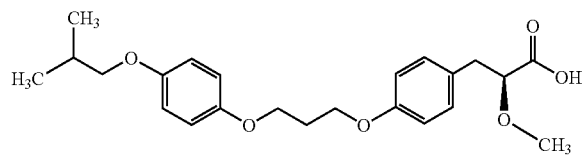

(2S)-3-{4-[3-(4-Hydroxy-phenoxy)-propoxy]-phenyl}-2-methoxy-propionic acid ethyl ester (Example 263, Step B) was coupled under the ester J with 1-bromo-2-methylpropane to afford the title compound. ¹H-NMR (CDCl₃, 200.15

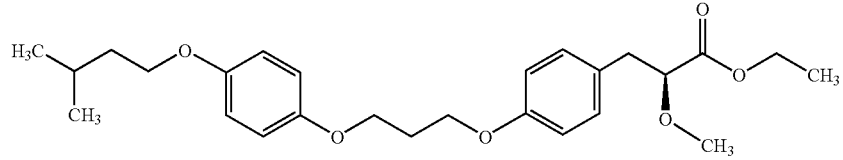

MHz): δ 7.14 (d, 2H, J=8.6), 6.86–6.82 (m, 6H), 4.11 (q, 4H, J=6.2), 3.98 (dd, 1H, J=7.3, 4.6), 3.66 (d, 2H, J=6.5), 3.40 (s, 3H), 3.10 (dd, 1H, J=14.5, 4.6), 2.95 (dd, 1H, J=14.5, 7.3), 2.21 (qn, 2H, J=6.2), 2.11–1.98 (m, 1H), 1.01 (d, 6H, J=6.7).

Example 265

(2S)-3-{4-[3-(4-Isopropoxy-phenoxy)-propoxy]-phenyl}-2-methoxy-propionic acid

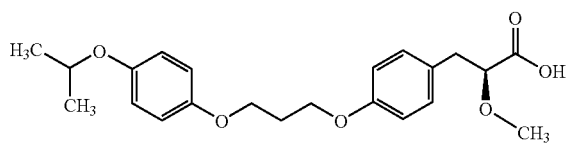

The title compound was prepared from (2S)-3-{4-[3-(4-hydroxy-phenoxy)-propoxy]-phenyl}-2-methoxy-propionic acid ethyl ester (Example 263, Step B) and 2-bromopropene following the procedure described for Example 264. $^1$H-NMR (CDCl$_3$, 200.15 MHz): δ 7.14 (d, 2H, J=8.3), 6.86–6.82 (m, 6H), 4.40 (qn, 1H, J=5.9), 4.11 (q, 4H, J=5.9), 3.98 (dd, 1H, J=7.3, 4.6), 3.40 (s, 3H), 3.10 (dd, 1H, J=14.2, 4.3), 3.01–2.90 (dd, 1H, J=14.2, 7.2), 2.22 (qn, 2H, J=5.9), 1.30 (d, 6H, J=6.2).

Example 266

(2S)-3-{4-[3-(4-Cyclohexylmethoxy-phenoxy)-propoxy]-phenyl}-2-methoxy-propionic acid

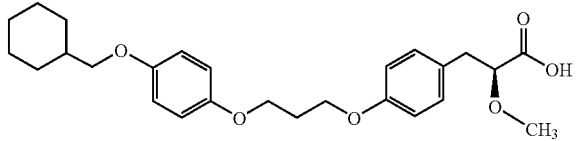

The title compound was prepared from (2S)-3-{4-[3-(4-hydroxy-phenoxy)-propoxy]-phenyl}-2-methoxy-propionic acid ethyl ester (Example 263, Step B) and (bromomethyl)cyclohexane following the procedure described for Example 264.

$^1$H-NMR (CDCl$_3$, 200.15 MHz): δ 7.14 (d, 2H, J=8.6), 6.86–6.81 (m, 6H), 4.11 (q, 4H, J=6.2), 3.99 (dd, 1H, J=7.3, 4.6), 3.70 (d, 2H, J=6.2), 3.40 (s, 3H), 3.10 (dd, 1H, J=14.5, 4.6), 2.96 (dd, 1H, J=14.2, 7.3), 2.23 (qn, 2H, J=6.2), 1.88–1.67 (m, 6H), 1.39–0.94 (m, 5H).

Example 267

(2S)-2-Methoxy-3-{4-[3-(4-phenetyloxy-phenoxy)-propoxy]-phenyl}-propionic acid

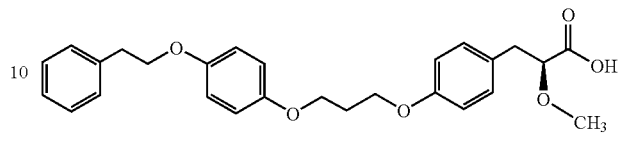

The title compound was prepared from (2S)-3-{4-[3-(4-hydroxy-phenoxy)-propoxy]-phenyl}-2-methoxy-propionic acid ethyl ester (Example 263, Step B) and (1-bromoethyl)benzene following the procedure described for Example 264. $^1$H-NMR (CDCl$_3$; 300.15 MHz): δ 7.32–7.26 (m, 5H), 7.14 (d, 2H, J=8.5), 6.86–6.82 (m, 6H), 4.15–4.08 (m, 6H), 4.00 (dd, 1H, J=6.9, 4.4), 3.41 (s, 3H), 3.14–3.05 (m, 3H), 2.97 (dd, 1H, J=14.5, 6.9), 2.22 (qn, 2H, J=6.1).

Example 268

(2S)-3-(4-{3-[4-(3-Dimethylamino-propoxy)-phenoxy]-propoxy}-phenyl)-2-methoxy-propionic acid

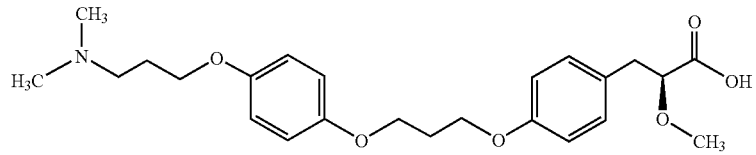

Step A

Methanesulfonic acid 3-dimethylamino-propyl ester

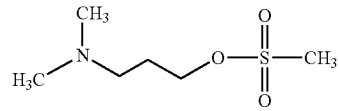

3-Dimethylamino-1-propanol (0.98 mmol, 0.12 mL) was dissolved in THF (2 mL). Triethylamine (1.47 mmol, 0.20 mL) was added, and the mixture was cooled at 0° C. Methanesulfonyl chloride (1.08 mmol, 0.08 mL). Was added and the bath removed. The mixture was warmed to room temperature and stirred for 2 hours. Hexanes were added and the precipitates were removed by filtration through celite (hexanes). The filtrate was concentrated to afford the title compound. $^1$H-NMR (CDCl$_3$, 200.15 MHz): δ 4.29 (t, 2H, J=6.4), 3.00 (s, 3H), 2.39 (t, 2H, J=7.0), 2.22 (s, 6H), 1.90 (qn, 2H, J=6.7).

Step B (2S)-3-(4-{3-[4-(3-Dimethylamino-propoxy)-phenoxy]-propoxy}-phenyl)-2-methoxy-propionic acid The title compound was prepared from (2S)-3-{4-[3-(4-hydroxy-phenoxy)-propoxy]-phenyl}-2-methoxy-propionic acid ethyl ester (Example 263, Step B) and methanesulfonic acid 3-dimethylaminopropyl ester (Step A) following the procedure described for Example 264. ¹H-NMR (CDCl₃, 200.15 MHz): δ 7.14 (d, 2H, J=7.8), 6.83–6.77 (m, 6H), 4.10–4.04 (m, 5H), 3.95–3.89 (m, 4H), 3.37 (s, 3H), 3.16–3.13 (m, 2H), 3.06–2.99 (m, 2H), 2.77 (s, 6H), 2.21–2.15 (m, 4H).

Example 269

(2S)-3-{4-[3-(4-Carboxymethoxy-phenoxy)-propoxy]-phenyl}-2-methoxy-propionic acid

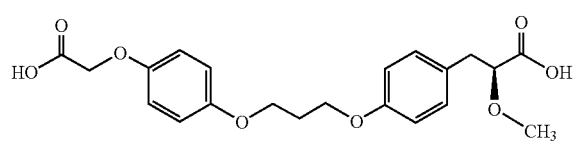

Step A

Methanesulfonyloxy-acetic acid ethyl ester

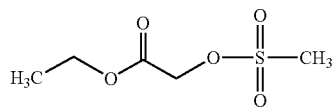

The title compound was prepared following the procedure described for methanesulfonic acid 3-dimethylamino-propyl ester (Example 268, Step A) starting from ethyl glycolate. ¹H-NMR (CDCl₃, 200.15 MHz): δ 4.75 (s, 2H), 4.27 (q, 2H, J=7.3), 3.20 (s, 3H), 1.31 (t, 3H, J=7.3).

Step B (2S)-3-{4-[3-(4-Carbomethoxy-phenoxy)-propoxy]-phenyl}-2-methoxy-propionic acid

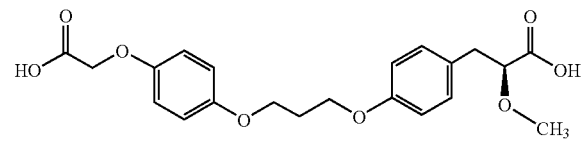

The title compound was prepared from (2S)-3-{4-[3-(4-hydroxy-phenoxy)-propoxy]-phenyl}-2-methoxy-propionic acid ethyl ester (Example 263, Step B) and methane-sulfonyloxy-acetic acid ethyl ester (Step A) by following the procedure described for Example 264. ¹H-NMR (MeOD, 200.15 MHz): δ 7.13 (d, 2H, J=8.6), 6.86–6.81 (m, 6H), 4.57 (s, 2H), 4.15–4.06 (m, 4H), 3.91 (dd, 1H, J=7.8, 4.8), 3.31 (s, 3H), 2.99 (dd, 1H, J=14.2, 4.6), 2.85 (dd, 1H, J=14.2, 7.5), 2.17 (qn, 2H, J=6.2).

Example 270

(2S)-3-(4-{3-[4-(1H-Indol-5-phenoxy]-propoxy}-phenyl)-2-methoxy-propionic acid

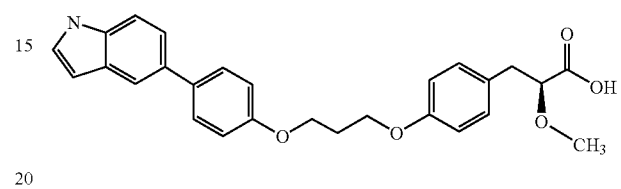

Step A (2S)-3-{4-[3-(4-Iodo-phenoxy)-propoxy]-phenyl}-2-methoxy-propionic acid ethyl ester

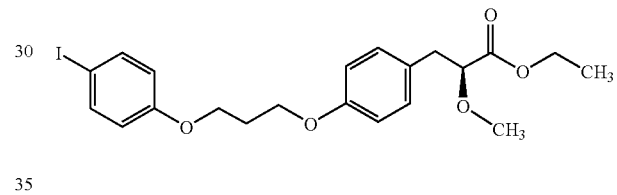

(2S)-3-[4-(3-Bromo-propoxy)-phenyl]-2-methoxy-propionic acid ethyl ester Example 173, Step A) and 4-iodophenol were treated under ester K (Cs₂CO₃) to afford the title compound. ¹H-NMR (CDCl₃, 200.15 MHz): δ 7.54 (d, 2H, J=8.9), 7.13 (d, 2H, J=8.6), 6.82 (d, 2H, J=8.9), 6.68 (d, 2H, J=9.1), 4.23–4.08 (m, 6H), 3.90 (dd, 1H, J=7.3, 5.9), 3.35 (s, 3H), 2.97–2.93 (m, 2H), 2.23 (qn, 2H, J=6.2), 1.23 (t, 3H, J=7.0).

Step B (2S)-3-(4-{3-[4-(1H-Indol-5-yl)-phenoxy]-propoxy}-phenyl)-2-methoxy-propionic acid ethyl ester

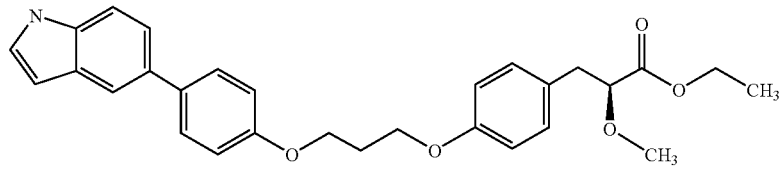

To a stirred mixture of (2S)-3-{4-[3-(4-iodo-phenoxy)-propoxy]-phenyl}-2-methoxy-propionic acid ethyl ester (0.10 mmol, 50 mg) (Step A), 5-indolyl-boronic acid (0.114 mmol, 18 mg) and powered cesium carbonate (0.23 mmol, 35 mg) in DME (0.5 mL) was added Pd(PPh₃)₄ (0.003 mmol, 4 mg). The mixture was flushed with nitrogen and maintained under nitrogen while being heated at reflux in a 100° C. oil bath. The mixture was stirred for 6 hours, and then cooled to room temperature and diluted with ethyl acetate and water. The organic layer was dried (Na₂SO₄) and concentrated. The crude product was purified by chromatography on silica gel (CH₂Cl₂/EtOAc 96:4) to afford the title compound ¹H-NMR (CDCl₃, 200.15 MHz): δ 8.20 (broad s, 1H), 7.80 (d, 1H, J=0.8), 7.56 (d, 3H, J=8.9), 7.41 (d, 2H, J=1.6), 7.23 (dd, 1H, J=3.2, 2.4), 7.15 (d, 3H, J=8.6), 6.99 (d, 2H, J=8.9), 6.85 (d, 3H, J=8.6), 6.60–6.58 (m, 1H), 4.24–4.11 (m, 8H), 3.92 (dd, 1H, J=7.3, 5.9), 3.35 (s, 4H), 2.98–2.94 (m, 3H), 2.28 (qn, 2H, J=5.9), 1.24 (t, 4H, J=7.3).

Step C (2S)-3-(4-{3-[4-(1H-Indol-5-yl)-phenoxy]-propoxy}-phenyl)-2-methoxy-propionic acid The title compound was obtained from (2S)-3-(4-{3-[4-(1H-indol-5-yl)-phenoxy]-propoxy}-phenyl)-2-methoxy-propionic acid ethyl ester (Step B) by following the standard hydrolysis procedure C (NaOH). ¹H-NMR (CDCl₃, 200.15 MHz): δ 8.17 (broad s, 1H), 7.80 (s, 1H), 7.56 (d, 2H, J=8.6), 7.42 (s, 2H), 7.24–7.21 (m, 1H), 7.15 (d, 2H, J=8.6), 6.98 (d, 2H, J=8.6), 6.86 (d, 2H, J=8.6), 6.59—6.59 (m, 1H), 4.23–4.13 (m, 4H), 3.98 (dd, 1H, J=7.3, 4.3), 3.39 (s, 3H), 3.10 (dd, 1H, J=14.5, 4.0), 2.95 (dd, 1H, J=14.5, 7.3), 2.27 (qn, 2H, J=6.2).

Example 271

(2S)-2-Methoxy-3-{4-[3-(4-pyridin-3-yl-phenoxy)-propoxy]-phenyl}-propionic acid

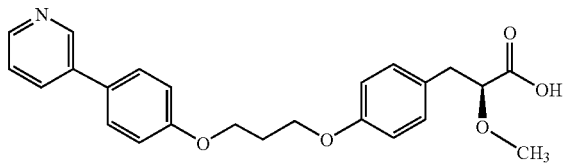

The title compound was prepared from (2S)-3-{4-[3-(4-iodo-phenoxy)-propoxy]-phenyl}-2-methoxy-propionic acid ethyl ester (Example 270, Step A) and 3-pyridyl boronic acid by following the procedure described for Example 270 (Steps B and C). ¹H-NMR (MeOD, 300.15 MHz): δ 8.76 (s, 1H), 8.46 (s, 1H), 8.05 (d, 1H, J=8.1), 7.60 (d, 2H, J=8.7), 7.49 (dd, 1H, J=7.7, 4.8), 7.19 (d, 2H, J=8.5), 7.09 (d, 2H, J=8.7), 6.85 (d, 2H, J=8.5), 4.24 (t, 2H, J=6.1), 4.17 (t, 2H, J=6.3), 3.74 (dd, 1H, J=8.7, 3.8), 3.27 (s, 3H), 2.97 (dd, 1H, J=14.3, 3.8), 2.81 (dd, 1H, J=14.1, 8.5), 2.26 (qn, 2H, J=6.0).

Example 272

(2S)-2-Methoxy-3-{4-[3-(4-pyridin-4-yl-phenoxy)-propoxy]-phenyl}-propionic acid

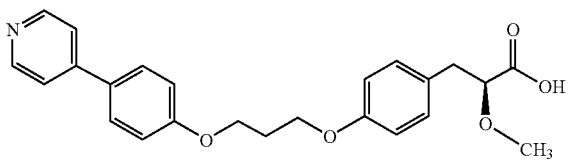

The title compound was prepared from (2S)-3-{4-[3-(4-iodo-phenoxy)-propoxy]-phenyl}-2-methoxy-propionic acid ethyl ester (Example 270, Step A) and 4-pyridyl boronic acid by following the procedure described for Example 270 (Steps B and C). ¹H-NMR (CDCl₃, 200.15 MHz): δ 8.67–8.65 (m, 2H), 8.16 (d, 2H, J=6.6), 7.90 (d, 2H, J=8.8), 7.16–7.09 (m, 4H), 6.82 (d, 2H, J=8.8), 4.26 (t, 2H, J=6.2), 4.13 (t, 2H, J=6.2), 3.90 (dd, 1H, J=7.7, 4.8), 2.97 (dd, 1H, J=14.3, 5.1), 2.83 (dd, 1H, J=14.3, 7.7), 2.24 (qn, 2H, J=5.9).

Example 273

(2S)-2-Methoxy-3-{4-[3-(4-quinolin-8-yl-phenoxy)-propoxy]-phenyl}-propionic acid

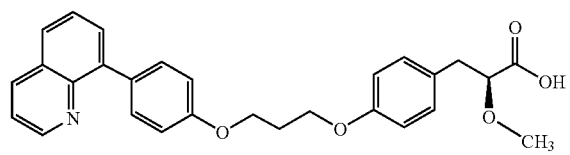

The title compound was prepared from (2S)-3-{4-[3-(4-iodo-phenoxy)-propoxy]-phenyl}-2-methoxy-propionic acid ethyl ester (Example 270, Step A) and 8-quinoline boronic acid by following the procedure described for Example 270 (Steps B and C). ¹H-NMR (MeOD, 300.15 MHz): δ 8.82 (d, 1H, J=2.6), 8.39 (d, 1H, J=8.1), 7.92 (d, 1H, J=7.9), 7.74–7.63 (m, 2H), 7.58–7.51 (m, 3H), 7.18 (d, 2H, J=8.5), 7.08 (d, 2H, J=8.7), 6.88 (d, 2H, J=8.7), 4.28 (t, 2H, J=6.0), 4.20 (t, 2H, J=6.3), 3.90–3.80 (m, 1H), 3.30 (s, 3H), 3.04–2.84 (m, 2H), 2.29 (qn, 2H, J=6.3).

Example 274

(2S)-3-{4-[3-(4'-Cyano-biphenyl-4-yloxy)-propoxy]-phenyl}-2-methoxy-propionic acid

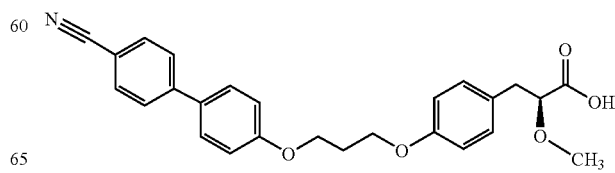

Step A (2S)-3-{4-[3-(4'-Cyano-biphenyl-4-yloxy)-propoxy]-phenyl}-2-methoxy-propionic acid ethyl ester

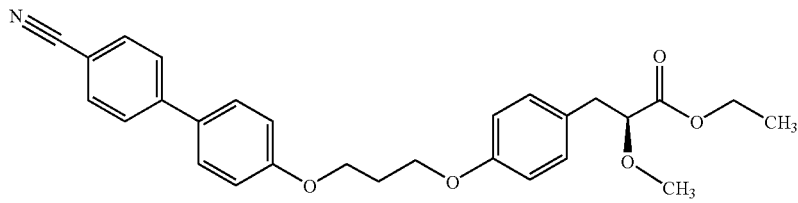

(2S)-3-[4-(3-Bromo-propoxy)-phenyl]-2-methoxy-propionic acid ethyl ester (Example 173, Step A) and 4'-hydroxy-4-biphenylcarbonitrile were treated under Mitsunobu standard conditions B (DIAD, toluene) to give the title compound. $^1$H-NMR (CDCl$_3$, 200.15 MHz): δ 7.71–7.60 (m, 4H), 7.52 (d, 2H, J=8.9), 7.14 (d, 2H, J=8.9), 7.00 (d, 2H, J=8.9), 6.83 (d, 2H, J=8.6), 4.24–4.12 (m, 6H), 3.90 (dd, 1H, J=7.3, 5.9), 3.34 (s, 3H), 2.97–2.93 (m, 2H), 2.27 (qn, 2H, J=6.2), 1.23 (t, 3H, J=7.3).

Step B (2S)-3-{4-[3-(4'-Cyano-biphenyl-4-yloxy)-propoxy]-phenyl}-2-methoxy-propionic acid The title compound was prepared from (2S)-3-{4-[3-(4'-cyano-biphenyl-4-yloxy)-propoxy]-phenyl}-2-methoxy-propionic acid ethyl ester (Step A) via the standard hydrolysis procedure C (NaOH). $^1$H-NMR (MeOD, 300.15 MHz): δ 7.77 (s, 4H), 7.64 (d, 2H, J=8.7), 7.18 (d, 2H, J=8.5), 7.07 (d, 2H, J=8.7), 6.86 (d, 2H, J=8.3), 4.24 (t, 2H, J=6.3), 4.17 (t, 2H, J=6.3), 3.84–3.74 (m, 1H), 3.03–2.81 (m, 2H), 2.26 (qn, 2H, J=6.0).

Example 275

(2S)-2-Methoxy-3-(4-{3-[4'-(1H-tetrazol-5-yl)biphenyl-4-yloxy]-propoxy}-phenyl)-propionic acid

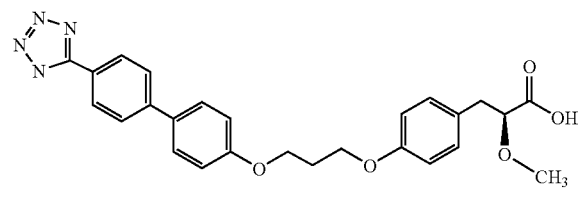

Step A (2S)-2-Methoxy-3-(4-{3-[4'-(1H-tetrazol-5-yl)biphenyl-4-yloxy]-propoxy}-phenyl)-propionic acid ethyl ester

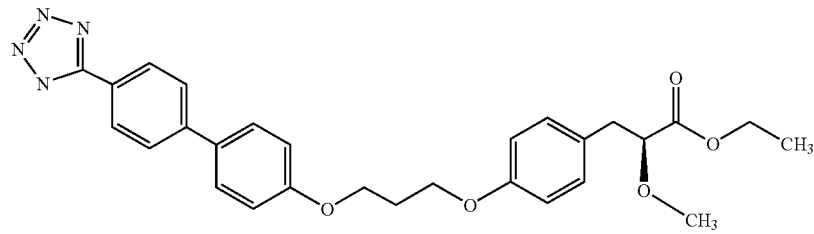

Azidotributyltin (0.72 mmol, 0.2 mL) was added to a solution of (2S)-3-{4-[3-(4'-cyano-biphenyl-4-yloxy)-propoxy]-phenyl}-2-methoxy-propionic acid ethyl ester (0.36 mmol, 0.17 g) (Example 274, Step A) in toluene (1 mL). The mixture was heated at 60° C. for 48 hours. The mixture was allowed to reach room temperature and 1N HCl was added. The mixture was heated at reflux for 24 additional hours. Upon cooling, water was added and the aqueous phase was extracted with ethyl acetate. The organic layer was dried (Na$_2$SO$_4$), filtered and evaporated. The crude product was purified by chromatography on silica gel (hexanes/ethyl acetate/acetic acid 3.2:10%) to afford the title product. $^1$H-NMR (CDCl$_3$, 200.15 MHz): δ 8.12 (d, 2H, J=8.3), 7.65 (d, 2H, J=8.6), 7.51 (d, 2H, J=8.9), 7.11 (d, 2H, J=8.6), 6.95 (d, 2H, J=8.6), 6.79 (d, 2H, 8.6), 4.25–4.06 (m, 7H), 3.97 (dd, 1H, J=7.0, 5.4), 3.37 (s, 3H), 2.99–2.96 (m, 2H), 2.22 (qn, 2H, J=5.9), 1.25 (t, 3H, J=7.2).

Step B (2S)-2-Methoxy-3-(4-{3-[4'-(1H-tetrazol-5-yl)biphenyl-4-yloxy]-propoxy}-phenyl)-propionic acid The title compound was prepared from (2S)-2-methoxy-3-(4-{3-[4'-(1H-tetrazol-5-yl)biphenyl-4-yloxy]-propoxy}-phenyl)-propionic acid ethyl ester (Step A) via the standard hydrolysis procedure C (NaOH). $^1$H-NMR (MeOD, 300.15 MHz): δ 8.09 (d, 2H, J=8.3), 7.70 (d, 2H, J=8.3), 7.62 (d, 2H, J=8.7), 7.18 (d, 2H, J=8.5), 7.05 (d, 2H, J=8.7), 6.86 (d, 2H, J=8.7), 4.23 (t, 2H, J=6.0), 4.17 (t, 2H, J=6.1), 3.83 (dd, 1H, J=8.3, 4.2), 3.36 (s, 3H), 2.99 (dd, 1H, J=14.1, 4.0), 2.84 (dd, 1H, J=13.9, 8.1), 2.26 (qn, 2H, J=6.3).

Example 276

(2S)-3-{4-[3-(4-Imidazol-1-yl-phenoxy)-propoxy]-phenyl}-2-methoxy-propionic acid

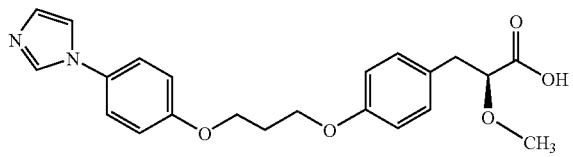

3-[4-(3-Bromo-propoxy)-phenyl]-2-methoxy-propionic acid ethyl ester (Example 173, Step A) and 4-(imidazol-1-yl)phenol were treated under ester J to give the title compound. $^1$H-NMR (CDCl$_3$, 200.15 MHz): δ 8.11 (s, 1H), 7.31–7.16 (m, 7H), 6.99 (d, 2H, J=8.9), 6.82 (d, 2H, J=8.6), 4.19 (t, 2H, J=6.2), 4.12 (t, 2H, J=5.9), 3.95 (dd, 1H, J=7.3, 4.8), 3.39 (s, 3H), 3.08 (dd, 1H, J=14.4, 4.8), 2.96 (dd, 1H, J=14.2, 7.6), 2.26 (qn, 2H, J=5.9).

Example 277

(2S)-3-(4-{3-[4-(1,3-Dioxo-1,3-dihydro-isoindol-2-yl)-phenoxy]-propoxy}-phenyl)-2-methoxy-propionic acid

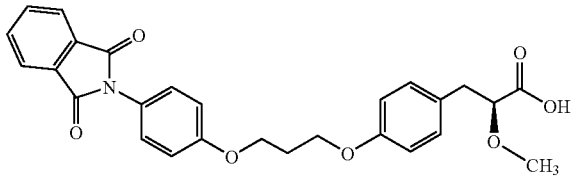

The title compound was obtained from (2S)-3-[4-(3-Bromo-propoxy)-phenyl]-2-methoxy-propionic acid ethyl ester (Example 173, Step A) and N-(4-hydroxyphenyl) phtalimide by following the procedure described for Example 276. $^1$H-NMR (CDCl$_3$, 300.15 MHz): δ 7.97–7.92 (m, 2H), 7.81–7.77 (m, 2H), 7.32 (d, 2H, J=8.9), 7.15 (d, 2H, J=8.5), 7.02 (d, 2H, J=8.9), 6.85 (d, 2H, J=8.5), 4.20 (t, 2H, J=6.0), 4.16 (t, 2H, J=6.0), 3.99 (dd, 1H, J=7.3, 4.4), 3.41 (s, 3H), 3.11 (dd, 1H, J=14.3, 4.4), 2.97 (dd, 1H, J=14.3, 7.1), 2.27 (qn, 2H, J=6.0).

Example 278

(2S)-3-(4-{3-[4-(4-Acetyl-piperazin-1-yl)-phenoxy]-propoxy}-phenyl)-2-methoxy-propionic acid

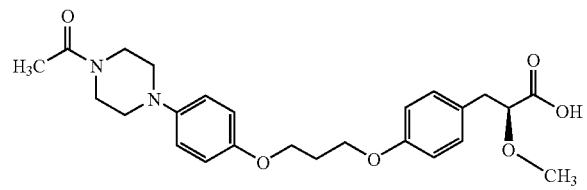

The title compound was obtained from (2S)-3-[4-(3-Bromo-propoxy)-phenyl]-2-methoxy-propionic acid ethyl ester (Example 173, Step A) and 1-acetyl-4-(4-hydroxyphenyl)piperazine by following the procedure described for Example 276. $^1$H-NMR (CDCl$_3$, 300.15 MHz): δ 7.14 (d, 2H, J=8.5), 6.90–6.80 (m, 5H), 4.15–4.09 (m, 3H), 3.98 (dd, 1H, J=6.7, 4.9), 3.79–3.76 (m, 2H), 3.63–3.60 (m, 2H), 3.40 (s, 3H), 3.11–2.93 (m, 6H), 2.14 (s, 3H).

Example 279

(2S)-2-Methoxy-3-{4-[3-(4-piperazin-1-yl-phenoxy)-propoxy]-phenyl}-propionic acid

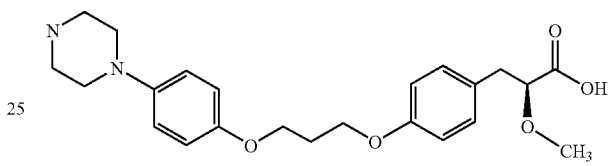

Step A (2S)-2-Methoxy-3-{4-[3-(4-piperazin-1-yl-phenoxy)-propoxy]-phenyl}-propionic acid ethyl ester

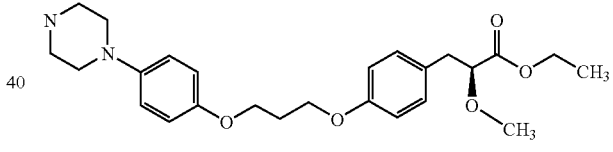

3-[4-(3-Bromo-propoxy)-phenyl]-2-methoxy-propionic acid ethyl ester (Example 173, Step A) and 1-(4-hydroxyphenyl)-piperazine were treated under ester K to give the title compound. $^1$H-NMR (CDCl$_3$, 200.15 MHz): δ 8.01 (s, 1H), 7.13 (d, 2H, J=8.6), 6.88–6.75 (m, 6H), 4.30 (t, 2H, J=6.4), 4.17 (q, 2H, J=7.0), 4.02 (t, 2H, J=5.9), 3.94–3.87 (m, 1H), 3.64–3.60 (m, 4H), 3.34 (s, 3H), 2.98–2.96 (m, 4H), 2.18–2.04 (m, 2H), 1.23 (t, 3H, J=7.3).

Step B (2S)-2-Methoxy-3-{4-[3-(4-piperazin-1-yl-phenoxy)-propoxy]-phenyl}-propionic acid The title compound was prepared from (2S)-2-methoxy-3-{4-[3-(4-piperazin-1-yl-phenoxy)-propoxy]-phenyl}-propionic acid ethyl ester (Step A) by standard hydrolysis procedure C (NaOH). ¹H-NMR (MeOD 300.15 MHz): δ 7.18 (d, 2H, J=8.5), 6.89–6.83 (m, 4H), 6.72 (d, 2H, J=9.1), 4.30 (t, 2H, J=6.3), 4.07 (t, 2H, J=6.1), 3.86–3.82 (m, 1H), 3.62–3.59 (m, 4H), 3.36 (s, 3H), 3.07–2.83 (m, 6H), 2.12 (qn, 2H, J=6.3).

Example 280

(2S)-2-Methoxy-3-{4-[3-(4-morpholin-4-yl-phenoxy)-propoxy]-phenyl}-propionic acid

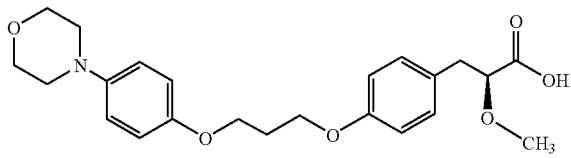

Step A (2S)-2-Methoxy-3-{4-[3-(4-morpholin-4-yl-phenoxy)-propoxy]-phenyl}-propionic acid ethyl ester

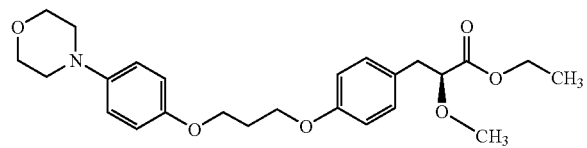

A mixture of (2S)-3-{4-[3-(4-iodo-phenoxy)-propoxy]-phenyl}-2-methoxy-propionic acid ethyl ester (1.03 mmol, 0.5 g), morpholine (1.24 mmol, 0.11 mL), Pd(OAc)₂ (0.05 mmol, 12 mg), 2,2'-bis(diphenylphsphino)-1,1'-binaphthyl (0.08 mmol, 48 mg) and cesium carbonate (1.45 mmol, 471 mg) in DMF (2 mL) was heated at 110° C. for 14 hours. The mixture was purified through a silica gel column (hexanes/ethyl acetate 7:3) to afford the title compound. ¹H-NMR (CDCl₃, 200.15 MHz): δ 7.11 (d, 2H, J=8.8), 6.85 (broad s, 2H), 6.80 (d, 4H, J=8.8), 4.21–4.04 (m, 6H), 3.91–3.80 (m, 5H), 3.32 (s, 3H), 3.10–2.95 (m, 4H), 2.94–2.91 (m, 2H), 2.20 (qn, 2H, J=5.9), 1.23 (t, 3H, J=7.2).

Step B (2S)-2-Methoxy-3-{4-[3-(4-morpholin-4-yl-phenoxy)-propoxy]-phenyl}-propionic acid The title compound was prepared from (2S)-2-ethoxy-3-{4-[3-(4-morpholin-4-yl-phenoxy)-propoxy]-phenyl}-propionic acid ethyl ester (Step A) by standard hydrolysis procedure C (NaOH). ¹H-NMR (CDCl₃, 200.15 MHz): δ 9.90 (s, 1H), 7.30 (d, 2H, J=9.1), 7.10 (d, 2H, J=8.4), 6.91 (d, 2H, J=9.1), 6.75 (d, 2H, J=8.8), 4.18–3.90 (m, 9H), 3.43–3.33 (m, 7H), 3.02 (dd, 1H, J=14.3, 4.8), 2.90 (dd, 1H, J=14.3, 7.0), 2.18 (qn, 2H, J=5.9).

Example 281

(2S)-3-{4-[3-(Biphenyl-4-yloxy)-propoxy]-2-chlorophenyl}-2-ethoxy-propionic acid

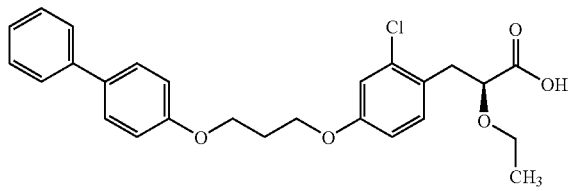

Step A

3-[4-(3-(Biphenyl-4-yloxy)-propoxy]-2-chloro-phenyl}-2-hydroxy-propionic acid

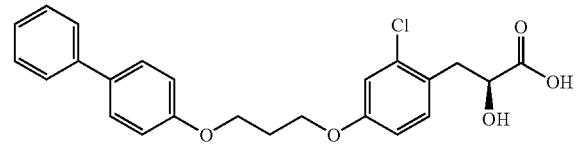

Boron tribromide (0.03 mmol, 0.03 mL) was added to a solution of 3-{4-[3-(biphenyl-4-yloxy)-propoxy]-2-chlorophenyl}-2-methoxy-propionic acid (0.06 mmol, 25.5 mg) (Example 191) in CH₂Cl₂ (0.4 mL) at −78° C. The mixture was warmed to temperature gradually and stirred for 12 hours. The solvent was concentrated to dryness to afford the title compound. ¹H-NMR (CDCl₃, 200.15 MHz): δ 7.56–7.18 (m, 8H), 6.99–6.95 (m, 3H), 6.79–6.75 (m, 1H), 4.58–4.42 (m, 1H), 4.25–4.12 (m, 4H), 3.34–2.92 (m, 2H), 2.30–2.22 (m, 2H).

Step B

3-{4-[3-(Biphenyl-4-yloxy)-propoxy]-2-chloro-phenyl}-2-ethoxy-propionic acid

Ethyl iodide (0.6 mmol, 0.05 mL) was added to a solution of 3-{4-[3-(biphenyl-4-yloxy)-propoxy]-2-chloro-phenyl}-2-hydroxy-propionic acid (Step A) and Ag₂O (0.09 mmol, 21 mg) in DMF (0.5 mL). The mixture was heated at 50° C. for 24 hours. The mixture was warmed to room temperature, and 1N HCl was added until pH 3. The aqueous phase was extracted with ethyl acetate (3×10 mL). The combined organic layers were dried (Na₂SO₄), filtered and evaporated. The crude was purified by chromatography on silica gel (CH₂Cl₂) to afford the title compound. ¹H-NMR (CDCl₃, 300.15 MHz): δ 7.56–7.51 (m, 4H), 7.44–7.39 (m, 2H), 7.30 (t, 1H, J=7.3), 7.20 (d, 1H, J=8.5), 6.99 (d, 2H, J=8.7), 6.95 (d, 1H, J=2.4), 6.77 (dd, 1H, J=8.5, 2.4), 4.21–4.13 (m, 5H), 3.64–3.54 (m, 1H), 3.44–3.34 (m, 1H), 3.29 (dd, 1H, J=14.1, 4.2), 3.01 (dd, 1H, J=14.1, 8.7), 2.28 (qn, 2H, J=6.0), 1.12 (t, 3H, J=6.9).

Example 282

3-{4-[3-(4-Benzoyl-phenoxy)-propoxy]-2-chlorophenyl}-2-ethoxy-propionic acid

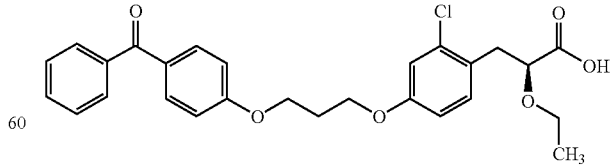

The title compound was prepared from 3-{4-[3-(4-benzoyl-phenoxy)-propoxy]-2-chloro-phenyl}-2-methoxy-propionic acid (Example 193) by following the same procedure as in Example 281 (Steps A and B). ¹H-NMR (CDCl₃, 300.15 MHz): δ 7.82 (d, 2H, J=8.7), 7.76 (d, 2H, J=8.1), 7.61–7.55 (m, 1H), 7.50–7.45 (m, 2H), 7.18 (d, 1H, J=8.5), 6.99–6.95 (m, 3H), 6.77 (dd, 1H, J=8.5, 2.4), 4.25 (t, 2H, J=5.9), 4.17–4.14 (m, 3H), 3.61–3.38 (m, 2H), 3.29 (dd, 1H, J=14.1, 4.9), 3.02 (dd, 1H, J=14.1, 8.1), 2.31 (qn, 2H, J=5.9), 1.14 (t, 3H, J=7.1).

Example 283

(2S)-3-{4-[2-(biphenyl-4-yloxy)-ethoxy]-phenyl}-2-methoxy-propionic acid

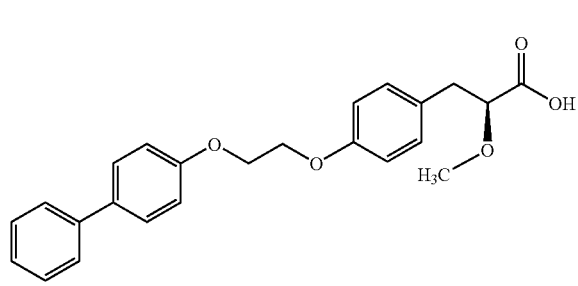

Step 1: (2S)-3-(4-hydroxy-phenyl)-2-methoxy-propionic acid ethyl ester

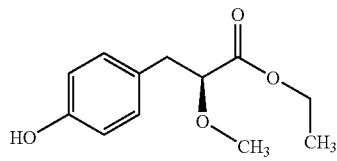

The compound of (2S)-3-(4-hydroxy-phenyl)-2-methoxy-propionic acid (5.1 mmol) was dissolved in 50 ml of ethanol and 0.3 ml (5.6 mmol) of sulfuric acid was added. The mixture was stirred at room temperature for 18 hours and then concentrated. The mixture was diluted with water (55 ml) and NaHCO$_3$ was added (310 mg, 3.7 mmol). This mixture was extracted with ethyl acetate (4×20 mL), and the combined organic layers were dried (MgSO$_4$) and then concentrated to produce a yellow oil. $^1$H-NMR (CDCl$_3$, 200.15 MHz): 7.07 (d, 2H, J=8.6), 6.72 (d, 2H, J=8.6), 5.42 (br s, 1H), 4.18 (q, 2H, J=7.3), 3.92 (dd, 1H, J=6.7, 5.9), 3.36 (s, 3H), 2.95 (d, 2H, J=6.7), 1.23 (t, 3H, J=7.3).

Step 2: (2S)-3-[4-(2-bromo-ethoxy)-phenyl]-2-methoxy-propionic acid ethyl ester

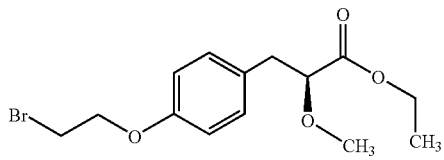

A mixture containing (2S)-3-(4-hydroxy-phenyl)-2-methoxy-propionic acid ethyl ester obtained in Step 1 (0.223 mol, 50 mg), potassium carbonate (0.446 mol, 50 mg), magnesium sulfate (powdered, 50 mg, 1 g/g), ethylene dibromide (3.35 mol. 628 mg) and EtOH (25 mL) was heated at reflux (78–76° C.) for 24 hours and cool to room temperature. The mixture was heated again to reflux (76.5–77° C.) and 2 mL of ethylene dibromide was added. The mixture was heated for another 12 hours at 79.5–80.1° C. and then cooled to room temperature and vacuum filtered. The filtrate was concentrated under vacuum, and the residue was purified by column chromatography (silica gel, hexanes/ethyl acetate 6:1, Rf 027) to produce a colorless oil. MS (ES) for C$_{14}$H$_{19}$BrO$_4$ [M+Na]$^+$: 353.0.

Step 3: (2S)-3-{4-[2-(biphenyl-4-yloxy)-ethoxy]-phenyl}-2-methoxy-propionic acid

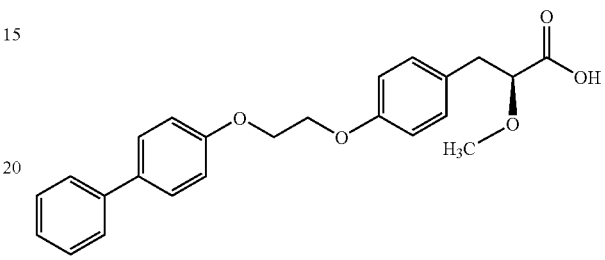

A solution of biphenyl-4-ol (0.39 mmol, 68 mg) in 10 ml of DMF in was treated with (2S)-3-[4-(2-bromo-ethoxy)-phenyl]-2-methoxy-propionic acid ethyl ester obtained in Step 2 (0.33 mmol, 100 mg) and cesium carbonate (0.66 mmol, 214 mg) in a round bottom flask. The reactants were filtered and was washed with DMF several times and the solvent was evaporated under vacuo. The residue was reconstituted in a mixture of ethanol (20 ml) and NaOH (1M) (8 ml), and then stirred at room temperature until TLC indicated the disappearance of starting material. Ethanol was removed under vacuum, and the aqueous solution was diluted with 20 ml of brine and washed with diethyl ether (3×15 mL). The aqueous phase was acidified with 1N HCl (pH 1–2) and extracted with ethyl acetate (3×15 mL). The organic layer was dried (MgSO$_4$) and concentrated under vacuum to yield the title compound. MS (ES) for C$_{24}$H$_{24}$O$_5$ [M+Na]$^+$: 415.4.

Example 284

(2S)-2-methoxy-3-{4-[3-(3-trifluoromethyl-phenoxy)-propoxy]-phenyl}-propionic acid

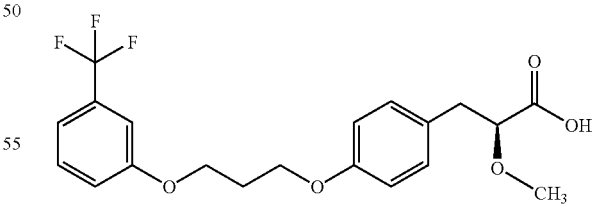

Step 1: 3-bromopropan-1-ol

The compound of 1,3-propanodiol (10.26 g, 134.8 mmol) was dissolved in benzene (150 mL), and HBr 48% (16.84 mL) was added. The mixture was refluxed under aceotropic removal of water for 24 hours. The solvent was distilled at atmospheric pressure, and the residue was diluted with ether and (150 mL) and washed with water (3×50) mL. The organic layer was dried over MgSO$_4$ and concentrated to

303 afford a yellowish oil. ¹H-NMR (CDCl₃, 200.15 MHz): 3.80 (t, 2H, J=6.4), 3.54 (t, 2H, J=6.5), 2.10 (qn, 2H, J=6.4).

Step 2: (2S)-3-[4-(3-bromo-propoxy)-phenyl]-2-methoxy-propionic acid ethyl ester

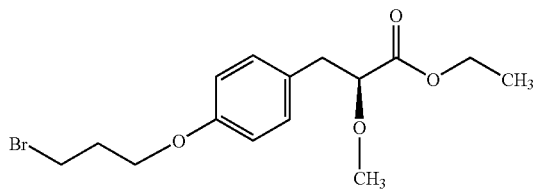

A solution of triphenylphosphine (4.77 mmol, 1250 mg) in 50 mL of dry toluene was treated at 0° C. with diisopropilazodicarboxylate (4.77 mmol, 964.5 mg) and stirred for about 20 minutes. A solution of (2S)-3-(4-hydroxy-phenyl)-2-methoxy-propionic acid ethyl ester (Example 283, Step 1) (4.46 mmol, 1000 mg) and 3-bromo-propan-1-ol (4.77 mmol, 663 mg) in 10 mL of dry THF was added, and the mixture was stirred at room temperature overnight. The mixture was concentrated to dryness under vacuum and purified by silica gel chromatography (silica gel, hexanes/ethyl acetate 6:1). The fraction with Rf 0.4 corresponding to the coupled compound was combined and concentrated to dryness to afford a yellow oil. MS (ES) for $C_{15}H_{21}BrO_4$ [M+Na]⁺: 367.2.

Step 3: (2S)-2-methoxy-3-{4-[3-(3-trifluoromethyl-phenoxy)-propoxy]-phenyl}-propionic acid

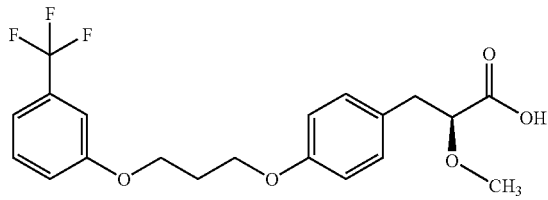

The title compound was prepared from (2S)-3-[4-(3-bromo-propoxy)-phenyl]-2-methoxy-propionic acid ethyl ester (Example 284, Step 2) and 3-trifluoromethyl-phenol via the same procedure used for the preparation of (2S)-3-{4-[2-(Biphenyl-4-yloxy)-ethoxy]-phenyl}-2-methoxy-propionic acid (Example 283, Step 3) to produce a yellow solid. MS (ES) for $C_{20}H_{21}F_3O_5$ [M+NH₄]⁺: 421.4.

Example 285

(2S)-2-methoxy-3-[4-(3-phenoxy-propoxy)-phenyl]-propionic acid

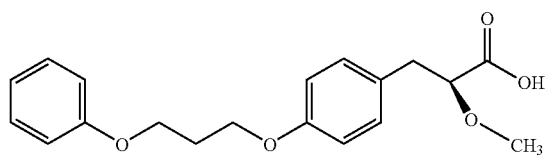

304

A solution of (2S)-3-[4-(3-bromo-propoxy)-phenyl]-2-methoxy-propionic acid ethyl ester (Example 284, Step 2) (0.1 mmol, 32 mg) in 0.7 ml of DM in a 16×100 mm tube was treated with phenol (0.15 mmol, 15 mg), cesium carbonate (0.3 mmol, 95 mg). The mixture was stirred at room temperature overnight and the reactants were filtered and washed with DMF a several times. The solvent was evaporated under vacuum, and the residue was reconstituted in a mixture of ethanol (2 ml) and NaOH (1M, 1 ml), which was stirred at room temperature until temperature until reaction was completed by HPLC-MS. Upon completion, HCl (1M) was added pH=3) and the solvents were eliminated under vacuum. The residue was reconstituted in CH₂Cl₂/H₂O and filtered through a hidrofobic syringer. The organic layer was separated, concentrated and purified by HPLC-MS to afford the title compound as a colorless oil. MS (ES) for $C_{19}H_{22}O_5$ [M+NH₄]⁺: 348.4.

Example 286

(2S)-3-{4-[3-(biphenyl-3-yloxy)-propoxy]-phenyl}-2-methoxy-propionic acid

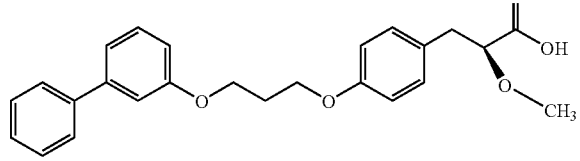

The title compound was prepared from (2S)-3-[4-(3-bromo-propoxy)-phenyl]-2-methoxy-propionic acid ethyl ester (Example 284, Step 2) and biphenyl-3-ol via the same procedure used for the preparation of (2S)-2-methoxy-3-[4-(3-phenoxy-propoxy)-phenyl]-propionic acid (Example 285, Step 1), to produce a colorless oil. MS (ES) for $C_{25}H_{25}O_5$ [M+Na]+429.4.

Example 287

(2S)-2-methoxy-3-{4-[3-(2-methyl-benzothiazol-5-yloxy)-propoxy]-phenyl}-propionic acid

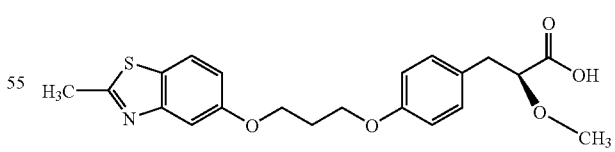

The title compound was prepared from (2S)-3-[4-(3-bromo-propoxy)-phenyl]-2-methoxy-propionic acid ethyl ester (Example 284, Step 2) and 2-methyl-benzothiazol-5-ol via the same procedure used for the preparation of (2S)-2-methoxy-3-[4-(3-phenoxy-propoxy)-phenyl]-propionic acid Example 285, Step 1), to produce a colorless oil. MS (ES) for $C_{21}H_{23}NO_5S$ [M+H]⁺: 402.4.

Example 288

(2S)-2-methoxy-3-{4-[3-(3-morpholin-4-yl-phenoxy)-propoxy]-phenyl}-propionic acid

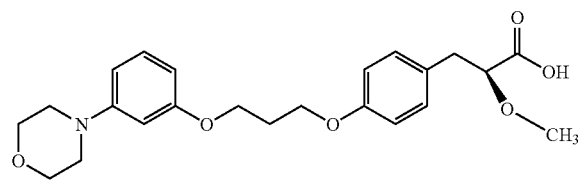

The title compound was prepared from (2S)-3-[4-(3-bromo-propoxy)-phenyl]-2-methoxy-propionic acid ethyl ester (Example 284, Step 2) and 3-Morpholin-4-yl-phenol via the same procedure used for the preparation of (2S)-2-methoxy-3-[4-(3-phenoxy-propoxy)-phenyl]-propionic acid (Example 285, Step 1), to produce a colorless oil.
MS (ES) for $C_{23}H_{29}NO_6$ [M+H]$^+$: 416.4.

Example 289

(2S)-2-methoxy-3-{4-[3-(5,6,7,8-tetrahydro-naphthalen-2-yloxy)-propoxy]-phenyl}-propionic acid

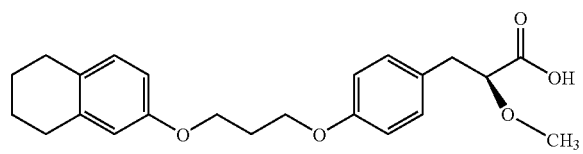

The title compound was prepared from (2S)-3-[4-(3-bromo-propoxy)-phenyl]-2-methoxy-propionic acid ethyl ester (Example 284, Step 2) and 5,6,7,8-tetrahydro-naphthalen-2-ol via the same procedure used for the: preparation of (2S)-3-{4-[2-(biphenyl-4-yloxy)-ethoxy]-phenyl}-2-methoxy-propionic acid (Example 283, Step 3), to produce a white solid.
MS (ES) for $C_{23}H_{28}O_5$ [M+Na]$^+$: 402.4.

Example 290

2-methoxy-3-{4-[2-(4-phenoxy-phenoxy)-ethoxy]-phenyl}-propionic acid

Chiral

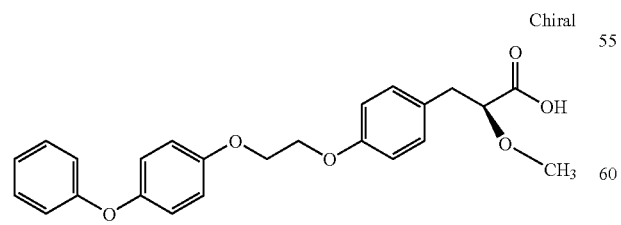

The title compound was prepared from (2S)-3-[4-(2-bromo-ethoxy)-phenyl]-2-methoxy-propionic acid ethyl ester (Example 283, Step 2) and 4-phenoxy-phenol via the same procedure used for the preparation of (2S)-3-{4-[2-(biphenyl-4-yloxy)-ethoxy]-phenyl}-2-methoxy-propionic acid (Example 283, Step 3) to produce a white solid.
MS (ES) for $C_{24}H_{24}O_6$ [M+NH$_4$]$^+$: 426.0.

Example 291

3-{3-[3-(biphenyl-4-yloxy)-propoxy]-phenyl}-2-methoxy-propionic acid (isomer 1)

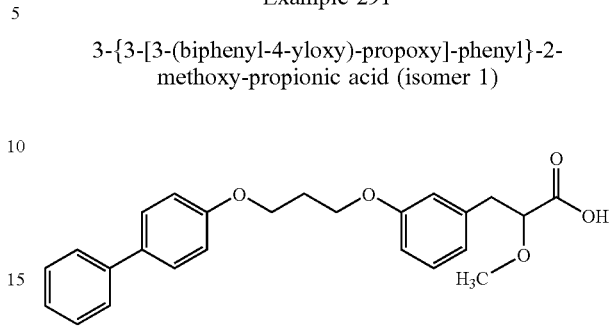

Step 1: 3-(3-benzyloxy-phenyl)-3-hydroxy-2-methoxy-propionic acid methyl ester

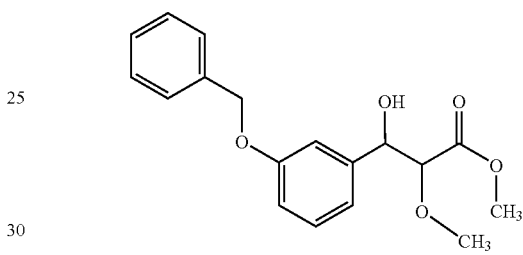

Sodium trimethylsilylamide 1M in THF (20.73 mL, 20.73 mmol) was added to a 2-neck round bottom flask under nitrogen. The flask was placed in an acetone bath cooled to about −78° C. A solution of methyl 2-methoxyacetate (2.34 mL, 23.55 mmol) and 3-benzyloxybenzaldehyde (4.0 g, 18.85 mmol) in dry THF (24 mL) was added dropwise via cannula over 10 minutes. The mixture was stirred at −78° C. for 3 hours. HPLC-MS showed the presence of starting aldehyde at this time. Additional 10 mL of NaHDMS were added, and the mixture was stirred for another hour, and then HCl 3N (50 mL) was added to the mixture at −78° C. The bath was removed, and the mixture was extracted with diethyl ether (4×50 mL). The combined organic layers were dried over MgSO$_4$ and concentrated to afford an oil that was purified by chromatography (silica gel, hexanes/ethyl acetate 3:1). Rf. 0.13. (two isomers) $^1$H-NMR (CDCl$_3$, 200.15 MHz): 7.45–7.22 (m, 12H), 7.05–6.89 (m, 6H), 5.07 (d, 4H, J=1.1), 4.93 (dd, 2H, J=11.8, 5.9), 3.97 (d, 1H, J=5.6), 3.89 (d, 1H, J=5.4), 3.67 (s, 3H), 3.65 (s, 3H), 3.40 (s, 3H), 3.37 (s, 3H), 2.92 (br s, 1H), 2.83 (br s, 1H).

Step 2: 3-(3-benzyloxy-phenyl)-2-methoxy-acrylic acid methyl ester

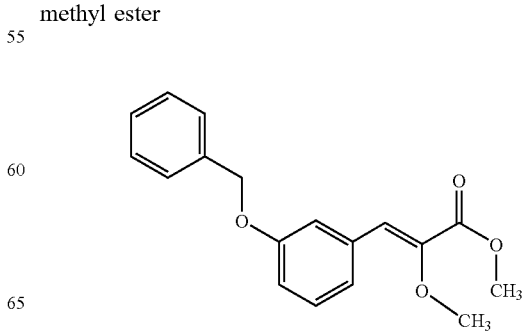

The compounds of 3-(3-benzyloxy-phenyl)-3-hydroxy-2-methoxy-propionic acid methyl ester (Example 291, Step 1) (4.06 g, 12.84 mmol), triethylamine (7.15 mL, 51.33 mmol) and 4-(N,N-dimethylamino)pyridine (0.157 g, 128 mmol) were dissolved in dichloromethane (20 mL) in a round bottom flask and then cooled to 0° C. under ice bath. Mesyl chloride (1.093 mL, 14.1 mmol) was added dropwise via syringe, and the mixture was stirred at room temperature until no starting aldol is observed by HPLC-MS (4 days, 0.2 additional mL of MsCl were added each day). The mixture was diluted with 200 mL of diethyl ether, washed with HCl (1N, 3×40 mL) and 40 mL of brine, and dried over MgSO$_4$ Concentration of the mixture afforded 3.96 g. of a 2.5:1 mixture of the acrylate and a single isomer of the mesylate intermediate which was directly used in the next Step. $^1$H-NMR (CDCl$_3$, 200.15 MHz): 7.46–7.26 (m, 8H), 6.99–6.93 (m, 1H), 5.10 (s, 2H), 3.85 (s, 3H), 3.72 (s, 3H).

Step 3: 3-(3-benzyloxy-phenyl)-2-methoxy-propionic acid methyl ester

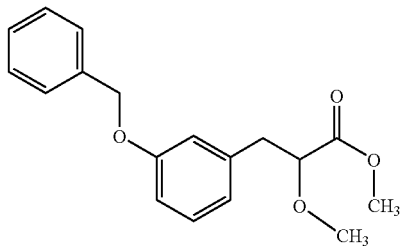

A solution of 3-(3-benzyloxy-phenyl)-2-methoxy-acrylic acid methyl ester (Example 291, Step 2) (3.96 g) in methanol (10 mL) was placed in a round bottom flask equipped with a reflux condenser. The mixture was cooled to 0° C. and Mg turnings (6.45 g) were added. The mixture was initially stirred vigorously and then further stirred at room temperature for about an hour. The solvent was evaporated under vacuum, and 100 mL of diethyl ether were added to the resulting solid. HCl (3N, 100 mL) was added and the solution was stirred for one minute. The organic layer was separated from the slurry, and 100 mL of diethyl ether and HCl (3N, 100 mL) were added to the remaining slurry. The procedure was repeated until the entire solid was dissolved. The combined ethereal extracts were washed with brine and dried over MgSO$_4$. Concentration of the mixture afforded a yellow oil which was about 90% pure bye NMR. $^1$H-NMR (CDCl$_3$, 200.15 MHz): 7.45–7.17 (m, 6H), 6.88–6.81 (m, 3H), 5.05 (s, 2H), 3.97 (dd, 1H, J=7.3, 5.4), 3.72 (s, 3H), 3.34 (s, 3H), 3.00 (d, 1H, J=5.1), 2.99 (d, 1H, J=7.8).

Step 4: 3-(3-hydroxy-phenyl)-2-methoxy-propionic acid methyl ester

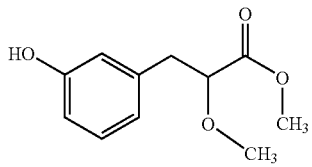

The compounds of 3-(3-benzyloxy-phenyl)-2-methoxy-propionic acid methyl ester (Example 291, Step 3) (3.15 g, 10.49 mmol) and Pd 10% on activated carbon (0.558 g, 0.524 mmol) were placed in a 250-ml round bottom flask equipped with a magnetic stirring bar. 100 mL of methanol was added, and hydrogen was bubbled through the solution for 10 minutes. The flask was sealed with a rubber septum, and a balloon containing 250 mL of hydrogen was connected to the flask through a needle. The mixture was stirred at room temperature for 5 hours and then concentrated to dryness under vacuum. The residue was taken up in ethyl acetate and filtered through a pad of celite. Concentration of the mixture afforded an oil, $^1$H-NMR (CDCl$_3$, 200.15 MHz): 7.15 (dt, 1H, J=1.1, 7.0), 6.79–6.68 (m, 3H), 5.27 (br s, 1H), 3.98 (dd, 1H, J=7.5, 5.6), 3.73 (s, 3H), 3.35 (s, 3H), 2.97 (d, 1H, J=3.8), 2.97 (d, 1H, J=9.1).

Step 5: [1,3,2]dioxathiane 2,2-dioxide

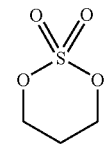

Thionyl chloride (36 mL, 491 mmol) was, added to a solution of 1,3-propanodiol (30 g, 394 mmol) in CCl$_4$ (278 mL) via syringe. The mixture was heated at reflux for 1.5 hours and cooled to 0° C. to evaporate the solvent under vacuum. The residue was dissolved in a mixture of CCl$_4$/CH$_3$CN/H$_2$O (2:2:3=500 mL) and cooled to 0° C. Ruthenium trichloride trihydrate (0.556 g, 2.68 mmol) was added followed by addition of solid NaIO$_4$ (14.35 g, 197 mmol). The mixture was stirred at room temperature for 1 hour and then H$_2$O (1 L) was added. The aqueous phase was extracted with diethyl ether (4×300 mL). The combined organic layers were washed with brine (2×100 mL), dried (MgSO$_4$), and filtered through a pad of silica gel to remove the ruthenium salts. The solvent was evaporated, and hexanes (200 mL) was added to the resulting oil. After cooling, a gray solid was precipitated, which was filtered and washed with hexanes. Recrystallization from hexanes/ether yielded a white crystaline solid. $^1$H-NMR (200.15 MHz, CDCl$_3$): d 4.73 (t, 4H, J=5.6), 2.13 (qn, 2H, J=5.6).

Step 6: 3-(biphenyl-4-yloxy)-propan-1-ol

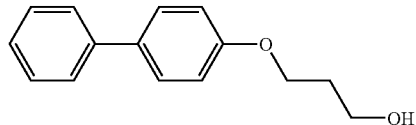

A solution of 4-phenylphenol (4.9 g, 29.0 mmol) and potassium tert-butoxide (3.64 g, 30.3 mmol) in THF (100 mL) was stirred at room temperature for 30 minutes. The solution was cooled at 0° C. and [1,3,2]dioxathiane 2,2-dioxide (Example 291, Step 5) (3.6 g, 26.34 mmol) in THF (25 mL) was added. The mixture was stirred at room temperature for 5 hours, and the solvent was removed under vacuum. The residue was dissolved in 6N HCl (15 mL) and heated at 100° C. for 16 hours. The mixture was cooled to room temperature, and the aqueous phase was extracted with ethyl acetate (3×30 mL). The combined organic layers were washed with H$_2$O (3×25 mL) and brine (25 mL), dried (MgSO$_4$), filtered, and concentrated to produce a white solid. $^1$H-NMR (200.15 MHz, CDCl$_3$): d 7.57–7.49 (m, 4H), 7.45–7.37 (m, 3H), 6.98 (dd, 2H, J=6.72, 2.14), 4.17 (t, 2H, J=5.9), 3.88 (q, 2H, J=5.9), 2.07 (qn, 2H, J=5.9).

Step 7: 4-(3-bromo-propoxy)-biphenyl

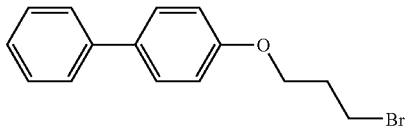

Triphenylphosphine (1.61 g, 6.14 mmol) was added to a solution of 3-(biphenyl-4-yloxy)-propan-1-ol (Example 291, Step 6) (1.00 g, 4.38 mmol) and carbon tetrabromide (1.81 g, 5.47 mmol) in CH2Cl2 (20 mL) at 0° C. The mixture was warmed to room temperature and stirred for about an hour and then extracted with ethyl acetate (50 mL). The organic layer was washed with $H_2O$ (3×50 mL) and brine (3×25 mL), and then dried ($MgSO_4$), filtered and concentrated. The crude product was purified by silica gel column chromatography (silica gel, hexanes/ethyl acetate, 9:1) to produce 4-(3-bromo-propoxy)-biphenyl. $^1$H-NMR (200.15 MHz, $CDCl_3$): d 7.57–7.29 (m, 7H), 6.98 (dd, 2H, J=6.72, 1.88), 4.45 (t, 2H, J=5.92), 3.62 (t, 2H, J=6.44), 2.34 (qn, 2H, J=5.92).

Step 8: 3-{3-[3-(biphenyl-4-yloxy)-propoxy]-phenyl}-2-methoxy-propionic acid (Isomer 1)

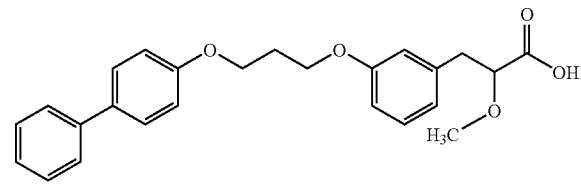

The title compound was prepared from 4-(3-bromo-propoxy)-biphenyl (Example 291, Step 7) and 3-(3-hydroxy-phenyl)-2-methoxy-propionic acid methyl ester (Example 291, Step 4) (0.3 g, 1.42 mmol) via the same procedure used for the preparation of (2S)-3-{4-[2-(biphenyl-4-yloxy)-ethoxy]-phenyl}-2-methoxy-propionic acid (Example 283, Step 3). The crude material was submitted to chiral HPLC separation to afford the single enantiomer of isomer 1. $^1$H-NMR ($CDCl_3$, 200.15 MHz): 7.57–7.17 (m, 7H), 6.99 (dd, 2H, J=6.7, 2.2), 6.85–6.80 (m, 3H), 4.19 (dd, 4H, J=13.4, 6.4), 4.03 (dd, 1H, J=7.3, 4.3), 3.40 (s, 3H), 0.14 (dd, 1H, J=14.0, 4.3), 2.98 (dd, 1H, J=14.8, 7.5), 2.28 (qui, 2H, J=5.9).

Example 292

3-{3-[3-(biphenyl-4-yloxy)-propoxy]-phenyl}-2-methoxy-propionic acid (Isomer 2)

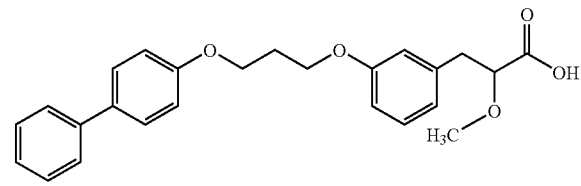

The title compound was prepared from 4-(3-bromo-propoxy)-biphenyl (Example 291, Step 7), and 3-(3-hydroxy-phenyl)-2-methoxy-propionic acid methyl ester (Example 291, Step 4) via the same procedure used for the preparation of (2S)-3-{4-[2-(biphenyl-4-yloxy)-ethoxy]-phenyl}-2-methoxy-propionic acid (Example 283, Step 3). The crude material was submitted to chiral HPLC separation to afford the single enantiomer of isomer 2. $^1$H-NMR ($CDCl_3$, 200.15 MHz): 7.57–7.17 (m, 7H), 6.99 (dd, 2H, J=6.7, 2.2), 6.85–6.80 (m, 3H), 4.19 (dd, 4H, J=13.4, 6.4), 4.03 (dd, 1H, J=7.3, 4.3), 3.40 (s, 3H), 0.14 (dd, 1H, J=14.0, 4.3), 2.98 (dd, 1H, J=14.8, 7.5), 2.28 (qn, 2H, J=5.9).

Example 293

(2S)-3-{4-[3-(2-cyano-phenoxy)-propoxy]-phenyl}-2-methoxy-propionic acid

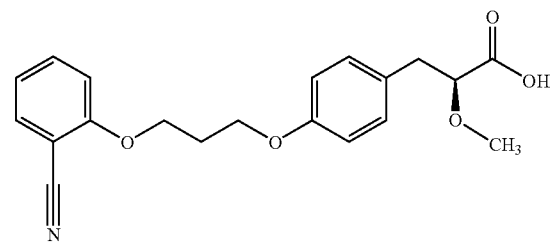

The title compound was prepared from (2S)-3-[4-(3-bromo-propoxy)-phenyl]-2-methoxy-propionic acid ethyl ester (Example 284, Step 2) and 2-hydroxy-benzonitrile via the same procedure used for the preparation of (2S)-2-methoxy-3-[4-(3-phenoxy-propoxy)-phenyl]-propionic acid (Example 285, Step 1), to produce a colorless oil.

MS (ES) for $C_{20}H_{21}NO_5$ $[M+NH_4]^+$: 373.4.

Example 294

(2S)-2-methoxy-3-{4-[3-(2-methoxy-phenoxy)-propoxy]-phenyl}-propionic acid

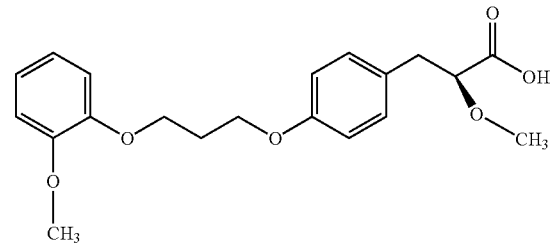

The title compound was prepared from (2S)-3-[4-(3-bromo-propoxy)-phenyl]-2-methoxy-propionic acid ethyl ester (Example 284, Step 2) and 2-methoxy-phenol via the same procedure used for the preparation of (2S)-2-methoxy-3-[4-(3-phenoxy-propoxy)-phenyl]-propionic acid (Example 285, Step 1), to produce a colorless oil. MS (ES) for $C_{20}H_{24}O_6$ $[M+NH_4]^+$: 378.4.

Example 295

(2S)-2-{3-[4-(2-carboxy-2-methoxy-ethyl)-phenoxy]-propoxy}-benzoic acid

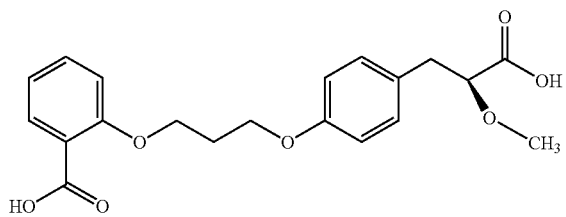

The title compound was prepared from (2S)-3-[4-(3-bromo-propoxy)-phenyl]-2-methoxy-propionic acid ethyl ester (Example 284, Step 2) and 2-hydroxy-benzoic acid methyl ester via the same procedure used for the preparation of (2S)-2-methoxy-3-[4-(3-phenoxy-propoxy)-phenyl]-propionic acid (Example 285, Step 1), to produce a colorless oil.
MS (ES) for $C_{20}H_{22}O_7$ $[M+H]^+$: 375.2.

Example 296

(2S)-3-{4-[3-(3-cyano-phenoxy)-propoxy]-phenyl}-2-methoxy-propionic acid

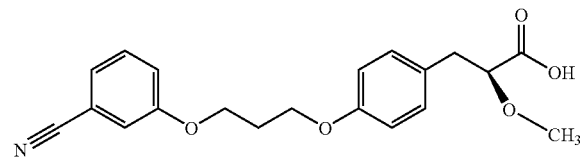

The title compound was prepared from (2S)-3-[4-(3-bromo-propoxy)-phenyl]-2-methoxy-propionic acid ethyl ester (Example 284, Step 2) and 3-hydroxy-benzonitrile via the same procedure used for the preparation of (2S)-2-methoxy-3-[4-(3-phenoxy-propoxy)-phenyl]-propionic acid (Example 285, Step 1), to produce a colorless oil.
MS (ES) for $C_{20}H_{21}NO_5$ $[M+NH_4]^+$: 373.4.

Example 297

(2S)-3-{4-[3-(3-dimethylamino-phenoxy)-propoxy]-phenyl}-2-methoxy-propionic acid

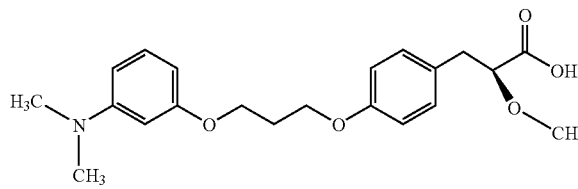

The title compound was prepared from (2S)-3-[4-(3-bromo-propoxy)-phenyl]-2-methoxy-propionic acid ethyl ester (Example 284, Step 2) and 3-dimethylamino-phenol via the same procedure used for the preparation of (2S)-2-methoxy-3-[4-(3-phenoxy-propoxy)-phenyl]-propionic acid (Example 285, Step 1), to produce a colorless oil.
MS (ES) for $C_{21}H_{27}NO_5$ $[M+H]^+$: 374.4.

Example 298

(2S)-3-{3-[4-(2-carboxy-2-methoxy-ethyl)-phenoxy]-propoxy}-benzoic acid

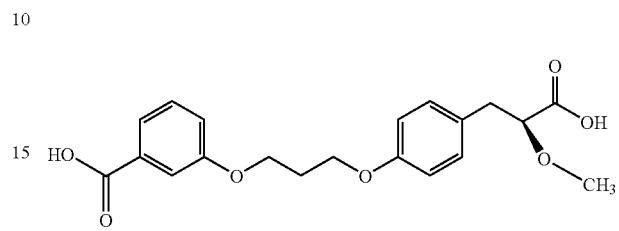

The title compound was prepared from (2S)-3-[4-(3-bromo-propoxy)-phenyl]-2-methoxy-propionic acid ethyl ester (Example 284, Step 2) and 3-hydroxy-benzoic acid methyl ester via the same procedure used for the preparation of (2S)-2-methoxy-3-[4-(3-phenoxy-propoxy)-phenyl]-propionic acid (Example 285, Step 1), to produce a colorless oil.
MS (ES) for $C_{20}H_{22}O_7$ $[M+Na]^+$: 397.4.

Example 299

(2S)-3-{4-[3-(indan-5-yloxy)-propoxy]-phenyl}-2-methoxy-propionic acid

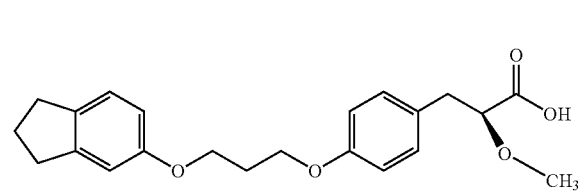

The title compound was prepared from (2S)-3-[4-(3-bromo-propoxy)-phenyl]-2-methoxy-propionic acid ethyl ester (Example 284, Step 2) and indan-5-ol via the same procedure used for the preparation of (2S)-2-methoxy-3-[4-(3-phenoxy-propoxy)-phenyl]-propionic acid (Example 285, Step 1), to produce a colorless oil.
MS (ES) for $C_{22}H_{26}O_5$ $[M+Na]^+$: 393.4.

Example 300

(2S)-2-methoxy-3-{4-[3-(naphthalen-2-yloxy)-propoxy]-phenyl}-propionic acid

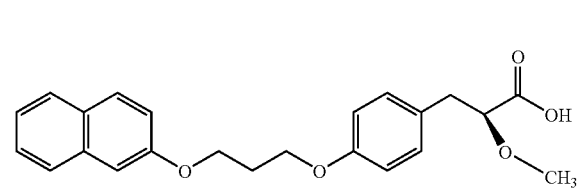

The title compound was prepared from (2S)-3-[4-(3-bromo-propoxy)-phenyl]-2-methoxy-propionic acid ethyl ester Example 284, Step 2) and naphthalen-2-ol via the same procedure used for the preparation of (2S)-2-methoxy-3-[4-

Example 301

(2S)-3-{4-[3-(1H-indol-5-yloxy-propoxy]-phenyl}-2-methoxy-propionic acid

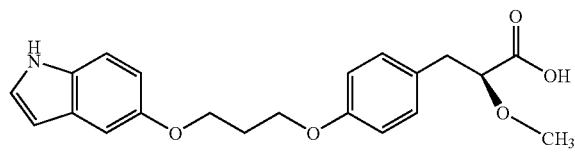

The title compound was prepared from (2S)-3-[4-(3-bromo-propoxy)-phenyl]-2-methoxy-propionic acid ethyl ester (Example 284, Step 2) and 1H-indol-5-ol via the same procedure used for the preparation of (2S)-2-methoxy-3-[4-(3-phenoxy-propoxy)-phenyl]-propionic acid (Example 285, Step 1), to produce a colorless oil. MS (ES) for $C_{21}H_{23}O_5$ [M+H]$^+$: 370.4.

Example 302

(2S)-2-methoxy-3-{4-[3-(quinolin-6-yloxy)-propoxy]-phenyl}-propionic acid

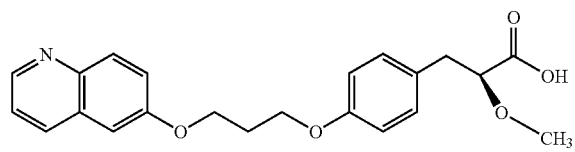

The title compound was prepared from (2S)-3-[4-(3-bromo-propoxy)-phenyl]-2-methoxy-propionic acid ethyl ester (Example 284, Step 2) and quinolin-6-ol via the same procedure used for the preparation of (2S)-2-methoxy-3-[4-(3-phenoxy-propoxy)-phenyl]-propionic acid (Example 285, Step 1), to produce a colorless oil. MS (ES) for $C_{22}H_{23}NO_5$ [M+H]$^+$: 382.4.

Example 303

(2S)-2-methoxy-3-{4-[3-(3-methoxy-phenoxy)-propoxy]-phenyl}-propionic acid

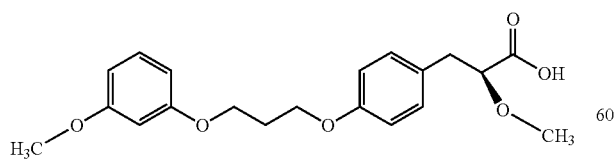

The title compound was prepared from (2S)-3-[4-(3-bromo-propoxy)-phenyl]-2-methoxy-propionic acid ethyl ester (Example 284, Step 2) and 3-methoxy-phenol via the same procedure used for the preparation of (2S)-2-methoxy-3-[4-(3-phenoxy-propoxy)-phenyl]-propionic acid (Example 285, Step 1), to produce a colorless oil. MS (ES) for $C_{23}H_{24}O_5$ [M+Na]$^+$: 403.4.

Example 304

(2S)-3-{4-[3-(3-fluoro-phenoxy)-propoxy]-phenyl}-2-methoxy-propionic acid

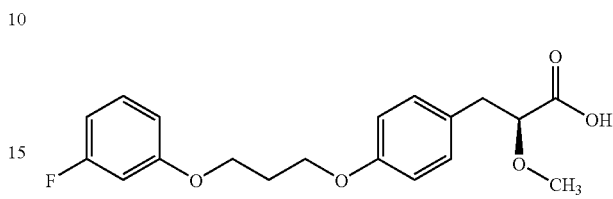

The title compound was prepared from (2S)-3-[4-(3-bromo-propoxy)-phenyl]-2-methoxy-propionic acid ethyl ester (Example 284, Step 2) and 3-fluoro-phenol via the same procedure used for the preparation of (2S)-2-methoxy-3-[4-(3-phenoxy-propoxy)-phenyl]-propionic acid (Example 285, Step 1), to produce a colorless oil. MS (ES) for $C_{19}H_{21}FO_5$ [M+Na]$^+$: 371.4.

Example 305

(2S)-3-{4-[3-(2-isopropyl-phenoxy)-propoxy]-phenyl}-2-methoxy-propionic acid

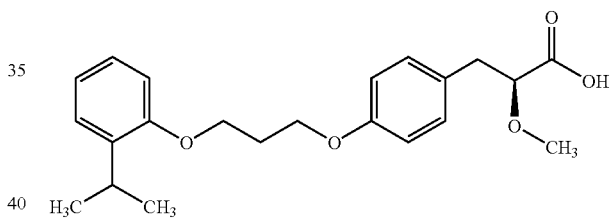

The title compound was prepared from (2S)-3-[4-(3-bromo-propoxy)-phenyl]-2-methoxy-propionic acid ethyl ester (example 284, Step 2) and 2-isopropyl-phenol via the same procedure used for the preparation of (2S)-2-methoxy-3-[4-(3-phenoxy-propoxy)-phenyl]-propionic acid (example 285, Step 1), to produce a colorless oil. MS (ES) for $C_{22}H_{28}O_5$ [M+NH$_4$]$^+$: 390.4.

Example 306

(2S)-2-methoxy-3-[4-(2-phenoxy-ethoxy)-phenyl]-propionic acid

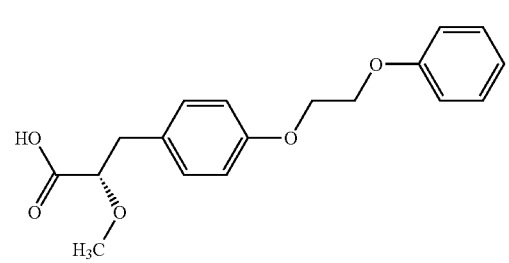

The title compound was prepared from (2S)-3-[4-(2-bromo-ethoxy)-phenyl]-2-methoxy-propionic acid ethyl ester Example 283, Step 2) and phenol via the same procedure used for the preparation of (2S)-2-methoxy-3-[4-(3-phenoxy-propoxy)-phenyl]-propionic acid (Example 285, Step 1), to produce a white solid. MS (ES) for $C_{18}H_{20}O_5$ [M+Na]$^+$: 339.3.

Example 307

(2S)-3-{4-[2-(2-cyano-phenoxy)-ethoxy]-phenyl}-2-methoxy-propionic acid

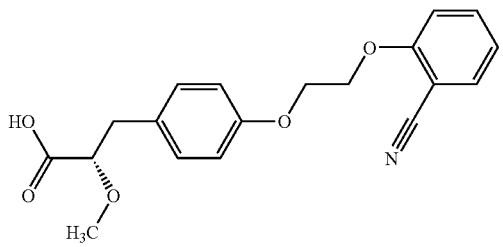

The title compound was prepared from (2S)-3-[4-(2-bromo-ethoxy)-phenyl]-2-methoxy-propionic acid ethyl ester (Example 283, Step 2) and 2-hydroxy-benzonitrile via the same procedure used for the preparation of (2S)-2-methoxy-3-[4-(3-phenoxy-propoxy)-phenyl]-propionic acid (Example 285, Step 1), to produce a colorless oil.
MS (ES) for $C_{19}H_{19}NO_5$ [M–H]$^-$: 340.3.

Example 308

(2S)-2-methoxy-3-{4-[2-(2-methoxy-phenoxy)-ethoxy]-phenyl}-propionic acid

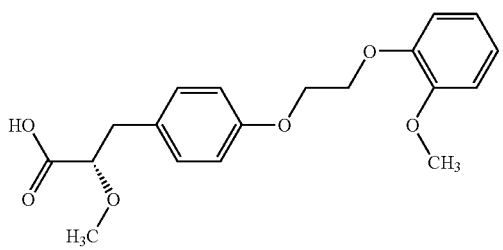

The title compound was prepared from (2S)-3-[4-(2-bromo-ethoxy)-phenyl]-2-methoxy-propionic acid ethyl ester (Example 283, Step 2) and 2-methoxy-phenol via the same procedure used for the preparation of (2S)-2-methoxy-3-[4-(3-phenoxy-propoxy)-phenyl]-propionic acid (Example 285, Step 1), to produce a white solid. MS (ES) for $C_{19}H_{22}O_6$ [M+Na]$^+$: 369.4.

Example 309

(2S)-3-{4-[2-(biphenyl-2-yloxy)-ethoxy]-phenyl}-2-methoxy-propionic acid

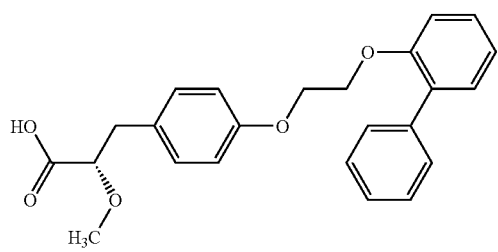

The title compound was prepared from (2S)-3-[4-(2-bromo-ethoxy)-phenyl]-2-methoxy-propionic acid ethyl ester (Example 283, Step 2) and biphenyl-2-ol via the same procedure used for the preparation of (2S)-2-methoxy-3-[4-(3-phenoxy-propoxy)-phenyl]-propionic acid (Example 285, Step 1), to produce a colorless oil. MS (ES) for $C_{24}H_{24}O_5$ [M+Na]$^+$: 415.4.

Example 310

(2S)-2-{2-[4-(2-carboxy-2-methoxy-ethyl)-phenoxy]-ethoxy}-benzoic acid

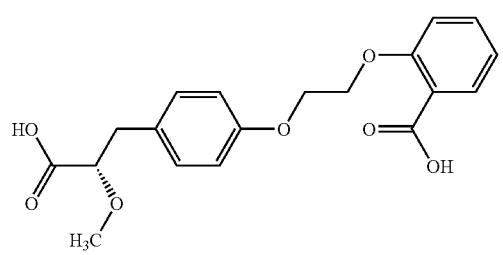

The title compound was prepared from (2S)-3-[4-(2-bromo-ethoxy)-phenyl]-2-methoxy-propionic acid ethyl ester (Example 283, Step 2) and 2-hydroxy-benzoic acid methyl ester via the same procedure used for the preparation of (2S)-2-methoxy-3-[4-(3-phenoxy-propoxy)-phenyl]-propionic acid (Example 285, Step 1), to produce a colorless oil.
MS (ES) for $C_{19}H_{20}O_7$ [M+Na]$^+$: 383.3.

Example 311

(2S)-3-{4-[2-(2-isopropyl-phenoxy)-ethoxy]-phenyl}-2-methoxy-propionic acid

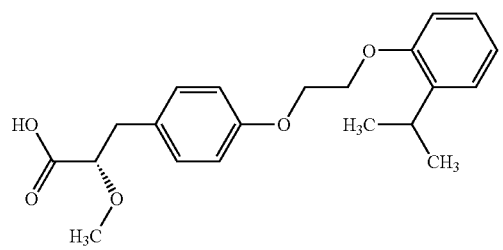

The title compound was prepared from (2S)-3-[4-(2-bromo-ethoxy)-phenyl]-2-methoxy-propionic acid ethyl ester (Example 283, Step 2) and 2-isopropyl-phenol via the same procedure used for the preparation of (2S)-2-methoxy-3-[4-(3-phenoxy-propoxy)-phenyl]-propionic acid (Example 285, Step 1), to produce a white solid. MS (ES) for $C_{21}H_{26}O_5$ [M+Na]$^+$: 381.4.

Example 312

(2S)-3-{4-[2-(3-cyano-phenoxy)-ethoxy]-phenyl}-2-methoxy-propionic acid

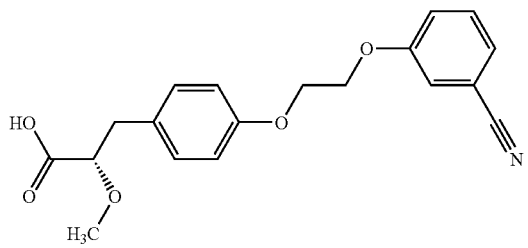

The title compound was prepared from (2S)-3-[4-(2-bromo-ethoxy)-phenyl]-2-methoxy-propionic acid ethyl ester (Example 283, Step 2) and 3-hydroxy-benzonitrile via the same procedure used for the preparation of (2S)-2-methoxy-3-[4-(3-phenoxy-propoxy)-phenyl]-propionic acid (Example 285, Step 1), to produce a white solid.

MS (ES) for $C_{19}H_{19}NO_5$ [M–H]$^-$: 340.3.

Example 313

(2S)-3-{4-[2-(3-dimethylamino-phenoxy)-ethoxy]-phenyl}-2-methoxy-propionic acid

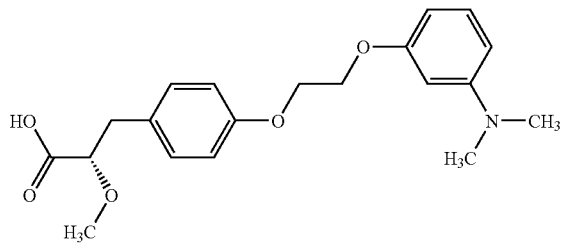

The title compound was prepared from (2S)-3-[4-(2-bromo-ethoxy)-phenyl]-2-methoxy-propionic acid ethyl ester (Example 283, Step 2) and 3-dimethylamino-phenol via the same procedure used for the preparation of (2S)-2-methoxy-3-[4-(3-phenoxy-propoxy)-phenyl]-propionic acid (Example 285, Step 1), to produce a yellow oil.

MS (ES) for $C_{21}H_{26}O_5$ [M+H]$^+$: 360.4.

Example 314

(2S)-3-{4-[2-(biphenyl-3-yloxy)-ethoxy]-phenyl}-2-methoxy-propionic acid

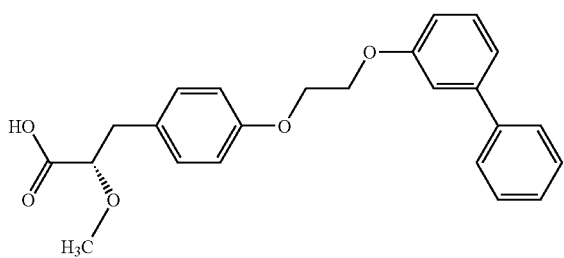

The title compound was prepared from (2S)-3-[4-(2-bromo-ethoxy)-phenyl]-2-methoxy-propionic acid ethyl ester (example 283, Step 2) and biphenyl-3-ol via the same procedure used for the preparation of (2S)-2-methoxy-3-[4-(3-phenoxy-propoxy)-phenyl]-propionic acid. (Example 285, Step 1), to produce a white solid. MS (ES) for $C_{24}H_{24}O_5$ [M–H]$^-$: 391.4.

Example 315

(2S)-3-{2-[4-(2-carboxy-2-methoxy-ethyl)-phenoxy]-ethoxy}-benzoic acid

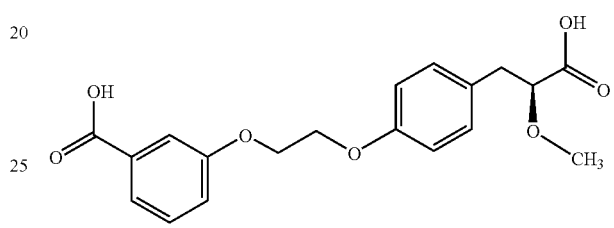

The title compound was prepared from (2S)-3-[4-(2-bromo-ethoxy)-phenyl]-2-methoxy-propionic acid ethyl ester (Example 283, Step 2) and 3-hydroxy-benzoic acid methyl ester via the same procedure used for the preparation of (2S)-2-methoxy-3-[4-(3-phenoxy-propoxy)-phenyl]-propionic acid (Example 285, Step 1), to produce a white solid.

MS (ES) for $C_{19}H_{20}O_7$ [M–H]$^-$: 359.3.

Example 316

(2S)-3-{4-[2-(indan-5-yloxy)-ethoxy]-phenyl}-2-methoxy-propionic acid

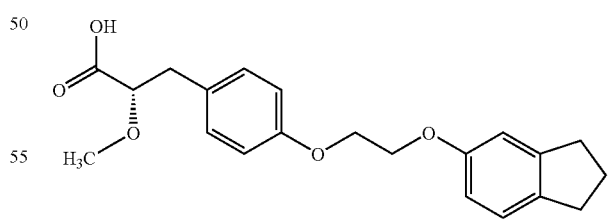

The title compound was prepared from (2S)-3-[4-(2-bromo-ethoxy)-phenyl]-2-methoxy-propionic acid ethyl ester (Example 283, Step 2) and indan-5-ol via the same procedure used for the preparation of (2S)-2-methoxy-3-[4-(3-phenoxy-propoxy)-phenyl]-propionic acid (Example 285, Step 1), to produce a colorless oil. MS (ES) for $C_{21}H_{24}O_5$ [M–H]$^-$: 355.3.

Example 317

(2S)-2-methoxy-3-{4-[2-(naphthalen-2-yloxy)-ethoxy]-phenyl}-propionic acid

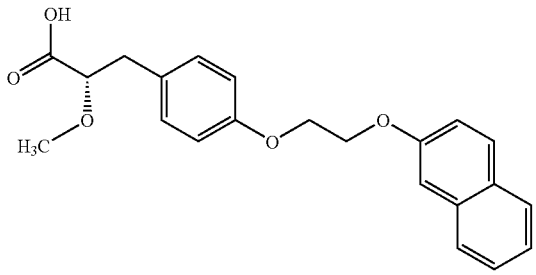

The title compound was prepared from (2S)-3-[4-(2-bromo-ethoxy)-phenyl]-2-methoxy-propionic acid ethyl ester (Example 283, Step 2) and naphthalen-2-ol via the same procedure used for the preparation of (2S)-2-methoxy-3-[4-(3-phenoxy-propoxy)-phenyl]-propionic acid (Example 285, Step 1), to produce a white solid. MS (ES) for $C_{22}H_{22}O_5$ [M+NH$_4$]$^+$: 389.3.

Example 318

(2S)-2-Methoxy-3-{4-[2-(quinolin-6-yloxy)-ethoxy]-phenyl}-propionic acid

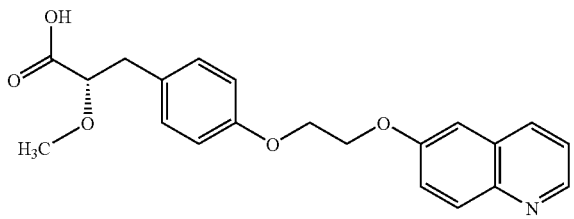

The title compound was prepared from (2S)-3-[4-(2-bromo-ethoxy)-phenyl]-2-methoxy-propionic acid ethyl ester (Example 283, Step 2) and quinolin-6-ol via the same procedure used for the preparation of (2S)-2-methoxy-3-[4-(3-phenoxy-propoxy)-phenyl]-propionic acid (Example 285, Step 1), to produce a white solid. MS (ES) for $C_{21}H_{21}NO_5$ [M+H]$^+$: 368.3.

Example 319

(2S)-2-Methoxy-3-{4-[2-(3-morpholin-4-yl-phenoxy)-ethoxy]-phenyl}-propionic acid

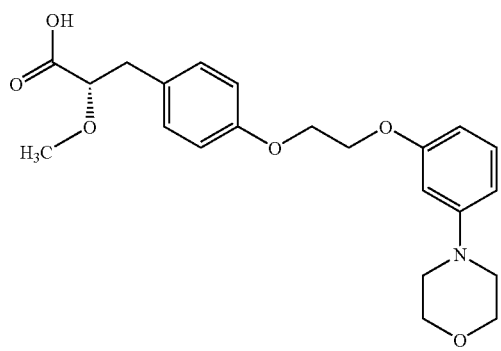

The title compound was prepared from (2S)-3-[4-(2-bromo-ethoxy)-phenyl]-2-methoxy-propionic acid ethyl ester (Example 283, Step 2) and 3-morpholin-4-yl-phenol via the same procedure used for the preparation of (2S)-2-methoxy-3-[4-(3-phenoxy-propoxy)-phenyl]-propionic acid (Example 285, Step 1), to produce a yellow oil.

MS (ES) for $C_{22}H_{27}NO_6$ [M+H]+402.4.

Example 320

(2S)-2-methoxy-3-{4-[2-(2-methyl-benzothiazol-5-yloxy)-ethoxy]-phenyl}-propionic acid

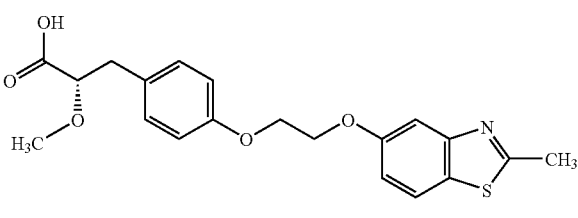

The title compound was prepared from (2S)-3-[4-(2-bromo-ethoxy)-phenyl]-2-methoxy-propionic acid ethyl ester (Example 283, Step 2) and 2-methyl-benzothiazol-5-ol via the same procedure used for the preparation of (2S)-2-methoxy-3-[4-(3-phenoxy-propoxy)-phenyl]-propionic acid (Example 285, Step 1), to produce a yellow oil.

MS (ES) for $C_{20}H_{21}NO_5S$ [M+H]$^+$: 388.3.

Example 321

(2S)-2-methoxy-3-{4-[2-(3-methoxy-phenyl)-ethoxy]-phenyl}-propionic acid

Example 322

(2S)-3-{4-[2-(3-fluoro-phenoxy)-ethoxy]-phenyl}-2-methoxy-propionic acid

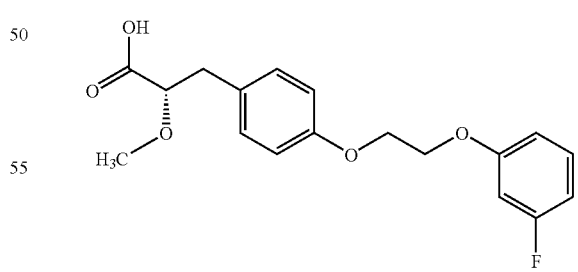

The title compound was prepared from (2S)-3-[4-(2-bromo-ethoxy)-phenyl]-2-methoxy-propionic acid ethyl ester (Example 283, Step 2) and 3-fluoro-phenol via the same procedure used for the preparation of (2S)-2-methoxy-3-[4-(3-phenoxy-propoxy)-phenyl]-propionic acid (Example 285, Step 1), to produce a white solid. MS (ES) for $C_{18}H_{19}FO_5$ [M−H]$^-$: 333.3.

Example 323

2-methoxy-3-[3-(3-phenoxy-propoxy)-phenyl]-propionic acid (isomer 1)

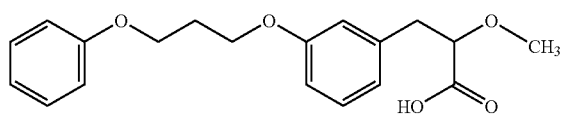

Step 1: 3-[3-(3-bromo-propoxy)-phenyl]-2-methoxy-propionic acid methyl ester

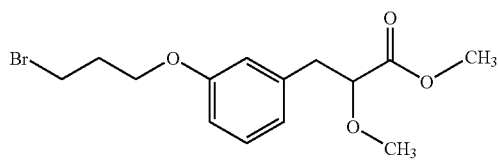

The title compound was prepared from 3-bromo-propan-1-ol (Example 284, Step 1) and 3-(3-hydroxy-phenyl)-2-methoxy-propionic acid methyl ester (Example 291, Step 4) via the same procedure used for the preparation of (2S)-3-[4-(3-bromo-propoxy)-phenyl]-2-methoxy-propionic acid ethyl ester (Example 284, Step 2). $^1$H-NMR (CDCl$_3$, 200.15 MHz): 7.26–7.16 (m, 1H), 6.80 (t, 3H, J=7.3), 4.09 (t, 2H, J=5.9), 3.97 (dd, 1H, J=7.3, 5.4), 3.73 (s, 3H), 3.60 (t, 2H, J=6.4), 3.36 (s, 3H), 3.00 (s, 1H), 2.97 (d, 1H, J=3.2), 2.31 (qn, 2H, J=6.2).

Step 2: (Isomer-1) 2-methoxy-3-[3-(3-phenoxy-propoxy)-phenyl]-propionic acid

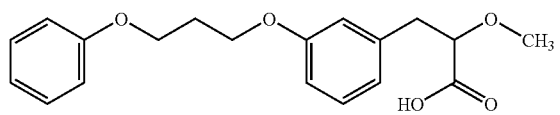

The title compound was prepared from 3-[3-(3-bromo-propoxy)-phenyl]-2-methoxy-propionic acid methyl ester (Example 323, Step 1) and phenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{19}$H$_{22}$O$_5$ [M+Na]$^+$: 353.3.

Example 324

3-{3-[3-(2-cyano-phenoxy)-propoxy]-phenyl}-2-methoxy-propionic acid (isomer 1)

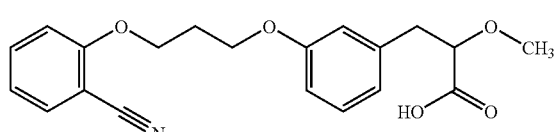

The title compound was prepared from 3-[3-(3-bromo-propoxy)-phenyl]-2-methoxy-propionic acid methyl ester (Example 323, Step 1) and 2-cianophenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{20}$H$_{21}$NO$_5$ [M+Na]$^+$: 378.3.

Example 325

3-{3-[3-(3-cyano-phenoxy)-propoxy-]phenyl}-2-methoxy-propionic acid (isomer 1)

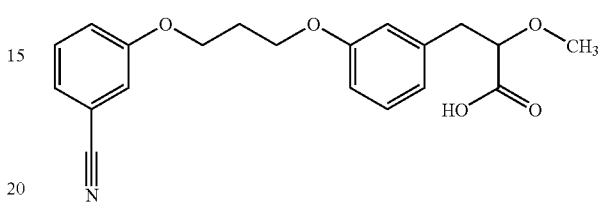

The title compound was prepared from 3-[3-(3-bromo-propoxy)-phenyl]-2-methoxy-propionic acid methyl ester Example 323, Step 1) and 3-cianophenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{20}$H$_{21}$NO$_5$ [M+Na]$^+$: 378.3.

Example 326

2-methoxy-3-[3-(3-phenoxy-propoxy)-phenyl]-propionic acid (isomer 2)

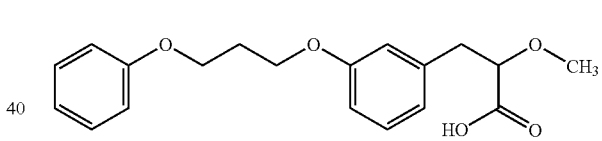

The title compound was prepared from 3-[3-(3-bromo-propoxy)-phenyl]-2-methoxy-propionic acid methyl ester (Example 323, Step 1) and phenol via the same procedure used for the preparation of (2S)-2-methoxy-3-[4-(3-phenoxy-propoxy)-phenyl]-propionic acid (Example 285, Step 1). The enantiomers were separated by chiral HPLC.

MS (ES) for C$_{19}$H$_{22}$O$_5$ [M+Na]$^+$: 353.3.

Example 327

3-{3-[3-(2-cyano-phenyl)-propoxy]-phenyl}-2-methoxy-propionic acid (isomer 2)

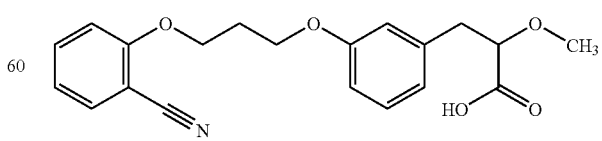

The title compound was prepared from 3-[3-(3-bromo-propoxy)-phenyl]-2-methoxy-propionic acid methyl ester (Example 323, Step 1) and 2-cianophenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{21}NO_5$ [M+Na]$^+$: 378.3

Example 328

3-{3-[3-(3-cyano-phenoxy)-propoxy]-phenyl}-2-methoxy-propionic acid (isomer 2)

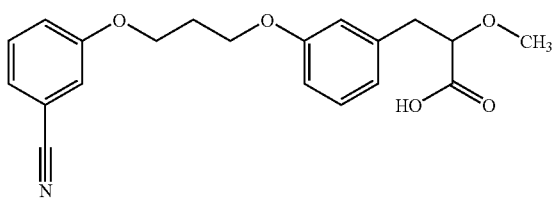

The title compound was prepared from 3-[3-(3-bromo-propoxy)-phenyl]-2-methoxy-propionic acid methyl ester (Example 323, Step 1) and 3-cianophenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{21}NO_5$ [M+Na]$^+$: 378.3

Example 329

2-methoxy-3-{3-[3-(2-methoxy-phenoxy)-propoxy]-phenyl}-propionic acid (isomer 1)

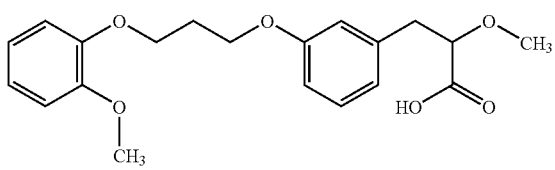

The title compound was prepared from 3-[3-(3-bromo-propoxy)-phenyl]-2-methoxy-propionic acid methyl ester (Example 323, Step 1) and 2-methoxyphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{24}O_6$ [M+Na]$^+$: 383.4.

Example 330

2-methoxy-3-{3-[3-(2-methoxy-phenoxy)-propoxy]-phenyl}-propionic acid (isomer 2)

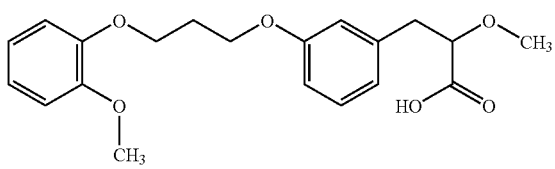

The title compound was prepared from 3-[3-(3-bromo-propoxy)-phenyl]-2-methoxy-propionic acid methyl ester (Example 323, Step 1) and 2-methoxyphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{24}O_6$ [M+Na]$^+$: 383.4.

Example 331

3-{3-[3-(2-isopropyl-phenoxy)-propoxy]-phenyl}-2-methoxy-propionic acid (isomer 1)

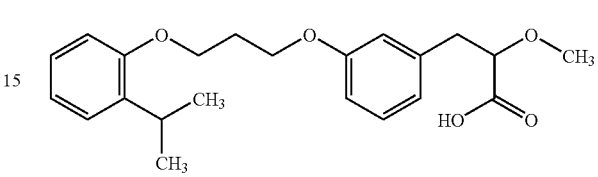

The title compound was prepared from 3-[3-(3-bromo-propoxy)-phenyl]-2-methoxy-propionic acid methyl ester (Example 323, Step 1) and 2-isopropylphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{22}H_{28}O_5$ [M+Na]$^+$: 395.4.

Example 332

3-{3-[3-(2-isopropyl-phenoxy)-propoxy]-phenyl}-2-methoxy-propionic acid (isomer 2)

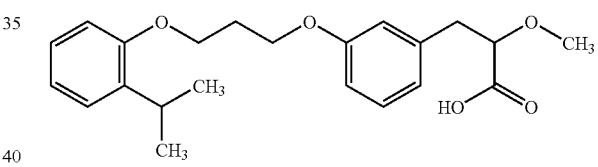

The title compound-was prepared from 3-[3-(3-bromo-propoxy)-phenyl]-2-methoxy-propionic acid methyl ester (Example 323, Step 1) and 2-isopropylphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{22}H_{28}O_5$ [M+Na]$^+$: 395.4.

Example 333

3-{3-[3-2-carboxy-2-methoxy-ethyl)-phenoxy]-propoxy}-benzoic acid (isomer 1)

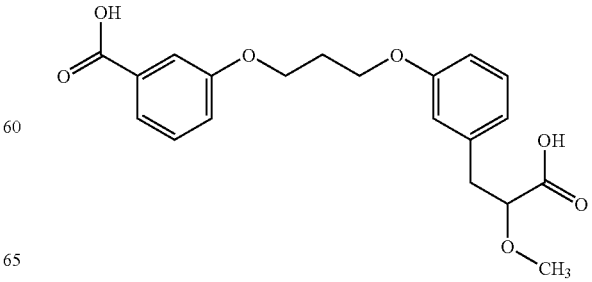

The title compound was prepared from 3-[3-(3-bromo-propoxy)-phenyl]-2-methoxy-propionic acid methyl ester (Example 323, Step 1) and 3-hydroxybenzoic acid methyl ester via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{22}O_7$ [M+Na]$^+$: 397.4.

Example 334

3-{3-[3-(2-carboxy-2-methoxy-ethyl)-phenoxy]-propoxy}-benzoic acid (isomer 2)

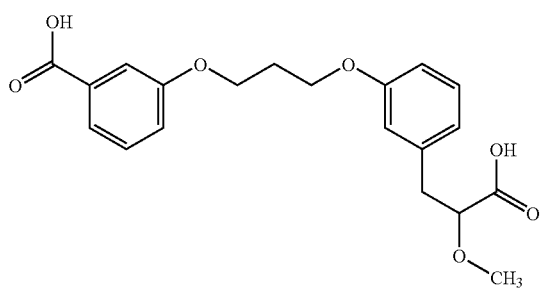

The title compound was prepared from 3-[3-(3-bromo-propoxy)-phenyl]-2-methoxy-propionic acid methyl ester (Example 323, Step 1) and 3-hydroxybenzoic acid methyl ester via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{22}O_7$ [M+Na]$^+$: 397.4.

Example 335

2-methoxy-3-{3-[3-(3-methoxy-phenoxy)-propoxy]-phenyl}-propionic acid (isomer 1)

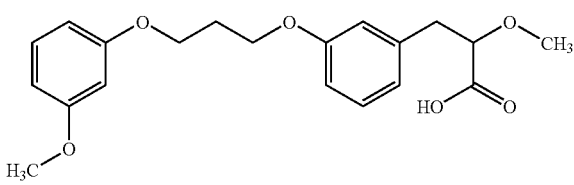

The title compound was prepared from 3-[3-(3-bromo-propoxy)-phenyl]-2-methoxy-propionic acid methyl ester (example 323, Step 1) and 3-methoxyphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{24}O_6$ [M+Na]$^+$: 383.3.

Example 336

2-methoxy-3-{3-[3-(3-methoxy-phenoxy)-propoxy]-phenyl}-propionic acid (isomer 2)

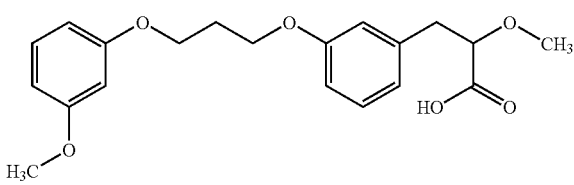

The title compound was prepared from 3-[3-(3-bromo-propoxy)-phenyl]-2-methoxy-propionic acid methyl ester (Example 323, Step 1) and 3-methoxyphenol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{20}H_{24}O_6$ [M+Na]$^+$: 383.3.

Example 337

2-methoxy-3-{3-[3-(naphthalen-2-yloxy)-propoxy]-phenyl}-propionic acid (isomer 1)

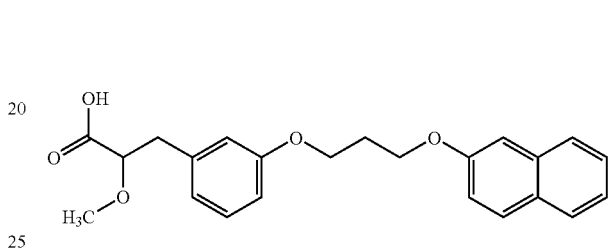

The title compound was prepared from 3-[3-(3-bromo-propoxy)-phenyl]-2-methoxy-propionic acid methyl ester (Example 323, Step 1) and 2-naphthol via the same procedure used for the preparation of (2S)-2-methoxy-3-[4-(3-phenoxy-propoxy)-phenyl]-propionic acid (Example 285, Step 1). The enatiomers were separated by chiral HPLC.

$^1$H-NMR (CDCl$_3$, 200.15 MHz): 7.78–7.69 (m, 3H), 7.47–7.12 (m, 5H), 6.84–6.81 (m, 3H), 4.28 (t, 2H, J=5.9), 4.19 (t, 2H, J=5.9), 4.02 (dd, 1H, J=7.5, 4.0), 3.38 (s, 3H), 3.13 (dd, 1H, J=14.2, 4.3), 2.97 (dd, 1H, J=14.2, 7.5), 2.33 (qn, 2H, J=6.2). MS (ES) for $C_{23}H_{24}O_5$ [M+H]$^+$: 381.2.

Example 338

2-methoxy-3-{3-[3-naphthalen-2-yloxy)-propoxy]-phenyl}-propionic acid (isomer 2)

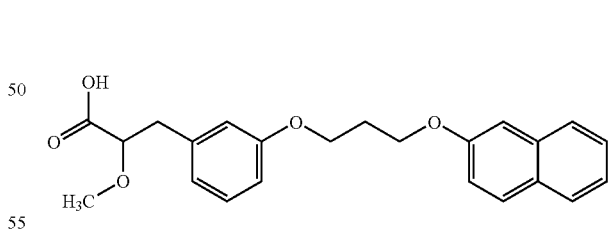

The title compound was prepared from 3-[3-(3-bromo-propoxy)-phenyl]-2-methoxy-propionic acid methyl ester (Example 323, Step 1) and 2-naphthol via the same procedure used for the preparation, of (2S)-2-methoxy-3-[4-(3-phenoxy-propoxy)-phenyl]-propionic acid (Example 285, Step 1). The enatiomers were separated by chiral HPLC.

$^1$H-NMR (CDCl$_3$, 200.15 MHz): 7.78–7.69 (m, 3H), 7.47–7.12 (m, 5H), 6.84–6.81 (m, 3H), 4.28 (t, 2H, J=5.9), 4.19 (t, 2H, J=5.9), 4.02 (dd, 1H, J=7.5, 4.0), 3.38 (s, 3H), 3.13 (dd, 1H, J=14.2, 4.3), 2.97 (dd, 1H, J=14.2, 7.5), 2.33 (qn, 2H, J=6.2). MS (ES) for $C_{23}H_{24}O_5$ [M+H]$^+$: 381.2.

Example 339

2-methoxy-3-{3-[3-(2-methyl-benzothiazol-5-yloxy)-propoxy]-phenyl}-propionic acid (isomer 1)

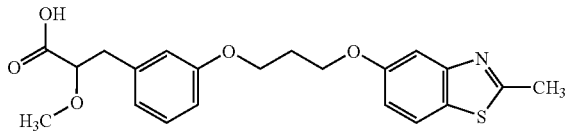

The title compound was prepared from 3-[3-(3-bromo-propoxy)-phenyl]-2-methoxy-propionic acid methyl ester (Example 323, Step 1) and 2-methyl-benzothiazol-5-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{21}H_{23}NO_5S$ [M+H]$^+$: 402.1.

Example 340

2-methoxy-3-{3-[3-(2-methyl-benzothiazol-5-yloxy)-propoxy]-phenyl}-propionic acid (isomer 2)

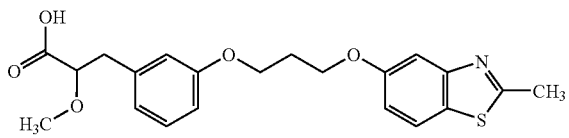

The title compound was prepared from 3-[3-(3-bromo-propoxy)-phenyl]-2-methoxy-propionic acid methyl ester (Example 323, Step 1) and 2-methyl-benzothiazol-5-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{21}H_{23}NO_5S$ [M+H]$^+$: 402.1.

Example 341

3-{3-[3-(2-chloro-phenoxy)-propoxy]-phenyl}-2-methoxy-propionic acid (isomer 1)

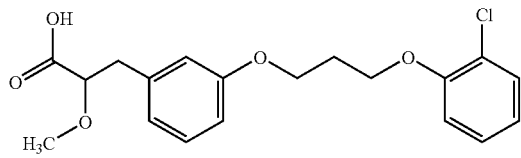

The title compound was prepared from 3-[3-(3-bromo-propoxy)-phenyl]-2-methoxy-propionic acid methyl ester (Example 323, Step 1) and 2-chlorophenol via the same procedure used for the preparation of (2S)-2-methoxy-3-[4-(3-phenoxy-propoxy)-phenyl]-propionic acid (Example 285, Step 1). The enatiomers were separated by chiral HPLC. $^1$H-NMR (CDCl$_3$, 200.15 MHz): 7.35 (dd, 1H, J=8.1, 1.9), 7.24–7.16 (m, 2H), 6.97–6.80 (m, 5H), 4.22 (t, 2H, J=5.9), 4.20 (t, 2H, J=5.9), 4.02 (dd, 1H, J=7.3, 4.0), 3.39 (s, 3H), 3.13 (dd, 1H, J=14.2, 3.8), 2.97 (dd, 1H, J=14.0, 7.8), 2.30 (qn, 2H, J=6.2).

MS (ES) for $C_{19}H_{21}ClO_5$ [M+Na]$^+$: 387.2.

Example 342

3-{3-[3-(2-chloro-phenoxy)-propoxy]-phenyl}-2-methoxy-propionic acid (isomer 2)

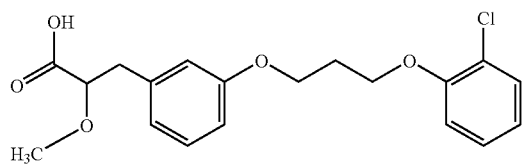

The title compound was prepared from 3-[3-(3-bromo-propoxy)-phenyl]-2-methoxy-propionic acid methyl ester (Example 323, Step 1) and 2-chlorophenol via the same procedure used for the preparation of (2S)-2-methoxy-3-[4-(3-phenoxy-propoxy)-phenyl]-propionic acid (Example 285, Step 1). The enatiomers were separated by chiral HPLC. $^1$H-NMR (CDCl$_3$, 200.15 MHz): 7.35 (dd, 1H, J=8.1, 1.9), 7.24–7.16 (m, 2H), 6.97–6.80 (m, 5H), 4.22 (t, 2H, J=5.9), 4.20 (t, 2H, J=5.9), 4.02 (dd, 1H, J=7.3, 4.0), 3.39 (s, 3H), 3.13 (dd, 1H, J=14.2, 3.8), 2.97 (dd, 1H, J=14.0, 7.8), 2.30 (qn, 2H, J=6.2).

MS (ES) for $C_{19}H_{21}ClO_5$ [M+Na]$^+$: 387.2.

Example 343

3-{3-[3-(3,4-dimethyl-phenoxy)-propoxy]-phenyl}-2-methoxy-propionic acid (isomer 1)

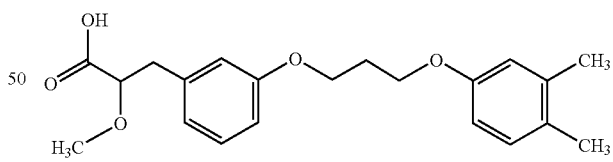

The title compound was prepared from 3-[3-(3-bromo-propoxy)-phenyl]-2-methoxy-propionic acid methyl ester (Example 323, Step 1) and 3,4-dimethylphenol via the same procedure used for the preparation of (2S)-2-methoxy-3-[4-(3-phenoxy-propoxy)-phenyl]-propionic acid (Example 285, Step 1). The enatiomers were separated by chiral HPLC. $^1$H-NMR (CDCl$_3$, 200.15 MHz): 7.18 (d, 1H, J=7.5), 7.02 (d, 1H, J=8.3), 6.84–6.62 (m, 5H), 4.14 (t, 2H, J=6.4), 4.12 (t, 2H, J=5.9), 4.02 (dd, 1H, J=7.3, 4.0), 3.39 (s, 3H), 3.13 (dd, 1H, J=14.2, 4.6), 2.97 (dd, 1H, J=14.0, 7.5), 2.23 (q, 1H, J=6.2.1), 2.22 (s, 3H), 2.18 (s, 3H). MS (ES) for $C_{21}H_{26}O_5$ [M+Na]$^+$: 381.2.

Example 344

3-{3-[3-(3,4-dimethyl-phenoxy)-propoxy]-phenyl}-2-methoxy-propionic acid (isomer 2)

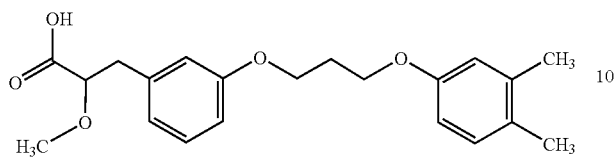

The title compound was prepared from 3-[3-(3-bromo-propoxy)-phenyl]-2-methoxy-propionic acid methyl ester (Example 323, Step 1) and 3,4-dimethylphenol via the same procedure used for the preparation of (2S)-2-methoxy-3-[4-(3-phenoxy-propoxy)-phenyl]-propionic acid (Example 285, Step 1). The enatiomers were separated by chiral HPLC. $^1$H-NMR (CDCl$_3$, 200.15 MHz): 7.18 (d, 1H, J=7.5), 7.02 (d, 1H, J=8.3), 6.84–6.62 (m, 5H), 4.14 (t, 2H, J=6.4), 4.12 (t, 2H, J=5.9), 4.02 (dd, 1H, J=7.3, 4.0), 3.39 (s, 3H), 3.13 (dd, 1H, J=14.2, 4.6), 2.97 (dd, 1H, J=14.0, 7.5), 2.23 (q, 1H, J=6.2.1), 2.22 (s, 3H), 2.18 (s, 3H). MS (ES) for C$_{21}$H$_{26}$O$_5$ [M+Na]$^+$: 381.2.

Example 345

2-{3-[3-(2-carboxy-2-methoxy-ethyl)-phenoxy]-propoxy}-benzoic acid (isomer 1)

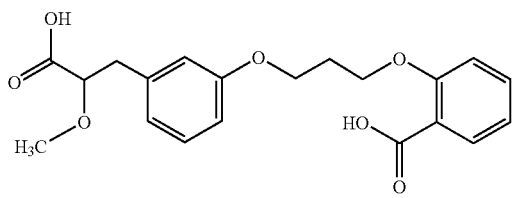

The title compound was prepared from 3-[3-(3-bromo-propoxy)-phenyl]-2-methoxy-propionic acid methyl ester (Example 323, Step 1) and 2-hydroxy-benzoic acid via the same procedure used for the preparation of (2S)-2-methoxy-3-[4-(3-phenoxy-propoxy)-phenyl]-propionic acid (example 285, Step 1). The enatiomers were separated by chiral HPLC. MS (ES) for C$_{20}$H$_{22}$O$_7$ [M+H]$^+$: 375.2.

Example 346

2-{3-[3-(2-carboxy-2-methoxy-ethyl)-phenoxy]-propoxy}-benzoic acid (isomer 2)

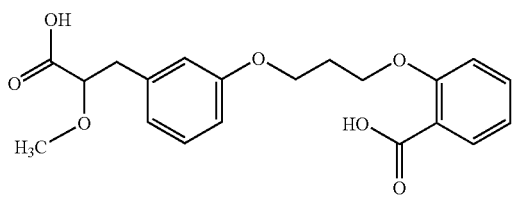

The title compound was prepared from 3-[3-(3-bromo-propoxy)-phenyl]-2-methoxy-propionic acid methyl ester (Example 323, Step 1) and 2-hydroxy-benzoic acid via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{20}$H$_{22}$O$_7$ [M+H]$^+$: 375.2.

Example 347

3-{3-[3-(biphenyl-3-yloxy)-propoxy]-phenyl}-2-methoxy-propionic acid (isomer 1)

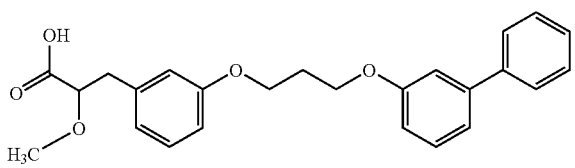

The title compound was prepared from 3-[3-(3-bromo-propoxy)-phenyl]-2-methoxy-propionic acid methyl ester (Example 323, Step 1) and biphenyl-3-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{25}$H$_{26}$O$_5$ [M+Na]$^+$: 429.2.

Example 348

3-{3-[3-(biphenyl-3-yloxy)-propoxy]-phenyl}-2-methoxy-propionic acid (isomer 2)

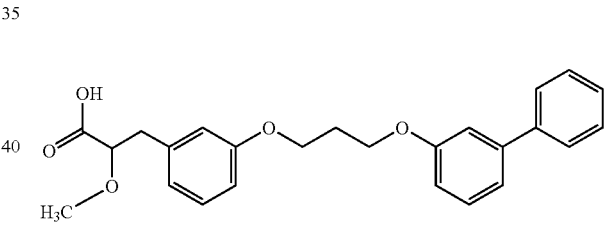

The title compound was prepared from 3-[3-(3-bromo-propoxy)-phenyl]-2-methoxy-propionic acid methyl ester (Example 323, Step 1) and biphenyl-3-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{25}$H$_{26}$O$_5$ [M+Na]$^+$: 429.2.

Example 349

2-methoxy-3-{3-[3-(quinolin-6-yloxy)-propoxy]-phenyl}-propionic acid (isomer 1)

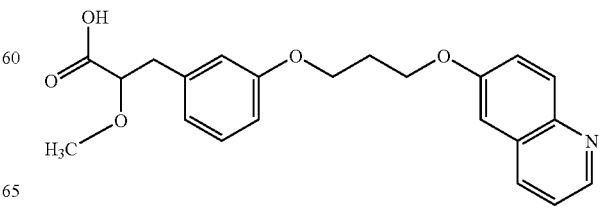

The title compound was prepared from 3-[3-(3-bromo-propoxy)-phenyl]-2-methoxy-propionic acid methyl ester (Example 323, Step 1) and quinolin-6-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{22}$H$_{23}$NO$_5$ [M+H]$^+$: 382.2.

Example 350

2-methoxy-3-{3-[3-(quinolin-6-yloxy)-propoxy]-phenyl}-propionic acid (isomer 2)

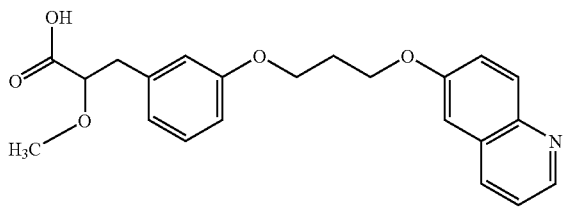

The title compound was prepared from 3-[3-(3-bromo-propoxy)-phenyl]-2-methoxy-propionic acid methyl ester Example 323, Step 1) and quinolin-6-ol via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{22}$H$_{23}$NO$_5$ [M+H]$^+$: 382.2.

Example 351

3-{3-[2-(2-isopropyl-phenoxy)-ethoxy]-phenyl}-2-methoxy-propionic acid (isomer 2)

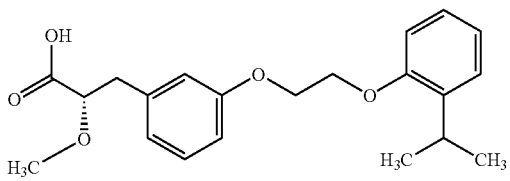

Step 1: 3-[3-(2-bromo-ethoxy)-phenyl]-2-methoxy-propionic acid methyl ester

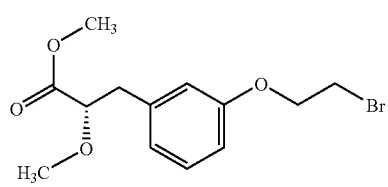

The title compound was prepared from 3-(3-hydroxy-phenyl)-2-methoxy-propionic acid methyl ester (Example 291, Step 4) (4.76 mol, 1000 mg) via the same procedure used for the preparation of (2S)-3-[4-(2-bromo-ethoxy)-phenyl]-2-methoxy-propionic acid ethyl ester (Example 283, Step 2). MS (ES) for C$_{13}$H$_{17}$BrO$_4$ [M+NH$_4$]$^+$: 334:2.

Step 2: 3-{3-[2-(2-isopropyl-phenoxy)-ethoxy]-phenyl}-2-methoxy-propionic acid (isomer 2)

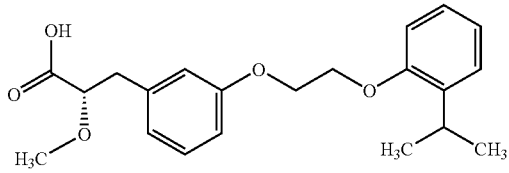

The title compound was prepared from 2-isopropyl-phenol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{21}$H$_{26}$O$_5$ [M−H]$^−$:357.2.

Example 352

2-methoxy-3-{3-[2-(3-methoxy-phenoxy)-ethoxy]-phenyl}-propionic acid (isomer 1)

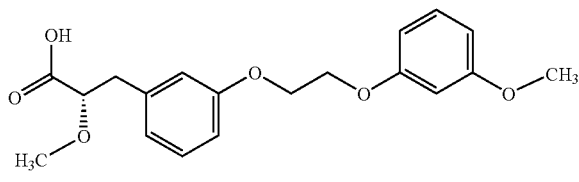

The title compound was prepared from 3-methoxy-phenol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{19}$H$_{22}$O$_6$ [M−H]$^−$: 345.1.

Example 353

3-{3-[2-(3-fluoro-phenoxy)-ethoxy]-phenyl}-2-methoxy-propionic acid (isomer 1)

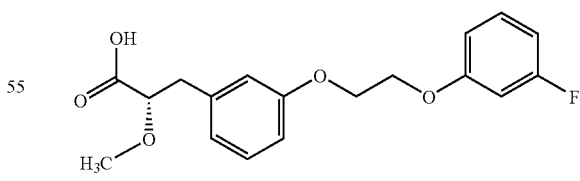

The title compound was prepared from 3-fluoro-phenol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for C$_{18}$H$_{19}$FO$_5$ [M−H]$^−$: 333.1.

Example 354

2-methoxy-3-{3-[2-(5,6,7,8-tetrahydro-naphthalen-2-yloxy-ethoxy]-phenyl}-propionic acid (isomer 1)

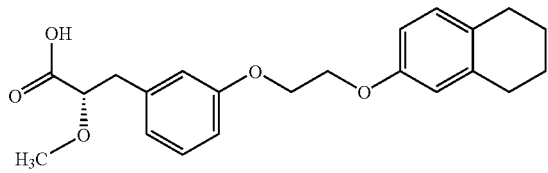

The title compound was prepared from 5,6,7,8-tetrahydro-naphthalen-2-ol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{22}H_{26}O_5$ [M–H]−: 369.2.

Example 355

2-methoxy-3-{3-[2-(3-methoxy-phenoxy)-ethoxy]-phenyl}-propionic acid (isomer 2)

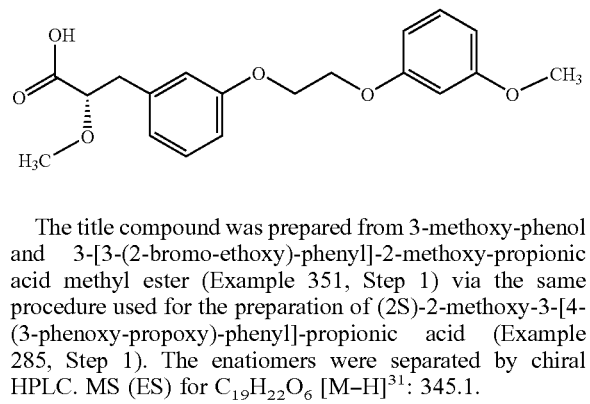

The title compound was prepared from 3-methoxy-phenol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{19}H_{22}O_6$ [M–H]$^{31}$: 345.1.

Example 356

3-{3-[2-(3-fluoro-phenoxy)-ethoxy]-phenyl}-2-methoxy-propionic acid (isomer 2)

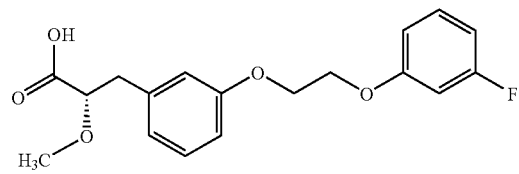

The title compound was prepared from 3-fluoro-phenol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{18}H_{19}FO_5$ [M–H]−: 333.1.

Example 357

2-methoxy-3-{3-[2-(5,6,7,8-tetrahydro-naphthalen-2-yloxy)-ethoxy]-phenyl}-propionic acid (isomer 2)

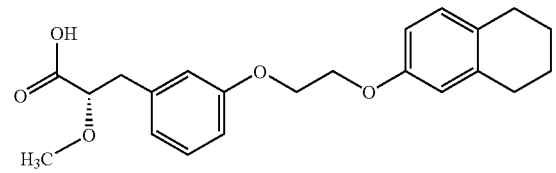

The title compound was prepared from 5,6,7,8-tetrahydro-naphthalen-2-ol and 3-[3-(2-bromo-ethoxy)-phenyl]-2-methoxy-propionic acid methyl ester (Example 351, Step 1) via the same procedure used for the preparation of (2S)-2-methoxy-3-[4-(3-phenoxy-propoxy)-phenyl]-propionic acid (Example 285, Step 1). The enatiomers were separated by chiral HPLC. MS (ES) for $C_{22}H_{26}O_5$ [M–H]−: 369.2.

Example 358

(2S)-2-methoxy-3-{4-[2-(4-trifluoromethyl-phenoxy)-ethoxy]-phenyl}-propionic acid

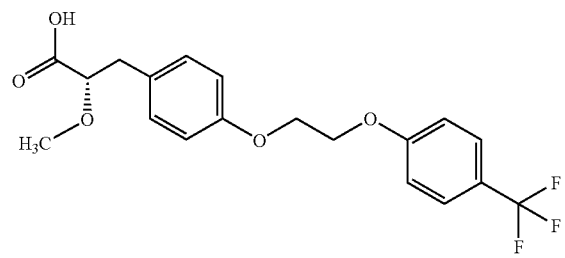

The title compound was prepared from (2S)-3-[4-(2-bromo-ethoxy)-phenyl]-2-methoxy-propionic acid ethyl ester (Example 283, Step 2) and 4-trifluoromethyl-phenol via the same procedure used for the preparation of (2S)-2-methoxy-3-[4-(3-phenoxy-propoxy)-phenyl]-propionic acid (Example 285, Step 1), to produce a white solid.
MS (ES) for $C_{19}H_{19}F_3O_5$ [M+Na]+: 407.2.

Example 359

(2S)-2-methoxy-3-(4-{2-[4-(1-methyl-1-phenyl-ethyl)-phenoxy]-ethoxy}-phenyl)-propionic acid

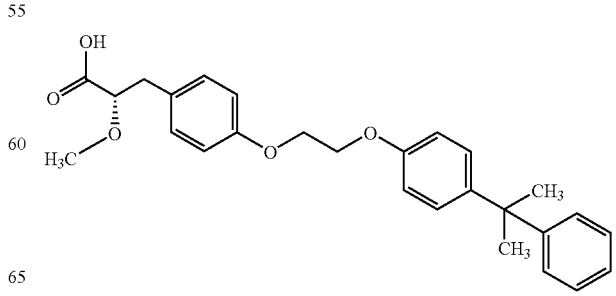

The title compound was prepared from (2S)-3-[4-(2-bromo-ethoxy)-phenyl]-2-methoxy-propionic acid ethyl ester (Example 283, Step 2) and 4-(1-methyl-1-phenyl-ethyl)-phenol via the same procedure used for the preparation of (2S)-2-methoxy-3-[4-(3-phenoxy-propoxy)-phenyl]-propionic acid (Example 285, Step 1), to produce a white solid.

MS (ES) for $C_{27}H_{30}O_5$ [M+Na]$^+$: 457.2.

Example 360

(2S)-3-{4-[2-(4-benzyl-phenoxy)-ethoxy]-phenyl}-2-methoxy-propionic acid

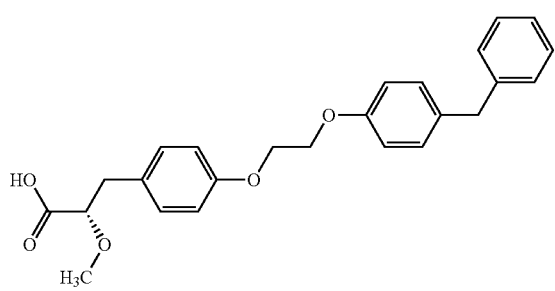

The title compound was prepared from (2S)-3-[4-(2-bromo-ethoxy)-phenyl]-2-methoxy-propionic acid ethyl ester (Example 283, Step 2) and 4-benzyl-phenol via the same procedure used for the preparation of (2S)-2-methoxy-3-[4-(3-phenoxy-propoxy)-phenyl]-propionic acid (Example 285, Step 1), to produce a white solid. MS (ES) for $C_{25}H_{26}O_5$ [M+Na]$^+$: 429.3.

Example 361

(2S)-2-methoxy-3-{4-[2-(4-oxo-2-phenyl-4H-chromen-7-yloxy)-ethoxy]-phenyl}-propionic acid

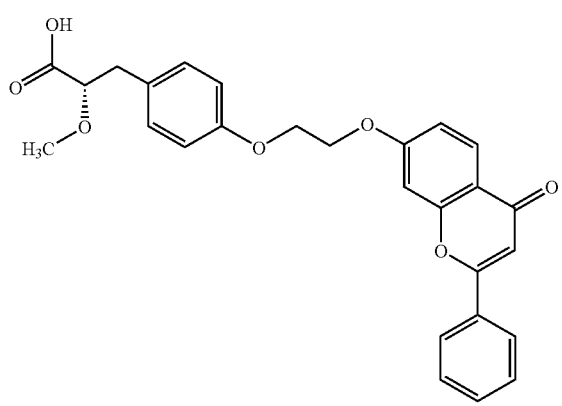

The title compound was prepared from (2S)-3-[4-(2-bromo-ethoxy)-phenyl]-2-methoxy-propionic acid ethyl ester (Example 283, Step 2) and 7-hydroxy-2-phenyl-chromen-4-one via the same procedure used for the preparation of (2S)-2-methoxy-3-[4-(3-phenoxy-propoxy)-phenyl]-propionic acid (Example 285, Step 1), to produce a yellow solid.

MS (ES) for $C_{27}H_{24}O_7$ [M+H]$^+$: 461.3.

Example 362

(2S)-3-{4-[2-(4-cyclopentyl-phenoxy)-ethoxy]-phenyl}-2-methoxy-propionic acid

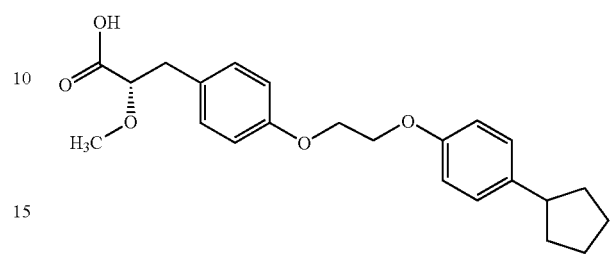

The title compound was prepared from (2S)-3-[4-(2-bromo-ethoxy)-phenyl]-2-methoxy-propionic acid ethyl ester (Example 283, Step 2) and 1-cyclopentyl-4-methoxy-benzene via the same procedure used for the preparation of (2S)-2-methoxy-3-[4-(3-phenoxy-propoxy)-phenyl]-propionic acid (Example 285, Step 1), to produce a white solid.

MS (ES) for $C_{23}H_{28}O_5$ [M+Na]$^+$: 407.3.

Example 363

(2S)-3-{4-[2-(9H-fluoren-2-yloxy)-ethoxy]-phenyl}-2-methoxy-propionic acid

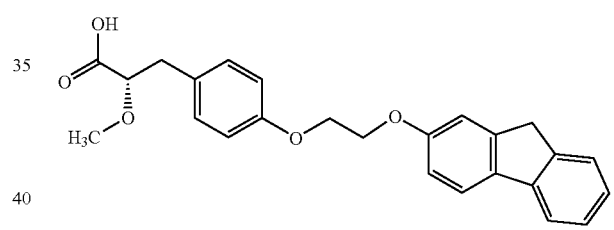

The title compound was prepared from (2S)-3-[4-(2-bromo-ethoxy)-phenyl]-2-methoxy-propionic acid ethyl ester (Example 283, Step 2) and 9H-fluoren-2-ol via the same procedure used for the preparation of (2S)-2-methoxy-3-[(3-phenoxy-propoxy)-phenyl]-propionic acid (Example 285, Step 1), to produce a white solid. MS (ES) for $C_{25}H_{24}O_5$ [M+Na]$^+$: 427.3.

Example 364

(2S)-3-[4-(2-butyl-phenoxy)-ethoxy-phenyl]-2-methoxy-propionic acid

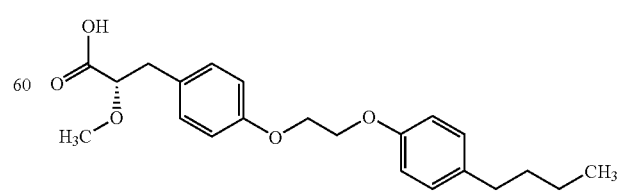

The title compound was prepared from (2S)-3-[4-(2-bromo-ethoxy)-phenyl]-2-methoxy-propionic acid ethyl ester (Example 283, Step 2) and 4-butyl-phenol via the same procedure used for the preparation of (2S)-2-methoxy-3-[4-(3-phenoxy-propoxy)-phenyl]-propionic acid (Example 285, Step 1), to produce a white solid. MS(ES) for $C_{22}H_{28}O_5$ [M+Na]$^+$: 395.3.

Example 365

(2S)-3-{4-[2-(2'-fluoro-biphenyl-4-yloxy)-ethoxy]-phenyl}-2-methoxy-propionic acid

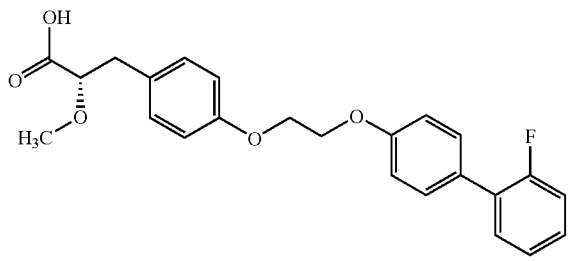

The title compound was prepared from (2S)-3-[4-(2-bromo-ethoxy)-phenyl]-2-methoxy-propionic acid ethyl ester (Example 283, Step 2) and 2'-fluoro-biphenyl-4-ol via the same procedure used for the preparation of (2S)-2-methoxy-3-[4-(3-phenoxy-propoxy)-phenyl]-propionic acid (Example 285, Step 1), to produce a white solid.

MS (ES) for $C_{24}H_{23}FO_5$ [M+Na]$^+$: 433.3.

Example 366

(2S)-3-(4-{2-[4-(2,2-dimethyl-propionyl)-phenoxy]-ethoxy}-phenyl)-2-methoxy-propionic acid

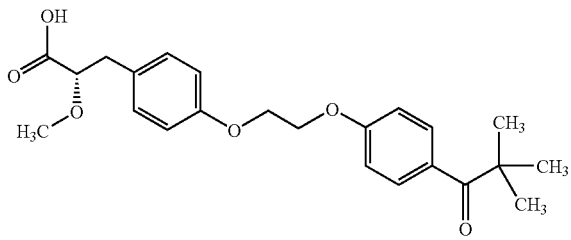

The title compound was prepared from (2S)-3-[4-(2-bromo-ethoxy)-phenyl]-2-methoxy-propionic acid ethyl ester (Example 283, Step 2) and 1-(4-hydroxy-phenyl)-2,2-dimethyl-propan-1-one via the same procedure used for the preparation of (2S)-2-methoxy-3-[4-(3-phenoxy-propoxy)-phenyl]-propionic acid (Example 285, Step 1), to produce a colorless oil. MS (ES) for $C_{23}H_{28}O_6$ [M+H]$^+$: 401.4.

Example 367

3-(4-{2-[4-(2,2-dimethyl-propionylamino)-phenoxy]-ethoxy}-phenyl)-2-methoxy-propionic acid

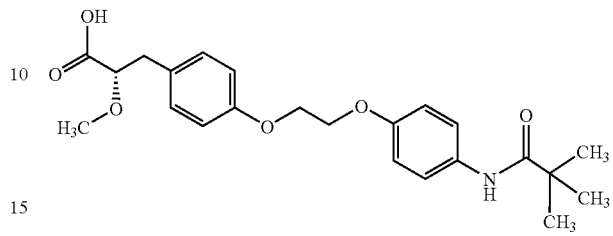

The title compound was prepared from (2S)-3-[4-(2-bromo-ethoxy)phenyl]-2-methoxy-propionic acid ethyl ester (Example 283, Step 2) and N-(4-hydroxy-phenyl)-2,2-dimethyl-propionamide via the same procedure used for the preparation of (2S)-2-methoxy-3-[4-(3-phenoxy-propoxy)-phenyl]-propionic acid (Example 285, Step 1), to produce a white solid. MS (ES) for $C_{23}H_{29}NO_6$ [M+H]$^+$: 416.4.

Example 368

(2S)-3-(4-{2-[4-(cyclopentanecarbonyl-amino)-phenoxy]-ethoxy}-phenyl)-2-methoxy-propionic acid

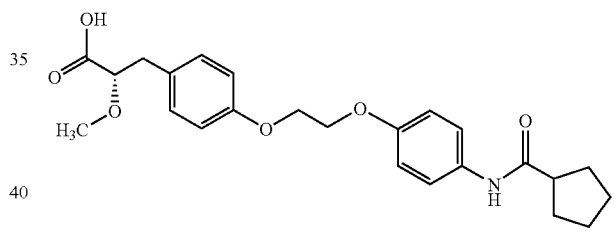

The title compound was prepared from (2S)-3-[4-(2-bromo-ethoxy)-phenyl]-2-methoxy-propionic acid ethyl ester (Example 283, Step 2) and cyclopentanecarboxylic acid (4-hydroxy-phenyl)-amide via the same procedure used for the preparation of (2S)-2-methoxy-3-[4-(3-phenoxy-propoxy)-phenyl]-propionic acid (Example 285, Step 1), to produce a white solid. MS (ES) for $C_{24}H_{29}NO_6$ [M+H]$^+$: 428.3.

Example 369

(2S)-3-[4-(2-{4-[(furan-2-carbonyl)-amino]-phenoxy}-ethoxy)-phenyl]-2-methoxy-propionic acid

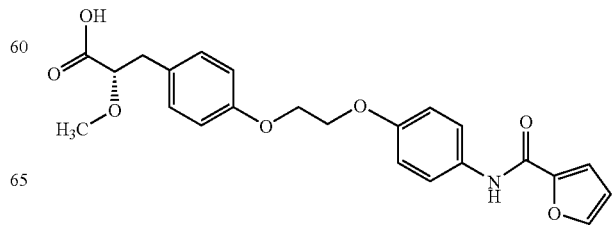

The title compound was prepared from (2S)-3-[4-(2-bromo-ethoxy)-phenyl]-2-methoxy-propionic acid ethyl ester (Example 283, Step 2) and furan-2-carboxylic acid (4-hydroxy-phenyl)-amide via the same procedure used for the preparation of (2S)-2-methoxy-3-[4-(3-phenoxy-propoxy)-phenyl]-propionic acid (Example 285, Step 1) to produce a white solid. MS (ES) for $C_{23}H_{23}NO_7$ [M+H]$^+$: 426.3.

Example 370

(2S)-2-methoxy-3-[4-(2-{4-[(pyridine-3-carbonyl)-amino]-phenoxy}-ethoxy)-phenyl]-propionic acid

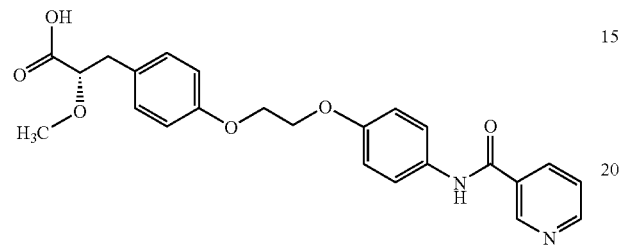

The title compound was prepared from (2S)-3-[4-(2-bromo-ethoxy)-phenyl]-2-methoxy-propionic acid ethyl ester (Example 283, Step 2) and N-(4-hydroxy-phenyl)-nicotinamide via the same procedure used for the preparation of (2S)-2-methoxy-3-[4-(3-phenoxy-propoxy)-phenyl]-propionic acid (Example 285, Step 1), to produce a white solid. MS (ES) for $C_{24}H_{24}N_2O_6$ [M+H]+: 437.3.

Example 371

(2S)-2-methoxy-3-{4-[2-(2-pyrrolidin-1-yl-phenoxy)-ethoxy]-phenyl}-propionic acid

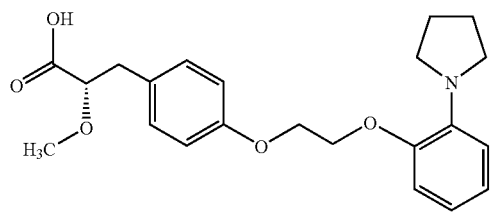

The title compound was prepared from (2S)-3-[4-(2-bromo-ethoxy)-phenyl]-2-methoxy-propionic acid ethyl ester (Example 283, Step 2) and 2-pyrrolidin-1-yl-phenol via the same procedure used for the preparation of (2S)-2-methoxy-3-[4-(3-phenoxy-propoxy)-phenyl]-propionic acid (Example 285, Step 1), to produce a yellow oil.
MS (ES) for $C_{22}H_{27}NO_5$ [M+H]$^+$: 386.3.

Example 372

(2S)-2-methoxy-3-{4-[2-(pyridin-2-yloxy)-ethoxy]-phenyl}-propionic acid

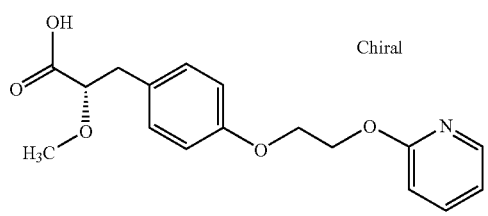

The title compound was prepared from (2S)-3-[4-(2-bromo-ethoxy)-phenyl]-2-methoxy-propionic acid ethyl ester (Example 283, Step 2) and pyridin-2-ol via the same procedure used for the preparation of (2S)-2-Methoxy-3-[4-(3-phenoxy-propoxy)-phenyl]-propionic acid (Example 285, Step 1); to produce a colorless oil. MS (ES) for $C_{17}H_{19}NO_5$ [M+H]$^+$: 318.3.

Example 373

(2S)-2-methoxy-3-{4-[2-(2-morpholin-4-yl-phenoxy)-ethoxy]-phenyl}-propionic acid

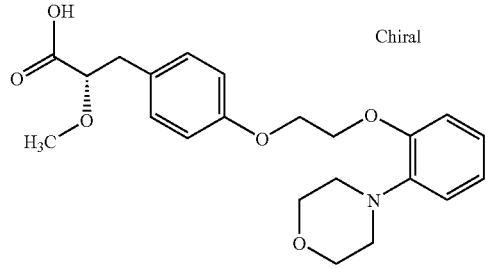

The title compound was prepared from (2S)-3-[4-(2-bromo-ethoxy)-phenyl]-2-methoxy-propionic acid ethyl ester (Example 283, Step 2) and 2-morpholin-4-yl-phenol via the same procedure used for the preparation of (2S)-2-methoxy-3-[4-(3-phenoxy-propoxy)-phenyl]-propionic acid (Example 285, Step 1), to produce a colorless oil.
MS (ES) for $C_{22}H_{27}NO_6$ [M+H]$^+$: 402.3.

Example 374

(2S)-3-{4-[2-(4'-tert-butyl-biphenyl-4-yloxy)-ethoxy]-phenyl}-2-methoxy-propionic acid

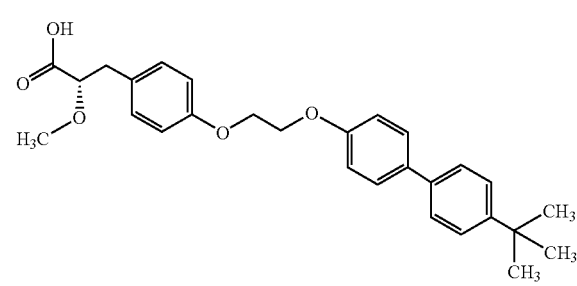

The title compound was prepared from (2S)-3-[4-(2-bromo-ethoxy)-phenyl]-2-methoxy-propionic acid ethyl ester Example 283, Step 2) and 4'-tert-butyl-biphenyl-4-ol via the same procedure used for the preparation of (2S)-2-methoxy-3-[4-(3-phenoxy-propoxy)-phenyl]-propionic acid (Example 285, Step 1), to produce a white solid.

MS (ES) for $C_{28}H_{32}O_5$ [M–H]$^-$: 447.2.

Example 375

(2S)-2-ethoxy-3-{4-[2-(4-phenoxy-phenoxy)-ethoxy]-phenyl}-propionic acid

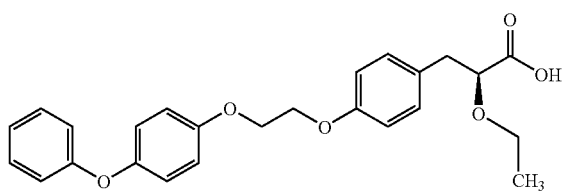

Step 1: 3-(4-benzyloxy-phenyl)-2-ethoxy-3-hydroxy-propionic acid ethyl ester

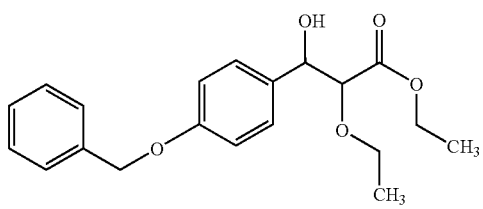

The title compound was prepared from 4-benzyloxybenzaldehyde, lithium diisopropylamide and ethyl 2-ethoxyacetate via the same procedure used for the preparation of 3-(3-benzyloxy-phenyl)-3-hydroxy-2-methoxy propionic acid methyl ester (Example 291, Step 1). MS (ES) for $C_{20}H_{24}O_5$ [M+H$_2$O–H]$^+$: 327, [M+Na]$^+$: 367.4.

Step 2: 3-(4-benzyloxy-phenyl)-2-ethoxy-acrylic acid ethyl ester

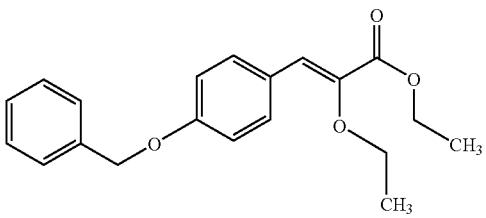

The title compound was prepared from 3-(4-benzyloxy-phenyl)-2-ethoxy-3-hydroxy-propionic acid ethyl ester (Example 375, Step 1) via the same procedure used for the preparation of 3-(4-benzyloxy-phenyl)-2-ethoxy-acrylic acid methyl ester. MS (ES) for $C_{20}H_{22}O_4$ [M+H]$^+$: 327.2.

Step 3: 3-(4-benzyloxy-phenyl)-2-ethoxy-propionic acid methyl ester

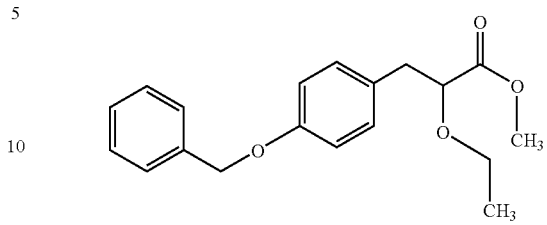

The title compound was prepared from 3-(4-benzyloxy-phenyl)-2-ethoxy-acrylic acid ethyl ester (Example 375, Step 2) (3.3 gr, 10.12 mmol) via the same procedure used for the preparation of 3-(3-benzyloxy-phenyl)-2-methoxy-propionic acid methyl ester (Example 291, Step 3) to produce an oil that was purified by chromatography (silica gel, hexanes/ethyl acetate 6:1) to produce two compounds: 3-(4-benzyloxy-phenyl)-propionic acid methyl ester (1.5 gr, Rf aprox. 0.65) and the desired compound (1.5 gr, Rf aprox. 0.2).

MS (ES) for $C_{19}H_{22}O_4$ [M+NH$_4$]$^+$: 332.3.

Step 4: 2-ethoxy-3-(4-hydroxy-phenyl)-propionic acid methyl ester

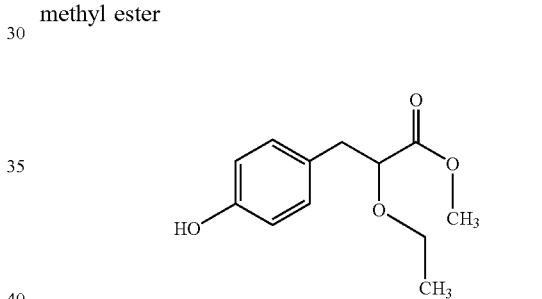

The title compound was prepared from 3-(4-benzyloxy-phenyl)-2-ethoxy-propionic acid methyl ester (example 375, Step 3) via the same procedure used for the preparation of 3-(3-hydroxy-phenyl)-2-methoxy-propionic acid methyl ester (Example 291, Step 4) to produce a yellow oil. MS (ES) for $C_{12}H_{16}O_4$ [M+H]$^+$: 225.2, [M+NH$_4$]$^+$: 242.2, [M+Na]$^+$: 247.2.

Step 5: 4-(2-bromo-ethoxy)-phenoxyphenyl

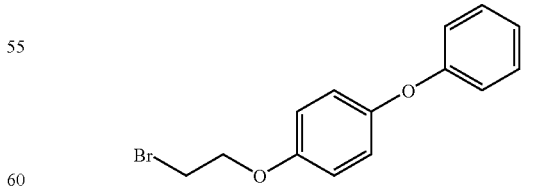

The title compound was prepared from 4-phenoxy-phenol via the same procedure used for the preparation of (2S)-3-[4-(2-bromo-ethoxy)-phenyl]-2-methoxy-propionic acid ethyl ester (Example 283, Step 2) to produce a white solid. MS (ES) for $C_{14}H_{13}BrO_2$ [M–H]$^-$: 291.0.

Step 6: (2S)-2-ethoxy-3-{4-[2-(4-phenoxy-phenoxy)-ethoxy]-phenyl}-propionic acid

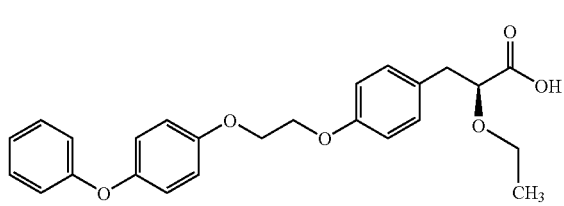

The title compound was prepared from 2-ethoxy-3-(4-hydroxy-phenyl)-propionic acid methyl ester Example 375, Step 4) and 4-(2-bromo-ethoxy)-phenoxyphenyl (Example 375, Step 5) via the same procedure used for the preparation of (2S)-3-{4-[2-(biphenyl-4-yloxy)-ethoxy]-phenyl}-2-methoxy-propionic acid (Example 283, Step 3). The crude material was submitted to chiral HPLC separation to afford the single enantiomer isomer 2. MS (ES) for $C_{25}H_{26}O_6$ [M–H]$^-$: 421.4.

Example 376

(2R)-2-ethoxy-3-{4-[2-(4-phenoxy-phenoxy)-ethoxy]-phenyl}-propionic acid

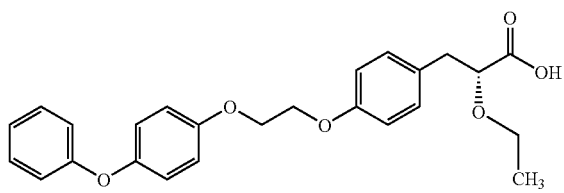

The title compound was prepared from 2-ethoxy-3-(4-hydroxy-phenyl)-propionic acid methyl ester (Example 375, Step 4) and 4-(2-bromo-ethoxy)-phenoxyphenyl (Example 375, Step 5) via the same procedure used for the preparation of (2S)-3-{4-[2-(biphenyl-4yloxy)-ethoxy]-phenyl}-2-methoxy-propionic acid (Example 283, Step 3). The crude material was submitted to chiral HPLC separation to afford the single enantiomer isomer 1. MS (ES) for $C_{25}H_{26}O_6$ [M–H]$^-$: 421.4.

Example 377

(2S)-3-{4-[2-(biphenyl-4-yloxy)-ethoxy]-phenyl}-2-propoxy-propionic acid

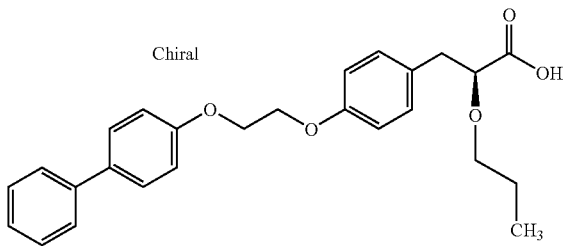

Step 1: 4-(2-bromo-ethoxy)biphenyl

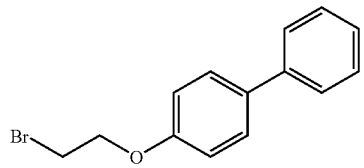

The title compound was prepared from biphenyl-4-ol via the same procedure used for the preparation of (2S)-3-[4-(2-bromo-ethoxy)-phenyl]-2-methoxy-propionic acid ethyl ester (Example 283, Step 2) to produce a white solid. MS (ES) for $C_{14}H_{13}BrO$ [M–H]$^-$: 279.1.

Step 2: (2S)-3-(4-benzyl-phenyl)-2-hydroxy-propionic acid ethyl ester

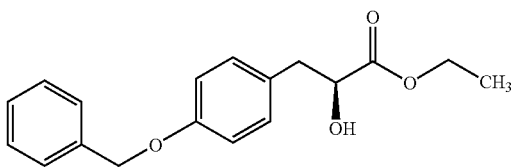

The title compound was prepared from (2S)-3-(4-benzyloxy-phenyl)-2-hydroxy-propionic acid via the same procedure used for the preparation of (2S)-3-(4-hydroxy-phenyl)-2-methoxy-propionic acid ethyl ester (Example 283, Step 1) to afford the product as a yellow oil. $^1$H-NMR (CDCl$_3$, 200.15 MHz): 7.35–7.55 (m, 5H), 7.20 (d, 2H, J=8.3), 6.79 (d, 2H, J=8.3), 4.99 (s, 2H), 4.41 (dd, 1H, J=6.5, 4.4), 4.19 (c, 2H, J=6.9), 2.92 (2dd, 2H, J=16.1, 4.4), 1.23 (t, 3H, J=6.9).

Step 3: (2S)-3-(4-benzyloxy-phenyl)-2-propoxy-propionic acid ethyl ester

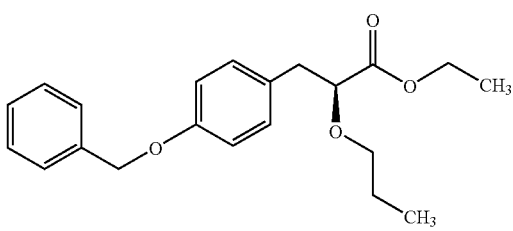

Propyl iodide (41.6 mmol) was added at room temperature to a solution of (2S)-3-(4-benzyloxy-phenyl)-2-hydroxy-propionic acid ethyl ester (Example 377, Step 2) (8.3 mmol) and silver oxide (12.45 mmol) in 40 mL of DMF. The mixture was heated at 50° C. for 24 hours. After that the mixture was cooled to room temperature, 300 ml of ethyl acetate and 200 ml of water were added. The aqueous layer was separated and the organic layer were washed with brine (3×100 ml), and then dried over (MgSO$_4$), filtered and concentrated under vacuum. The crude was purified by chromatography (silica gel, hexanes/ethyl acetate 6:1) to produce a yellow oil. $^1$H-NMR (CDCl$_3$, 200.15 MHz): 7.42–7.31 (m, 5 H), 7.17 (d, 2 H, J=8.6 Hz), 6.90 (d, 2 H, J=8.6 Hz), 5.05 (s, 2 H), 4.17 (q, 2 H, J=7.0 Hz), 3.97 (dd, 1 H, J=7.0, 6.2 Hz), 3.53 (dt, 1 H, J=8.9, 6.4 Hz), 3.23 (dt, 1 H, J=9.1, 6.7 Hz), 2.97 (d, 2 H, J=6.7 Hz), 1.66–1.48 (m, 2 H), 1.23 (t, 3 H, J=7.3 Hz), 0.86 (t, 3 H, J=7.5 Hz).

Step 4: (2S)-3-(4-hydroxy-phenyl)-2-propoxy-propionic acid ethyl ester

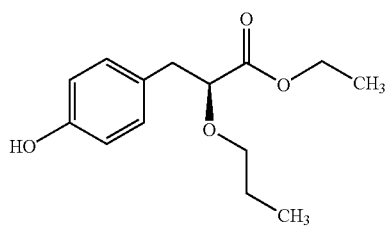

The title compound was prepared from (2S)-3-(4-beyloxy-phenyl)-2-propoxy-propionic acid ethyl ester (Example 377, Step 3) via the same procedure used for the preparation of 3-(3-hydroxy-phenyl)-2-methoxy-propionic acid methyl ester (Example 291, Step 4) to produce a yellow oil. MS (ES) for $C_{14}H_{20}O_4$ [M+H]$^+$: 253.1.

Step 5: (2S)-3-{4-[2-(biphenyl-4-yloxy)-ethoxy]-phenyl}-2-propoxy-propionic acid

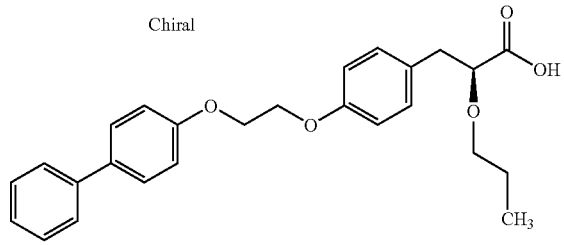

The title compound was prepared from 4-(2-bromo-ethoxy)-biphenyl (Example 377, Step 1) and (2S)-3-(4-hydroxy-phenyl)-2-propoxy-propionic acid ethyl ester (Example 377, Step 4) via the same procedure used for the preparation of (2S)-3-{4-[2-(biphenyl-4-yloxy)-ethoxy]-phenyl}-2-methoxy-propionic acid (Example 283, Step 3) to produce a white solid. MS (ES) for $C_{26}H_{28}O_5$ [M+H]$^+$: 421.0, [M+NH$_4$]$^+$: 438.0, [M+Na]$^+$: 443.0, [M–H]$^-$: 3239.2.

Example 378

3-{3-[3-(biphenyl-4-yloxy)-propoxy]-phenyl}-2-ethoxy-propionic acid (isomer 1)

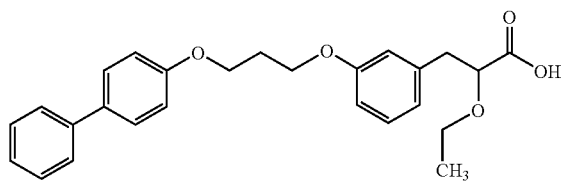

Step 1: 3-(3-benzyloxy-phenyl)-2-ethoxy-3-hydroxy-propionic acid ethyl ester

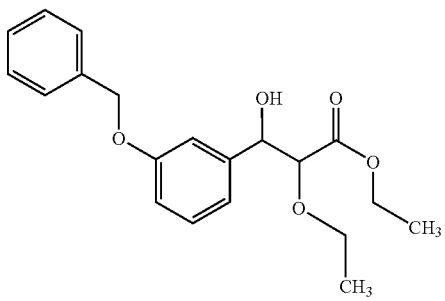

The title compound was prepared from 3-benzyloxy-benzaldehyde and ethyl ethoxyacetate via the same procedure used for the preparation of 3-(3-benzyloxy-phenyl)-3-hydroxy-2-methoxy-propionic acid methyl ester (Example 291, Step 1) to afford the title compound as a colorless oil.

Step 2: 3-(3-benzyloxy-phenyl)-2-ethoxy-acrylic acid ethyl ester

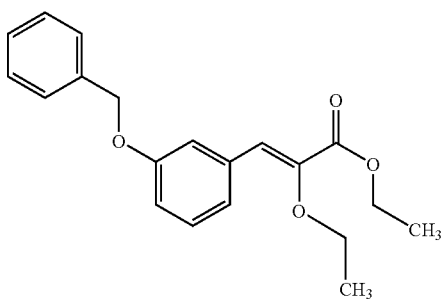

The title compound was prepared from 3-(3-benzyloxy-phenyl)-2-ethoxy-3-hydroxy-propionic acid ethyl ester (Example 378, Step 1) via the same procedure used for the preparation of 3-(3-benzyloxy-phenyl)-2-methoxy-acrylic acid methyl ester (Example 291, Step 2) to afford the title compound as a colorless oil.

Step 3: 3-(3-benzyloxy-phenyl)-2-ethoxy-propionic acid methyl ester

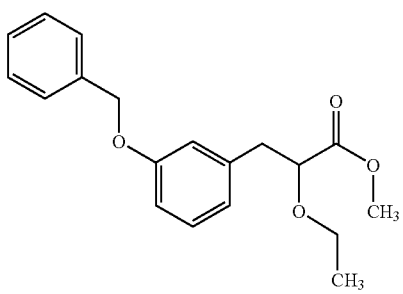

The title compound was prepared from 3-(3-benzyloxy-phenyl)-2-ethoxy-acrylic acid ethyl ester Example 378, Step 2) via the same procedure used for the preparation of 3-(3-benzyloxy-phenyl)-2-methoxy-propionic acid methyl ester (Example 291, Step 3) to afford the title compound as a colorless oil.

Step 4: 2-ethoxy-3-(3-hydroxy-phenyl)-propionic acid methyl ester

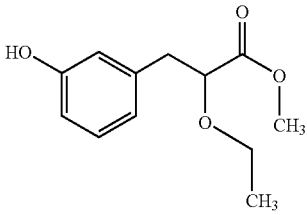

The title compound was prepared from 3-(3-benzyloxy-phenyl)-2-ethoxy-propionic acid methyl ester (Example 378, Step 3) via the same procedure used for the preparation of 3-(3-hydroxy-phenyl)-2-methoxy-propionic acid methyl ester (Example 291, Step 4) to afford the title compound as a yellow oil. MS (ES) for $C_{12}H_{16}O_4$ [M+H]$^+$: 225.1.

Step 5: (3-{3-[3-(biphenyl-4-yloxy)-propoxy]-phenyl}-2-ethoxy-propionic acid (isomer 1)

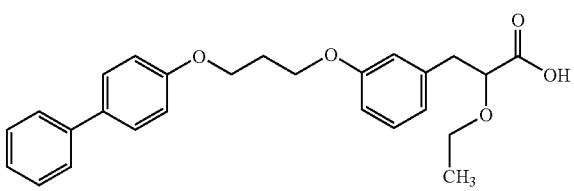

The title compound was prepared from 3-(biphenyl-4-yloxy)-propan-1-ol (Example 291, Step 6) and 2-ethoxy-3-(3-hydroxy-phenyl)-propionic acid methyl ester (Example 378, Step 4) via the same procedure used for the preparation of (2S)-3-{4-[2-(biphenyl-4-yloxy)-ethoxy]-phenyl}-2-methoxy-propionic acid (Example 283, Step 3) to produce a white solid. The crude material was submitted to chiral HPLC separation to afford the single enantiomer isomer 1. (ES) for $C_{26}H_{28}O_5$ [M+NH$_4$]$^+$: 438.0, [M+Na]$^+$: 443.0.

Example 379

3-{3-[3-(biphenyl-4-yloxy)-propoxy]-phenyl}-2-ethoxy-propionic acid (isomer 2)

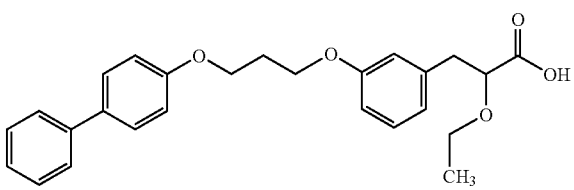

The title compound was prepared from 3-(biphenyl-4-yloxy)-propan-1-ol (Example 291, Step 6) and 2-ethoxy-3-(3-hydroxy-phenyl)-propionic acid methyl ester (Example 378, Step 4) via the same procedure used for the preparation of (2S)-3-{4-[2-(biphenyl-4-yloxy)-ethoxy]-phenyl}-2-methoxy-propionic acid (Example 283, Step 3) to produce a white solid. The crude material was submitted to chiral HPLC separation to afford the single enantiomer isomer 2. MS (ES) for $C_{26}H_{28}O_5$ [M+NH$_4$]$^+$: 438.0, [M+Na]$^+$: 443.0.

Example 380

Binding Assay:

DNA-dependent binding was carried out using Scintillation Proximity Assay (SPA) technology. PPARγ as well as its heterodimeric partner RXRα were prepared using a baculovirus expression system. A biotinylated complementary oligonucleotide duplex representing the human consensus PPR response element was used for binding receptor dimer to Yttrium silicate streptavidin-coated SPA beads. The 5'-3' strand had the sequence: $^{5'}$TAATGTAGGTAATAGT-TCAATAGGTCAAAGG$^{3'}$ (SEQ ID NO: 1); biotin was bound to the first A at the 3' end of the complementary 3'-5' strand. The PPARγ labeled ligand was $^3$H-(s)-3-{4-[3-(biphenyl-4-yloxy)-propoxy]-phenyl}-2-methoxy-propionic acid with specific activity of 24 Ci/mmol. The binding assay was carried out on 96 well dishes. Per well, 100 ng of oligonucleotide was preincubated with 3 μg SPA beads in a binding buffer containing 10 mM HEPES pH 7.8, 80 mM KCl, 0.5 mM MgCl$_2$, 1 mM DTT, 0.5% CHAPS and 16.6 μg bovine serum albumin for 30 minutes at room temperature. The mixture was then spun at 2000 rpm for 3 minutes to pellet the beads-oligo mix. The supernatant was removed, and the beads-oligo pellet was resuspended in the same binding buffer as above but also containing 14% glycerol, 5 μg sheared salmon sperm DNA and 2.5 μg of each receptor, PPARγ and RXRα. A saturation binding assay was carried out using increasing amounts of $^3$H-(s)-3-{4-[3-(biphenyl-4-yloxy)-propoxy]-phenyl}-2-methoxy-propionic acid in the reaction to obtain 0.39 nM to 402 nM of $^3$H-(s)-3-{4-[3-(biphenyl-4-yloxy)-propoxy]-phenyl}-2-methoxy-propionic acid. Non-specific binding was measured in the presence of 10 μM of unlabeled (s)-3-{4-[3-(biphenyl-4-yloxy)-propoxy]-phenyl}-2-methoxy-propionic acid. A K$_d$ value was calculated from the saturation binding experiments after plotting specific binding versus concentration of labeled ligand. Competition binding reactions were carried in the presence of 30,000 cpm of $^3$H-(s)-3-{4-[3-(biphenyl-4-yloxy)-propoxy]-phenyl}-2-methoxy-propionic acid and 5 nM to 10 μM of competing compounds. The IC$_{50}$ (nM) values for competing compounds were calculated after deduction of non-specific binding (measured in the presence of 10 μM unlabeled $^3$H-(s)-3-{4-[3-(biphenyl-4-yloxy)-propoxy]-phenyl}2-methoxy-propionic acid), and the data normalized to total binding (if the absence of any unlabeled compound). The $^3$H-(s)-3-{4-[3-(biphenyl-4-yloxy)-propoxy]-phenyl}-2-methoxy propionic acid was effective in determining the binding affinity of PPAR subtypes in the range of 5 nM to 10000 nM. For example, PPAR compounds with IC$_{50}$ values less than 500 nM were identified as ligands for PPAR gamma.

Preparation of $^3$H-(s)-3-{4-[3-(biphenyl-4-yloxy-propoxy]-phenyl}-2-methoxy-propionic acid

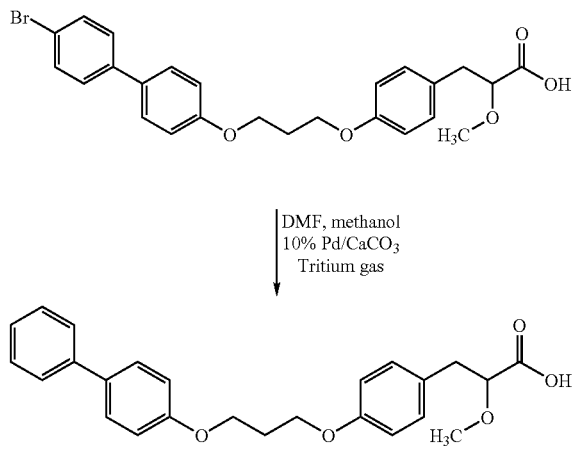

In a reaction vessel (s)-3-{4-[3-(4'-bromo-biphenyl-4-yloxy)-propoxy]-phenyl}-2-methoxy-propionic acid (6.1 mg) was combined with 10% Pd/CaCO$_3$ (18.6 mg), DMF (0.5 ml) and methanol (0.5 ml). The mixture was stirred under 10 Ci of tritium gas for about 4.5 hours. The catalyst was removed by filtration, and the labile activity was removed by repeated rotary evaporations with methanol. The final residue was dissolved in ethanol. The crude product was purified by reverse phase HPLC eluting with a water/acetonitrile/TFA gradient system. The major UV and radioactive peak was collected and rotary evaporated to dryness. The resulting residue was dissolved in ethanol (yield: 102 mCi)

Example 381

Binding and Cotransfection Studies

The in vitro potency of compounds in modulating PPARα and PPARγ receptors were determined by the procedures detailed below. DNA-dependent binding (ABCD binding) was carried out using Scintillation Proximity Assay (SPA) technology with PPAR receptors. Tritium-labeled PPARα and PPARγ agonists were used as radioligands for generating displacement curves and IC$_{50}$ values with compounds of the present invention. Cotransfection assays were carried out in CV-1 cells. The reporter plasmid contained an acylCoA oxidase (AOX) PPRE and TK promoter upstream of the luciferase reporter cDNA. Appropriate PPARs and RXRα were constitutively expressed using plasmids containing the CMV promoter. Since for PPARα and PPARβ/δ, interference by endogenous PPARγ in CV-1 cells is an issue, in order to eliminate such interference, a GAL4 chimeric system was used in which the DNA binding domain of the transfected PPAR is replaced by that of GAL4, and the GAL4 response element was utilized in place of the AOX PPRE. Cotransfection efficacy was determined relative to PPAR-isotope specific reference compounds. Efficacies were determined by computer fit to a concentration-response curve, or in some cases at a single high concentration of agonist (10 µM). Typical range for concentration determination IC$_{50}$ is in the range of 1 nM to 10 µM. For binding or cotransfection studies with receptors other than PPARs, similar assays were carried out using appropriate ligands, receptors, reporter constructs for that particular receptor.

These studies were carried out to evaluate the ability of compounds of the present invention to bind to and/or activate various nuclear transcription factors, particularly huPPARα ("hu" indicates "human") and huPPARγ. These studies provided in-vitro data concerning efficacy and selectivity of compounds of the present invention. Furthermore, binding and cotransfection data for compounds of the present invention were compared with corresponding data for marketed compounds that act on either huPPARα or huPPARγ. Binding and cotransfection data for representative compounds of the present invention were compared with corresponding data for reference compounds to determine the binding.

The concentration of test compound required to effect 50% maximal activation of PPARα (IC$_{50}$α) and PPARγ (IC$_{50}$γ) was determined. Many of the compounds of the present invention are selective agonists for PPARγ or are co-agonists of PPARα/PPARγ.

Evaluation of Triglyceride and Cholesterol Levels in HuapoAI Transgenic Mice

Five to six week old male mice, transgenic for human apoAI [C57B1/6-tgn(apoa1)1rub, Jackson Laboratory, Bar Harbor, Me.] were housed five per cage (10"×20"×8" with aspen chip bedding) with food (Purina 5001) and water available at all times. After an acclimation period of 2 weeks, animals were individually identified by ear notches, weighed and assigned to groups based on body weight. Beginning the following morning, mice were dosed daily by oral gavage for 7 days using a 20 gauge, 1½" curved disposable feeding needle. Treatments were test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice were weighed and dosed. Three hours after dosing, animals were anesthetized by inhalation of isoflurane (2–4%) and blood obtained via cardiac puncture (0.7–1.0 ml). Whole blood was transferred to serum separator tubes (Vacutainer SST), chilled on ice and permitted to clot. Serum, was obtained after centrifugation at 4° C. and frozen until analysis for triglycerides, total cholesterol, compound levels and serum lipoprotein profiled by fast protein liquid, chromatography (FPLC) coupled to an inline detection system. After sacrifice by cervical dislocation, the liver, heart and epididymal fat pads were excised and weighed.

The animals dosed with vehicle had average triglycerides values of about 60 to 80 mg/dl, which were reduced by the positive control fenofibrate (33–58 mg/dl with a mean reduction of 37%). The animals dosed with vehicle have average total serum cholesterol values of about 140 to 180 mg/dl, which were increased by fenofibrate (about 190 to 280 mg/dl with a mean elevation of 41%). When subject to FPLC analysis, pooled sera from vehicle-treated hu apoAI transgenic mice had a high-density lipoprotein cholesterol (HDLc) peak area which ranged from 47 v-sec to 62 v-sec. Fenofibrate increased the amount of HDLc (68–96 v-sec with a mean percent increase of 48%). Test compounds were evaluated in terms of percent increase in the area under the curve. Representative compounds of the present invention were tested using the above method or substantially similar methods.

Evaluation of Glucose Levels in db/db Mice

Five week old male diabetic (db/db) mice [C57BlKs/j-m+/+Lepr(db), Jackson Laboratory, Bar Harbor, Me.] or lean littermates (db+) were housed 6 per cage (10"×20"×8" with aspen chip bedding) with food (Purina 5015) and water available at all times. After an acclimation period of 2 weeks, animals were individually identified by ear notches, weighed and bled via the tail vein for determination of initial glucose levels. Blood was collected (100 µl) from unfasted animals by wrapping each mouse in a towel, cutting the tip of the tail with a scalpel, and milking blood from the tail into a heparinized capillary tube balanced on the edge of the bench. Sample was discharged into a heparinized microtainer with gel separator (VWR) and retained on ice. Plasma was obtained after centrifugation at 4° C. and glucose was measured immediately. Remaining plasma was frozen until the completion of the experiment, and glucose and triglycerides were assayed in all samples. Animals were grouped based on initial glucose levels and body weights. Beginning the following morning, mice were dosed daily by oral gavage for 7 days using a 20 gauge, 1½" curved disposable feeding needle. Treatments were test compounds (30 mg/kg), a positive control agent (30 mg/kg) or vehicle [1% carboxymethylcellulose (w/v)/0.25% Tween80 (w/v); 0.3 ml/mouse]. On day 7, mice were weighed and bled (tail vein) for about 3 hours after dosing. Twenty-four hours after the $7^{th}$ dose (i.e., day 8), animals were bled again (tail vein). Samples obtained from conscious animals on days 0, 7 and 8 were assayed for glucose. After 24 hour bleed, animals were weighed and dosed for the final time. Three hours after dosing on day 8, animals were anesthetized by inhalation of isoflurane, and blood obtained was via cardiac puncture (0.5–0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed.

The animals dosed with vehicle-had average triglycerides values of about 170 to 230 mg/dl, which were reduced by the positive PPARγ control (about 70 to 120 mg/dl with a mean reduction of 50%). Male db/db mice are hyperglycemic (average glucose of about 680 to 730 mg/dl on the $7^{th}$ day of treatment), while lean animals have average glucose levels between about 190 and 230 mg/dl. Treatment with the positive control agent reduced glucose significantly (about 350 to 550 mg/dl with a mean decrease towards normalization of 56%).

Glucose was measured colorimetrically by using commercially purchased reagents (Sigma #315-500). According to the manufacturers, the procedures were modified from published work (McGowan et al. *Clin Chem,* 20:470–5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte coupled with a color reaction first described by Trinder (Trinder, P. *Ann Clin Biochem,* 6:24 (1969)). The absorbance of the dye produced was linearly related to the analyte in the sample. The assays was further modified for use in a 96 well format. Standards (Sigma #339-11, Sigma #16-11, and Sigma #CC0534 for glucose, triglycerides and total cholesterol, respectively), quality control plasma (Sigma # A2034), and samples-(2 or 5 µl well) were measured in duplicate using 200 µl of reagent. An additional aliquot of sample, pipetted to a third well and diluted in 200 µl water, provided ai blank for each specimen. Plates were incubated at room temperature (18, 15, and 10 minutes for glucose, triglycerides and total cholesterol, respectively) on a plate shaker and absorbance read at 500 nm (glucose and total cholesterol) or 540 nm (triglycerides) on a plate reader. Sample absorbance was compared to a standard curve (100–800, 10–500, and 100–400 mg/dl for glucose, triglycerides and total cholesterol, respectively). Values for the quality control sample wee consistently within the expected range and the coefficient of variation for samples is below 10%. All samples from an experiment were assayed at the same time to minimize inter-assay variability.

Serum lipoproteins were separated and cholesterol was quantitated with an in-line detection system. Sample was applied to a Superose® 6 HR 10/30 size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min was mixed with the column effluent through a T-connection, and the mixture was passed through a 15 m×0.5 mm id knitted tubing reactor immersed in a 37° C. water bath. The colored product produced in the presence of cholesterol was monitored in the flow stream at 505 nm, and the analog voltage from the monitor was converted to a digital signal for collection and analysis. The change in voltage corresponding to change in cholesterol concentration was plotted against time, and the area under the curve corresponding to the elution of VLDL, LDL and HDL was calculated (Perkin Elmer Turbochrome software).

While this invention has been particularly shown and described with references to preferred embodiments thereof, it will be understood by those skilled in the art that various changes in form and details maybe made therein without departing from the scope of the invention encompassed by the appended claims.

What is claimed is:

1. A compound represented by the following structural formula:

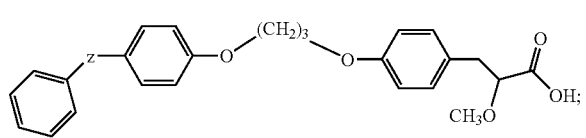

or pharmaceutically acceptable salts, hydrates, stereoisomers and solvates thereof, wherein Z is —O— or —CO—.

2. A compound represented by the following structural formula

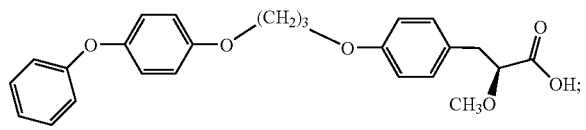

or pharmaceutically acceptable salts, hydrates and solvates thereof.

3. A compound selected from the group consisting of (S)-2-Methoxy-3-{4-[3-(4-phenoxy-phenoxy)-propoxy]-phenyl}-propionic acid, represented by the following structural formula:

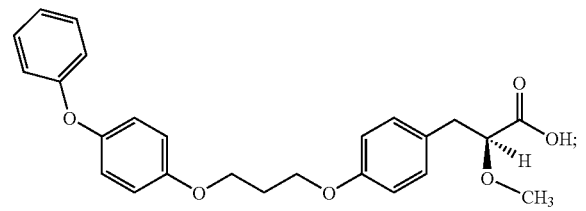

(S)-3-{4-[3 (Biphenyl-4-yloxy)-propoxy]-phenyl}-2-methoxy-propionic acid, represented by the following structural formula:

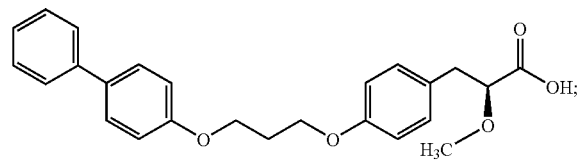

(S)-3-{4-[3-(Biphenyl-4-yloxy)-prop-1-ynyl]-phenyl}-2-methoxy-propionic acid, represented by the following structural formula:

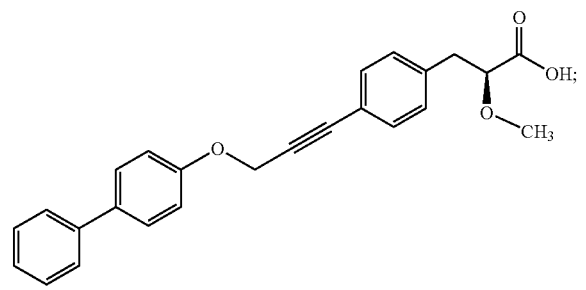

(S)-3-{4-[3-(4-Benzoyl-phenoxy)-propoxy]-phenyl}-2-methoxy-propionic acid, represented by the following structural formula:

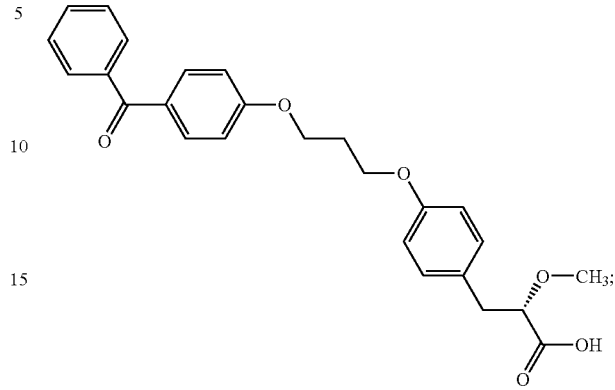

(S)-3-(4-{3-[4-(4-Fluoro-benzoyl)-phenoxy]-propoxy}-phenyl)-2-methoxy-propionic acid, represented by the following structural formula:

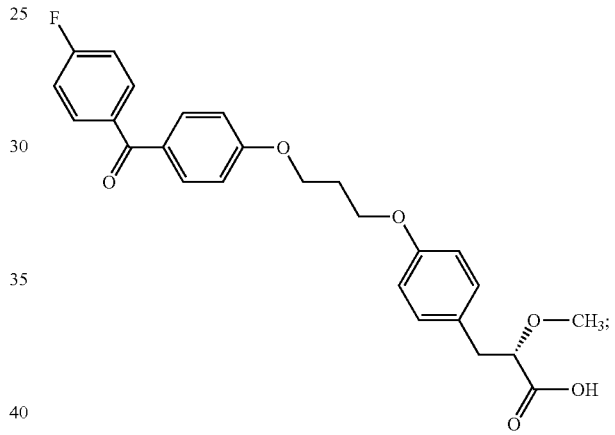

(S)-3-{4-[3-(4-Benzoyl-phenoxy)-propoxy]-3-methoxy-phenyl}-2-methoxy-propionic acid, which is represented by the following structural formula:

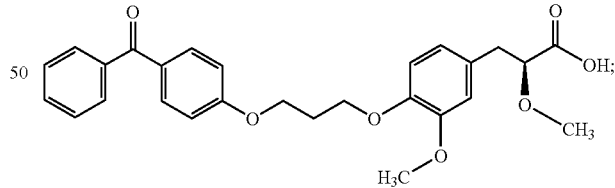

(S)-3-{4-[4-(Biphenyl-4-yloxy)-but-1-ynyl]-phenyl}-2-methoxy-propionic acid, which is represented by the following structural formula:

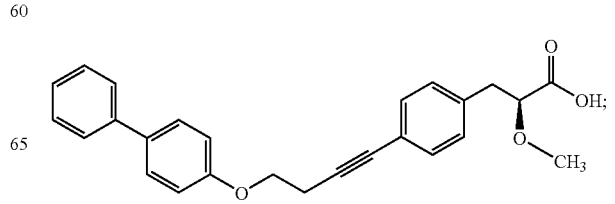

(S)-3-{4-[3-(4-Benzyl-phenoxy)-propoxy]-phenyl}-2-methoxy-propionic acid, which is represented by the following structural formula:

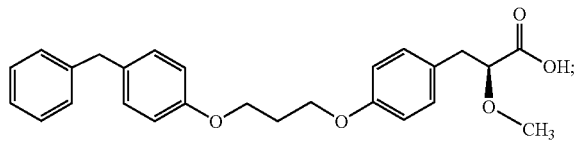

(S)-3-{4-[3-(4-Benzoyl-phenoxy)-prop-1-ynyl]-phenyl}-2-methoxy-propionic acid, which is represented by the following structural formula:

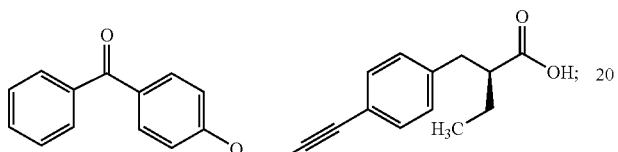

(S)-2-Methoxy-3-{4-[3-(4-phenoxy-phenoxy)-prop-1-ynyl]-phenyl}-propionic acid, which is represented by the following structural formula:

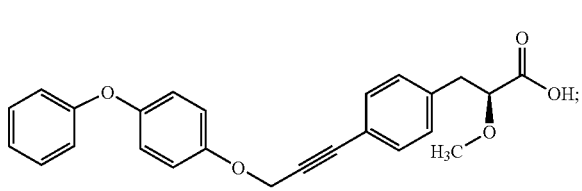

(S)-3-{4-[3-(Biphenyl-4-yloxy)-propoxy]-2-fluoro-phenyl}-2-methoxy-propionic acid, which is represented by the following structural formula:

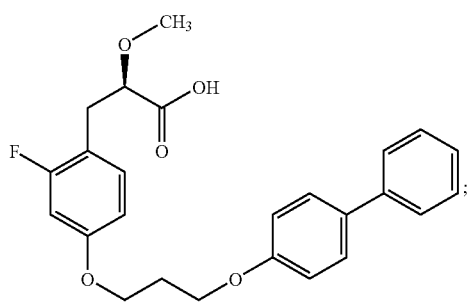

(S)-3-{4-[3-(4-Butyl-phenoxy)-propoxy]-phenyl}-2-methoxy-propionic acid, which is represented by the following structural formula:

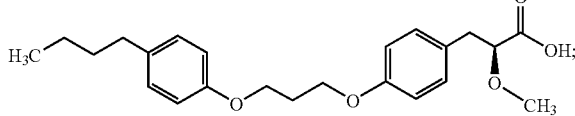

(S)-2-Methoxy-3-{4-[4-(4-phenoxy-phenoxy)-but-1-ynyl]-phenyl}-propionic acid, which is represented by the following structural formula:

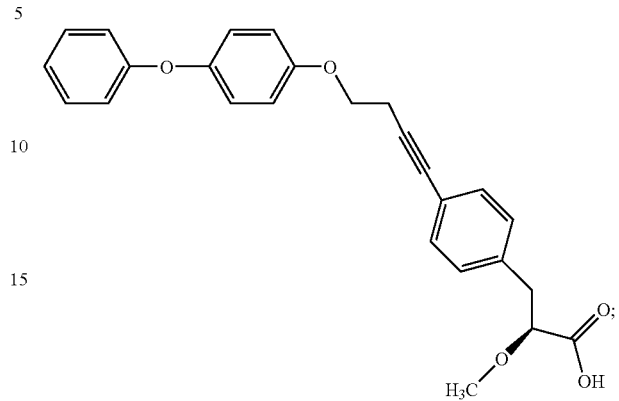

(2S)-3-(4-{2-[4-(4-Fluoro-benzoyl)-phenoxy]-cyclopentyloxy}-phenyl)-2-methoxy-propionic acid, which is represented by the following structural formula:

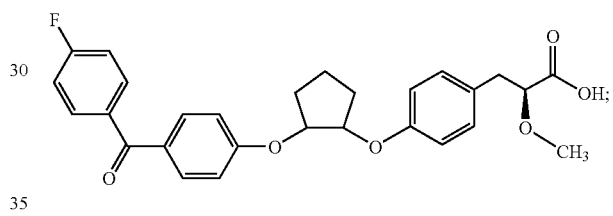

(S)-3-{4-[5-(Biphenyl-4-yloxy)-pent-1-ynyl]-phenyl}-2-methoxy-propionic acid, which is represented by the following structural formula:

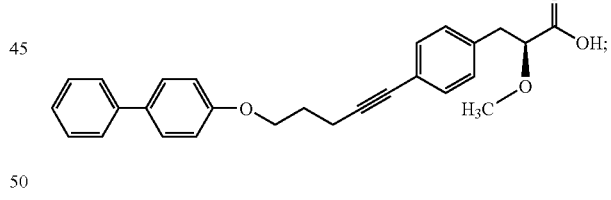

(S)-3-{4-[2-(4-Benzoyl-phenoxy)-ethoxy]-phenyl}-2-methoxy-propionic acid, which is represented by the following structural formula:

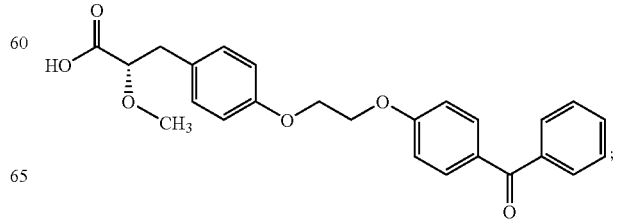

(S)-3-{4-[5-(Biphenyl-4-yloxy)-pentanoyl]-phenyl}-2-methoxy-propionic acid, represented by the following structural formula:

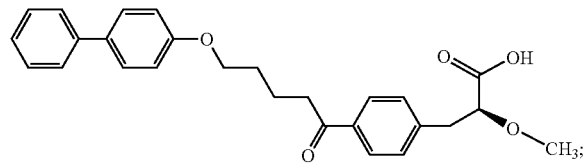

(S)-3-{4-[3-(Biphenyl-4-yloxy)-cyclopentyloxy]-phenyl}-2-methoxy-propionic acid, represented by the following structural formula:

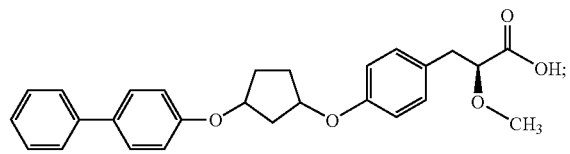

(S)-3-{4-[4-(4-Benzoyl-phenoxy)-but-1-ynyl]-phenyl}-2-methoxy-propionic acid, represented by the following structural formula:

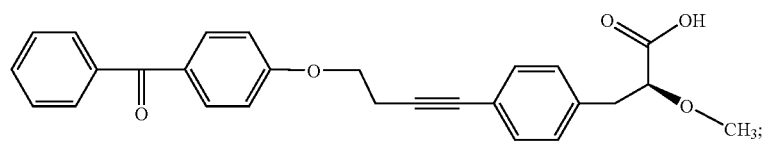

(S)-3-{4-[4-(4-Benzoyl-phenoxy)-butyryl]-phenyl}-2-methoxy-propionic acid, represented by the following structural formula:

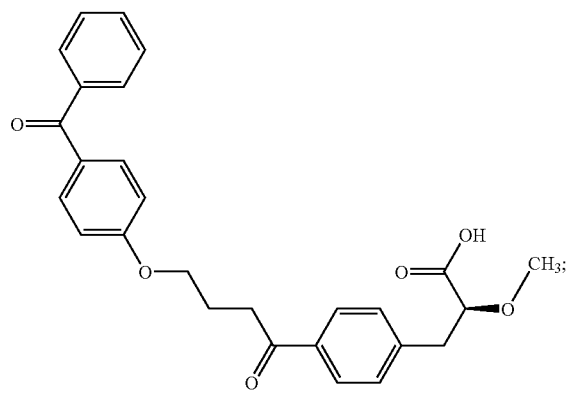

(S)-2-Methoxy-3-{4-[5-(4-phenoxy-phenoxy)-pent-1-ynyl]-phenyl}-propionic acid, represented by the following structural formula:

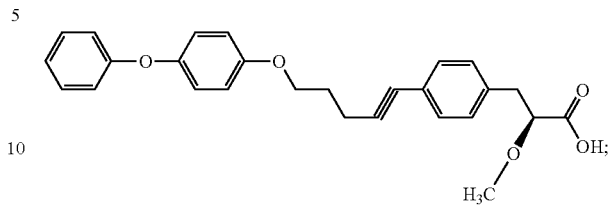

(S)-3-{4-[5-(4-Benzoyl-phenoxy)-pent-1-ynyl]-phenyl}-2-methoxy-propionic acid, represented by the following structural formula:

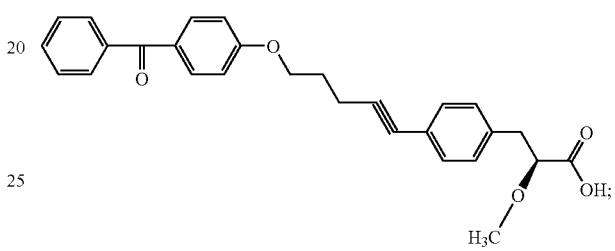

(S)-3-{4-[3-(Biphenyl-4-yloxy)-propoxy]-3-methoxy-phenyl}-2-methoxy-propionic acid, represented by the following structural formula:

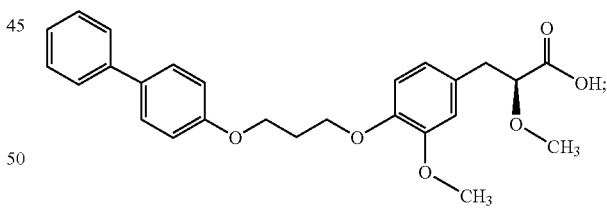

(S)-2-Methoxy-3-{3-methoxy-4-[3-(4-phenoxy-phenoxy)-propoxy]-phenyl}-propionic acid, represented by the following structural formula:

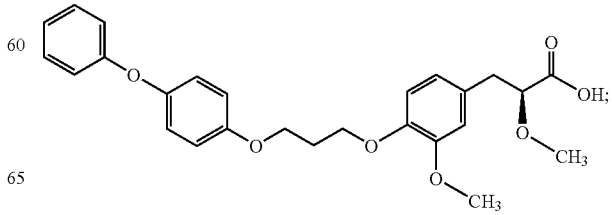

(S)-3-{4-[4-(4-Benzoyl-phenoxy)-butoxy]-phenyl}-2-methoxy-propionic acid, represented by the following structural formula:

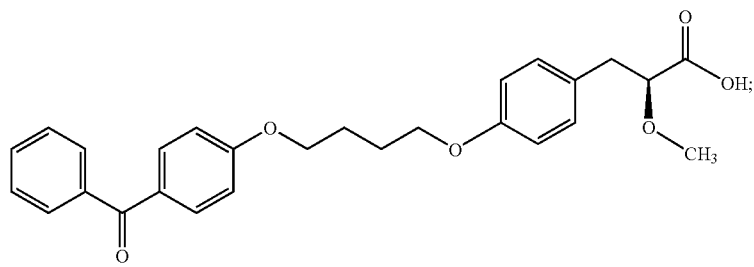

(S)-3-{4-[5-(4-Benzoyl-phenoxy)-pentanoyl]-phenyl}-2-methoxy-propionic acid, represented by the following structural formula:

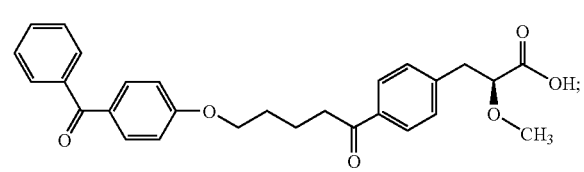

(S)-2-Methoxy-3-{4-[3-(4-phenylacetyl-phenoxy)-propoxy]-phenyl}-propionic acid, represented by the following structural formula:

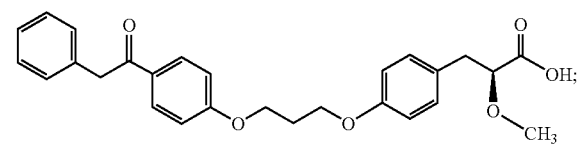

2-Methoxy-3-(4-{3-[4-(4-trifluoromethyl-phenoxy)-phenoxy]-propoxy}-phenyl)-propionic acid, represented by the following structural formula:

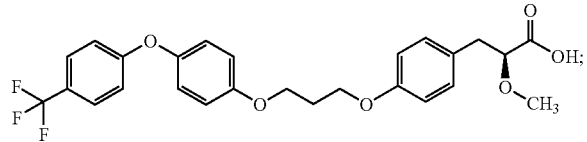

3-(4-{4-[4-(Hydroxyimino-phenyl-methyl)-phenoxy]-but-1-ynyl}-phenyl)-2-methoxy-propionic acid, represented by the following structural formula:

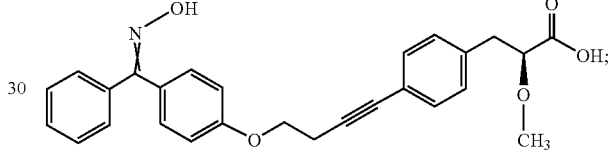

2-Methoxy-3-{4-[1-methyl-2-(4-phenoxy-phenoxy)-propoxy]-phenyl}-propionic acid, represented by the following structural formula:

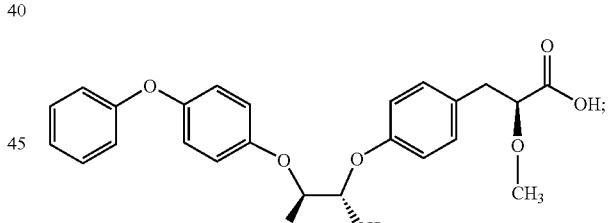

3-{4-[2-(4-Benzoyl-phenoxy)-1-methyl-propoxy]-phenyl}-2-methoxy-propionic acid, represented by the following structural formula:

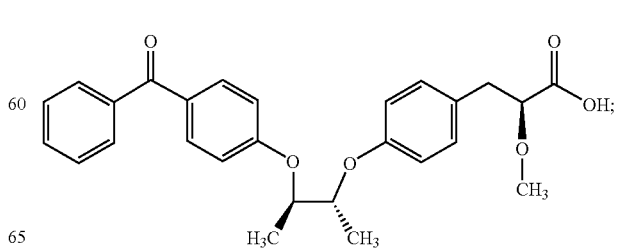

Sodium 3-{4-[3-(4-benzoyl-phenoxy)-propoxy]-phenyl}-2-methoxy-propionate, represented by the following structural formula:

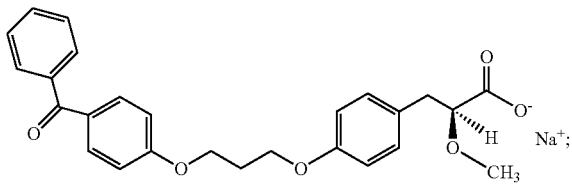

3-{4-[3-(Biphenyl-4-yloxy)-cyclopentyloxy]-phenyl}-2S-methoxy-propionic acid, represented by the following structural formula:

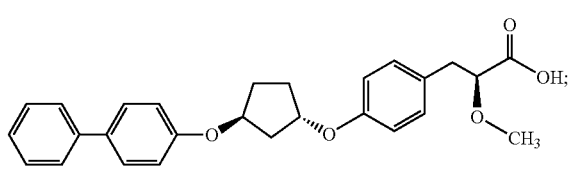

3-{4-[3-(Biphenyl-4-yloxy)-cyclopentyloxy]-phenyl}-2S-methoxy-propionic acid, represented by the following structural formula:

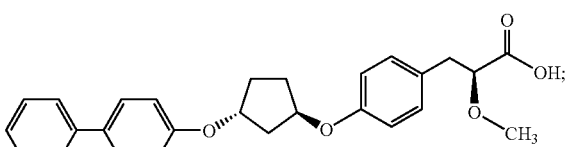

Sodium (S)-2-methoxy-3-{4-[6-(4-phenoxy-phenoxy)-hex-1-ynyl]-phenyl}-propionate, represented by the following structural formula:

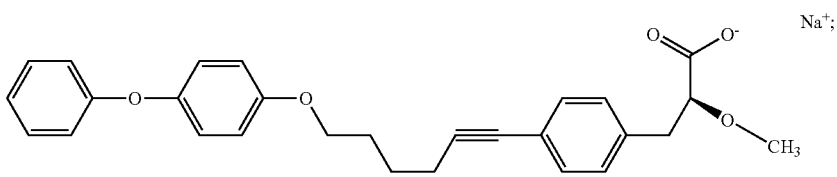

Sodium (S)-3-{4-[6-(4-benzoyl-phenoxy)-hex-1-ynyl]-phenyl}-2-methoxy-propionate, represented by the following structural formula:

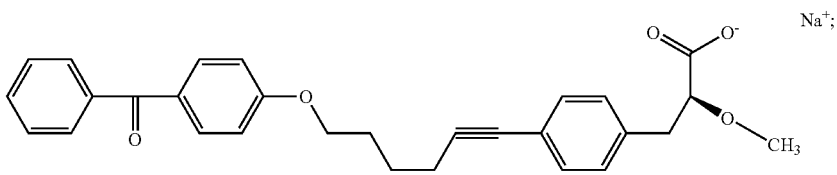

Sodium (S)-3-{4-[6-(biphenyl-4-yloxy)-hex-1-ynyl]-phenyl}-2-methoxy-propionate, represented by the following structural formula:

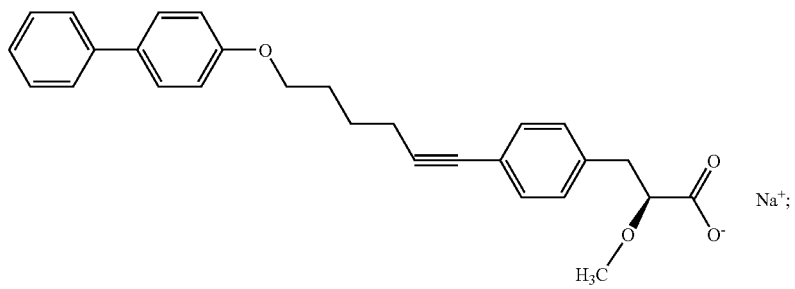

(S)-3-(4-{3-[4-(4-Hydroxy-benzoyl)-phenoxy]-propoxy}-phenyl)-2-methoxy-propionic acid, represented by the following structural formula:

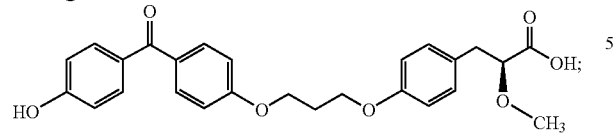

Sodium (S)-2-methoxy-3-{4-[6-(4-phenoxy-phenoxy)-hexanoyl]-phenyl}-propionate, represented by the following structural formula:

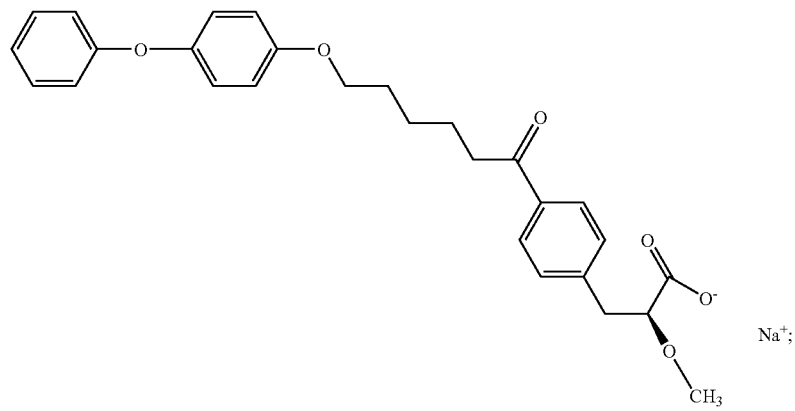

(S)-2-Methoxy-3-{4-[3-(9-oxo-9H-fluoren-2-yloxy)-prop-1-ynyl]-phenyl}-propionic acid, represented by the following structural formula:

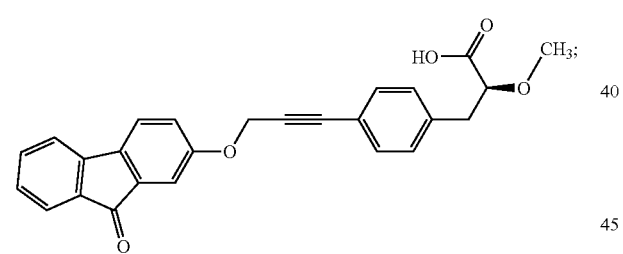

(S)-2-Methoxy-3-{4-[3-(4-oxo-2-phenyl-4H-chromen-7-yloxy)-prop-1-ynyl]-phenyl}-propionic acid, represented by the following structural formula:

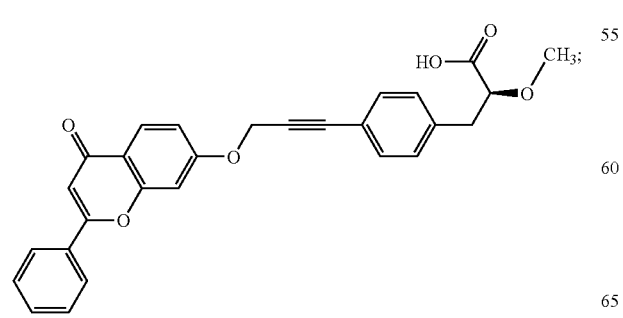

(S)-3-{4-[3-(4-Dibenzofuran-2-yl-phenoxy)-propoxy]-phenyl}-2-methoxy-propionic acid, represented by the following structural formula:

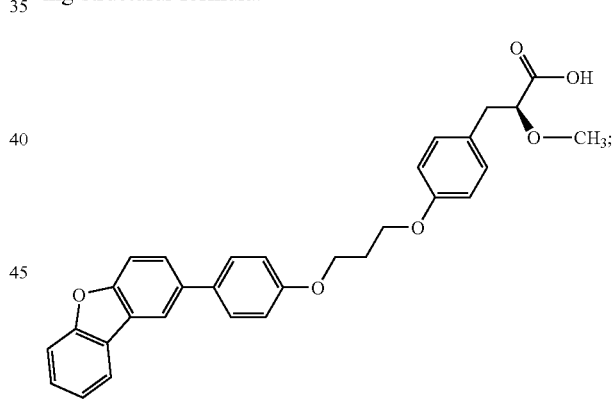

(S)-3-{4-[3-(4'-tert-Butyl-biphenyl-4-yloxy)-propoxy]-phenyl}-2-methoxy-propionic acid, represented by the following structural formula:

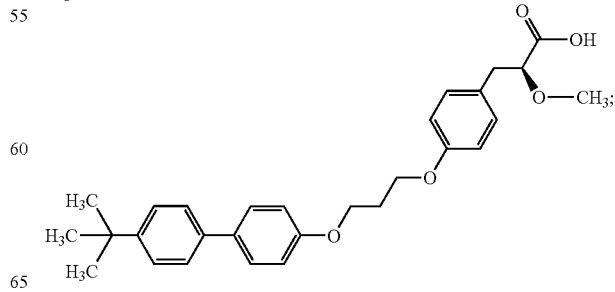

(R)-2-Methoxy-3-{4-[3-(4-phenoxy-phenoxy)-propoxy]-phenyl}-propionic acid, represented by the following structural formula:

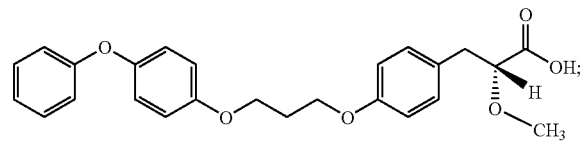

Sodium (S)-2-methoxy-3-{4-[3-(4-phenylacetyl-phenoxy)-cyclopentyloxy]-phenyl}-propionate, represented by the following structural formula:

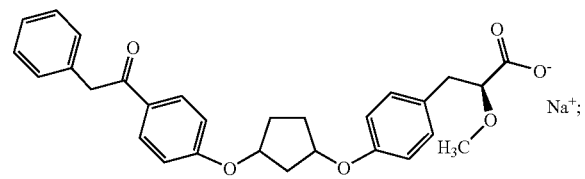

Sodium (S)-3-(4-{3-[4-(2-fluoro-benzoyl)-phenoxy]-propoxy}-phenyl)-2-methoxy-propionate, represented by the following structural formula:

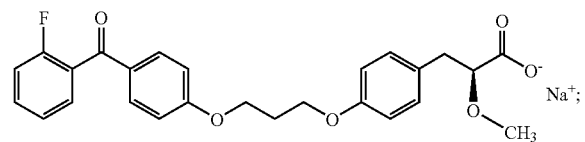

(S)-2-Methoxy-3-{2-methoxy-4-[3-(4-phenoxy-phenoxy)-propoxy]-phenyl}-propionic acid, represented by the following structural formula:

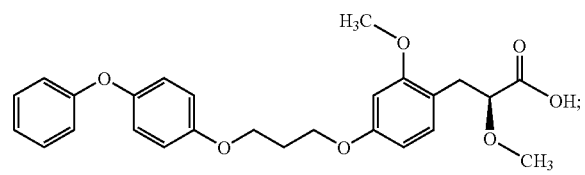

Sodium (S)-3-{4-[4-(4-benzoyl-phenoxy)-but-1-ynyl]-phenyl}-2-methoxy-propionate, represented by the following structural formula:

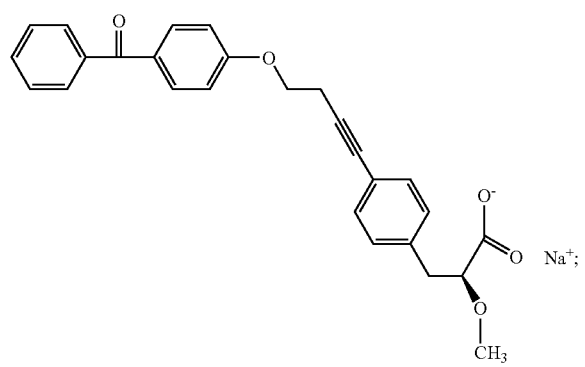

Sodium (S)-3-{6-[3-(biphenyl-4-yloxy)-propoxy]-2'-methoxy-biphenyl-3-yl}-2-methoxy-propionate, represented by the following structural formula:

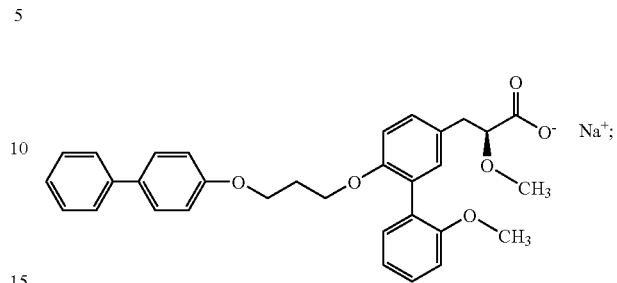

Sodium (S)-3-{4-[3-(4-benzoyl-phenoxy)-propoxy]-3-chloro-phenyl}-2-methoxy-propionate, represented by the following structural formula:

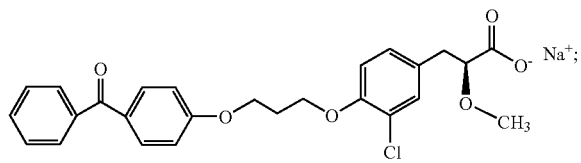

Sodium (S)-2-methoxy-3-{4-[3-(4-oxo-2-phenyl-4H-chromen-6-yloxy)-prop-1-ynyl]-phenyl}-propionate, represented by the following structural formula:

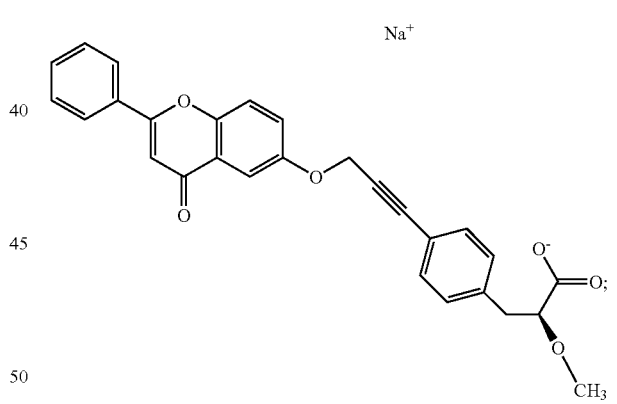

(S)-3-{4-[3-(4'-Hydroxy-biphenyl-4-yloxy)-propoxy]-phenyl}-2-methoxy-propionic acid, represented by the following structural formula:

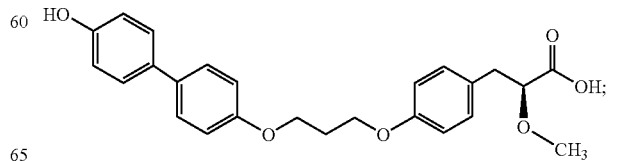

Sodium (S)-2-methoxy-3-(4-{3-[4-(4-trifluoromethyl-phenoxy)-phenoxy]-prop-1-ynyl}-phenyl)-propionate, represented by the following structural formula:

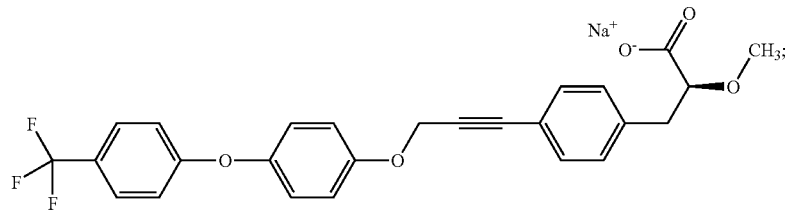

(S)-4'-{3-[4-(2-Carboxy-2-methoxy-ethyl)-phenoxy]-propoxy}-biphenyl-4-carboxylic acid, represented by the following structural formula:

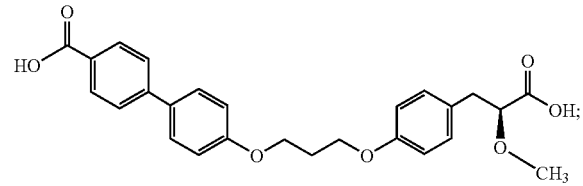

Sodium (S)-2-ethoxy-3-{4-[3-(4-phenoxy-phenoxy)-propoxy]-phenyl}-propionate, represented by the following structural formula:

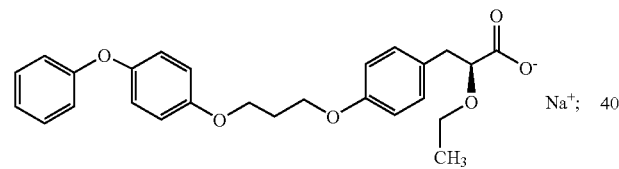

(S)-2-Methoxy-3-{2-methoxy-4-[3-(4-phenoxy-phenoxy)-propoxy]-phenyl}-propionic acid 2-dimethylamino-ethyl ester, represented by the following structural formula:

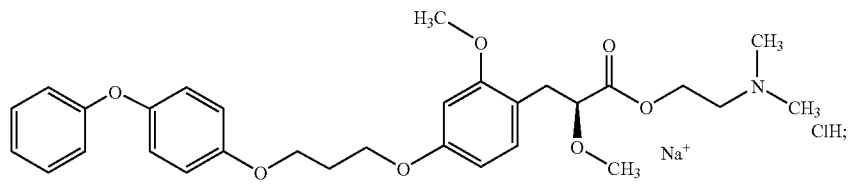

Sodium (S)-3-[4-(3-{4-[(4-fluoro-phenyl)-hydroxy-methyl]-phenoxy}-propoxy)-phenyl]-2-methoxy-propionate, represented by the following structural formula:

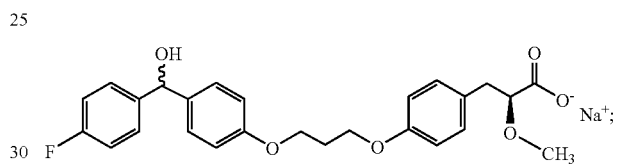

(S)-2-Methoxy-3-(4-{3-[4-(naphthalene-1-carbonyl)-phenoxy]-propoxy}-phenyl)-propionic acid, represented by the following structural formula:

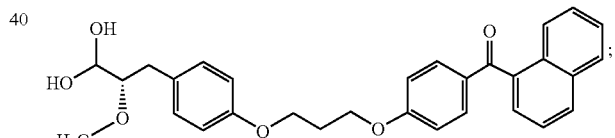

(S)-2-Methoxy-3-(4-{3-[4-(4-methyl-benzoyl)-phenoxy]-propoxy}-phenyl)-propionic acid, represented by the following structural formula:

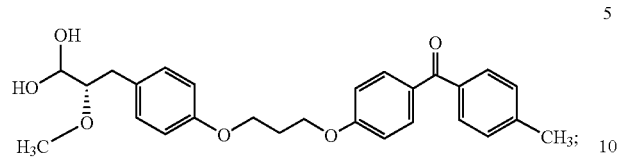

(S)-2-Methoxy-3-(4-{3-[4-(3-phenyl-propionyl)-phenoxy]-propoxy}-phenyl)-propionic acid, represented by the following structural formula:

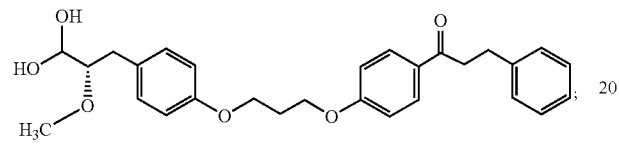

(S)-3-(4-{3-[4-(2,4-Dimethoxy-benzoyl)-phenoxy]-propoxy}-phenyl)-2-methoxy-propionic acid, represented by the following structural formula:

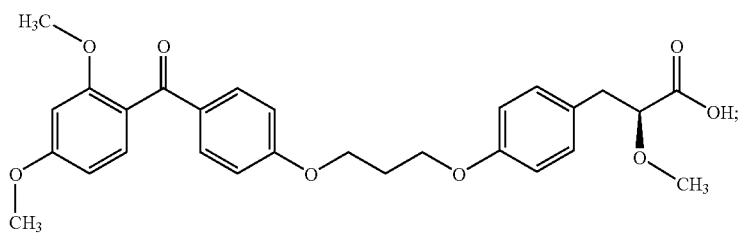

(S)-3-{3-Chloro-4-[3-(4-oxo-2-phenyl-4H-chromen-6-yloxy)-propoxy]-phenyl}-2-methoxy-propionic acid, represented by the following structural formula:

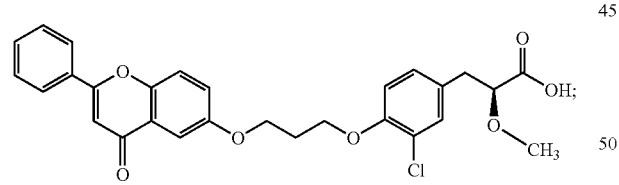

(S)-3-{4-[3-(4-Benzoyl-phenoxy)-propoxy]-2-chloro-phenyl}-2-methoxy-propionic acid, represented by the following structural formula:

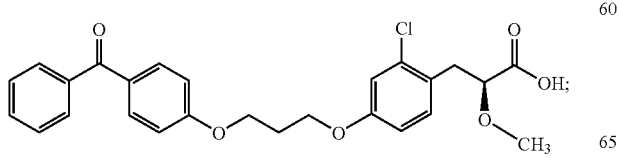

(S)-2-Methoxy-3-(3-methoxy-4-{3-[4-(4-trifluoromethyl-phenoxy)-phenoxy]-propoxy}-phenyl)-propionic acid, represented by the following structural formula:

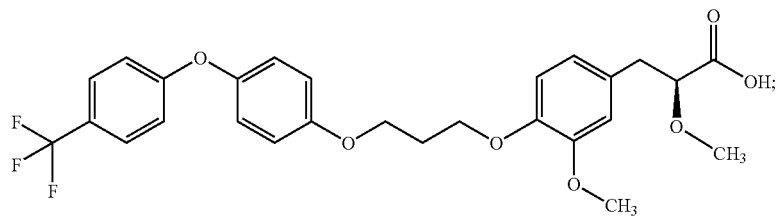

(S)-2-Methoxy-3-(4-{3-[4-(3-methyl-butoxy)-phenoxy]-propoxy}-phenyl)-propionic acid, represented by the following structural formula:

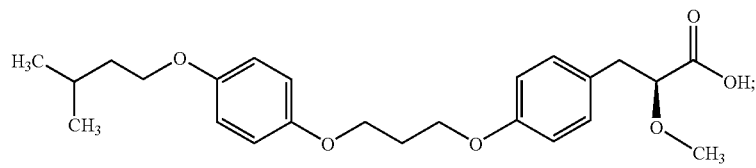

(S)-2-Methoxy-3-{4-[3-(4-phenethyloxy-phenoxy)-propoxy]-phenyl}-propionic acid, represented by the following structural formula:

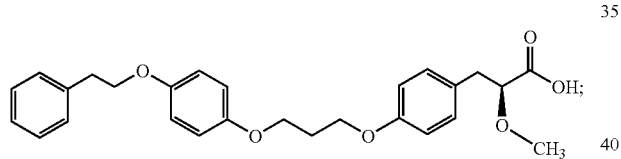

3-{4-[3-(4-Benzoyl-phenoxy)-propoxy]-2-chloro-phenyl}-2-methoxy-propionic acid, represented by the following structural formula:

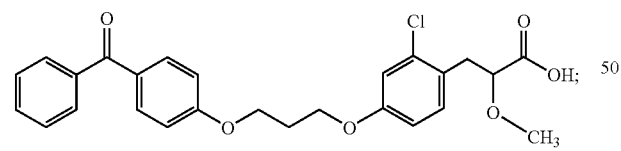

Sodium (S)-3-{4-[3-(biphenyl-4-yloxy)-cyclohexyloxy]-phenyl}-2-methoxy-propionate, represented by the following structural formula:

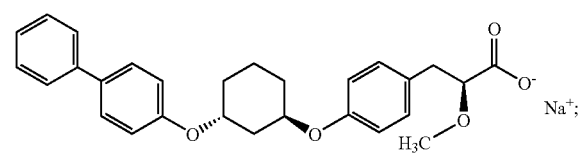

Sodium (S)-3-{4-[3-(2-carboxy-phenoxy)-propoxy]-phenyl}-2-methoxy-propionate, represented by the following structural formula:

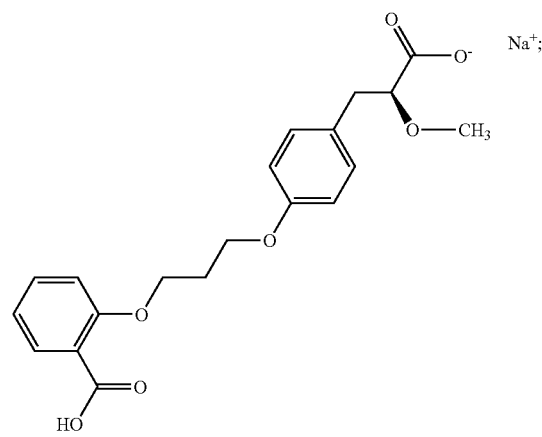

2-Methoxy-3-{2-methoxy-4-[3-(4-phenoxy-phenoxy)-propoxy]-phenyl}-propionic acid, represented by the following structural formula:

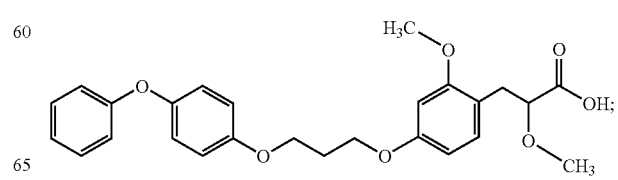

3-{4-[3-(4-Phenoxy-phenoxy)-propoxy]-phenyl}-2-propoxy-propionic acid, represented by the following structural formula:

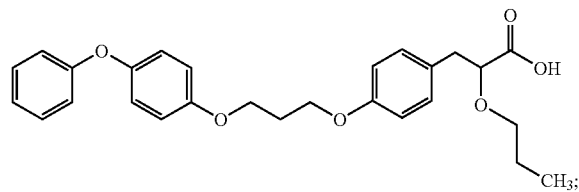

3-{4-[3-(4-Benzoyl-phenoxy)-propoxy]-phenyl}-2-ethoxy-propionic acid, represented by the following structural formula:

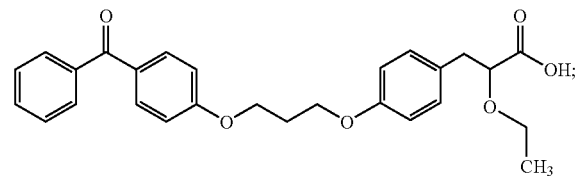

(S)-2-Isopropoxy-3-{4-[3-(4-phenoxy-phenoxy)-propoxy]-phenyl}-propionic acid, represented by the following structural formula:

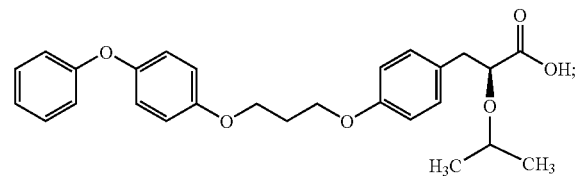

(S)-3-{4-[3-(4-Benzyl-phenoxy)-propoxy]-phenyl}-2-ethoxy-propionic acid, represented by the following structural formula:

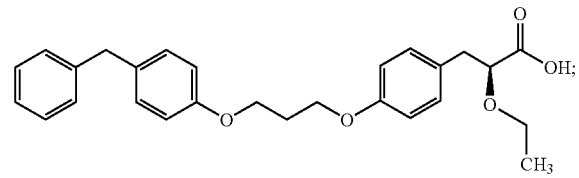

(S)-3-{4-[3-(4-Benzoyl-phenoxy)-propoxy]-3-chloro-phenyl}-2-ethoxy-propionic acid, represented by the following structural formula:

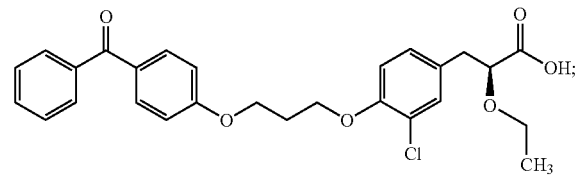

(S)-3-{4-[2-(Biphenyl-4-yloxy)-ethoxy]-phenyl}-2-methoxy-propionic acid, represented by the following structural formula:

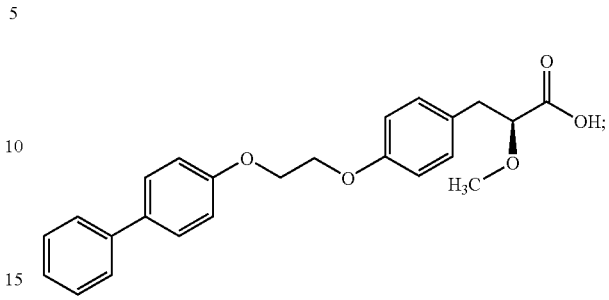

(S)-2-Methoxy-3-{4-[3-(5,6,7,8-tetrahydro-naphthalen-2-yloxy)-propoxy]-phenyl}-propionic acid, represented by the following structural formula:

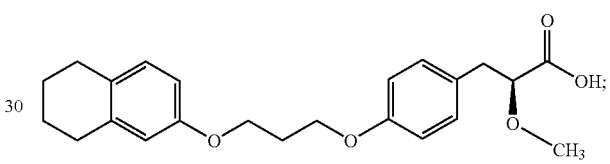

(S)-2-Methoxy-3-{4-[2-(4-phenoxy-phenoxy)-ethoxy]-phenyl}-propionic acid, represented by the following structural formula:

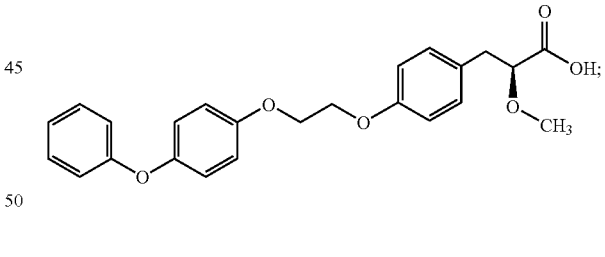

3-{3-[3-(Biphenyl-4-yloxy)-propoxy]-phenyl}-2-methoxy-propionic acid, represented by the following structural formula:

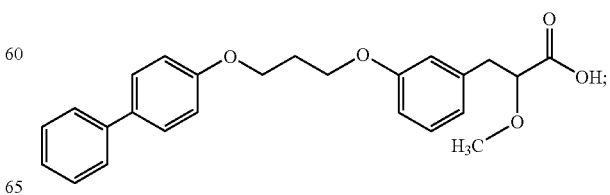

(S)-3-{4-[3-(3-Dimethylamino-phenoxy)-propoxy]-phenyl}-2-methoxy-propionic acid, represented by the following structural formula:

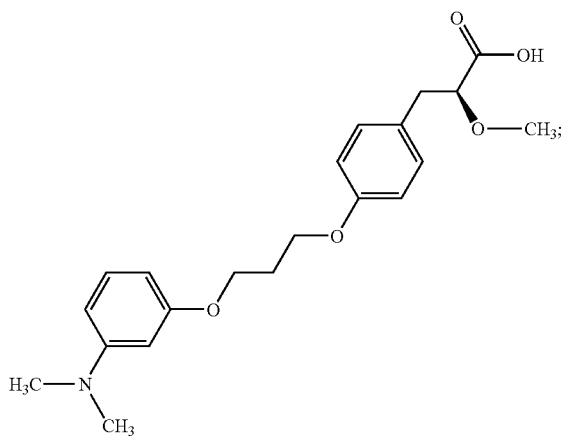

(S)-3-{4-[2-(Biphenyl-4-yloxy)-ethoxy]-phenyl}-2-ethoxy-propionic acid, represented by the following structural formula:

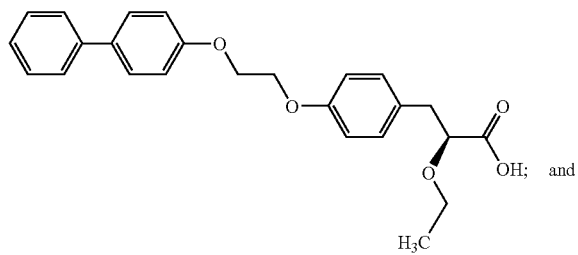

and (S)-3-{4-[2-(Biphenyl-4-yloxy)-ethoxy]-phenyl}-2-propoxy-propionic acid, represented by the following structural formula:

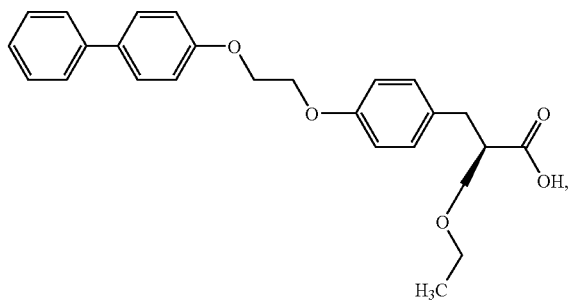

or a pharmaceutically acceptable salts, hydrates and solvates of the foregoing compounds.

4. A compound represented by the following structural formula:

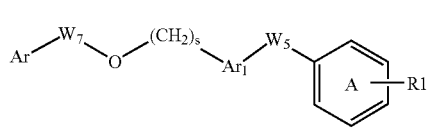

(XL)

or pharmaceutically acceptable salts, hydrates, stereoisomers and solvates thereof, wherein:

Ar is represented by a structural formula selected from:

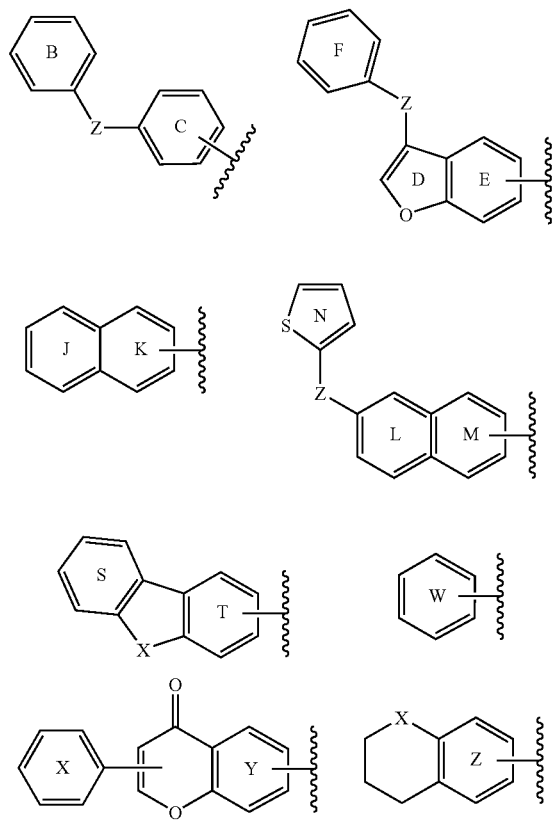

$R_1$ is $-(CH_2)_n-CH(OR_2)-(CH_2)_mE$, $-(CH)=C(OR_2)-(CH_2)_mE$, $-(CH_2)_n-CH(Y)-(CH_2)_mE$ or $-(CH)=C(Y)-(CH_2)_mE$; wherein E is $COOR_3$, $C_1-C_3$-alkylnitrile, carboxamide, sulfonamide or acylsulfonamide and wherein sulfonamide and acylsulfonamide are optionally substituted with one or more substituents independently selected from: C1–C6 alkyl, haloalkyl and aryl-C0-4-alkyl;

$R_2$ is $-H$, an aliphatic group, a substituted aliphatic group, an aromatic group, a substituted aromatic group, $-COR_4$, $-COOR_4$, $-CONR_5R_6$, $-C(S)R_4$, $-C(S)OR_4$ or $-C(S)NR_5R_6$;

Y is $-O-$, $-CH_2-$, $-CH_2CH_2-$ or $-CH=CH-$ and is bonded to a carbon atom in Phenyl Ring A that is ortho to $R_1$;

$R_3-R_6$ are independently $-H$, an aliphatic group, a substituted aliphatic group, an aromatic group or a substituted aromatic group;

n and m are independently 0, 1 or 2;

Ring B-Z are independently substituted or unsubstituted;

X is $-O-$, $-S-$, $-CH_2-$ or $-C(O)-$;

Z is a covalent bond, $-O-$, $(-CH_2)_q-$, $-CH(CH_3)(CH_2)_q-$, $-(CH_3)_2(CH_2)_q-$, $-(CH_2)_qCH(CH_3)-$, $-(CH_2)_qC(CH_3)_2-$, $-O(CH_2)_q-$, $-(CH_2)_qO-$, $-(CH_2)_qNH-$, $-(CH_2)_qNH-$, $-(CH_2)_qCHR_{20}-$, $-CHR_{20}(CH_2)_q-$, $-(CH_2)_qCR_{20}R_{20}-$, $-(CH_2)_qCR_{20}R_{20}-$, $-(CH_2)_qNR_{20}-$, $-NR_{20}(CH_2)_q-$, —$(CH_2)_qC(=NOH)—$, —$C(=NOH)(CH_2)_q—$, —$CH(OH)—(CH_2)_q—$, —$(CH_2)_q—CH(OH)—$, —$CO—(CH_2)_q—$, —$(CH_2)_q—CO—$, —$COO—(CH_2)_q—$, —$OCO—(CH_2)_q—$, —$(CH_2)_q—OCO—$, —$(CH_2)_q—COO—$, —$(CH_2)_qCO—NH—$, —$(CH_2)_qNH—CO—$, —$(CH_2)_qCONR_{20}—$, —$CONR_{20}(CH_2)_q—$, —$(CH_2)_qNR_{20}CO—$ or —$NR_{20}CO(CH_2)_q—$;

q is, 0, 1, 2 or 3; and each $R_{20}$ is independently a C1–C5 alkyl group or a halogenated C1–C5 alkyl group;

s is 0, 1 or 2;

$Ar_1$ is a substituted or unsubstituted arylene group;

$W_6$ is a covalent bond, —$W_1$—, —$CH_2W_1$— or —$W_1CH_2$—;

$W_7$ is a covalent bond or $CH_2$—; and $W_1$ is —O—, —C(O)—, —$OCH_2$—, —$CH_2$—, —$NR_8$—, —$NR_8CO$—, —$NR_8CH$—, —$C(=NOH)$— or —$CH(NR_7R_8)$—.

5. The compound of claim 4 wherein $R_1$ is —$(CH_2)_n—CH(OR_2)—(CH_2)_mCOOR_3$, —$(CH)=C(OR_2)—(CH_2)_mCOOR_3$, —$(CH_2)_n—CH(Y)—(CH_2)_mCOOR_3$ or —$(CH)=C(Y)—(CH_2)_mCOOR_3$.

6. The compound of claim 5 wherein the compound is represented by the following structural formula:

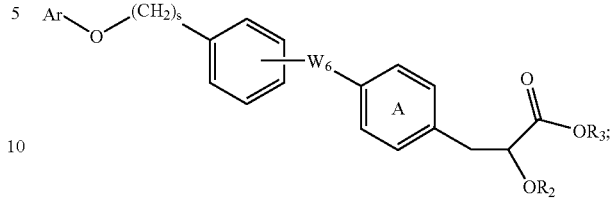

wherein s is 0 or 1 and $W_6$ is a covalent bond, —O—, —$CH_2O$— or —$OCH_2$—.

7. A pharmaceutical composition comprising the compound of claim 2 or a pharmaceutically acceptable salt, solvate or hydrate thereof, and a pharmaceutically acceptable carrier.

8. A method for lowering blood-glucose in a subject comprising the step of administering to the subject an effective amount of the compound of claim 2.

* * * * *

UNITED STATES PATENT AND TRADEMARK OFFICE
CERTIFICATE OF CORRECTION

PATENT NO. : 7,192,982 B2 Page 1 of 1
APPLICATION NO. : 10/479262
DATED : March 20, 2007
INVENTOR(S) : Dawn Alisa Brooks et al.

It is certified that error appears in the above-identified patent and that said Letters Patent is hereby corrected as shown below:

Column 375
Line 60, delete
"
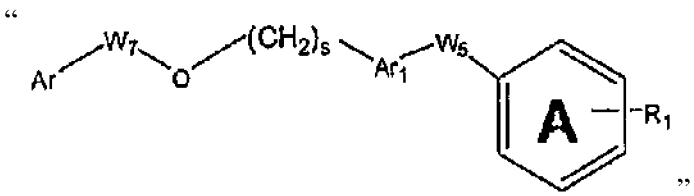
"

and insert
--
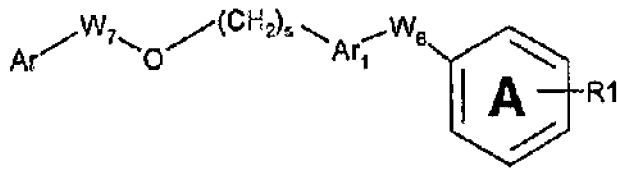
--

Column 376
Line 59, delete "Ring B-Z" and insert --Rings B-Z--

Signed and Sealed this

Nineteenth Day of June, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 31
<212> TYPE: DNA
<213> ORGANISM: Human

<400> SEQUENCE: 1
taatgtaggt aatagttcaa taggtcaaag g                        31